US007202334B1

(12) United States Patent
Mitcham et al.

(10) Patent No.: US 7,202,334 B1

(45) Date of Patent: Apr. 10, 2007

(54) COMPOSITIONS AND METHODS FOR THE THERAPY AND DIAGNOSIS OF OVARIAN CANCER

(75) Inventors: Jennifer L. Mitcham, Redmond, WA (US); Gordon E. King, Seattle, WA (US); Paul A. Algate, Issaquah, WA (US); Steven P. Fling, Bainbridge Island, WA (US); Marc W. Retter, Carnation, WA (US); Gary R. Fanger, Mill Creek, WA (US); Steven G. Reed, Bellevue, WA (US)

(73) Assignee: Corixa Corporation, Hamilton, MT (US)

( * ) Notice: Subject to any disclaimer, the term of this patent is extended or adjusted under 35 U.S.C. 154(b) by 371 days.

(21) Appl. No.: 09/636,801

(22) Filed: Aug. 10, 2000

Related U.S. Application Data

(63) Continuation-in-part of application No. 09/617,747, filed on Jul. 17, 2000, now abandoned, which is a continuation-in-part of application No. 09/404,879, filed on Sep. 24, 1999, now Pat. No. 6,468,546.

(51) Int. Cl.
*A61K 39/00* (2006.01)

(52) U.S. Cl. .................... 530/350; 530/828; 424/184.1; 424/185.1; 424/277.1; 436/501; 436/64; 436/813; 435/7.1

(58) Field of Classification Search ................ 530/300, 530/350, 810; 424/184.1; 514/2–12; 436/510, 436/64, 813

See application file for complete search history.

(56) References Cited

U.S. PATENT DOCUMENTS 5,082,767 A * 1/1992 Hatfield et al. ................ 435/6

FOREIGN PATENT DOCUMENTS

| | | |
|---|---|---|
| EP | 1033401 A2 | 9/2000 |
| WO | WO 99/25877 | 5/1999 |
| WO | WO-99/63008 A2 * | 12/1999 |
| WO | WO 99/63088 | 12/1999 |
| WO | WO 00/12758 | 3/2000 |
| WO | WO 00/55629 | 9/2000 |
| WO | WO 00/73454 | 12/2000 |
| WO | WO 00/76531 | 12/2000 |
| WO | WO 01/16318 | 3/2001 |
| WO | WO 01/18542 | 3/2001 |
| WO | WO 01/40269 | 6/2001 |
| WO | WO 01/57272 | 8/2001 |
| WO | WO 01/94641 | 12/2001 |
| WO | WO 02/02587 | 1/2002 |
| WO | WO 02/02624 | 1/2002 |
| WO | WO 02/10187 | 2/2002 |
| WO | WO 02/16429 | 2/2002 |
| WO | WO 02/16581 | 2/2002 |

OTHER PUBLICATIONS

Biochemistry. Lehninger, A. (1970) Worth Publishers, New York, pp. 57-62 and 718.*

Nagata et al. BBRC (1999) vol. 261, pp. 445-451.*

Bookman et al., "Biological therapy of ovarian cancer: Current directions," *Seminars in Oncology*, 25(3):381-396, 1998.

Gillespie et al., "Mage, Bage and Gage: Tumour antigen expression in benign and malignant ovarian tissue," *British Journal of Cancer*, 78(6):816-821, Sep., 1998.

Heller et al., "Discovery and analysis of inflammatory disease-related genes using cDNA microarrays," *Proc. Natl. Acad. Sci. USA 94*:2150-2155, Mar., 1997.

Ishikawa et al., "Prediction of the coding sequence of unidentified human genes. The complete sequence of 100 new cDNA clones from brain which can code for large proteins i vitro," *DNA Res.*, 5:169-176, 1998.

Jin et al., "Human T cell leukemia virus type 1 oncoprotein tax targets the human mitotic checkpoint protein MAD1," *Cell 93*:81-91, Apr. 3, 1998.

Köhler et al., "Immotherapy of Ovarian Carcinoma with the Monoclonal Anti-Idiotype Antibody ACA125—Results of the Phase LB Study," *Gebrutshilfe und Fraenheilkunde*, 58(4):180-186, Apr. 1998+(English Abstract).

Ma et al., "Use of encapsulated single chain antibodies for induction of anti-idiotypic humoral and cellular immune responses," *Journal of Pharmaceutical Sciences*, 87(11):1375 1378, Nov., 1998.

Parker et al., "Scheme for ranking potential HLA-A2 binding peptides based on independent binding of individual peptide side-chains," *The Journal of Immunology 152*(1):163-175, Jan. 1, 1994.

Peoples et al., "Ovarian cancer-associated lymphocyte recognition of folate binding protein peptides," *Annals of Surgical Oncology*, 5(8):743-750, Dec., 1998.

Schena et al., "Parallel human genome analysis: Microarray-based expression monitoring of 1000 genes," *Proc. Natl. Acad. Sci.*, 93:10614-10619, Oct., 1996.

LifeSeq Accession No. 027245.1, May 1999.

Life Seq Accession No. 2798803H1, Mar. 1997.

Frankel, A.E. et al., "Targeted Toxins," *Clinical Cancer Research 6*: 326-334, Feb. 2000.

(Continued)

*Primary Examiner*—Mary K. Zeman
(74) *Attorney, Agent, or Firm*—Seed IP Law Group PLLC

(57) ABSTRACT

Compositions and methods for the therapy and diagnosis of cancer, such as ovarian cancer, are disclosed. Compositions may comprise one or more ovarian carcinoma proteins, immunogenic portions thereof, polynucleotides that encode such portions or antibodies or immune system cells specific for such proteins. Such compositions may be used, for example, for the prevention and treatment of diseases such as ovarian cancer. Methods are further provided for identifying tumor antigens that are secreted from ovarian carcinomas and/or other tumors. Polypeptides and polynucleotides as provided herein may further be used for the diagnosis and monitoring of ovarian cancer.

7 Claims, 101 Drawing Sheets

OTHER PUBLICATIONS

GenBank Accession No. AA075632, Dec. 23, 1997. Available at www.ncbi.nlm.nih.gov/entrz .

GenBank Accession No. AA404225, Aug. 8, 1997. Available at www.ncbi.nlm.nih.gov/entrz .

GenBank Accession No. NM_024626, Sep. 3, 2004. Available at www.ncbi.nlm.nih.gov/entrz .

GenBank Accession No. NP_078902, Sep. 3, 2004. Available at www.ncbi.nlm.nih.gov/entrz .

GenBank Accession No. XM_018334, Oct. 16, 2001. Available at www.ncbi.nlm.nih.gov/entrz .

GenBank Accession No. XP_018334, Oct. 16, 2001. Available at www.ncbi.nlm.nih.gov/entrz .

* cited by examiner 11729.1 contg

TTAGAGAGGCACAGAAGGAAGAAGAGTTAAAAGCAGCAAAGCCGGGTTTTTTTGTTTTGTTTTGTTTTGTTTTGTT
TTGAGATGGAGTCTCACTCTGTTGCCCAAGCTGGAGTACAACGGCATGATCTCAGCTCGCTGCAACCTCCGCCTCC
CACGTTCAAGTGATTCTCCTGCCTCAGCCTCCCAAGTAGCTGGGATTACAGGCGCCCGCCACCACGCTCAGCTAAT
TTTTTTTGTATTTTTAGTAGAGACAGGGTTTCACCAGGTTGGCCAGGCTGCTCTTGAACTCCTGACCTCAGGTGAT
CCACCCGCCTCGGCCTCCCAAAGTGCTGGGATTACAGGCGTGAGCCACCACGCCCGGCCCCCAAAGCTGTTTCTTT
TGTCTTTAGCGTAAAGCTCTCCTGCCATGCAGTATCTACATAACTGACGTGACTGCCAGCAAGCTCAGTCACTCCG
TGGTC 11729-45.21.21.cons1

TAGGATGTGTTGGACCCTCTGTGTCAAAAAAAACCTCACAAAGAATCCCCTGCTCATTACAGAAGAAGATGCATTT
AAAATATGGGTTATTTTCAACTTTTTATCTGAGGACAAGTATCCATTAATTATTGTGTCAGAAGAGATTGAATACC
TGCTTAAGAAGCTTACAGAAGCTATGGGAGGAGGTTGGCAGCAAGAACAATTTGAACATTATAAAATCAACTTTGA
TGACAGTAAAAATGGCCTTTCTGCATGGGAACTTATTGAGCTTATTGGAAATGGACAGTTTAGCAAAGGCATGGAC
CGGCAGACTGTGTCTATGGCAATTAATGAAGTCTTTAATGAACTTATATTAGATGTGTTAAAGCAGGGTTACATGA
TGAAAAAGGGCCACAGACGGAAAAACTGGACTGAAAGATGGTTTGTACTAAAACCCAACATAATTTCTTACTATGT
GAGTGAGGATCTGAAGGATAAGAAAGGAGACATTCTCTTGGATGAAAATTGCTGTGTAGAGTCCTTGCCTGACAAA
GATGGAAA 11729-45.21.21.cons2

TTAGAGAGGCACAGAAGGAAGAAGAGTTAAAAGCAGCAAAGCCGGGTTTTTTTGTTTTGTTTTGTTTTGTTTTGTT
TTGAGATGGAGTCTCACTCTGTTGCCCAAGCTGGAGTACAACGGCATGATCTCAGCTCGCTGCAACCTCCGCCTCC
CACGTTCAAGTGATTCTCCTGCCTCAGCCTCCCAAGTAGCTGGGATTACAGGCGCCCGCCACCACGCTCAGCTAAT
TTTTTTTGTATTTTTAGTAGAGACAGGGTTTCACCAGGTTGGCCAGGCTGCTCTTGAACTCCTGACCTCAGGTGAT
CCACCCGCCTCGGCCTCCCAAAGTGCTGGGATTACAGGCGTGAGCCACCACGCCCGGCCCCCAAAGCTGTTTCTTT
TGTCTTTAGCGTAAAGCTCTCCTGCCATGCAGTATCTACATAACTGACGTGACTGCCAGCAAGCTCAGTCACTCCG
TGGTC 11731.1contig TCTTTTTCTTTCGATTTCCTTCAATTTGTCACGTTTGATTTTATGAAGTTGTTCAAGGGCTAACTGCTGTGTATTA
TAGCTTTCTCTGAGTTCCTTCAGCTGATTGTTAAATGAATCCATTTCTGAGAGCTTAGATGCAGTTTCTTTTTCAA
GAGCATCTAATTGTTCTTTAAGTCTTTGGCATAATTCTTCCTTTTCTGATGACTTTTTATGAAGTAAACTGATCCC
TGAATCAGGTGTGTTACTGAGCTGCATGTTTTTAATTCTTTCGTTTAATAGCTGCTTCTCAGGGACCAGATAGATA
AGCTTATTTTGATATTCCTTAAGCTCTTGTTGAAGTTGTTTGATTTCCATAATTTCCAGGTCACACTGTTTATCCA
AAACTTCTAGCTCAGTCTTTTGTGTTTGCTTTCTGATTTGGACATCTTGTAGTCTGCCTGAGATCTGCTGATGXTT
TCCATTCACTGCTTCCAGTTCCAGGTGGAGACTTTXCTTTCTGGAGCTCAGCCTGACAATGCCTTCTTGXTCCCT

*Fig. 1A*

11731.2contig

AGCCAGATGGCTGAGAGCTGCAAGAAGAAGTCAGGATCATGATGGCTCAGTTTCCCACAGCGATGAATGGAGGGCC
AAATATGTGGGCTATTACATCTGAAGAACGTACTAAGCATGATAAACAGTTTGATAACCTCAAACCTTCAGGAGGT
TACATAACAGGTGATCAAGCCCGTACTTTTTTCCTACAGTCAGGTCTGCCGGCCCCGGTTTTAGCTGAAATATGGG
CCTTATCAGATCTGAACAAGGATGGGAAGATGGACCAGCAAGAGTTCTCTATAGCTATGAAACTCATCAAGTTAAA
GTTGCAGGGCCAACAGCTGCCTGTAGTCCTCCCTCCTATCATGAAACAACCCCCTATGTTCTCTCCACTAATCTCT
GCTCGTTTTGGGATGGGAAGCATGCCCAATCTGTCCATTCATCAGCCATTGCCTCCAGTTGCACCTATAGCAACAC
CCTTGTCTTCTGCTACTTCAGGGACCAGTATTCCTCCCCTAATGATGCCTGCTCCCCTAGTGCCTTCTGTTAGTA 11734.1contig AATAGATTTAATGCAGAGTGTCAACTTCAATTGATTGATAGTGGCTGCCTAGAGTGCTGTGTTGAGTAGGTTTCTG
AGGATGCACCCTGGCTTGAAGAGAAAGACTGGCAGGATTAACAATATCTAAAATCTCACTTGTAGGAGAAACCACA
GGCACCAGAGCTGCCACTGGTGCTGGCACCAGCTCCACCAAGGCCAGCGAAGAGCCCAAATGTGAGAGTGGCGGTC
AGGCTGGCACCAGCACTGAAGCCACCACTGGTGCTGGCACTGGCACTGGCACTGTTATTGGTACTGGTACTGGCAC
CAGTGCTGGCACTGCCACTCTCTTGGGCTTTGGCTTTAGCTTCTGCTCCCGCCTGGATCCGGGCTTTGGCCCAGGG
TCCGATATCAGCTTCGTCCCAGTTGCAGGGCCCGGCAGCATTCTCCGAGCCGAGCCCAATGCCCATTCGAGCTCTA
ATCTCGGCCCTAGCCTTGGCTTCAGCTGCAGCCTCAGCTGCAGCCTTCAAATCCGCTTCCATCGCCTCTCGGTAC 11734.2contig GCCAAGAAAGCCCGAAAGGTGAAGCATCTGGATGGGGAAGAGGATGGCAGCAGTGATCAGAGTCAGGCTTCTGGAA
CCACAGGTGGCCGAAGGGTCTCAAAGGCCCTAATGGCCTCAATGGCCCGCAGGGCTTCAAGGGGTCCCATAGCCTT
TTGGGCCCGCAGGGCATCAAGGACTCGGTTGGCTGCTTGGGCCCGGAGAGCCTTGCTCTCCCTGAGATCACCTAAA
GCCCGTAGGGGCAAGGCTCGCCGTAGAGCTGCCAAGCTCCAGTCATCCCAAGAGCCTGAAGCACCACCACCTCGGG
ATGTGGCCCTTTTGCAAGGGAGGGCAAATGATTTGGTGAAGTACCTTTTGGCTAAAGACCAGACGAAGATTCCCAT
CAAGCGCTCGGACATGCTGAAGGACATCATCAAAGAATACACTGATGTGTACCCCGAAATCATTGAACGAGCAGGC
TATTCCTTGGAGAAGGTATTTGGGATTCAATTGAAGGAAATTGATAAGAATGACCACTTGTACATTCTTCTCAGC 11736.1contg GAGGTCTCACTATGTTGCCCAGGCTGTTCTTGAACTCCTGGGATCAAGCAATCCACCCATGTTGGTCTCCAAAAGT
GCTGGGATCATAGGCGTGAGCCACCTCACCCAGCCACCAATTTTCAATCAGGAAGACTTTTTCCTTCTTCAAGAAG
TGAAGGGTTTCCAGAGTATAGCTACACTATTGCTTGCCTGAGGGTGACTACAAAATTGCTTGCTAAAAGGTTAGGA
TGGGTAAAGAATTAGATTTTCTGAATGCAAAAATAAAATGTGAACTAATGAACTTTAGGTAATACATATTCATAAA
ATAATTATTCACATATTTCCTGATTTATCACAGAAATAATGTATGAAATGCTTTGAGTTTCTTGGAGTAAACTCCA
TTACTCATCCCAAGAAACCATATTATAAGTATCACTGATAATAAGAACAACAGGACCTTGTCATAAATTCTGGATA
AGAGAAATAGTCTCTGGGTGTTTGXTCTTAATTGATAAAATTTACTTGTCCATCTTTTAGTTCAGAATCACAAAA

*Fig. 1B*

11736.2contig

AAGCGGAAATGAGAAAGGAGGGAAAATCATGTGGTATTGAGCGGAAAACTGCTGGATGACAGGGCTCAGTCCTGTT
GGAGAACTCTGGGTGGTGCTGTAGAACAGGGCCACTCACAGTGGGGTGCACAGACCAGCACGGCTCTGTGACCTGT
TTGTTACAGGTCCATGATGAGGTAAACAATACACTGAGTATAAGGGTTGGTTTAGAAACTCTTACAGCAATTTGAC
AAAGTAATCTTCTGTGCAGTGAATCTAAGAAAAAAATTGGGGCTGTATTTGTATGTTCCTTTTTTTCATTTCATGT
TCTGAGTTACCTATTTTTATTGCATTTTACAAAAGCATCCTTCCATGAAGGACCGGAAGTTAAAAACAAAGCAGGT
CCTTTATCACAGCACTGTCGTAGAACACAGTTCAGAGTTATCCACCCAAGGAGCCAGGGAGCTGGGCTAAACCAAA
GAATTTTGCTTTTGGTTAATCATCAGGTACTTGAGTTGGAATTGTTTTAATCCCATCATTACCAGGCTGGAXGTG 11739-1&2

CCGCGGCTCCTGTCCAGACCCTGACCCTCCCTCCCAAGGCTCAACCGTCCCCCAACAACCGCCAGCCTTGTACTGA
TGTCGGCTGCGAGAGCCTGTGCTTAAGTAAGAATCAGGCCTTATTGGAGACATTCAAGCAAAGGTTGGACAACTAC
TTTTCCAGAACAGAAAGGAAACTCATGCATCAGAAAAGGTGACTAATAAAGGTACCAGAAGAATATGGCTGCACAA
ATACCAGAATCTGATCAGATAAAACAGTTTAAGGAATTTCTGGGGACCTACAATAAACTTACAGAGACCTGCTTTT
TGGACTGTGTTAGAGACTTCACAACAAGAGAAGTAAAACCTGAAGAGACCACCTGTTCAGAACATTGCTTACAGAA
ATATTTAAAAATGACACAAAGAATATCCATGAGATTTCAGGAATATCATATTCAGCAGAATGAAGCCCTGGCAGCC
AAAGCAGGACTCCTTGGCCAACCACGATAGAGAAGTCCTGATGGATGAACTTTTGATGAAAGATTGCCAACAGCTG
CTTTATTGGAAATGAGGACTCATCTGATAGAATCCCCTGAAAGCAGTAGCCACCATGTTCAACCATCTGTCATGAC
TGTTTGGCAAATGGAAACCGCTGGAGAAACAAAATTGCTATTTACCAGGAATAATCACAATAGAAGGTCTTATTGT
TCAGTGAAATAATAAGATGCAACATTTGTTGAGGCCTTATGATTCAGCAGCTTGGTCACTTGATTAGAAAAATAAA
CCATTGTTTCTTCAATTGTGACTGTTAATTTTAAAGCAACTTATGTGTTCGATCATGTATGAGATAGAAAAATTTT
TATTACTCAAAGTAAAATAAATGGA 11740.1.contig GAAAAAAAATATAAAACACACTTTTGCGAAAACGGTGGCCCTAAAAGAGGAAAAGAATTTCACCAATATAAATCCA
ATTTTATGAAAACTGACAATTTAATCCAAGAATCACTTTTGTAAATGAAGCTAGCAAGTGATGATATGATAAAATA
AACGTGGAGGAAATAAAAACACAAGACTTGGCATAAGATATATCCACTTTTGATATTAAACTTGTGAAGCATATTC
TTCGACAAATTGTGAAAGCGTTCCTGATCTTGCTTGTTCTCCATTTCAAATAAGGAGGCATATCACATCCCAAGAG
TAACAGAAAAAGAAAAAAGACATTTTTGCATTTTGAGATGAACCAAAGACACAAAACAAAACGAACAAAGTGTCAT
GTCTAATTCTAGCCTCTGAAATAAACCTTGAACATCTCCTACAAGGCACCGTGATTTTTGTAATTCTAACCTGAAG
AAATGTGATGACTTTTGTGGACATGAAAATCAGATGAGAAAACTGTGGTCTTTCCAAAGCCTGAACTCCCCTGAAA
ACCTTTGCA

*Fig. 1C*

11766.1.contig

CTGGGATCATTTCTCTTGATGTCATAAAAGACTCTTCTTCTTCCTCTTCATCCTCTTCTTCATCCTCTTCTGTACA
GTGCTGCCGGGTACAACGGCTATCTTTGTCTTTATCCTGAGATGAAGATGATGCTTCTGTTTCTCCTACCATAACT
GAAGAAATTTCGCTGGAAGTCGTTTGACTGGCTGTTTCTCTGACTTCACCTTCTTTGTCAAACCTGAGTCTTTTTA
CCTCATGCCCCTCAGCTTCCACAGCATCTTCATCTGGATGTTTATTTTTCAAAGGGCTCACTGAGGAAACTTCTGA
TTCAGAGGTCGAAGAGTCACTGTGATTTTTCTCCTCATTTTGCTGCAAATTTGCCTCTTTGCTGTCTGTGCTCTCA
GGCAACCCATTTGTTGTCATGGGGGCTGACAAAGAAACCTTTGGTCGATTAAGTGGCCTGGGTGTCCCAGGCCCAT
TTATATTAGACCTCTCAGTATAGCTTGGTGAATTTCCAGGAAACATAACACCATTCATTCGATTTAAACTATTGGA
ATTGGTTTT 11766.2.contig GAGGGTTGGTGGTAGCGGCTTGGGGAGGTGCTCGCTCTGTCGGTCTTGCTCTCTCGCACGCTTCCCCCGGCTCCCT
TCGTTTCCCCCCCCCGGTCGCCTGCGTGCCGGAGTGTGTGCGAGGGAGGGGGAGGGCGTCGGGGGGGTGGGGGGAG
GCGTTCCGGTCCCCAAGAGACCCGCGGAGGGAGGCGGAGGCTGTGAGGGACTCCGGGAAGCCATGGACGTCGAGAG
GCTCCAGGAGGCGCTGAAAGATTTTGAGAAGAGGGGGAAAAAGGAAGTTTGTCCTGTCCTGGATCAGTTTCTTTGT
CATGTAGCCAAGACTGGAGAAACAATGATTCAGTGGTCCCAATTTAAAGGCTATTTTATTTTCAAACTGGAGAAAG
TGATGGATGATTTCAGAACTTCAGCTCCTGAGCCAAGAGGTCCTCCCAACCCTAATGTCGA 11773.2.contig AAGCAGGCGGCTCCCGCGCTCGCAGGGCCGTGCCACCTGCCCGCCCGCCCGCTCGCTCGCTCGCCCGCCGCGCCGC
GCTGCCGACCGCCAGCATGCTGCCGAGAGTGGGCTGCCCCGCGCTGCCGXTGCCG 11775-1&2

ATCTCTTGTATGCCAAATATTTAATATAAATCTTTGAAACAAGTTCAGATGAAATAAAAATCAAAGTTTGCAAAAA
CGTGAAGATTAACTTAATTGTCAAATATTCCTCATTGCCCCAAATCAGTATTTTTTTTATTTCTATGCAAAAGTAT
GCCTTCAAACTGCTTAAATGATATATGATATGATACACAAACCAGTTTTCAAATAGTAAAGCCAGTCATCTTGCAA
TTGTAAGAAATAGGTAAAAGATTATAAGACACCTTACACACACACACACACACACACACGTGTGCACGCCAATGAC
AAAAAACAATTTGGCCTCTCCTAAAATAAGAACATGAAGACCCTTAATTGCTGCCAGGAGGGAACACTGTGTCACC
CCTCCCTACAATCCAGGTAGTTTCCTTTAATCCAATAGCAAATCTGGGCATATTTGAGAGGAGTGATTCTGACAGC
CACGTTGAAATCCTGTGGGGAACCATTCATGTCCACCCACTGGTGCCCTGAAAAAATGCCAATAATTTTTCGCTCC
CACTTCTGCTGCTGtCTCTTCCACATCCTCACATAGACCCCAGACCCGCTGGCCCCTGGCTGGGCATCGCATTGCT
GGTAGAGCAAGTCATAGGTCTCGTCTTTGACGTCACAGAAGCGATACACCAAATTGCCTGGTCGGTCATTGTCATA
ACCAGAGA

*Fig. 1D*

11777.1&2.cons

CAGACGGGGTTTCACTATGTTGGCTAGGCTGGTCTTGAACTCCTGACTTCAGGTGATCTGCCTGCCTTGGCCTCCC
AAAGTGCTGGGATTACAGGCATAAGCCACTGCGCCCGGCTGATCTGATGGTTTCATAAGGCTTTTCCCCCTTTTGC
TCAGCACTTCTCCTTCCTGCCGCCATGTGAAGAAGGACATGTTTGCTTCCCCTTCCACCACGATTGTAAGTTGTTT
CCTGAGGCCTCCCCGGCCATGCTGAACTGTGAGTCAATTAAACCTCTTTCCTTTATAAATTATCCAGTTTTGGGTA
TGTCTTTATTAGTAGAATGAGAACAGACTAATACAACCCTTAAAGGAGACTGACGGAGAGGATTCTTCCTGGATCC
CAGCACTTCCTCTGAATGCTACTGACATTCTTCTTGAGGACTTTAAACTGGGAGATAGAAAACAGATTCCATGGCT
CAGCAGCCTGAGAGCAGGGAGGGAGCCAAGCTATAGATGACATGGGCAGCCTCCCCTGAGGCCAGGTGTGGCCGAA
CCTGGGCAGTGCTGCcACCCACCCCACCAGGGCCAAGTCCTGTCCTTGGAGAGCCAAGCCTCAATCACTGCTAGCC
TCAAGTGTCCCCAAGCCACAGTGGCTAGGGGGACTCAGGGAACAGTTCCCAGTCTGCCCTACTTCTCTTACCTTTA
CCCCTCATACCTCCAAAGTAGACCATGTTCATGAGGTCCAAAGG 11779.2.contig AAGCGAGGAAGCCACTGCGGCTCCTGGCTGAAAAGCGGCGCCAGGCTCGGGAACAGAGGGAACGCGAAGAACAGGA
GCGGAAGCTGCAGGCTGAAAGGGACAAGCGAATGCGAGAGGAGCAGCTGGCCCGGGAGGCTGAAGCCCGGGCTGAA
CGTGAGGCCGAGGCGCGGAGACGGGAGGAGCAGGAGGCTCGAGAGAAGGCGCAGGCTGAGCAGGAGGAGCAGGAGC
GACTGCAGAAGCAGAAAGAGGAAGCCGAAGCCCGGTCCCGGGAAGAAGCTGAGCGCCAGCGCCAGGAGCGGGAAAA
GCACTTTCAGAAGGAGGAACAGGAGAGACAAGAGCGAAGAAAGCGGCTGGAGGAGATAATGAAGAGGACTCGGAAA
TCAGAAGCCGCCGAAACCAAGAAGCAGGATGCAAAGGAGACCGCAGCTAACAATTCCGGCCCAGACCCTTGTGAAA
GCTGTAGAGACTCGGCCCTCTGGGCTTCCAGAAAGGATTCTATTGCAGAAAGGAAGGAGCTXGGCCCCCCAXGGA 11781 & 37.cons CTCTGTGGAAAACTGATGAGGAATGAATTTACCATTACCCATGTTCTCATCCCCAAGCAAAGTGCTGGGTCTGATT
ACTGCAACACAGAGAACGAAGAAGAACTTTTCCTCATACAGGATCAGCAGGGCCTCATCACACTGGGCTGGATTCA
TACTCACCCCACACAGACCGCGTTTCTCTCCAGTGTCGACCTACACACTCACTGCTCTTACCAGATGATGTTGCCA
GAGTCAGTAGCCATTGTTTGCTCCCCCAAGTTCCAGGAAACTGGATTCTTTAAACTAACTGACCATGGACTAGAGG
AGATTTCTTCCTGTCGCCAGAAAGGATTTCATCCACACAGCAAGGATCCACCTCTGTTCTGTAGCTGCAGCCACGT
GACTGTTGTGGACAGAGCAGTGACCATCACAGACCTTCGATGAGCGTTTGAGTCCAACACCTTCCAAGAACAACAA
AACCATATCAGTGTACTGTAGCCCCTTAATTTAAGCTTTCTAGAAAGCTTTGGAAGTTTTTGTAGATAGTAGAAAG
GGGGGCATCACXTGAGAAAGAGCTGATTTTGTATTTCAGGTTTGAAAAGAAATAACTGAACATATTTTTTAGGCAA
GTCAGAAAGAGAACATGGTCACCCAAAAGCAACTGTAACTCAGAAATTAAGTTACTCAGAAATTAAGTAGCTCAGA
AATTAAGAAAGAATGGTATAATGAACCCCCATATACCCTTCCTTCTGGATTCACCAATTGTTAACATTTTTTTCCT
CTCAGCTATCCTTCTAATTTCTCTCTAATTTCAATTTGTTTATATTTACCTCTGGGCTCAATAAGGGCATCTGTGC
AGAAATTTGGAAGCCATTTAGAAAATCTTTTGGATTTTCCTGTGGTTTATGGCAATATGAATGGAGCTTATTACTG
GGGTGAGGGACAGCTTACTCCATTTGACCAGATTGTTTGGCTAACACATCCCGAAGAATGATTTTGTCAGGAATTA
TTGTTATTTAATAAATATTTCAGGATATTTTTCCTCTACAATAAAGTAACAAT

CTCTGTGGAAAACTGATGAGGAATGAATTTACCATTACCCATGTTCTCATCCCCAAGCAAAGTGCTGGGTCTGATT
ACTGCAACACAGAGAACGAAGAAGAACTTTTCCTCATACAGGATCAGCAGGGCCTCATCACACTGGGCTGGATTCA
TACTCACCCCACACAGACCGCGTTTCTCTCCAGTGTCGACCTACACACTCACTGCTCTTACCAGATGATGTTGCCA
GAGTCAGTAGCCATTGTTTGCTCCCCCAAGTTCCAGGAAACTGGATTCTTTAAACTAACTGACCATGGACTAGAGG
AGATTTCTTCCTGTCGCCAGAAAGGATTTCATCCACACAGCAAGGATCCACCTCTGTTCTGTAGCTGCAGCCACGT
GACTGTTGTGGACAGAGCAGTGACCATCACAGACCTTCGATGAGCGTTTGAGTCCAACACCTTCCAAGAACAACAA
AACCATATCAGTGTACTGTAGCCCCTTAATTTAAGCTTTCTAGAAAGCTTTGGAAGTTTTTGTAGATAGTAGAAAG
GGGGGCATCACCTGAGAAAGAGCTGATTTTGTATTTCAGGTTTGAAAAGAAATAACTGAACATATTTTTTAGGCAA
GTCAGAAAGAGAACATGGTCACCCAAAAGCAACTGTAACTCAGAAATTAAGTTACTCAGAAATTAAGTAGCTCAGA
AATTAAGAAAGAATGGTATAATGAACCCCCATATACCCTTCCTTCTGGATTCACCAATTGTTAACATTTTTTTCCT
CTCAGCTATCCTTCTAATTTCTCTCTAATTTCAATTTGTTTATATTTACCTCTGGGCTCAATAAGGGCATCTGTGC
AGAAATTTGGAAGCCATTTAGAAAATCTTTTGGATTTTCCTGTGGTTTATGGCAATATGAATGGAGCTTATTACTG
GGGTGAGGGACAGCTTACTCCATTTGACCAGATTGTTTGGCTAACACATCCCGAAGAATGATTTTGTCAGGAATTA
TTGTTATTTAATAAATATTTCAGGATATTTTTCCTCTACAATAAAGTAACAATTA 11784-1 & 2

GGACGACAAGGCCATGGCGATATCGGATCCGAATTCAAGCCTTTGGAATTAAATAAACCTGGAACAGGGAAGGTGA
AAGTTGGAGTGAGATGTCTTCCATATCTATACCTTTGTGCACAGTTGAATGGGAACTGTTTGGGTTTAGGGCATCT
TAGAGTTGATTGATGGAAAAAGCAGACAGGAACTGGTGGGAGGTCAAGTGGGGAAGTTGGTGAATGTGGAATAACT
TACCTTTGTGCTCCACTTAAACCAGATGTGTTGCAGCTTTCCTGACATGCAAGGATCTACTTTAATTCCACACTCT
CATTAATAAATTGAATAAAAGGGAATGTTTTGGCACCTGATATAATCTGCCAGGCTATGTGACAGTAGGAAGGAAT
GGTTTCCCCTAACAAGCCCAATGCACTGGTCTGACTTTATAAATTATTTAATAAAATGAACTATTATC 11785.2.contig GGCAGTGACATTCACCATCATGGGAACCACCTTCCCTTTTCTTCAGGATTCTCTGTAGTGGAAGAGAGCACCCAGT
GTTGGGCTGAAAACATCTGAAAGTAGGGAGAAGAACCTAAAATAATCAGTATCTCAGAGGGCTCTAAGGTGCCAAG
AAGTCTCACTGGACATTTAAGTGCCAACAAAGGCATACTTTCGGAATCGCCAAGTCAAAACTTTCTAACTTCTGTC
TCTCTCAGAGACAAGTGAGACTCAAGAGTCTACTGCTTTAGTGGCAACTACAGAAAACTGGTGTTACCCAGAAAAA
CAGGAGCAATTAGAAATGGTTCCAATATTTCAAAGCTCCGCAAACAGGATGTGCTTTCCTTTGCCCATTTAGGGTT
TCTTCTCTTTCCTTTCTCTTTATTAACCACT

*Fig. 1F*

11718-1&2 cons

TGCGCTGAAAACAACGGCCTCCTTTACTGTTAAAATGCAGCCACAGGTGCTTAGCCGTGGGCATCTCAACCACCAG
CCTCTGTGGGGGGCAGGTGGGCGTCCCTGTGGGCCTCTGGGCCCACGTCCAGCCTCTGTCCTCTGCCTTCCGTTCT
TCGACAGTGTTCCCGGCATCCCTGGTCACTTGGTACTTGGCGTGGGCCTCCTGTGCTGCTCCAGCAGCTCCTCCAG
GXGGTCGGCCCGCTTCACCGCAGCCTCATGTTGTGTCCGGAGGCTGCTCACGGCCTCCTCCTTCCTCGCGAGGGCT
GTCTTCACCCTCCGGXGCACCTCCTCCAGCTCCAGCTGCTGGCGGGCCTGCAGCGTGGCCAGCTCGGCCTTGGCCT
GCCGCGTCTCCTCCTCARAGGCTGCCAGCCGGTCCTCGAACTCCTGGCGGATCACCTGGGCCAGGTTGCTGCGCTC
GCTAGAAAGCTGCTCGTTCACCGCCTGCGCATCCTCCAGCGCCCGCTCCTTCTGCCGCACAAGGCCCTGCAGACGC
AGATTCTCGCCCTCGGCcTCCCCAAGCTGGCCCTTCAGCTCCGAGCACCGCTCCTGAAGCTTCCGCTCCGACTGCT
CCAGCTCGGAGAGCTCGGCCTCGTACTTGTCCCGTAAGCGCTTGATGCGGCTCTCGGCAGCCTTCTCACTCTCCTC
CTTGGCCAGCGCCATGTCGGCCTCCAGCCGGTGAATGACCAGCTCAATCTCCTTGTCCCGGCCTTTCCGGATTTCT
TCCCTCAGCTCCTGTTCCCGGTTCAGCAGCCACGCCTCCTCCTTCCTGGTGCGGCCGGCCTCCCACGCCTGCCTCT
CCAGCTCCAGCTGCTGCTTCAGGGTATTCAGCTCCATCTGGCGGGCCTGCAGCGTGGCCA 13690.4

CAACTTATTACTTGAAATTATAATATAGCCTGTCCGTTTGCTGTTTCCAGGCTGTGATATATTTTCCTAGTGGTTT
GACTTTAAAAATAAATAAGGTTTAATTTTCTCCCC 13693.1

TGCAAGTCACGGGAGTTTATTTATTTAATTTTTTTCCCCAGATGGAGACTCTGTCGCCCAGGCTGGAGTGCAATGG
TGTGATCTTGGCTCACTGCAACCTCCACCTCCTGGGTTCAAGCGATTCTCCTGCCACAGCCTCCCGAGTAGCTGGG
ATTACAGGTGCCCGCCACCACACCCAGCTAATTTTTATATTTTTAGTAAAGACAGGGTTTCCCCATGTTGGCCAGG
CTGGTCTTGAACTTCTGACCTCAGGTGATCCACCTGCCTCGGCCTCCCAAAGTGTTGGGATTACAGGCGTGAGCTA
CCCGTGCCTGGCCAGCCACTGGAGTTTAAAGGACAGTCATGTTGGCTCCAGCCTAAGGCGGCATTTTCCCCCATCA
GAAAGCCCGCGGCTCCTGTACCTCAAAATAGGGCACCTGTAAAGTCAGTCAGTGAAGTCTCTGCTCTAACTGGCCA
CCCGGGGCCATTGGCNTCTGACACAGCCTTGCCAGGANGCCTGCATCTGCAAAAGAAAAGTTCACTTCCTTTCCG 13694.1

CAGAGAATCTKAGAAAGATGTCGCGTTTTCTTTTAATGAATGAGAGAAGCCCATTTGTATCCCTGAATCATTGAGA
AAAGGCGGCGGTGGCGACAGCGGCGACCTAGGGATCGATCTGGAGGGACTTGGGGAGCGTGCAGAGACCTCTAGCT
CGAGCGCGAGGGACCTCCCGCCGGGATGCCTGGGGAGCAGATGGACCCTACTGGAAGTCAGTTGGATTCAGATTTC
TCTCAGCAAGATACTCCTTGCCTGATAATTGAAGATTCTCAGCCTGAAAGCCAGGTTCTAGAGGATGATTCTGGTT
CTCACTTCAGTATGCTATCTCGACACCTTCCTAATCTCCAGACGCACAAAGAAAATCCTGTGTTGGATGTTGNGTC
CAATCCTTGAACAAACAGCTGGAGAAGAACGAGGAGACCGGTAATAGTGGGTTCAATGAACATTTGAAAGAAAACC
AGGTTGCAGACCCTG

GACTGTCCTGAACAAGGGACCTCTGACCAGAGAGCTGCAGGAGATGCAGAGTGGTGGCAGGAGTGGAAGCCAAAGA
ACACCCACCTTCCTCCCTTGAAGGAGTAGAGCAACCATCAGAAGATACTGTTTTATTGCTCTGGTCAAACAAGTCT
TCCTGAGTTGACAAAACCTCAGGCTCTGGTGACTTCTGAATCTGCAGTCCACTTTCCATAAGTTCTTGTGCAGACA
ACTGTTCTTTTGCTTCCATAGCAGCAACAGATGCTTTGGGGCTAAAAGGCATGTCCTCTGACCTTGCAGGTGGTGG
ATTTTGCTCTTTTACAACATGTACATCCTTACTGGGCTGTGCTGTCACAGGGATGTCCTTGCTGGACTGTTCTGCT
ATGGGGATATCTTCGTTGGACTGTTCTTCATGCTTAATTGCAGTATTAGCATCCACATCAGACAGCCTGGTATAAC
CAGAGTTGGTGGTTACTGATTGTAGCTGCTCTTTGTCCACTTCATATGGCACAAGTATTTTCCTCAACATCCTGGC
TCTGGGAAG 13695.1

GAAATGTATATTTAATCATTCTCTTGAACGATCAGAACTCTRAAATCAGTTTTCTATAACARCATGTAATACAGTC
ACCGTGGCTCCAAGGTCCAGGAAGGCAGTGGTTAACACATGAAGAGTGTGGGAAGGGGGCTGGAAACAAAGTATTC
TTTTCCTTCAAAGCTTCATTCCTCAAGGCCTCAATTCAAGCAGTCATTGTCCTTGCTTTCAAAAGTCTGTGTGTGC
TTCATGGAAGGTATATGTTTGTTGCCTTAATTTGAATTGTGGCCAGGAAGGGTCTGGAGATCTAAATTCAGAGTAA
GAAAACCTGAGCTAGAACTCAGGCATTTCTCTTACAGAACTTGGCTTGCAGGGTAGAATGAANGGAAAGAAACTTA
GAAGCTCAACAAGCTGAAGATAATCCCATCAGGCATTTCCCATAGGCCTTGCAACTCTGTTCACTGAGAGATGTTA
TCCTG 13695.2

AGTCTGGAGTGAGCAAACAAGAGCAAGAAACAARRAGAAGCCAAAAGCAGAAGGCTCCAATATGAACAAGATAAAT
CTATCTTCAAAGACATATTAGAAGTTGGGAAAATAATTCATGTGAACTAGACAAGTGTGTTAAGAGTGATAAGTAA
AATGCACGTGGAGACAAGTGCATCCCCAGATCTCAGGGACCTCCCCCTGCCTGTCACCTGGGGAGTGAGAGGACAG
GATAGTGCATGTTCTTTGTCTCTGAATTTTTAGTTATATGTGCTGTAATGTTGCTCTGAGGAAGCCCCTGGAAAGT
CTATCCCAACATATCCACATCTTATATTCCACAAATTAAGCTGTAGTATGTACCCTAAGACGCTGCTAATTGACTG
CCACTTCGCAACTCAGGGGCGGCTGCATTTTAGTAATGGGTCAAATGATTCACTTTTTATGATGCTTCCCAAGGTG
CCTTGGCTTCTCTTCCCAACTGACAAATGCCCAAGTTGAGAAAAATGATCATAATTTTAGCATAAACCGAGCAATC
GGCGACCCC 13697.1

TAGCTGTCTTCCTCACTCTTATGGCAATGACCCCATATCTTAATGGATTAAGATAATGAAAGTGTATTTCTTACAC
TCTGTATCTATCACCAGAAGCTGAGGTGATAGCCCGCTTGTCATTGTCATCCATATTCTGGGACTCAGGCGGGAAC
TTTCTGGAATATTGCCAGGGAGCATGGCAGAGGGGCACAGTGCATTCTGGGGGAATGCACATTGGCTCAGCCTGGG
TAATGAGTGATATACATTACCTCTGTTCACAACTCATTGCCCAGCACCAGTCACAAGGCCCCACCAAATACCAGAG
CCCAAGAAATGTAGTCCTGTTGATATGGTTTTGCTGTGTCCCAACCCAAATCTCATCTTGAATTGTAAGCTCCCAT
AATTCCCATGTGTTGTGGGAGGGACCTGGTG

ATCATGAGGATGTTACCAAAGGGATGGTACTAAACCATTTGTATTCGTCTGTTTTCACACTGCTTTGAAGATACTA
CCTGAGACTGGGTAATTTATAAACAAAAGAGATTTAATTGACTCACAGTTCTGCATGGCTGAAGAGGCCTCAGGAA
ACTTACAGTCATGGTGGAAGGCAAAGGAGGAGCAAGGCATGTCTTACATGTCAGTAGGAGAGAGAGCGAGAGCAGG
AGAACCTGCCACTTATAAACCATTCAGATCTCATAACTCCCTATCATGAGAAAAACATGGAGGAAACCACCCTCAT
GATCCAATCACCTCCCGCCAGGTCCCTCCCTCGACACGTGGGGATTATAATTCAGGATTAGAGGGACACAGAGACA
AACCATATCATCATTCATGAGAAATCCACCCTCATAGTCCAATCAGCTCCTACCAGGCCCCACCTCCAACACTGGG
GATTGCAATTCAACATGAGATTTGGATGGGGACACAGATTCAAACCATATCATAC 13699.1&2

CATGGCCTTTCTCCTTAGAGGCCAGAGGTGCTGCCCTGGCTGGGAGTGAAGCTCCAGGCACTACCAGCTTTCCTGA
TTTTCCCGTTTGGTCCATGTGAAGAGCTACCACGAGCCCCAGCCTCACAGTGTCCACTCAAGGGCAGCTTGGTCCT
CTTGTCCTGCAGAGGCAGGCTGGTGTGACCCTGGGAACTTGACCCGGGAACAACAGGTGGCCCAGAGTGAGTGTGG
CCTGGCCCCTCAACCTAGTGTCCGTCCTCCTCTCTCCTGGAGCCAGTCTTGAGTTTAAAGGCATTAAGTGTTAGAT
ACAAGCTCCTTGTGGCTGGAAAAACACCCCTCTGCTGATAAAGCTCAGGGGGCACTGAGGAAGCAGAGGCCCCTTG
GGGGTGCCCTCCTGAAGAGAGCGTCAGGCCATCAGCTCTGTCCCTCTGGTGCTCCCACGTCTGTTCCTCACCCTCC
ATCTCTGGGAGCAGCTGCACCTGACTGGCCACGCGGGGGCAGTGGAGGCACAGGCTCAGGGTGGCCGGGCTACCTG
GCACCCTATGGCTTACAAAGTAGAGTTGGCCCAGTTTCCTTCCACCTGAGGGGAGCACTCTGACTCCTAACAGTCT
TCCTTGCCCTGCCATCATCTGGGGTGGCTGGCTGTCAAGAAAGGCCGGGCATGCTTTCTAAACACAGCCACAGGAG
GCTTGTAGGGCATCTTCCAGGTGGGGAAACAGTCTTAGATAAGTAAGGTGACTTGCCTAAGGCCTCCCAGCACCCT
TGATCTTGGAGTCTCACAGCAGACTGCATGTSAACAACTGGAACCGAAAACATGCCTCAGTATAAAA 13703.3

CCAGAACCTCCTTCTCTTTGGAGAATGGGGAGGCCTCTTGGAGACACAGAGGGTTTCACCTTGGATGACCTCTAGA
GAAATTGCCCAAGAAGCCCACCTTCTGGTCCCAACCTGCAGACCCCACAGCAGTCAGTTGGTCAGGCCCTGCTGTA
GAAGGTCACTTGGCTCCATTGCCTGCTTCCAACCAATGGGCAGGAGAGAAGGCCTTTATTTCTCGCCCACCCATTC
TCCTGTACCAGCACCTCCGTTTTCAGTCAGYGTTGTCCAGCAACGGTACCGTTTACACAGTCA 13705.1

TGCATGTAGTTTTATTTATGTGTTTTSGTCTGGAAAACCAAGTGTCCCAGCAGCATGACTGAACATCACTCACTTC
CCCTACTTGATCTACAAGGCCAACGCCGAGAGCCCAGACCAGGATTCCAAACACACTGCACGAGAATATTGTGGAT
CCGCTGTCAGGTAAGTGTCCGTCACTGACCCARACGCTGTTACGTGGCACATGACTGTACAGTGCCACGTAACAGC
ACTGTACTTTTCTCCCATGAACAGTTACCTGCCATGTATCTACATGATTCAGAACATTTTGAACAGTTAATTCTGA
CACTTGAATAATCCCATCAAAAACCGTAAAATCACTTTGATGTTTGTAACGACAACATAGCATCACTTTACGACAG
AATCATCTGGAAAAACAGAACAACGAATACATACATCTTAAAAAATGCTGGGGTGGGCCAGGCACAGCTTCACGCC
TGTAATCCCAGCACTTTGGGAGGCTTAAGCGGGTG

TGGGGCGGAAAGAAGCCAAGGCCAAGGAGCTGGTGCGGCAGCTGCAGCTGGAGGCCGAGGAGCAGAGGAAGCAGAA
GAAGCGGCAGAGTGTGTCGGGCCTGCACAGATACCTTCACTTGCTGGATGGAAATGAAAATTACCCGTGTCTTGTG
GATGCAGACGGTGATGTGATTTCCTTCCCACCAATAACCAACAGTGAGAAGACAAAGGTTAAGAAAACGACTTCTG
ATTTGTTTTTGGAAGTAACAAGTGCCACCAGTCTGCAGATTTGCAAGGATGTCATGGATGCCCTCATTCTGAAAAT
GGCAAGAAATGAAAAAGTACACTTTAGAAAATAAAGAGGAAGGATCACTCTCAGATACTGAAGCCGATGCAGTCTC
TGGACAACTTCCAGATCCCACAACGAATCCCAGTGCTGGAAAGGACGGGCCCTTCCTTCTGGTGGTGGAACANGTC
CCGGTGGTGGATCTTGGAANGGAACCTGAANGTGGTGTACCCCGTCCAAGGCCGACCTTGGCCAC 13707.4

TCCCGCGCTCGCAGGGCNCGTGCCACCTGCCYGTCCGCCCGCTCGCTCGCTCGCCCGCCGCGCCGCGCTGCCGACC
GYCAGCATGCTGCCGAGAGTGGGCTGCCCCGCGCTGCCGCTGCCGCCGCCGCCGCTGCTGCCGCTGCTGCCGCTGC
TGCTGCTGC 13708.1&2

GGCGGGTAGGCATGGAACTGAGAAGAACGAAGAAGCTTTCAGACTACGTGGGGAAGAATGAAAAAACCAAAATTAT
CGCCAAGATTCAGCAAAGGGGACAGGGAGCTCCAGCCCGAGAGCCTATTATTAGCAGTGAGGAGCAGAAGCAGCTG
ATGCTGTACTATCACAGAAGACAAGAGGAGCTCAAGAGATTGGAAGAAAATGATGATGATGCCTATTTAAACTCAC
CATGGGCGGATAACACTGCTTTGAAAAGACATTTTCATGGAGTGAAAGACATAAAGTGGAGACCAAGATGAAGTTC
ACCAGCTGATGACACTTCCAAAGAGATTAGCTCACCT 13709.1

TCTGAAGGTTAAATGTTTCATCTAAATAGGGATAATGRTAAACACCTATAGCATAGAGTTGTTTGAGATTAAATGA
GATAATACATGTAAAATTATGTGCCTGGCATACAGCAAGATTGTTGTTGTTGTTGATGATGATGATGATGATGATA
ATATTTTTCTATCCCCAGTGCACAACTGCTTGAACCTATTAGATAATCAATACATGTTTCTTGAACTGAGATCAAT
TTCCCCATGTTGTCTGACTGATGAAGCCCTACATTTTCTTCTAGAGGAGATGACATTTGAGCAAGATCTTAAAGAA
AATCAGATGCCTTCACCTGACCACTGCTTGGTGATCCCATGGCACTTTGTACATCTCTCCATTAGCTCTCATCTCA
CCAGCCCATCATTATTGTATGTGCTGCCTTCTGAAGCTTGCAGCTGGCTACCATCMGGTAGAATAAAAATCATCCT
TTCATAAAATAGTGACCCTCCTTTTTTATTTGCATTTCCCAAAGCCAAGCACCGTGGGANGGTAG

TATGAAGAAGGGAAAAGAAGATAATTTGTGAAAGAAATGGGTCCAGTTACTAGTCTTTGAAAAGGGTCAGTCTGTA
GCTCTTCTTAATGAGAATAGGCAGCTTTCAGTTGCTCAGGGTCAGATTTCCTTAGTGGTGTATCTAATCACAGGAA
ACATCTGTGGTTCCCTCCAGTCTCTTTCTGGGGGACTTGGGCCCACTTCTCATTTCATTTAATTAGAGGAAATAGA
ACTCAAAGTACAATTTACTGTTGTTTAACAATGCCACAAAGACATGGTTGGGAGCTATTTCTTGATTTGTGTAAAA
TGCTGTTTTTGTGTGCTCATAATGGTTCCAAAAATTGGGTGCTGGCCAAAGAGAGATACTGTTACAGAAGCCAGCA
AGAAGACCTCTGTTCATTCACACCCCCGGGGATATCAGGAATTGACTCCAGTGTGTGCAAATCCAGTTTGGCCTAT
CTTCT 13712.1&2

TGAGGGACTGATTGGTTTGCTCTCTGCTATTCAATTCCCCAAGCCCACTTGTTCCTGCAGCGTCCTCCTTCTCATT
CCCTTTAGTTGTACCCTCTCTTTCATCTGAGACCTTTCCTTCTTGATGTCGCCTTTTCTTCTTCTTGCTTTTTCTG
ATGTTCTGCTCAGCATGTTCTGGGTGCTTCTCATCTGCATCATTCCTTTCAGATGCTGTAGCTTCTTCCTCCTCTT
TCTGCCTCCTTTTCTTTTTCTTTTTTTGGGGGGCTTGCTCTCTGACTGCAGTTGAGGGGCCCCAGGGTCCTGGCC
TTTGAGACGAGCCAGGAAGGCCTGCTCCTGGGCCTCTAGGCGAGCAAGCTTGGCCTTCATTGTGATCCCAAGACGG
GCAGCCTTGTGTGCTGTTCGCCCCTCACAGGCTTGGAGCAGCATCTCATCAGTCAGAATCTTTGGGGACTTGGACC
CCTGGTTGTCGTCATCACTGCAGCTCTCCAAGTCTTTGTTTGGCTTCTCTCCACCTGAAGTCAATGTAGCCATCTT
CACAAACTTCTGATACAGCAAGTTGGGCTTGGGATGATTATAACGGGTGGTCTCCTTAGAAAGGCTCCTTATCTGT
ACTCCATCCTGCCCAGTTTCCACTACCAAGTTGGCCGCAGTCTTGTTGAAGAGCTCATTCCACCAGTGGTTTGTGA
ACTCCTTGGCAGGGTCATGTCCTACCCCATGAGTGTCTTGCTTCAGYGTCACCCTGAGAGCCTGAGTGATACCATT
CTCCTTCCG 13714.1&2

GACAACATGAAATAAATCCTAGAGGACAAAATTAAACTCAATAGAGTGTAGTCTAGTTAAAAACTCGAAAAATGAG
CAAGTCTGGTGGGAGTGGAGGAAGGGCTATACTATAAATCCAAGTGGGCCTCCTGATCTTAACAAGCCATGCTCAT
TATACACATCTCTGAACTGGACATACCACCTTTACGCAGGAAACAGGGCTTGGAACTTCTAAGGGAAATTAACATG
CACCACCCACATCTAACCTACCTGCCGGGTAGGTACCATCCCTGCTTCGCTGAAATCAGTGCTC 13716.1&2

TTGGAATTAAATAAACCTGGAACAGGGAAGGTGAAAGTTGGAGTGAGATGTCTTCCATATCTATACCTTTGTGCAC
AGTTGAATGGGAACTGTTTGGGTTTAGGGCATCTTAGAGTTGATTGATGGAAAAAGCAGACAGGAACTGGTGGGAG
GTCAAGTGGGGAAGTTGGTGAATGTGGAATAACTTACCTTTGTGCTCCACTTAAACCAGATGTGTTGCAGCTTTCC
TGACATGCAAGGATCTACTTTAATTCCACACTCTCATTAATAAATTGAATAAAAGGGAATGTTTTGGCACCTGATA
TAATCTGCCAGGCTATGTGACAGTAGGAAGGAATGGTTTCCCCTAACAAGCCCAATGCACTGGTCTGACTTTATAA
ATTATTTAATAAAATGAACTATTATC

*Fig. 1K*

AAACTGGACCTGCAACAGGGACATGAATTTACTGCARGGTCTGAGCAAGCTCAGCCCCTCTACCTCAGGGCCCCAC
AGCCATGACTACCTCCCCCAGGAGCGGGAGGGTGAAGGGGGCCTGTCTCTGCAAGTGGAGCCAGAGTGGAGGAATG
AGCTCTGAAGACACAGCACCCAGCCTTCTCGCACCAGCCAAGCCTTAACTGCCTGCCTGACCCTGAACCAGAACCC
AGCTGAACTGCCCCTCCAAGGGACAGGAAGGCTGGGGGAGGGAGTTTACAACCCAAGCCATTCCACCCCCTCCCCT
GCTGGGGAGAATGACACATCAAGCTGCTAACAATTGGGGGAAGGGGAAGGAAGAAAACTCTGAAAACAAAATCTTG
T 13722.3

CATGCGTTTCACCACTGTTGGCCAGGCTGGTCTCGAACTCCTGGCCTCAAGCAATCCACCCGCCTCAGCCTCCAAA
AGTGCTGGGATTACAGATGTGAGCCATGGCACCATGCCAAAAGGCTATATTCCTGGCTCTGTGTTTCCGAGACTGC
TTTTAATCCCAACTTCTCTACATTTAGATTAAAAAATATTTTATTCATGGTCAATCTGGAACATAATTACTGCATC
TTAAGTTTCCACTGATGTATATAGAAGGCTAAAGGCACAATTTTTATCAAATCTAGTAGAGTAACCAAACATAAAA
TCATTAATTACTTTCAACTTAATAACTAATTGACATTCCTCAAAAGAGCTGTTTTCAATCCTGATAGGTTCTTTAT
TTTTTCAAAATATATTTGCCATGGGATGCTAATTTGCAATAAGGCGCATAATGAGAATACCCCAAACTGGA 13722.4

GTTGGACCCCCAGGGACTGGAAAGACACTTCTTGCCCGAGCTGTGGCGGGAGAAGCTGATGTTCCTTTTTATTATG
CTTCTGGATCCGAATTTGATGAGATGTTTGTGGGTGTGGGAGCCAGCCGTATCAGAAATCTTTTTAGGGAAGCAAA
GGCGAATGCTCCTTGTGTTATATTTATTGATGAATTAGATTCTGTTGGTGGGAAGAGAATTGAATCTCCAATGCAT
CCATATTCAAGGCAGACCATAAATCAACTTCTTGCTGAAATGGATGGTTTTAAACCCAATGAAGGAGTTATCATAA
TAGGAGCCACAAACTTCCCAGAGGCATTAGATAATGCCTTAATACCGTCCTGGTCGTTTTGACATGCAAGTTACAG
TTCCAAGGCCAGATGTAAAAGGTCGAACAGAAATTTTGAAATGGTATCTCAATAAAATAAAGTTTGATCAATCCCG
TTGATCCAGAAATTATAGCCTCGAGGTACTGGTGGCTTTTCCGGAAGCAGAGTTGGGAGAATCTT 13724-13698-13748

GCCTACAACATCCAGAAAGAGTCTACCCTGCACCTGGTGCTSCGTCTCAGAGGTGGGATGCAGATCTTCGTGAAGA
CCCTGACTGGTAAGACCATCACTCTCGAAGTGGAGCCGAGTGACACCATYGAGAACGTCAAAGCAAAGATCCARGA
CAAGGAAGGCRTYCCTCCTGACCAGCAGAGGTTGATCTTTGCCGGAAAGCAGCTGGAAGATGGDCGCACCCTGTCT
GACTACAACATCCAGAAAGAGTCYACCCTGCACCTGGTGCTCCGTCTCAGAGGTGGGATGCARATCTTCGTGAAGA
CCCTGACTGGTAAGACCATCACCCTCGAGGTGGAGCCCAGTGACACCATCGAGAATGTCAAGGCAAAGATCCAAGA
TAAGGAAGGCATCCCTCCTGATCAGCAGAGGTTGATCTTTGCTGGGAAACAGCTGGAAGATGGACGCACCCTGTCT
GACTACAACATCCAGAAAGAGTCCACTCTGCACTTGGTCCTGCGCTTGAGGGGGGGTGTCTAAGTTTCCCCTTTTA
AGGTTTCMACAAATTTCATTGCACTTTCCTTTCAATAAAGTTGTTGCATTCCC 13730.1

GAACTGGGCCCTGAGCCCAAGTCATGCCTTGTGTCCGCATCTGCCGTGTCACCTCTGTKCCTGCCCCTCACCCCTC
CCTCCTGGTCTTCTGAGCCAGCACCATCTCCAAATAGCCTATTCCTTCCTGCAAATCACACACACATGCGGGCCAC
ACATACCTGCTGCCCTGGAGATGGGGAAGTAGGAGAGATGAATAGAGGCCCATACATTGTACAGAAGGAGGGGCAG
GTGCAGATAAAAGCAGCAGACCCAGCGGCAGCTGAGGTGCATGGAGCACGGTTGGGGCCGGCATTGGGCTGAGCAC
CTGATGGGCCTCATCTCGTGAATCCTCGAGGCAGCGCCACAGCAGAGGAGTTAAGTGGCACCTGGGCCGAGCAGAG
CAGGAGACTGAGGGTCAGAGTGGAGGCTAAGCTGCCCTGGAACTCCTCAATCTTGCCTGCCCCCTAGTATGAAGCC
CCCTTCCTGCCCCTACAATTCCTGA 13732.1

ATGGATCTTACTTTGCCACCCAGGTTGGAGTGCAGTGCTGCAATCTTGGCTCACTGCAGCCTTAACCTCCCAGGCT
CAAGCTATCCTCCTGCCAAAGCCTTCCACATAGCTGGGACTACAGGTACACNGCCACCACACCCAGCTAAAATTTT
TGTATTTTTTGTAGAGACGGGATCTCGCCACGTTGCCCAGGCTGGTCCCATCCTGACCTCAAGCAGATCTGCCCAC
CTCAGCCCCCCAACGTGCTAGGATTACAGGCGTGAGCCACCGCACCCAGCCTTTGTTTTGCTTTTAATGGAATCAC
CAGTTCCCCTCCGTGTCTCAGCAGCAGCTGTGAGAAATGCTTTGCATCTGTGACCTTTATGAAGGGGAACTTCCAT
GCTGAATGAGGGTAGGATTACATGCTCCTGTTTCCCGGGGGTCAAGAAAGCCTCAGACTCCAGCATGATAAGCAGG
GTGAG 13732.2

ATAGGGGCTTTAAGGAGGGAATTCAGGTTCAATGAGGTCGTAAGGCCAGGGCTCTTATCCAGTAAGACTGGGGTCC
TTAGATGAGAAAGAGACACCCGAGGTCCTTCTCTCTGCCGTGTGAGGATGCATCAAGAAGGCGGCCGTCTGCAAGC
GAAGGAGAGGCCGCACCAGAAACCGACACCTTCATCTTGGACTTGCAGCCTCTAGAACTGAGAAAATAACTGTCTG
TTGGTTAAGCCACCCAGTTTGTAGTATTCTCTTATGGCTTCCTAAGCAGACTAACAAACAAACACCCAAAATTAAC
TGATGGCTTCGCTGTCTTCTGTAAAAATTGCTATGAGAGAACTTTTCACTCACTGTTTTGCAGTTTCTCCCTCAGT
CCCTGGTTCTTTCTTCTCACATAATCCCAATTTCAATTTATAGTTCATGGCCCAGGCAGAGTCATTCATCACGGCA
TCTCCTGAGCTAAACCAGCACCTGCTCTGCTCACTTCTTGACTGGCTGCTCATCATCAGCCCTCTTGCAGAGATTT
CATTTCCTCCCGTGCCAGGTACTTCACGCACCAAGCTCA

GGATAATGAAGTTGTTTTATTTAGCTTGGACAAAAAGGCATATTCCTCTATTTTCTTATACAACAAATATCCCCAA
AATAAAGCAAGCATATATATCTTGAATGTGTAATAATCCAGTGATAAACAAGAGCAGTACTTTAAAAGAAAAAAAA
ATATGTATTTCTGTCAGGTTAAAATGAGAATCAAAACCATTTACTCTGCTAACTCATTATTTTTTGCTTTCTTTTT
GGTTAAGAGAGGCAATGCAATACACTGAAAAAGGTTTTTATCTTATCTGGCATTGGAATTAGACATATTCAAACCC
CAGCCCCCATTTCCAAACTTTAAGACCACAAACAAGTAATTTACTTTTCTGAACATTGGTTTTTTCTGGAAAATGG
GAATTATAAAATAGACTTTGCAGACTCTTATGAGATTAAATAAGATAATGTATGAAATTCTTTCTTCTTTTTTACT
TCTTTTTCCTTTTTGAGATGGAGTCTCACCCCGTCACCCAGGCTGGAGTACAGTG 13735.2

CCACTGCACTCCAGCCTGGGTGACGGAGTGAGACTCTGTCTCAAAAAAACAAACAAACAAACAAACAAAAAACTGA
AAAGGAAATAGAGTTCCTCTTTCCTCATATATGAATATATTATTTCAACAGATTGTTGATCACCTACCATATGCTT
GGTATTGTTCTAATTGCTGGGGATACAGCAAGAGGTTCTGCAGAACTTCATGGAGCATGAAAGTAAATAAACAAAG
TTAATTTCAAGGCCAGGCATGGTTGCTCACACCTTTAGTCCCAGCACTTTGGGAGGCTGAGGCAGGTGGATCACTT
GGGCCCAGGAGTTCAAGGCTGCAGTGAGCCAAGATTGTGCCACTACTCTCCAGGCTGGGCAACAGAGCAAGACCCT
GTCTCAGGGGGAACAAAAAGTTAATTTCAGATTTTGTTAAGTGCTGTAAAGGAAGTAAATAGGTTGATATTCAAGA
GAGCACCTGAAGGCCAGGCGTGGTGGCTCACGCCTGTGGTCTAACGCTTTGGGAAGCCCGAGCGGGCGGATCACAA
GGTCAGGAGAATTTTGGCCAGGCATGGTG 13736.1

AGAATCCATTTATTGGGTTTTAAACTAGTTACACAACTGAAATCAGTTTGGCACTACTTTATACAGGGATTACGCC
TGTGTATGCCGACACTTAAATACTGTACCAGGACCACTGCTGTGCTTAGGTCTGTATTCAGTCATTCAGCATGTAG
ATACTAAAAATATACTGTAGTGTTCCTTTAAGGAAGACTGTACAGGGTGTGTTGCAAGATGACATTCACCAATTTG
TGAATTATTTCAACCCAGAAGATACCTTTCACTCTATAAACTTGTCATAGGCAAACATGTGGTGTTAGCATTGAGA
GATGCACACAAAAATGTTACATAAAAGTTCAGACATTCTAATGATAAGTGAACTGAAAAAAAAAAAAACCCCACAT
CTCAATTTTTGTAACAAGATAAAGAAAATAATTTAAAAACACAAAAAATGGCATTCAGTGGGTACAAAGCC 13737.1&2

CAAATATTTAATATAAATCTTTGAAACAAGTTCAGAKGAAATAAAAATCAAAGTTTGCAAAAACGTGAAGATTAAC
TTAATTGTCAAATATTCCTCATTGCCCCAAATCAGTATTTTTTTTATTTCTATGCAAAAGTATGCCTTCAAACTGC
TTAAATGATATATGATATGATACACAAACCAGTTTTCAAATAGTAAAGCCAGTCATCTTGCAATTGTAAGAAATAG
GTAAAAGATTATAAGACACCTTACACACACACACACACACACACACACACGTGTGCACcGCCAATGACAAAAAAACA
ATTTGGCCTCTCCTAAAATAAGAACATGAAGACCCTTAATTGCTGCCAGGAGGGAACACTGTGTCACCCCTCCCTA
CAATCCAGGTAGTTTCCTTTAATCCAATAGCAAATCTGGGCATATTTGAGAGGAGTGATTCTGACAGCCACSGTTG
AAATCCTGTGGGGAACCATTCATGTCCACCCACTGGTGCCCTGAAAAAATGCCAATAATTTTTCGCTCCCACTTCT
GCTGCTGTCTCTTCCACATCCTCACATAGACCCCAGACCCGCTGGCCCCTGGCTGGGCATCGCATTGCTGGTAGAG
CAAGTCATAGGTCTCGTCTTTGACGTCACAGAAGCGATACACCAAATTGCCTGGTCGGTCATTGTCATAACCAG

TTTGACTTTAGTAGGGGTCTGAACTATTTATTTTACTTTGCCMGTAATATTTARACCYTATATATCTTTCATTATG
CCATCTTATCTTCTAATGBCAAGGGAACAGWTGCTAAMCTGGCTTCTGCATTWATCACATTAAAAATGGCTTTCTT
GGAAAATCTTCTTGATATGAATAAAGGATCTTTTAVAGCCATCATTTAAAGCMGGNTTCTCTCCAACACGAGTCTG
CTSASGGGGGGKGAGCTGTGAACTCTGGCTGAAGGCTTTCCCATACACACTGCAATGACMTGGTTTCTGACCAGBG
TGAGTTA 13738.2

AGAGAAGCCCCATAAATGCAATCAGTGTGGGAAGGCCTTCAGTCAGAGCTCAAGCCTTTTCCTCCATCATCGGGTT
CATACTGGAGAGAAACCCTATGTATGTAATGAATGCGGCAGAGCCTTTGGTTTTAACTCTCATCTTACTGAACACG
TAAGGATTCACACAGGAGAAAAACCCTATGTTTGTAATGAGTGCGGCAAAGCCTTTCGTCGGAGTTCCACTCTTGT
TCAGCATCGAAGAGTTCACACTGGGGAGAAGCCCTACCAGTGCGTTGAATGTGGGAAAGCTTTCAGCCAGAGCTCC
CAGCTCACCCTACATCAGCCGAGTTCACACTGGAGAGAAGCCCTATGACTGTGGTGACTGTGGGAAGGCCTTCAGC
CGGAGGTCAACCCTCATTCAGCATCAGAAAGTTCACAGCGGAGAGACTCGTAAGTGCAGAAAACATGGTCCAGCCT
TTGTTCATGGCTCCAGCCTCACAGCAGATGGACAGATTCCCACTGGAGAGAAGCACGGCAGAACCTTTAACCATGG
TGCAAATCTCATTCTGCGCTGGACAGTTC 13739.1&2

GAGACAGGGTCTCACTTTGTCACCCAGGCTGGAATGCAGTGGTGCGATCTTACGTAGCTCACTGCAGCCCTGACCT
CCTGGACTCAAACAATTCTCCTGCCTCAGCCCTGCAAGTAGCTGGGACTGTGGGTGCATGCCACCATGCCTGGCTA
ACTTTTGTAGTTTTTGTAAAGATGGGGTTTTGCCATGTTGCACATGCTGGTCTTGAACTCCTGAGCTCAAACGATC
TGCCCACCTCGGCCTCCCAGAATGTTGGGATTACAGGGGTAAACCACCACGCCTGGCCCCATTAGGGTATTCTTAG
CATCCACTTGCTCACTGAGATTAATCATAAGAGATGATAAGCACTGGAAGAAAAAAATTTTTACTAGGCTTTGGAT
ATTTTTTTCCTTTTTCAGCTTTATACAGAGGATTGGATCTTTAGTTTTCCTTTAACTGATAATAAAACATTGAAAG
GAAATAAGTTTACCTGAGATTCACAGAGATAACCGGCATCACTCCCTTGCTCAATTCCAGTCTTTACCACATCAAT
TATTTTCAGAGGTGCAGGATAAAGGCCTTTAGTCTGCTTTCGCACTTTTTCTTCCACTTTTTTGTAAACCTGTTGC
CTGACAAATGGAATTGACAGCGTATGCCATGACTATTCCATTTGTCAGGCATACGCTGTCAATTTTTCCACCAATC
CCTTGTCTCTCTTTGGAGAGATCTTCTTATCAGCTAGTCCTTTGGCAAAAGTAATTGCAACTTCTTCTAGGTATTC
TATTGTCCGTTCCACTGGTGGAACCCCTGGGACCAGGACTAAAACCTCCAG 13741.1

ATCTCATATATATATTTCTTCCTGACTTTATTTGCTTGCTTCTGNCACGCATTTAAAATATCACAGAGACCAAAAT
AGAGCGGCTTTCTGGTGGAACGCATGGCAGTCACAGGACAAAATACAAAACTAGGGGGCTCTGTCTTCTCATACAT
CATACAATTTTCAAGTATTTTTTTTATGTACAAAGAGCTACTCTATCTGAAAAAAAATTAAAAAATAAATGAGACA
AGATAGTTTATGCATCCTAGGAAGAAAGAATGGGAAGAAAGAACGGGGCAGTTGGGTACAGATTCCTGTCCCCTGT
TCCCAGGGACCACTACCTTCCTGCCACTGAGTTCCCCCACAGCCTCACCCATCATGTCACAGGGCAAGTGCCAGGG
TAGGTGGGGACCAGTGGAGACAGGAACCAGCAACATACTTTGGCCTGGAAGATAAGGAGAAAGTCTCAGAAACACA
CTGGTGGGAAGCAATCCCACNGGCCGTGCCCCANGAGCTTCCCACCTGCTGCTGGCTCCCTGGGTGGCTTTGGGAA
CAGCTTGGGCAGGCCCTTTTGGGTGGGGNCCAACTGGGCCTTTGGGCCCGTGTGGAAAG

*Fig. 1O*

13742.1
AAACATTGAGATGGAATGATAGGGTTTCCCAGAATCAGGTCCATATTTTAACTAAATGAAAATTATGATTTATAGC
CTTCTCAAATACCTGCCATACTTGATATCTCAACCAGAGCTAATTTTACCTCTTTACAAATTAAATAAGCAAGTAA
CTGGATCCACAATTTATAATACCTGTCAATTTTTTCTGTATTAAACCTCTATCATAGTTTAAGCCTATTAGGGTAC
TTAATCCTTACAAATAAACAGGTTTAAAATCACCTCAATAGGCAACTGCCCTTCTGGTTTTCTTCTTTGACTAAAC
AATCTGAATGCTTAAGATTTTCCACTTTGGGTGCTAGCAGTACACAGTGTTACACTCTGTATTCCAGACTTCTTAA
ATTATAGAAAAAGGAATGTACACTTTTTGTATTCTTTCTGAGCAGGGCCGGGAGGCAACATCATCTACCATGGTAG
GGACTTGTATGCATGGACTACTTTA

14351.1
ACTCTGTCGCCCAGGCTGGAGCCCABTGGMGCGATCTCGACTCCCTGCAAGCTMCGCCTCACAGGWTCATGCCATT
CTCCTGCCTCAGCATCTGGAGTAGCTGGGACTACAGGCGCCAGCCACCATGCCCAGCTAATTTTT

14351.2
ACCTTAAAGACATAGGAGAATTTATACTGGGAGAGAAAGCTTACAAATGTAAGGTTTCTGACAAGACTTGGGAGTG
ATTCACACCTGGAACAACATACTGGACTTCACACTGGABAGAAACCTTACAAGTGTAATGAGTGTGGCAAAGCCTT
TGGCAAGCAGTCAACACTTATTCACCATCAGGCAATTCA

14354.2
AGTCAGGATCATGATGGCTCAGTTTCCCACAGCGATGAATGGAGGGCCAAATATGTGGGCTATTACATCTGAAGAA
CGTACTAAGCATGATAAACAGTTTGATAACCTCAAACCTTCAGGAGGTTACATAACAGGTGATCAAGCCCGTACTT
TTTTCCTACAGTCAGGTCTGCCGGCCCCGGTTTTAGCTGAAATATGGGCCTTATCAGATCTGAACAAGGATGGGAA
GATGGACCAGCAAGAGTTCTCTATAGCTATGAAACTCATCAAGTTAAAGTTGCAGGGCCAACAGCTGCCTGTAGTC
CTCCCTCCTATCATGAAACAACCCCCTATGTTCTCTCCACTAATCTCTGCTCGTTTTGGGATGGGAAGCATGCCCA
ATCTGTCCATTCATCAGCCATTGCCTCCAGTTGCACCTATAGCAACACCCTTGTCTTCTGCTACTTCAGGGACCAG
TATTCCTCCCTAATGATGCCTGCT

14354.1
CTTTCGATTTCCTTCAATTTGTCACGTTTGATTTTATGAAGTTGTTCAAGGGCTAACTGCTGTGTATTATAGCTTT
CTCTGAGTTCCTTCAGCTGATTGTTAAATGAATCCATTTCTGAGAGCTTAGATGCAGTTTCTTTTTTCAAGAGCATC
TAATTGTTCTTTAAGTCTTTGGCATAATTCTTCCTTTTCTGATGACTTTCTATGAAGTAAACTGATCCCTGAATCA
GGTGTGTTACTGAGCTGCATGTTTTTAATTCTTTCGTTTAATAGCTGCTTCTCAGGGACCAGATAGATAAGCTTAT
TTTGATATTCCTTAAGCTCTTGGTGAAGTTGTTCGATTTCCATAATTTCCAGGTCACACTGGTTATCCCAAACTTC
T 16431.1.2

TGGAGGTGAAACGGAGGCAAGAAAGGGGGCTACCTCAGGAGCGAGGGACAAAGGGGGCGTGAGGCACCTAGGCCGC
GGCACCCCGGCGACAGGAAGCCGTCCTGAACCGGGCTACCGGGTAGGGGAAGGGCCCGCGTAGTCCTCGCAGGGCC
CCAGAGCTGGAGTCGGCTCCACAGCCCCGGGCCGTCGGCTTCTCACTTCCTGGACCTCCCCGGCGCCCGGGCCTGA
GGACTGGCTCGGCGGAGGGAGAAGAGGAAACAGACTTGAGCAGCTCCCCGTTGTCTCGCAACTCCACTGCCGAGGA
ACTCTCATTTCTTCCCTCGCTCCTTCACCCCCCACCTCATGTAGAAAGGTGCTGAAGCGTCCGGAGGGAAGAAGAA
CCTGGGCTACCGTCCTGGCCTTCCCMCCCCCTTCCCGGGGCGCTTTGGTGGGCGTGGAGTTGGGGTTGGGGGGGTG
GGTGGGGGTTCTTTTTTGGAGTGCTGGGGAACTTTTTTCCCTTCTTCAGGTCAGGGGAAAGGGAATGCCCAATTCA
GAGAGACATGGGGGCAAGAAGGACGGGAGTGGAGGAGCTTCTGGAACTTTGCAGCCGTCATCGGGAGGCGGCAGCT
CTAACAGCAGAGAGCGTCACCGCTTGGTATCGAAGCACAAGCGGCATAAGTCCAAACACTCCAAAGACATGGGGTT
GGTGACCCCCGAAGCAGCATCCCTGGGCACAGTTATCAAACCTTTGGTGGAGTATGATGATATCAGCTCTGATTCC
GACACCTTCTCCGATGACATGGCCTTCAAACTAGACCGAAGGGAGAACGACGAACGTCGTGGATCAGATCGGAGCG
ACCGCCTGCACAAACATCGTCACCACCAGCACAGGCGTTCCCGGGACTTACTAAAAGCTAAACAGACCG 16432-1

GACATGTTTGCCTGCAGGGGACCAGAGACAATGGGATTAGCCAGTGCTCACTGTTCTTTATGCTTCCAGAGAGGAT
GGGGACAGCTCTCAGGTCAGAATCCAGGCTGAGAAGGCCATGCTGGTTGGGGGCCCCCGGAAGCACGGTCCGGATC
CTCCCTGGCATCAGCGTAGACCCGCTGCTCAGGCTTGGGGTACCAAACTCATGCTCTGTACTGTTTTGGCCCCATG
CGGTGAGAGGAAAACCTAGAAAAAGATTGGTCGTGCTAAGGAATCAGCTGCCCCCTCATCCTCCGCATCCAATGCT
GGTGACAACATATTCCCTCTCCCAGGACACAGACTCGGTGACTCCACACTGGGCTGAGTGGCCTCTGGAGGCTCGT
GGCCTAAGGCAGGGCTCCGTAAGGCTGATCGGCTGAACTGGGTGGGGTGAGGGTTTCTGACCCTTCGCTTCCCATC
CCATAACCGCTGTCAATGAGCTCACACTGTGGTCA 16432-2

GATGGCATGGTCGTTGCTAATGTGCCTGCTGGGATGGAGCACTTCCTCCTGTGAGCCCAGGGGACCCGCCTGTCCC
TGGAGCTTGGGGCAAGGAGGGAAGAGTGATACCAGGAAGGTGGGGCTGCAGCCAGGGGCCAGAGTCAGTTCAGGGA
GTGGTCCTCGGCCCTCAAAGCTCCTCCGGGGACTGCTCAGGAGTGATGGTGCCCTGGAGTTTGCCCCAACTTCCCT
GGCCACCCTGGAAGGTGCCTGGCTGCTCCAGGCCTCTAGGCTGGGCTGATGGGTTTCTCCAGGACACAAGTATCAT
TAAAGCCACCCTCTCCTCAGCTTGTCAGGCCGCACATGTGGGACAGGCTGTGCTCACAACCCCCTCGCCTGCCCTG
CCCTCCATCAGGAGGAGCCAGTGGAACCTTCGGAAAGCTCCCAGCATCTCAGCAGCCCTCAAAAGTCGTCCTGGGG
CAAGCTCTGGTTCTCCTGACTGGAGGTCATCTGGGCTTGGCCTGCTCTCTCTCGC 17184.3

TAAAAAAGTGTAACAAAGGTTTATTTAGACTTTCTTCATGCCCCCAGATCCAGGATGTCTATGTAAACCGTTATCT
TACAAAGAAAGCACAATATTTGGTATAAACTAAGTCAGTGACTTGCTTAACTGAAATAGCGTCCATCCAAAAGTGG
GTTTAAGGTAAAACTACCTGACGATATTGGCGGGGATCCTGCAGTTTGGACTGCTTGCCGGGTTTGTCCAGGGTTC
CGGGTCTGTTCTTGGCACTCATGGGGACAGGCATCCTGCTCGTCTGTGGGGCCCCGCTGGAGCCCTTACGTGAAGC
TGAAGGTATCGACCSTAGGGGGCTCTAGGGCAGTGGGACCTTCATCCGGAACTAACAAGGGTCGGGGAGAGGCCTC
TTGGGCTATGTGGG

CAAGCGTTCCTTTATGGATGTAAATTCAAACAGTCATGCTGAGCCATCCCGGGCTGACAGTCACGTTWAAGACACT
AGGTCGGGCGCCACAGTGCCACCCAAGGAGAAGAAGAATTTGGAATTTTTCCATGAAGATGTACGGAAATCTGATG
TTGAATATGAAAATGGCCCCCAAATGGAATTCCAAAAGGTTACCACAGGGGCTGTAAGACCTAGTGACCCTCCTAA
GTGGGAAAGAGGAATGGAGAATAGTATTTCTGATGCATCAAGAACATCAGAATATAAAACTGAGATCATAATGAAG
GAAAATTCCATATCCAATATGAGTTTACTCAGAGACAGTAGAAACTATTCCCAGG 17185.1

TAGGAATAACAAATGTTTATTCAGAAATGGATAAGTAATACATAATCACCCTTCATCTCTTAATGCCCCTTCCTCT
CCTTCTGCACAGGAGACACAGATGGGTAACATAGAGGCATGGGAAGTGGAGGAGGACACAGGACTAGCCCACCACC
TTCTCTTCCCGGTCTCCCAAGATGACTGCTTATAGAGTGGAGGAGGCAAACAGGTCCCCTCAATGTACCAGATGGT
CACCTATAGCACCAGCTCCAGATGGCCACGTGGTTGCAGCTGGACTCAATGAAACTCTGTGACAACCAGAAGATAC
CTGCTTTGGGATGAGAGGGAGGATAAAGCCATGCAGGGAGGATATTTACCATCCCTACCCTAAGCACAGTGCAAGC
AGTGAGCCCCCGGCTCCCAGTACCTGAAAAACCAAGGCCTACTGNCTTTTGGATGCTCTCTTGGGCCACG 17188.2

AAGCCTCCTGCCCTGGAAATCTGGAGCCCCTTGGAGCTGAGCTGGACGGGGCAGGGAGGGGCTGAGAGGCAAGACC
GTCTCCCTCCTGCTGCAGCTGCTTCCCCAGCAGCCACTGCTGGGCACAGCAGAAACGCCAGCAGAGAAAATGGGAG
CCGAGAGTCCTTAGCCCTGGAGCTGAGGCTGCCTCTGGGCTGACCCGCTGGCTGTACGTGGCCAGAACTGGGGTTG
GCATCTGGCATCCATTTGAGGCCAGGGTGGAGGAAAGGGAGGCCAACAGAGGAAAACCTATTCCTGCTGTGACAAC
ACAGCCCTTGTCCCACGCAGCCTAAGTGCAGGGAGCGTGATGAAGTCAGGCAGCCAGTCGGGGAGGACGAGGTAAC
TCAGCAGCAATGTCACCTTGTAGCCTATGCGCTCAATGGCCCGGAGGGGCAGCAACCCCCCGCACACGTCAGCCAA
CAGCAGTGCCTCTGCAGGCACCAAGAGAGCGATGATGGACTTGAGCGCCGTGTTC 17190.1

GTTTGGCAGAAGACATGTTTAATAACATTTTCATATTTAAAAAATACAGCAACAATTCTCTATCTGTCCACCATCT
TGCCTTGCCCTTCCTGGGGCTGAGGCAGACAAAGGAAAGGTAATGAGGTTAGGGCCCCCAGGCGGGCTAAGTGCTA
TTGGCCTGCTCCTGCTCAAAGAGAGCCATAGCCAGCTGGGCACGGCCCCCTAGCCCCTCCAGGTTGCTGAGGCGGC
AGCGGTGGTAGAGTTCTTCACTGAGCCGTGGGCTGCAGTCTCGCAGGGAGAACTTCTGCACCAGCCCTGGCTCTAC
GGCCCGAAAGAGGTGGAGCCCTGAGAACCGGAGGAAAACATCCATCACCTCCAGCCCCTCCAGGGCTTCCTCCTCT
TCCTGGCCTGCCAGTTCACCTGCCAGCCGGGCTCGGGCCGCCAGGTAGTCAGCGTTGTAGAAGCAGCCCTCCGCAG
AAGCCTGCCGGTCAAATCTCCCCGCTATAGGAGCCCCCCGGGAGGGGTCAGCACC

CAAGTTGAACGTCAGGCTTGGCAGAGGTGGAGTGTAGATGAAAACAAAGGTGTGATTATGAAGAGGATGTGAGTCC
TTTGGGTGTAGGAGAGAAAGGCTGTTGAGCTTCTATTTCAAGATACTTTTACCTGTGCAAAAAGCACATTTTCCAC
CTCCTTCTCATGGCATTTGTGTAAGGTGAGTATGATTCCTATTCCATCTGCATTTTAGAGGTGAAGAATAACGTAC
AAGGGATTCAGTGATTAGCAAGGGACCCCTCACTAAGTGTTGATGGAGTTAGGACAGAGCTCAGCTGTTTGAATCT
CAGAGCCCAGGCAGCTGGAGCTGGGTAGGATCCTGGAGCTGGCACTAATGTGAGGTGCATTCCCTCCAACCCAGGC
TCAGATCCGGAACCTGACCGTGCTGACCCCCGAAGGGGAGGCAGGGCTGAGCTGGCCCGTTGGGCTCCCTGCTCCT
TTCACACCACACTCTCGCTTTGAGGTGCTGGGCTGGGACTACTTCACAGAGCAGC 17191.2&89.2

TGGCCTGGGCAGGATTGGGAGAGAGGTAGCTACCCGGATGCAGTCCTTTGGGATGAAGACTATAGGGTATGACCCC
ATCATTTCCCCAGAGGTCTCGGCCTCCTTTGGTGTTCAGCAGCTGCCCCTGGAGGAGATCTGGCCTCTCTGTGATT
TCATCACTGTGCACACTCCTCTCCTGCCCTCCACGACAGGCTTGCTGAATGACAACACCTTTGCCCAGTGCAAGAA
GGGGGTGCGTGTGGTGAACTGTGCCCGTGGAGGGATCGTGGACGAAGGCGCCCTGCTCCGGGCCCTGCAGTCTGGC
CAGTGTGCCGGGGCTGCACTGGACGTGTTTACGGAAGAGCCGCCACGGGACCGGGCCTTGGTGGACCATGAGAATG
TCATCAGCTGTCCCCACCTGGGTGCCAGCACCAAGGAGGCTCAGAGCCGCTGTGGGGAGGAAATTGCTGTTCAGTT
CGTGGACATGGTGAAGGGGAAATCTCTCACGGGGGTTGTGAATGCCCAGGCCCTT

*Fig. 1S*

AGCCAGATGGCTGAGAGCTGCAAGAAGAAGTCAGGATCATGATGGCTCAGTTTCCCACAGCGATGAATGGAGGGCC
AAATATGTGGGCTATTACATCTGAAGAACGTACTAAGCATGATAAACAGTTTGATAACCTCAAACCTTCAGGAGGT
TACATAACAGGTGATCAAGCCCGTACTTTTTTCCTACAGTCAGGTCTGCCGGCCCCGGTTTTAGCTGAAATATGGG
CCTTATCAGATCTGAACAAGGATGGGAAGATGGACCAGCAAGAGTTCTCTATAGCTATGAAACTCATCAAGTTAAA
GTTGCAGGGCCAACAGCTGCCTGTAGTCCTCCCTCCTATCATGAAACAACCCCCTATGTTCTCTCCACTAATCTCT
GCTCGTTTTGGGATGGGAAGCATGCCCAATCTGTCCATTCATCAGCCATTGCCTCCAGTTGCACCTATAGCAACAC
CCTTGTCTTCTGCTACTTCAGGGACCAGTATTCCTCCCCTAATGATGCCTGCTCCCCTAGTGCCTTCTGTTAGTAC
ATCCTCATTACCAAATGGAACTGCCAGTCTCATTCAGCCTTTATCCATTCCTTATTCTTCTTCAACATTGCCTCAT
GCATCATCTTACAGCCTGATGATGGGAGGATTTGGTGGTGCTAGTATCCAGAAGGCCCAGTCTCTGATTGATTTAG
GATCTAGTAGCTCAACTTCCTCAACTGCTTCCCTCTCAGGGAACTCACCTAAGACAGGGACCTCAGAGTGGGCAGT
TCCTCAGCCTTCAAGATTAAAGTATCGGCAAAAATTTAATAGTCTAGACAAAGGCATGAGCGGATACCTCTCAGGT
TTTCAAGCTAGAAATGCCCTTCTTCAGTCAAATCTCTCTCAAACTCAGCTAGCTACTATTTGGACTCTGGCTGACA
TCGATGGTGACGGACAGTTGAAAGCTGAAGAATTTATTCTGGCGATGCACCTCACTGACATGGCCAAAGCTGGACA
GCCACTACCACTGACGTTGCCTCCCGAGCTTGTCCCTCCATCTTTCAGAGGGGGAAAGCAAGTTGATTCTGTTAAT
GGAACTCTGCCTTCATATCAGAAAACACAAGAAGAAGAGCCTCAGAAGAAACTGCCAGTTACTTTTGAGGACAAAC
GGAAAGCCAACTATGAACGAGGAAACATGGAGCTGGAGAAGCGACGCCAAGTGTTGATGGAGCAGCAGCAGAGGGA
GGCTGAACGCAAAGCCCAGAAAGAGAAGGAAGAGTGGGAGCGGAAACAGAGAGAACTGCAAGAGCAAGAATGGAAG
AAGCAGCTGGAGTTGGAGAAACGCTTGGAGAAACAGAGAGAGCTGGAGAGACAGCGGGAGGAAGAGAGGAGAAAGG
AGATAGAAAGACGAGAGGCAGCAAAACAGGAGCTTGAGAGACAACGCCGTTTAGAATGGGAAAGACTCCGTCGGCA
GGAGCTGCTCAGTCAGAAGACCAGGGAACAAGAAGACATTGTCAGGCTGAGCTCCAGAAAGAAAAGTCTCCACCTG
GAACTGGAAGCAGTGAATGGAAAACATCAGCAGATCTCAGGCAGACTACAAGATGTCCAAATCAGAAAGCAAACAC
AAAAGACTGAGCTAGAAGTTTTGGATAAACAGTGTGACCTGGAAATTATGGAAATCAAACAACTTCAACAAGAGCT
TAAGGAATATCAAAATAAGCTTATCTATCTGGTCCCTGAGAAGCAGCTATTAAACGAAAGAATTAAAAACATGCAG
CTCAGTAACACACCTGATTCAGGGATCAGTTTACTTCATAAAAAGTCATCAGAAAAGGAAGAATTATGCCAAAGAC
TTAAAGAACAATTAGATGCTCTTGAAAAAGAAACTGCATCTAAGCTCTCAGAAATGGATTCATTTAACAATCAGCT
GAAGGAACTCAGAGAAAGCTATAATACACAGCAGTTAGCCCTTGAACAACTTCATAAAATCAAACGTGACAAATTG
AAGGAAATCGAAAGAAAAAGATTAGAGCAAAAAAAAAAAAA

*Fig. 2A*

ATGGCAGTGACATTCACCATCATGGGAACCACCTTCCCTTTTCTTCAGGATTCTCTGTAGTGGAAGAGAGCACCCA
GTGTTGGGCTGAAAACATCTGAAAGTAGGGAGAAGAACCTAAAATAATCAGTATCTCAGAGGGCTCTAAGGTGCCA
AGAAGTCTCACTGGACATTTAAGTGCCAACAAAGGCATACTTTCGGAATCGCCAAGTCAAAACTTTCTAACTTCTG
TCTCTCTCAGAGACAAGTGAGACTCAAGAGTCTACTGCTTTAGTGGCAACTACAGAAAACTGGTGTTACCCAGAAA
AACAGGAGCAATTAGAAATGGTTCCAATATTTCAAAGCTCCGCAAACAGGATGTGCTTTCCTTTGCCCATTTAGGG
TTTCTTCTCTTTCCTTTCTCTTTATTAACCACTA

*Fig. 2B*

ATATCTAGAAGTCTGGAGTGAGCAAACAAGAGCAAGAAACAAAAAGAAGCCAAAAGCAGAAGGCTCCAATATGAAC
AAGATAAATCTATCTTCAAAGACATATTAGAAGTTGGGAAAATAATTCATGTGAACTAGACAAGTGTGTTAAGAGT
GATAAGTAAAATGCACGTGGAGACAAGTGCATCCCCAGATCTCAGGGACCTCCCCCTGCCTGTCACCTGGGGAGTG
AGAGGACAGGATAGTGCATGTTCTTTGTCTCTGAATTTTTAGTTATATGTGCTGTAATGTTGCTCTGAGGAAGCCC
CTGGAAAGTCTATCCCAACATATCCACATCTTATATTCCACAAATTAAGCTGTAGTATGTACCCTAAGACGCTGCT
AATTGACTGCCACTTCGCAACTCAGGGGCGGCTGCATTTTAGTAATGGGTCAAATGATTCACTTTTTATGATGCTT
CCAAAGGTGCCTTGGCTTCTCTTCCCAACTGACAAATGCCAAAGTTGAGAAAAATGATCATAATTTTAGCATAAAC
AGAGCAGTCGGCGACACCGATTTTATAAATAAACTGAGCACCTTCTTTTTAAACAAACAAATGCGGGTTTATTTCT
CAGATGATGTTCATCCGTGAATGGTCCAGGGAAGGACCTTTCACCTTGACTATATGGCATTATGTCATCACAAGCT
CTGAGGCTTCTCCTTTCCATCCTGCGTGGACAGCTAAGACCTCAGTTTTCAATAGCATCTAGAGCAGTGGGACTCA
GCTGGGGTGATTTCGCCCCCCATCTCCGGGGGAATGTCTGAAGACAATTTTGTTACCTCAATGAGGGAGTGGAGGA
GGATACAGTGCTACTACCAACTAGTGGATAAAGGCCAGGGATGCTGCTCAACCTCCTACCATGTACAGGACGTCTC
CCCATTACAACTACCCAATCCGAAGTGTCAACTGTGTCAGGACTAAGAAACCCTGGTTTTGAGTAGAAAAGGGCCT
GGAAAGAGGGGAGCCAACAAATCTGTCTGCTTCCTCACATTAGTCATTGGCAAATAAGCATTCTGTCTCTTTGGCT
GCTGCCTCAGCACAGAGAGCCAGAACTCTATCGGGCACCAGGATAACATCTCTCAGTGAACAGAGTTGACAAGGCC
TATGGGAAATGCCTGATGGGATTATCTTCAGCTTGTTGAGCTTCTAAGTTTCTTTCCCTTCATTCTACCCTGCAAG
CCAAGTTCTGTAAGAGAAATGCCTGAGTTCTAGCTCAGGTTTTCTTACTCTGAATTTAGATCTCCAGACCCTTCCT
GGCCACAATTCAAATTAAGGCAACAAACATATACCTTCCATGAAGCACACACAGACTTTTGAAAGCAAGGACAATG
ACTGCTTGAATTGAGGCCTTGAGGAATGAAGCTTTGAAGGAAAAGAATACTTTGTTTCCAGCCCCCTTCCCACACT
CTTCATGTGTTAACCACTGCCTTCCTGGACCTTGGAGCCACGGTGACTGTATTACATGTTGTTATAGAAAACTGAT
TTTAGAGTTCTGATCGTTCAAGAGAATGATTAAATATACATTTCCTA

*Fig. 2C*

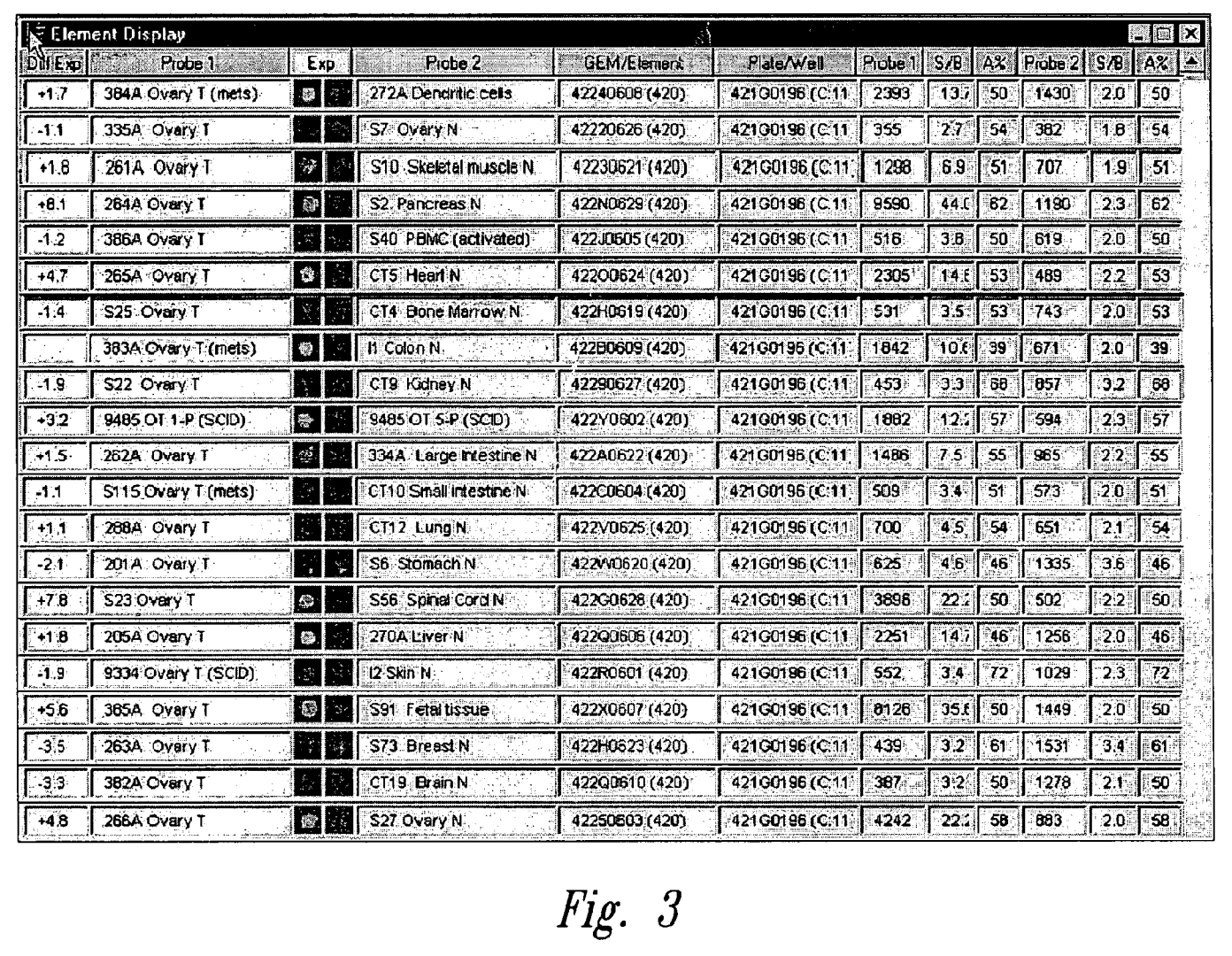

Element Display

| Diff Exp | Probe 1 | Exp | Probe 2 | GEM/Element | Plate/Well | Probe 1 | S/B | A% | Probe 2 | S/B | A% |
|---|---|---|---|---|---|---|---|---|---|---|---|
| +1.7 | 384A Ovary T (mets) | | 272A Dendritic cells | 42240608 (420) | 421G0196 (C11 | 2393 | 13.7 | 50 | 1430 | 2.0 | 50 |
| -1.1 | 335A Ovary T | | S7 Ovary N | 42220626 (420) | 421G0196 (C11 | 355 | 2.7 | 54 | 382 | 1.8 | 54 |
| +1.8 | 261A Ovary T | | S10 Skeletal muscle N | 42230621 (420) | 421G0196 (C11 | 1298 | 6.9 | 51 | 707 | 1.9 | 51 |
| +8.1 | 264A Ovary T | | S2 Pancreas N | 422N0629 (420) | 421G0196 (C11 | 9590 | 44. | 62 | 1190 | 2.3 | 62 |
| -1.2 | 386A Ovary T | | S40 PBMC (activated) | 422J0605 (420) | 421G0196 (C11 | 516 | 3.8 | 50 | 619 | 2.0 | 50 |
| +4.7 | 265A Ovary T | | CT5 Heart N | 422O0624 (420) | 421G0196 (C11 | 2305 | 14. | 53 | 489 | 2.2 | 53 |
| -1.4 | S25 Ovary T | | CT4 Bone Marrow N | 422H0619 (420) | 421G0196 (C11 | 531 | 3.5 | 53 | 743 | 2.0 | 53 |
| | 383A Ovary T (mets) | | I1 Colon N | 422B0609 (420) | 421G0196 (C11 | 1842 | 10. | 39 | 671 | 2.0 | 39 |
| -1.9 | S22 Ovary T | | CT9 Kidney N | 42290627 (420) | 421G0196 (C11 | 453 | 3.3 | 68 | 857 | 3.2 | 68 |
| +3.2 | 9485 OT 1-P (SCID) | | 9485 OT 5-P (SCID) | 422Y0602 (420) | 421G0196 (C11 | 1882 | 12. | 57 | 594 | 2.3 | 57 |
| +1.5 | 262A Ovary T | | 334A Large Intestine N | 422A0622 (420) | 421G0196 (C11 | 1486 | 7.5 | 55 | 965 | 2.2 | 55 |
| -1.1 | S115 Ovary T (mets) | | CT10 Small Intestine N | 422C0604 (420) | 421G0196 (C11 | 509 | 3.4 | 51 | 573 | 2.0 | 51 |
| +1.1 | 288A Ovary T | | CT12 Lung N | 422V0625 (420) | 421G0196 (C11 | 700 | 4.5 | 54 | 651 | 2.1 | 54 |
| -2.1 | 201A Ovary T | | S6 Stomach N | 422W0620 (420) | 421G0196 (C11 | 625 | 4.6 | 46 | 1335 | 3.6 | 46 |
| +7.8 | S23 Ovary T | | S56 Spinal Cord N | 422G0628 (420) | 421G0196 (C11 | 3896 | 22. | 50 | 502 | 2.2 | 50 |
| +1.8 | 205A Ovary T | | 270A Liver N | 422Q0606 (420) | 421G0196 (C11 | 2251 | 14.7 | 46 | 1256 | 2.0 | 46 |
| -1.9 | 9334 Ovary T (SCID) | | I2 Skin N | 422R0601 (420) | 421G0196 (C11 | 552 | 3.4 | 72 | 1029 | 2.3 | 72 |
| +5.6 | 365A Ovary T | | S91 Fetal tissue | 422X0607 (420) | 421G0196 (C11 | 8126 | 35. | 50 | 1449 | 2.0 | 50 |
| -3.5 | 263A Ovary T | | S73 Breast N | 422H0623 (420) | 421G0196 (C11 | 439 | 3.2 | 61 | 1531 | 3.4 | 61 |
| -3.3 | 382A Ovary T | | CT19 Brain N | 422Q0610 (420) | 421G0196 (C11 | 387 | 3.2 | 50 | 1278 | 2.1 | 50 |
| +4.8 | 266A Ovary T | | S27 Ovary N | 42250603 (420) | 421G0196 (C11 | 4242 | 22. | 58 | 883 | 2.0 | 58 |

*Fig. 3*

TCGAGCGGCCGCCCGGGCAGGTCCTTCAGACTTGGACTGTGTCACACTGCCAGGCTTCCAGGGCTCCAACTTGCAG
ACGGCCTGTTGTGGGACAGTCTCTGTAATCGCGAAAGCAACCATGGAAGACCTGGGGGAAAACACCATGGTTTTAT
CCACCCTGAGATCTTTGAACAACTTCATCTCTCAGCGTGCGGAGGGAGGCTCTGGACTGGATATTTCTACCTCGGC
CGCGACCACGCT

*Fig. 4*

TAGCGYGGTCGCGGCCGAGGYCTGCTTYTCTGTCCAGCCCAGGGCCTGTGGGGTCAGGGCGGTGGGTGCAGATGGC
ATCCACTCCGGTGGCTTCCCCATCTTTCTCTGGCCTGAGCAAGGTCAGCCTGCAGCCAGAGTACAGAGGGCCAACA
CTGGTGTTCTTGAACAAGGGCCTTAGCAGGCCCTGAAGGRCCCTCTCTGTAGTGTTGAACTTCCTGGAGCCAGGCC
ACATGTTCTCCTCATACCGCAGGYTAGYGATGGTGAAGTTGAGGGTGAAATAGTATTMANGRAGATGGCTGGCARA
CCTGCCCGGGCGGCCGCTCSAAATCC

*Fig. 5*

AGCGTGGTCGCGGCCGAGGTGTCCTTCAGGGTCTGCTTATGCCCTTGTTCAAGAACACCAGTGTCAGCTCTCTGTA
CTCTGGTTGCAGACTGACCTTGCTCAGGCCTGAGAAGGATGGGGCAGCCACCAGAGTGGATGCTGTCTGCACCCAT
CGTCCTGACCCCAAAAGCCCTGGACTGGACAGAGAGCGGCTGTACTGGAAGCTGAGCCAGCTGACCCACGGCATCA
CTGAGCTGGGCCCCTACACCCTGGACAGGGACAGTCTCTATGTCAATGGTTTCACCCATCGGAGCTCTGTACCCAC
CACCAGCACCGGGGTGGTCAGCGAGGAGCCATTCAACCTGCCCGGGCGGCCGCTCGA

TTGGGGNTTTMGAGCGGCCGCCCGGGCAGGTACCGGGGTGGTCAGCGAGGAGCCATTCACACTGAACTTCACCATC
AACAACCTGCGGTATGAGGAGAACATGCAGCACCCTGGCTCCAGGAAGTTCAACACCACGGAGAGGGTCCTTCAGG
GCCTGCTCAGGTCCCTGTTCAAGAGCACCAGTGTTGGCCCTCTGTACTCTGGCTGCAGACTGACTTTGCTCAGACT
TGAGAAACATGGGGCAGCCACTGGAGTGGACGCCATCTGCACCCTCCGCCTTGATCCCACTGGTCCTGGACTGGAC
AGAGAGCGGCTATACTGGGAGCTGAGCCAGTCCTCTGGCGGNGACNCCNCTT

Fig. 7B

AGCGTGGTCGCGGCCGAGGTCCAGTCGCAGCATGCTCTTTCTCCTGCCCACTGGCACAGTGAGGAAGATCTCTGCT
GTCAGTGAGAAGGCTGTCATCCACTGAGATGGCAGTCAAAAGTGCATTTAATACACCTAACGTATCGAACATCATA
GCTTGGCCCAGGTTATCTCATATGTGCTCAGAACACTTACAATAGCCTGCAGACCTGCCCGGGCGGCCGCTCGA

*Fig. 7A and 7B*

TGTGGTGTTGAACTTCCTGGAGNCAGGGTGACCCATGTCCTCCCCATACTGCAGGTTGGTGATGGTGAAGTTGAGG
GTGAATGGTACCAGGAGAGGGCCAGCAGCCATAATTGTSGRGCKGSMGMSSGAGGMWGGWGTYYCWGAGGTTCYRA
RRTCCACTGTGGAGGTCCCAGGAGTGCTGGTGGTGGGCACAGAGSTCYGATGGGTGAAACCATTGACATAGAGACT
GTTCCTGTCCAGGGTGTAGGGGCCCAGCTCTTYRATGYCATTGGYCAGTTKGCTYAGCTCCCAGTACAGCCRCTCT
CKGYYGMGWCCAGSGCTTTTGGGGTCAAGATGATGGATGCAGATGGCATCCACTCCAGTGGCTGCTCCATCCTTCT
CGGACCTGAGAGAGGTCAGTCTGCAGCCAGAGTACAGAGGGCCAACACTGGTGTTCTTTGAATA

*Fig. 8*

TCGAGCGGCCGCCCGGGCAGGTCAGGAAGCACATTGGTCTTAGAGCCACTGCCTCCTGGATTCCACCTGTGCTGCG
GACATCTCCAGGGAGTGCAGAAGGGAAGCAGGTCAAACTGCTCAGATCAGTCAGACTGGCTGTTCTCAGTTCTCAC
CTGAGCAAGGTCAGTCTGCAGCCAGAGTACAGAGGGCCAACACTGGTGTTCTTGAACAAGGGCTTGAGCAGACCCT
GCAGAACCCTCTTCCGTGGTGTTGAACTTCCTGGAAACCAGGGTGTTGCATGTTTTTCCTCATAATGCAAGGTTGG
TGATGG

*Fig. 9*

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 42100188 (D3) | +7.0 | 205A Ovary T | | | 270A Liver N | 422Q0606 | 8620 | 1240 | 57.7 | 65 | 2.2 | 65 |
| 42100188 (D3) | +5.9 | S23 Ovary T | | | S56 Spinal Cord N | 422G0628 | 5894 | 1002 | 35.3 | 89 | 3.9 | 89 |
| 42100188 (D3) | +5.7 | 385A Ovary T | | | S91 Fetal tissue | 422X0607 | 12151 | 2121 | 54.3 | 73 | 2.8 | 73 |
| 42100188 (D3) | +5.1 | 426A Ovary T (met | | | 415A Aorta N | 422X0611 | 7487 | 1480 | 53.0 | 73 | 9.7 | 73 |
| 42100188 (D3) | +3.5 | 263A Ovary T | | | S73 Breast N | 422H0623 | 7302 | 2116 | 39.2 | 84 | 4.5 | 84 |
| 42100188 (D3) | +3.3 | 383A Ovary T (met | | | I1 Colon N | 422B0609 | 3714 | 1113 | 20.4 | 83 | 2.6 | 83 |
| 42100188 (D3) | +3.0 | 9334 Ovary T (SCII | | | I2 Skin N | 422R0601 | 2435 | 814 | 12.1 | 75 | 2.1 | 75 |
| 42100188 (D3) | +2.6 | 384A Ovary T (met | | | 272A Dendritic cell | 42240608 | 4578 | 1754 | 25.0 | 69 | 2.3 | 69 |
| 42100188 (D3) | +2.2 | 264A Ovary T | | | S2 Pancreas N | 422N0629 | 7904 | 3596 | 38.5 | 81 | 5.6 | 81 |
| 42100188 (D3) | +2.0 | 386A Ovary T | | | S40 PBMC (activat | 422J0605 | 2191 | 1081 | 14.0 | 90 | 2.9 | 90 |
| 42100188 (D3) | +2.0 | S115 Ovary T (mets | | | CT10 Small intestin | 422C0604 | 1979 | 971 | 10.4 | 80 | 2.7 | 80 |
| 42100188 (D3) | +2.0 | 265A Ovary T | | | CT5 Heart N | 422O0624 | 1911 | 964 | 13.9 | 93 | 3.4 | 93 |
| 42100188 (D3) | +2.0 | 335A Ovary T | | | S7 Ovary N | 42220626 | 1666 | 817 | 9.8 | 100 | 3.0 | 100 |
| 42100188 (D3) | -1.9 | 428A Ovary T (met | | | 243A Esophagus N | 42240612 | 1827 | 3480 | 13.4 | 97 | 9.5 | 97 |
| 42100188 (D3) | +1.6 | 261A Ovary T | | | S10 Skeletal muscl | 42230621 | 5914 | 3653 | 30.4 | 86 | 6.0 | 86 |
| 42100188 (D3) | +1.6 | 266A Ovary T | | | S27 Ovary N | 42250603 | 2039 | 1274 | 11.9 | 50 | 2.6 | 50 |
| 42100188 (D3) | +1.6 | S22 Ovary T | | | CT9 Kidney N | 42290627 | 1736 | 1072 | 11.0 | 92 | 4.0 | 92 |
| 42100188 (D3) | +1.4 | 9485 OT 1-P (SCID | | | 9485 OT 5-P (SCID | 422Y0602 | 4204 | 3074 | 23.0 | 93 | 7.7 | 93 |
| 42100188 (D3) | +1.4 | 262A Ovary T | | | 334A Large Intestir | 422A0622 | 3002 | 2101 | 16.6 | 89 | 4.0 | 89 |
| 42100188 (D3) | +1.3 | S25 Ovary T | | | CT4 Bone Marrow | 422H0619 | 1643 | 1297 | 9.6 | 90 | 3.1 | 90 |
| 42100188 (D3) | +1.2 | 429A Ovary T (met | | | 364A Ovary N | 422I0614 | 2521 | 2084 | 22.0 | 65 | 23.9 | 65 |
| 42100188 (D3) | +1.2 | 382A Ovary T | | | CT19 Brain N | 422Q0610 | 2072 | 1663 | 10.9 | 88 | 2.3 | 88 |
| 42100188 (D3) | +1.2 | 288A Ovary T | | | CT12 Lung N | 422V0625 | 1840 | 1473 | 10.7 | 87 | 3.8 | 87 |
| 42100188 (D3) | +1.1 | 201A Ovary T | | | S6 Stomach N | 422W0620 | 1329 | 1204 | 9.1 | 90 | 3.5 | 90 |

*Fig. 10*

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 421B0181 {C3} | +18.3 | 385A Ovary T | | | S91 Fetal tissue | 422X0607 | 26711 | 1424 | 103.3 | 54 | 2.0 | 54 |
| 421B0181 {C3} | +11.5 | S23 Ovary T | | | S56 Spinal Cord N | 422G0628 | 13559 | 1179 | 65.3 | 68 | 3.9 | 68 |
| 421B0181 {C3} | +11.1 | 426A Ovary T (mets) | | | 415A Aorta N | 422X0611 | 14125 | 1273 | 67.3 | 61 | 5.6 | 61 |
| 421B0181 {C3} | +10.8 | 205A Ovary T | | | 270A Liver N | 422Q0606 | 16121 | 1488 | 93.1 | 43 | 2.3 | 43 |
| 421B0181 {C3} | +5.1 | 263A Ovary T | | | S73 Breast N | 422H0623 | 11326 | 2235 | 58.2 | 68 | 4.4 | 68 |
| 421B0181 {C3} | +4.6 | 384A Ovary T (mets) | | | 272A Dendritic cells | 42240608 | 6583 | 1424 | 24.5 | 40 | 2.1 | 40 |
| 421B0181 {C3} | +4.4 | 264A Ovary T | | | S2 Pancreas N | 422N0629 | 9865 | 2245 | 40.9 | 64 | 3.6 | 64 |
| 421B0181 {C3} | +4.4 | 429A Ovary T (mets) | | | 364A Ovary N | 422I0614 | 2803 | 638 | 22.6 | 60 | 7.4 | 60 |
| 421B0181 {C3} | +4.2 | 261A Ovary T | | | S10 Skeletal muscle | M2230621 | 8271 | 1949 | 39.5 | 68 | 3.6 | 68 |
| 421B0181 {C3} | +3.8 | S115 Ovary T (mets) | | | CT10 Small intestine | M22C0604 | 2281 | 607 | 11.6 | 60 | 2.1 | 60 |
| 421B0181 {C3} | +2.5 | 265A Ovary T | | | CT5 Heart N | 422O0624 | 3192 | 1293 | 19.2 | 68 | 4.0 | 68 |
| 421B0181 {C3} | -2.3 | S22 Ovary T | | | CT9 Kidney N | 42290627 | 565 | 1276 | 3.6 | 70 | 3.9 | 70 |
| 421B0181 {C3} | +2.2 | 266A Ovary T | | | S27 Ovary N | 42250603 | 2774 | 1260 | 14.3 | 46 | 2.7 | 46 |
| 421B0181 {C3} | +2.1 | 9334 Ovary T (SCID) | | | I2 Skin N | 422R0601 | 1774 | 837 | 8.4 | 56 | 2.1 | 56 |
| 421B0181 {C3} | +1.9 | 9485 OT 1-P (SCID) | | | 9485 OT 5-P (SCID) | 422Y0602 | 6967 | 3726 | 41.5 | 70 | 9.2 | 70 |
| 421B0181 {C3} | +1.6 | 382A Ovary T | | | CT19 Brain N | 422Q0610 | 2313 | 1471 | 6.2 | 50 | 1.9 | 50 |
| 421B0181 {C3} | +1.6 | 288A Ovary T | | | CT12 Lung N | 422V0625 | 1657 | 1054 | 9.7 | 69 | 2.9 | 69 |
| 421B0181 {C3} | -1.5 | S25 Ovary T | | | CT4 Bone Marrow N | 422H0619 | 848 | 1243 | 4.5 | 65 | 2.7 | 65 |
| 421B0181 {C3} | +1.4 | 262A Ovary T | | | 334A Large Intestine | 422A0622 | 3171 | 2214 | 16.8 | 69 | 3.8 | 69 |
| 421B0181 {C3} | +1.2 | 386A Ovary T | | | S40 PBMC (activated | 422J0605 | 630 | 544 | 4.2 | 53 | 1.9 | 53 |
| 421B0181 {C3} | -1.2 | 335A Ovary T | | | S7 Ovary N | 42220626 | 592 | 730 | 3.7 | 75 | 2.6 | 75 |
| 421B0181 {C3} | -1.0 | 201A Ovary T | | | S6 Stomach N | 422W0620 | 1197 | 1237 | 7.8 | 65 | 3.5 | 65 |
| 421B0181 {C3} | -1.0 | 428A Ovary T (mets) | | | 243A Esophagus N | 42240612 | 783 | 797 | 4.5 | 95 | 2.4 | 95 |
| 421B0181 {C3} | | 383A Ovary T (mets) | | | I1 Colon N | 422B0609 | 3470 | 862 | 8.9 | 24 | 1.7 | 24 |

*Fig. 11*

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 42110182 (H7) | +16.7 | 426A Ovary T (met: | 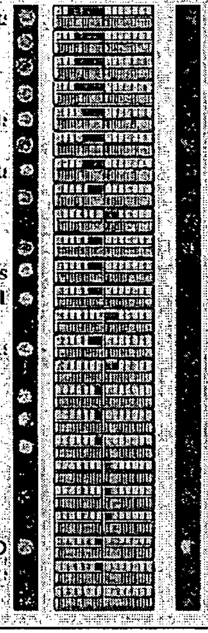 | | 415A Aorta N | 422X0611 | 7706 | 462 | 46.3 | 75 | 3.5 | 75 |
| 42110182 (H7) | +10.7 | 205A Ovary T | | | 270A Liver N | 422Q0606 | 10171 | 950 | 61.2 | 41 | 1.8 | 41 |
| 42110182 (H7) | +9.9 | 385A Ovary T | | | S91 Fetal tissue | 422X0607 | 14415 | 1459 | 62.1 | 48 | 2.2 | 48 |
| 42110182 (H7) | +8.8 | S23 Ovary T | | | S56 Spinal Cord N | 422G0628 | 7781 | 880 | 47.3 | 73 | 3.4 | 73 |
| 42110182 (H7) | +6.4 | 383A Ovary T (met: | | | 11 Colon N | 422B0609 | 4807 | 748 | 27.6 | 47 | 2.2 | 47 |
| 42110182 (H7) | +5.1 | 263A Ovary T | | | S73 Breast N | 422H0623 | 9815 | 1909 | 57.1 | 74 | 4.2 | 74 |
| 42110182 (H7) | +4.9 | 429A Ovary T (met: | | | 364A Ovary N | 422I0614 | 2661 | 543 | 20.3 | 61 | 6.7 | 61 |
| 42110182 (H7) | +3.5 | 264A Ovary T | | | S2 Pancreas N | 422N0629 | 7934 | 2274 | 38.8 | 71 | 3.9 | 71 |
| 42110182 (H7) | -2.9 | S25 Ovary T | | | CT4 Bone Marrow | 422H0619 | 480 | 1375 | 3.5 | 80 | 3.0 | 80 |
| 42110182 (H7) | +2.8 | 261A Ovary T | | | S10 Skeletal muscl | 42230621 | 8993 | 3245 | 34.6 | 69 | 5.1 | 69 |
| 42110182 (H7) | +2.5 | S115 Ovary T (mets | | | CT10 Small intestin | 422C0604 | 1864 | 738 | 8.1 | 67 | 2.2 | 67 |
| 42110182 (H7) | +2.3 | 9334 Ovary T (SCII | | | 12 Skin N | 422R0601 | 2552 | 1113 | 12.7 | 41 | 2.6 | 41 |
| 42110182 (H7) | -2.3 | S22 Ovary T | | | CT9 Kidney N | 42290627 | 386 | 889 | 3.2 | 69 | 3.4 | 69 |
| 42110182 (H7) | +2.2 | 384A Ovary T (met: | | | 272A Dendritic cell | 42240608 | 3516 | 1567 | 18.7 | 55 | 2.2 | 55 |
| 42110182 (H7) | -2.2 | 382A Ovary T | | | CT19 Brain N | 422Q0610 | 608 | 1320 | 4.2 | 60 | 2.3 | 60 |
| 42110182 (H7) | +1.9 | 265A Ovary T | | | CT5 Heart N | 422O0624 | 2063 | 1080 | 13.6 | 87 | 3.5 | 87 |
| 42110182 (H7) | +1.8 | 266A Ovary T | | | S27 Ovary N | 42250603 | 1550 | 847 | 7.0 | 58 | 2.1 | 58 |
| 42110182 (H7) | +1.5 | 262A Ovary T | | | 334A Large Intestir | 422A0622 | 2559 | 1651 | 13.2 | 73 | 3.2 | 73 |
| 42110182 (H7) | -1.4 | 386A Ovary T | | | S40 PBMC (activat | 422J0605 | 534 | 738 | 3.9 | 62 | 2.2 | 62 |
| 42110182 (H7) | -1.3 | 288A Ovary T | | | CT12 Lung N | 422V0625 | 893 | 1120 | 5.3 | 66 | 3.1 | 66 |
| 42110182 (H7) | -1.3 | 335A Ovary T | | | S7 Ovary N | 42220626 | 440 | 567 | 3.3 | 60 | 2.2 | 60 |
| 42110182 (H7) | +1.2 | 9485 OT 1-P (SCID | | | 9485 OT 5-P (SCID | 422Y0602 | 4188 | 3529 | 21.6 | 66 | 9.5 | 66 |
| 42110182 (H7) | +1.1 | 428A Ovary T (met: | | | 243A Esophagus N | 42240612 | 725 | 689 | 6.2 | 65 | 2.8 | 65 |
| 42110182 (H7) | -1.0 | 201A Ovary T | | | S6 Stomach N | 422W0620 | 1008 | 1018 | 7.4 | 62 | 3.2 | 62 |

*Fig. 12*

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 421V0189 {D1} | +33.2 | 426A Ovary T (mets | 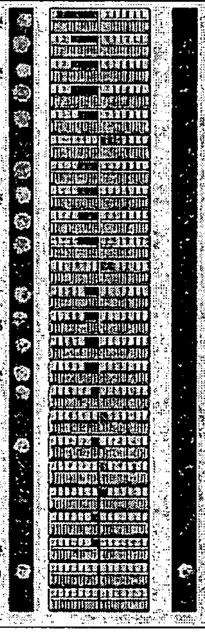 | | 415A Aorta N | 422X0611 | 8072 | 243 | 55.2 | 67 | 2.4 | 67 |
| 421V0189 {D1} | +13.7 | S23 Ovary T | | | S56 Spinal Cord N | 422G0628 | 7367 | 537 | 42.6 | 69 | 2.5 | 69 |
| 421V0189 {D1} | +12.6 | 429A Ovary T (mets | | | 364A Ovary N | 422I0614 | 2850 | 227 | 21.7 | 64 | 3.5 | 64 |
| 421V0189 {D1} | +8.0 | 385A Ovary T | | | S91 Fetal tissue | 422X0607 | 11711 | 1469 | 54.0 | 58 | 2.2 | 58 |
| 421V0189 {D1} | +7.3 | 263A Ovary T | | | S73 Breast N | 422H0623 | 6949 | 952 | 37.8 | 69 | 2.6 | 69 |
| 421V0189 {D1} | -5.8 | S25 Ovary T | | | CT4 Bone Marrow | 422H0619 | 208 | 1210 | 2.1 | 44 | 2.9 | 44 |
| 421V0189 {D1} | +5.0 | 205A Ovary T | | | 270A Liver N | 422Q0606 | 8676 | 1737 | 52.3 | 57 | 2.6 | 57 |
| 421V0189 {D1} | +4.5 | 383A Ovary T (mets | | | 11 Colon N | 422B0609 | 3149 | 707 | 17.4 | 57 | 2.0 | 57 |
| 421V0189 {D1} | +4.4 | 261A Ovary T | | | S10 Skeletal muscl | 4223O621 | 6332 | 1443 | 29.1 | 77 | 2.9 | 77 |
| 421V0189 {D1} | +4.2 | 264A Ovary T | | | S2 Pancreas N | 422N0629 | 7612 | 1809 | 38.1 | 79 | 3.3 | 79 |
| 421V0189 {D1} | -3.2 | 382A Ovary T | | | CT19 Brain N | 422Q0610 | 468 | 1508 | 3.4 | 60 | 2.3 | 60 |
| 421V0189 {D1} | +2.9 | 9334 Ovary T (SCII | | | 12 Skin N | 422R0601 | 2500 | 860 | 12.3 | 51 | 2.1 | 51 |
| 421V0189 {D1} | +2.5 | S115 Ovary T (mets | | | CT10 Small intestin | 422C0604 | 1424 | 569 | 6.7 | 61 | 2.1 | 61 |
| 421V0189 {D1} | +2.4 | 265A Ovary T | | | CT5 Heart N | 422O0624 | 1742 | 723 | 11.8 | 70 | 2.8 | 70 |
| 421V0189 {D1} | +2.3 | 384A Ovary T (mets | | | 272A Dendritic cells | 42240608 | 3083 | 1342 | 17.0 | 62 | 2.0 | 62 |
| 421V0189 {D1} | +1.9 | 266A Ovary T | | | S27 Ovary N | 42250603 | 1370 | 732 | 8.0 | 47 | 2.0 | 47 |
| 421V0189 {D1} | -1.9 | 386A Ovary T | | | S40 PBMC (activat | 422J0605 | 307 | 580 | 2.6 | 41 | 2.0 | 41 |
| 421V0189 {D1} | +1.7 | 262A Ovary T | | | 334A Large Intestir | 422A0622 | 2097 | 1202 | 11.2 | 86 | 2.7 | 86 |
| 421V0189 {D1} | -1.3 | 335A Ovary T | | | S7 Ovary N | 42220626 | 373 | 470 | 2.9 | 47 | 2.0 | 47 |
| 421V0189 {D1} | -1.1 | 288A Ovary T | | | CT12 Lung N | 422V0625 | 969 | 1094 | 5.6 | 72 | 2.9 | 72 |
| 421V0189 {D1} | +1.1 | 201A Ovary T | | | S6 Stomach N | 422W0620 | 750 | 672 | 5.6 | 62 | 2.4 | 62 |
| 421V0189 {D1} | +1.1 | 428A Ovary T (mets | | | 243A Esophagus N | 42240612 | 498 | 446 | 4.2 | 73 | 2.1 | 73 |
| 421V0189 {D1} | -1.0 | 9485 OT 1-P (SCID | | | 9485 OT 5-P (SCID | 422Y0602 | 3117 | 3174 | 16.7 | 91 | 8.2 | 91 |
| 421V0189 {D1} | | S22 Ovary T | | | CT9 Kidney N | 42290627 | 224 | 409 | 2.3 | 48 | 2.3 | 48 |

Fig. 13

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 421H0187 {E11} | +20.2 | 426A Ovary T (met: | | | 415A Aorta N | 422X0611 | 5441 | 270 | 36.3 | 50 | 2.3 | 50 |
| 421H0187 {E11} | +10.0 | S23 Ovary T | | | S56 Spinal Cord N | 422G0628 | 5318 | 533 | 27.1 | 56 | 2.3 | 56 |
| 421H0187 {E11} | +8.3 | 429A Ovary T (met: | | | 364A Ovary N | 422I0614 | 1252 | 150 | 10.1 | 58 | 2.5 | 58 |
| 421H0187 {E11} | +5.7 | 385A Ovary T | | | S91 Fetal tissue | 422X0607 | 9507 | 1668 | 35.8 | 45 | 2.1 | 45 |
| 421H0187 {E11} | +4.4 | 205A Ovary T | | | 270A Liver N | 422Q0606 | 5456 | 1235 | 31.1 | 50 | 2.0 | 50 |
| 421H0187 {E11} | +4.2 | 265A Ovary T | | | CT5 Heart N | 422O0624 | 1834 | 438 | 11.9 | 48 | 2.0 | 48 |
| 421H0187 {E11} | -4.1 | 382A Ovary T | | | CT19 Brain N | 422Q0610 | 309 | 1259 | 2.6 | 48 | 2.0 | 48 |
| 421H0187 {E11} | +3.6 | 261A Ovary T | | | S10 Skeletal muscl | 42230621 | 3733 | 1036 | 17.7 | 55 | 2.3 | 55 |
| 421H0187 {E11} | +3.4 | 263A Ovary T | | | S73 Breast N | 422H0623 | 4163 | 1239 | 23.0 | 62 | 3.0 | 62 |
| 421H0187 {E11} | +2.5 | S115 Ovary T (mets | | | CT10 Small intestin | 422C0604 | 1565 | 627 | 8.8 | 47 | 2.1 | 47 |
| 421H0187 {E11} | +2.1 | 264A Ovary T | | | S2 Pancreas N | 422N0629 | 3455 | 1630 | 14.9 | 60 | 3.0 | 60 |
| 421H0187 {E11} | +2.1 | 384A Ovary T (met: | | | 272A Dendritic cell | 42240608 | 2667 | 1270 | 13.4 | 44 | 1.9 | 44 |
| 421H0187 {E11} | -2.1 | S22 Ovary T | | | CT9 Kidney N | 42290627 | 291 | 605 | 2.4 | 51 | 2.5 | 51 |
| 421H0187 {E11} | -1.7 | 386A Ovary T | | | S40 PBMC (activat | 422J0605 | 410 | 687 | 3.2 | 47 | 2.0 | 47 |
| 421H0187 {E11} | +1.6 | 9334 Ovary T (SCII | | | I2 Skin N | 422R0601 | 1622 | 984 | 7.9 | 44 | 2.2 | 44 |
| 421H0187 {E11} | +1.5 | 262A Ovary T | | | 334A Large Intestir | 422A0622 | 1892 | 1245 | 10.1 | 50 | 2.6 | 50 |
| 421H0187 {E11} | -1.5 | 288A Ovary T | | | CT12 Lung N | 422V0625 | 604 | 908 | 4.1 | 62 | 2.6 | 62 |
| 421H0187 {E11} | -1.4 | 428A Ovary T (met: | | | 243A Esophagus N | 42240612 | 236 | 325 | 2.7 | 78 | 1.9 | 78 |
| 421H0187 {E11} | -1.3 | 335A Ovary T | | | S7 Ovary N | 42220626 | 382 | 501 | 2.9 | 58 | 2.0 | 58 |
| 421H0187 {E11} | -1.2 | 201A Ovary T | | | S6 Stomach N | 422W0620 | 558 | 677 | 4.2 | 58 | 2.3 | 58 |
| 421H0187 {E11} | +1.0 | 9485 OT 1-P (SCID | | | 9485 OT 5-P (SCID | 422Y0602 | 2582 | 2493 | 15.1 | 57 | 6.3 | 57 |
| 421H0187 {E11} | | 383A Ovary T (met: | | | I1 Colon N | 422B0609 | 2261 | 562 | 12.5 | 38 | 1.7 | 38 |
| 421H0187 {E11} | | 266A Ovary T | | | S27 Ovary N | 42250603 | 1739 | 965 | 9.7 | 36 | 2.2 | 36 |
| 421H0187 {E11} | | S25 Ovary T | | | CT4 Bone Marrow | 422H0619 | 283 | 845 | 2.2 | 44 | 2.2 | 44 |

ACGGTTTCAATGGACACTTTTATTGTTTACTTAATGGATCATCAATTTTGTCTCACTACCTACAAATGGAATTTCA
TCTTGTTTCCATGCTGAGTAGTGAAACAGTGACAAAGCTAATCATAATAACCTACATCAAAAGAGAACTAAGCTAA
CACTGCTCACTTTCTTTTTAACAGGCAAAATATAAATATATGCACTCTAXAATGCACAATGGTTTAGTCACTAAAA
AATTCAAATGGGATCTTGAAGAATGTATGCAAATCCAGGGTGCAGTGAAGATGAGCTGAGATGCTGTGCAACTGTT
TAAGGGTTCCTGGCACTGCATCTCTTGGCCACTAGCTGAATCTTGACATGGAAGGTTTTAGCTAATGCCAAGTGGA
GATGCAGAAAATGCTAAGTTGACTTAGGGGCTGTGCACAGGAACTAAAAGGCAGGAAAGTACTAAATATTGCTGAG
AGCATCCACCCCAGGAAGGACTTTACCTTCCAGGAGCTCCAAACTGGCACCACCCCCAGTGCTCACATGGCTGACT
TTATCCTCCGTGTTCCATTTGGCACAGCAAGTGGCAGTG 11721-2

AAGGCTGGTGGGTTTTTGATCCTGCTGGAGAACCTCCGCTTTCATGTGGAGGAAGAAGGGAAGGGAAAAGATGCTT
CTGGGAACAAGGTTAAAGCCGAGCCAGCCAAAATAGAAGCTTTCCGAGCTTCACTTTCCAAGCTAGGGGATGTCTA
TGTCAATGATGCTTTTGGCACTGCTCACAGAGCCCACAGCTCCATGGTAGGAGTCAATCTGCCACAGAAGGCTGGT
GGGTTTTTGATGAAGAAGGAGCTGAACTACTTTGCAAAGGCCTTGGAGAGCCCAGAGCGACCCTTCCTGGCCATCC
TGGGCGGAGCTAAAGTTGCAGACAAGATCCAGCTCATCAATAATATGCTGGACAAAGTCAATGAGATGATTATTGG
TGGTGGAATGGCTTTTACCTTCCTTAAGGTGCTCAACAACATGGAGATTGGCACTTCTCTGTTTGATGAAGAGGGA
GCCAAGATTGTCAAAGACCTAATGTCCAAAGCTGAGAAGAATGGTGTGAAGATTACCTTGCCTGTTGACTTTGTCA
CTGCTGACAAGTTTGATGA 11724-1

TTTGTTCCTTACATTTTTCTAAAGAGTTACTTAAATCAGTCAACTGGTCTTTGAGACTCTTAAGTTCTGATTCCAA
CTTAGCTAATTCATTCTGAGAACTGTGGTATAGGTGGCGTGTCTCTTCTAGCTGGGACAAAAGTTCTTTGTTTTCC
CCCTGTAGAGTATCACAGACCTTCTGCTGAAGCTGGACCTCTGTCTGGGCCTTGGACTCCCAAATCTGCTTGTCAT
GTTCAAGCCTGGAAATGTTAATCTTTAATTCTTCCATATGGATGGACATCTGTCTAAGTTGATCCTTTAGAACACT
GCAATTATCTTCTTTGAGTCTAATTTCTTCTTCTTTGCTTTGAATCGCATCACTAAACTTCCTCTCCCATTTCTTA
GCTTCATCTATCACCCTGTCACGATCATCCTGGAGGGAAGACATGCTCTTAGTAAAGGCTGCAAGCTGGGTCACAG
TACTGTCCAAGTTTTCCTGAAGTTGCTGAACTTCCTTGTCTTTCTTGTTCAAAGTAACCTGAATCTCTCCAATTGT
CTCTTCCAAGTGGACTTTTTCTCTGCGCAAAGCATCCAG 11724-2

TCATTGCCTGTGATGGCATCTGGAATGTGATGAGCAGCCAGGAAGTTGTAGATTTCATTCAATCAAAGGATTCAGC
ATGTGGTGGAAGCTGTGAGGCAAGAGAAACAAGAACTGTATGGCAAGTTAAGAAGCACAGAGGCAAACAAGAAGGA
GACAGAAAAGCAGTTGCAGGAAGCTGAGCAAGAAATGGAGGAAATGAAAGAAAAGATGAGAAAGTTTGCTAAATCT
AAACAGCAGAAAATCCTAGAGCTGGAAGAAGAGAATGACCGGCTTAGGGCAGAGGTGCACCCTGCAGGAGATACAG
CTAAAGAGTGTATGGAAACACTTCTTTCTTCCAATGCCAGCATGAAGGAAGAACTTGAAAGGGTCAAAATGGAGTA
TGAAACCCTTTCTAAGAAGTTTCAGTCTTTAATGTCTGAGAAAGACTCTCTAAGTGAAGAGGTTCAAGATTTAAAG
CATCAGATAGAAGGTAATGTATCTAAACAAGCTAACCTAGAGGCCACCGAGAAACATGATAACCAAACGAATGTCA
CTGAAGAGGGAACACAGTCTATACCAGGT

AAGCCAATAATCACCATTTATTACTTAATATATGCCAACCACTGTACTTGGCAGTTCACAAATTCTCACCGTTACA
ACAACCCCATGAGGTATTTATTCCCATTCTATAGATAGGGAAACCACAGCTCAAGTAAGTTAGGAAACTGAGCCAA
GTATACACAGAATACGAAGTGGCAAAACTAGAAGGAAAGACTGACACTGCTATCTGCTGGCCTCCAGTGTCCTGGC
TCTTTTCACACGGGtTCAATGTCTCCAGCGCTGCTGCTGCTGCTGCATTACCATGCCCTCATTGTTTTTCTTCCTC
TGGTGTTCAACTGCATCCTTCAAAGAATCTAACTCATTCCAGAGACCACTTATTTCTTTCTCTCTTTCTGAAATTA
CTTTTAATAATTCTTCATGAGGGGGAAAAGAAGATGCCTGTTGGTAGTTTTGTTGTTTAAGCTGCTCAATTTGGGA
CTTAAACAATTTGTTTTCATCTTGTACATCCTGTAACAGCTGTGTTTTGCTAGAAAGATCACTCTCCCTCTCTTTT
AGCATGGCTTCTAACCTCTTCAATTCATTTTCCTTTTCTTTCAACACAATCTCAAGTTCTTCAAACTGTGATGCAG
AAGAGGCCTCTTTCAAGTTATGTTGTGCTACTTCCTGAACATGTGCTTTTAAAGATTCATTTTCTTCTTGAAGATC
CTGTAACCACTTCCCTGTATTGGCTAGGTCTTTCTCTTTCTCTTCCAAAACAGCCTTCATGGTATTCATCTGTTCC
TCTTTTCCTTTTAATAAGTTCAGGAGCTTCAGAAC 11726-1&2

CAAGCTTTTTTTTTTTTTTTTAAAAAGTGTTAGCATTAATGTTTTATTGTCACGCAGATGGCAACTGGGTTTATGTC
TTCATATTTTATATTTTTGTAAATTAAAAAAATTACAAGTTTTAAATAGCCAATGGCTGGTTATATTTTCAGAAAA
CATGATTAGACTAATTCATTAATGGTGGCTTCAAGCTTTTCCTTATTGGCTCCAGAAAATTCACCCACCTTTTGTC
CCTTCTTAAAAAACTGGAATGTTGGCATGCATTTGACTTCACACTCTGAAGCAACATCCTGACAGTCATCCACATC
TACTTCAAGGAATATCACGTTGGAATACTTTTCAGAGAGGGAATGAAAGAAAGGCTTGATCATTTTGCAAGGCCCA
CACCACGTGGCTGAGAAGTCAACTACTACAAGTTTATCACCTGCAGCGTCCAAGGCTTCCTGAAAAGCAGTCTTGC
TCTCGATCTGCTTCACCATCTTGGCTGCTGGAGTCTGACGAGCGGCTGTAAGGACCGATGGAAATGGATCCAAAGC
ACCAAACAGAGCTTCAAGACTCGCTGCTTGGCTTGAATTCGGATCCGATATCGCCATGGCCT 11727-1&2

AAGTGTTAGCATTAATGTTTTATTGTCACGCAGATGGCAACTGGGTTTATGTCTTCATATTTTATATTTTTGTAAA
TTAAAAAAATTMCAAGTTTTAAATAGCCAATGGCTGGTTATATTTTCAGAAAACATGATTAGACTAATTCATTAAT
GGTGGCTTCAAGCTTTTCCTTATTGGCTCCAGAAAATTCACCCACCTTTTGTCCCTTCTTAAAAAACTGGAATGTT
GGCATGCATTTGACTTCACACTCTGAAGCAACATCCTGACAGTCATCCACATCTACTTCAAGGAATATCACGTTGG
AATACTTTTCAGAGAGGGAATGAAAGAAAGGCTTGATCATTTTGCAAGGCCCACACCACGTGGCTGAGAAGTCAAC
TACTACAAGTTTATCACCTGCAGCGTCCAAGGCTTCCTGAAAAGCAGTCTTGCTCTCGATCTGCTTCACCATCTTG
GCTGCTGGAGTCTGACGAGCGGCTGTAAGGACCGATGGAAATGGATCCAAAGCACCAAACAGAGCTTCAAGACTCG
CTGCTTGGCATGAATTCGGATCCGA

TACAAACTTTATTGAAACGCACACGCGCACACACACAAACACCCCTGTGGATAGGGAAAAGCACCTGGCCACAGGG
TCCACTGAAACGGGGAGGGGATGGCAGCTTGTAATGTGGCTTTTGCCACAACCCCCTTCTGACAGGGAAGGCCTTA
GATTGAGGCCCCACCTCCCATGGTGATGGGGAGCTCAGAATGGGGTCCAGGGAGAATTTGGTTAGGGGGAGGTGCT
AGGGAGGCATGAGCAGAGGGCACCCTCCGAGTGGGGTCCCGAGGGCTGCAGAGTCTTCAGTACTGTCCCTCACAGC
AGCTGTCTCAAGGCTGGGTCCCTCAAAGGGGCGTCCCAGCGCGGGGCCTCCCTGCGCAAACACTTGGTACCCCTGG
CTGCGCAGCGGAAGCCAGCAGGACAGCAGTGGCGCCGATCAGCACAACAGACGCCCTGGCGGTAGGGACAGCAGGC
CCAGCCCTGTCGGTTGTCTCGGCAGCAGGTCTGGTTATCATGGCAGAAGTGTCCTTCCCACACTTCACGTCCTTCA
CACCCACGTGAXGGCTACXGGCCAGGAAG 11728.2.40.19.19

CCCGTGGGTGCCATCCACGGAGTTGTTACCTGATCTTTGGAAGCAGGATCGCCCGTCTGCACTGCAGTGGAAGCCC
CGTGGGCAGCAGTGATGGCCATCCCCGCATGCCACGGCCTCTGGGAAGGGGCAGCAACTGGAAGTCCCTGAGACGG
TAAAGATGCAGGAGTGGCCGGCAGAGCAGTGGGCATCAACCTGGCAGGGGCCACCCAGATGCCTGCTCAGTGTTGT
GGGCCATTTGTCCAGAAGGGGACGGCAGCAGCTGTAGCTGGCTCCTCCGGGGTCCAGGCAGCAGGCCACAGGGCAG
AACTGACCATCTGGGCACCGCGTTCCAGCCACCAGCCCTGCTGTTAAGGCCACCCAGCTCACCAGGGTCCACATGG
TCTGCCTGCGTCCGACTCCGCGGTCCTTGGGCCCTGATGGTTCTACCTGCTGTGAGCTGCCCAGTGGGAAGTATGG
CTGCTGCCAATGCCCAACGCCACCTGCTGCTCCGATCACCTGCACTGCTGCCCCAAGACACTGTGTGTGACCTGAT
CCAGAGTAAGTGCCTCTCCAAGGAGAACG 11730-1

GAATCACCTTTCTGGTTTAGCTAGTACTTTGTACAGAACAATGAGGTTTCCCACAGCGGAGTCTCCCTGGGCTCTG
TTTGGCTCTCGGTAAGGCAGGCCTACACCTTTTCCTCTCCTCTATGGAGAGGGGAATATGCATTAAGGTGAAAAGT
CACCTTCCAAAAGTGAGAAAGGGATTCGATTGCTGCTTCAGGACTGTGGAATTATTTGGAATGTTTTACAAATGGT
TGCTACAAAACAACAAAAAAGGTAATTACAAAATGTGTACATCACAACATGCTTTTTAAAGACATTATGCATTGTG
CTCACATTCCCTTAAATGTTGTTTCCAAAGGTGCTCAGCCTCTAGCCCAGCTGGATTCTCCGGGAAGAGGCAGAGA
CAGTTTGGCGAAAAAGACACAGGGAAGGAGGGGGTGGTGAAAGGAGAAAGCAGCCTTCCAGTTAAAGATCAGCCCT
CAGTTAAAGGTCAGCTTCCCGCAXGCTGGCCTCAXGCGGAGTCTGGGTCAGAGGGAGGAGCAGCAGCAGGGTGGGA
CTGGGGCGT 11730-2

AACCGGAGCGCGAGCAGTAGCTGGGTGGGCACCATGGCTGGGATCACCACCATCGAGGCGGTGAAGCGCAAGATCC
AGGTTCTGCAGCAGCAGGCAGATGATGCAGAGGAGCGAGCTGAGCGCCTCCAGCGAGAAGTTGAGGGAGAAAGGCG
GGCCCGGGAACAGGCTGAGGCTGAGGTGGCCTCCTTGAACCGTAGGATCCAGCTGGTTGAAGAAGAGCTGGACCGT
GCTCAGGAGCGCCTGGCCACTGCCCTGCAAAAGCTGGAAGAAGCTGAAAAAGCTGCTGATGAGAGTGAGAGAGGTA
TGAAGGTTATTGAAAACCGGGCCTTAAAAGATGAAGAAAAGATGGAACTCCAGGAAATCCAACTCAAAGAAGCTAA
GCACATTGCAGAAGAGGCAGATAGGAAGTATGAAGAGGTGGCTCGTAAGTTGGTGATCATTGAAGGAGACTTGGAA
CGCACAGAGGAACGAGCTGAGCTGGCAGAGTCCCGTTGCCGAGAGATGGATGAGCAGATTAGACTGATGGACCAGA
ACCTGAAGTGTCTGAGTGC

*Fig. 15C*

11732.1contig

GAGAACTTGGCCTTTATTGTGGGCCCAGGAGGGCACAAAGGTCAGGAGGCCCAAGGGAGGGATCTGGTTTTCTGGA
TAGCCAGGTCATAGCATGGGTATCAGTAGGAATCCGCTGTAGCTGCACAGGCCTCACTTGCTGCAGTTCCGGGGAG
AACACCTGCACTGCATGGCGTTGATGACCTCGTGGTACACGACAGAGCCATTGGTGCAGTGCAAGGGCACGCGCAT
GGGCTCCGTCCTCGAGGGCAGGCAGCAGGAGCATTGCTCCTGCACATCCTCGATGTCAATGGAGTACACAGCTTTG
CTGGCACACTTTCCCTGGCAGTAATGAATGTCCACTTCCTCTTGGGACTTACAATCTCCCACTTTGATGTACTGCA
CCTTGGCTGTGATGTCTTTGCAATCAGGCTCCTCACATGTGTCACAGCAGGTGCCTGGAATTTTCACGATTTTGCC
TCCTTCAGCCAGACACTTGTGTTCATCAAATGGTGGGCAGCCCGTGACCCTCTTCTCCCAGATGTACTCTCCTCT 11732.2contig GCCTGGACCTTGCCGGATCAGTGCCACACAGTGACTTGCTTGGCAAATGGCCAGACCTTGCTGCAGAGTCATCGTG
TCAATTGTGACCATGGACCCCGGCCTTCATGTGCCAACAGCCAGTCTCCTGTTCGGGTGGAGGAGACGTGTGGCTG
CCGCTGGACCTGCCCTTGTGTGTGCACGGGCAGTTCCACTCGGCACATCGTCACCTTCGATGGGCAGAATTTCAAG
CTTACTGGTAGCTGCTCCTATGTCATCTTTCAAAACAAGGAGCAGGACCTGGAAGTGCTCCTCCACAATGGGGCCT
GCAGCCCCGGGGCAAAACAAGCCTGCATGAAGTCCATTGAGATTAAGCATGCTGGCGTCTCTGCTGAGCTGCACAG
TAACATGGAGATGGCAGTGGATGGGAGACTGGTCCTTGCCCCGTACGTTGGTGAAAACATGGAAGTCAGCATCTAC
GGCGCTATCATGTATGAAGTCAGGTTTACCCATCTTGGCCACATCCTCACATACACCGCCXCAAAACAACGAGTT 11735-1-2

AGATCAACCTCTGCTGGTCAGGAGGAATGCCTTCCTTGTCTTGGATCTTTGCTTTGACGTTCTCGATAGTRWCAaC
TKKRYTSRAMSKMAAGKGYRATGRWMTTKSYWGWRASYKTMWWMRSGRARAYTTaGaCAYCCCMCCTCWgAGaCGS
AGKACCARGTGCAgAgGTGGACTCTTTCTGGATGTTGTAGTCAGACAGGGTGCGTCCATCTTCCAGCTGTTTCCCA
GCAAAGATCAACCTCTGCTGATCAGGAGGGATGCCTTCCTTATCTTGGATCTTTGCCTTGACATTCTCGATGGTGT
CACTGGGCTCCACCTCGAGGGTGATGGTCTTACCAGTCAGGGTCTTCACGAAGATYTGCATCCCACCTCTGAGACG
GAGCACCAGGTGCAGGGTRGACTCTTTCTGGATGTTGTAGTCAGACAGGGTGCGYCCATCTTCCAGCTGcTTTCCS
aGCAAAGATCAACCTCTGCTGGTCAGGAGGRATGCCTTCCTTGTCYTGGATCTTTGCYTTGACRTTCTCRATGGTG
TCACTCGGCTCCACTTCGAGAGTGATGGTCTTACCAGTCAGGGTCTTCACGAAGATCTGCATCCCACCTCTAA 11740.2.contig AAGTCACAAACAGACAAAGATTATTACCAGCTGCAAGCTATATTAGAAGCTGAACGAAGAGACAGAGGTCATGATT
CTGAGATGATTGGAGACCTTCAAGCTCGAATTACATCTTTACAAGAGGAGGTGAAGCATCTCAAACATAATCTCGA
AAAAGTGGAAGGAGAAAGAAAAGAGGCTCAAGACATGCTTAATCACTCAGAAAAGGAAAAGAATAATTTAGAGATA
GATTTAAACTACAAACTTAAATCATTACAACAACGGTTAGAACAAGAGGTAAATGAACACAAAGTAACCAAAGCTC
GTTTAACTGACAAACATCAATCTATTGAAGAGGCAAAGTCTGTGGCAATGTGTGAGATGGAAAAAAAGCTGAAAGA
AGAAAGAGAAGCTCGAGAGAAGGCTGAAAATCGGGTTGTTCAGATTGAGAAACAGTGTTCCATGCTAGACGTTGAT
CTGAAGCAATCTCAGCAGAAACTAGAACATTTGACTGGAAATAAAGAAAGGATGGAGGATGAAGTTAAGAATCTA

*Fig. 15D*

11765.2&64.2.contig

CGCCTCCACCATGTCCATCAGGGTGACCCAGAAGTCCTACAAGGTGTCCACCTCTGGCCCCCGGGCCTTCAGCAGC
CGCTCCTACACGAGTGGGCCCGGTTCCCGCATCAGCTCCTCGAGCTTCTCCCGAGTGGGCAGCAGCAACTTTCGCG
GTGGCCTGGGCGGCGGCTATGGTGGGGCCAGCGGCATGGGAGGCATCACCGCAGTTACGGTCAACCAGAGCCTGCT
GAGCCCCCTTGTCCTGGAGGTGGACCCCAACATCCAGGCCGTGCGCACCCAGGAGAAGGAGCAGATCAAGACCCTC
AACAACAAGTTTGCCTCCTTCATAGACAAGGTACGGTTCCTGGAGCAGCAGAACAAGATGCTGGAGACCAAGTGGA
GCCTCCTGCAGCAGCAGAAGACGGCTCGAAGCAACATGGACAACATGTTCGAGAGCTACATCAACARCCTTAGGCG
GCAGCTGGAGACTCTGGGCCAGGAGAAGCTGAAGCTGGAGGCGGAGCTTGGCAACATGCAGGGGCTGGTGGAGGAC
TTCAAGAACAAGTATGAGGATGAGATCAATAAGCGTACAGAGATGGAGAACGAATTTGTCCTCATCAAGAAGGATG
TGGATGAAGCTTACATGAACAAGGTAGAGCTGGAGTCTCGCCTGGAAGGGCTGACCGACGAGATCAACTTCCTCAG
GCAGCTGTATGAAGAGGAGATCCGGGAGCTGCAGTCCCAGATCTCGGACACATCTGTGGTGCTGTCCATGGACAAC
AGCCGCTCCCTGGACATGGACAGCATCATTGCTGAGGTCAAGGCACAGTACGAGGATATTGCCAACCGCAGCCGGG
CTGAGGCTGAGAGCATGTACCAGGTCAAGTATGAGGAGCTGCAGAGCCTGGCTGGGAAGCACGGGGATGACCTGCG
GCGCACAAAGACTGAGATCTCTGAGATGAACCCGGAACATCAGCCCGGCTXCAGGCTGAGATTGAGGGCCTCAAAG
GCCAGAXGGCTTXCCTGGAXGXCCGCCAT 11767.2.contig CCCGGAGCCAGCCAACGAGCGGAAAATGGCAGACAATTTTTCGCTCCATGATGCGTTATCTGGGTCTGGAAACCCA
AACCCTCAAGGATGGCCTGGCGCATGGGGGAACCAGCCTGCTGGGGCAGGGGGCTACCCAGGGGCTTCCTATCCTG
GGGCCTACCCCGGGCAGGCACCCCCAGGGGCTTATCCTGGACAGGCACCTCCAGGCGCCTACCCTGGAGCACCTGG
AGCTTATCCCGGAGCACCTGCACCTGGAGTCTACCCAGGGCCACCCAGCGGCCCTGGGGCCTACCCATCTTCTGGA
CAGCCAAGTGCCACCGGAGCCTACCCTGCCACTGGCCCCTATGGCGCCCCTGCTGGGCCACTGATTGTGCCTTATA
ACCTGCCTTTGCCTGGGGGAGTGGTGCCTCGCATGCTGATAACAATTCTGGGCACGGTGAAGCCCAATGCAAACAG
AATTGCTTTAGATTTCCAAAGAGGGAATGATGTTGCCTTCCACTTTAACCCACGCTTCAATGAGAACAACAGGAGA
GTCATTGGTTGCAATACAAAGCTGGATAA 11768-1&2

GGGAATGCAACAACTTTATTGAAAGGAAAGTGCAATGAAATTTGTTGAAACCTTAAAAGGGGAAACTTAGACACCC
CCCCTCRAgCGMAGKACCARGTGCARAgGTGGACTCTTTCTGGATGTTGTAGTCAGACAGGGTRCGWCCATCTTCC
AGCTGTTTYCCRGCAAAGATCAACCTCTGCTGATCAGGAGGRATGCCTTCCTTATCTTGGATCTTTGCCTTGACAT
TCTCGATGGTGTCACTGGGCTCCACCTCGAGGGTGATGGTCTTACCAGTCAGGGTCTTCACGAAGATYTGCATCCC
ACCTCTGAGACGGAGCACCAGGTGCAGGGTRGACTCTTTCTGGATGTTGTAGTCAGACAGGGTGCGYCCATCTTCC
AGCTGcTTTCCSaGCAAAGATCAACCTCTGCTGGTCAGGAGGRATGCCTTCCTTGTCYTGGATCTTTGCYTTGACR
TTCTCAATGGTGTCACTCGGCTCCACTTCGAGAGTGATGGTCTTACCAGTCAGGGTCTTCACGAAGATCTGCATCC
CACCTCTAAGACGGAGCACCAGGTGCAGGGTGGACTCTTTCTGGATGgTTGTAGTCAGACAGGGTGCGTCCATCTT
CCAGCTGTTTCCCAGCAAAGATCAACCT

AGGTTGATCTTTGCTGGGAAACAGCTGGAAGATGGACGCACCCTGTCTGACTACAAcCATCCAGAAAGAGTCCACC
CTGCACCTGGTGCTCCGTCTTAGAGGTGGGATGCAGATCTTCGTGAAGACCCTGACTGGTAAGACCATCACTCTCG
AAGTGGAGCCGAGTGACACCATTGAGAAYGTCAARGCAAAGATCCARGACAAGGAAGGCATYCCTCCTGACCAGCA
GAGGTTGATCTTTGCtSGGAAAgCAGCTGGAAGATGGRCGCACCCTGTCTGACTACAACATCCAGAAAGAGTCYAC
CCTGCACCTGGTGCTCCGTCTCAGAGGTGGGATGCARATCTTCGTGAAGACCCTGACTGGTAAGACCATCACCCTC
GAGGTGGAGCCCAGTGACACCATCGAGAATGTCAAGGCAAAGATCCAAGATAAGGAAGGCATCCCTCCTGATCAGC
AGAGGTTGATCTTTGCTGGGAAACAGCTGGAAGATGGACGCACCCTGTCTGACTACAACATCCAGAAAGAGTCCAC
cTYTGCACYTGGTMCTBCGtCTYaGAGGKGGGRTGcaaaTCTWMGTKWagaCaCtCaCTKKYAAGRYYaTCAMCMW
tgAKKTCgAKYSCASTKWCaCTWTCRAKAAMGTYRWWGCAWagaTCCMAGACAAGGAAGGCATTCCTCCTGACCAG
CAGAGGTTGATCT 11769.1.contig ATGGAGTCTCACTCTGTCGACCAGGCTGGAGCGCTGTGGTGCGATATCGGCTCACTGCAGTCTCCACTTCCTGGGT
TCAAGCGATCCTCCTGCCTCAGCCTCCCGAGTAGCTGGGACTACAGGCAGGCGTCACCATAATTTTTGTATTTTTA
GTAGAGACATGGTTTCGCCATGTTGGCTGGGCTGGTCTCGAACTCCTGACCTCAAGTGATCTGTCCTGGCCTCCCA
AAGTGTTGGGATTACAGGCGAAAGCCAACGCTCCCGGCCAGGGAACAACTTTAGAATGAAGGAAATATGCAAAAGA
ACATCACATCAAGGATCAATTAATTACCATCTATTAATTACTATATGTGGGTAATTATGACTATTTCCCAAGCATT
CTACGTTGACTGCTTGAGAAGATGTTTGTCCTGCATGGTGGAGAGTGGAGAAGGGCCAGGATTCTTAGGTT 11769.2.contig AGCGCGGTCTTCCGGCGCGAGAAAGCTGAAGGTGATGTGGCCGCCCTCAACCGACGCATCCAGCTCGTTGAGGAGG
AGTTGGACAGGGCTCAGGAACGACTGGCCACGGCCCTGCAGAAGCTGGAGGAGGCAGAAAAAGCTGCAGATGAGAG
TGAGAGAGGAATGAAGGTGATAGAAAACCGGGCCATGAAGGATGAGGAGAAGATGGAGATTCAGGAGATGCAGCTC
AAAGAGGCCAAGCACATTGCGGAAGAGGCTGACCGCAAATACGAGGAGGTAGCTCGTAAGCTGGTCATCCTGGAGG
GTGAGCTGGAGAGGGCAGAGGAGCGTGCGGAGGTGTCTGAACTAAAATGTGGTGACCTGGAAGAAGAACTCAAGAA
TGTTACTAACAATCTGAAATCTCTGGAGGCTGCATCTGAAAAGTATTCTGAAAAGGAGGACAAATATGAAGAAGAA
ATTAAACTTCTGTCTGACAAACTGAAAGAGGCTGAGACCCGTGCTGAATTTGCAGAGAGAACGGTTGCAAAACTGG
AAAAGACAATTGATGACCTGGAAGAGAAACTTGCCCAGC 11770.1.contig GTGCACAGGTCCCATTTATTGTAGAAAATAATAATAATTACAGTGATGAATAGCTCTTCTTAAATTACAAAACAGA
AACCACAAAGAAGGAAGAGGAAAAACCCCAGGACTTCCAAGGGTGAAGCTGTCCCCTCCTCCCTGCCACCCTCCCA
GGCTCATTAGTGTCCTTGGAAGGGGCAGAGGACTCAGAGGGGATCAGTCTCCAGGGGCCCTGGGCTGAAGCGGGTG
AGGCAGAGAGTCCTGAGGCCACAGAGCTGGGCAACCTGAGCCGCCTCTCTGGCCCCCTCCCCCACCACTGCCCAAA
CCTGTTTACAGCACCTTCGCCCCTCCCCTCTAAACCCGTCCATCCACTCTGCACTTCCCAGGCAGGTGGGTGGGCC
AGGCCTCAGCCATACTCCTGGGCGCGGGTTTCGGTGAGCAAGGCACAGTCCCAGAGGTGATATCAAGGCCT

*Fig. 15F*

11770.2.contig

GCAAGGAACTGGTCTGCTCACACTTGCTGGCTTGCGCATCAGGACTGGCTTTATCTCCTGACTCACGGTGCAAAGG
TGCACTCTGCGAACGTTAAGTCCGTCCCCAGCGCTTGGAATCCTACGGCCCCCACAGCCGGATCCCCTCAGCCTTC
CAGGTCCTCAACTCCCGTGGACGCTGAACAATGGCCTCCATGGGGCTACAGGTAATGGGCATCGCGCTGGCCGTCC
TGGGCTGGCTGGCCGTCATGCTGTGCTGCGCGCTGCCCATGTGGCGCGTGACGGCCTTCATCGGCAGCAACATTGT
CACCTCGCAGACCATCTGGGAGGGCCTATGGATGAACTGCGTGGTGCAGAGCACCGGCCAGATGCAGTGCAAGGTG
TACGACTCGCTGCTGGCACTGCCGCAGGACCTGCAGGCGGCCCGCGCCCTCGTCATCATCA 11773.1.contig TGCAAAAGGGACACAGGGGTTCAAAAATAAAAATTTCTCTTCCCCCTCCCCAAACCTGTACCCCAGCTCCCCGACC
ACAACCCCCTTCCTCCCCCGGGGAAAGCAAGAAGGAGCAGGTGTGGCATCTGCAGCTGGGAAGAGAGAGGCCGGGG
AGGTGCCGAGCTCGGTGCTGGTCTCTTTCCAAATATAAATACXTGTGTCAGAACTGGAAAATCCTCCAGCACCCAC
CACCCAAGCACTCTCCGTTTTCTGCCGGTGTTTGGAGAGGGGCGGGGGGCAGGGGCGCCAGGCACCGGCTGGCTGC
GGTCTACTGCATCCGCTGGGTGTGCACCCCGCGAGCCTCCTGCTGCTCATTGTAGAAGAGATGACACTCGGGGTCC
CCCCGGATGGTGGGGGCTCCCTGGATCAGCTTCCCGGTGTTGGGGTTCACACACCAGCACTCCCCACGCTGCCCGT
TCAGAGACATCTTGCACTGTTTGAGGTTGTACAGGCCATGCTTGTCACAGTTG 11778.1.contig GGGTTGGAGGGACTGGTTCTTTATTTCAAAAAGACACTTGTCAATATTCAGTATCAAAACAGTTGCACTATTGATT
TCTCTTTCTCCCAATCGGCCCCAAAGAGACCACATAAAAGGAGAGTACATTTTAAGCCAATAAGCTGCAGGATGTA
CACCTAACAGACCTCCTAGAAACCTTACCAGAAAATGGGGACTGGGTAGGGAAGGAAACTTAAAAGATCAACAAAC
TGCCAGCCCACGGACTGCAGAGGCTGTCACAGCCAGATGGGGTGGCCAGGGTGCCACAAACCCAAAGCAAAGTTTC
AAAATAATATAAAATTTAAAAAGTTTTGTACATAAGCTATTCAAGATTTCTCCAGCACTGACTGATACAAAGCACA
ATTGAGATGGCACTTCTAGAGACAGCAGCTTCAAACCCAGAAAAGGGTGATGAGATGAGTTTCACATGGCTAAATC
AGTGGCAAAAACACAGTCTTCTTTCTTTCTTTCTTTCAAGGAGGCAGGAAAGCAATTAAGTGGTCACCTCAACATA
AGGGGGACATGATCCATTCTGTAAGCAGTTGTGAAGGGG 11778-2&30-2

CAGGAACCGGAGCGCGAGCAGTAGCTGGGTGGGCACCATGGCTGGGATCACCACCATCGAGGCGGTGAAGCGCAAG
ATCCAGGTTCTGCAGCAGCAGGCAGATGATGCAGAGGAGCGAGCTGAGCGCCTCCAGCGAGAAGTTGAGGGAGAAA
GGCGGGCCCGGGAACAGGCTGAGGCTGAGGTGGCCTCCTTGAACCGTAGGATCCAGCTGGTTGAAGAAGAGCTGGA
CCGTGCTCAGGAGCGCCTGGCCACTGCCCTGCAAAAGCTGGAAGAAGCTGAAAAAGCTGCTGATGAGAGTGAGAGA
GGTATGAAGGTTATTGAAAACCGGGCCTTAAAAGATGAAGAAAAGATGGAACTCCAGGAAATCCAACTCAAAGAAG
CTAAGCACATTGCAGAAGAGGCAGATAGGAAGTATGAAGAGGTGGCTCGTAAGTTGGTGATCATTGAAGGAGACTT
GGAACGCACAGAGGAACGAGCTGAGCTGGCAGAGTCCCGTTGCCGAGAGATGGATGAGCAGATTAGACTGATGGAC
CAGAACCTGAAGTGTCTGAGTGC

*Fig. 15G*

11782.1.contig

ATCTACGTCATCAATCAGGCTGGAGACACCATGTTCAATCGAGCTAAGCTGCTCAATATTGGCTTTCAAGAGGCCT
TGAAGGACTATGATTACAACTGCTTTGTGTTCAGTGATGTGGACCTCATTCCGATGGACGACCGTAATGCCTACAG
GTGTTTTTCGCAGCCACGGCACATTTCTGTTGCAATGGACAAGTTCGGGTTTAGCCTGCCATATGTTCAGTATTTT
GGAGGTGTCTCTGCTCTCAGTAAACAACAGTTTCTTGCCATCAATGGATTCCCTAATAATTATTGGGGTTGGGGAG
GAGAAGATGACGACATTTTTAACAGATTAGTTCATAAAGGCATGTCTATATCACGTCCAAATGCTGTAGTAGGGAG
GTGTCGAATGATCCGGCATTCAAGAGACAAGAAAAATGAGCCCAATCCTCAGAGGTTTGACCGGATCGCACATACA
AAGGAAACGATGCGCTTCGATGGTTTGAACTCACTTACCTACAAGGTGTTGGATGTCAGAGATACCCGTTATATAC
CCAAATCAC 11782.2.contig CTAGACCTCTAATTAAAAGGCACAATCATGCTGGAGAATGAACAGTCTGACCCCGAGGGCCACAGCGAATTTTAGG
GAAGGAGGCAAAGAGGTGAGAAGGGAAAGGAAAGAAGGAAGGAAGGAGAACAATAAGAACTGGAGACGTTGGGTGG
GTCAGGGAGTGTGGTGGAGGCTCGGAGAGATGGTAAACAAACCTGACTGCTATGAGTTTTCAACCCCATAGTCTAG
GGCCATGAGGGCGTCAGTTCTTGGTGGCTGAGGGTCCTTCCACCCAGCCCACCTGGGGGAGTGGAGTGGGGAGTTC
TGCCAGGTAAGCAGATGTTGTCTCCCAAGTTCCTGACCCAGATGTCTGGCAGGATAACGCTGACCTGTTCCCTCAA
CAAGGGACCTGAAAGTAATTTTGCTCTTTAC 11783-1 & 2

CCGAATTCAAGCGTCAACGATCCYTCCCTTACCATCAAATCAATTGGCCACCAATGGTACTGAACCTACGAGTACA
CCGACTACgGGCGGACTAATCTTCAACTCCTACATACTTCCCCCATTATTCCTAGAACCAGGCGACCTGCGACTCC
TTGACGTTGACAATCGAGTAGTACTCCCGATTGAAGCCCCCATTCGTATAATAATTACATCACAAGACGTCTTGCA
CTCATGAGCTGTCCCCACATTAGGCTTAAAAACAGATGCAATTCCCGGACGTCTAAGCCAAACCACTTTCACCGCT
ACACGACCGGGGGTATACTACGGTCAATGCTCTGAAATCTGTGGAGCAAACCACAGTTTCATGCCCATCGTCCTAG
AATTAATTCCCCTAAAAATCTTTGAAATAGGGCCCGTATTTACCCTATAGCACCCCCTCTACCCCCTCTAG 11786.1.contig GCTCTTCACACTTTTATTGTTAATTCTCTTCACATGGCAGATACAGAGCTGTCGTCTTGAAGACCACCACTGACCA
GGAAATGCCACTTTTACAAAATCATCCCCCCTTTTCATGATTGGAACAGTTTTCCTGACCGTCTGGGAGCGTTGAA
GGGTGACCAGCACATTTGCACATGCAAAAAAGGAGTGACCCCAAGGCCTCAACCACACTTCCCAGAGCTCACCATG
GGCTGCAGGTGACTTGCCAGGTTTGGGGTTCGTGAGCTTTCCTTGCTGCTGCGGTGGGGAGGCCCTCAAGAACTGA
GAGGCCGGGGTATGCTTCATGAGTGTTAACATTTACGGGACAAAAGCGCATCATTAGGATAAGGAACAGCCACAGC
ACTTCATGCTTGTGAGGGTTAGCTGTAGGAGCGGGTGAAAGGATTCCAGTTTATGAAAATTTAAAGCAAACAACGG
TTTTTAGCTGGGTGGGAAACAGGAAAACTGTGATGTCGGCCAATGACCACCATTTTTCTGCCCATGTGAAGGTCCC
CATGAAACC

*Fig. 15H*

11786.2.contig

CAAGCGCTTGGCGTTTGGACCCAGTTCAGTGAGGTTCTTGGGTTTTGTGCCTTTGGGGATTTTGGTTTGACCCAGG
GGTCAGCCTTAGGAAGGTCTTCAGGAGGAGGCCGAGTTCCCCTTCAGTACCACCCCTCTCTCCCCACTTTCCCTCT
CCCGGCAACATCTCTGGGAATCAACAGCATATTGACACGTTGGAGCCGAGCCTGAACATGCCCCTCGGCCCCAGCA
CATGGAAAACCCCCTTCCTTGCCTAAGGTGTCTGAGTTTCTGGCTCTTGAGGCATTTCCAGACTTGAAATTCTCAT
CAGTCCATTGCTCTTGAGTCTTTGCAGAGAACCTCAGATCAGGTGCACCTGGGAGAAAGACTTTGTCCCCACTTAC
AGATCTATCTCCTCCCTTGGGAAGGGCAGGGAATGGGGACGGTGTATGGAGGGGAAGGGATCTCCTGCGCCCTTCA
TTGCCACACTTGGTGGGACCATGAACATCTTTAGTGTCTGAGCTTCTCAAATTACTGCAATAGGA 13691.1&2

AGCGTCAAATCAGAATGGAAAAGACTCAAAACCATCATCAACACCAAGATCAAAAGGACAAGRATCCTTCAAGAAA
CAGGAAAAAACTCCTAAAACACCAAAAGGACCTAGTTCTGTAGAAGACATTAAAGCAAAAATGCAAGCAAGTATAG
AAAAAGGTGGTTCTCTTCCCAAAGTGGAAGCCAAATTCATCAATTATGTGAAGAATTGCTTCCGGATGACTGACCA
AGAGGCTATTCAAGATCTCTGGCAGTGGAGGAAGTCTCTTTAAGAAAATAGTTTAAACAATTTGTTAAAAAATTTT
CCGTCTTATTTCATTTCTGTAACAGTTGATATCTGGCTGTCCTTTTTATAATGCAGAGTGAGAACTTTCCCTACCG
TGTTTGATAAATGTTGTCCAGGTTCTATTGCCAAGAATGTGTTGTCCAAAATGCCTGTTTAGTTTTTAAAGATGGA
ACTCCACCCTTTGCTTGGTTTTAAGTATGTATGGAATGTTATGATAGGACATAGTAGTAGCGGTGGTCAGACATGG
AAATGGTGGGSMGACAAAAATATACATGTGAAATAA 13692.1&2

TCCGAATTCCAAGCGAATTATGGACAAACGATTCCTTTTAGAGGATTACTTTTTTCAATTTCGGTTTTAGTAATCT
AGGCTTTGCCTGTAAAGAATACAACGATGGATTTTAAATACTGTTTGTGGAATGTGTTTAAAGGATTGATTCTAGA
ACCTTTGTATATTTGATAGTATTTCTAACTTTCATTTCTTTACTGTTTGCAGTTAATGTTCATGTTCTGCTATGCA
ATCGTTTATATGCACGTTTCTTTAATTTTTTTAGATTTTCCTGGATGTATAGTTTAAACAACAAAAAGTCTATTTA
AAACTGTAGCAGTAGTTTACAGTTCTAGCAAAGAGGAAAGTTGTGGGGTTAAACTTTGTATTTTCTTTCTTATAGA
GGCTTCTAAAAAGGTATTTTTATATGTTCTTTTTAACAAATATTGTGTACAACCTTTAAAACATCAATGTTTGGAT
CAAAACAAGACCCAGCTTATTTTCTGC 13693.2

TGTGGTGGCGCGGGCTGAGGTGGAGGCCCAGGACTCTGACCCTGCCCCTGCCTTCAGCAAGGCCCCCGGCAGCGCC
GGCCACTACGAACTGCCGTGGGTTGAAAAATATAGGCCAGTAAAGCTGAATGAAATTGTCGGGAATGAAGACACCG
TGAGCAGGCTAGAGGTCTTTGCAAGGGAAGGAAATGTGCCCAACATCATCATTGCGGGCCCTCCAGGAACCGGCAA
GACCACAAGCATTCTGTGCTTGGCCCGGGCCCTGCTGGGCCCAGCACTCAAAGATGCCATGTTGGAACTCAATGCT
TCAAATGACAGGGGCATTGACGTTGTGAGGAATAAAATTAAAATGTTTGCTCAACAAAAAGTCACTCTTCCCAAAG
GCCGACATAAGATCATCATTCTGGATGAAGCAGACAGCATGACCGACGGAGCCCAGCAAGCCTTGAGGAGAACCAT
GGAAATCTACTCTAAAACCACTCGTTCGCCCTTGCTTGTAATGCTTCGGATAAGATCATCGAGCC

CTTTGCAAAGCTTTTATTTCATGTCTGCGGCATGGAATCCACCTGCACATGGCATCTTAGCTGTGAAGGAGAAAGC
AGTGCACGAGAAGGAATGAGTGGGCGGAACCAACGGCCTCCACAAGCTGCCTTCCAGCAGCCTGCCAAGGCCATGG
CAGAGAGAGACTGCAAACAAACACAAGCAAACAGAGTCTCTTCACAGCTGGAGTCTGAAAGCTCATAGTGGCATGT
GTGAATCTGACAAAATTAAAAGTGTGCATAGTCCATTACATGCATAAAACACTAATAATAATCCTGTTTACACGTG
ACTGCAGCAGGCAGGTCCAGCTCCACCACTGCCCTCCTGCCACATCACATCAAGTGCCATGGTTTAGAGGGTTTTT
CATATGTAATTCTTTTATTCTGTAAAAGGTAACAAAATATACAGAACAAAACTTTCCCTTTTTAAAACTAATGTTA
CAAATCTGTATTATCACTTGGATATAAATAGTATATAAGCTGATC 13700.1

CAAGGGATATATGTTGAGGGTACRGRGTGACACTGAACAGATCACAAAGCACGAGAAACATTAGTTCTCTCCCTCC
CCAGCGTCTCCTTCGTCTCCCTGGTTTTCCGATGTCCACAGAGTGAGATTGTCCCTAAGTAACTGCATGATCAGAG
TGCTGKCTTTATAAGACTCTTCATTCAGCGTATCCAATTCAGCAATTGCTTCATCAAATGCCGTTTTTGCCAGGCT
ACAGGCCTTTTCAGGAGAGTTTAGAATCTCATAGTAAAAGACTGAGAAATTTAGTGCCAGACCAAGACGAATTGGG
TGTGTAGGCTGCATTNCTTTCTTACTAATTTCAAATGCTTCCTGGTAAGCCTGCTGGGAGTTCGACACAAGTGGTT
TGTTTGTTGCTCCAGATGCCACTTCAGAAAGATACCTAAAATAATCTCCTTTCATTTTCAAAGTAGAACAC 13700.2

TCCGGAGCCGGGGTAGTCGCCGCCGCCGCCGCCGGTGCAGCCACTGCAGGCACCGCTGCCGCCGCCTGAGTAGTGG
GCTTAGGAAGGAAGAGGTCATCTCGCTCGGAGCTTCGCTCGGAAGGGTCTTTGTTCCCTGCAGCCCTCCCACGGGA
ATGACAATGGATAAAAGTGAGCTGGTACAGAAAGCCAAACTCGCTGAGCAGGCTGAGCGATATGATGATATGGCTG
CAGCCATGAAGGCAGTCACAGAACAGGGGCATGAACTCTCCAACGAAGAGAGAAATCTGCTCTCTGTTGCCTACAA
GAATGTGGTAAGGCCGCCCGCCGCTCTTCCTGGCGTGTCATCTCCAGCATTGAGCAGAAAACAGAGAGGAATGAGA
AGAAGCAGCAGATGGGCAAAGAGTACCGTGAGAAGATAGAGGCAGAACTGCAGGACATCTGCAATGATGTTCTGGA
GCTTGTTGGACAAATATCTTATTCCAATGCTACACAACCCAGAAA 13701.1

AAAAAGCAGCARGTTCAACACAAAATAGAAATCTCAAATGTAGGATAGAACAAAACCAAGTGTGTGAGGGGGGAAG
CAACAGCAAAAGGAAGAAATGAGATGTTGCAAAAAAGATGGAGGAGGGTTCCCCTCTCCTCTGGGGACTGACTCAA
ACACTGATGTGGCAGTATACACCATTCCAGAGTCAGGGGTGTTCATTCTTTTTTGGGAGTAAGAAAAGGTGGGGAT
TAAGAAGACGTTTCTGGAGGCTTAGGGACCAAGGCTGGTCTCTTTCCCCCCTCCCAACCCCCTTGATCCCTTTCTC
TGATCAGGGGAAAGGAGCTCGAATGAGGGAGGTAGAGTTGGAAAGGGAAAGGATTCCACTTGACAGAATGGGACAG
ACTCCTTCCCA

TGGCAATAGCACAGCCATCCAGGAGCTCTTCARGCGCATCTCGGAGCAGTTCACTGCCATGTTCCGCCGGAAGGCC
TTCCTCCACTGGTACACAGGCGAGGGCATGGACGAGATGGAGTTCACCGAGGCTGAGAGCAACATGAACGACCTCG
TCTCTGAGTATCAAGCAGTACCAGGATGCCACCGCAGAAGAGGAGGAGGATTTCGGTGAGGAGGCCGAAGAGGAGG
CCTAAGGCAGAGCCCCCATCACCTCAGGCTTCTCAGTTCCCTTAGCCGTCTTACTCAACTGCCCCTTTCCTCTCCC
TCAGAATTTGTGTTTGCTGCCTCTATCTTGTTTTTTGTTTTTTCTTCTGGGGGGGTCTAGAACAGTGCCTGGCACA
TAGTAGGCGCTCAATAAATACTTGGTTGNTGAATGTCTCCT 13702.2

AGCTGGCGCTAGGGCTCGGTTGTGAAATACAGCGTRGTCAGCCCTTGCGCTCAGTGTAGAAACCCACGCCTGTAAG
GTCGGTCTTCGTCCATCTGCTTTTTTCTGAAATACACTAAGAGCAGCCACAAAACTGTAACCTCAAGGAAACCATA
AAGCTTGGAGTGCCTTAATTTTTAACCAGTTTCCAATAAAACGGTTTACTACCT 13704.2-13740.2

GGAGATGAAGATGAGGAAGCTGAGTCAGCTACGGGCARGCGGGCAGCTGAAGATGATGAGGATGACGATGTCGATA
CCAAGAAGCAGAAGACCGACGAGGATGACTAGACAGCAAAAAAGGAAAAGTTAAA 13706.1

GATGAAAATTAAATACTTAAATTAATCAAAAGGCACTACGATACCACCTAAAACCTACTGCCTCAGTGGCAGTAKG
CTAAKGAAGATCAAGCTACAGSACATYATCTAATATGAATGTTAGCAATTACATAKCARGAAGCATGTTTGCTTTC
CAGAAGACTATGGNACAATGGTCATTWGGGCCCAAGAGGATATTTGGCCNGGAAAGGATCAAGATAGATNAANGTA
AAG 13706.2

GAGTAGCAACGCAAAGCGCTTGGTATTGAGTCTGTGGGSGACTTCGGTTCCGGTCTCTGCAGCAGCCGTGATCGCT
TAGTGGAGTGCTTAGGGTAGTTGGCCAGGATGCCGAATATCAAAATCTTCAGCAGGCAGCTCCCACCAGGACTTAT
CTCASAAAATTGCTGACCGCCTGGGCCTGGAGCTAGGCAAGGTGGTGACTAAGAAATTCAGCAACCAGGAGACCTG
TGTGGAAATTGGTGAAAGTGTACCGTGGAGAGGATGTCTACATTGTTCAGAGTGGNTGTGGCGAAATCAATGACAA
TTTAATGGAGCTTTTGATCATGATTAATGCCTGCAAGATTGCTTCAGCCAGCCGGGTTACTGCAGTCATCCCATGC
TTCCCTTATGCCCCGGCAGGATAAGAAAGATNAGAGCCGGGCCGCCAATCTCAGCCAAGCTTGGTGCAAATATGCT
ATCTGTAGCAGTGCAGATCATATTATCACCATGGACCTACATGCTTCTCAAATTCANGGCTTTTT

ATGCAAAAGGGGACACAGGGGGTTCAAAAATAAAAATTTCTCTTCCCCCTCCCCAAACCTGTACCCCAGCTCCCCG
ACCACAACCCCCTTCCTCCCCCGGGGAAAGCAAGAAGGAGCAGGTGTGGCATCTGCAGCTGGGAAGAGAGAGGCCG
GGGAGGTGCCGAGCTCGGTGCTGGTCTCTTTCCAAATATAAATACGTGTGTCAGAACTGGAAAATCCTCCAGCACC
CACCACCCAAGCACTCTCCGTTTTCTGCCGGTGTTTGGAGAGGGGCGGNGGGCAGGGGCGCCAGGCACCGGCTGGC
TGCGGTCTACTGCATCCGCTGGGTGTGCACCCCGCGA 13710.2

AGGTTGGAGAAGGTCATGCAGGTGCAGATTGTCCAGGSKCAGCCACAGGGTCAAGCCCAACAGGCCCAGAGTGGCA
CTGGACAGACCATGCAGGTGATGCAGCAGATCATCACTAACACAGGAGAGATCCAGCAGATCCCGGTGCAGCTGAA
TGCCGGCCAGCTGCAGTATATCCGCTTAGCCCAGCCTGTATCAGGCACTCAAGTTGTGCAGGGACAGATCCAGACA
CTTGCCACCAATGCTCAACAGATTACACAGACAGAGGTCCAGCAAGGACAGCAGCAGTTCAAGCCAGTTCACAAGA
TGGACAGCAGCTCTACCAGATCCAGCAAGTCACCATGCCTGCGGGCCANGACCTCGCCAGCCCATGTTCATCCAGT
CAAGCCAACCAGCCCTTCNACGGGCAGGCCCCCCAGGTGACCGGCGACTGAAGGGCCTGAGCTGGCAAGGCCAANG
ACACCCAACACAATTTTTGCCATACAGCCCCCAGGCAATGGGCACAGCCTTTCTTCCCAGAGGAC 13710-1

TGAGATTTATTGCATTTCATGCAGCTTGAAGTCCATGCAAAGGRGACTAGCACAGTTTTTAATGCATTTAAAAAAT
AAAAGGGAGGTGGGCAGCAAACACACAAAGTCCTAGTTTCCTGGGTCCCTGGGAGAAAAGAGTGTGGCAATGAATC
CACCCACTCTCCACAGGGAATAAATCTGTCTCTTAAATGCAAAGAATGTTTCCATGGCCTCTGGATGCAAATACAC
AGAGCTCTGGGGTCAGAGCAAGGGATGGGGAGAGGACCACGAGTGAAAAAGCAGCTACACACATTCACCTAATTCC
ATCTGAGGGCAAGAACAACGTGGCAAGTCTTGGGGGTAGCAGCTGTT 13711.1

TCCAGACATGCTCCTGTCCTAGGCGGGGAGCAGGAACCAGACCTGCTATGGGAAGCAGAAAGAGTTAAGGGAAGGT
TTCCTTTCATTCCTGTTCCTTCTCTTTTGCTTTTGAACAGTTTTTAAATATACTAATAGCTAAGTCATTTGCCAGC
CAGGTCCCGGTGAACAGTAGAGAACAAGGAGCTTGCTAAGAATTAATTTTGCTGTTTTTCACCCCATTCAAACAGA
GCTGCCCTGTTCCCTGATGGAGTTCCATTCCTGCCAGGGCACGGCTGAGTAACACGAAGCCATTCAAGAAAGGCGG
GTGTGAAATCACTGCCACCCCATGGACAGACCCCTCACTCTTCCTTCTTAGCCGCAGCGCTACTTAATAAATATAT
TTATACTTTGAAATTATGATAACCGATTTTTCCCATGCGGCATCCTAAGGGCACTTGCCAGCTCTTATCCGGACAG
TCAAGCACTGTTGTTGGACAACAGATAAAGGAAAAGAAAAAGAAGAAAACAACCGCAACTTCTGT

TGAGACGGACCACTGGCCTGGTCCCCCCTCATKTGCTGTCGTAGGACCTGACATGAAACGCAGATCTAGTGGCAGA
GAGGAAGATGATGAGGAACTTCTGAGACGTCGGCAGCTTCAAGAAGAGCAATTAATGAAGCTTAACTCAGGCCTGG
GACAGTTGATCTTGAAAGAAGAGATGGAGAAAGAGAGCCGGGAAAGGTCATCTCTGTTAGCCAGTCGCTACGATTC
TCCCATCAACTCAGCTTCACATATTCCATCATCTAAAACTGCATCTCTCCCTGGCTATGGAAGAAATGGGCTTCAC
CGGCCTGTTTCTACCGACTTCGCTCAGTATAACAGCTATGGGGATGTCAGCGGGGGAGTGCGAGATTACCAGACAC
TTCCAGATGGCCACATGCCTGCAATGAGAATGGACCGAGGAGTGTCTATGCCCAACATGTTGGAACCAAAGATATT
TCCATATGAAATGCTCATGGTGACCAACAGAGGGCCGAAACCAAATCTCAGAGAGGTGGACAGAA 13713.1&2

TCACTTTATTTTTCTTGTATAAAAACCCTATGTTGTAGCCACAGCTGGAGCCTGAGTCCGCTGCACGGAGACTCTG
GTGTGGGTCTTGACGAGGTGGTCAGTGAACTCCTGATAGGGAGACTTGGTGAATACAGTCTCCTTCCAGAGGTCGG
GGGTCAGGTAGCTGTAGGTCTTAGAAATGGCATCAAAGGTGGCCTTGGCGAAGTTGCCCAGGGTGGCAGTGCAGCC
CCGGGCTGAGGTGTAGCAGTCATCGATACCAGCCATCATGAG 13715.4

CTGGAATATAGACCCGTGATCGACAAAACTTTGAACGAGGCTGACTGTGCCACCGTCCCGCCAGCCATTCGCTCCT
ACTGATGAGACAAGATGTGGTGATGACAGAATCAGCTTTTGTAATTATGTATAATAGCTCATGCATGTGTCCATGT
CATAACTGTCTTCATACGCTTCTGCACTCTGGGGAAGAAGGAGTACATTGAAGGGAGATTGGCACCTAGTGGCTGG
GAGCTTGCCAGGAACCCAGTGGCCAGGGAGCGTGGCACTTACCTTTGTCCCTTGCTTCATTCTTGTGAGATGATAA
AACTGGGCACAGCTCTTAAATAAAATATAAATGAACA 13717.1&2

TGAATGGGGAGGAGCTGACCCAGGAAATGGAGCTTGNGGAGACCAGGCCTGCAGGGGATGGAACCTTCCAGAAGTG
GGCATCTGTGGTGGTGCCTCTTGGGAAGGAGCAGAAGTACACATGCCATGTGGAACATGAGGGGCTGCCTGAGCCC
CTCACCCTGAGATGGGGCAAGGAGGAGCCTCCTTCATCCACCAAGACTAACACAGTAATCATTGCTGTTCCGGTTG
TCCTTGGAGCTGTGGTCATCCTTGGAGCTGTGATGGCTTTTGTGATGAAGAGGAGGAGAAACACAGGTGGAAAAGG
AGGGGACTATGCTCTGGCTCCAGGCTCCCAGAGCTCTGATATGTCTCTCCCAGATTGTAAAGTGTGAAGACAGCTG
CCTGGTGTGGACTTGGTGACAGACAATGTCTTCACACATCTCCTGTGACATCCAGAGACCTCAGTTCTCTTTAGTC
AAGTGTCTGATGTTCCCTGTGAGTCTGCGGGCTCAAAGTGAAGAACTGTGGAGCCCAGTCCACCCCTGCACACCAG
GACCCTATCCCTGCACTGCCCTGTGTTCCCTTCCACAGCCAACCTTGCTGCTCCAGCCAAACATTGGTGGACATCT
GCAGCCTGTCAGCTCCATGCTACCCTGACCTTCAACTCCTCACTTCCACACTGAGAATAATAATTTGAATGTGGGT
GGCTGGAGAGATGGCTCAGCGCTGACTGCTCTTCCAAAGGTCCTGAGTTCAAATCCCAGCAACCACATGGTGGCTC
ACAACCATCTGTAATGGGATCTAATACCCTCTTCTGCAGTGTCTGAAGACASCTACAGTGTACTTACATATAATAA
TAAATAAG

GGCCGGGCGCGCGCGCCCCCGCCACACGCACGCCGGGCGTGCCAGTTTATAAAGGGAGAGAGCAAGCAGCGAGTCT
TGAAGCTCTGTTTGGTGCTTTGGATCCATTTCCATCGGTCCTTACAGCCGCTCGTCAGACTCCAGCAGCCAAGATG
GTGAAGCAGATCGAGAGCAAGACTGCTTTTCAGGAAGCCTTGGACGCTGCAGGTGATAAACTTGTAGTAGTTGACT
TCTCAGCCACGTGGTGTGGGCCTTGCAAAATGATCAAGCCTTTCTTTCATTCCCTCTCTGAAAAGTATTCCAACGT
GATATTCCTTGAAGTAGATGTGGATGACTGTCAGGATGTTGCTTCAGAGTGTGAAGTCAAATGCATGCCAACATTC
CAGTTTTTTAAGAAGGGACAAAAGGTGGGTGAATTTTCTGGAGCCAATAAGGAAAAGCTTGAAGCCACCATTAATG
AATTAGTCTAATCATGTTTTCTGAAAATATAACCAGCCATTGGCTATTTAAAACTTGTAATTTTTTTAATTTACAA
AAATATAAAATATGAAGACATAAACCCMGTTGCCATCTGCGTGACAATAAAACATTAATGCTAACACTT 13721.1

TCACATAAGAAATTTAAGCAAGTTACRCTATCTTAAAAAACACAACGAATGCATTTTAATAGAGAAACCCTTCCCT
CCCTCCACCTCCCTCCCCCACCCTCCTCATGAATTAAGAATCTAAGAGAAGAAGTAACCATAAAACCAAGTTTTGT
GGAATCCATCATCCAGAGTGCTTACATGGTGATTAGGTTAATATTGCCTTCTTACAAAATTTCTATTTTAAAAAAA
ATTATAACCTTGATTGCTTATTACAAAAAAATTCAGTACAAAAGTTCAATATATTGAAAAATGCTTTTCCCCTCCC
TCACAGCACCGTTTTATATATAGCAGAGAATAATGAAGAGATTGCTAGTCTAGATGGGGCAATCTTCAAATTACAC
CAAGACGCACAGTGGTTTATTTACCCTCCCCTTCTCATAAG 13721.2

GGAAAGGATTCAAGAATTAGAGGACTTGCTTGCTRRAGAAAAAGACAACTCTCGTCGCATGCTGACAGACAAAGAG
AGAGAGATGGCGGAAATAAGGGATCAAATGCAGCAACAGCTGAATGACTATGAACAGCTTCTTGATGTAAAGTTAG
CCCTGGACATGGAAATCAGTGCTTACAGGAAACTCTTAGAAGGCGAAGAAGAGAGGTTGAAGCTGTCTCCAAGCCC
TTCTTCCCGTGTGACAGTATCCCGAGCATCCTCAAGTCGTAGTGTACCGTACAACTAGAGGAAAGCGGAAGAGGGT
TGATGTGGAAGAATCAGAGGCGAAGTAGTAGTGTTAGCATCTCTCATTCCGCCTCAACCACTGGAAATGTTTGCAT
CGAAGAAATTGATGTTGATGGGAAATTTATCCCGCTTGAAGAACACTTCTGAACAGGATCAACCAATGGGAAGGCT
TGGGAGATGATCAGAAAAATTGGAGACACATCAGTCAGTTATAAATATACCTCAA 13723.1

CATGGGTTTCACCAGGTTGGCCAGGCTGCTCTTGAACTSCTGACCTCAGGTGATCCACCCGCCTCGGCCTCCCAAA
GTGCTGGGATTACAGGCGTGAGCCACCACGCCCGGCCCCCAAAGCTGTTTCTTTTGTCTTTAGCGTAAAGCTCTCC
TGCCATGCAGTATCTACATAACTGACGTGACTGCCAGCAAGCTCAGTCACTCCGTGGTCTTTTTCTCTTTCCAGTT
CTTCTCTCTCTCTTCAAGTTCTGCCTCAGTGAAAGCTGCAGGTCCCCAGTTAAGTGATCAGGTGAGGGTTCTTTGA
ACCTGGTTCTATCAGTCGAATTAATCCTTCATGATGG

GATGTGTTGGACCCTCTGTGTCAAAAAAAACCTCACAAAGAATCCCCTGCTCATTACAGAAGAAGATGCATTTAAA
ATATGGGTTATTTTCAACTTTTTATCTGAGGACAAGTATCCATTAATTATTGTGTCAGAAGAGATTGAATACCTGC
TTAAGAAGCTTACAGAAGCTATGGGAGGAGGTTGGCAGCAAGAACAATTTGAACATTATAAAATCAACTTTGATGA
CAGTAAAAATGGCCTTTCTGCATGGGAACTTATTGAGCTTATTGGAAATGGACAGTTTAGCAAAGGCATGGACCGG
CAGACTGTGTCTATGGCAATTAATGAAGTCTTTAATGAACTTATATTAGATGTGTTAAAGCAGGGTTACATGATGA
AAAAGGGCCACAGACGGAAAAACTGGACTGAAAGATGGTTTGTACTAAAACCCAACATAATTTCTTACTATGTGAG
TGAGGATCTGAAGGATAAGAAAGGAGACATTCTCTTGGATGAAAATTGCTGTGTAGAAGTCCTTGCCTGACAAAAG
ATGGAAAGAAATGCCTTTT 13725.1

GACTGGTTCTTTATTTCAAAAAGACACTTGTCAATATTCAGTRTCAAAACAGTTGCACTATTGATTTCTCTTTCTC
CCAATCGGCCCCAAAGAGACCACATAAAAGGAGAGTACATTTTAAGCCAATAAGCTGCAGGATGTACACCTAACAG
ACCTCCTAGAAACCTTACCAGAAAATGGGGACTGGGTAGGGAAGGAAACTTAAAAGATCAACAAACTGCCAGCCCA
CGGACTGCAGAGGCTGTCACAGCCAGATGGGGTGGCCAGGGTGCCACAAACCCAAAGCAAAGTTTCAAAATAATAT
AAAATTTAAAAAGTTTTGTACATAAGCTATTCAAGATTTCTCCAGCACTGACTGATACAAAGCACAATTGAGATGG
CACTTCTAGAGACAGCAGCTTCAAACCCAGAAAAGGGTGATGAGATGAAGTTTCACATGGCTAAATCAGTGGCAAA
AACACAGTCTTCTTTCTTTCTTTCTTTCAAGGANGCAGGAAAGCAATTAAGTGGTCACCTTAACATAAGGGGGAC 13725.2

TGGGTGGGCACCATGGCTGGGATCACCACCATCGAGGCGGTGAAGCGCAAGATCCAGGTTCTGCAGCAGCAGGCAG
ATGATGCAGAGGAGCGAGCTGAGCGCCTCCAGCGAGAAGTTGAGGGAGAAAGGCGGGCCCGGGAACAGGCTGAGGC
TGAGGTGGCCTCCTTGAACCGTAGGATCCAGCTGGTTGAAGAAGAGCTGGACCGTGCTCAGGAGCGCCTGGCCACT
GCCCTGCAAAAGCTGGAAGAAGCTGAAAAAGCTGCTGATGAGAGTGAGAGAGGTATGAAGGTTATTGAAAACCGGG
CCTTAAAAGATGAAGAAAAGATGGAACTCCAGGAAATCCAACTCAAAGAAGCTAAGCACATTGCAGAAGAGGCAGA
TAGGAAGTATGAAGAGGTGGCTCGTAAGTTGGTGATCATTGAAGGAGACTTGGAACCGCACAGAAGGAACGAGCTT
GAGCTTGGCAAAAGTCCCGTTGCCCAGAGATGGGATGAACCAGATTAGACTGATGGACCANAACC 13726.1&2

AGGGGCNGCGGGTGCGTGGGCCACTGGGTGACCGACTTAGCCTGGCCAGACTCTCAGCACCTGGAAGCGCCCCGAG
AGTGACAGCGTGAGGCTGGGAGGGAGGACTTGGCTTGAGCTTGTTAAACTCTGCTCTGAGCCTCCTTGTCGCCTGC
ATTTAGATGGCTCCCGCAAAGAAGGGTGGCGAGAAGAAAAAGGGCCGTTCTGCCATCAACGAAGTGGTAACCCGAG
AATACACCATCAACATTCACAAGCGCATCCATGGAGTGGGCTTCAAGAAGCGTGCACCTCGGGCACTCAAAGAGAT
TCGGAAATTTGCCATGAAGGAGATGGGAACTCCAGATGTGCGCATTGACACCAGGCTCAACAAAGCTGTCTGGGCC
AAAGGAATAAGGAATGTGCCATACCGAATCCGGTGTGCGGCTGTCCAGAAAACGTAATGAGGATGAAGATTCACCA
AATAAGCTATATACTTTGGTTACCTATGTACCTGTTACCACTTTCAAAAATCTACAGACAGTCAATGTGGATGAGA
ACTAATCGCTGATCGTCAGATCAAATAAAGTTATAAAAT

TCGGGAGCCACACTTGGCCCTCTTCCTCTCCAAAGSGCCAGAACCTCCTTCTCTTTGGAGAATGGGGAGGCCTCTT
GGAGACACAGAGGGTTTCACCTTGGATGACCTCTAGAGAAATTGCCCAAGAAGCCCACCTTCTGGTCCCAACCTGC
AGACCCCACAGCAGTCAGTTGGTCAGGCCCTGCTGTAGAAGGTCACTTGGCTCCATTGCCTGCTTCCAACCAATGG
GCAGGAGAGAAGGCCTTTATTTCTCGCCCACCCATTCCTCCTGTACCAGCACCTCCGTTTTCAGTCAGTGTTGTCC
AGCAACGGTACCGTTTACACAGTCACCTCAGACACACCATTTCACCTCCCTTGCCAAGCTGTTAGCCTTAGAGTGA
TTGCAGTGAACACTGTTTACACACCGTGAATCCATTCCCATCAGTCCATTCCAGTTGGCACCAGCCTGAACCATTT
GGTACCTGGTGTTAACTGGAGTCCTGTTTACAAGGTGGAGTCGGGGCTTGCTGACTTCTCTTCATTTGAGGGCAC 13727.2

ACCTAGACAGAAGGTGGGTGAGGGAGGACTGGTAGGAGGCTGAGGCAATTCCTTGGTAGTTTGTCCTGAAACCCTA
CTGGAGAAGTCAGCATGAGGCACCTACTGAGAGAAGTGCCCAGAAACTGCTGACTGCATCTGTTAAGAGTTAACAG
TAAAGAGGTAGAAGTGTGTTTCTGAATCAGAGTGGAAGCGTCTCAAGGGTCCCACAGTGGAGGTCCCTGAGCTACC
TCCCTTCCGTGAGTGGGAAGAGTGAAGCCCATGAAGAACTGAGATGAAGCAAGGATGGGGTTCCTGGGCTCCAGGC
AAGGGCTGTGCTCTCTGCAGCAGGGAGCCCCACGAGTCAGAAGAAAAGAACTAATCATTTGTTGCAAGAAACCTTG
CCCGGATACTAGCGGAAAACTGGAGGCGGNGGTGGGGGCACAGGAAAGTGGAAGTGATTTGATGGAGAGCAGAGAA
GCCTATGCACAGTGGCCGAGTCCACTTGTAAAGTG 13728.1&2

TTCAAGCAATTGTAACAAGTATATGTAGATTAGAGTGAGCAAAATCATATACAATTTTCATTTCCAGTTGCTATTT
TCCAAATTGTTCTGTAATGTCGTTAAAATTACTTAAAAATTAACAAAGCCAAAAATTATATTTATGACAAGAAAGC
CATCCCTACATTAATCTTACTTTTCCACTCACCGGCCCATCTCCTTCCTCTTTTTCCTAACTATGCCATTAAAACT
GTTCTACTGGGCCGGGCGTGTGGCTCATGCCTGTAATCCCAGCATTTTGGGAGGCCAAGGCAGGCGGATCATGAGG
TCAAGAGATTGAGACCATCCTGGCCAACATGGTGAAACCCCGCCTCGACTAAGAATACAAAAATTAGCTGGGCATG
GTGGCGCATGCCTGTAGTCTCAGCTACTCGGGAGGCTGAGGCAGAAGAATCGCTTGAACCCGGGAGGCAGAGGATG
CAGTGAGCCCCGATCGCGCCACTGCACTCTAGCCTGGGCGACAGACTGAGACTCTGCTC 13731.1&2

TGTGCCAGTCTACAGGCCTATCAGCAGCGACTCCTTCAGCAACAGATGGGGTCCCCTGTTCAGCCCAACCCCATGA
GCCCCCAGCAGCATATGCTCCCAAATCAGGCCCAGTCCCCACACCTACAAGGCCAGCAGATCCCTAATTCTCTCTC
CAATCAAGTGCGCTCTCCCCAGCCTGTCCCTTCTCCACGGCCACAGTCCCAGCCCCCCCACTCCAGTCCTTCCCCA
AGGATGCAGCCTCAGCCTTCTCCACACCACGTTTCCCCACAGACAAGTTCCCCACATCCTGGACTGGTAGTTGCCC
AGGCCAACCCCATGGAACAAGGGCATTTTGCCAGCC

TGTAAAAACTTGTTTTTAATTTTGTATAAAATAAAGGTGGTCCATGCCCACGGGGGCTGTAGGAAATCCAAGCAGACCA
GCTGGGGTGGGGGGATGTAGCCTACCTCGGGGGACTGTCTGTCCTCAAAACGGGCTGAGAAGGCCCGTCAGGGGCCCAG
GTCCCACAGAGAGGCCTGGGATACTCCCCCAACCCGAGGGGCAGACTGGGCAGTGGGGAGCCCCCATCGTGCCCCAGAG
GTGGCCACAGGCTGAAGGAGGGGCCTGAGGCACCGCAGCCTGCAACCCCCAGGGCTGCAGTCCACTAACTTTTTACAGA
ATAAAAGGAACATGGGGATGGGGAAAAAAGCACCAGGTCAGGCAGGGCCCGAGGGCCCCAGATCCCAGGAGGGCCAGGA
CTCAGGATGCCAGCACCACCCTAGCAGCTCCCACAGCTCCTGGCACAGGAGGCCGCCACGGATTGGCACAGGCCGCTGC
TGGCCATCACGCCACATTTGGAGAACTTGTCCCGACAGAGGTCAGCTCGGAGGAGCTCCTCGTGGGCACACACTGTACG
AACACAGATCTCCTTGTTAATGACGTACACACGGCGGAGGCTGCGGGGACAGGGCACGGGAGGTCTCAGCCCCACTT 13736.2

ATGGCTGCTGGATTTAGGTGGTAATAGGGGCTGTGGGCCATAAATCTGAAGCCTTGAGAACCTTGGGTCTGGAGAGCCA
TGAAGAGGGAAGGAAAAGAGGGCAAGTCCTGAACCTAACCAATGACCTGATGGATTGCTCGACCAAGACACAGAAGTGA
AGTCTGTGTCTGTGCACTTCCCACAGACTGGAGTTTTTGGTGCTGAATAGAGCCAGTTGCTAAAAAATTGGGGGTTTGG
TGAAGAAATCTGATTGTTGTGTGTATTCAATGTGTGATTTTAAAAATAAACAGCAACAACAATAAAAACCCTGACTGGC
TGTTTTTTCCCTGTATTCTTTACAACTATTTTTTGACCCTCTGAAAATTATTATACTTCACCTAAATGGAAGACTGCTG
TGTTTGTGGAAATTTTTGTAATTTTTTAATTTATTTTATTCTCTCTCCTTTTTATTTTGCCTGCAGAATCCGTTGAGAGA
CTAATAAGGCTTAATATTTAATTGATTTGTTTAATATGTATATAAAT 13744.2-13696.2

GGCATGCGAGCGCACTCGGCGGACGCAAGGGCGGCGGGGAGCACACGGAGCACTGCAGGCGCCGGGTTGGGACAGCGTC
TTCGCTGCTGCTGGATAGTCGTGTTTTCGGGGATCGAGGATACTCACCAGAAACCGAAAATGCCGAAACCAATCAATGT
CCGAGTTACCACCATGGATGCAGAGCTGGAGTTTGCAATCCAGCCAAATACAACTGGAAAACAGCTTTTTGATCAGGTG
GTAAAGACTATCGGCCTCCGGGAAGTGTGGTACTTTGGCCTCCACTATGTGGATAATAAAGGATTTCCTACCTGGCTGA
AGCTGGATAAGAAGGTGTCTGCCCAGGAGGTCAGGAAGGAGAATCCCCTCCAGTTCAAGTTCCGGGCCAAaGTTCTACC
CTGAAGATGTGGCTGAGGAGCTCATCCAGGACATCACCCAGAAACTTTTCTTCCTTCAAGTGAAGGAAGGAATCCTTAG
CGATGAGATCTACTGCCCCCCTTGARACTGCCGTGCTCTTGGGGTCCTACGCTTGTGCATGCCAAGTTTGGGGACTACC
ACCAAGAAG 13746.1&2-13720.1&2

GAAGGAGTCGGGATACTCAGCATTGATGCACCCCAATTTCAAAGCGGCATTCTTCGGCAGGTCTCTGGGACAATCTCTA
GGGTCACTACCTGGAAACTCGTTAGGGTACAACTGAATGCTGAAAGGAAAGAACACCTGCAGAACCGGACAGAAATTCA
CCCCGGCGATCAGCTGATTGATCTCGGTCGACCAGAAGTCATGGCTAAAGATGACGAGGACGTTGTCAATTCCCTGGGC
TTTTCGAAGTGAGTCCAGCAGCAGTCTGAGGTATTCGGGCCGGTTATGCACCTGGACCACCAGCACCAGCTCCCGGGGG
GCCCAGGTGCCAGCCTTATCTACATTCCTCAGGGTCTGATCAAAGTTCAGCTGGTACACCAGGGACCGGTACCGCAGCG
TCAGGTTGTCCGCTCGGGCTGGGGGACCGCCGGGACCAGGGAAGCCGCCGACACGTTGGAGACCCTGCGGATGCCCACA
GCCACAGAGGGGTGGTCCCCACCGCGGCCGCCGGCACCCCGCGCGGGTTCGGCGTCCAGCAACGGTGGGGCGAGGGCCT
CGTTCTTCCTTTGTCGCCCATTGCTGCTCCAGAGGACGAAGCCGCAGGCGGCCACCACGAGCGTCAGGATTAGCACCTT
CCGTTTGTAGATGCGGAACCTCATGGTCTCCAGGGCCGGGAGCGCAGCTACAGCTCGAGCGTCGGCGCCGCCGCTAGGA
GCCGCGGCTCGGCTTCGTCTCCGTCCTCTCCATTCAGCACCACGGGTCCCGGAAAAAGCTCAGCCSCGGTCCCAACCGC
ACCCTAGCTTCGTTACCTGCGCCTCGCTTG

CAGATTTTTATTTGCAGTCGTCACTGGGGCCGTTTCTTGCTGCTTATTTGTCTGCTAGCCTGCTCTTCCAGCTGCA
TGGCCAGGCGCAAGGCCTTGATGACATCTCGCAGGGCTGAGAAATGCTTGGCTTGCTGGGCCAGAGCAGATTCCGC
TTTGTTCACAAAGGTCTCCAGGTCATAGTCTGGCTGCTCGGTCATCTCAGAGAGCTCAAGCCAGTCTGGTCCTTGC
TGTATGATCTCCTTGAGCTCTTCCATAGCCTTCTCCTCCAGCTCCCTGATCTGAGTCATGGCTTCGTTAAAGCTGG
ACATCTGGGAAGACAGTTCCTCCTCTTCCTTGGATAAATTGCCTGGAATCAGCGCCCCGTTAGAGCAGGCTTCCAT
CTCTTCTGTTTCCATTTGAATCAACTGCTCTCCACTGGGCCCACTGTGGGGGCTCAGCTCCTTGACCCTGCTGCAT
ATCTTAAGGGTGTTTAAAGGATATTCACAGGAGCTTATGCCTGGT 14347.2

CTCCTCTTGGTACATGAACCCAAGTTGAAAGTGGACTTAACAAAGTATCTGGAGAACCAAGCATTCTGCTTTGACT
TTGCATTTGATGAAACAGCTTCGAATGAAGTTGTCTACAGGTTCACAGCAAGGCCACTGGTACAGACAATCTTTGA
AGGTGGAAAAGCAACTTGTTTTGCATATGGCCAGACAGGAAGTGGCAAGACACATACTATGGGCGGAGACCTCTCT
GGGAAAGCCCAGAATGCATCCAAAGGGATCTATGCCATGGCCTTCCGGGACGTCTTCTTCTGAAGAATCAACCCTG
CTACCGGAAGTTGGGCCTGGAAGTCTATGTGACATTCTTCGAGATCTACAATGGGAAGCTGTTTGACCTGCTCAAC
AAGAAGGCCAAGCTTGCGCGTGCTGGAAGACGGCAAGCAACAGGTGCAAGTGGTGGGGGCTTGCAGGAACATCTGG
NTAACTCTGCTTGATGATGGCANTCAAGATGATCGACATGGGCAGCGCCTGCAGA 14348.2&14350.1&2

TCCCGAATTCAAGCGACAAATTGGAWAGTGAAATGGAAGATGCCTATCATGAACATCAGGCAAATCTTTTGCGCCA
AGATCTGATGAGACGACAGGAAGAATTAAGACGCATGGAAGAACTTCACAATCAAGAAATGCAGAAACGTAAAGAA
ATGCAATTGAGGCAAGAGGAGGAACGACGTAGAAGAGAGGAAGAGATGATGATTCGTCAACGTGAGATGGAAGAAC
AAATGAGGCGCCAAAGAGAGGAAAGTTACAGCCGAATGGGCTACATGGATCCACGGGAAAGAGACATGCGAATGGG
TGGCGGAGGAGCAATGAACATGGGAGATCCCTATGGTTCAGGAGGCCAGAAATTTCCACCTCTAGGAGGTGGTGGT
GGCATAGGTTATGAAGCTAATCCTGGCGTTCCACCAGCAACCATGAGTGGTTCCATGATGGGAAGTGACATGCGTA
CTGAGCGCTTTGGGCAGGGAGGTGCGGGGCCTGTGGGTGGACAGGGTCCTAGAGGAATGGGGCCTGGAACTCCAGC
AGGATATGGTAGAGGGAGAGAAGAGTACGAAGGC 14349.1&2

TTCGTGAAGACCCTGACTGGTAAGACCATCACTCTCGAAGTGGAGCCCGAGTGACACCATTGAGAATGTCAAGGCA
AAGATCCAAGACAAGGAAGGCATCCCTCCTGACCAGCAKAGGTTGATCTTTGCTGGGAAACAGCTGGAAGATGGAC
GCACCCTGTCTGACTACAACATCCAGAAAGAGTCCACCCTGCACCTGGTGCTCCGTCTCAGAGGTGGGATGCAAAT
CTTCGTGAAGACCCTGACTGGTAAGACCATCACCCTCGAGGTGGAGCCCAGTGACACCATCGAGAATGTCAAGGCA
AAGATCCAAGATAAGGAAGGCATCCCTCCTGATCAGCAGAGGTTGATCTTTGCTGGGAAACAGCTGGAAGATGGAC
GCACCCTGTCTGACTACAACATCCAGAAAGAGTCCACTCTGCACTTGGTCCTGCGCTTGAGGGGGGGTGTCTAAGT
TTCCCCTTTTAAGGTTTCAACAAATTTCATTGCACTTTCCTTTCAATAAAGTTGTTGCATTC

*Fig. 15R*

GCGCGGGTGCGTGGGCCACTGGGTGACCGACTTAGCCTGGCCAGACTCTCAGCACCTGGAAGCGCCCCGAGAGTGA
CAGCGTGAGGCTGGGAGGGAGGACTTGGCTTGAGCTTGTTAAACTCTGCTCTGAGCCTCCTTGTCGCCTGCATTTA
GATGGCTCCCGCAAAGAAGGGTGGCGAGAAGAAAAAGGGCCGTTCTGCCATCAACGAAGTGGTAACCCGAGAATAC
ACCATCAACATTCACAAGCGCATCCATGGAGTGGGCTTCAAGAAGCGTGCACCTCGGGCACTCAAAGAGATTCGGA
AATTTGCCATGAAGGAGATGGGAACTCCAGATGTGCGCATTGACACCAGGCTCAACAAAGCTGTCTGGGCCAAAGG
AATAAGGAATGTGCCATACCGAATCCGTGTGCGGCTGTCCAGAAAACGTAATGAGGATGAAGATTCACCAAATAAG
CTATATACTTTGGTTACCTATGTACCTGTTACCACTTTCAAAAATCTACAGACAGTCAATGTGGATGAGAACTAAT
CGCTGATCGT 14353.1

AATTCTTTATTTAAATCAACAAACTCATCTTCCTCAAGCCCCAGACCATGGTAGGCAGCCCTCCCTCTCCATCCCC
TCACCCCACCCCTTAGCCACAGTGAAGGGAATGGAAAATGAGAAGCCACGAGGGCCCCTGCCAGGGAAGGCTGCCC
CAGATGTGTGGTGAGCACAGTCAGTGCAGCTGTGGCTGGGGCAGCAGCTGCCACAGGCTCCTCCCTATAAATTAAG
TTCCTGCAGCCACAGCTGTGGGAGAAGCATACTTGTAGAAGCAAGGCCAGTCCAGCATCAGAAGGCAGAGGCAGCA
TCAGTGACTCCCAGCCATGGAATGAACGGAGGACACAGAGCTCAGAGACAGAACAGGCCAGGGGGAAGAAGGAGAG
ACAGAATAGGCCAGGGCATGGCGGTGAGGGA 14353.2

TGATGAATCTGGGTGGGCTGGCAGTAGCCCGAGATGATGGGCTCTTCTCTGGGGATCCCAACTGGTTCCCTAAGAA
ATCCAAGGAGAATCCTCGGAACTTCTCGGATAACCAGCTGCAAGAGGGCAAGAACGTGATCGGGTTACAGATGGGC
ACCAACCGCGGGGCGTCTCANGCAGGCATGACTGGCTACGGGATGCCACGCCAGATCCTCTGATCCCACCCCAGGC
CTTGCCCCTGCCCTCCCACGAATGGTTAATATATATGTAGATATATATTTTAGCAGTGACATTCCCAGAGAGCCCC
AGAGCTCTCAAGCTCCTTTCTGTCAGGGTGGGGGGTTCAAGCCTGTCCTGTCACCTCTGAAGTGCCTGCTGGCATC
CTCTCCCCCATGCTTACTAATACATTCCCTTCCCCATAGCC 17182.1&2

AGCGGAGCTCCCTCCCCTGGTGGCTACAACCCACACACGCCAGGCTCAGGCATCGAGCAGAACTCCAGCGACTGGG
TAACCACTGACATTCAGGTGAAGGTGCGGGACACCTACCTGGATACACAGGTGGTGGGACAGACAGGTGTCATCCG
CAGTGTCACGGGGGGCATGTGCTCTGTGTACCTGAAGGACAGTGAGAAGGTTGTCAGCATTTCCAGTGAGCACCTG
GAGCCTATCACCCCCACCAAGAACAACAAGGTGAAAGTGATCCTGGGCGAGGATCGGGAAGCCACGGGCGTCCTAC
TGAGCATTGATGGTGAGGATGGCATTGTCCGTATGGACCTTGATGAGCAGCTCAAGATCCTCAACCTCCGCTTCCT
GGGGAAGCTCCTGGAAGCCTGAAGCAGGCAGGGCCGGTGGACTTCGTCGGATGAAGAGTGATCCTCCTTCCTTCCC
TGGCCCTTGGCTGTGACACAAGATCCTCCTGCAGGGCTAGGCGGATTGTTCTGGATTTCCTTTTGTTTTTCCTTTT
AGGTTTCCATCTTTTCCCTCCCTGGTGCTCATTGGAATCTGAGTAGAGTCTGGGGGAGGGTCCCCACCTTCCTGTA
CCTCCTCCCCACAGCTTGCTTTTGTTGTACCGTCTTTCAATAAAAAGAAGCTGTTTGGTCTA

GGTTCACAGCACTGCTGCTTGTGTGTTGCCGGCCAGGAATTCCAGGCTCACAAGGCTATCTTAGCAGCTCGTTCTC
CGGTTTTTAGTGCCATGTTTGAACATGAAATGGAGGAGAGCAAAAAGAATCGAGTTGAAATCAATGATGTGGAGCC
TGAAGTTTTTAAGGAAATGATGTGCTTCATTTACACGGGGAAGGCTCCAAACCTCGACAAAATGGCTGATGATTTG
CTGGCAGCTGCTGACAAGTATGCCCTGGAGCGCTTAAAGGTCATGTGTGAGGATGCCCTCTGCAGTAACCTGTCCG
TGGAGAACGCTGCAGAAATTCTCATCCTGGCCGACCTCCACAGTGCAGATCAGTTGAAAACTCAGGCAGTGGATTT
CATCAACTATCATGCTTCGGATGTCTTGGAGACCTCTTGGG 17186.1&2

TCGTAGCCATTTTTCTGCTTCTTTGGAGAATGACGCCACACTGACTGCTCATTGTCGTTGGTTCCATGCCAATTGG
TGAAATAGAACCTCATCCGGTAGTGGAGCCGGAGGGACATCTTGTCATCAACGGTGATGGTGCGATTTGGAGCATA
CCAGAGCTTGGTGTTCTCGCCATACAGGGCAAAGAGGTTGTGACAAAGAGGAGAGATACGGCATGCCTGTGCAGCC
CTGATGCACAGTTCCTCTGCTGTGTACTCTCCACTGCCCAGCCGGAGGGGCTCCCTGTCCGACAGATAGAAGATCA
CTTCCACCCCTGGCTTG 17187.1&2

TGGCACACTGCTCTTAAGAAACTATGAWGATCTGAGATTTTTTTGTGTATGTTTTTGACTCTTTTGAGTGGTAATC
ATATGTGTCTTTATAGATGTACATACCTCCTTGCACAAATGGAGGGGAATTCATTTTCATCACTGGGAGTGTCCTT
AGTGTATAAAAACCATGCTGGTATATGGCTTCAAGTTGTAAAAATGAAAGTGACTTTAAAAGAAAATAGGGGATGG
TCCAGGATCTCCACTGATAAGACTGTTTTTAAGTAACTTAAGGACCTTTGGGTCTACAAGTATATGTGAAAAAAAT
GAGACTTACTGGGTGAGGAAATTCATTGTTTAAAGATGGTCGTGTGTGTGTGTGTGTGTGTGTGTGTTGTGTTGTG
TTTTGTTTTTTAAGGGAGGGAATTTATTATTTACCGTTGCTTGAAATTACTGKGTAAATATATGTYTGATAATGAT
TTGCTYTTTGVCMACTAAAATTAGGVCTGTATAAGTWCTARATGCMTCCCTGGGKGTTGATYTTCCMAGATATTGA
TGATAMCCCTTAAAATTGTAACCYGCCTTTTTCCCTTTGCTYTCMATTAAAGTCTATTCMAAAG 17191.1&89.1

GGGGGTAGGCTCTTTATTAGACGGTTATTGCTGTACTACAGGGTCAGAGTGCAGTGTAAGCAGTGTCAGAGGCCCG
CGTTCAGCCCAAGAATGTGGATTTTCTCTCCCTATTGATCACAGTGGGTGGGTTTCTTCAGAAAAGCCCCAGAGGC
AGGGACCAGTGAGCTCCAAGGTTAGAAGTGGAACTGGAAGGCTTCAGTCACATGCTGCTTCCACGCTTCCAGGCTG
GGCAGCAAGGAGGAGATGCCCATGACGTGCCAGGTCTCCCCATCTGACACCAGTGAAGTCTGGTAGGACAGCAGCC
GCACGCCTGCCTCTGCCAGGAGGCCAATCATGGTAGGCAGCATTGCAGGGTCAGAGGTCTGAGTCCGGAATAGGAG
CAGGGGCAGGTCCCTGCGGAGAGGCACTTCTGGCCTGAAGACAGCTCCATTGAGCCCCTGCAGTACAGGYGTAGTG
CCTTGGACCAAGCCCACAGCCTGGTAAGGGGCGCCTGCCAGGGCCACGGCCAGGAGGCA

TAATTTCTTAGTCGTTTGGAATCCTTAAGCATGCAAAAGCTTTGAACAGAAGGGTTCACAAAGGAACCAGGGTTGT
CTTATGGCATCCAGTTAAGCCAGAGCTGGGAATGCCTCTGGGTCATCCACATCAGGAGCAGAAGCACTTGACTTGT
CGGTCCTGCTGCCACGGTTTGGGCGCCCACCACGCCCACGTCCACCTCGTCCTCCCCTGCCGCCACGTCCTGGGCG
GCCAAGGTCTCCAAAATTGATCTCCAGCTGAGACGTTATATCATTTGCTGGCTTCCGGAAATGATGGTCCATAACC
GAATCTTCAGCATGAGCCTCTTCACTCTTTGATTTATGAAGAACAAATCCCTTCTTCCACTGCCCATCAGCACCTT
CATTTGGTTTTCGGATATTAAATTCTACTTTTGCCCGGTCCTTATTTTGAATAGCCTTCCACTCATCCAAAGTCAT
CTCTTTTGGACCCTCCTCTTTTACCTCTTCAACTTCATTCTCCTTATTTTCAGTGTCTGCCACTGGATGATGTTCT
TCACCTTCAGGTGTTTCCTCAGTCACATTTGATTGATCCAAGTCAGTTAATTCGTCTTTGACAGTTCCCCAGTTGT
GAGATCCGCTACCTCCACGTTTGTCCTCGTGCTTCAGGCCAGATCTATCACTTCCACTATGCCTATCAAATTCACG
TTTGCCACGAGAATCAAATCCATCTCCTCGGCCCATTCCACGTCCACGGCCCCCTCGACCTCTTCCAAGACCACCA
CGACCTCGAATAGGTCGGTCAATAATCGGTCTATCAACTGAAAATTCGCCTCCTTCACCCTTTTCTTCAAGTGGCT
TTTCGAATCTTCGTTCACGAGGTGGTCGCCTTTCTGGTCTTCTATCAATTATTTTCCCTTCACCCTGAAGTTGTTG
ATCAGGTCTTCTTCCAACTCGTGC

17193

AAGCGGATGGACCTGAGTCAGCCGAATCCTAGCCCCTTCCCTTGGGCCTGCTGTGGTGCTCGACATCAGTGACAGA
CGGAAGCAGCAGACCATCAAGGCTACGGGAGGCCCGGGGCGCTTGCGAAGATGAAGTTTGGCTGCCTCTCCTTCCG
GCAGCCTTATGCTGGCTTTGTCTTAAATGGAATCAAGACTGTGGAGACGCGCTGGCGTCCTCTGCTGAGCAGCCAG
CGGAACTGTACCATCGCCGTCCACATTGCTCACAGGGACTGGGAAGGCGATGCCTGTCGGGAGCTGCTGGTGGAGA
GACTCGGGATGACTCCTGCTCAGATTCAGGCCTTGCTCAGGAAAGGGGAAAAGTTTGGTCGAGGAGTGATAGCGGG
ACTCGTTGACATTGGGGAAACTTTGCAATGCCCCGAAGACTTAACTCCCGATGAGGTTGTGGAACTAGAAAATCAA
GCTGCACTGACCAACCTGAAGCAGAAGTACCTGACTGTGATTTCAAACCCCAGGTGGTTACTGGAGCCCATACCTA
GGAAAGGAGGCAAGGATGTATTCCAGGTAGACATCCCAGAGCACCTGATCCCTTTGGGGCATGAAGTGTGACAAGT
GTGGGCTCCTGAAAGGAATGTTCCRGAGAAACCAGCTAAATCATGGCACCTTCAATTTGCCATCGTGACGCAGACC
TGTATAAATTAGGTTAAAGATGAATTTCCACTGCTTTGGAGAGTCCCACCCACTAAGCACTGTGCATGTAAACAGG
TTCCTTTGCTCAGATGAAGGAAGTAGGGGGTGGGGCTTTCCTTGTGTGATGCCTCCTTAGGCACACAGGCAATGTC
TCAAGTACTTTGACCTTAGGGTAGAAGGCAAAGCTGCCAGTAAATGTCTCAGCATTGCTGCTAATTTTGGTCCTGC
TAGTTTCTGGATTGTACAAATAAATGTGTTGTAGATGA

*Fig. 15U*

16443.1.edit

TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGTACACCTGTGGTTCTCGGGGCTGCCCTTTGGCTTTGGAGATGGTTTTCT
CGATGGGGGCTGGGAGGGCTTTGTTGGAGACCTTGCACTTGTACTCCTTGCCATTCAACCAGTCCTGGTGCANGAC
GGTGAGGACGCTNACCACACGGTACGNGCTGGTGTACTGCTCCTCCCGCGGCTTTGTCTTGGCATTATGCACCTCC
ACGCCGTCCACGTACCAATTGAACTTGACCTCAGGGTCTTCGTGGCTCACGTCCACCACCACGCATGTAACCTCAA
ANCTCGGNCGCGANCACGC 16443.2.edit AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GTGTGGTCAGCGTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAGCCCCGAGAACCACAGGTGTACACCCTG
CCCCCATCCCGGGAGGAGATGACCAAGAACCAGGTCAGCCTGACCTGCCTGGTCAAAGGCTTCTATCCCAGCGACA
TCGCCCGTGGAGTGGGAGAGCAATGGGCAGCCGGAGAACAACTACAAGACCACGCCTCCCGTGCTGGACTCCGACA
CCTGCCGGGCGGCCGCTCGA 16444.2.edit AGCGTGGTTNCGGCCGAGGTCCCAACCAAGGCTGCANCCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGGGCGGNCGCTCGA 16445.1.edit AGCGTGGTCGCGGCCGAGGTCAAGAACCCCGCCCGCACCTGCCGTGACCTCAAGATGTGCCACTCTGACTGGAAGA
GTGGAGAGTACTGGATTGACCCCAACCAAGGCTGCAACCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGGGCGGCCGCTCGA

*Fig. 15V*

16445.2.edit

TCGAGCGGTCGCCCGGGCAGGTCCACATCGGCAGGGTCGGAGCCCTGGCCGCCATACTCGAACTGGAATCCATCGG
NCATGCTCTCGCCGAACCAGACATGCCTCTTGNCCTTGGGGTTCTTGCTGATGTACCAGNTCTTCTGGGCCACACT
GGGCTGAGTGGGGTACACGCAGGTCTCACCANTCTCCATGTTGCANAAGACTTTGATGGCATCCAGGTTGCAGCCT
TGGTTGGGGTCAATCCAGTACTCTCCACTCTTCCAGACAGAGTGGCACATCTTGAGGTCACGGCAGGTGCGGGCGG
GGTTCTTGACCTCGGTCGCGACCACGCT 16446.1.edit TCGAGCGGCCGCCCGGGCAGGTCCTCCTCAGAGCGGTAGCTGTTCTTATTGCCCCGGCAGCCTCCATAGATNAAGT
TATTGCANGAGTTCCTCTCCACGTCAAAGTACCAGCGTGGGAAGGATGCACGGCAAGGCCCAGTGACTGCGTTGGC
GGTGCAGTATTCTTCATAGTTGAACATATCGCTGGAGTGGACTTCAGAATCCTGCCTTCTGGGAGCACTTGGGACA
GAGGAATCCGCTGCATTCCTGCTGGTGGACCTCGGCCGCGACCACGCT 16446.2.edit AGCGTGGTCGCGGCCGAGGTCCACCAGCAGGAATGCAGCGGATTCCTCTGTCCCAAGTGCTCCCAGAAGGCAGGAT
TCTGAAGACCACTCCAGCGATATGTTCAACTATGAAGAATACTGCACCGCCAACGCAGTCACTGGGCCTTGCCGTG
CATCCTTCCCACGCTGGTACTTTGACGTGGAGAGGAACTCCTGCAATAACTTCATCTATGGAGGCTGCCGGGGCAA
TAAGAACAGCTACCGCTCTGAGGAGGACCTGCCCGGGCGGCCGCTCGA 16447.1.edit TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGCCAGAATGGCACATCTTGAGGTCACGGCANGTGCGGGCGG
GGTTCTTGACCTCGGCCGCGACCACGCT

*Fig. 15W*

16447.2.edit

AGCGTGGTCGCGGCCGAGGTCAAGAAACCCCGCCCGCACCTGCCGTGACCTCAAGATGTGCCACTCTGGCTGGAAG
AGTGGAGAGTACTGGATTGACCCCAACCAAGGCTGCAACCTGGATGCCATCAAAGTCTTCTGCAACATGGAGACTG
GTGAGACCTGCGTGTACCCCACTCAGCCCAGTGTGGCCCAGAAGAACTGGTACATCAGCAAGAACCCCAAGGACAA
GAGGCATGTCTGGCTCGGCGAGAGCATGACCGATGGATTCCAGTTCGAGTATGGCGGCCAGGGCTCCGACCCTGCC
GATGTGGACCTGCCCGGGCGGCCGCTCGA 16449.1.edit AGCGTGGTCGCGGCCGAGGTCCTGTCAGAGTGGCACTGGTAGAAGNTCCAGGAACCCTGAACTGTAAGGGTTCTTC
ATCAGTGCCAACAGGATGACATGAAATGATGTACTCAGAAGTGTCCTGNAATGGGGCCCATGANATGGTTGNCTGA
GAGAGAGCTTCTTGTCCTACATTCGGCGGGTATGGTCTTGGCCTATGCCTTATGGGGGTGGCCGTTGNGGGCGGTG
NGGTCCGCCTAAAACCATGTTCCTCAAAGATCATTTGTTGCCCAACACTGGGTTGCTGACCANAAGTGCCAGGAAG
CTGAATACCATTTCCAGTGTCATACCCAGGGTGGGTGACGAAAGGGGTCTTTTGAACTGTGGAAGGAACATCCAAG
ATCTCTGNTCCATGAAGATTGGGGTGTGGAAGGGTTACCAGTTGGGGAAGCTCGCTGTCTTTTTCCTTCCAATCAN
GGGCTCGCTCTTCTGAATATTCTTCAGGGCAATGACATAAATTGTATATTCGGTTCCCGGTTCCAGGCCAG 16450.1.edit TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGANGAACATGGNTTT
AGGCGGACCACACCGGCCACAACGGGCACCCCCATAAGGCATAGGCCAAGAACATACCCGNCGAATGTAGGACAAG
AAGCTCTNTCTCANACAANCATCTCATGGGCCCCATTCCANGACACTTCTGAGTACATCANTTCATGGCATCCTGG
TGGCACTGATAAAAACCCTTACAGTTA 16450.2.edit AGCGTGGTCGCGGGCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
NGGGCTCGCTCTTCTGATTATTCTTCAGGGCAATGACATAAATTGTATATTCGGNTCCCGGGTNCAGCCAATAATA
ATAACCCTCTGTGACACCANGGCGGGGCCGAAGGANCACT

*Fig. 15X*

16451.1.edit

AGCGTGGTCGCGGCCGAGGTCCTCACCAGAGGTACCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTANGCTTTGGAAGTGGTCATTTCAGATGTGATTCATCTAGATGGTGCCATGACAATGGTG
TGAACTACAAGATTGGAGAGAAGTGGGACCGTCAGGGAGAAAATGGACCTGCCCGGGCGGCCGCTCGA 16451.2.edit TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGNTGACAGAGTTGCCCACGGTAACAACCTCTTCCCGAACCTTATGCCTCTGCTGG
TCTTTCAGTGCCTCCACTATGATGTTGTAGGTGGTACCTCTGGTGAGGACCTCGGCCGCGACCACGCT 16452.1.edit AGCGTGGCCGCGGCCGAGGTCCATTGGCTGGAACGGCATCAACTTGGAAGCCAGTGATCGTCTCAGCCTTGGTTCT
CCAGCTAATGGTGATGGNGGTCTCAGTAGCATCTGTCACACGAGCCCTTCTTGGTGGGCTGACATTCTCCAGAGTG
GTGACAACACCCTGAGCTGGTCTGCTTGTCAAAGTGTCCTTAAGAGCATAGACACTCACTTCATATTTGGCGNCCA
CCATAAGTCCTGATACAACCACGGAATGACCTGTCAGGAAC 16452.2.edit TCGAGCGGCCGCCCGGGCAGGTCCTCAGACCGGGTTCTGAGTACACAGTCAGTGTGGTTGCCTTGCACGATGATAT
GGAGAGCCAGCCCCTGATTGGAACCCAGTCCACAGCTATTCCTGCACCAACTGACCTGAAGTTCACTCAGGTCACA
CCCACAAGCCTGAGCGCCCAGTGGACACCACCCAATGTTCAGCTCACTGGATATCGAGTGCGGGTGACCCCCAAGG
AGAAGACCGGACCAATGAAAGAAATCAACCTTGCTCCTGACAGCTCATCCGTGGTTGTATCAGGACTTATGGCGGC
CACCAAATATGAAGTGAGTGTCTATGCTCTTAAGGACACTTTGACAAGCAGACCAGCTCAGGGTGTTGTCACCACT
CTGGAGAATGTCAGCCCACCAAGAAGGGCTCGTGTGACAGATGCTACTGAGACCACCATCACCATTAGCTGGAGAA
CCAAGACTGAGACGATCACTGGCTTCCAAGTTGATGCCGTTCCAGCCAATGGACCTCGGCCGCGACCACGCTT

*Fig. 15Y*

16453.1.edit

AGCGTGGTCGCGGCCGAGGTCTGGCCGAACTGCCAGTGTACAGGGAAGATGTACATGTTATAGNTCTTCTCGAAGT
CCCGGGCCAGCAGCTCCACGGGGTGGTCTCCTGCCTCCAGGCGCTTCTCATTCTCATGGATCTTCTTCACCCGCAG
CTTCTGCTTCTCAGTCAGAAGGTTGTTGTCCTCATCCCTCTCATACAGGGTGACCAGGACGTTCTTGAGCCAGTCC
CGCATGCGCAGGGGGAATTCGGTCAGCTCAGAGTCCAGGCAAGGGGGGATGTATTTGCAAGGCCCGATGTAGTCCA
AGTGGAGCTTGTGGCCCTTCTTGGTGCCCTCCAAGGTGCACTTTGTGGCAAAGAAGTGGCAGGAAGAGTCGAAGGT
CTTGTTGTCATTGCTGCACACCTTCTCAAACTCGCCAATGGGGGCTGGGCAGACCTGCCCGGGCGGCCGCTCGA 16453.2.edit TCGAGCGGCCGCCCGGGCAGGTCTGCCCAGCCCCCATTGGCGAGTTTGAGAAGGNGTGCAGCAATGACAACAAGAC
CTTCGACTCTTCCTGCCACTTCTTTGCCACAAAGTGCACCCTGGAGGGCACCAAGAAGGGCCACAAGCTCCACCTG
GACTACATCGGGCCTTGCAAATACATCCCCCCTTGCCTGGACTCTGAGCTGACCGAATTCCCCCTGCGCATGCGGG
ACTGGCTCAAGAACGTCCTGGTCACCCTGTATGAGAGGGATGAGGACAACAACCTTCTGACTGAGAAGCANAAGCT
GCGGGTGAAGAANATCCATGAGAATGANAAGCGCCTGNAGGCANGAGACCACCCCGTGGAGCTGCTGGCCCGGGAC
TTCGAGAAGAACTATAACATGTACATCTTCCCTGTACACTGGCAGTTCGGCCAGACCTCGGCCGCGACCACGCT 16454.1.edit AGCGTGGNTGCGGACGACGCCCACAAAGCCATTGTATGTAGTTTTANTTCAGCTGCAAANAATACCNCCAGCATCC
ACCTTACTAACCAGCATATGCAGACA 16454.2.edit TCGAGCGGTCGCCCGGGCAGGTCTGGGCGGATAGCACCGGGCATATTTTGGAATGGATGAGGTCTGGCACCCTGAG
CAGCCCAGCGAGGACTTGGTCTTAGTTGAGCAATTTGGCTAGGAGGATAGTATGCAGCACGGTTCTGAGTCTGTGG
GATAGCTGCCATGAAGNAACCTGAAGGAGGCGCTGGCTGGTANGGGTTGATTACAGGGCTGGGAACAGCTCGTACA
CTTGCCATTCTCTGCATATACTGGNTAGTGAGGCGAGCCTGGCGCTCTTCTTTGCGCTGAGCTAAAGCTACATACA
ATGGCTTTGNGGACCTCGGCCGCGACCACGCTT

*Fig. 15Z*

16455.1.edit

TCGAGCGGCCGCCCGGGCAGGTCCATTTTCTCCCTGACGGTCCCACTTCTCTCCAATCTTGTAGTTCACACCATTG
TCATGACACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAAGTTGCCCACGGTAACAACCTCTTCCCGAACCTTATGCCTCTGCTG
GTCTTTCAAGTGCCTCCACTATGATGTTGTAGGTGGCACCTCTGGTGAGGACCTCGGCCGCGACCACGCT 16455.2.edit AGCGTGGTTTGCGGCCGAGGTCCTCACCANAGGTGCCACCTACAACATCATAGTGGAGGCACTGAAAGACCAGCAG
AGGCATAAGGTTCGGGAAGAGGTTGTTACCGTGGGCAACTCTGTCAACGAAGGCTTGAACCAACCTACGGATGACT
CGTGCTTTGACCCCTACACAGNTTCCCATTATGCCGTTGGAGATGAGTGGGAACGAATGTCTGAATCAGGCTTTAA
ACTGTTGTGCCAGTGCTTANGCTTTGGAAGTGGTCATTTCAGATGTGATTCATCTANATGGTGTCATGACAATGGT
GNGAACTACAAGATTGGAGAGAAGTGGNACCGTCAGGGGANAAAATGGACCTGCCCGGGCGGCNCGCTCGA 16456.1.edit AGCGTGGTCGCGGCCGAGGTCTGGCTTNCTGCTCANGTGATTATCCTGAACCATCCAGGCCAAATAAGCGCCGGCT
ATGCCCCTGNATTGGATTGCCACACGGCTCACATTGCATGCAAGTTTGCTGAGCTGAAGGAAAAGATTGATC 16456.2.edit TCGAGCGGCCGCCCGGGCAGGTCCAATTGAAACAAACAGTTCTGAGACCGTTCTTCCACCACTGATTAAGAGTGGG
GNGGCGGGTATTAGGGATAATATTCATTTAGCCTTCTGAGCTTTCTGGGCAGACTTGGTGACCTTGCCAGCTCCAG
CAGCCTTCTGGTCCACTGCTTTGATGACACCCACCGCAACTGTCTGTCTCATATCACGAACAGCAAAGCGACCCAA
AGGTGGATAGTCTGAGAAGCTCTCAACACACATGGGCTTGCCAGGAACCATATCAACAATGGGCAGCATCACCAGA
CTTCAAGAATTTAAGGGCCATCTTCCAGCTTTTTACCAGAACGGCGATCAATCTTTTCCTTCAGCTCAGCAAACTT
GCATGCAATGTGAGCCG

*Fig. 15AA*

16459.1.edit

```
TCGAGCGGCCGCCCGGGCAGGTCCAGAGGGCTGTGCTGAAGTTTGCTGCTGCCACTGGAGCCACTCCAATTGCTGG
CCGCTTCACTCCTGGAACCTTCACTAACCAGATCCAGGCAGCCTTCCGGGAGCCACGGCTTCTTGTGGNTACTGAC
CCCAGGGCTGACCACCAGCCTCTCACGGAGGCATCTTATGTTAACCTACCTACCATTGCGCTGTGTAACACAGATT
CTCCTCTGCGCTATGTGGACATTGCCATCCCATGCAACAACAAGGGAGCTCACTCAGNGGGGTTTGATGTGGTGGA
TGCTGGCTCGGGAAGTTCTGCGCATGCGTGGCACCATTTCCCGTGAACACCCATGGGANGNCATGCCTGATCTGGA
CTTCTACAGAGATCCTGAAGAGATTGAAAAAGAAGAACAGGCTGNTTGCTGANAAAGCAAGTGACCAAGGANGAAA
TTTCANGGGTGAAANGGACTGCTCCCGCTCCTGAATTCACTGCTACTCAACCTGANGNTGCAGACTGGTCTTGAAG
GNGNACANGGGCCCTCTGGGCCTATTTAAGCANCTTCGGTCGCGAACACGNT
```

16459.2.edit

```
AGCGTGNGTCGCGGCCGAGGTGCTGAATAGGCACAGAGGGCACCTGTACACCTTCAGACCAGTCTGCAACCTCAGG
CTGAGTAGCAGTGAACTCAGGAGCGGGAGCAGTCCATTCACCCTGAAATTCCTCCTTGGNCACTGCCTTCTCAGCA
GCAGCCTGCTCTTCTTTTTCAATCTCTTCAGGATCTCTGTAGAAGTACAGATCAGGCATGACCTCCCATGGGTGTT
CACGGGAAATGGTGCCACGCATGCGCAGAACTTCCCGAGCCAGCATCCACCACATCAAACCCACTGAGTGAGCTCC
CTTGTTGTTGCATGGGATGGGCAATGTCCACATAGCGCAGAGGAGAATCTGTGTTACACAGCGCAATGGTAGGTAG
GTTAACATAAGATGCCTCCGCGAGAAGCTGGTGGTCAGCCCTGGGGTCAAGTAACCACAAGAAGCCGTGGCTCCCG
GAAGGCTGCCTGGATCTGGTTAGTGAAGGNTCCAGGAGTGAAGCGGCCAACAATTGGAGTGGCTTCAGTGGCAAGC
AGCAAACTTCAGCACAAGCCCTCTGGACCTGCCCGGCGGCCGCTCGA
```

16460.1.edit

```
TCGAGCGGCCGCCCGGGCAGGTCCATTTTCTCCCTGACGGNCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCNTCCCCGAACCTTATGCCTCTGCTG
GGCTTTCAGNGCCTCCACTATGATGNTGTAGGGGGGCACCTCTGGNGANGACCTCGGCCGCGACCACGCT
```

16460.2.edit

```
AGCGTGGTCGCGGCCGAGGTCCTCACCAGAGGTGCCACCTACAACATCATAGTGGAGGCACTGAAAGACCAGCAGA
GGCATAAGGCTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTANGCTTTGGAAGTGGGTCATTTCAGATGTGATTCATCTAGATGGTGCCATGACAATGGN
GNGAACTACAAGATTGGAGAGAAGTGGNACCGNCAGGGAGAAAATGGACCTGCCCGGGCGGCCGCTCGA
```

*Fig. 15BB*

16461.1.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGNTGCAACCTTG
GTTGGGGTCAATCCAGTACTCTCCACTCTTCCAGCCAGAGTGGCACATCTTGAGGTCACGGCAGGTGCGGNCGGGG
GNTTTTGCGGCTGCCCTCTGGNCTTCGGNTGTNCTCNATCTGCTGGCTCA 16461.2.edit TCGAGCGGCCGCCCGGGCAGGTCTCGCGGTCGCACTGGTGATGCTGGTCCTGTTGGTCCCCCCGGCCCTCCTGGAC
CTCCTGGCCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTGAGCCAGCAGATCGAGAACATCCGGAGCCCAGAGGGCAGNCGCAAGAACCCCGCCCGCACCTGCCGTG
ACCTCAAGATGTGCCACTCTGACTGGAAGAGTGGAGAGTACTGGATTGACCCCAACCAAGCTGCAACCTGGATGCC
ATCAAAGTCTTCTGCAACATGGAGACTGGTGAGACCTGCGTGTACCCCACTCAGCCCAGTGTGGCCCAAAAGAACT
GGTACATCAGCAAGAACCCCAAGGACAAGAAGCATGTCTGGTTCGGCGAGAACATGACCGATGGATTCCAGTTCGA
GTATGGCGGGCAGGGCTCCGACCCTGCCGATGGGGACCTTGGCCGCGAACACGCT 16463.1.edit AGCGTGGNNGCGGCCGAGGTATAAATATCCAGNCCATATCCTCCCTCCACACGCTGANAGATGAAGCTGTNCAAAG
ATCTCAGGGTGGANAAAACCAT 16463.2.edit TCGAGCGGCCGCCCGGGCAGGTCCTTCAGACTTGGACTGTGTCACACTGCCAGGCTTCCAGGGCTCCAACTTGCAG
ACGGCCTGTTGTGGGACAGTCTCTGTAATCGCGAAAGCAACCATGGAAGACCTGGGGGAAAACACCATGGTTTTAT
CCACCCTGAGATCTTTGAACAACTTCATCTCTCAGCGTGCGGAGGGAGGCTCTGGACTGGATATTTCTACCTCGGC
CGCGACCACGCT

*Fig. 15CC*

16464.1.edit

CGAGCGGGCGACCGGGCAGGTNCAGACTCCAATCCANANAACCATCAAGCCAGATGTCAGAAGCTACACCATCACA
GGTTTACAACCAGGCACTGACTACAAGANCTACCTGCACACCTTGAATGACAATGCTCGGAGCTCCCCTGTGGTCA
TCGACGCCTCCACTGCCATTGATGCACCATCCAACCTGCGTTTCCTGGCCACCACACCCAATTCCTTGCTGGTATC
ATGGCAGCCGCCACGTGCCAGGATTACCGGTACATCATCNAGTATGANAAGCCTGGGCCTCCTCCCAGAGAAGNGG
TCCCTCGGCCCCGCCCTGNTGTCCCANAGGNTACTATTACTGNGCCNGCAACCGGCAACCGATATCNATTTTGNCA
TTGGCCTTCAACAATAATTA 16464.2.edit AGCGTGGTTCGCGGCCGANGTCCTGTCAGAGTGGCACTGGTAGAAGTTCCAGGAACCCTGAACTGTAAGGGTTCTT
CATCAGNGCCAACAGGATGACATGAAATGATGTACTCAGAAGTGTCCTGGAATGGGGCCCATGAGATGGTTGTCTG
AGAGAGAGCTTCTTGNCCTGTCTTTTTCCTTCCAATCAGGGGCTCGCTCTTCTGATTATTCTTCAGGGCAATGACA
TAAATTGTATATTCGGGTCCCGGNTCCAGGCCAGTAATAGTANCCTCTGTGACACCAGGGCGGNGCCGAGGGACCA
CTTCTCTGGGAGGAGACCCAGGCTTCTCATACTTGATGATGTAACCGGTAATCCTGGCACGTGGCGGCTGCCATGA
TACCAGCAAGGAATTGGGGTGTGGTGGCCAGGAAACGCAGGTTGGATGGNGCATCAATGGCAGTGGAGGCCGTCGA
TGACCACAGGGGGAGCTCCGACATTGTCATTCAAGGTG 16465.1.edit AGCGTGGNCGCGGCCGAGGTGCAGCGCGGGCTGTGCCACCTTCTGCTCTCTGCCCAACGATAAGGAGGGTNCCTGC
CCCCAGGAGAACATTAACTNTCCCCAGCTCGGCCTCTGCCGG 16465.2.edit TCGAGCGGCCGCCCGGGCAGGTTTTTTTTGCTGAAAGTGGNTACTTTATTGGNTGGGAAAGGGAGAAGCTGTGGTC
AGCCCAAGAGGGAATACAGAGNCCCGAAAAAGGGGAGGGCAGGTGGGCTGGAACCAGACGCAGGGCCAGGCAGAAA
CTTTCTCTCCTCACTGCTCAGCCTGGTGGTGGCTGGAGCTCANAAATTGGGAGTGACACAGGACACCTTCCCACAG
CCATTGCGGCGGCATTTCATCTGGCCAGGACACTGGCTGTCCACCTGGCACTGGTCCCGACAGAAGCCCGAGCTGG
GGAAAGTTAATGTTCACCTGGGGGCAGGAACCCTCCTTATCATTGNGCAGAGAGCAGAAGGTGGCACAGCCCGCGC
TGCACCTCGGCCGCGACCACGCT 16466.2.edit TCGAGCGGCCGCCCGGGCAGGTCCACCATAAGTCCTGATACAACCACGGATGAGCTGTCAGGAGCAAGGTTGATTT
CTTTCATTGGTCCGGNCTTCTCCTTGGGGGNCACCCGCACTCGATATCCAGTGAGCTGAACATTGGGTGGCGTCCA
CTGGGCGCTCAGGCT 16467.2.edit TCGAGCGGTTCGCCCGGGCAGGTCCACCACACCCAATTCCTTGCTGGTATCATGGCAGCCGCCACGTGCCAGGATT
ACCGGCTACATCATCAAGTATGAGAAGCCTGGGTCTCCTCCCAGAGAAGCGGTCCCTCGGCCCCGCCCTGGTGTCA
CAGAGGCTACTATTACTGGCCTGGAACCGGGAACCGAATATACAATTTATGTCATTGNCCTGAAGAATAATCANNA
ANAGCGANCCCCTGATTGGAAGGA

*Fig. 15DD*

01_16469.edit

AGCGTGGTCGCGGCCGAGGTTGTACAAGCTTTTTTTTTTTTTTTTTTTTTTTTTTTTTTTTTTTTTTTTTTTTTT
TTTTTTTTTTTTTTT

02_16469.edit

TCGAGCGGNCGCCCGGGCAGGTCTGCCAACACCAAGATTGGCCCCCGCCGCATCCACACAGTCCGTGTGCGGGGAG
GTAACAAGAAATACCGTGCCCTGAGGTTGGACGTGGGGAATTTCTCCTGGGGCTCAGAGTGTTGTACTCGTAAAAC
AAGGATCATCGATGTTGTCTACAATGCATCTAATAACGAGCTGGTTCGTACCAAGACCCTGGTGAAGAATTGCATC
GTGCTCATCGACAGCACACCGTACCGACAGTGGTACGAGTCCCACTATGCGCTGCCCCTGGGCCGCAAGAAGGGAG
CCAAGCTGACTCCTGAGGAAGAAGAGATTTTAAACAAAAAACGATCTAANAAAAAAAAAACAAT

03_16470.edit

AGCGTGGTCGCGGCCGAGGTGAAATGGTATTCAGCTTCCTGGCACTTCTGGTCAGCAACCCAGTGTTGGGCAACAA
ATGATCTTTGAGGAACATGGTTTTAGGCGGACCACACCGCCCACAACGGCCACCCCCATAAGGCATAGGCCAAGAC
CATACCCGCCGAATGTAGGACAAGAAGCTCTCTCTCAGACAACCATCTCATGGGCCCCATTCCAGGACACTTCTGA
GTACATCATTTCATGTCATCCTGTTGGCACTGATGAAGAACCCTTACAGTTCAGGGTTCCTGGAACTTCTACCAGT
GCCACTCTGACAGGACCTGCCCGGGCGGCCGCTCGA

04_16470.edit

TCGAGCGGCCGCCCGGGCAGGTCCTGTCAGAGTGGCACTGGTAGAAGTTCCAGGAACCCTGAACTGTAAGGGTTCT
TCATCAGTGCCAACAGGATGACATGAAATGATGTACTCAGAAGTGTCCTGGAATGGGGCCCATGAGATGGTTGTCT
GAGAGAGAGCTTCTTGTCCTACATTCGGCGGGTATGGTCTTGGCCTATGCCTTATGGGGGTGGCCGTTGTGGGCGG
TGTGGTCCGCCTAAAACCATGTTCCTCAAAGATCATTTGTTGCCCAACACTGGGTTGCTGACCAGAAGTGCCAGGA
AGCTGAATACCATTTCACCTCGGCCGCGACCACGCTA

05_16471.edit

TCGAGCGGCCGCCCGGGCAGGTCTCCCTTCTTGCGGCCCAGGGGCAGCGCATAGTGGGACTCGTACCACTGTCGGT
ACGGTGTGCTGTCGATGAGCACGATGCAATTCTTCACCAGGGTCTTGGTACGAACCAGCTCGTTATTAGATGCATT
GTAGACAACATCGATGATCCTTGTTTTACGAGTACAACACTCTGAGCCCCAGGAGAAATTCCCCACGTCCAACCTC
AGGGCACGGTATTTCTTGTTACCTCCCCGCACACGGACTGTGTGGATGCGGCGGGGGCCAAGCTGACTCCTGAGGA
AGAAGAGATTTTAAACAAAAAACGATCTAAAAAAATTCAGAAGAAATATGATGAAAGGAAAAAGAATGCCAAAATC
AGCAGTCTCCTGGAGGAGCAGTTCCAGCAGGGCAAGCTTCTTGCGTGCATCGCTTCAAGGCCGGGACAGTGTGACC
GAGCAGATGGCTATGTGCTAGAGGGCAAAGAAGTGGAGTTCTATCTTAAGAAAATCAGGGCCCAGAATGGTGNGTC
TTCAACTAATCCAAAGGGGAGTTTCAGACCAGTGCAATCAGCAAAAACATTGATACTGNTGGCCAAATTTATTGGT
GCAGGGCTTGCACANTANGANNGGCTGGGTCTTGGGGCTTGGATTGGNACAAGCTTTGGCAGCCTTTTCTTTGGTT
TTGCCAAAAACCTTTTGNTGAAGANGANACCTNGGGCGGACCCCTTAACCGATTCCACNCCNGGNGGCGTTCTANG
GNCCCNCTTG

*Fig. 15EE*

06_16471.edit

AGCGTGGTCGCGGCCGAGGTCTGCTGCTTCAGCGAAGGGTTTCTGGCATAACCAATGATAAGGCTGCCAAAGACTG
TTCCAATACCAGCACCAGAACCAGCCACTCCTACTGTTGCAGCACCTGCACCAATAAATTTGGCAGCAGTATCAAT
GTCTCTGCTGATTGCACTGGTCTGAAACTCCCTTTGGATTAGCTGAGACACACCATTCTGGGCCCTGATTTTCCTA
AGATAGAACTCCAACTCTTTGCCCTCTAGCACATAGCCATCTGCTCGGTCACACTGTCCCGGCCTTGAAGCGATGC
ACGCAAGAAGCTTGCCCTGCTGGAACTGCTCCTCCAGGAGACTGCTGATTTTGGCATTCTTTTTCCTTTCATCATA
TTTCTTCTGAATTTTTTTAGATCGTTTTTTGTTTAAAATCTCTTCTTCCTCAGGAGTCAGCTTGGCCCCCGCCGCA
TCCACACAGTCCGTGTGCGGGGAGGTAACAAGAAATACCGTGCCCTGAGGTTGGACGTGGGGAATTTCTCCTGGGG
CTCAGAGTGGTGTACTCGTAAAACAAGGATCATCGATGGTGNCTACAATGCATCTAATAACGAGCTGGGTCGGACC
CAAAGAACCTGGNGAANAAATGGATCGNCTCATCGACAGGACACCGTACCCGACAGGGGNACGANTCCCACTATGC
GCTTGCCCCTGGGCCGCAANAAAGGAAAACTGCCCGGGCGGCCNTCGAAAGCCCAATTNTGGAAAAAATCCATCAC
ACTGGGNGGCCNGTCGAGCATGCATNTANAGGGGCCCATTCCCCCTNANN

07_16472.edit

TCGAGCGGCCGCCCGGGCAGGTCCCCAACCAAGGCTGCAACCTGGATGCCATCAAAGTCTTCTGCAACATGGAGAC
TGGTGAGACCTGCGTGTACCCCACTCAGCCCAGTGTGGCCCAGAAGAACTGGTACATCAGCAAGAACCCCAAGGAC
AAGAGGCATGTCTGGTTCGGCGAGAGCATGACCGATGGATTCCAGTTCGAGTATGGCGGCCAGGGCTCCGACCCTG
CCGATGTGGACCTCGGCCGCGACCACGCT

08_16472.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGACCTGCCCGGGCGGCCGCTCGA

09_16473.edit

TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGAGGAACATGGNTTT
AGGCGGACCACACCGCCCACAACGGCCACCCCCATAAGGCATAGGCCAAGACCATACCCGCCGAATGTAGGACAAG
AAGCTNTNTNTCANACACCATNTNATGGGCCCCATTCCAGGACACTTCTGAGTACATCATTTATGNCATCTGTGGC
ACTTGATGAAAACCCTTACAGTTCAGGGTTCTGGAACTTTTACCAGGCCTNTTACAGGACTNGGCCGGACNCCTTA
AGCCNATTNCACCCTGGGGCGTTCTANGGTCCCACTCGNNCACTGGNGAAAATGGCTACTGTN

*Fig. 15FF*

11_16474.edit

AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGNGAAACTCCNAGGACANGAGGGCTAAATTCCATGAAGTTTGTGGATGGCCTGATGATCCACAAT
CGGAGACCCTGTTAACTACTACCGTCTNACCNCCTGCTGTNCNCCCCCNTTTCTGCTNAANACATNGGGNTNNTNC
TTGNCCNTCCTTGGGTNGAANATNNAATNGCCTNCCCNTTCNTANCNCTACTNGNTCCANANTTGGCCTTTAAANA
ATCCNCCTTGCCTTNNNCACTGTTCANNTNTTTNNTCGTAAACCCTATNANTTNNATTANATNNTNNNNNNCTCAC
CCCCCTCNTCATTNANCCNATANGCTNNNAANTCCTTNANNCCTCCCNCCCNNTNCNCTCNTACTNANTNCTTCTN
NCCCATTACNNAGCTCTTTCNTTTAANATAATGNNGCCNNGCTCTNCATNTCTACNATNTGNNNAATNCCCCCNCC
CCCNANCGNNTTTTTGACCTNNNAACCTCCTTTCCTCTTCCCTNCNNAAATTNCNNANTTCCNCNTTCCNNCNTTT
CGGNTNNTCCCATNCTTTCCANNNCTTCANTCTANCNCNCTNCAACTTATTTTCCTNTCATCCCTTNTTCTTTACA
NNCCCCCTNNTCTACTCNNCNNTTNCATTANATTTGAAACTNCCACNNCTANTTNCCTCNCTCTACNNTTTTATTT
TNCGNTCNCTCTACNTAATANTTTAATNANTTNTCN

12_16474.edit

TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAAGCAGTGTCAACGTAGTAAGTTAACAGGGTCTCCGCTGTGGATCA
TCAGGCCATCCACAAACTTCATGGATTTAGCCCTCTGTCCTCGGAGTTTCCCAGACACCACAACCTCGCAGCCTTT
GGCCCCACTCTCCATGATGAACCGCAGCACACCATAGCAGGCCCTCCGCACAAGCAAGCCCTCCTAAGAATTTGTA
ACGCANANACTCTGCTGGCAATGGCACACAAACCTCTAGTGGACCTCGGNCGCGACCACGC

13_16475.edit

TCGAGCGGCCGCCCGGGCAGGTCTGGTCCAGGATAGCCTGCGAGTCCTCCTACTGCTACTCCAGACTTGACATCAT
ATGAATCATACTGGGGAGAATAGTTCTGAGGACCAGTAGGGCATGATTCACAGATTCCAGGGGGGCCAGGAGAACC
AGGGGACCCTGGTTGTCCTGGAATACCAGGGTCACCATTTCTCCCAGGAATACCAGGAGGGCCTGGATCTCCCTTG
GGGCCTTGAGGTCCTTGACCATTAGGAGGGCGAGTAGGAGCAGTTGGAGGCTGTGGGCAAACTGCACAACATTCTC
CAAATGGAATTTCTGGGTTGGGGCAGTCTAATTCTTGATCCGTCACATATTATGTCATCGCAGAGAACGGATCCTG
AGTCACAGACACATATTTGGCATGGTTCTGGCTTCCAGACATCTCTATCCGNCATAGGACTGACCAAGATGGGAAC
ATCCTCCTTCAACAAGCTTNCTGTTGTGCCAAAAATAATAGTGGGATGAAGCAGACCGAGAAGTANCCAGCTCCCC
TTTTTGCACAAAGCNTCATCATGTCTAAATATCAGACATGAGACTTCTTTGGGCAAAAAAGGAGAAAAAGAAAAAG
CAGTTCAAAGTANCCNCCATCAAGTTGGTTCCTTGCCCNTTCAGCACCCGGGCCCCGTTATAAAACACCTNGGGCC
GGACCCCCCTT

*Fig. 15GG*

14_16475.edit

AGCGTGGTCGCGGCCGAGGTGTTTTATGACGGGCCCGGTGCTGAAGGGCAGGGAACAACTTGATGGTGCTACTTTG
AACTGCTTTTCTTTTCTCCTTTTTGCACAAAGAGTCTCATGTCTGATATTTAGACATGATGAGCTTTGTGCAAAAG
GGGAGCTGGCTACTTCTCGCTCTGCTTCATCCCACTATTATTTTGGCACAACAGGAAGCTGTTGAAGGAGGATGTT
CCCATCTTGGTCAGTCCTATGCGGATAGAGATGTCTGGAAGCCAGAACCATGCCAAATATGTGTCTGTGACTCAGG
ATCCGTTCTCTGCGATGACATAATATGTGACGATCAAGAATTAGACTGCCCCAACCCAGAAATTCCATTTGGAGAA
TGTTGTGCAGTTTGCCCACAGCCTCCAACTGCTCCTACTCGCCCTCCTAATGGTCAAGGACCTCAAGGCCCCAAGG
GAGATCCAGGCCCTCCTGGTATTCCTGGGAGAAATGGTGACCCTGGTATTCCAGGACAACCAGGGTCCCCTGGTTC
TCCTGGCCCCCCTGGAATCNGGNGAATCATGCCCTACTGGTCCTCAAACTATTCTCCCANATGATTCATATGATGT
CAAGTCTGGGATAGCNAGTANGGANGGACTCGCAGGCTATTCTGGACCANACCTGCCGGGGGGGCGTTCGAAAGCC
CGAATCTGCANANNTNCNTTCACACTGGCGGCCGTCGAGCTGCTTTAAAAGGGCCATTCCNCCTTTAGNGNGGGGG
ANTACAATTACTNGGCGGCGTTTTANANCGCGNGNCTGGGAAAT

15_16476.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAGTGGCACATCTTGAGGTCACGGCAGGTGCGGGCGGGG
TTCTTGCGGCTGCCCTCTGGGCTCCGGATGTTCTCGATCTGCTGGCTCAGGCTCTTGAGGGTGGTGTCCACCTCGA
GGTCACGGTCACGAACCACATTGGCATCATCAGCCCGGTAGTAGCGGCCACCATCGTGAGCCTTCTCTTGANGTGG
CTGGGGCAGGAACTGAAGTCGAAACCAGCGCTGGGAGGACCAGGGGGACCAANAGGTCCAGGAAGGGCCCGGGGGG
GACCAACAGGACCAGCATCACCAAGTGCGACCCGCGAGAACCTGCCCGGCCGNCCGCTCGAA

16_16476.edit

TCGAGCGNNCGCCCGGGCAGGTCTCGCGGTCGCACTGGTGATGCTGGTCCTGTTGGTCCCCCCGGCCCTCCTGGAC
CTCCTGGTCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTGAGCCAGCAGATCGAGAACATCCGGAGCCCAGAGGGCAGCCGCAAGAACCCCGCCCGCACCTGCCGTG
ACCTCAAGATGTGCCACTCTGACTGGAAGAGTGGAGAGTACTGGATTGACCCCAACCAAGGCTGCAACCTGGATGC
CATCAAAGTCTTCTGCAACATGGAGACTGGTGAGACCTGCGTGTACCCCACTCAGCCCAGTGTGGCCCAGAAGAAC
TGGTACATCAGCAAGAACCCCAAGGACAAGAGGCATGTCTGGTTCGGCGAGAGCATGACCGATGGATTCCAGTTCG
AGTATGGCGGCCAGGGCTCCCACCCTGCCGATGTGGACCTCCGGCCGCGACCACCCTT

*Fig. 15HH*

17_16477.edit

TNGAGCGGCCGCCCGGGCAGGNTGNNAACGCTGGTCCTGCTGGTCCTCCTGGCAAGGCTGGTGAAGATGGTCACCC
TGGAAAACCCGGACGACCTGGTGAGAGAGGAGTTGTTGGACCACAGGGTGCTCGTGGTTTCCCTGGAACTCCTGGA
CTTCCTGGCTTCAAAGGCATTAGGGGACACAATGGTCTGGATGGATTGAAGGGACAGCCCGGTGCTCCTGGTGTGA
AGGGTGAACCTGGTGCCCCTGGTGAAAATGGAACTCCAGGTCAAACAGGAGCCCGTGGGCTTCCTGGTGAGAGAGG
ACCGTGTTGGTGCCCCTGGCCCANACCTCGGCCGCGACCACGCTAAGCCCGAATTTCCAGCACACTGGNGGCCGTT
ACTANTGGATCCGAGCTCGGTACCAAGCTTGGCGTAATCATGGTCATAGCTGTTTCCTGNGTGAAATTGTTATCCG
CTCACAATTTCACACANCATACGAAGCCGGAAAGCATAAAGTGTAAAGCCTTGGGGTGCTAATGAGTGAGCTAACT
CNCATTAAATTGCGTTGCGCTCACTGCCCGCTTTTCCANNNGGGAAACCNTGGCNTNGCCNGCTTGCNTTAANTGA
AATCCGCCNACCCCCGGGGAAAAGNCGGTTTGCNGTATTGGGGCNCTTTTTCCCTTTCCTCGGNTTACTTGANTTA
NTGGGCTTTGGNCGNTTCGGGTTGNGGCGANCNGGTTCAACNTCACNCCAAAGGNGGNAANACGGTTTTCCCANAA
TCCGGGGGNTANCCCAANGNAAAACATNNGNCNAANGGGCT

18_16477.edit

AGCGTGGTTNGCGGCCGAGGTCTGGGCCAGGGGCACCAACACGTCCTCTCTCACCAGGAAGCCCACGGGCTCCTGT
TTGACCTGGAGTTCCATTTTCACCAGGGGCACCAGGTTCACCCTTCACACCAGGAGCACCGGGCTGTCCCTTCAAT
CCATNCAGACCATTGTGNCCCCTAATGCCTTTGAAGCCAGGAAGTCCAGGAGTTCCAGGGAAACCACCGAGCACCC
TGTGGTCCAACAACTCCTCTCTCACCAGGTCGTCCGGGTTTTCCAGGGTGACCATCTTCACCAGCCTTGCCAGGAG
GACCAGCAGGACCAGCGTTACCAACCTGCCCGGGCGGCCGCTCGA

21_16479.edit

TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCTTCCCGAACCTTATGCCTCTGCTGG
TCTTTCAGTGCCTCCACTATGATGTTGTAGGTGGCACCTCTGGTGAGGACCTCGGCCGCGACCACGCT

22_16479.edit

AGCGTGGTCGCGGCCGAGGTCCTCACCAGAGGTGCCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTAGGCTTTGGAAGTGGTCATTTCAAGATGTGATTCATCTAGATGGTGCCATGACAATGGT
GTGAACTACAAGATTGGAGAGAAGTGGGACCGTCAGGGAGAAAATGGACCTGCCCGGGCCGGCCGCTCGA

*Fig. 15II*

24_16480.edit

TCGAGCGNNCGCCCGGGCAGGTCCAGTAGTGCCTTCGGGACTGGGTTCACCCCCAGGTCTGCGGCAGTTGTCACAG
CGCCAGCCCCGCTGGCCTCCAAAGCATGTGCAGGAGCAAATGGCACCGAGATATTCCTTCTGCCACTGTTCTCCTA
CGTGGTATGTCTTCCCATCATCGTAACACGTTGCCTCATGAGGGTCACACTTGAATTCTCCTTTTCCGTTCCCAAG
ACATGTGCAGCTCATTTGGCTGGCTCTATAGTTTGGGGAAAGTTTGTTGAAACTGTGCCACTGACCTTTACTTCCT
CCTTCTCTACTGGAGCTTTCGTACCTTCCACTTCTGCTGTTGGTAAAATGGTGGATCTTCTATCAATTTCATTGAC
AGTACCCACTTCTCCCAAACATCCAGGGAAATAGTGATTTCAGAGCGATTAGGAGAACCAAATTATGGGGCAGAAA
TAAGGGGCTTTTCCACAGGTTTTCCTTTGGAGGAAGATTTCAGTGGTGACTTTAAAAGAATACTCAACAGTGTCTT
CATCCCCATAGCAAAAGAAGAAACNGTAAATGATGGAANGCTTCTGGAGATGCCNNCATTTAAGGGACNCCCAGAA
CTTCACCATCTACAGGACCTACTTCAGTTTACANNAAGNCACATANTCTGACTCANAAAGGACCCAAGTAGCNCCA
TGGNCAGCACTTTNAGCCTTTCCCCTGGGGAAAANNTTACNTTCTTAAANCCTNGGCCNNGACCCCCTTAAGNCCA
AATTNTGGAAAANTTCCNTNCNNCTGGGGGGCNGTTCNACATGCNTTTNAAGGGCCCAATTNCCCCNT

25_16481.edit

TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGTACACCTGTGGTTCTCGGGGCTGCCCTTTGGCTTTGGAGATGGTTTTCT
CGATGGGGGCTGGGAGGGCTTTGTTGGAGACCTTGCACTTGTACTCCTTGCCATTCAGCCAGTCCTGGTGCAGGAC
GGTGAGGACGCTGACCACACGGTACGTGCTGTTGTACTGCTCCTCCCGCGGCTTTGTCTTGGCATTATGCACCTCC
ACGCCGTCCACGTACCAGTTGAACTTGACCTCAGGGTCTTCGTGGCTCACGTCCACCACCACGCATGTAACCTCAG
ACCTCGGCCGCGACCACGCT

26_16481.edit

AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GTGTGGTCAGCGTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAAGCCCCGAGAACCACAGGTGTACACCCT
GCCCCCATCCCGGGAGGAGATGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCCGTGCTGGACTCCGACA
CCTGCCCGGGCGGCCGCTCGA

27_16482.edit

TCGAGCGGCCGCCCGGGCAGGTTGAATGGCTCCTCGCTGACCACCCCGGTGCTGGTGGTGGGTACAGAGCTCCGAT
GGGTGAAACCATTGACATAGAGACTGTCCCTGTCCAGGGTGTAGGGGCCCAGCTCAGTGATGCCGTGGGTCAGCTG
GCTCAGCTTCCAGTACAGCCGCTCTCTGTCCAGTCCAGGGCTTTTGGGGTCAGGACGATGGGTGCAGACAGCATCC
ACTCTGGTGGCTGCCCCATCCTTCTCAGGCCTGAGCAAGGTCAGTCTGCAACCAGAGTACAGAGAGCTGACACTGG
TGTTCTTGAACAAGGGCATAAGCAGACCCTGAAGGACACCTCGGCCGCGACCACGCT

*Fig. 15JJ*

28_16482.edit
```
AGCGTGGTCGCGGCCGAGGTGTCCTTCAGGGTCTGCTTATGCCCTTGTTCAAGAACACCAGTGTCAGCTCTCTGTA
CTCTGGTTGCAGACTGACCTTGCTCAGGCCTGAGAAGGATGGGGCAGCCACCAGAGTGGATGCTGTCTGCACCCAT
CGTCCTGACCCCAAAAGCCCTGGACTGGACAGAGAGCGGCTGTACTGGAAGCTGAGCCAGCTGACCCACGGCATCA
CTGAGCTGGGCCCCTACACCCTGGACAGGGACAGTCTCTATGTCAATGGTTTCACCCATCGGAGCTCTGTACCCAC
CACCAGCACCGGGGTGGTCAGCGAGGAGCCATTCAACCTGCCCGGGCGGCCGCTCGA
```

29_16483.edit
```
AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
GGGGCTCGCTCTTCTGATTATTCTTCAGGGCAATGACATAAATTGTATATTCGGTCCCGGTTCCAGGCCAGTAATA
GTAGCCTCTGTGACACCAGGGCGGGGCCGAGGGACCCTTCTNTTGGAAGAGACCAGCTTCTCATACTTGATGATGA
GNCCGGTAATCCTGGCACGTGGNGGTTGCATGATNCCACCAAGGAAATNGGNGGGGGNGGACCTGCCCGGCGGCCG
TTCNAAAGCCCAATTCCACACACTTGGNGGCCGTACTATGGATCCCACTCNGTCCAACTTGGNGGAATATGGCATA
ACTTTT
```

31_16484.edit
```
TCGAGCGGCCGCCCGGGCAGGTCCTTGACCTTTTCAGCAAGTGGGAAGGTGTAATCCGTCTCCACAGACAAGGCCA
GGACTCGTTTGTACCCGTTGATGATAGAATGGGGTACTGATGCAACAGTTGGGTAGCCAATCTGCAGACAGACACT
GGCAACATTGCGGACACCCTCCAGGAAGCGAGAATGCAGAGTTTCCTCTGTGATATCAAGCACTTCAGGGTTGTAG
ATGCTGCCATTGTCGAACACCTGCTGGATGACCAGCCCAAAGGAGAAGGGGGAGATGTTGAGCATGTTCAGCAGCG
TGGCTTCGCTGGCTCCCACTTTGTCTCCAGTCTTGATCAGACCTCGGCCGCGACCACGCT
```

37_16487.edit
```
AGCGTGGTCGCGGCCGAGGTCTGTCCTACAGTCCTCAGGACTCTACTCCCTCAGCAGCGTGGTGACCGTGCCCTCC
AGCAACTTCGGCACCCAGACCTACACCTGCAACGTAGATCACAAGCCCAGCAACACCAAGGTGGACAAGAGAGTTG
AGCCCAAATCTTGTGACAAAACTCACACATGCCCACCGTGCCCAGCACCTGAACTCCTGGGGGGACCGTCAGTCTT
CCTCTTCCCCCGCATCCCCCTTCCAAACCTGCCCGGGCGGCCGCTCG
```

*Fig. 15KK*

38_16487.edit

CGAGCGGCCGCCCGGGCAGGTTTGGAAGGGGGATGCGGGGGAAGAGGAAGACTGACGGTCCCCCCAGGAGTTCAGG
TGCTGGGCACGGTGGGCATGTGTGAGTTTTGTCACAAGATTTGGGCTCAACTCTCTTGTCCACCTTGGTGTTGCTG
GGCTTGTGATCTACGTTGCAGGTGTAGGTCTGGGTGCCGAAGTTGCTGGAGGGCACGGTCACCACGCTGCTGAGGG
AGTAGAGTCCTGAGGACTGTAGGACAGACCTCGGCCGCGACCACGCT

39_16488.edit

NGGNNGGTCCGGNCNGNCAGGACCACTCNTCTTCGAAATA

41_16489.edit

AGCGTGGTCGCGGCCGAGGTCCTCACTTGCCTCCTGCAAAGCACCGATAGCTGCGCTCTGGAAGCGCAGATCTGTT
TTAAAGTCCTGAGCAATTTCTCGCACCAGACGCTGGAAGGGAAGTTTGCGAATCAGAAGTTCAGTGGACTTCTGAT
AACGTCTAATTTCACGGAGCGCCACAGTACCAGGACCTGCCCGGGCGGCCGCTCGA

42_16489.edit

TCGAGCGGCCGCCCGGGCAGGTCCTGGTACTGNGGCGCTCCGTGAAATTAGACGTTATCAGAAGTCCACTGAACTT
CTGATTCGCAAACTTCCCTTCCAGCGTCTGGTGCGAGAAATTGCTCAGGACTTTAAAACAGATCTGCGCTTCCAGA
GCGCAGCTATCGGTGCTTTGCAGGAGGCAAGTGAGGACCTCGGCCGCGACCACGCT

45_16491.edit

TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCTCGGCCGCGACCACGCT

*Fig. 15LL*

46_16491.edit

GTGGGNTTGAACCCNTTTNANCTCCGCTTGGTACCGAGCTCGGATCCACTAGTAACGGCCGCCAGTGTGCTGGAAT
TCGGCTTAGCGTGGTCGCGGCCGAGGTCAAGAACCCCGCCCGCACCTGCCGTGACCTCAAGATGTGCCACTCTGAC
TGGAAGAGTGGAGAGTACTGGATTGACCCCAACCAAGGCTGCAACCTGGATGCCATCAAAGTCTTCTGCAACATGG
AGACTGGTGAGACCTGCGTGTACCCCACTCAGCCCAGTGTGGCCCAGAAGAACTGGTACATCAGCAAGAACCCCAA
GGACAAGAGGCATGTCTGGTTCGGCGAGAGCATGACCGATGGATTCCAGTTCGAGTATGGCGGCCAGGGCTCCGAC
CCTGCCGATGTGGACCTGCCCGGGCGGCCGCTCGA

47_16492.edit

AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGACCAGGACCAACAAAAAC
TAAAACTGCAGGTCCAGATCAAACAGAAATGACTATTGAAGGCTTGCAGCCCACAGTGGAGTATGTGGTTAAGTGT
CTATGCTCAGAATCCAAGCGGAGAGAAGTCAGCCTCTGGTTCAGACTGNAAGTAACCAACATTGATCGCCTAAAGG
ACTGGCATTCACTGATGNGGATGCCGATTCCATCAAAATTGNTTGGGAAAACCCACAGGGGCAAGTTTNCANGTCN
AGGNGGACCTACTCGAGCCCTGAGGATGGAATCCTTGACTNTTCCTTNNCCTGATGGGGAAAAAAAACCTTNAAAA
CTTGAAGGACCTGCCCGGGCGGCCGTNCAAAACCCAATTCCACCCCCTTGGGGGCGTTCTATGGGNCCCACTCGGA
CCAAACTTGGGGTAAN

48_16492.edit

TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGGCATCCACATCAGTGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAGTTTTTGTTGGTCCTGGTCCATTTTTGGGAGTGGTGGTTACTCTGT
AACCAGTAACAGGGGAACTTGAAGGCAGCCACTTGACACTAATGCTGTTGTCCTGAACATCGGTCACTTGCATCTG
GGATGGTTTGTCAATTTCTGTTCGGTAATTAATGGAAATTGGCTTGCTGCTTGCGGGGCTTGTCTCCACGGCCAGT
GACAGCATACACAGTGATGGTATAATCAACTCCAGGTTTAAGCCGCTGATGGTAGCTGAAACTTTGCTCCAGGCAC
AAGTGAACTCCTGACAGGGCTATTTCCTNCTGTTCTCCGTAAGTGATCCTGTAATATCTCACTGGGACAGCAGGAN
GCATTCCAAAACTTCGGGCGNGACCCCCTAAGCCGAATTNTGCAATATNCATCACACTGGCGGGCGCTCGANCATT
CATTAAAAGGCCCAATCNCCCCTATAGGGAGTNTANTACAATTNG

*Fig. 15MM*

49_16493.edit

TCGAGCGGCCGCCCGGGCAGGTCACTTTTGGTTTTTGGTCATGTTCGGTTGGTCAAAGATAAAAACTAAGTTTGAG
AGATGAATGCAAAGGAAAAAAATATTTTCCAAAGTCCATGTGAAATTGTCTCCCATTTTTTTGGCTTTTGAGGGGG
TTCAGTTTGGGTTGCTTGTCTGTTTCCGGGTTGGGGGGAAAGTTGGTTGGGTGGGAGGGAGCCAGGTTGGGATGGA
GGGAGTTTACAGGAAGCAGACAGGGCCAACGTCG

55_16496.edit

AGCGTGGTCGCGGCCGAGGTCCTCACCAGAGGTGCCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTAGGCTTTGGAAGTGGTCATTTCAGATGTGATTCATCTAGATGGTGCCATGACAATGGTG
TGAACTACAAGATTGGAGAGAAGTGGGACCGTCAGGGAGAAAATGGACCTGCCCGGGCGGCCGCTCGA

56_16496.edit

TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCTTCCCGAACCTTATGCCTCTGCTGG
TCTTTCAGTGCCTCCACTATGATGTTGTAGGTGGCACCTCTGGTGAGGACCTCGGCCGCGACCACGCT

59_16498.edit

TCGAGCGGCCGCCCGGGCAGGTCCACCATAAGTCCTGATACAACCACGGATGAGCTGTCAGGAGCAAGGTTGATTT
CTTTCATTGGTCCGGTCTTCTCCTTGGGGGTCACCCGCACTCGATATCCAGTGAGCTGAACATTGGGTGGTGTCCA
CTGGGCGCTCAGGCTTGTGGGTGTGACCTGAGTGAACTTCAGGTCAGTTGGTGCAGGAATAGTGGTTACTGCAGTC
TGAACCAGAGGCTGACTCTCTCCGCTTGGATTCTGAGCATAGACACTAACCACATACTCCACTGTGGGCTGCAAGC
CTTCAATAGTCATTTCTGTTTGATCTGGACCTGCAGTTTTAGTTTTTGTTGGTCCTGGTCCATTTTTGGGAGTGGT
GGTTACTCTGTAACCAGTAACAGGGGAACTTGAAGGCAGCCACTTGACACTAATGCTGTTGTCCTGAACATCGGTC
ACTTGCATCTGGGATGGTTTGNCAATTTCTGTTCGGTAATTAATGGAAATTGGCTTGCTGCTTGCGGGGCTGTCTC
CACGGCCAGTGACAGCATACACAGNGATGGNATNATCAACTCCAAGTTTAAGGCCCTGATGGTAACTTTAAACTTG
CTCCCAGCCAGNGAACTTCCGGACAGGGTATTTCTTCTGGTTTTCCGAAAGNGANCCTGGAATNNTCTCCTTGGAN
CAGAAGGANCNTCCAAAACTTGGGCCGGAACCCCTT

*Fig. 15NN*

60_16473.edit

AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
GGGGCTCGCTCTTCTGATTATTCTTCAGGGCAATGACATAAATTGTATATTCGGTTCCCGGTTCCAGGCCAGTAAT
AGTAGCCTCTTGTGACACCAGGCGGGGCCCANGGACCACTTCTCTGGGANGAGACCCAGCTTCTCATACTTGATGA
TGTAACCCGGTAATCCTGCACGTGGCGGCTGNCATGATACCANCAAGGAATTGGGTGNGGNGGACCTGCCCGGCGG
CCCTCNA

60_16498.edit

AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGACCAGGACCAACAAAAAC
TAAAACTGCAGGTCCAGATCAAACAGAAATGACTATTGAAGGCTTGCAGCCCACAGTGGAGTATGTGGTTAGTGTC
TATGCTCAGAATCCAAGCGGAGAGAGTCAGCCTCTGGTTCAGACTGCAGTAACCACTATTCCTGCACCAACTGACC
TGAAGTTCACTCAGGTCACACCCACAAGCCTGAGCCGCCAGTGGACACCACCCAATGTTCACTCACTGGATATCGA
GTGCGGGTGACCCCCAAGGAGAAGACCCGGACCCATGAAAGAAATCAACCTTGCTCCTGACAGCTCATCCGNGGGT
GTATCAGGACTTATGGGGGACTGCCCCGGCNGGCCGNTCGAAANCGAATTNTGAAATTTCCTTCNCACTGGGNGGC
GNTTCGAGCTTNCTTNTANANGGCCCAATTCNCCTNTAGNGGGTCGTN

61_16499.edit

AGCGTGGTCGCGGCCGAGGTCNAGG

62_16483.edit

TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGAGGAACATGGTTTT
AGGCGGACCACACCGCCCACAACGGGCACCCCCATAAGGNATAGGCCAAGACCATACCCCGCCGAATGTAGGACAA
GAAGCTCTNTCTCAACAACCATCTCATGGGCCCCATTCCAGGACACTTCTGAGTACATCATTTCATGTCATCCTGG
TGGGCACTTGATGAANAACCCTTACAGTTCAGGGTTCCTGGAACTTCTACCAGNGCCACTTCTGACAGGANCTTGG
GCGNGACCACCCT

*Fig. 15OO*

63_16500.edit

AGCGTGGTCGCGGCCGAGGTCCATTTTCTCCCTGACGGTCCCACTTCTCTCCAATCTTGTAGTTCACACCATTGTC
ATGGCACCATCTAGATGAATCACATCTGAAATGACCACTTCCAAAGCCTAAGCACTGGCACAACAGTTTAAAGCCT
GATTCAGACATTCGTTCCCACTCATCTCCAACGGCATAATGGGAAACTGTGTAGGGGTCAAAGCACGAGTCATCCG
TAGGTTGGTTCAAGCCTTCGTTGACAGAGTTGCCCACGGTAACAACCTCTTCCCGAACCTTATGCCTCTGCTGGTC
TTTCAGTGCCTCCACTATGATGTTGTAGGTGGCACCTCTGGTGAGGACCTGCCCGGGCGGCCCGCTCGA

64_16493.edit

AGCGTGGTCGCGGCCGAGGTGTGCCCCAGACCAGGAATTCGGCTTCGACGTTGGCCCTGTCTGCTTCCTGTAAACT
CCCTCCATCCCAACCTGGCTCCCTCCCACCCAACCAACTTTCCCCCCAACCCGGAAACAGACAAGCAACCCAAACT
GAACCCCCTCAAAAGCCAAAAAAATGGGAGACAATTTCACATGGACTTTGGAAAATATTTTTTTCCTTTGCATTCA
TCTCTCAAACTTAGTTTTTATCTTTGACCAACCGAACATGACCAAAAACCAAAAGTGACCTGCCCGGGCGGCCGCT
CGA

64_16500.edit

TCGAGCGGCCGCCCGGGCAGGTCCTCACCAGAGGTGCCACCTACAACATCATAGTGGAGGCACTGAAAGACCAGCA
GAGGCATAAGGTTCGGGAAGAGGTTGTTACCGTGGGCAACTCTGTCAACGAAGGCTTGAACCAACCTACGGATGAC
TCGTGCTTTGACCCCTACACAGTTTCCCATTATGCCGTTGGAGATGAGTGGGAACGAATGTCTGAATCAGGCTTTA
AACTGTTGTGCCAGTGCTTAGGCTTTGGAAGTGGTCATTTCAGATGTGATTCATCTAGATGGTGCCATGACAATGG
TGTGAACTACAAGATTGGAGAGAAGTGGGACCGTCAGGGAGAAAATGGACCTCGGCCGCGACCACGCT

*Fig. 15PP*

16501.edit

TCGAGCGGCCGCCCGGGCAGGTACCGGGGTGGTCAGCGAGGAGCCATTCACACTGAACTTCACCATCAACAACCTG
CGGTATGAGGAGAACATGCAGCACCCTGGCTCCAGGAAGTTCAACACCACGGAGAGGGTCCTTCAGGGCCTGCTCA
GGTCCCTGTTCAAGAGCACCAGTGTTGGCCCTCTGTACTCTGGCTGCAGACTGACTTTGCTCAGACCTGAGAAACA
TGGGGCAGCCACTGGAGTGGACGCCATCTGCACCCTCCGCCTTGATCCCACTGGTNCTGGACTGGACANANAGCGG
CTATACTTGGGAGCTGANCCNAACCTTTGGCGGNGACNCCNCTT 16501.2.edit GAGGACTGGCTCAGCTCCCAGTATAGCCGCTCTCTGTCCAGTCCAGGACCAGTGGGATCAAGGCGGAGGGTGCAGA
TGGCGTCCACTCCAGTGGCTGCCCCATGTTTCTCAAGTCTGAGCAAAGNCAGTCTGCAGCCAGAGTACAGAGGGCC
AACACTGGTGCTCTTGAACAGGGACCTGAGCAGGCCCTGAAGGACCCTCTCCGTGGTGTTGAACTTCCTGGAGCCA
GGGTGCTGCATGTTCTCCTCATACCGCAGGTTGTTGATGGTGAAGTTCAGTGTGAATGGCTCCTCGCTGACCACCC 16502.1.edit AGCGTGGTCGCGGCCGAGGTCCACCACACCCAATTCCTTGCTGGTATCATGGCAGCCGCCACGTGCCAGGATTACC
GGCTACATCATCAAGTATGAGAAGCCTGGGTCTCCTCCCAGAGAAGTGGTCCCTCGGCCCCGCCCTGGTGTCACAG
AGGCTACTATTACTGGCCTGGAACCGGGAACCGAATATACAATTTATGTCATTGCCCTGAAGAATAATCAGAAGAG
CGAGCCCCTGATTGGAAGGAAAAAGACAGACGAGCTTCCCCAACTGGTAACCCTTCCACACCCCAATCTTCATGGA
CCANANANCTTGGATNGTCCTTTCACNGGTTNAAAAAACCCTTTTCGCCCCCCCACCTTGGGGATTAACCTTGGGA
AANGGGGATTTNACCNTTCC 16502.2.edit TCGAGCGGCCGCCCGGGCAGGTCCTGTCAGAGTGGCACTGGTAGAAGTTCCAGGAACCCTGAACTGTAAGGGTTCT
TCATCAGTGCCAACAGGATGACATGAAATGATGTACTCAGAAGTGTCCTGGAATGGGGCCCATGAGATGGTTGTCT
GAGAGAGAGCTTCTTGTCCTACATTCGGCGGGTATGGTCTTGGCCTATGCCTTATGGGGGTGGCCGTTGTGGGCGG
TGTGGTCCGCCTAAAACCATGTTCCTCAAAGATCATTTGTTGCCCAACACTGGGTTGCTGACCAGAAGTGCCAGGA
AGCTGAATACCATTTCCAGTGTCATACCCAGGGNGGGTGACCAAAGGGGGTCNTTTNGACCTGGNGAAAGGAACCA
TCCAAAANCTCTGNCCCATG

*Fig. 15QQ*

16503.1.edit

AGCGTGGNCGCGGCCGAGGTCTGAGGATGTAAACTCTTCCCAGGGGAAGGCTGAAGTGCTGACCATGGTGCTACTG
GGTCCTTCTGAGTCAGATATGTGACTGATGNGAACTGAAGTAGGTACTGTAGATGGTGAAGTCTGGGTGTCCCTAA
ATGCTGCATCTCCAGAGCCTTCCATCATTACCGTTTCTTCTTTTGCTATGGGATGAGACACTGTTGAGTATTCTCT
AAAGTCACCACTGAAATCTTCCTCCAAAGGAAAACCTGTGGAAAAGCCCCTTATTTCTGCCCCATAATTTGGTTCT
CCTAATCNCTCTGAAATCACTATTTCCCTGGAANGTTTGGGAAAAANNGGGCNACCTGNCANTGGAAANTGGATAN
AAAGATCCCACCATTTTACCCAACNAGCAGAAAGTGGGAANGGTACCGAAAAGCTCCAAGTAANAAAAAGGAGGGA
AGTAAAGGTCAAGTGGGCACCAGTTTCAAACAAAACTTTCCCCAAACTATANAACCCA 16503.2.edit AAGCGGCCGCCCGGGCAGGNNCAGNAGTGCCTTCGGGACTGGGNTCACCCCCAGGTCTGCGGCAGTTGTCACAGCG
CCAGCCCCGCTGGCCTCCAAAGCATGTGCAGGAGCAAATGGCACCGAGATATTCCTTCTGCCACTGTTCTCCTACG
TGGTATGTCTTCCCATCATCGTAACACGTTGCCTCATGAGGGTCACACTTGAATTCTCCTTTTCCGTTCCCAAGAC
ATGTGCAGCTCATTTGGCTGGCTCTATAGTTTGGGGAAAGTTTGTTGAAACTGTGCCACTGACCTTTACTTCCTCC
TTCTCTACTGGAGCTTTCCGTACCTTCCACTTCTGCTGNTGGNAAAAAGGGNGGAACNTCTTATCAATTTCATTGG
ACAGTANCCCNCTTTCTNCCCAAAACATNCAAGGGAAAATATTGATTNCNAGAGCGGATTAAGGAACAACCCNAAT
TATGGGGGCCAGAAATAAAGGGGGCTTTTCCACAGGTNTTTTCCT 16504.1.edit TCGAGCGGCCGCCCGGGCAGGTCTGCAGGCTATTGTAAGTGTTCTGAGCACATATGAGATAACCTGGGCCAAGCTA
TGATGTTCGATACGTTAGGTGTATTAAATGCACTTTTGACTGCCATCTCAGTGGATGACAGCCTTCTCACTGACAG
CAGAGATCTTCCTCACTGTGCCAGTGGGCAGGAGAAAGAGCATGCTGCGACTGGACCTCGGCCGCGACCACGCT 16504.2.edit AGCGTGGTCGCGGCCGAGGTCCAGTCGCAGCATGCTCTTTCTCCTGCCCACTGGCACAGTGAGGAAGATCTCTGCT
GTCAGTGAGAAGGCTGTCATCCACTGAGATGGCAGTCAAAAGTGCATTTAATACACCTAACGTATCGAACATCATA
GCTTGGCCCAGGTTATCTCATATGTGCTCAGAACACTTACAATAGCCTGCAGACCTGCCCGGGCGGCCGCTCGA

*Fig. 15RR*

16505.1.edit

CGAGCGGCCGCCCGGGCAGGTCCAGACTCCAATCCAGAGAACCACCAAGCCAGATGTCAGAAGCTACACCATCACA
GGTTTACAACCAGGCACTGACTACAAGATCTACCTGTACACCTTGAATGACAATGCTCGGAGCTCCCCTGTGGTCA
TCGACGCCTCCACTGCCATTGATGCACCATCCAACCTGCGTTTCCTGGCCACCACACCCAATTCCTTGCTGGTATC
ATGGCAGCCGCCACGTGCCAGGATTACCGGCTACATCATCAAGTATGAGAAGCCTGGGTCTCCTCCCAGAGAAGTG
GTCCCTCGGCCCCGCCCTGGTGNCACAGAAGCTACTATTACTGGCCTGGAACCGGGAACCGAATATACAATTTATG
TCATTGCCCTGAAGAATAATCANAAGAGCGAGCCCCTGATTGGAAGG 16505.2.edit AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTGTCTTTTTCCTTCCAATCAGGGGCTCGCTCTTCTGATTATTCTTCAGGGCAATGACAT
AAATTGTATATTCGGTTCCCGGTTCCAGGCCAGTAATAGTAGCCTCTGTGACACCAGGGCGGGGCCGAGGGACCAC
TTCTCTGGGAGGAGACCCAGGCTTCTCATACTTGATGATGTANCCGGTAATCCTGGCACCGTGGCGGCTGCCATGA
TACCAGCAAGGAATTGGGTGTGGTGGCCAAGAAACGCAGGTTGGATGGTGCATCAATGGCAGTGGAGGCGTCGATN
ACCACAGGGGAGCTCCGANCATTGTCATTCAAGGTGGACAGGTAGAATCTTGTAATCAGGTGCCTGGTTTGTAAAC
CTG 16506.1.edit TCGAGCGGCCGCCCGGGCAGGTTTCGTGACCGTGACCTCGAGGTGGACACCACCCTCAAGAGCCTGAGCCAGCAGA
TCGAGAACATCCGGAGCCCAGAGGGCAGCCGCAAGAACCCCGCCCGCACCTGCCGTGACCTCAAGATGTGCCACTC
TGACTGGAAGAGTGGAGAGTACTGGATTGACCCCAACCAAGGCTGCAACCTGGATGCCATCAAAGTCTTCTGCAAC
ATGGAGACTGGTGAGACCTGCGTGTACCCCACTCAGCCCAGTGTGGCCCAGAAGAACTGGTACATCAGCAAGAACC
CCAAGGACAAGAAGCATGTCTGGTTCGGCGAAAGCATGACCGATGGATTCCAGTTCGAGTATGGCGGCCAGGGCTC
CGACCCTGCCGATGTGGACCTCGGCCGCGACCACGCTAAGCCCGAATTCCAGCACACTGGCGGCCGTTACTAGTGG
GATCCGAGCTTCGGTACCAAGCTTGGCGTAATCATGGGNCATAGCTGTTTCCTGNGTGAAAATGGTATTCCGCTTC
ACAATTTCCCAC 16506.2.edit AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAGTGGCACATCTTGAGGTCACGGCAGGTGCGGGCGGGG
TTCTTGCGGCTGCCCTCTGGGCTCCGGATGTTCTCGATCTGCTGGCTCAAGCTCTTGAAGGGTGGTGTCCACCTCG
AGGTCACGGTCACGAAACCTGCCCGGGCGGCCGCTCGA

*Fig. 15SS*

16507.1.edit

AGCGTGGTCGCGGCCGAGGTCAAGAACCCCGCCCGCACCTGCCGTGACCTCAAGATGTGCCACTCTGACTGGAAGA
GTGGAGAGTACTGGATTGACCCCAACCAAGGCTGCAACCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGNGCCGGNCCGCTCGAAAAGCCCNAATTTCCAGNCACACTTGGCCGGCCGTTACTACTG 16507.2.edit TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCTCGGCCGCGACCACGCT 16508.1.edit CGAGCGGCCGCCCGGGCAGGTCCCCCCCCTTTTTTTTTTTTTTTTTTTTTTTTTTTTTTTTTTTTTTTTTTTTTTTTT
TTTTTTTTTTTTTTTTTT 16508.2.edit AGCGTGGTCGCGGCCGAGGTCTGGCATTCCTTCGACTTCTCTCCAGCCGAGCTTCCCAGAACATCACATATCACTG
CAAAAATAGCATTGCATACATGGATCAGGCCAGTGGAAATGTAAAGAAGGCCCTGAAGCTGATGGGGTCAAATGAA
GGTGAATTCAAGGCTGAAGGAAATAGCAAATTCACCTACACAGTTCTGGAGGATGGTTGCACGAAACACACTGGGG
AATGGAGCAAAACAGTCTTTGAATATCGAACACGCAAGGCTGTGAGACTACCTATTGTAGATATTGCACCCTATGA
CATTGGTGGTCCTGATCAAGAATTTGGTGTGGACGTTGGCCCTGTTTGCTTTTTATAAACCAAACTCTATCTGAAA
TCCCAACAAAAAAAATTTAACTCCATATGTGNTCCTCTTGTTCTAATCTTGGCAACCAGTGCAAGTGACCGACAAA
ATTCCAGTTATTTATTTCCAAAATGTTTGGAAACAGTATAATTTGACAAAGAAAAAAGGATACTTCTCTTTTTTTG
GCTGGTCCACCAAATACAATTCAAAAGGCTTTTTGGTTTTATTTTTTTANCCAATTCCAATTTCAAAATGTCTCAA
TGGNGCTTATAATAAAATAAACTTTCACCCTTNTTTTNTGAT

*Fig. 15TT*

16509.1.edit

AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAAGTAACCACCACTCCCAAAAATGGACCAGGACCAACAAAAA
CTAAAACTGCAGGTCCAGATCAAACAGAAAATGGACTATTGAAGGCTTGCAGCCCACAGTGGAAGTATGTGGNTAG
GNGTCTATGCTCAGAATCCCAAGCCGGAGAAAGTCAGCCTTCTGGTTTAGACTGCAGTAACCAACATTGATCGCCC
TAAAGGACTGGNCATTCACTTGGATGGTGGATGTCCAATTC 16509.2.edit TCGAGCGGCCGCCCGGGCAGGTCCTTGCAGCTCTGCAGNGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGNGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAAGTTTTTGGTGGTCCTGNCCCATTTTTGGGAAGTGGGGGGTTACTC
TGTAACCAGTAACAGGGGAACTTGAAGGCAGCCACTTGACACTAATGCTGTTGTCCTGAACATCGGTCACTTGCAT
CTGGGGATGGTTTTGACAATTTCTGGTTCGGCAAATTAATGGAAATTGGCTTGCTGCTTGGCGGGGCTGNCTCCAC
GGGCCAGTGACAGCATAC 16510.1.edit TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGTGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAAGTTTTTGTTGGNCCTGNNCCATTTTTGGGGAAGGGGTGGTTACTC
TTGTAACCAGTAACAGGGGAACTTGAAGCAGCCACTTGACACTAATGCTGGTGGCCTGAACATCGGTCACTTGCAT
CTGGGATGGTTTGGTCAATTTCTGTTCGGTAATTAATGGGAAATTGGCTTACTGGCTTGCGGGGGCTGTCTCCACG
GNCAGTGACAAGCATACACAGGNGATGGGTATAATCAACTCCAGGTTTAAGGCCNCTGATGGTA 16510.2.edit AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGTAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGGACCAGGACCAACAAAAA
ACTAAAACTGCANGGTCCAGATCAAACAGAAATGACTATTGAAGGCTTGCAGCCCACAGTGGAGTATGTGGGTTAG
TGTCTATGCTCAGAATNCCAAGCGGAGAGAGTCAGCCTCTGGTTCAGACT

*Fig. 15UU*

16511.1.edit

TCGAGCGGCCGCCCGGGCAGGTCAGCGCTCTCAGGACGTCACCACCATGGCCTGGGCTCTGCTCCTCCTCACCCTC
CTCACTCAGGGCACAGGGTCCTGGGCCCAGTCTGCCCTGACTCAGCCTCCCTCCGCGTCCGGGTCTCCTGGACAGT
CAGTCACCATCTCCTGCACTGGAACCAGCAGTGACGTTGGTGCTTATGAATTTGTCTCCTGGTACCAACAACACCC
AGGCAAGGCCCCCAAACTCATGATTTCTGAGGTCACTAAGCGGCCCTCAGGGGTCCCTGATCGCTTCTCTGGCTCC
AAGTCTGGCAACACGGCCTCCCTGACCGTCTCTGGGCTCCANGCTGAGGATGANGCTGATTATTACTGGAAGCTCA
TATGCAGGCAACAACAATTGGGTGTTCGGCGGAAGGGACCAAGCTGACCGTNCTAAGGTCAAGCCCAAGGCTTGCC
CCCCTCGGTCACTCTGTTCCCACCCTCCTCTGAAGAAGCTTTCAAGCCAACAANGNCACACTGGGTGTGTCTCATA
AGTGGACTTTCTACCC 16511.2.edit AGCGTGGTCGCGGCCGAGGTCTGTAGCTTCTGTGGGACTTCCACTGCTCAGGCGTCAGGCTCAGGTAGCTGCTGGC
CGCGTACTTGTTGTTGCTTTGNTTGGAGGGTGTGGTGGTCTCCACTCCCGCCTTGACGGGGCTGCTATCTGCCTTC
CAGGCCACTGTCACGGCTCCCGGGTAGAAGTCACTTATGAGACACACCAGTGTGGCCTTGTTGGCTTGAAGCTCCT
CAGAGGAGGGTGGGAACAGAGTGACCGAGGGGGCAGCCTTGGGCTGACCTAGGACGGTCAGCTTGGTCCCTCCGCC
GAACACCCAATTGTTGTTGCCTGCATATGAGCTGCAGTAATAATCAGCCTCATCCTCAGCCTGGAGCCCAGAGACN
GTCAAGGGAGGCCCGTGTTTGCCAAGACTTGGAAGCCAGANAAGCGATCAGGGACCCCTGAGGGCCGCTTTACNGA
CCTCAAAAAATCATGAATTTGGGGGGCCTTTGCCTGGGNGTTGGTTGGTNACCAGNAAAACAAAATTTCATAAAGC
ACCAACGTCACTGCTGGTTTCCAGTGCANGAANATGGTGAACTGAANTGTCC 16512.1.edit AGCGTGGTCGCGGCCGAGGTCCAGCATCAGGAGCCCCGCCTTGCCGGCTCTGGTCATCGCCTTTCTTTTTGTGGCC
TGAAACGATGTCATCAATTCGCAGTAGCAGAACTGCCGTCTCCACTGCTGTCTTATAAGTCTGCAGCTTCACAGCC
AATGGCTCCCATATGCCCAGTTCCTTCATGTCCACCAAAGTACCCGTCTCACCATTTACACCCCAGGTCTCACAGT
TCTCCTGGGTGTGCTTGGCCCGAAGGGAGGTAAGTANACGGATGGTGCTGGTCCCACAGTTCTGGATCAGGGTACG
AGGAATGACCTCTAGGGCCTGGGCNACAAGCCCTGTATGGACCTGCCCGGGCGGGCCCGCTCGA 16512.2.edit TCGAGCGGCCGCCCGGGCAGGTCCATACAGGGCTGTTGCCCAGGCCCTAGAGGNCATTCCTTGTACCCTGATCCAG
AACTGTGGGACCAGCACCATCCGTCTACTTACCTCCCTTCGGGCCAAGCACACCCAGGAGAACTGTGAGACCTGGG
GTGTAAATGGNGAGACGGGTACTTTGGTGGACATGAAGGAACTGGGCATATGGGAGCCATTGGCTGNGAAGCTGCA
NACTTATAAGACAGCAGTGGAGACGGCAGTTCTGCTACTGCGAATTGATGACATCGTTTCAGGCCACAAAAAGAAA
GGCGATGACCANAGCCGGCAAGGCGGGGCTTCCTGATGCTGGACCTCGGCCGCCGACCACGCTT

*Fig. 15VV*

16514.1.edit

AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGGGAAACTCCGAGGACAGAGGGCTAAATCCATGAAGTTTGTGGATGGCCTGATGATCCACAGCGG
AGACCCTGTTAACTACTACGTTGACACTGCTGTGCGCCACGTGTTGCTCANACAGGGTGTGCTGGGCATCAAGGTG
AAGATCATGCTGCCCTGGGACCCANCTGGCAAAAATGGCCCTTAAAAACCCCTTGCCNTGACCACGTGAACCATTT
GTGNGAACCCCAAGATGAANATACTTGCCCACCACCCCCCATTC 16514.2.edit TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAGCAGTGTCAACGTAGTAGTTAACAGGGTCTCCGCTGTGGATCATC
AGGCCATCCACAAACTTCATGGATTTAGCCCTCTGTCCTCGGAGTTTCCCAAAACACCACAACCTCGCCAGCCTTT
GGGCCCCACTTCTTCATGAATGAAACCGCAGCACACCATTANCAAGGCCCTTCCGCACAGGNAAGCCCTTCCTAAG
GAGTTTTGTAAACGCAAAAAACTCTTGCCTGGGGCAAATGGGCACACAGACCTNTANTNGGACCTTGGNCCGCGAA
CCACCGCTT 16515.1.edit AGCGTGGTCGCGGCCGAGGTCTGGCCCTCCTGGCAAGGCTGGTGAAGATGGTCACCCTGGAAAACCCGGACGACCT
GGTGAGAGAGGAGTTGTTGGACCACAGGGTGCTCGTGGTTTCCCTGGAACTCCTGGACTTCCTGGCTTCAAAGGCA
TTAGGGGACACAATGGTCTGGATGGATTGAAGGGACAGCCCGGTGCTCCTGGTGTGAAGGGTGAACCTGGNGCCCC
TGGTGAAAATGGAACTCCAGGTCAAACAGGAGCCCGNGGGCTTCCTGGNGAGAGAGGACGTGTTGGTGCCCCTGGC
CCANACCTGCCCGGGCGGCCGCTCNAAAAGCCGAAATCCAGNACACTGGCGGCCGNTACTANTGGAATCCGAACTT
CGGTACCAAAGCTTGGCCGTAATCATGGCCATAGCTTGTTCCCTGGGGNGGAAATTGGTATTCCGCTNCCAATTCC
ACACAACATACCGAACCCGGAAAGCATTAAAGTGTAAAAGCCCTGGGGGGGCCTAAATGANGTGAGCNTAACTCNC
ATTTAATTGGCGTTGCGCTTCACTGCCCCGCTTTTCCAGTCCGGGNA 16515.2.edit TCGAGCGGCCGCCCGGGCAGGTCTGGGCCAGGGGCACCAACACGTCCTCTCTCACCAGGAAGCCCACGGGCTCCTG
TTTGACCTGGAGTTCCATTTTCACCAGGGGCACCAGGTTCACCCTTCACACCAGGAGCACCGGGCTGTCCCTTCAA
TCCATCCAGACCATTGTGNCCCCTAATGCCTTTGAAGCCAGGAAGTCCAGGAGTTCCAGGGAAACCACGAGCACCC
TGTGGTCCAACAACTCCTCTCTCACCAGGTCGTCCGGGTTTTCCAGGGTGACCATCTTCACCAGCCTTGCCAGGAG
GGCCAGACCTCGGCCGCGACCACGCT

*Fig. 15WW*

16516.1.edit

ANCGTGGTCGCGGCCGAGGTCCTCACCAGAGGTGNCACCTACAACATCATAGTGGAGGCACTGAAAGACCANCAGA
GGCATAAGGTTCGGGAAGAGG 16516.2.edit TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGTCCACGGTAACAACCTCTTCCCGAACCTTATGCCTCTGCTGG
TCTTTCAGTGCCTCCACTATGATGTTGTAGGTGGCACCTCTGGTGAGGACCTCNGNCCNGAACAACGCTTAAGCCC
GNATTCTGCAGAATAATCCCATCACACTTGGCGGCCGCTTCGANCATGCATCNTAAAAGGGGCCCCAATTTCCCCC
TTATAAGNGAANCCGTATTTNCCAATTTCACTGGNCCCGCCGNTTTTACAAACGNCGGTGAACTGGGGAAAAAACCC
TGGCGGTTACCCAACTTTAATCGCCNTTGGCAGCACAATCCCCCCTTTTCGNCCANCNTGGGCGTAAATAACCGAA
AA 16517.1.edit

ANCGNGGTCGCGGCCGANGTNTTTTTTCTTNTTTTTTT 16518.1.edit

AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GGGNGGTCAGCGTCCTCACCGTCCTGCACCAGAATTGGTTGAATGGCAAGGAGTACAAGNGCAAGGTTTCCAACAA
AGCCNTCCCAGCCCCCNTCGAAAAAACCATTTCCAAAGCCAAAGGGCAGCCCCGAGAACCACAGGTGTACACCCTG
CCCCCATCCCGGGAGGAAAAGANCAANAACCNGGTTCAGCCTTAACTTGCTTGGTCNAANGCTTTTTATCCCAACG
NACTTCCCCCNTGGAANTGGGAAAAACCAATGGGCCAANCCGAAAAACAATTACAANAACCCC 16518.2.edit TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGAACACCTGGGGTTCTCGGGGCTTGCCCTTTGGTTTTGAANATGGTTTTC
TCGATGGGGGCTGGAAGGGCTTTGTTGNAAACCTTGCACTTGACTCCTTGCCATTCACCCAGNCCTGGNGCAGGAC
GGNGAGGACNCTNACCACACGGAACCGGGCTGGTGGACTGCTCC

*Fig. 15XX*

16519.1.edit

AGCGTGGTCGCGGACGANGTCCTGTCAGAGTGGNACTGGTAGAAGTTCCANGAACCCTGAACTGTAAGGGTTCTTC
ATCAGTGCCAACAGGATGACATGAAATGATGTACTCAGAAGNGNCCTGGAATGGGGCCCATGANATGGTTGCC 16519.2.edit TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGGCACCCCCCCTGGGTATGAACCTGGGAA
AANGGNANTTAANCTTTCCTGGCA 16520.1.edit AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGGTNCCCTGGTACTGGGTTACAGANTAACCACCACTCCCAAAAATGGACCAGGAACCACAAAAA
CTTAAACTGCAGGGTCCAGATCAAAACAGAAATGACTATTGAANGCTTGCAGCCCACAGTGGGAGTATGNGGGTAG
TGNCTATGCTTCAGAATCCAAGCGGAAAAANGTCAAGCCTTNTGGGTTCAA 16520.2.edit TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGTGAATGCCAGTCCTTTAGGGCGATCAATGTTGGTTACTGCAGNCTGAACCAGAGG
CTGACTCTCTCCGCTTGGATTCTGAGCATAGACACTAACCACATACTCCACTGTGGGCTGCAANCCTTCAATAANN
CATTTCTGTTTGATCTGGACC 16521.2.edit TCGAGCGGCCGCCCGGGCAGGTCTGGTGGGGTCCTGGCACACGCACATGGGGGNGTTGNTCTNATCCAGCTGCCCA
GCCCCCATTGGCGAGTTTGAGAAGGTGTGCAGCAATGACAACAANACCTTCGACTCTTCCTGCCACTTCTTTGCCA
CAAAGTGCACCCTGGAGGGCACCAAGAAGGGCCACAAGCTCCACCTGGACTACATCGGGCCTTGCAAATACATCCC
CCCTTGCCTGGACTCTGAGCTGACCGAATTCCCCCTTGCGCATGCGGGACTGGCTCAAGAACCGTCCTGGCACCCT
TGTATGANAGGGATGAAGACACNACCC

*Fig. 15YY*

16522.1.edit

AGCGTGGTCGCGGCCGAGGTCTGTCCTACAGTCCTCAGGACTCTACTCCCTCAGCAGCGTGGTGACCGTGCCCTCC
AGCAACTTCGGCACCCAGACCTACACCTGCAACGTAGATCACAAGCCCAGCAACACCAAGGTGGACAAGAGAGTTG
AGCCCAAATCTTGTGACAAAACTCACACATGCCCACCGTGCCCAGCACCTGAACTCCTGGGGGGACCGTCAGTCTT
CCTCTTCCCCCGCATCCCCCTTCCAAACCTGCCCGGGCGGCCGCTCGAAAGCCGAATTCCAGCACACTGGCGGCCG
GTACTAGTGGANCCNAACTTGGNANCCAACCTGGNGGAANTAATGGGCATAANCTGTTTCTGGGGGGAAATTGGTA
TCCNGTTTACAATTCCCNCACAACATACGAGCCGGAAGCATAAAAGNGTAAAAGCCTGGGGGNGGCCTANTGAAGT
GAAGCTAAACTCACATTAATTNGCGTTGCCGCTCACTGGCCCGCTTTTCCAGC 16522.2.edit TCGAGCGGCCGCCCGGGCAGGTTTGGAAGGGGGATGCGGGGGAAGAGGAAGACTGACGGTCCCCCCAGGAGTTCAG
GTGCTGGGCACGGTGGGCATGTGTGAGTTTTGTCACAAGATTTGGGCTCAACTCTCTTGTCCACCTTGGTGTTGCT
GGGCTTGTGATCTACGTTGCAGGTGTAGGTCTGGGNGCCGAAGTTGCTGGAGGGCACGGTCACCACGCTGCTGAGG
GAGTAGAGTCCTGAGGACTGTANGACAGACCTCGGCCGNGACCACGCTAAGCCGAATTCTGCAGATATCCATCACA
CTGGCGGCCGCTCCGAGCATGCATTTTAGAGG 16523.1.edit

AGCGTGGNCGCGGACGANGACAACAACCCC 16523.2.edit

TCGAGCGGCCGCCCGGGCAGGNCCACATCGGCAGGGTCGGAGCCCTGGCCGCCATACTCGAACTGGAATCCATCGG
TCATGCTCTTGCCGAACCAGACATGCCTCTTGTCCTTGGGGTTCTTGCTGATGNACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCT 16524.1.edit AGCGTGGTCGCGGCCGAGGTCCAGCCTGGAGATAANGGTGAAGGTGGTGCCCCCGGACTTCCAGGTATAGCTGGAC
CTCGTGGTAGCCCTGGTGAGAGAGGTGAAACTGGCCCTCCAGGACCTGCTGGTTTCCCTGGTGCTCCTGGACAGAA
TGGTGAACCTGGNGGTAAAGGAGAAAGAGGGGCTCCGGNTGANAAAGGTGAAGGAGGCCCTCCTGNATTGGCAGGG
GCCCCANGACTTAGAGGTGGAGCTGGCCCCCCTGGCCCCGAAGGAGGAAAGGGTGCTGCTGGTCCTCCTGGGCCAC
CTGG

*Fig. 15ZZ*

16524.2.edit

TCGAGCGGCCGCCCGGGCAGGTCTGGGCCAGGAGGACCAATAGGACCAGTAGGACCCCTTGGGCCATCTTTCCCTG
GGACACCATCAGCACCTGGACCGCCTGGTTCACCCTTGTCACCCTTTGGACCAGGACTTCCAAGACCTCCTCTTTC
TCCAGGCATTCCTTGCAGACCAGGAGTACCANCAGCACCAGGTGGCCCAGGAGGACCAGCAGCACCCTTTCCTCCT
TCGGGACCAGGGGGACCAGCTCCACCTCTAAGTCCTGGGGCCCCTGCCAATCCAGGAGGGCCTCCTTCACCTTTCT
CACCCGGAGCCCCTCTTTCT 16526.1.edit TCGAGCGGCCGCCCGGGCAGGTCCACCGGGATATTCGGGGGTCTGGCAGGAATGGGAGGCATCCAGAACGAGAAGG
AGACCATGCAAAGCCTGAACGACCGCCTGGCCTCTTACCTGGACAGAGTGAGGAGCCTGGAGACCGACAACCGGAG
GCTGGAGAGCAAAATCCGGGAGCACTTGGAGAAGAAGGGACCCCAGGTCAGAGACTGGAGCCATTACTTCAAGATC
ATCGAGGACCTGAGGGCTCANATCTTCGCAAATACTGCNGACAATGCCCG 16526.2.edit ATGCGNGGTCGCGGCCGANGACCANCTCTGGCTCATACTTGACTCTAAAGNCNTCACCAGNANTTACGGNCATTGC
CAATCTGCAGAACGATGCGGGCATTGTCCGCANTATTTGCGAAGATCTGAGCCCTCAGGNCCTCGATGATCTTGAA
GTAANGGCTCCAGTCTCTGACCTGGGGTCCCTTCTTCTCCAAGTGCTCCCGGATTTTGCTCTCCAGCCTCCGGTTC
TCGGTCTCCAAGNCTTCTCACTCTGTCCAGGAAAAGAGGCCAGGCGGNCGATCAGGGCTTTTGCATGGACT 16527.1.edit AGCGTGGTCGCGGCCGAGGTTGTACAAGCTTTTTTTTTTTTTTTTTTTTTTTTTTTTTTTTTTTTTTTTTTTTTTT
TTTTTTTTTTTTTTTTTTTTTTTTT 16527.2.edit TCGAGCGGCCGCCCGGGCAGGTCTGCCAACACCAAGATTGGCCCCCGCCGCATCCACACAGTTNGTGTGCGGGGAG
GTAACAAGAAATACCGTGCCCTGAGGNTGGACGNGGGGAATTTCTCCTGGGGCTCAGAGTGTTGTACTCGTAAAAC
AAGGATCATCGATGTTGTCTACAATGCATCTAATAACGAGCTGGTTCGTACCAAGACCCTGGTGAAGAATTGCATC
GTGCTCATNGACAGCACACCGTACCGACAGTGGGTACCGAAGTCCCACTATGCNCCT

*Fig. 15AAA*

16528.1.edit

TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAG 16528.2.edit AGCGTGNTCNCGGCCGAGGATGGGGAAGCTCGNCTGTCTTTTTCCTTCCAATCAGGGGCTNNNTCTTCTGATTATT
CTTCAGGGCAANGACATAAATTGTATATTCGGNTCCCGGTTCCAGNCCAGTAATAGTAGCCTCTGTGACACCAGGG
CGGGGCCGAGGGACCACTTCTCTGGGAGGAGACCCAGGCTTCTCATACTTGATGATGAAGCCGGTAATCCTGGCAC
GTGGGCGGCTGCCATGATACCACCAANGAATTGGGTGTGGTGGACCTGCCCGGGCGGGCCGCTCGAAAANCCGAAT
TCNTGCAAGAATATCCATCACACTTGGGCGGGCCGNTCGAACCATGCATCNTAAAAGGGCCCCAATTTCCCCCCTA
TTAGGNGAAGCCNCATTTAACAAATTCCACTTGG 16529.1.edit TCGAGCGGCCGCCCGGGCAGGTCTCGCGGTCGCACTGGTGATGCTGGTCCTGTTGGTCCCCCCGGCCCTCCTGGAC
CTCCTGGTCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTTGAGCCAGCAGAATCGAAAACATTCGGAACCCAAGAAGGGCAAGCCCGCAAAGAAACCCCGCCCGCAC
CTGGCCGNGAACCTCCAAGAANGTGCCCACNTCTTGACTGGGAAAAAAAGGGAAAANTACTTGGAATTGGAC 16529.2.edit AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAAGTGGCACATCTTGAGGTCACGGCAGGGTGCGGGCGG
GGTTCTTGCGGGCTGCCCTTCTGGGCTCCCGGAATGTTCTNNGAACTTGCTGG

*Fig. 15BBB*

16530.1.edit

AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGGGAAACTCCGAGGACAGAGGGCTAAATCCATGAAGTTTGTGGATGGCCTGATGATCCACAGCGG
AGACCCTGTTAACTACTACGTTGACACTTGCTTGTGCGCCACGTGTTGCTCANACANGGGTGGGCTGGGCATCAAG
GNG 16530.2.edit TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAGCAAGTGTCAACGTAAGTAAGTTAACAGGGTCTCCGCTGTGGATC
ATCAGGCCATCCACAAACTTCATGGATTTAACCCTCTGTCCTCGGAG 16531.1.edit TCGAGCGGCCGCCCGGGCAGGTGTTTCAGAGGTTCCAAGGTCCACTGTGGAGGTCCCAGGAGTGCTGGTGGTGGGC
ACAGAGGTCCGATGGGTGAAACCATTGACATAGAGACTGTTCCTGTCCAGGGTGTAGGGGCCCAGCTCTTTGATGC
CATTGGCCAGTTGGCTCAGCTCCCAGTACAGCCGCTCTCTGTTGAGTCCAGGGCTTTTGGGGTCAAGATGATGGAT
GCAGATGGCATCCACTCCAGTGGCTGCTCCATCCTTCTCGGACCTGAGAGAGGTCAGTCTGCAGCCAGAGTACAGA
GGGCCAACACTGGTGTTCTTTGAATA 16531.2.edit AGCGTGGTCGCGGCCGAGGTCTGTACTGGGAGCTAAGCAAACTGACCAATGACATTGAAGAGCTGGGCCCCTACAC
CCTGGACAGGAACAGTCTCTATGTCAATGGTTTCACCCATCAGAGCTCTGTGNCCACCACCAGCACTCCTGGGACC
TCCACAGTGGATTTCAGAACCTCAGGGACTCCATCCTCCCTCTCCAGCCCCACAATTATGGCTGCTGGCCCTCTCC
TGGTACCATTCACCCTCAACTTCACCATCACCAACCTGCAGTATGGGGAGGACATGGGTCACCCTGNCTCCAGGAA
GTTCAACACCACA 16532.1.edit TCGAGCGGCCGCCCGGACAGGTCTGGGCGGATAGCACCGGGCATATTTTGGAATGGATGAGGTCTGGCACCCTGAG
CAGTCCAGCGAGGACTTGGTCTTAGTTGAGCAATTTGGCTAGGAGGATAGTATGCAGCACGGNTCTGAGNCTGTGG
GATAGCTGCCATGAAGTAACCTGAAGGAGGTGCTGGCTGGTANGGGTTGATTACAGGGTTGGGAACAGCTCGTACA
CTTGCCATTCTCTGCATATACTGGTTAGTGAGGTGAGCCTGGCCCTCTTCTTTTG

*Fig. 15CCC*

01_16558.3.edit

AGCGTGGTCGCGGCCGAGGTGAGCCACAGGTGACCGGGGCTGAAGCTGGGGCTGCTGGNCCTGCTGGTCCTG

02_16558.4.edit

CAGCNGCTCCNACGGGGCCTGNGGGACCAACAACACCGTTTTCACCCTTAGGCCCTTTGGCTCCTCTTTCTCCTTT
AGCACCAGGTTGACCAGCAGCNCCANCAGGACCAGCAAATCCATTGGGGCCAGCAGGACCGACCTCACCACGTTCA
CCAGGGCTTCCCCGAGGACCAGCAGGACCAGCAGGACCAGCAGCCCCAGCTTCGCCCCGGTCACCTGTGGCTCACC
TCGGCCGCGACCACGCT

03_16535.1.edit

TCGAGCGGTCGCCCGGGCAGGTCCACCGGGATAGCCGGGGGTCTGGCAGGAATGGGAGGCATCCAGAACGAGAAGG
AGACCATGCAAAGCCTGAACGACCGCCTGGCCTCTTACCTGGACAGAGTGAGGAGCCTGGAGACCGANAACCGGAG
GCTGGANAGCAAAATCCGGGAGCACTTGGAGAAGAAGGGACCCCAGGTCAAGAGACTGGAGCCATTACTTCAAGAT
CATCGAGGGACCTGGAGG

04_16535.2.edit

AGCGNGGTCGCGGCCGAGGTCCAGCTCTGTCTCATACTTGACTCTAAAGTCATCAGCAGCAAGACGGGCATTGTCA
ATCTGCAGAACGATGCGGGCATTGTCCGCAGTATTTGCGAAGATCTGAGCCCTCAGGTCCTCGATGATCTTGAAGT
AATGGCTCCAGTCTCTGACCTGGGGTCCCTTCTTCTCCAAGTGCTCCCGGATTTTGCTCTCCAGCCTCCGGTTCTC
GGTCTCCAGGCTCCTCACTCTGTCCAGGTAAGAAGGCCCAGGCGGTCGTTCAGGCTTTGCATGGTCTCCTTCTCGT
TCTGGATGCCTCCCATTCCTGCCAGACCC

05_16536.1.edit

TCGAGCGGCCGCCCGGGCAGGTCAGGAAGCACATTGGTCTTAGAGCCACTGCCTCCTGGATTCCACCTGTGCTGCG
GACATCTCCAGGGAGTGCAGAAGGGAAGCAGGTCAAACTGCTCAGATCAGTCAGACTGGCTGTTCTCAGTTCTCAC
CTGAGCAAGGTCAGTCTGCAGCCAGAGTACAGAGGGCCAACACTGGTGTTCTTGAACAAGGGCTTGAGCAGACCCT
GCAGAACCCTCTTCCGTGGTGTTGAACTTCCTGGAAACCAGGGTGTTGCATGTTTTTCCTCATAATGCAAGGTTGG
TGATGG

*Fig. 15DDD*

07_16537.1.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACCGCAGGTCTCACCAGTCTCCATGTTGCAGAAGACTTTGATGGCATCCAGGTTGCAGCCTT
GGTTGGGGTCAATCCAGTACTCTCCACTCTTCCAGTCAGAAGTGGGCACATCTTGAGGTCACCGGCAGGTGCCGGG
CCGGGGGTTCTTGCGGCTTGCCCTCTGGGCTCCGGATGTTCTCGATCTGCTTGGCTCAGGCTCTTGAGGGTGGGTG
TCCACCTCGAGGTCACGGTCACCGAAACCTGCCCGGGCGGCCCGCTCGA

08_16537.2.edit

TCGAGCGGTCGCCCGGGCAGGTTTCGTGACCGTGACCTCGAGGTGGACACCACCCTCAAGAGCCTGAGCCAGCAGA
TCGAGAACATCCGGAGCCCAGAGGGCAGCCGCAAGAACCCCGCCCGCACCTGCCGTGACCTCAAGATGTGCCACTC
TGACTGGAAGAGTGGAGAGTACTGGATTGACCCCAACCAAGGCTGCAACCTGGATGCCATCAAAGTCTTCTGCAAC
ATGGAGACTGGTGAGACCTGCGTGTACCCCACTCAGCCCAGTGTGGGCCCAGAAGAAACTGGTACATCAGCAAGGA
ACCCCAAGGACAAGAGGCATTGTCTTGGTTCGGCGAGNAGCATGACCCGATGGATTCCAGTTTCGAGTATTGGCGG
CCAGGGCTTCCCGACCCTTGCCGATGTGGACCTCGGCCGCGACCACCGCT

*Fig. 15EEE*

O8E Surface Expression

O8E Surface Expression

O8E expression in HEK293 Cells
(probed with anti-O8E rabbit polyclonal sera #2333L)

08E Rabbits 01212000

Date:1/21/99

| Antigen on Plate | Sera Sample | Antibody Dilutions | | | | | | | | | | | |
|---|---|---|---|---|---|---|---|---|---|---|---|---|---|
| | | 1:1000 | 1:2000 | 1:4000 | 1:8000 | 1:16000 | 1:32000 | 1:64000 | 1:128000 | 1:256000 | 1:512000 | 1:1024000 | 1:2048000 |
| 08E (#632-24) | Preimmune sera (#2576L):11/10/99 | 0.13 | 0.09 | 0.08 | 0.07 | 0.07 | 0.07 | 0.07 | 0.06 | 0.07 | 0.07 | 0.07 | 0.07 |
| | | 0.10 | 0.08 | 0.07 | 0.07 | 0.07 | 0.07 | 0.07 | 0.06 | 0.06 | 0.07 | 0.06 | 0.07 |
| | Average | 0.11 | 0.08 | 0.07 | 0.07 | 0.07 | 0.07 | 0.07 | 0.06 | 0.07 | 0.07 | 0.06 | 0.07 |
| | α-08E (#2576K):1/11/2000 | 2.92 | 2.81 | 2.74 | 2.70 | 2.58 | 2.08 | 1.61 | 1.01 | 0.68 | 0.40 | 0.24 | 0.15 |
| | | 2.93 | 2.77 | 2.74 | 2.69 | 2.48 | 2.08 | 1.57 | 1.00 | 0.66 | 0.40 | 0.23 | 0.16 |
| | Average | 2.93 | 2.79 | 2.74 | 2.69 | 2.53 | 2.08 | 1.59 | 1.00 | 0.67 | 0.40 | 0.23 | 0.16 |
| | Preimmune sera (#2333L):11/10/99 | 0.09 | 0.07 | 0.06 | 0.06 | 0.07 | 0.07 | 0.07 | 0.07 | 0.07 | 0.07 | 0.07 | 0.07 |
| | | 0.08 | 0.07 | 0.06 | 0.07 | 0.10 | 0.07 | 0.07 | 0.07 | 0.07 | 0.07 | 0.07 | 0.07 |
| | Average | 0.08 | 0.07 | 0.06 | 0.06 | 0.08 | 0.07 | 0.07 | 0.07 | 0.07 | 0.07 | 0.07 | 0.07 |
| | α-08E (#2333L):1/11/2000 | 2.73 | 2.75 | 2.64 | 2.48 | 2.30 | 1.78 | 1.41 | 0.92 | 0.58 | 0.32 | 0.20 | 0.14 |
| | | 2.73 | 2.76 | 2.51 | 2.60 | 2.37 | 1.93 | 1.44 | 0.88 | 0.58 | 0.35 | 0.20 | 0.14 |
| | Average | 2.73 | 2.76 | 2.57 | 2.54 | 2.33 | 1.85 | 1.43 | 0.90 | 0.58 | 0.33 | 0.20 | 0.14 |

*Fig. 23* affi-pure O8E #2576L 739.87A&B

| Date: 5/2/2000 | | |
|---|---|---|
| Antibody Name<br>Rabbit #, Bleed Date<br>Purification Method<br>Buffer<br>Notebook | O8E polyclonal<br>2576L, 1/11/2000<br>affinity<br>PBS<br>#705, p150 | |
| lot #<br>Antibody Concentration<br>Initial Amount | 739.87A<br>1.4mg/ml<br>18mg | 739.87B<br>1.7mg/ml<br>3mg |

| Antigen on Plate | Sera Sample | Antibody Dilutions | | | | | | | | | | | |
|---|---|---|---|---|---|---|---|---|---|---|---|---|---|
| | | 1:1000 | 1:2000 | 1:4000 | 1:8000 | 1:16000 | 1:32000 | 1:64000 | 1:128000 | 1:256000 | 1:512000 | 1:1024000 | 1:2048000 |
| O8E #632-24 | preimmune sera (2576L) | 0.15 | 0.11 | 0.09 | 0.08 | 0.08 | 0.07 | 0.07 | 0.07 | 0.07 | 0.08 | 0.07 | 0.08 |
| | | 0.14 | 0.10 | 0.09 | 0.08 | 0.07 | 0.07 | 0.07 | 0.07 | 0.07 | 0.07 | 0.07 | 0.07 |
| | Average | 0.14 | 0.10 | 0.09 | 0.08 | 0.07 | 0.07 | 0.07 | 0.07 | 0.07 | 0.08 | 0.07 | 0.08 |
| | α-O8E (2576K):2/8/2000 | 2.74 | 2.71 | 2.63 | 2.49 | 2.29 | 1.87 | 1.39 | 0.92 | 0.57 | 0.33 | 0.20 | 0.14 |
| | | 2.72 | 2.68 | 2.64 | 2.47 | 2.26 | 1.93 | 1.42 | 0.94 | 0.57 | 0.34 | 0.21 | 0.14 |
| | Average | 2.73 | 2.70 | 2.63 | 2.48 | 2.27 | 1.90 | 1.41 | 0.93 | 0.57 | 0.34 | 0.21 | 0.14 |
| | affinity pure α-O8E poly salt peak 739-87A | 2.69 | 2.60 | 2.50 | 2.21 | 1.83 | 1.34 | 0.99 | 0.64 | 0.38 | 0.22 | 0.15 | 0.11 |
| | | 2.59 | 2.48 | 2.38 | 2.21 | 1.82 | 1.33 | 1.00 | 0.62 | 0.37 | 0.22 | 0.14 | 0.11 |
| | Average | 2.64 | 2.54 | 2.44 | 2.21 | 1.83 | 1.34 | 1.00 | 0.63 | 0.37 | 0.22 | 0.15 | 0.11 |
| | affinity pure α-O8E poly acid peak 739-67B | 2.46 | 2.39 | 2.40 | 2.34 | 2.08 | 1.73 | 1.29 | 0.81 | 0.49 | 0.29 | 0.19 | 0.13 |
| | | 2.65 | 2.66 | 2.61 | 2.45 | 2.14 | 1.76 | 1.30 | 0.82 | 0.48 | 0.29 | 0.19 | 0.13 |
| | Average | 2.56 | 2.53 | 2.51 | 2.39 | 2.11 | 1.74 | 1.30 | 0.81 | 0.49 | 0.29 | 0.19 | 0.13 |

*Fig. 24*

COMPOSITIONS AND METHODS FOR THE THERAPY AND DIAGNOSIS OF OVARIAN CANCER

CROSS REFERENCE TO RELATED APPLICATIONS

This application is a continuation-in-part of U.S. application Ser. No. 09/617,747, filed Jul. 17, 2000, now abandoned, which is a continuation-in-part of U.S. application Ser. No. 09/404,879, filed Sep. 24, 1999, now U.S. Pat. No. 6,468,546.

TECHNICAL FIELD

The present invention relates generally to ovarian cancer therapy. The invention is more specifically related to polypeptides comprising at least a portion of an ovarian carcinoma protein, and to polynucleotides encoding such polypeptides, as well as antibodies and immune system cells that specifically recognize such polypeptides. Such polypeptides, polynucleotides, antibodies and cells may be used in vaccines and pharmaceutical compositions for treatment of ovarian cancer.

BACKGROUND OF THE INVENTION

Ovarian cancer is a significant health problem for women in the United States and throughout the world. Although advances have been made in detection and therapy of this cancer, no vaccine or other universally successful method for prevention or treatment is currently available. Management of the disease currently relies on a combination of early diagnosis and aggressive treatment, which may include one or more of a variety of treatments such as surgery, radiotherapy, chemotherapy and hormone therapy. The course of treatment for a particular cancer is often selected based on a variety of prognostic parameters, including an analysis of specific tumor markers. However, the use of established markers often leads to a result that is difficult to interpret, and high mortality continues to be observed in many cancer patients.

Immunotherapies have the potential to substantially improve cancer treatment and survival. Such therapies may involve the generation or enhancement of an immune response to an ovarian carcinoma antigen. However, to date, relatively few ovarian carcinoma antigens are known and the generation of an immune response against such antigens has not been shown to be therapeutically beneficial.

Accordingly, there is a need in the art for improved methods for identifying ovarian tumor antigens and for using such antigens in the therapy of ovarian cancer. The present invention fulfills these needs and further provides other related advantages.

SUMMARY OF THE INVENTION

Briefly stated, this invention provides compositions and methods for the therapy of cancer, such as ovarian cancer. In one aspect, the present invention provides polypeptides comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished. Within certain embodiments, the ovarian carcinoma protein comprises a sequence that is encoded by a polynucleotide sequence selected from the group consisting of SEQ ID NOs:1–81, 313–331, 359, 366, 379, 385–387, 391 and complements of such polynucleotides.

The present invention further provides polynucleotides that encode a polypeptide as described above or a portion thereof, expression vectors comprising such polynucleotides and host cells transformed or transfected with such expression vectors.

Within other aspects, the present invention provides pharmaceutical compositions and vaccines. Pharmaceutical compositions may comprise a physiologically acceptable carrier or excipient in combination with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs:1–81, 313–331, 359, 366, 379, 385–387 or 391; (ii) a polynucleotide encoding such a polypeptide; (iii) an antibody that specifically binds to such a polypeptide; (iv) an antigen-presenting cell that expresses such a polypeptide and/or (v) a T cell that specifically reacts with such a polypeptide. Vaccines may comprise a non-specific immune response enhancer in combination with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs:1–81, 313–331, 359, 366, 379, 385–387 or 391; (ii) a polynucleotide encoding such a polypeptide; (iii) an anti-idiotypic antibody that is specifically bound by an antibody that specifically binds to such a polypeptide; (iv) an antigen-presenting cell that expresses such a polypeptide and/or (v) a T cell that specifically reacts with such a polypeptide.

The present invention further provides, in other aspects, fusion proteins that comprise at least one polypeptide as described above, as well as polynucleotides encoding such fusion proteins.

Within related aspects, pharmaceutical compositions comprising a fusion protein or polynucleotide encoding a fusion protein in combination with a physiologically acceptable carrier are provided.

Vaccines are further provided, within other aspects, comprising a fusion protein or polynucleotide encoding a fusion protein in combination with a non-specific immune response enhancer.

Within further aspects, the present invention provides methods for inhibiting the development of a cancer in a patient, comprising administering to a patient a pharmaceutical composition or vaccine as recited above.

The present invention further provides, within other aspects, methods for stimulating and/or expanding T cells, comprising contacting T cells with (a) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs:1–387 or 391; (b) a polynucleotide encoding such a polypeptide and/or (c) an antigen presenting cell that expresses such a polypeptide under conditions and for a time sufficient to permit the stimulation and/or expansion of T cells. Such polypeptide, polynucleotide and/or antigen presenting cell(s) may be present within a pharmaceutical composition or vaccine, for use in stimulating and/or expanding T cells in a mammal.

Within other aspects, the present invention provides methods for inhibiting the development of ovarian cancer in a patient, comprising administering to a patient T cells prepared as described above.

Within further aspects, the present invention provides methods for inhibiting the development of ovarian cancer in a patient, comprising the steps of: (a) incubating $CD4^+$ and/or $CD8^+$ T cells isolated from a patient with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs: 1–387 or 391; (ii) a polynucleotide encoding such a polypeptide; or (iii) an antigen-presenting cell that expresses such a polypeptide; such that T cells proliferate; and (b) administering to the patient an effective amount of the proliferated T cells, and thereby inhibiting the development of ovarian cancer in the patient. The proliferated cells may be cloned prior to administration to the patient.

The present invention also provides, within other aspects, methods for identifying secreted tumor antigens. Such methods comprise the steps of: (a) implanting tumor cells in an immunodeficient mammal; (b) obtaining serum from the immunodeficient mammal after a time sufficient to permit secretion of tumor antigens into the serum; (c) immunizing an immunocompetent mammal with the serum; (d) obtaining antiserum from the immunocompetent mammal; and (e) screening a tumor expression library with the antiserum, and therefrom identifying a secreted tumor antigen. A preferred method for identifying a secreted ovarian carcinoma antigen comprises the steps of: (a) implanting ovarian carcinoma cells in a SCID mouse; (b) obtaining serum from the SCID mouse after a time sufficient to permit secretion of ovarian carcinoma antigens into the serum; (c) immunizing an immunocompetent mouse with the serum; (d) obtaining antiserum from the immunocompetent mouse; and (e) screening an ovarian carcinoma expression library with the antiserum, and therefrom identifying a secreted ovarian carcinoma antigen.

The present invention also discloses antibody epitopes recognized by the O8E polyclonal anti-sera which epitopes are presented herein as SEQ ID NOs: 394–415.

Further disclosed by the present invention are 10-mer and 9-mer peptides predicted to bind HLA-0201 which peptides are disclosed herein as SEQ ID NOs: 416–435 and SEQ ID NOs: 436–455, respectively.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 1A–1S (SEQ ID NOs:1–71) depict partial sequences of polynucleotides encoding representative secreted ovarian carcinoma antigens.

FIGS. 2A–2C depict full insert sequences for three of the clones of FIG. 1. FIG. 2A shows the sequence designated O7E (11731; SEQ ID NO:72), FIG. 2B shows the sequence designated O9E (11785; SEQ ID NO:73) and FIG. 2C shows the sequence designated O8E (13695; SEQ ID NO:74).

FIG. 3 presents results of microarray expression analysis of the ovarian carcinoma sequence designated O8E.

FIG. 4 presents a partial sequence of a polynucleotide (designated 3g; SEQ ID NO:75) encoding an ovarian carcinoma sequence that is a splice fusion between the human T-cell leukemia virus type I oncoprotein TAX and osteonectin.

FIG. 5 presents the ovarian carcinoma polynucleotide designated 3f (SEQ ID NO:76).

FIG. 6 presents the ovarian carcinoma polynucleotide designated 6b (SEQ ID NO:77).

FIGS. 7A and 7B present the ovarian carcinoma polynucleotides designated 8e (SEQ ID NO:78) and 8h (SEQ ID NO:79).

FIG. 8 presents the ovarian carcinoma polynucleotide designated 12c (SEQ ID NO:80).

FIG. 9 presents the ovarian carcinoma polynucleotide designated 12h (SEQ ID NO:81).

FIG. 10 is a chart that depicts results of microarray expression analysis of the ovarian carcinoma sequence designated 3f.

FIG. 11 is a chart that depicts results of microarray expression analysis of the ovarian carcinoma sequence designated 6b.

FIG. 12 is a chart that depicts results of microarray expression analysis of the ovarian carcinoma sequence designated 8e.

FIG. 13 is a chart that depicts results of microarray expression analysis of the ovarian carcinoma sequence designated 12c.

FIG. 14 is a chart that depicts results of microarray expression analysis of the ovarian carcinoma sequence designated 12h.

FIGS. 15A–15EEE depict partial sequences of additional polynucleotides encoding representative secreted ovarian carcinoma antigens (SEQ ID NOs:82–310).

DETAILED DESCRIPTION OF THE INVENTION

Figure 16:
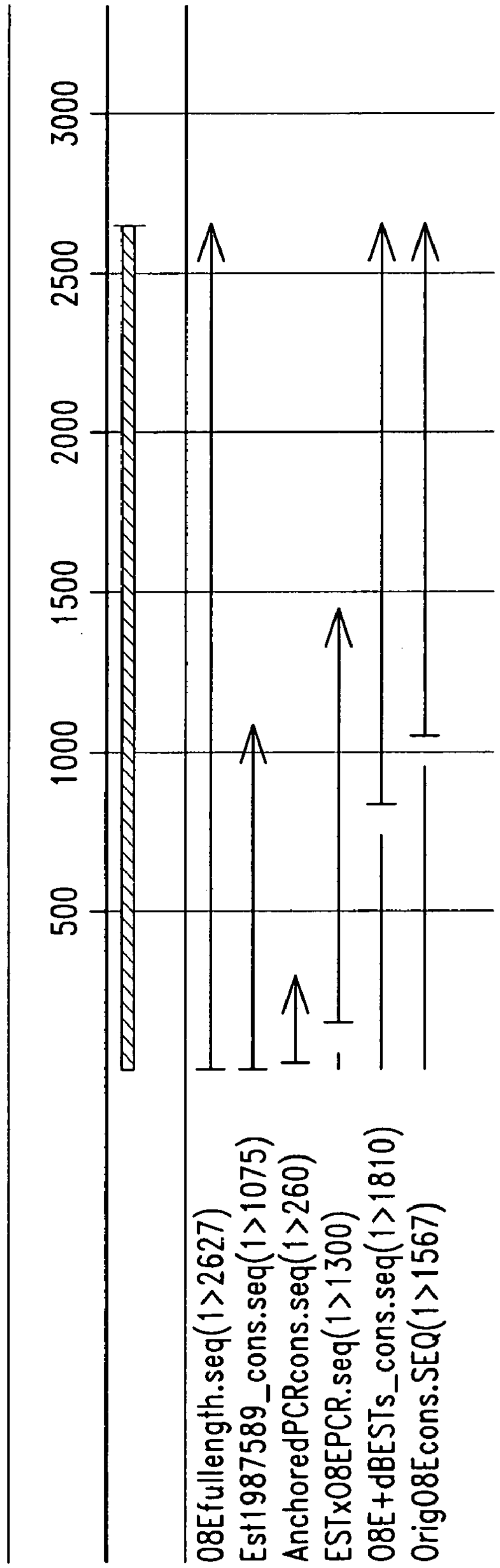
FIG. 16 is a diagram illustrating the location of various partial O8E sequences within the full length sequence.

As noted above, the present invention is generally directed to compositions and methods for the therapy of cancer, such as ovarian cancer. The compositions described herein may include immunogenic polypeptides, polynucleotides encoding such polypeptides, binding agents such as antibodies that bind to a polypeptide, antigen presenting cells (APCs) and/or immune system cells (e.g., T cells).

Polypeptides of the present invention generally comprise at least an immunogenic portion of an ovarian carcinoma protein or a variant thereof. Certain ovarian carcinoma proteins have been identified using an immunoassay technique, and are referred to herein as ovarian carcinoma antigens. An "ovarian carcinoma antigen" is a protein that is expressed by ovarian tumor cells (preferably human cells) at a level that is at least two fold higher than the level in normal ovarian cells. Certain ovarian carcinoma antigens react detectably (within an immunoassay, such as an ELISA or Western blot) with antisera generated against serum from an immunodeficient animal implanted with a human ovarian tumor. Such ovarian carcinoma antigens are shed or secreted from an ovarian tumor into the sera of the immunodeficient animal. Accordingly, certain ovarian carcinoma antigens provided herein are secreted antigens. Certain nucleic acid sequences of the subject invention generally comprise a DNA or RNA sequence that encodes all or a portion of such a polypeptide, or that is complementary to such a sequence.

The present invention further provides ovarian carcinoma sequences that are identified using techniques to evaluate altered expression within an ovarian tumor. Such sequences may be polynucleotide or protein sequences. Ovarian carcinoma sequences are generally expressed in an ovarian tumor at a level that is at least two fold, and preferably at least five fold, greater than the level of expression in normal ovarian tissue, as determined using a representative assay provided herein. Certain partial ovarian carcinoma polynucleotide sequences are presented herein. Proteins encoded by genes comprising such polynucleotide sequences (or complements thereof) are also considered ovarian carcinoma proteins.

Antibodies are generally immune system proteins, or antigen-binding fragments thereof, that are capable of binding to at least a portion of an ovarian carcinoma polypeptide as described herein. T cells that may be employed within the compositions provided herein are generally T cells (e.g., $CD4^+$ and/or $CD8^+$) that are specific for such a polypeptide. Certain methods described herein further employ antigen-presenting cells (such as dendritic cells or macrophages) that express an ovarian carcinoma polypeptide as provided herein.

Ovarian Carcinoma Polynucleotides

Any polynucleotide that encodes an ovarian carcinoma protein or a portion or other variant thereof as described herein is encompassed by the present invention. Preferred polynucleotides comprise at least 15 consecutive nucleotides, preferably at least 30 consecutive nucleotides, and more preferably at least 45 consecutive nucleotides, that encode a portion of an ovarian carcinoma protein. More preferably, a polynucleotide encodes an immunogenic portion of an ovarian carcinoma protein, such as an ovarian carcinoma antigen. Polynucleotides complementary to any such sequences are also encompassed by the present invention. Polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an ovarian carcinoma protein or a portion thereof) or may comprise a variant of such a sequence. Polynucleotide variants may contain one or more substitutions, additions, deletions and/or insertions such that the immunogenicity of the encoded polypeptide is not diminished, relative to a native ovarian carcinoma protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native ovarian carcinoma protein or a portion thereof.

The percent identity for two polynucleotide or polypeptide sequences may be readily determined by comparing sequences using computer algorithms well known to those of ordinary skill in the art, such as Megalign, using default parameters. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned. Optimal alignment of sequences for comparison may be conducted, for example, using the Megalign program in the Lasergene suite of bioinformatics software (DNASTAR, Inc., Madison, Wis.), using default parameters. Preferably, the percentage of sequence identity is determined by comparing two optimally aligned sequences over a window of comparison of at least 20 positions, wherein the portion of the polynucleotide or polypeptide sequence in the window may comprise additions or deletions (i.e., gaps) of 20% or less, usually 5 to 15%, or 10 to 12%, relative to the reference sequence (which does not contain additions or deletions). The percent identity may be calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native ovarian carcinoma protein (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques. For example, an ovarian carcinoma polynucleotide may be identified, as described in more detail below, by screening a late passage ovarian tumor expression library with antisera generated against sera of immunocompetent mice after injection of such mice with sera from SCID mice implanted with late passage ovarian tumors. Ovarian carcinoma polynucleotides may also be identified using any of a variety of techniques designed to evaluate differential gene expression. Alternatively, polynucleotides may be amplified from cDNA prepared from ovarian tumor cells. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., an ovarian carcinoma cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}$p) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Additional techniques include capture PCR (Lagerstrom et al., *PCR Methods Applic.* 1: 111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence.

Certain nucleic acid sequences of cDNA molecules encoding portions of ovarian carcinoma antigens are provided in FIGS. 1A–1S (SEQ ID NOS:1 to 71) and FIGS. 15A to 15EEE (SEQ ID NOs:82 to 310). The sequences provided in FIGS. 1A–1S appear to be novel. For sequences in FIGS. 15A–15EEE, database searches revealed matches having substantial identity. These polynucleotides were isolated by serological screening of an ovarian tumor cDNA expression library, using a technique designed to identify secreted tumor antigens. Briefly, a late passage ovarian tumor expression library was prepared from a SCID-derived human ovarian tumor (OV9334) in the vector λ-screen (Novagen). The sera used for screening were obtained by injecting immunocompetent mice with sera from SCID mice implanted with one late passage ovarian tumors. This technique permits the identification of cDNA molecules that encode immunogenic portions of secreted tumor antigens.

The polynucleotides recited herein, as well as full length polynucleotides comprising such sequences, other portions of such full length polynucleotides, and sequences complementary to all or a portion of such full length molecules, are specifically encompassed by the present invention. It will be apparent to those of ordinary skill in the art that this technique can also be applied to the identification of antigens that are secreted from other types of tumors.

Other nucleic acid sequences of cDNA molecules encoding portions of ovarian carcinoma proteins are provided in FIGS. 4–9 (SEQ ID NOs:75–81), as well as SEQ ID NOs:313–384. These sequences were identified by screening a microarray of cDNAs for tumor-associated expression (i.e., expression that is at least five fold greater in an ovarian tumor than in normal ovarian tissue, as determined using a representative assay provided herein). Such screens were performed using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). SEQ ID NOs:311 and 391 provide full length sequences incorporating certain of these nucleic acid sequences.

Any of a variety of well known techniques may be used to evaluate tumor-associated expression of a cDNA. For example, hybridization techniques using labeled polynucleotide probes may be employed. Alternatively, or in addition, amplification techniques such as real-time PCR may be used (see Gibson et al., *Genome Research* 6:995–1001, 1996;

Heid et al., *Genome Research* 6:986–994, 1996). Real-time PCR is a technique that evaluates the level of PCR product accumulation during amplification. This technique permits quantitative evaluation of mRNA levels in multiple samples. Briefly, mRNA is extracted from tumor and normal tissue and cDNA is prepared using standard techniques. Real-time PCR may be performed, for example, using a Perkin Elmer/Applied Biosystems (Foster City, Calif.) 7700 Prism instrument. Matching primers and fluorescent probes may be designed for genes of interest using, for example, the primer express program provided by Perkin Elmer/Applied Biosystems (Foster City, Calif.). Optimal concentrations of primers and probes may be initially determined by those of ordinary skill in the art, and control (e.g., β-actin) primers and probes may be obtained commercially from, for example, Perkin Elmer/Applied Biosystems (Foster City, Calif.). To quantitate the amount of specific RNA in a sample, a standard curve is generated alongside using a plasmid containing the gene of interest. Standard curves may be generated using the Ct values determined in the real-time PCR, which are related to the initial cDNA concentration used in the assay. Standard dilutions ranging from $10$–$10^6$ copies of the gene of interest are generally sufficient. In addition, a standard curve is generated for the control sequence. This permits standardization of initial RNA content of a tissue sample to the amount of control for comparison purposes.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding an ovarian carcinoma antigen, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo.

A portion of a sequence complementary to a coding sequence (i.e., an antisense polynucleotide) may also be used as a probe or to modulate gene expression. cDNA constructs that can be transcribed into antisense RNA may also be introduced into cells or tissues to facilitate the production of antisense RNA. An antisense polynucleotide may be used, as described herein, to inhibit expression of an ovarian carcinoma protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches*, Futura Publishing Co. (Mt. Kisco, N.Y.; 1994). Alternatively, an antisense molecule may be designed to hybridize with a control region of a gene (e.g., promoter, enhancer or transcription initiation site), and block transcription of the gene; or to block translation by inhibiting binding of a transcript to ribosomes.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Ovarian Carcinoma Polypeptides

Within the context of the present invention, polypeptides may comprise at least an immunogenic portion of an ovarian carcinoma protein or a variant thereof, as described herein. As noted above, certain ovarian carcinoma proteins are ovarian carcinoma antigens that are expressed by ovarian tumor cells and react detectably within an immunoassay (such as an ELISA) with antisera generated against serum from an immunodeficient animal implanted with an ovarian tumor. Other ovarian carcinoma proteins are encoded by ovarian carcinoma polynucleotides recited herein. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of an antigen that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of an ovarian carcinoma protein or a variant thereof. Preferred immunogenic portions are encoded by cDNA molecules isolated as described herein. Further immunogenic portions may generally be identified using well known techniques, such as those summarized in Paul, *Fundamental Immunology,* 3rd ed., 243–247 (Raven Press, 1993) and references cited therein. Such techniques include screening polypeptides for the ability to react with ovarian carcinoma protein-specific antibodies, antisera and/or T-cell lines or clones. As used herein, antisera and antibodies are "ovarian carcinoma protein-specific" if they specifically bind to an ovarian carcinoma protein (i.e., they react with the ovarian carcinoma protein in an ELISA or other immunoassay, and do not react detectably with unrelated proteins). Such antisera, antibodies and T cells may be prepared as described herein, and using well known techniques. An immunogenic portion of a native ovarian carcinoma protein is a portion that reacts with such antisera, antibodies and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length protein. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native ovarian carcinoma protein. A polypeptide "variant," as used herein, is a polypeptide that differs from a native ovarian carcinoma protein in one or more substitutions, deletions, additions and/or insertions, such that the immunogenicity of the polypeptide is not substantially diminished. In other words, the ability of a variant to react with ovarian carcinoma protein-specific antisera may be enhanced or unchanged, relative to the native ovarian carcinoma protein, or may be diminished by less than 50%, and preferably less than 20%, relative to the native ovarian carcinoma protein. Such variants may generally be identified by modifying one of the above polypeptide sequences and evaluating the reactivity of the modified polypeptide with ovarian carcinoma protein-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants preferably exhibit at least about 70%, more preferably at least about 90% and most preferably at least about 95% identity to the native polypeptide. Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. Coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied BioSystems, Inc. (Foster City, Calif.), and may be operated according to the manufacturer's instructions.

Within certain specific embodiments, a polypeptide may be a fusion protein that comprises multiple polypeptides as described herein, or that comprises one polypeptide as described herein and a known tumor antigen, such as an ovarian carcinoma protein or a variant of such a protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci.* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.,* 336:86–91, 1997).

Within preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen present cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to an ovarian carcinoma protein.

As used herein, an antibody, or antigen-binding fragment thereof, is said to "specifically bind" to an ovarian carcinoma protein if it reacts at a detectable level (within, for example, an ELISA) with an ovarian carcinoma protein, and does not react detectably with unrelated proteins under similar conditions. As used herein, "binding" refers to a noncovalent association between two separate molecules such that a "complex" is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents may be further capable of differentiating between patients with and without a cancer, such as ovarian cancer, using the representative assays provided herein. In other words, antibodies or other binding agents that bind to a ovarian carcinoma antigen will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, leukophoresis, urine and/or tumor biopsies) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas* exotoxin, *Shigella* toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Also provided herein are anti-idiotypic antibodies that mimic an immunogenic portion of an ovarian carcinoma protein. Such antibodies may be raised against an antibody, or antigen-binding fragment thereof, that specifically binds to an immunogenic portion of an ovarian carcinoma protein, using well known techniques. Anti-idiotypic antibodies that mimic an immunogenic portion of an ovarian carcinoma protein are those antibodies that bind to an antibody, or antigen-binding fragment thereof, that specifically binds to an immunogenic portion of an ovarian carcinoma protein, as described herein.

T Cells

Immunotherapeutic compositions may also, or alternatively, comprise T cells specific for an ovarian carcinoma protein. Such cells may generally be prepared in vitro or ex vivo, using standard procedures. For example, T cells may be present within (or isolated from) bone marrow, peripheral blood or a fraction of bone marrow or peripheral blood of a mammal, such as a patient, using a commercially available cell separation system, such as the CEPRATE™ system, available from CellPro Inc., Bothell Wash. (see also U.S. Pat. No. 5,240,856; U.S. Pat. No. 5,215,926; WO 89/06280; WO 91/16116 and WO 92/07243). Alternatively, T cells may be derived from related or unrelated humans, non-human animals, cell lines or cultures.

T cells may be stimulated with an ovarian carcinoma polypeptide, polynucleotide encoding an ovarian carcinoma polypeptide and/or an antigen presenting cell (APC) that expresses such a polypeptide. Such stimulation is performed under conditions and for a time sufficient to permit the generation of T cells that are specific for the polypeptide. Preferably, an ovarian carcinoma polypeptide or polynucleotide is present within a delivery vehicle, such as a microsphere, to facilitate the generation of specific T cells.

T cells are considered to be specific for an ovarian carcinoma polypeptide if the T cells kill target cells coated with an ovarian carcinoma polypeptide or expressing a gene encoding such a polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with an ovarian carcinoma polypeptide (200 ng/ml–100 μg/ml, preferably 100 ng/ml–25 μg/ml) for 3–7 days should result in at least a two fold increase in proliferation of the T cells and/or contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998). T cells that have been activated in response to an ovarian carcinoma polypeptide, polynucleotide or ovarian carcinoma polypeptide-expressing APC may be $CD4^+$ and/or $CD8^+$. Ovarian carcinoma polypeptide-specific T cells may be expanded using standard techniques. Within preferred embodiments, the T cells are derived from a patient or a related or unrelated donor and are administered to the patient following stimulation and expansion.

For therapeutic purposes, $CD4^+$ or $CD8^+$ T cells that proliferate in response to an ovarian carcinoma polypeptide, polynucleotide or APC can be expanded in number either in vitro or in vivo. Proliferation of such T cells in vitro may be accomplished in a variety of ways. For example, the T cells can be re-exposed to an ovarian carcinoma polypeptide, with or without the addition of T cell growth factors, such as interleukin-2, and/or stimulator cells that synthesize an ovarian carcinoma polypeptide. Alternatively, one or more T cells that proliferate in the presence of an ovarian carcinoma polypeptide can be expanded in number by cloning. Methods for cloning cells are well known in the art, and include limiting dilution. Following expansion, the cells may be administered back to the patient as described, for example, by Chang et al., *Crit. Rev. Oncol. Hematol.* 22:213, 1996.

Pharmaceutical Compositions and Vaccines

Within certain aspects, polypeptides, polynucleotides, binding agents and/or immune system cells as described herein may be incorporated into pharmaceutical compositions or vaccines. Pharmaceutical compositions comprise one or more such compounds or cells and a physiologically acceptable carrier. Vaccines may comprise one or more such compounds or cells and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as *Bacillus-Calmette-Guerrin*) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, IL-2 and IL-12) tend to favor the induction of cell mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Ribi ImmunoChem Research Inc. (Hamilton, Mont.; see U.S. Pat. Nos. 4,436,727; 4,877,611; 4,866,034 and 4,912,094). Also preferred is AS-2 (SmithKline Beecham). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Any vaccine provided herein may be prepared using well known methods that result in a combination of antigen, immune response enhancer and a suitable carrier or excipient.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80 and CD86).

APCs may generally be transfected with a polynucleotide encoding a ovarian carcinoma antigen (or portion or other variant thereof) such that the antigen, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Cancer Therapy

In further aspects of the present invention, the compositions described herein may be used for immunotherapy of cancer, such as ovarian cancer. Within such methods, pharmaceutical compositions and vaccines are typically administered to a patient. As used herein, a "patient" refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. Within certain preferred embodiments, a patient is afflicted with ovarian cancer. Such cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors with the administration of immuno response-modifying agents (such as tumor vaccines, bacterial adjuvants and/or cytokines).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into stem cells taken from a patient and clonally propagated in vitro for autologous transplant back into the same patient.

Routes and frequency of administration, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration), orally or in the bed of a resected tumor. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 100 μg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to an ovarian carcinoma antigen generally correlate with an improved clinical outcome. Such immune responses may generally be evaluated using standard proliferation, cytotoxicity or cytokine assays, which may be performed using samples obtained from a patient before and after treatment.

Screens for Identifying Secreted Ovarian Carcinoma Antigens

The present invention provides methods for identifying secreted tumor antigens. Within such methods, tumors are implanted into immunodeficient animals such as SCID mice and maintained for a time sufficient to permit secretion of tumor antigens into serum. In general, tumors may be implanted subcutaneously or within the gonadal fat pad of an immunodeficient animal and maintained for 1–9 months, preferably 1–4 months. Implantation may generally be performed as described in WO 97/18300. The serum containing secreted antigens is then used to prepare antisera in immunocompetent mice, using standard techniques and as described herein. Briefly, 50–100 μL of sera (pooled from three sets of immunodeficient mice, each set bearing a different SCID-derived human ovarian tumor) may be mixed 1:1 (vol:vol) with an appropriate adjuvant, such as RIBI-MPL or MPL+TDM (Sigma Chemical Co., St. Louis, Mo.) and injected intraperitoneally into syngeneic immunocompetent animals at monthly intervals for a total of 5 months. Antisera from animals immunized in such a manner may be obtained by drawing blood after the third, fourth and fifth immunizations. The resulting antiserum is generally precleared of *E. coli* and phage antigens and used (generally following dilution, such as 1:200) in a serological expression screen.

The library is typically an expression library containing cDNAs from one or more tumors of the type that was implanted into SCID mice. This expression library may be prepared in any suitable vector, such as λ-screen (Novagen). cDNAs that encode a polypeptide that reacts with the antiserum may be identified using standard techniques, and sequenced. Such cDNA molecules may be further characterized to evaluate expression in tumor and normal tissue, and to evaluate antigen secretion in patients.

The methods provided herein have advantages over other methods for tumor antigen discovery. In particular, all antigens identified by such methods should be secreted or released through necrosis of the tumor cells. Such antigens may be present on the surface of tumor cells for an amount of time sufficient to permit targeting and killing by the immune system, following vaccination.

Methods for Detecting Cancer

In general, a cancer may be detected in a patient based on the presence of one or more ovarian carcinoma proteins and/or polynucleotides encoding such proteins in a biological sample (such as blood, sera, urine and/or tumor biopsies) obtained from the patient. In other words, such proteins may be used as markers to indicate the presence or absence of a cancer such as ovarian cancer. In addition, such proteins may be useful for the detection of other cancers. The binding agents provided herein generally permit detection of the level of protein that binds to the agent in the biological sample. Polynucleotide primers and probes may be used to detect the level of mRNA encoding a tumor protein, which is also indicative of the presence or absence of a cancer. In general, an ovarian carcinoma-associated sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length ovarian carcinoma proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term “immobilization” refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with ovarian cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as ovarian cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 μg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use ovarian carcinoma polypeptides to detect antibodies that bind to such polypeptides in a biological sample. The detection of such ovarian carcinoma protein specific antibodies may correlate with the presence of a cancer.

A cancer may also, or alternatively, be detected based on the presence of T cells that specifically react with an ovarian carcinoma protein in a biological sample. Within certain methods, a biological sample comprising $CD4^+$ and/or $CD8^+$ T cells isolated from a patient is incubated with an ovarian carcinoma protein, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with an ovarian carcinoma protein (e.g., 5–25 μg/ml). It may be desirable to incubate another aliquot of a T cell sample in the absence of ovarian carcinoma protein to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding an ovarian carcinoma protein in a biological sample. For example, at least two oligonucleotide primers may be employed in a polymerase chain reaction (PCR) based assay to amplify a portion of an ovarian carcinoma protein cDNA derived from a biological sample, wherein at least one of the oligonucleotide primers is specific for (i.e., hybridizes to) a polynucleotide encoding the ovarian carcinoma protein. The amplified cDNA is then separated and detected using techniques well known in the art, such as gel electrophoresis. Similarly, oligonucleotide probes that specifically hybridize to a polynucleotide encoding an ovarian carcinoma protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding an ovarian carcinoma protein that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence provided herein. Techniques for both PCR based assays and hybridization assays are well known in the art (see, for example, Mullis et al., *Cold Spring Harbor Symp. Quant. Biol.,* 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample such as a biopsy tissue and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, ovarian carcinoma proteins and polynucleotides encoding such proteins may be used as markers for monitoring the progression of cancer. In this embodiment, assays as described above for the diagnosis of a cancer may be performed over time, and the change in the level of reactive polypeptide(s) evaluated. For example, the assays may be performed every 24–72 hours for a period of 6 months to 1 year, and thereafter performed as needed. In general, a cancer is progressing in those patients in whom the level of polypeptide detected by the binding agent increases over time. In contrast, the cancer is not progressing when the level of reactive polypeptide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple ovarian carcinoma protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to an ovarian carcinoma protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding an ovarian carcinoma protein in a biological sample. Such kits generally comprise at least one oligonucleotide probe or primer, as described above, that hybridizes to a polynucleotide encoding an ovarian carcinoma protein. Such an oligonucleotide may be used, for example, within a PCR or hybridization assay. Additional components that may be present within such kits include a second oligonucleotide and/or a diagnostic reagent or container to facilitate the detection of a polynucleotide encoding an ovarian carcinoma protein.

The following Examples are offered by way of illustration and not by way of limitation.

EXAMPLES

Example 1

Identification of Representative Ovarian Carcinoma Protein cDNAs

This Example illustrates the identification of cDNA molecules encoding ovarian carcinoma proteins.

Anti-SCID mouse sera (generated against sera from SCID mice carrying late passage ovarian carcinoma) was precleared of *E. coli* and phage antigens and used at a 1:200 dilution in a serological expression screen. The library screened was made from a SCID-derived human ovarian tumor (OV9334) using a directional RH oligo(dT) priming cDNA library construction kit and the % Screen vector (Novagen). A bacteriophage lambda screen was employed. Approximately 400,000 pfu of the amplified OV9334 library were screened.

196 positive clones were isolated. Certain sequences that appear to be novel are provided in FIGS. 1A–1S and SEQ ID NOs:1 to 71. Three complete insert sequences are shown in FIGS. 2A–2C (SEQ ID NOs:72 to 74). Other clones having known sequences are presented in FIGS. 15A–15EEE (SEQ ID NOs:82 to 310). Database searches identified the following sequences that were substantially identical to the sequences presented in FIGS. 15A–15EEE.

These clones were further characterized using microarray technology to determine mRNA expression levels in a variety of tumor and normal tissues. Such analyses were performed using a Synteni (Palo Alto, Calif.) microarray, according to the manufacturer's instructions. PCR amplification products were arrayed on slides, with each product occupying a unique location in the array. mRNA was extracted from the tissue sample to be tested, reverse transcribed and fluorescent-labeled cDNA probes were generated. The microarrays were probed with the labeled cDNA probes and the slides were scanned to measure fluorescence intensity. Data was analyzed using Synteni's provided GEMtools software. The results for one clone (13695, also referred to as O8E) are shown in FIG. 3.

Example 2

Identification of Ovarian Carcinoma cDNAs Using Microarray Technology

This Example illustrates the identification of ovarian carcinoma polynucleotides by PCR subtraction and microarray analysis. Microarrays of cDNAs were analyzed for ovarian tumor-specific expression using a Synteni (Palo Alto, Calif.) microarray, according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997).

A PCR subtraction was performed using a tester comprising cDNA of four ovarian tumors (three of which were metastatic tumors) and a driver of cDNA form five normal tissues (adrenal gland, lung, pancreas, spleen and brain). cDNA fragments recovered from this subtraction were subjected to DNA microarray analysis where the fragments were PCR amplified, adhered to chips and hybridized with fluorescently labeled probes derived from mRNAs of human ovarian tumors and a variety of normal human tissues. In this analysis, the slides were scanned and the fluorescence intensity was measured, and the data were analyzed using Syriteni's GEMtools software. In general, sequences showing at least a 5-fold increase in expression in tumor cells (relative to normal cells) were considered ovarian tumor antigens. The fluorescent results were analyzed and clones that displayed increased expression in ovarian tumors were further characterized by DNA sequencing and database searches to determine the novelty of the sequences.

Using such assays, an ovarian tumor antigen was identified that is a splice fusion between the human T-cell leukemia virus type I oncoprotein TAX (see Jin et al., *Cell* 93:81–91, 1998) and an extracellular matrix protein called osteonectin. A splice junction sequence exists at the fusion point. The sequence of this clone is presented in FIG. 4 and SEQ ID NO:75. Osteonectin, unspliced and unaltered, was also identified from such assays independently.

Further clones identified by this method are referred to herein as 3f, 6b, 8e, 8h, 12c and 12h. Sequences of these clones are shown in FIGS. 5 to 9 and SEQ ID NOs:76 to 81. Microarray analyses were performed as described above, and are presented in FIGS. 10 to 14. A full length sequence encompassing clones 3f, 6b, 8e and 12h was obtained by screening an ovarian tumor (SCID-derived) cDNA library. This 2996 base pair sequence (designated O772P) is presented in SEQ ID NO:311, and the encoded 914 amino acid protein sequence is shown in SEQ ID NO:312. PSORT analysis indicates a Type 1a transmembrane protein localized to the plasma membrane.

In addition to certain of the sequences described above, this screen identified the following sequences:

Table 1—Ovarian Carcinoma cDNAs Identified by Microarray Analysis

| Sequence | Comments |
|---|---|
| OV4vG11 (SEQ ID NO:313) | human clone 1119D9 on chromosome 20p12 |
| OV4vB11 (SEQ ID NO:314) | human UWGC:y14c094 from chromosome 6p21 |
| OV4vD9 (SEQ ID NO:315) | human clone 1049G16 chromosome 20q12-13.2 |
| OV4vD5 (SEQ ID NO:316) | human KIAA0014 gene |
| OV4vC2 (SEQ ID NO:317) | human KIAA0084 gene |
| OV4vF3 (SEQ ID NO:318) | human chromosome 19 cosmid R31167 |
| OV4VC1 (SEQ ID NO:319) | novel |
| OV4vH3 (SEQ ID NO:320) | novel |
| OV4vD2 (SEQ ID NO:321) | novel |
| O815P (SEQ ID NO:322) | novel |
| OV4vC12 (SEQ ID NO:323) | novel |
| OV4vA4 (SEQ ID NO:324) | novel |

-continued

| Sequence | Comments |
|---|---|
| OV4vA3 (SEQ ID NO:325) | novel |
| OV4v2A5 (SEQ ID NO:326) | novel |
| O819P (SEQ ID NO:327) | novel |
| O818P (SEQ ID NO:328) | novel |
| O817P (SEQ ID NO:329) | novel |
| O816P (SEQ ID NO:330) | novel |
| Ov4vC5 (SEQ ID NO:331) | novel |
| 21721 (SEQ ID NO:332) | human lumican |
| 21719 (SEQ ID NO:333) | human retinoic acid-binding protein II |
| 21717 (SEQ ID NO:334) | human26S proteasome ATPase subunit |
| 21654 (SEQ ID NO:335) | human copine I |
| 21627 (SEQ ID NO:336) | human neuron specific gamma-2 enolase |
| 21623 (SEQ ID NO:337) | human geranylgeranyl transferase II |
| 21621 (SEQ ID NO:338) | human cyclin-dependent protein kinase |
| 21616 (SEQ ID NO:339) | human prepro-megakaryocyte potentiating factor |
| 21612 (SEQ ID NO:340) | human UPH1 |
| 21558 (SEQ ID NO:341) | human RalGDS-like 2 (RGL2) |
| 21555 (SEQ ID NO:342) | human autoantigen P542 |
| 21548 (SEQ ID NO:343) | human actin-related protein (ARP2) |
| 21462 (SEQ ID NO:344) | human huntingtin interacting protein |
| 21441 (SEQ ID NO:345) | human 90K product (tumor associated antigen) |
| 21439 (SEQ ID NO:346) | human guanine nucleotide regulator protein (tim1) |
| 21438 (SEQ ID NO:347) | human Ku autoimmune (p70/p80) antigen |
| 21237 (SEQ ID NO:348) | human S-laminin |
| 21436 (SEQ ID NO:349) | human ribophorin I |
| 21435 (SEQ ID NO:350) | human cytoplasmic chaperonin hTRiC5 |
| 21425 (SEQ ID NO:351) | humanEMX2 |
| 21423 (SEQ ID NO:352) | human p87/p89 gene |
| 21419 (SEQ ID NO:353) | human HPBRII-7 |
| 21252 (SEQ ID NO:354) | human T1-227H |
| 21251 (SEQ ID NO:355) | human cullin I |
| 21247 (SEQ ID NO:356) | kunitz type protease inhibitor (KOP) |
| 21244-1 (SEQ ID NO:357) | human protein tyrosine phosphatase receptor F (PTPRF) |
| 21718 (SEQ ID NO:358) | human LTR repeat |
| OV2-90 (SEQ ID NO:359) | novel |
| Human zinc finger (SEQ ID NO:360) | |
| Human polyA binding protein (SEQ ID NO:361) | |
| Human pleitrophin (SEQ ID NO:362) | |
| Human PAC clone 278C19 (SEQ ID NO:363) | |
| Human LLRep3 (SEQ ID NO:364) | |
| Human Kunitz type protease inhib (SEQ ID NO:365) | |
| Human KIAA0106 gene (SEQ ID NO:366) | |
| Human keratin (SEQ ID NO:367) | |
| Human HIV-1TAR (SEQ ID NO:368) | |
| Human glia derived nexin (SEQ ID NO:369) | |
| Human fibronectin (SEQ ID NO:370) | |
| Human ECMproBM4O (SEQ ID NO:371) | |
| Human collagen (SEQ ID NO:372) | |
| Human alpha enolase (SEQ ID NO:373) | |
| Human aldolase (SEQ ID NO:374) | |
| Human transf growth factor BIG H3 (SEQ ID NO:375) | |
| Human SPARC osteonectin (SEQ ID NO:376) | |
| Human SLP1 leucocyte protease (SEQ ID NO:377) | |
| Human mitochondrial ATP synth (SEQ ID NO:378) | |
| Human DNA seq clone 461P17 (SEQ ID NO:379) | |
| Human dbpB pro Y box (SEQ ID NO:380) | |
| Human 40 kDa keratin (SEQ ID NO:381) | |
| Human arginosuccinate synth (SEQ ID NO:382) | |
| Human acidic ribosomal phosphoprotein (SEQ ID NO:383) | |
| Human colon carcinoma laminin binding pro (SEQ ID NO:384) | |

This screen further identified multiple forms of the clone O772P, referred to herein as 21013, 21003 and 21008. PSORT analysis indicates that 21003 (SEQ ID NO:386; translated as SEQ ID NO:389) and 21008 (SEQ ID NO:387; translated as SEQ ID NO:390) represent Type 1a transmembrane protein forms of O772P. 21013 (SEQ ID NO:385; translated as SEQ ID NO:388) appears to be a truncated form of the protein and is predicted by PSORT analysis to be a secreted protein.

Additional sequence analysis resulted in a full length clone for O8E (2627 bp, which agrees with the message size observed by Northern analysis; SEQ ID NO:391). This nucleotide sequence was obtained as follows: the original O8E sequence (OrigO8Econs) was found to overlap by 33 nucleotides with a sequence from an EST clone (IMAGE#1987589). This clone provided 1042 additional nucleotides upstream of the original O8E sequence. The link between the EST and O8E was confirmed by sequencing multiple PCR fragments generated from an ovary primary tumor library using primers to the unique EST and the O8E sequence (EST×O8EPCR). Full length status was further indicated when anchored PCR from the ovary tumor library gave several clones (AnchoredPCR cons) that all terminated upstream of the putative start methionine, but failed to yield any additional sequence information. FIG. 16 presents a diagram that illustrates the location of each partial sequence within the full length O8E sequence.

Two protein sequences may be translated from the full length O8E. For "a" (SEQ ID NO:393) begins with a putative start methionine. A second form "b" (SEQ ID NO:392) includes 27 additional upstream residues to the 5' end of the nucleotide sequence.

Example 3

This example discloses the identification and characterization of antibody epitopes recognized by the O8E polyclonal anti-sera.

Rabbit anti-sera was raised against *E. coli* derived O8E recombinant protein and tested for antibody epitope recognition against 20 or 21 mer peptides that correspond to the O8E amino acid sequence. Peptides spanning amino acid regions 31 to 65, 76 to 110, 136 to 200 and 226 to 245 of the full length O8E protein were recognized by an acid eluted peak and/or a salt eluted peak from affinity purified anti-O8E sera. Thus, the corresponding amino acid sequences of the above peptides constitute the antibody epitopes recognized by affinity purified anti-O8E antibodies.

Figure 17:
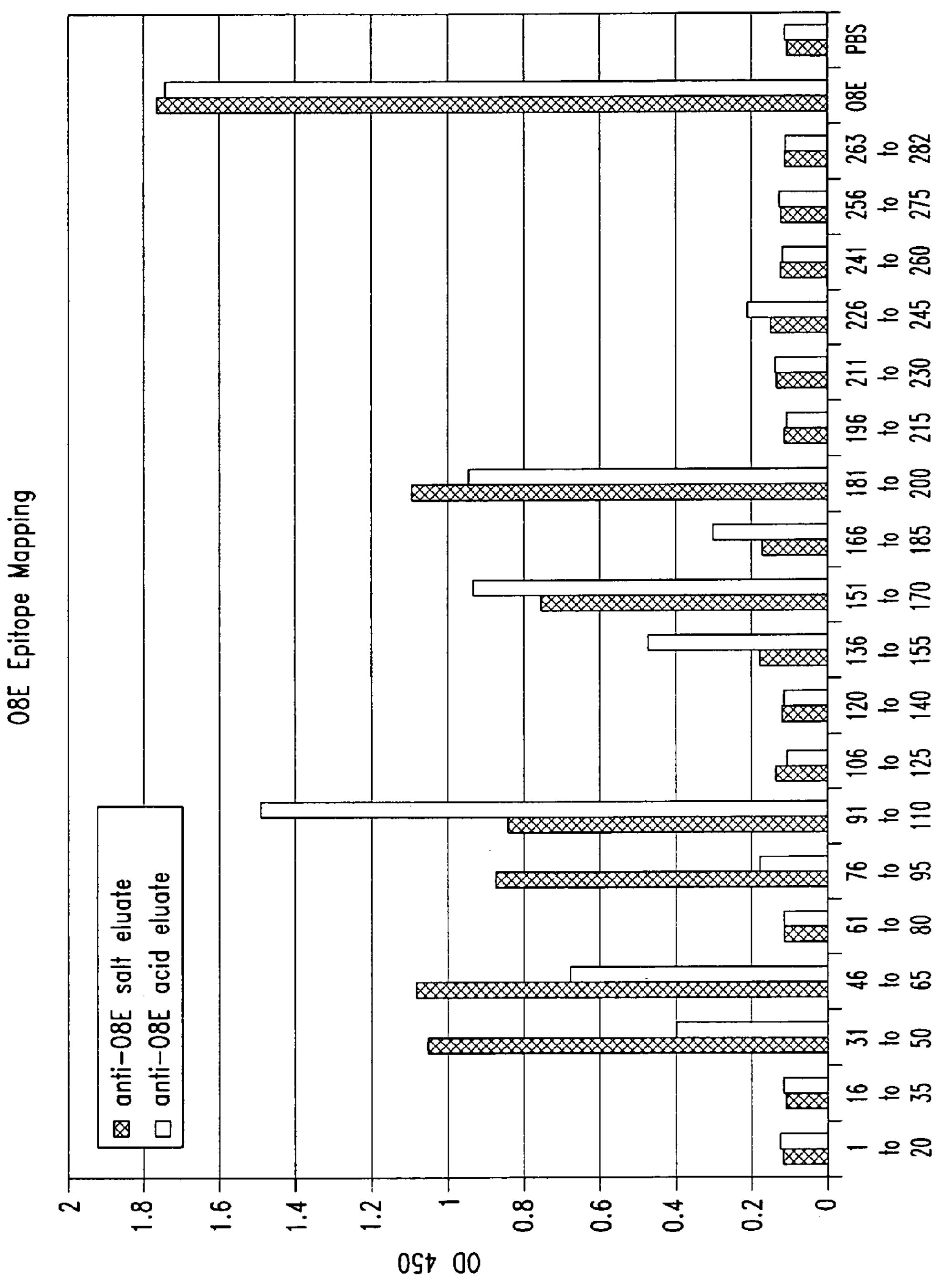
FIG. 17 is a graph illustrating the results of epitope mapping studies on O8E protein.

For epitope mapping, 20 or 21 mer peptides corresponding to the O8E protein were synthesized. For antibody affinity purification, rabbit anti-O8E sera was run over an O8E-sepharose column, then antibody was eluted with a salt buffer containing 0.5 M NaCl and 20 mM $PO_4$, followed by an acid elution step using 0.2 M Glycine, pH 2.3. Purified antibody was neutralized by the addition of 1M Tris, pH 8 and buffer exchanged into phosphate buffered saline (PBS). For enzyme linked immunosorbant assay (ELISA) analysis, O8E peptides and O8E recombinant protein were coated onto 96 well flat bottom plates at 2 μg/ml for 2 hours at room temperature (RT). Plates were then washed 5 times with PBS+0.1% Tween 20 and blocked with PBS+1% bovine serum albumin (BSA) for 1 hour. Affinity purified anti-O8E antibody, either an acid or salt eluted fraction, was then added to the wells at 1 μg/ml and incubated at RT for 1 hr. Plates were again washed, followed by the addition of donkey anti-rabbit-Ig-horseradish peroxidase (HRP) antibody for 1 hour at RT. Plates were washed, then developed by the addition of the chromagenic substrate 3, 3', 5,5'-tetramethylbenzidine (TMB) (described by Bos et al., *J. of Immunoassay* 2:187–204 (1981); available from Sigma (St. Louis, Mo.)). The reaction was incubated 15 minutes at RT and then stopped by the addition of 1 N $H_2SO_4$. Plates were read at an optical density of 450 (OD450) in an automated plate reader. The sequences of peptides corresponding to the OE8 antibody epitopes are disclosed herein as SEQ ID NOs: 394–415. Antibody epitopes recognized by the O8E polyclonal anti-sera are disclosed herein in FIG. 17.

Example 4

This example discloses IHC analysis of O8E expression in ovarian cancer tissue samples.

For immunohistochemistry studies, paraffin-embedded formalin fixed ovarian cancer tissue was sliced into 8 micron sections. Steam heat induced epitope retrieval (SHIER) in 0.1 M sodium citrate buffer (pH 6.0) was used for optimal staining conditions. Sections were incubated with 10% serum/PBS for 5 minutes. Primary antibody (anti-O8E rabbit affinity purified polyclonal antibody) was added to each section for 25 min followed by a 25 min incubation with an anti-rabbit biotinylated antibody. Endogenous peroxidase activity was blocked by three 1.5 min incubations with hydrogen peroxidase. The avidin biotin complex/horse radish peroxidase system was used along with DAB chromogen to visualize antigen expression. Slides were counterstained with hematoxylin. One (papillary serous carcinoma) of six ovarian cancer tissue sections displayed O8E immunoreactivity. O8E expression was localized to the plasma membrane.

Six ovarian cancer tissues were analyzed with the anti-O8E rabbit polyclonal antibody. One (papillary serous carcinoma) of six ovarian cancer tissue samples stained positive for O8E expression. O8E expression was localized to the surface membrane.

Example 5

This example discloses O8E peptides that are predicted to bind HLA-A2 and to be immunogenic for CD8 T cell responses in humans.

Potential HLA-A2 binding peptides of O8E were predicted by using the full-length open-reading frame (ORF) from O8E and running it through "Episeek," a program used to predict MHC binding peptides. The program used is based on the algorithm published by Parker, K. C. et al., *J. Immunol.* 152(1):163–175 (1994) (incorporated by reference herein in its entirety). 10-mer and 9-mer peptides predicted to bind HLA-0201 are disclosed herein as SEQ ID NOs: 416–435 and SEQ ID NOs: 436–455, respectively.

Example 6

This example discloses O8E cell surface expression measured by fluoresence activated cell sorting.

Figure 18:
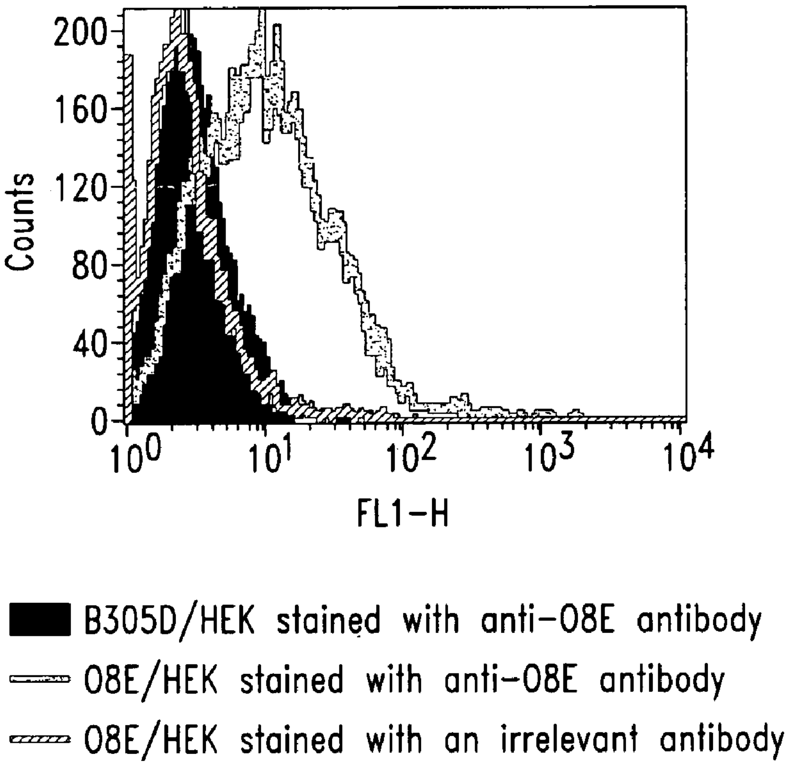
FIG. 18 is graph of a fluorescence activated cell sorting (FACS) analysis of O8E cell surface expression.
Figure 19:
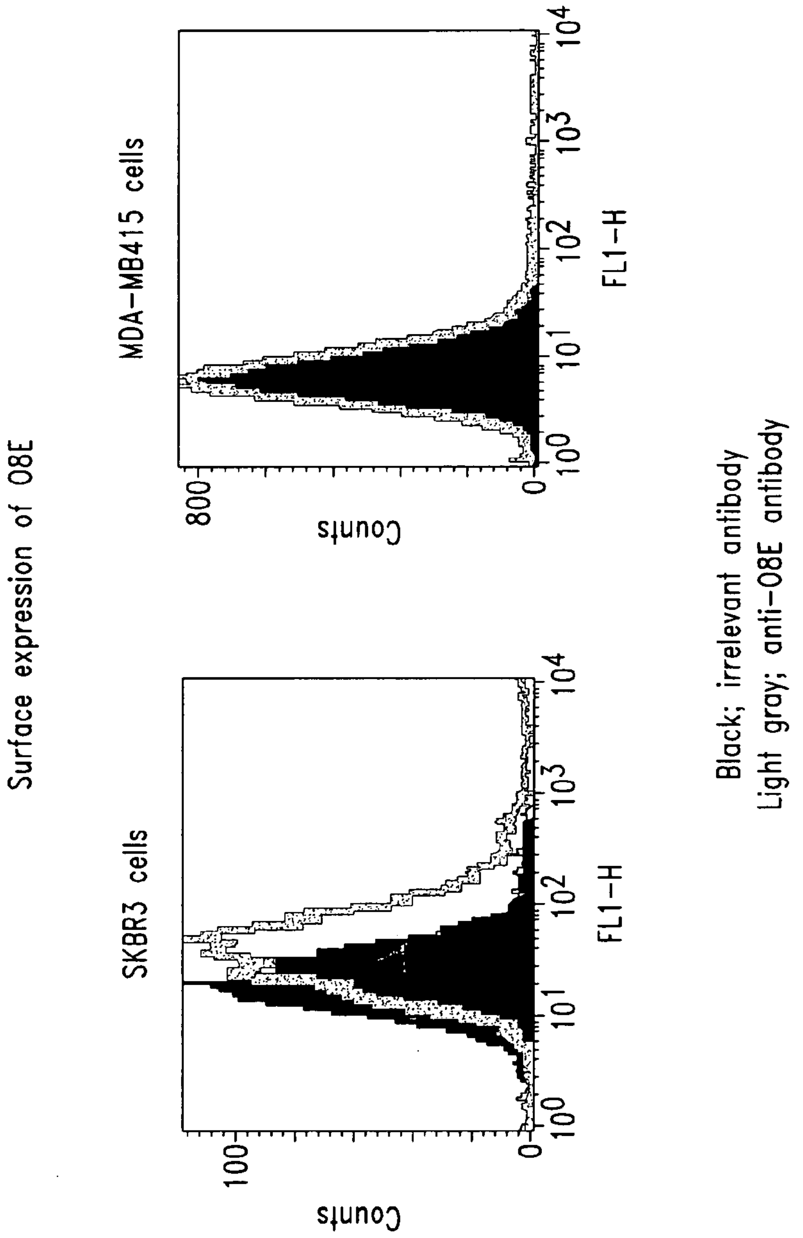
FIG. 19 is graph of a FACS analysis of O8E cell surface expression.

For FACS analysis, cells were washed with ice cold staining buffer (PBS/1% BSA/azide). Next, the cells were incubated for 30 minutes on ice with 10 micrograms/ml of affinity purified rabbit anti-B305D polyclonal antibody. The cells were washed 3 times with staining buffer and then incubated with a 1:100 dilution of a goat anti-rabbit Ig (H+L)-FITC reagent (Southern Biotechnology) for 30 minutes on ice. Following 3 washes, the cells were resuspended in staining buffer containing prodium iodide, a vital stain that allows for identification of permeable cells, and analyzed by FACS. O8E surface expression was confirmed on SKBR3 breast cancer cells and HEK293 cells that stably overexpress the cDNA for O8E. Neither MB415 cells nor HEK293 cells stably transfected with a control irrelevant plasmid DNA showed surface expression of O8E (FIGS. 18 and 19).

Example 7

This example further evaluates the expression and surface localization of O8E.

For expression and purification of antigen used for immunization, O8E expressed in an *E. coli* recombinant expression system was grown overnight in LB Broth with the appropriate antibiotics at 37° C. in a shaking incubator. The next morning, 10 ml of the overnight culture was added to 500 ml of 2×YT plus appropriate antibiotics in a 2 L-baffled Erlenmeyer flask. When the Optical Density (at 560 nanometers) of the culture reached 0.4–0.6 the cells were induced with IPTG (1 mM). 4 hours after induction with IPTG the cells were harvested by centrifugation. The cells were then washed with phosphate buffered saline and centrifuged again. The supernatant was discarded and the cells were either frozen for future use or immediately processed. Twenty milliliters of lysis buffer was added to the cell pellets and vortexed. To break open the *E. coli* cells, this mixture was then run through the French Press at a pressure of 16,000 psi. The cells were then centrifuged again and the supernatant and pellet were checked by SDS-PAGE for the partitioning of the recombinant protein. For protein that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole. The solubilized protein was added to 5 ml of nickel-chelate resin (Qiagen) and incubated for 45 min to 1 hour at room temperature with continuous agitation. After incubation, the resin and protein mixture were poured through a disposable column and the flow through was collected. The column was then washed with 10–20 column volumes of the solubilization buffer. The antigen was then eluted from the column using 8M urea, 10 mM tris pH 8.0 and 300 mM imidazole and collected in 3 ml fractions. A SDS-PAGE gel was run to determine which fractions to pool for further purification. As a final purification step, a strong anion exchange resin such as Hi-Prep Q (Biorad) was equilibrated with the appropriate buffer and the pooled fractions from above were loaded onto the column. Each antigen was eluted off of the column with an increasing salt gradient. Fractions were collected as the column was run and another SDS-PAGE gel was run to determine which fractions from the column to pool. The pooled fractions were dialyzed against 10 mM Tris pH 8.0. This material was then evaluated for acceptable purity as determined by SDS-PAGE or HPLC, concentration as determined by Lowry assay or Amino Acid Analysis, identity as determined by amino terminal protein sequence, and endotoxin level as determined by the *Limulus* (LAL) assay. The proteins were then vialed after filtration through a 0.22 micron filter and the antigens were frozen until needed for immunization.

For generation of polyclonal anti-sera, 400 micrograms of each prostate antigen was combined with 100 micrograms of muramyldipeptide (MDP). Equal volume of Incomplete Freund's Adjuvant (IFA) was added and then mixed. Every four weeks animals were boosted with 100 micrograms of antigen mixed with an equal volume of IFA. Seven days following each boost the animal was bled. Sera was generated by incubating the blood at 4° C. for 12–24 hours followed by centrifugation.

For characterization of polyclonal antisera, 96 well plates were coated with antigen by incubating with 50 microliters (typically 1 micrgram) at 4 C. for 20 hrs. 250 microliters of BSA blocking buffer was added to the wells and incubated at RT for 2 hrs. Plates were washed 6 times with PBS/0.01% tween. Anti-O8E rabbit sera or affinity purified anti-O8e antibody was diluted in PBS. Fifty microliters of diluted antibody was added to each well and incubated at RT for 30 min. Plates were washed as described above before 50 microliters of goat anti-rabbit horse radish peroxidase (HRP) at a 1:10000 dilution was added and incubated at RT for 30 min. Plates were washed as described above and 100 microliters of TMB microwell Peroxidase Substrate was added to each well. Following a 15 minute incubation in the dark at room temperature the colorimetric reaction was stopped with 100 microliters of 1N $H2SO_4$ and read immediately at 450 nm. All polyclonal antibodies showed immunoreactivity to the O8E antigen.

For recombinant expression in mammalian HEK293 cells, full length O8E cDNA was subcloned into the mammalian expression vectors pcDNA3.1+ and pCEP4 (Invitrogen) which were modified to contain His and FLAG epitope tags, respectively. These constructs were transfected into HEK293 cells (ATCC) using Fugene 6 reagent (Roche). Briefly, HEK293 cells were plated at a density of 100,000 cells/ml in DMEM (Gibco) containing 10% FBS (Hyclone) and grown overnight. The following day, 2 ul of Fugene6 was added to 100 ul of DMEM containing no FBS and incubated for 15 minutes at room temperature. The Fugene6/DMEM mixture was then added to 1 ug of O8E/pCEP4 or O8E/pcDNA3.1 plasmid DNA and incubated for 15 minutes at room temperature. The Fugene/DNA mix was then added to the HEK293 cells and incubated for 48–72 hrs at 37° C. with 7% CO2. Cells were rinsed with PBS then collected and pelleted by centrifugation. For Western blot analysis, whole cell lysates were generated by incubating the cells in Triton-X100 containing lysis buffer for 30 minutes on ice. Lysates were then cleared by centrifugation at 10,000 rpm for 5 minutes at 4 C. Samples were diluted with SDS-PAGE loading buffer containing beta-mercaptoethanol, then boiled for 10 minutes prior to loading the SDS-PAGE gel. Protein was transferred to nitrocellulose and probed using anti-O8E rabbit polyclonal sera #2333L at a dilution of 1:750. The blot was revealed with a goat anti-rabbit Ig coupled to HRP followed by incubation in ECL substrate.

For FACS analysis, cells were washed further with ice cold staining buffer (PBS+1% BSA+Azide). Next, the cells were incubated for 30 minutes on ice with 10ug/ml of Protein A purified anti-O8E polyclonal sera. The cells were washed 3 times with staining buffer and then incubated with a 1:100 dilution of a goat anti-rabbit Ig(H+L)-FITC reagent (Southern Biotechnology) for 30 minutes on ice. Following 3 washes, the cells were resuspended in staining buffer containing Propidium Iodide (PI), a vital stain that allows for the identification of permeable cells, and analyzed by FACS.

Figure 20:
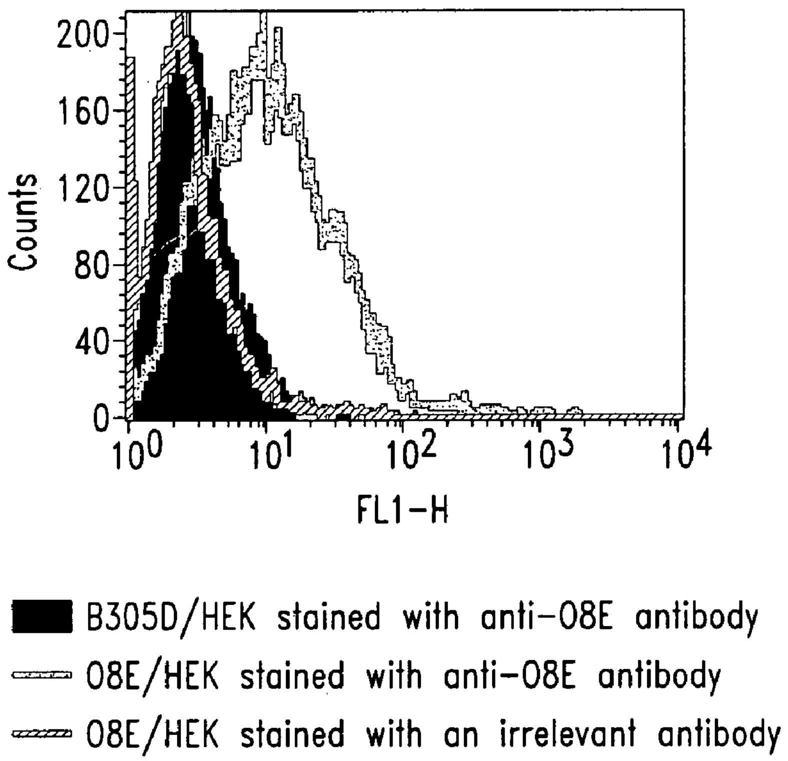
FIG. 20 shows FACS analysis results for O8E transfected HEK293 cells demonstrating cell surface expression of O8E.
Figure 21:
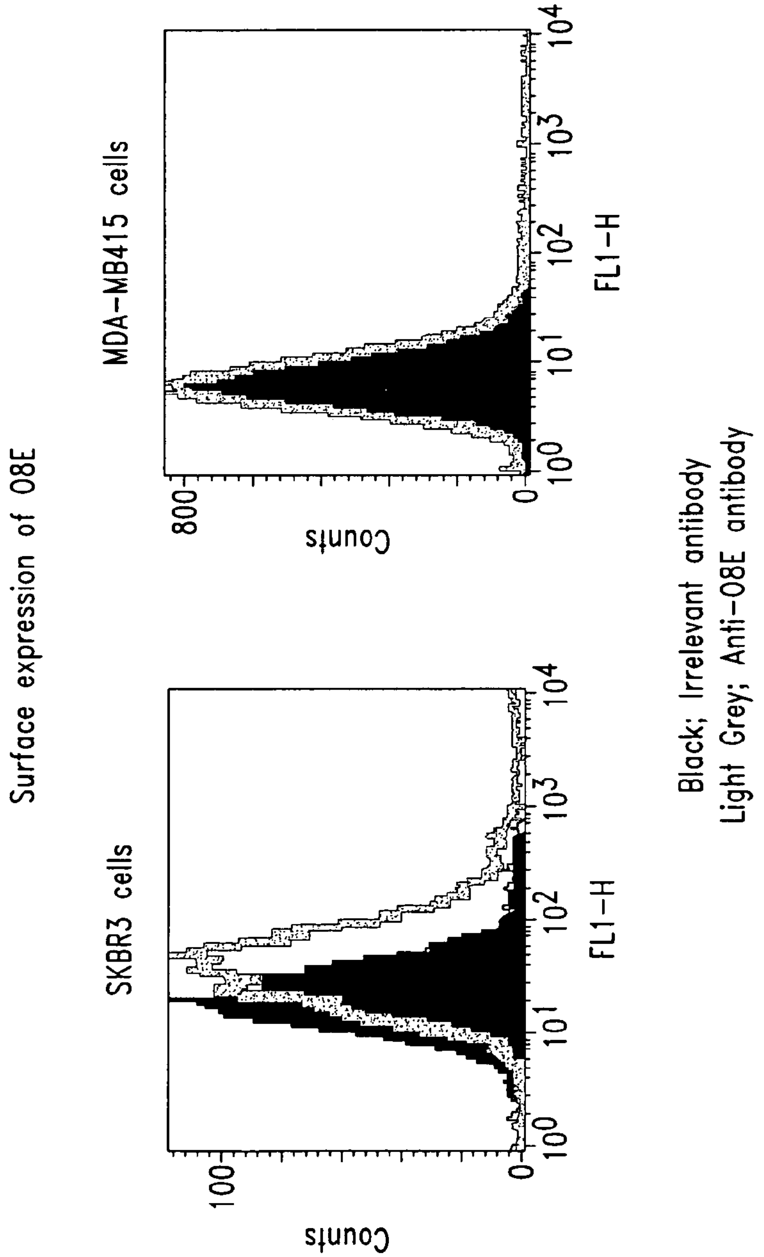
FIG. 21 shows FACS analysis results for SKBR3 breast tumor cells demonstrating cell surface expression of O8E.
Figure 22:
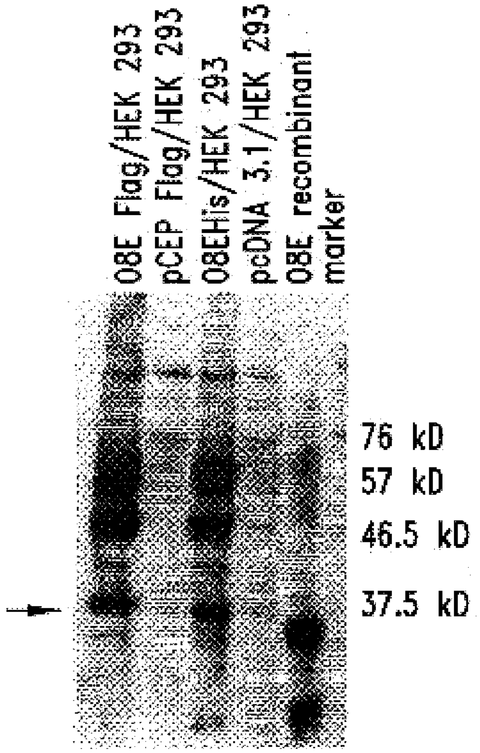
Figure 25:
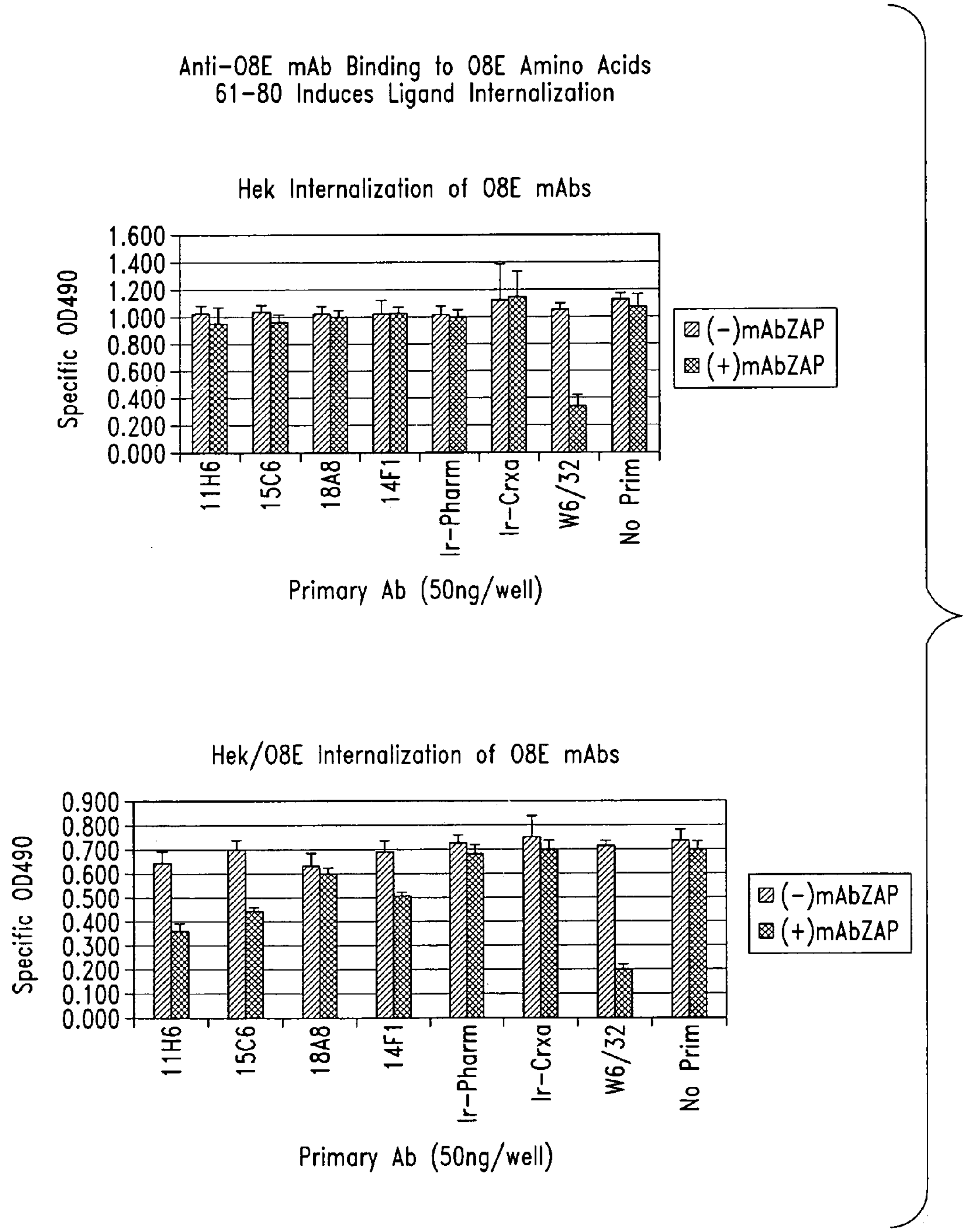

From these experiments, the results of which are illustrated in FIGS. 20–21, O8E expression was detected on the surface of tranfected HEK293 cells and SKBR3 cells by FACS analysis using rabit anti-O8E sera. Expression was also detected in tranfected HEK293 cell lysates by Western blot analysis (not shown).

From the foregoing it will be appreciated that, although specific embodiments of the invention have been described herein for purposes of illustration, various modifications may be made without deviating from the spirit and scope of the invention. Accordingly, the invention is not limited except as by the appended claims.

SUMMARY OF SEQUENCE LISTING

SEQ ID NOs:1–71 are ovarian carcinoma antigen polynucleotides shown in FIGS. 1A–1S.

SEQ ID NOs:72–74 are ovarian carcinoma antigen polynucleotide shown in FIGS. 2A–2C.

SEQ ID NO:75 is the ovarian carcinoma polynucleotide 3g (FIG. 4).

SEQ ID NO:76 is the ovarian carcinoma polynucleotide 3f (FIG. 5).

SEQ ID NO:77 is the ovarian carcinoma polynucleotide 6b (FIG. 6).

SEQ ID NO:78 is the ovarian carcinoma polynucleotide 8e (FIG. 7A).

SEQ ID NO:79 is the ovarian carcinoma polynucleotide 8h (FIG. 7B).

SEQ ID NO:80 is the ovarian carcinoma polynucleotide 12e (FIG. 8).

SEQ ID NO:81 is the ovarian carcinoma polynucleotide 12h (FIG. 9).

SEQ ID NOs:82–310 are ovarian carcinoma antigen polynucleotide shown in FIGS. 15A–15EEE.

SEQ ID NO:311 is a full length sequence of ovarian carcinoma polynucleotide O772P.

SEQ ID NO:312 is the O772P amino acid sequence.

SEQ ID NO:313–384 are ovarian carcinoma antigen polynucleotides.

SEQ ID NO:385–390 present sequences O772P forms.

SEQ ID NO:391 is a full length sequence of ovarian carcinoma polynucleotide O8E.

SEQ ID NOs:392–393 are protein sequences encoded by O8E.

The invention claimed is:

1. An isolated polypeptide comprising SEQ ID NO:392.

2. An isolated polypeptide comprising SEQ ID NO:392, or a variant thereof having at least 90% identity to SEQ ID NO: 392, wherein said variant reacts with an antibody that specifically binds the polypeptide of SEQ ID NO: 392.

3. An isolated polypeptide comprising SEQ ID NO: 392 or a variant thereof containing only conservative amino acid substitutions and having at least 90% identity to SEQ ID NO:392, wherein said variant reacts with an antibody that specifically binds the polypeptide of SEQ ID NO: 392.

4. A fusion polypeptide comprising a polypeptide according to any one of claims 2–3.

5. A composition comprising a polypeptide according to any one of claims 2–3 and at least one physiologically acceptable excipient.

6. A composition comprising a polypeptide according to any one of claims 2–3 and at least one adjuvant.

7. The composition of claim 6, wherein the adjuvant is selected from the group consisting of: an MPL, QS21 and AS-2.

* * * * *

SEQUENCE LISTING

```
<160> NUMBER OF SEQ ID NOS:  455

<210> SEQ ID NO 1
<211> LENGTH: 461
<212> TYPE: DNA
<213> ORGANISM: Homo sapien

<400> SEQUENCE: 1

ttagagaggc acagaaggaa gaagagttaa aagcagcaaa gccgggtttt tttgttttgt     60

tttgttttgt tttgttttga gatggagtct cactctgttg cccaagctgg agtacaacgg    120

catgatctca gctcgctgca acctccgcct cccacgttca agtgattctc ctgcctcagc    180

ctcccaagta gctgggatta caggcgcccg ccaccacgct cagctaattt tttttgtatt    240

tttagtagag acagggtttc accaggttgg ccaggctgct cttgaactcc tgacctcagg    300

tgatccaccc gcctcggcct cccaaagtgc tgggattaca ggcgtgagcc accacgcccg    360

gcccccaaag ctgtttcttt tgtctttagc gtaaagctct cctgccatgc agtatctaca    420

taactgacgt gactgccagc aagctcagtc actccgtggt c                        461


<210> SEQ ID NO 2
<211> LENGTH: 540
<212> TYPE: DNA
<213> ORGANISM: Homo sapien

<400> SEQUENCE: 2

taggatgtgt tggaccctct gtgtcaaaaa aaacctcaca aagaatcccc tgctcattac     60

agaagaagat gcatttaaaa tatgggttat tttcaacttt ttatctgagg acaagtatcc    120

attaattatt gtgtcagaag agattgaata cctgcttaag aagcttacag aagctatggg    180

aggaggttgg cagcaagaac aatttgaaca ttataaaatc aactttgatg acagtaaaaa    240

tggcctttct gcatgggaac ttattgagct tattggaaat ggacagttta gcaaaggcat    300

ggaccggcag actgtgtcta tggcaattaa tgaagtcttt aatgaactta tattagatgt    360

gttaaagcag ggttacatga tgaaaaaggg ccacagacgg aaaaactgga ctgaaagatg    420

gtttgtacta aaacccaaca taatttctta ctatgtgagt gaggatctga aggataagaa    480

aggagacatt ctcttggatg aaaattgctg tgtagagtcc ttgcctgaca aagatggaaa    540


<210> SEQ ID NO 3
<211> LENGTH: 461
<212> TYPE: DNA
```

-continued

<213> ORGANISM: Homo sapien

<400> SEQUENCE: 3
ttagagaggc acagaaggaa gaagagttaa aagcagcaaa gccgggtttt tttgttttgt 60
tttgttttgt tttgttttga gatggagtct cactctgttg cccaagctgg agtacaacgg 120
catgatctca gctcgctgca acctccgcct cccacgttca agtgattctc ctgcctcagc 180
ctcccaagta gctgggatta caggcgcccg ccaccacgct cagctaattt tttttgtatt 240
tttagtagag acagggtttc accaggttgg ccaggctgct cttgaactcc tgacctcagg 300
tgatccaccc gcctcggcct cccaaagtgc tgggattaca ggcgtgagcc accacgcccg 360
gcccccaaag ctgtttcttt tgtctttagc gtaaagctct cctgccatgc agtatctaca 420
taactgacgt gactgccagc aagctcagtc actccgtggt c 461

<210> SEQ ID NO 4
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 4
tctttttctt tcgatttcct tcaatttgtc acgtttgatt ttatgaagtt gttcaagggc 60
taactgctgt gtattatagc tttctctgag ttccttcagc tgattgttaa atgaatccat 120
ttctgagagc ttagatgcag tttctttttc aagagcatct aattgttctt taagtctttg 180
gcataattct tccttttctg atgacttttt atgaagtaaa ctgatccctg aatcaggtgt 240
gttactgagc tgcatgtttt taattctttc gtttaatagc tgcttctcag ggaccagata 300
gataagctta ttttgatatt ccttaagctc ttgttgaagt tgtttgattt ccataatttc 360
caggtcacac tgtttatcca aaacttctag ctcagtcttt tgtgtttgct ttctgatttg 420
gacatcttgt agtctgcctg agatctgctg atgntttcca ttcactgctt ccagttccag 480
gtggagactt tnctttctgg agctcagcct gacaatgcct tcttgntccc t 531

<210> SEQ ID NO 5
<211> LENGTH: 531
<212> TYPE: DNA
<213> ORGANISM: Homo sapien

<400> SEQUENCE: 5
agccagatgg ctgagagctg caagaagaag tcaggatcat gatggctcag tttcccacag 60
cgatgaatgg agggccaaat atgtgggcta ttacatctga agaacgtact aagcatgata 120
aacagtttga taacctcaaa ccttcaggag gttacataac aggtgatcaa gcccgtactt 180
ttttcctaca gtcaggtctg ccggccccgg ttttagctga aatatgggcc ttatcagatc 240
tgaacaagga tgggaagatg gaccagcaag agttctctat agctatgaaa ctcatcaagt 300
taaagttgca gggccaacag ctgcctgtag tcctccctcc tatcatgaaa caacccccta 360
tgttctctcc actaatctct gctcgttttg ggatgggaag catgcccaat ctgtccattc 420
atcagccatt gcctccagtt gcacctatag caacaccctt gtcttctgct acttcaggga 480
ccagtattcc tcccctaatg atgcctgctc ccctagtgcc ttctgttagt a 531

<210> SEQ ID NO 6
<211> LENGTH: 531

-continued

<212> TYPE: DNA
<213> ORGANISM: Homo sapien

<400> SEQUENCE: 6
aatagattta atgcagagtg tcaacttcaa ttgattgata gtggctgcct agagtgctgt 60
gttgagtagg tttctgagga tgcaccctgg cttgaagaga aagactggca ggattaacaa 120
tatctaaaat ctcacttgta ggagaaacca caggcaccag agctgccact ggtgctggca 180
ccagctccac caaggccagc gaagagccca aatgtgagag tggcggtcag gctggcacca 240
gcactgaagc caccactggt gctggcactg gcactggcac tgttattggt actggtactg 300
gcaccagtgc tggcactgcc actctcttgg gctttggctt tagcttctgc tcccgcctgg 360
atccgggctt tggcccaggg tccgatatca gcttcgtccc agttgcaggg cccggcagca 420
ttctccgagc cgagcccaat gcccattcga gctctaatct cggccctagc cttggcttca 480
gctgcagcct cagctgcagc cttcaaatcc gcttccatcg cctctcggta c 531

<210> SEQ ID NO 7
<211> LENGTH: 531
<212> TYPE: DNA
<213> ORGANISM: Homo sapien

<400> SEQUENCE: 7
gccaagaaag cccgaaaggt gaagcatctg gatggggaag aggatggcag cagtgatcag 60
agtcaggctt ctggaaccac aggtggccga agggtctcaa aggccctaat ggcctcaatg 120
gcccgcaggg cttcaagggg tcccatagcc ttttgggccc gcagggcatc aaggactcgg 180
ttggctgctt gggcccggag agccttgctc tccctgagat cacctaaagc ccgtaggggc 240
aaggctcgcc gtagagctgc caagctccag tcatcccaag agcctgaagc accaccacct 300
cgggatgtgg cccttttgca agggagggca aatgatttgg tgaagtacct tttggctaaa 360
gaccagacga agattcccat caagcgctcg gacatgctga aggacatcat caaagaatac 420
actgatgtgt accccgaaat cattgaacga gcaggctatt ccttggagaa ggtatttggg 480
attcaattga aggaaattga taagaatgac cacttgtaca ttcttctcag c 531

<210> SEQ ID NO 8
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 8
gaggtctcac tatgttgccc aggctgttct tgaactcctg ggatcaagca atccacccat 60
gttggtctcc aaaagtgctg ggatcatagg cgtgagccac ctcacccagc caccaatttt 120
caatcaggaa gactttttcc ttcttcaaga agtgaagggt ttccagagta tagctacact 180
attgcttgcc tgagggtgac tacaaaattg cttgctaaaa ggttaggatg ggtaaagaat 240
tagattttct gaatgcaaaa ataaaatgtg aactaatgaa ctttaggtaa tacatattca 300
taaaataatt attcacatat ttcctgattt atcacagaaa taatgtatga aatgctttga 360
gtttcttgga gtaaactcca ttactcatcc caagaaacca tattataagt atcactgata 420
ataagaacaa caggaccttg tcataaattc tggataagag aaatagtctc tgggtgtttg 480
ntcttaattg ataaaattta cttgtccatc ttttagttca gaatcacaaa a 531

-continued

<210> SEQ ID NO 9
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 9

```
aagcggaaat gagaaaggag ggaaaatcat gtggtattga gcggaaaact gctggatgac     60

agggctcagt cctgttggag aactctgggt ggtgctgtag aacagggcca ctcacagtgg    120

ggtgcacaga ccagcacggc tctgtgacct gtttgttaca ggtccatgat gaggtaaaca    180

atacactgag tataagggtt ggtttagaaa ctcttacagc aatttgacaa agtaatcttc    240

tgtgcagtga atctaagaaa aaaattgggg ctgtatttgt atgttccttt ttttcatttc    300

atgttctgag ttacctattt ttattgcatt ttacaaaagc atccttccat gaaggaccgg    360

aagttaaaaa caaagcaggt cctttatcac agcactgtcg tagaacacag ttcagagtta    420

tccacccaag gagccaggga gctgggctaa accaaagaat tttgcttttg gttaatcatc    480

aggtacttga gttggaattg ttttaatccc atcattacca ggctggangt g             531
```

<210> SEQ ID NO 10
<211> LENGTH: 861
<212> TYPE: DNA
<213> ORGANISM: Homo sapien

<400> SEQUENCE: 10

```
ccgcggctcc tgtccagacc ctgaccctcc ctcccaaggc tcaaccgtcc cccaacaacc     60

gccagccttg tactgatgtc ggctgcgaga gcctgtgctt aagtaagaat caggccttat    120

tggagacatt caagcaaagg ttggacaact acttttccag aacagaaagg aaactcatgc    180

atcagaaaag gtgactaata aaggtaccag aagaatatgg ctgcacaaat accagaatct    240

gatcagataa aacagtttaa ggaatttctg ggacctacaa ataaacttac agagacctgc    300

tttttggact gtgttagaga cttcacaaca agagaagtaa aacctgaaga gaccacctgt    360

tcagaacatt gcttacagaa atatttaaaa atgacacaaa gaatatccat gagatttcag    420

gaatatcata ttcagcagaa tgaagccctg gcagccaaag caggactcct tggccaacca    480

cgatagagaa gtcctgatgg atgaactttt gatgaaagat tgccaacagc tgctttattg    540

gaaatgagga ctcatctgat agaatcccct gaaagcagta gccaccatgt tcaaccatct    600

gtcatgactg tttggcaaat ggaaaccgct ggagaaacaa aattgctatt taccaggaat    660

aatcacaata gaaggtctta ttgttcagtg aaataataag atgcaacatt tgttgaggcc    720

ttatgattca gcagcttggt cacttgatta gaaaaataaa ccattgtttc ttcaattgtg    780

actgttaatt ttaaagcaac ttatgtgttc gatcatgtat gagatagaaa aatttttatt    840

actcaaagta aaataaatgg a                                              861
```

<210> SEQ ID NO 11
<211> LENGTH: 541
<212> TYPE: DNA
<213> ORGANISM: Homo sapien

<400> SEQUENCE: 11

```
gaaaaaaaat ataaaacaca cttttgcgaa aacggtggcc ctaaaagagg aaaagaattt     60

caccaatata aatccaattt tatgaaaact gacaatttaa tccaagaatc acttttgtaa    120
```

-continued atgaagctag caagtgatga tatgataaaa taaacgtgga ggaaataaaa acacaagact 180
tggcataaga tatatccact tttgatatta aacttgtgaa gcatattctt cgacaaattg 240
tgaaagcgtt cctgatcttg cttgttctcc atttcaaata aggaggcata tcacatccca 300
agagtaacag aaaaagaaaa aagacatttt tgcattttga gatgaaccaa agacacaaaa 360
caaaacgaac aaagtgtcat gtctaattct agcctctgaa ataaaccttg aacatctcct 420
acaaggcacc gtgatttttg taattctaac ctgaagaaat gtgatgactt ttgtggacat 480
gaaaatcaga tgagaaaact gtggtctttc caaagcctga actcccctga aaacctttgc 540
a 541

<210> SEQ ID NO 12
<211> LENGTH: 541
<212> TYPE: DNA
<213> ORGANISM: Homo sapien

<400> SEQUENCE: 12
ctgggatcat ttctcttgat gtcataaaag actcttcttc ttcctcttca tcctcttctt 60
catcctcttc tgtacagtgc tgccgggtac aacggctatc tttgtcttta tcctgagatg 120
aagatgatgc ttctgtttct cctaccataa ctgaagaaat ttcgctggaa gtcgtttgac 180
tggctgtttc tctgacttca ccttctttgt caaacctgag tctttttacc tcatgcccct 240
cagcttccac agcatcttca tctggatgtt tatttttcaa agggctcact gaggaaactt 300
ctgattcaga ggtcgaagag tcactgtgat ttttctcctc attttgctgc aaatttgcct 360
ctttgctgtc tgtgctctca ggcaacccat ttgttgtcat gggggctgac aaagaaacct 420
ttggtcgatt aagtggcctg ggtgtcccag gcccatttat attagacctc tcagtatagc 480
ttggtgaatt tccaggaaac ataacaccat tcattcgatt taaactattg gaattggttt 540
t 541

<210> SEQ ID NO 13
<211> LENGTH: 441
<212> TYPE: DNA
<213> ORGANISM: Homo sapien

<400> SEQUENCE: 13
gagggttggt ggtagcggct tggggaggtg ctcgctctgt cggtcttgct ctctcgcacg 60 cttccccccgg ctcccttcgt ttcccccccc cggtcgcctg cgtgccggag tgtgtgcgag 120 ggaggggggag ggcgtcgggg gggtgggggg aggcgttccg gtccccaaga gacccgcgga 180
gggaggcgga ggctgtgagg gactccggga agccatggac gtcgagaggc tccaggaggc 240
gctgaaagat tttgagaaga gggggaaaaa ggaagtttgt cctgtcctgg atcagtttct 300
ttgtcatgta gccaagactg gagaaacaat gattcagtgg tcccaattta aaggctattt 360
tattttcaaa ctggagaaag tgatggatga tttcagaact tcagctcctg agccaagagg 420
tcctcccaac cctaatgtcg a 441

<210> SEQ ID NO 14
<211> LENGTH: 131
<212> TYPE: DNA
<213> ORGANISM: Homo sapien
<220> FEATURE:
<221> NAME/KEY: misc_feature
<222> LOCATION: (1)...(131)
<223> OTHER INFORMATION: n = A,T,C or G -continued

<400> SEQUENCE: 14

```
aagcaggcgg ctcccgcgct cgcagggccg tgccacctgc ccgcccgccc gctcgctcgc     60

tcgcccgccg cgccgcgctg ccgaccgcca gcatgctgcc gagagtgggc tgccccgcgc    120

tgccgntgcc g                                                         131
```

<210> SEQ ID NO 15
<211> LENGTH: 692
<212> TYPE: DNA
<213> ORGANISM: Homo sapien

<400> SEQUENCE: 15

```
atctcttgta tgccaaatat ttaatataaa tctttgaaac aagttcagat gaaataaaaa     60

tcaaagtttg caaaaacgtg aagattaact taattgtcaa atattcctca ttgccccaaa    120

tcagtatttt ttttatttct atgcaaaagt atgccttcaa actgcttaaa tgatatatga    180

tatgatacac aaaccagttt tcaaatagta aagccagtca tcttgcaatt gtaagaaata    240

ggtaaaagat tataagacac cttacacaca cacacacaca cacacacgtg tgcacgccaa    300

tgacaaaaaa caatttggcc tctcctaaaa taagaacatg aagaccctta attgctgcca    360

ggagggaaca ctgtgtcacc cctccctaca atccaggtag tttcctttaa tccaatagca    420

aatctgggca tatttgagag gagtgattct gacagccacg ttgaaatcct gtggggaacc    480

attcatgtcc acccactggt gccctgaaaa aatgccaata atttttcgct cccacttctg    540

ctgctgtctc ttccacatcc tcacatagac cccagacccg ctggcccctg gctgggcatc    600

gcattgctgg tagagcaagt cataggtctc gtctttgacg tcacagaagc gatacaccaa    660

attgcctggt cggtcattgt cataaccaga ga                                  692
```

<210> SEQ ID NO 16
<211> LENGTH: 728
<212> TYPE: DNA
<213> ORGANISM: Homo sapien

<400> SEQUENCE: 16

```
cagacggggt ttcactatgt tggctaggct ggtcttgaac tcctgacttc aggtgatctg     60

cctgccttgg cctcccaaag tgctgggatt acaggcataa gccactgcgc ccggctgatc    120

tgatggtttc ataaggcttt tccccctttt gctcagcact tctccttcct gccgccatgt    180

gaagaaggac atgtttgctt ccccttccac cacgattgta agttgtttcc tgaggcctcc    240

ccggccatgc tgaactgtga gtcaattaaa cctctttcct ttataaatta tccagttttg    300

ggtatgtctt tattagtaga atgagaacag actaatacaa cccttaaagg agactgacgg    360

agaggattct tcctggatcc cagcacttcc tctgaatgct actgacattc ttcttgagga    420

ctttaaactg ggagatagaa aacagattcc atggctcagc agcctgagag cagggaggga    480

gccaagctat agatgacatg ggcagcctcc cctgaggcca ggtgtggccg aacctgggca    540

gtgctgccac ccaccccacc agggccaagt cctgtccttg gagagccaag cctcaatcac    600

tgctagcctc aagtgtcccc aagccacagt ggctaggggg actcagggaa cagttcccag    660

tctgccctac ttctcttacc tttacccctc atacctccaa agtagaccat gttcatgagg    720

tccaaagg                                                             728
```

<210> SEQ ID NO 17
<211> LENGTH: 531
<212> TYPE: DNA
<213> ORGANISM: Homo sapien -continued

```
<220> FEATURE:
<221> NAME/KEY: misc_feature
<222> LOCATION: (1)...(531)
<223> OTHER INFORMATION: n = A,T,C or G

<400> SEQUENCE: 17

aagcgaggaa gccactgcgg ctcctggctg aaaagcggcg ccaggctcgg gaacagaggg     60

aacgcgaaga acaggagcgg aagctgcagg ctgaaaggga caagcgaatg cgagaggagc    120

agctggcccg ggaggctgaa gcccgggctg aacgtgaggc cgaggcgcgg agacgggagg    180

agcaggaggc tcgagagaag gcgcaggctg agcaggagga gcaggagcga ctgcagaagc    240

agaaagagga agccgaagcc cggtcccggg aagaagctga gcgccagcgc caggagcggg    300

aaaagcactt tcagaaggag gaacaggaga gacaagagcg aagaaagcgg ctggaggaga    360

taatgaagag gactcggaaa tcagaagccg ccgaaaccaa gaagcaggat gcaaaggaga    420

ccgcagctaa caattccggc ccagaccctt gtgaaagctg tagagactcg gccctctggg    480

cttccagaaa ggattctatt gcagaaagga aggagctngg ccccccangg a             531


<210> SEQ ID NO 18
<211> LENGTH: 1041
<212> TYPE: DNA
<213> ORGANISM: Homo sapien
<220> FEATURE:
<221> NAME/KEY: misc_feature
<222> LOCATION: (1)...(1041)
<223> OTHER INFORMATION: n = A,T,C or G

<400> SEQUENCE: 18

ctctgtggaa aactgatgag gaatgaattt accattaccc atgttctcat ccccaagcaa     60

agtgctgggt ctgattactg caacacagag aacgaagaag aacttttcct catacaggat    120

cagcagggcc tcatcacact gggctggatt catactcacc ccacacagac cgcgtttctc    180

tccagtgtcg acctacacac tcactgctct taccagatga tgttgccaga gtcagtagcc    240

attgtttgct cccccaagtt ccaggaaact ggattcttta aactaactga ccatggacta    300

gaggagattt cttcctgtcg ccagaaagga tttcatccac acagcaagga tccacctctg    360

ttctgtagct gcagccacgt gactgttgtg gacagagcag tgaccatcac agaccttcga    420

tgagcgtttg agtccaacac cttccaagaa caacaaaacc atatcagtgt actgtagccc    480

cttaatttaa gctttctaga aagctttgga agtttttgta gatagtagaa agggggggcat    540

cacntgagaa agagctgatt ttgtatttca ggtttgaaaa gaaataactg aacatatttt    600

ttaggcaagt cagaaagaga acatggtcac ccaaaagcaa ctgtaactca gaaattaagt    660

tactcagaaa ttaagtagct cagaaattaa gaaagaatgg tataatgaac ccccatatac    720

ccttccttct ggattcacca attgttaaca tttttttcct ctcagctatc cttctaattt    780

ctctctaatt tcaatttgtt tatatttacc tctgggctca ataagggcat ctgtgcagaa    840

atttggaagc catttagaaa atctttttgga ttttcctgtg gtttatggca atatgaatgg    900

agcttattac tggggtgagg gacagcttac tccatttgac cagattgttt ggctaacaca    960

tcccgaagaa tgattttgtc aggaattatt gttatttaat aaatatttca ggatattttt   1020

cctctacaat aaagtaacaa t                                             1041


<210> SEQ ID NO 19
<211> LENGTH: 1043
<212> TYPE: DNA
<213> ORGANISM: Homo sapien
```

<400> SEQUENCE: 19
ctctgtggaa aactgatgag gaatgaattt accattaccc atgttctcat ccccaagcaa 60
agtgctgggt ctgattactg caacacagag aacgaagaag aacttttcct catacaggat 120
cagcagggcc tcatcacact gggctggatt catactcacc ccacacagac cgcgtttctc 180
tccagtgtcg acctacacac tcactgctct taccagatga tgttgccaga gtcagtagcc 240
attgtttgct cccccaagtt ccaggaaact ggattcttta aactaactga ccatggacta 300
gaggagattt cttcctgtcg ccagaaagga tttcatccac acagcaagga tccacctctg 360
ttctgtagct gcagccacgt gactgttgtg gacagagcag tgaccatcac agaccttcga 420
tgagcgtttg agtccaacac cttccaagaa caacaaaacc atatcagtgt actgtagccc 480
cttaatttaa gctttctaga aagctttgga agtttttgta gatagtagaa agggggggcat 540 cacctgagaa agagctgatt ttgtatttca ggtttgaaaa gaaataactg aacatatttt 600
ttaggcaagt cagaaagaga acatggtcac ccaaaagcaa ctgtaactca gaaattaagt 660
tactcagaaa ttaagtagct cagaaattaa gaaagaatgg tataatgaac cccatatac 720 ccttccttct ggattcacca attgttaaca tttttttcct ctcagctatc cttctaattt 780
ctctctaatt tcaatttgtt tatatttacc tctgggctca ataagggcat ctgtgcagaa 840
atttggaagc catttagaaa atcttttgga ttttcctgtg gtttatggca atatgaatgg 900
agcttattac tggggtgagg gacagcttac tccatttgac cagattgttt ggctaacaca 960
tcccgaagaa tgattttgtc aggaattatt gttatttaat aaatatttca ggatattttt 1020
cctctacaat aaagtaacaa tta 1043

<210> SEQ ID NO 20
<211> LENGTH: 448
<212> TYPE: DNA
<213> ORGANISM: Homo sapien

<400> SEQUENCE: 20
ggacgacaag gccatggcga tatcggatcc gaattcaagc ctttggaatt aaataaacct 60
ggaacaggga aggtgaaagt tggagtgaga tgtcttccat atctatacct ttgtgcacag 120
ttgaatggga actgtttggg tttagggcat cttagagttg attgatggaa aaagcagaca 180
ggaactggtg ggaggtcaag tggggaagtt ggtgaatgtg gaataactta cctttgtgct 240
ccacttaaac cagatgtgtt gcagctttcc tgacatgcaa ggatctactt taattccaca 300
ctctcattaa taaattgaat aaaagggaat gttttggcac ctgatataat ctgccaggct 360
atgtgacagt aggaaggaat ggtttcccct aacaagccca atgcactggt ctgactttat 420
aaattattta ataaaatgaa ctattatc 448

<210> SEQ ID NO 21
<211> LENGTH: 411
<212> TYPE: DNA
<213> ORGANISM: Homo sapien

<400> SEQUENCE: 21
ggcagtgaca ttcaccatca tgggaaccac cttccctttt cttcaggatt ctctgtagtg 60
gaagagagca cccagtgttg ggctgaaaac atctgaaagt agggagaaga acctaaaata 120
atcagtatct cagagggctc taaggtgcca agaagtctca ctggacattt aagtgccaac 180
aaaggcatac tttcggaatc gccaagtcaa aactttctaa cttctgtctc tctcagagac 240
aagtgagact caagagtcta ctgctttagt ggcaactaca gaaaactggt gttacccaga 300

-continued aaaacaggag caattagaaa tggttccaat atttcaaagc tccgcaaaca ggatgtgctt 360
tcctttgccc atttagggtt tcttctcttt cctttctctt tattaaccac t 411

<210> SEQ ID NO 22
<211> LENGTH: 896
<212> TYPE: DNA
<213> ORGANISM: Homo sapien
<220> FEATURE:
<221> NAME/KEY: misc_feature
<222> LOCATION: (1)...(896)
<223> OTHER INFORMATION: n = A,T,C or G

<400> SEQUENCE: 22
tgcgctgaaa acaacggcct cctttactgt taaaatgcag ccacaggtgc ttagccgtgg 60
gcatctcaac caccagcctc tgtggggggc aggtgggcgt ccctgtgggc ctctgggccc 120
acgtccagcc tctgtcctct gccttccgtt cttcgacagt gttcccggca tccctggtca 180
cttggtactt ggcgtgggcc tcctgtgctg ctccagcagc tcctccaggn ggtcggcccg 240
cttcaccgca gcctcatgtt gtgtccggag gctgctcacg gcctcctcct tcctcgcgag 300
ggctgtcttc accctccggn gcacctcctc cagctccagc tgctggcggg cctgcagcgt 360
ggccagctcg gccttggcct gccgcgtctc ctcctcarag gctgccagcc ggtcctcgaa 420
ctcctggcgg atcacctggg ccaggttgct gcgctcgcta gaaagctgct cgttcaccgc 480
ctgcgcatcc tccagcgccc gctccttctg ccgcacaagg ccctgcagac gcagattctc 540
gccctcggcc tccccaagct ggcccttcag ctccgagcac cgctcctgaa gcttccgctc 600
cgactgctcc agctcggaga gctcggcctc gtacttgtcc cgtaagcgct tgatgcggct 660
ctcggcagcc ttctcactct cctccttggc cagcgccatg tcggcctcca gccggtgaat 720
gaccagctca atctccttgt cccggccttt ccggatttct tccctcagct cctgttcccg 780
gttcagcagc cacgcctcct ccttcctggt gcggccggcc tcccacgcct gcctctccag 840
ctccagctgc tgcttcaggg tattcagctc catctggcgg gcctgcagcg tggcca 896

<210> SEQ ID NO 23
<211> LENGTH: 111
<212> TYPE: DNA
<213> ORGANISM: Homo sapien

<400> SEQUENCE: 23
caacttatta cttgaaatta taatatagcc tgtccgtttg ctgtttccag gctgtgatat 60
attttcctag tggtttgact ttaaaaataa ataaggttta attttctccc c 111

<210> SEQ ID NO 24
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 24
tgcaagtcac gggagtttat ttatttaatt tttttcccca gatggagact ctgtcgccca 60
ggctggagtg caatggtgtg atcttggctc actgcaacct ccacctcctg ggttcaagcg 120
attctcctgc cacagcctcc cgagtagctg ggattacagg tgcccgccac cacacccagc 180
taatttttat atttttagta aagacagggt ttccccatgt tggccaggct ggtcttgaac 240

-continued

```
ttctgacctc aggtgatcca cctgcctcgg cctcccaaag tgttgggatt acaggcgtga    300

gctacccgtg cctggccagc cactggagtt taaaggacag tcatgttggc tccagcctaa    360

ggcggcattt tcccccatca gaaagcccgc ggctcctgta cctcaaaata gggcacctgt    420

aaagtcagtc agtgaagtct ctgctctaac tggccacccg gggccattgg cntctgacac    480

agccttgcca ggangcctgc atctgcaaaa gaaaagttca cttcctttcc g             531
```

<210> SEQ ID NO 25
<211> LENGTH: 471
<212> TYPE: DNA
<213> ORGANISM: Homo sapien
<220> FEATURE:
<221> NAME/KEY: misc_feature
<222> LOCATION: (1)...(471)
<223> OTHER INFORMATION: n = A,T,C or G

<400> SEQUENCE: 25

```
cagagaatct kagaaagatg tcgcgttttc ttttaatgaa tgagagaagc ccatttgtat     60

ccctgaatca ttgagaaaag gcggcggtgg cgacagcggc gacctaggga tcgatctgga    120

gggacttggg gagcgtgcag agacctctag ctcgagcgcg agggacctcc cgccgggatg    180

cctggggagc agatggaccc tactggaagt cagttggatt cagatttctc tcagcaagat    240

actccttgcc tgataattga agattctcag cctgaaagcc aggttctaga ggatgattct    300

ggttctcact tcagtatgct atctcgacac cttcctaatc tccagacgca caaagaaaat    360

cctgtgttgg atgttgngtc caatccttga acaaacagct ggagaagaac gaggagaccg    420

gtaatagtgg gttcaatgaa catttgaaag aaaaccaggt tgcagaccct g             471
```

<210> SEQ ID NO 26
<211> LENGTH: 541
<212> TYPE: DNA
<213> ORGANISM: Homo sapien

<400> SEQUENCE: 26

```
gactgtcctg aacaagggac ctctgaccag agagctgcag gagatgcaga gtggtggcag     60

gagtggaagc caaagaacac ccaccttcct cccttgaagg agtagagcaa ccatcagaag    120

atactgtttt attgctctgg tcaaacaagt cttcctgagt tgacaaaacc tcaggctctg    180

gtgacttctg aatctgcagt ccactttcca taagttcttg tgcagacaac tgttcttttg    240

cttccatagc agcaacagat gctttggggc taaaaggcat gtcctctgac cttgcaggtg    300

gtggattttg ctcttttaca acatgtacat ccttactggg ctgtgctgtc acagggatgt    360

ccttgctgga ctgttctgct atggggatat cttcgttgga ctgttcttca tgcttaattg    420

cagtattagc atccacatca gacagcctgg tataaccaga gttggtggtt actgattgta    480

gctgctcttt gtccacttca tatggcacaa gtattttcct caacatcctg gctctgggaa    540

g                                                                    541
```

<210> SEQ ID NO 27
<211> LENGTH: 461
<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 27

```
gaaatgtata tttaatcatt ctcttgaacg atcagaactc traaatcagt tttctataac     60
```

-continued

```
arcatgtaat acagtcaccg tggctccaag gtccaggaag gcagtggtta acacatgaag    120

agtgtgggaa gggggctgga aacaaagtat tcttttcctt caaagcttca ttcctcaagg    180

cctcaattca agcagtcatt gtccttgctt tcaaaagtct gtgtgtgctt catggaaggt    240

atatgtttgt tgccttaatt tgaattgtgg ccaggaaggg tctggagatc taaattcaga    300

gtaagaaaac ctgagctaga actcaggcat ttctcttaca gaacttggct tgcagggtag    360

aatgaangga aagaaactta gaagctcaac aagctgaaga taatcccatc aggcatttcc    420

cataggcctt gcaactctgt tcactgagag atgttatcct g                        461
```

<210> SEQ ID NO 28
<211> LENGTH: 541
<212> TYPE: DNA
<213> ORGANISM: Homo sapien

<400> SEQUENCE: 28

```
agtctggagt gagcaaacaa gagcaagaaa caarragaag ccaaaagcag aaggctccaa     60

tatgaacaag ataaatctat cttcaaagac atattagaag ttgggaaaat aattcatgtg    120

aactagacaa gtgtgttaag agtgataagt aaaatgcacg tggagacaag tgcatcccca    180

gatctcaggg acctccccct gcctgtcacc tggggagtga gaggacagga tagtgcatgt    240

tctttgtctc tgaattttta gttatatgtg ctgtaatgtt gctctgagga agcccctgga    300

aagtctatcc caacatatcc acatcttata ttccacaaat taagctgtag tatgtaccct    360

aagacgctgc taattgactg ccacttcgca actcaggggc ggctgcattt tagtaatggg    420

tcaaatgatt cactttttat gatgcttccc aaggtgcctt ggcttctctt cccaactgac    480

aaatgcccaa gttgagaaaa atgatcataa ttttagcata aaccgagcaa tcggcgaccc    540

c                                                                    541
```

<210> SEQ ID NO 29
<211> LENGTH: 411
<212> TYPE: DNA
<213> ORGANISM: Homo sapien

<400> SEQUENCE: 29

```
tagctgtctt cctcactctt atggcaatga ccccatatct taatggatta agataatgaa     60

agtgtatttc ttacactctg tatctatcac cagaagctga ggtgatagcc cgcttgtcat    120

tgtcatccat attctgggac tcaggcggga actttctgga atattgccag ggagcatggc    180

agaggggcac agtgcattct gggggaatgc acattggctc agcctgggta atgagtgata    240

tacattacct ctgttcacaa ctcattgccc agcaccagtc acaaggcccc accaaatacc    300

agagcccaag aaatgtagtc ctgttgatat ggttttgctg tgtcccaacc caaatctcat    360

cttgaattgt aagctcccat aattcccatg tgttgtggga gggacctggt g             411
```

<210> SEQ ID NO 30
<211> LENGTH: 511
<212> TYPE: DNA
<213> ORGANISM: Homo sapien

<400> SEQUENCE: 30

```
atcatgagga tgttaccaaa gggatggtac taaaccattt gtattcgtct gttttcacac     60

tgctttgaag atactacctg agactgggta atttataaac aaaagagatt taattgactc    120

acagttctgc atggctgaag aggcctcagg aaacttacag tcatggtgga aggcaaagga    180
```

-continued

```
ggagcaaggc atgtcttaca tgtcagtagg agagagagcg agagcaggag aacctgccac    240

ttataaacca ttcagatctc ataactccct atcatgagaa aaacatggag gaaaccaccc    300

tcatgatcca atcacctccc gccaggtccc tccctcgaca cgtggggatt ataattcagg    360

attagaggga cacagagaca aaccatatca tcattcatga gaaatccacc ctcatagtcc    420

aatcagctcc taccaggccc cacctccaac actggggatt gcaattcaac atgagatttg    480

gatggggaca cagattcaaa ccatatcata c                                   511
```

<210> SEQ ID NO 31
<211> LENGTH: 827
<212> TYPE: DNA
<213> ORGANISM: Homo sapien

<400> SEQUENCE: 31

```
catggccttt ctccttagag gccagaggtg ctgccctggc tgggagtgaa gctccaggca     60

ctaccagctt tcctgatttt cccgtttggt ccatgtgaag agctaccacg agccccagcc    120

tcacagtgtc cactcaaggg cagcttggtc ctcttgtcct gcagaggcag gctggtgtga    180

ccctgggaac ttgacccggg aacaacaggt ggcccagagt gagtgtggcc tggcccctca    240

acctagtgtc cgtcctcctc tctcctggag ccagtcttga gtttaaaggc attaagtgtt    300

agatacaagc tccttgtggc tggaaaaaca cccctctgct gataaagctc agggggcact    360

gaggaagcag aggccccttg ggggtgccct cctgaagaga gcgtcaggcc atcagctctg    420

tccctctggt gctcccacgt ctgttcctca ccctccatct ctgggagcag ctgcacctga    480

ctggccacgc gggggcagtg gaggcacagg ctcagggtgg ccgggctacc tggcacccta    540

tggcttacaa agtagagttg gcccagtttc cttccacctg aggggagcac tctgactcct    600

aacagtcttc cttgccctgc catcatctgg ggtggctggc tgtcaagaaa ggccgggcat    660

gctttctaaa cacagccaca ggaggcttgt agggcatctt ccaggtgggg aaacagtctt    720

agataagtaa ggtgacttgc ctaaggcctc ccagcaccct tgatcttgga gtctcacagc    780

agactgcatg tsaacaactg gaaccgaaaa catgcctcag tataaaa                  827
```

<210> SEQ ID NO 32
<211> LENGTH: 291
<212> TYPE: DNA
<213> ORGANISM: Homo sapien

<400> SEQUENCE: 32

```
ccagaacctc cttctctttg gagaatgggg aggcctcttg gagacacaga gggtttcacc     60

ttggatgacc tctagagaaa ttgcccaaga agcccacctt ctggtcccaa cctgcagacc    120

ccacagcagt cagttggtca ggccctgctg tagaaggtca cttggctcca ttgcctgctt    180

ccaaccaatg ggcaggagag aaggccttta tttctcgccc acccattctc ctgtaccagc    240

acctccgttt tcagtcagyg ttgtccagca acggtaccgt ttacacagtc a             291
```

<210> SEQ ID NO 33
<211> LENGTH: 491
<212> TYPE: DNA
<213> ORGANISM: Homo sapien

<400> SEQUENCE: 33

```
tgcatgtagt tttatttatg tgttttsgtc tggaaaacca agtgtcccag cagcatgact     60

gaacatcact cacttcccct acttgatcta caaggccaac gccgagagcc cagaccagga    120

ttccaaacac actgcacgag aatattgtgg atccgctgtc aggtaagtgt ccgtcactga    180
```

-continued

```
cccaracgct gttacgtggc acatgactgt acagtgccac gtaacagcac tgtacttttc    240

tcccatgaac agttacctgc catgtatcta catgattcag aacattttga acagttaatt    300

ctgacacttg aataatccca tcaaaaaccg taaaatcact ttgatgtttg taacgacaac    360

atagcatcac tttacgacag aatcatctgg aaaaacagaa caacgaatac atacatctta    420

aaaaatgctg ggtgggccca ggcacagctt cacgcctgta atcccagcac tttgggaggc    480

ttaagcgggt g                                                         491


<210> SEQ ID NO 34
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 34

tggggcggaa agaagccaag gccaaggagc tggtgcggca gctgcagctg gaggccgagg     60

agcagaggaa gcagaagaag cggcagagtg tgtcgggcct gcacagatac cttcacttgc    120

tggatggaaa tgaaaattac ccgtgtcttg tggatgcaga cggtgatgtg atttccttcc    180

caccaataac caacagtgag aagacaaagg ttaagaaaac gacttctgat ttgtttttgg    240

aagtaacaag tgccaccagt ctgcagattt gcaaggatgt catggatgcc ctcattctga    300

aaatggcaag aaatgaaaaa gtacacttta gaaaataaag aggaaggatc actctcagat    360

actgaagccg atgcagtctc tggacaactt ccagatccca caacgaatcc cagtgctgga    420

aaggacgggc ccttccttct ggtggtggaa cangtcccgg tggtggatct tggaanggaa    480

cctgaangtg gtgtaccccg tccaaggccg accttggcca c                        521


<210> SEQ ID NO 35
<211> LENGTH: 161
<212> TYPE: DNA
<213> ORGANISM: Homo sapien
<220> FEATURE:
<221> NAME/KEY: misc_feature
<222> LOCATION: (1)...(161)
<223> OTHER INFORMATION: n = A,T,C or G

<400> SEQUENCE: 35

tcccgcgctc gcagggcncg tgccacctgc cygtccgccc gctcgctcgc tcgcccgccg     60

cgccgcgctg ccgaccgyca gcatgctgcc gagagtgggc tgccccgcgc tgccgctgcc    120

gccgccgccg ctgctgccgc tgctgccgct gctgctgctg c                        161


<210> SEQ ID NO 36
<211> LENGTH: 341
<212> TYPE: DNA
<213> ORGANISM: Homo sapien

<400> SEQUENCE: 36

ggcgggtagg catggaactg agaagaacga agaagctttc agactacgtg gggaagaatg     60

aaaaaaccaa aattatcgcc aagattcagc aaaggggaca gggagctcca gcccgagagc    120

ctattattag cagtgaggag cagaagcagc tgatgctgta ctatcacaga agacaagagg    180

agctcaagag attggaagaa aatgatgatg atgcctattt aaactcacca tgggcggata    240

acactgcttt gaaaagacat tttcatggag tgaaagacat aaagtggaga ccaagatgaa    300
```

-continued

```
gttcaccagc tgatgacact tccaaagaga ttagctcacc t                    341


<210> SEQ ID NO 37
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 37

tctgaaggtt aaatgtttca tctaaatagg gataatgrta aacacctata gcatagagtt     60

gtttgagatt aaatgagata atacatgtaa aattatgtgc ctggcataca gcaagattgt    120

tgttgttgtt gatgatgatg atgatgatga taatattttt ctatccccag tgcacaactg    180

cttgaaccta ttagataatc aatacatgtt tcttgaactg agatcaattt ccccatgttg    240

tctgactgat gaagccctac attttcttct agaggagatg acatttgagc aagatcttaa    300

agaaaatcag atgccttcac ctgaccactg cttggtgatc ccatggcact ttgtacatct    360

ctccattagc tctcatctca ccagcccatc attattgtat gtgctgcctt ctgaagcttg    420

cagctggcta ccatcmggta gaataaaaat catcctttca taaaatagtg accctccttt    480

tttatttgca tttcccaaag ccaagcaccg tgggancggta g                   521


<210> SEQ ID NO 38
<211> LENGTH: 461
<212> TYPE: DNA
<213> ORGANISM: Homo sapien

<400> SEQUENCE: 38

tatgaagaag ggaaaagaag ataatttgtg aaagaaatgg gtccagttac tagtctttga     60

aaagggtcag tctgtagctc ttcttaatga gaataggcag ctttcagttg ctcagggtca    120

gatttcctta gtggtgtatc taatcacagg aaacatctgt ggttccctcc agtctctttc    180

tgggggactt gggcccactt ctcatttcat ttaattagag gaaatagaac tcaaagtaca    240

atttactgtt gtttaacaat gccacaaaga catggttggg agctatttct tgatttgtgt    300

aaaatgctgt ttttgtgtgc tcataatggt tccaaaaatt gggtgctggc caaagagaga    360

tactgttaca gaagccagca agaagacctc tgttcattca cacccccggg gatatcagga    420

attgactcca gtgtgtgcaa atccagtttg gcctatcttc t                    461


<210> SEQ ID NO 39
<211> LENGTH: 769
<212> TYPE: DNA
<213> ORGANISM: Homo sapien

<400> SEQUENCE: 39

tgagggactg attggtttgc tctctgctat tcaattcccc aagcccactt gttcctgcag     60

cgtcctcctt ctcattccct ttagttgtac cctctctttc atctgagacc tttccttctt    120

gatgtcgcct tttcttcttc ttgctttttc tgatgttctg ctcagcatgt tctgggtgct    180

tctcatctgc atcattcctt tcagatgctg tagcttcttc ctcctctttc tgcctccttt    240

tctttttctt ttttttgggg ggcttgctct ctgactgcag ttgaggggcc ccagggtcct    300

ggcctttgag acgagccagg aaggcctgct cctgggcctc taggcgagca agcttggcct    360

tcattgtgat cccaagacgg gcagccttgt gtgctgttcg cccctcacag gcttggagca    420

gcatctcatc agtcagaatc tttggggact tggacccctg gttgtcgtca tcactgcagc    480
```

-continued tctccaagtc tttgtttggc ttctctccac ctgaagtcaa tgtagccatc ttcacaaact 540
tctgatacag caagttgggc ttgggatgat tataacgggt ggtctcctta gaaaggctcc 600
ttatctgtac tccatcctgc ccagtttcca ctaccaagtt ggccgcagtc ttgttgaaga 660
gctcattcca ccagtggttt gtgaactcct tggcagggtc atgtcctacc ccatgagtgt 720
cttgcttcag ygtcaccctg agagcctgag tgataccatt ctccttccg 769

<210> SEQ ID NO 40
<211> LENGTH: 292
<212> TYPE: DNA
<213> ORGANISM: Homo sapien

<400> SEQUENCE: 40
gacaacatga aataaatcct agaggacaaa attaaactca atagagtgta gtctagttaa 60
aaactcgaaa aatgagcaag tctggtggga gtggaggaag ggctatacta taaatccaag 120
tgggcctcct gatcttaaca agccatgctc attatacaca tctctgaact ggacatacca 180
cctttacgca ggaaacaggg cttggaactt ctaagggaaa ttaacatgca ccacccacat 240
ctaacctacc tgccgggtag gtaccatccc tgcttcgctg aaatcagtgc tc 292

<210> SEQ ID NO 41
<211> LENGTH: 406
<212> TYPE: DNA
<213> ORGANISM: Homo sapien

<400> SEQUENCE: 41
ttggaattaa ataaacctgg aacagggaag gtgaaagttg gagtgagatg tcttccatat 60
ctataccttt gtgcacagtt gaatgggaac tgtttgggtt tagggcatct tagagttgat 120
tgatggaaaa agcagacagg aactggtggg aggtcaagtg gggaagttgg tgaatgtgga 180
ataacttacc tttgtgctcc acttaaacca gatgtgttgc agctttcctg acatgcaagg 240
atctacttta attccacact ctcattaata aattgaataa aagggaatgt tttggcacct 300
gatataatct gccaggctat gtgacagtag gaaggaatgg tttcccctaa caagcccaat 360
gcactggtct gactttataa attatttaat aaaatgaact attatc 406

<210> SEQ ID NO 42
<211> LENGTH: 381
<212> TYPE: DNA
<213> ORGANISM: Homo sapien

<400> SEQUENCE: 42
aaactggacc tgcaacaggg acatgaattt actgcarggt ctgagcaagc tcagcccctc 60
tacctcaggg ccccacagcc atgactacct cccccaggag cgggagggtg aagggggcct 120
gtctctgcaa gtggagccag agtggaggaa tgagctctga agacacagca cccagccttc 180
tcgcaccagc caagccttaa ctgcctgcct gaccctgaac cagaacccag ctgaactgcc 240
cctccaaggg acaggaaggc tgggggaggg agtttacaac ccaagccatt ccacccccctc 300 ccctgctggg gagaatgaca catcaagctg ctaacaattg gggaagggg aaggaagaaa 360 actctgaaaa caaaatcttg t 381

<210> SEQ ID NO 43
<211> LENGTH: 451
<212> TYPE: DNA
<213> ORGANISM: Homo sapien -continued

<400> SEQUENCE: 43

```
catgcgtttc accactgttg gccaggctgg tctcgaactc ctggcctcaa gcaatccacc     60
cgcctcagcc tccaaaagtg ctgggattac agatgtgagc catggcacca tgccaaaagg    120
ctatattcct ggctctgtgt ttccgagact gcttttaatc ccaacttctc tacatttaga    180
ttaaaaaata ttttattcat ggtcaatctg gaacataatt actgcatctt aagtttccac    240
tgatgtatat agaaggctaa aggcacaatt tttatcaaat ctagtagagt aaccaaacat    300
aaaatcatta attactttca acttaataac taattgacat tcctcaaaag agctgttttc    360
aatcctgata ggttctttat tttttcaaaa tatatttgcc atgggatgct aatttgcaat    420
aaggcgcata atgagaatac cccaaactgg a                                   451
```

<210> SEQ ID NO 44
<211> LENGTH: 521
<212> TYPE: DNA
<213> ORGANISM: Homo sapien

<400> SEQUENCE: 44

```
gttggacccc cagggactgg aaagacactt cttgcccgag ctgtggcggg agaagctgat     60
gttccttttt attatgcttc tggatccgaa tttgatgaga tgtttgtggg tgtgggagcc    120
agccgtatca gaaatctttt tagggaagca aaggcgaatg ctccttgtgt tatatttatt    180
gatgaattag attctgttgg tgggaagaga attgaatctc caatgcatcc atattcaagg    240
cagaccataa atcaacttct tgctgaaatg gatggtttta aacccaatga aggagttatc    300
ataataggag ccacaaactt cccagaggca ttagataatg ccttaatacc gtcctggtcg    360
ttttgacatg caagttacag ttccaaggcc agatgtaaaa ggtcgaacag aaattttgaa    420
atggtatctc aataaaataa agtttgatca atcccgttga tccagaaatt atagcctcga    480
ggtactggtg gcttttccgg aagcagagtt gggagaatct t                        521
```

<210> SEQ ID NO 45
<211> LENGTH: 585
<212> TYPE: DNA
<213> ORGANISM: Homo sapien

<400> SEQUENCE: 45

```
gcctacaaca tccagaaaga gtctaccctg cacctggtgc tscgtctcag aggtgggatg     60
cagatcttcg tgaagaccct gactggtaag accatcactc tcgaagtgga gccgagtgac    120
accatygaga acgtcaaagc aaagatccar gacaaggaag gcrtycctcc tgaccagcag    180
aggttgatct ttgccggaaa gcagctggaa gatggdcgca ccctgtctga ctacaacatc    240
cagaaagagt cyaccctgca cctggtgctc cgtctcagag gtgggatgca ratcttcgtg    300
aagaccctga ctggtaagac catcaccctc gaggtggagc ccagtgacac catcgagaat    360
gtcaaggcaa agatccaaga taaggaaggc atccctcctg atcagcagag gttgatcttt    420
gctgggaaac agctggaaga tggacgcacc ctgtctgact acaacatcca gaaagagtcc    480
actctgcact tggtcctgcg cttgaggggg ggtgtctaag tttcccettt taaggtttcm    540
acaaatttca ttgcactttc ctttcaataa agttgttgca ttccc                    585
```

<210> SEQ ID NO 46
<211> LENGTH: 481
<212> TYPE: DNA
<213> ORGANISM: Homo sapien

<400> SEQUENCE: 46

-continued gaactgggcc ctgagcccaa gtcatgcctt gtgtccgcat ctgccgtgtc acctctgtkc 60
ctgcccctca cccctccctc ctggtcttct gagccagcac catctccaaa tagcctattc 120
cttcctgcaa atcacacaca catgcgggcc acacatacct gctgccctgg agatggggaa 180
gtaggagaga tgaatagagg cccatacatt gtacagaagg aggggcaggt gcagataaaa 240
gcagcagacc cagcggcagc tgaggtgcat ggagcacggt tggggccggc attgggctga 300
gcacctgatg ggcctcatct cgtgaatcct cgaggcagcg ccacagcaga ggagttaagt 360
ggcacctggg ccgagcagag caggagactg agggtcagag tggaggctaa gctgccctgg 420
aactcctcaa tcttgcctgc cccctagtat gaagcccccct tcctgcccct acaattcctg 480
a 481

<210> SEQ ID NO 47
<211> LENGTH: 461
<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 47
atggatctta ctttgccacc caggttggag tgcagtgctg caatcttggc tcactgcagc 60
cttaacctcc caggctcaag ctatcctcct gccaaagcct tccacatagc tgggactaca 120
ggtacacngc caccacaccc agctaaaatt tttgtatttt ttgtagagac gggatctcgc 180
cacgttgccc aggctggtcc catcctgacc tcaagcagat ctgcccacct cagcccccca 240
acgtgctagg attacaggcg tgagccaccg cacccagcct ttgttttgct tttaatggaa 300
tcaccagttc ccctccgtgt ctcagcagca gctgtgagaa atgctttgca tctgtgacct 360
ttatgaaggg gaacttccat gctgaatgag ggtaggatta catgctcctg tttcccgggg 420
gtcaagaaag cctcagactc cagcatgata agcagggtga g 461

<210> SEQ ID NO 48
<211> LENGTH: 571
<212> TYPE: DNA
<213> ORGANISM: Homo sapien

<400> SEQUENCE: 48
ataggggctt taaggaggga attcaggttc aatgaggtcg taaggccagg gctcttatcc 60
agtaagactg gggtccttag atgagaaaga gacacccgag gtccttctct ctgccgtgtg 120
aggatgcatc aagaaggcgg ccgtctgcaa gcgaaggaga ggccgcacca gaaaccgaca 180
ccttcatctt ggacttgcag cctctagaac tgagaaaata actgtctgtt ggttaagcca 240
cccagtttgt agtattctct tatggcttcc taagcagact aacaaacaaa cacccaaaat 300
taactgatgg cttcgctgtc ttctgtaaaa attgctatga gagaactttt cactcactgt 360
tttgcagttt ctccctcagt ccctggttct ttcttctcac ataatcccaa tttcaattta 420
tagttcatgg cccaggcaga gtcattcatc acggcatctc ctgagctaaa ccagcacctg 480
ctctgctcac ttcttgactg gctgctcatc atcagccctc ttgcagagat ttcatttcct 540
cccgtgccag gtacttcacg caccaagctc a 571

<210> SEQ ID NO 49
<211> LENGTH: 511
<212> TYPE: DNA

-continued

<213> ORGANISM: Homo sapien

<400> SEQUENCE: 49

```
ggataatgaa gttgttttat ttagcttgga caaaaaggca tattcctcta ttttcttata     60
caacaaatat ccccaaaata aagcaagcat atatatcttg aatgtgtaat aatccagtga    120
taaacaagag cagtacttta aaagaaaaaa aaatatgtat ttctgtcagg ttaaaatgag    180
aatcaaaacc atttactctg ctaactcatt attttttgct ttctttttgg ttaagagagg    240
caatgcaata cactgaaaaa ggtttttatc ttatctggca ttggaattag acatattcaa    300
accccagccc ccatttccaa actttaagac cacaaacaag taatttactt ttctgaacat    360
tggtttttc tggaaaatgg gaattataaa atagactttg cagactctta tgagattaaa    420
taagataatg tatgaaattc tttcttcttt tttacttctt tttccttttt gagatggagt    480
ctcaccccgt cacccaggct ggagtacagt g                                   511
```

<210> SEQ ID NO 50
<211> LENGTH: 561
<212> TYPE: DNA
<213> ORGANISM: Homo sapien

<400> SEQUENCE: 50

```
ccactgcact ccagcctggg tgacggagtg agactctgtc tcaaaaaaac aaacaaacaa     60
acaaacaaaa aactgaaaag gaaatagagt tcctctttcc tcatatatga atatattatt    120
tcaacagatt gttgatcacc taccatatgc ttggtattgt tctaattgct ggggatacag    180
caagaggttc tgcagaactt catggagcat gaaagtaaat aaacaaagtt aatttcaagg    240
ccaggcatgg ttgctcacac ctttagtccc agcactttgg gaggctgagg caggtggatc    300
acttgggccc aggagttcaa ggctgcagtg agccaagatt gtgccactac tctccaggct    360
gggcaacaga gcaagaccct gtctcagggg gaacaaaaag ttaatttcag attttgttaa    420
gtgctgtaaa ggaagtaaat aggttgatat tcaagagagc acctgaaggc caggcgtggt    480
ggctcacgcc tgtggtctaa cgctttggga agcccgagcg ggcggatcac aaggtcagga    540
gaattttggc caggcatggt g                                              561
```

<210> SEQ ID NO 51
<211> LENGTH: 451
<212> TYPE: DNA
<213> ORGANISM: Homo sapien

<400> SEQUENCE: 51

```
agaatccatt tattgggttt taaactagtt acacaactga aatcagtttg gcactacttt     60
atacagggat tacgcctgtg tatgccgaca cttaaatact gtaccaggac cactgctgtg    120
cttaggtctg tattcagtca ttcagcatgt agatactaaa aatatactgt agtgttcctt    180
taaggaagac tgtacagggt gtgttgcaag atgacattca ccaatttgtg aattatttca    240
acccagaaga tacctttcac tctataaact tgtcataggc aaacatgtgg tgttagcatt    300
gagagatgca cacaaaaatg ttacataaaa gttcagacat tctaatgata agtgaactga    360
aaaaaaaaaa aaccccacat ctcaattttt gtaacaagat aaagaaaata atttaaaaac    420
acaaaaaatg gcattcagtg ggtacaaagc c                                   451
```

<210> SEQ ID NO 52
<211> LENGTH: 682
<212> TYPE: DNA
<213> ORGANISM: Homo sapien -continued

<400> SEQUENCE: 52
caaatattta atataaatct ttgaaacaag ttcagakgaa ataaaaatca aagtttgcaa 60
aaacgtgaag attaacttaa ttgtcaaata ttcctcattg ccccaaatca gtattttttt 120
tatttctatg caaaagtatg ccttcaaact gcttaaatga tatatgatat gatacacaaa 180
ccagttttca aatagtaaag ccagtcatct tgcaattgta agaaataggt aaaagattat 240
aagacacctt acacacacac acacacacac acacacacgt gtgcaccgcc aatgacaaaa 300
aacaatttgg cctctcctaa aataagaaca tgaagaccct taattgctgc caggagggaa 360
cactgtgtca cccctcccta caatccaggt agtttccttt aatccaatag caaatctggg 420
catatttgag aggagtgatt ctgacagcca csgttgaaat cctgtgggga accattcatg 480
tccacccact ggtgccctga aaaaatgcca ataatttttc gctcccactt ctgctgctgt 540
ctcttccaca tcctcacata gaccccagac ccgctggccc ctggctgggc atcgcattgc 600
tggtagagca agtcataggt ctcgtctttg acgtcacaga agcgatacac caaattgcct 660
ggtcggtcat tgtcataacc ag 682

<210> SEQ ID NO 53
<211> LENGTH: 311
<212> TYPE: DNA
<213> ORGANISM: Homo sapien
<220> FEATURE:
<221> NAME/KEY: misc_feature
<222> LOCATION: (1)...(311)
<223> OTHER INFORMATION: n = A,T,C or G

<400> SEQUENCE: 53
tttgacttta gtaggggtct gaactattta ttttactttg ccmgtaatat ttaraccyta 60
tatatctttc attatgccat cttatcttct aatgbcaagg gaacagwtgc taamctggct 120
tctgcattwa tcacattaaa aatggctttc ttggaaaatc ttcttgatat gaataaagga 180
tcttttavag ccatcattta aagcmggntt ctctccaaca cgagtctgct sasggggggk 240
gagctgtgaa ctctggctga aggctttccc atacacactg caatgacmtg gtttctgacc 300
agbgtgagtt a 311

<210> SEQ ID NO 54
<211> LENGTH: 561
<212> TYPE: DNA
<213> ORGANISM: Homo sapien

<400> SEQUENCE: 54
agagaagccc cataaatgca atcagtgtgg gaaggccttc agtcagagct caagcctttt 60
cctccatcat cgggttcata ctggagagaa accctatgta tgtaatgaat gcggcagagc 120
ctttggtttt aactctcatc ttactgaaca cgtaaggatt cacacaggag aaaaaaccta 180
tgtttgtaat gagtgcggca aagcctttcg tcggagttcc actcttgttc agcatcgaag 240
agttcacact ggggagaagc cctaccagtg cgttgaatgt gggaaagctt tcagccagag 300
ctcccagctc accctacatc agccgagttc acactggaga gaagccctat gactgtggtg 360
actgtgggaa ggccttcagc cggaggtcaa ccctcattca gcatcagaaa gttcacagcg 420
gagagactcg taagtgcaga aaacatggtc cagcctttgt tcatggctcc agcctcacag 480
cagatggaca gattcccact ggagagaagc acggcagaac ctttaaccat ggtgcaaatc 540
tcattctgcg ctggacagtt c 561

-continued

<210> SEQ ID NO 55
<211> LENGTH: 811
<212> TYPE: DNA
<213> ORGANISM: Homo sapien

<400> SEQUENCE: 55
gagacagggt ctcactttgt cacccaggct ggaatgcagt ggtgcgatct tacgtagctc 60
actgcagccc tgacctcctg gactcaaaca attctcctgc ctcagccctg caagtagctg 120
ggactgtggg tgcatgccac catgcctggc taacttttgt agtttttgta aagatggggt 180
tttgccatgt tgcacatgct ggtcttgaac tcctgagctc aaacgatctg cccacctcgg 240
cctcccagaa tgttgggatt acaggggtaa accaccacgc ctggccccat tagggtattc 300
ttagcatcca cttgctcact gagattaatc ataagagatg ataagcactg gaagaaaaaa 360
atttttacta ggctttggat atttttttcc tttttcagct ttatacagag gattggatct 420
ttagttttcc tttaactgat aataaaacat tgaaaggaaa taagtttacc tgagattcac 480
agagataacc ggcatcactc ccttgctcaa ttccagtctt taccacatca attattttca 540
gaggtgcagg ataaaggcct ttagtctgct ttcgcacttt ttcttccact tttttgtaaa 600
cctgttgcct gacaaatgga attgacagcg tatgccatga ctattccatt tgtcaggcat 660
acgctgtcaa tttttccacc aatcccttgt ctctctttgg agagatcttc ttatcagcta 720
gtcctttggc aaaagtaatt gcaacttctt ctaggtattc tattgtccgt tccactggtg 780
gaacccctgg gaccaggact aaaacctcca g 811

<210> SEQ ID NO 56
<211> LENGTH: 591
<212> TYPE: DNA
<213> ORGANISM: Homo sapien
<220> FEATURE:
<221> NAME/KEY: misc_feature
<222> LOCATION: (1)...(591)
<223> OTHER INFORMATION: n = A,T,C or G

<400> SEQUENCE: 56
atctcatata tatatttctt cctgacttta tttgcttgct tctgncacgc atttaaaata 60
tcacagagac caaaatagag cggctttctg gtggaacgca tggcagtcac aggacaaaat 120
acaaaactag ggggctctgt cttctcatac atcatacaat tttcaagtat tttttttatg 180
tacaaagagc tactctatct gaaaaaaaat taaaaaataa atgagacaag atagtttatg 240
catcctagga agaaagaatg ggaagaaaga acggggcagt tgggtacaga ttcctgtccc 300
ctgttcccag ggaccactac cttcctgcca ctgagttccc ccacagcctc acccatcatg 360
tcacagggca agtgccaggg taggtgggga ccagtggaga caggaaccag caacatactt 420
tggcctggaa gataaggaga aagtctcaga aacacactgg tgggaagcaa tcccacnggc 480
cgtgccccan gagcttccca cctgctgctg gctccctggg tggctttggg aacagcttgg 540
gcaggccctt ttgggtgggg nccaactggg cctttgggcc cgtgtggaaa g 591

<210> SEQ ID NO 57
<211> LENGTH: 481
<212> TYPE: DNA
<213> ORGANISM: Homo sapien

<400> SEQUENCE: 57
aaacattgag atggaatgat agggtttccc agaatcaggt ccatatttta actaaatgaa 60
aattatgatt tatagccttc tcaaatacct gccatacttg atatctcaac cagagctaat 120

-continued tttacctctt tacaaattaa ataagcaagt aactggatcc acaatttata atacctgtca 180 atttttttctg tattaaacct ctatcatagt ttaagcctat tagggtactt aatccttaca 240
aataaacagg tttaaaatca cctcaatagg caactgccct tctggttttc ttctttgact 300
aaacaatctg aatgcttaag attttccact ttgggtgcta gcagtacaca gtgttacact 360
ctgtattcca gacttcttaa attatagaaa aaggaatgta cactttttgt attctttctg 420
agcagggccg ggaggcaaca tcatctacca tggtagggac ttgtatgcat ggactacttt 480
a 481

<210> SEQ ID NO 58
<211> LENGTH: 141
<212> TYPE: DNA
<213> ORGANISM: Homo sapien

<400> SEQUENCE: 58
actctgtcgc ccaggctgga gcccabtggm gcgatctcga ctccctgcaa gctmcgcctc 60
acaggwtcat gccattctcc tgcctcagca tctggagtag ctgggactac aggcgccagc 120
caccatgccc agctaatttt t 141

<210> SEQ ID NO 59
<211> LENGTH: 191
<212> TYPE: DNA
<213> ORGANISM: Homo sapien

<400> SEQUENCE: 59
accttaaaga cataggagaa tttatactgg gagagaaagc ttacaaatgt aaggtttctg 60
acaagacttg ggagtgattc acacctggaa caacatactg gacttcacac tggabagaaa 120
ccttacaagt gtaatgagtg tggcaaagcc tttggcaagc agtcaacact tattcaccat 180
caggcaattc a 191

<210> SEQ ID NO 60
<211> LENGTH: 480
<212> TYPE: DNA
<213> ORGANISM: Homo sapien

<400> SEQUENCE: 60
agtcaggatc atgatggctc agtttcccac agcgatgaat ggagggccaa atatgtgggc 60
tattacatct gaagaacgta ctaagcatga taaacagttt gataacctca aaccttcagg 120
aggttacata acaggtgatc aagcccgtac ttttttccta cagtcaggtc tgccggcccc 180
ggttttagct gaaatatggg ccttatcaga tctgaacaag gatgggaaga tggaccagca 240
agagttctct atagctatga aactcatcaa gttaaagttg cagggccaac agctgcctgt 300
agtcctccct cctatcatga aacaaccccc tatgttctct ccactaatct ctgctcgttt 360
tgggatggga agcatgccca atctgtccat tcatcagcca ttgcctccag ttgcacctat 420
agcaacaccc ttgtcttctg ctacttcagg gaccagtatt cctccctaat gatgcctgct 480

<210> SEQ ID NO 61
<211> LENGTH: 381
<212> TYPE: DNA
<213> ORGANISM: Homo sapien

<400> SEQUENCE: 61
ctttcgattt ccttcaattt gtcacgtttg attttatgaa gttgttcaag ggctaactgc 60

-continued

```
tgtgtattat agctttctct gagttccttc agctgattgt taaatgaatc catttctgag    120

agcttagatg cagtttcttt ttcaagagca tctaattgtt ctttaagtct ttggcataat    180

tcttcctttt ctgatgactt tctatgaagt aaactgatcc ctgaatcagg tgtgttactg    240

agctgcatgt ttttaattct ttcgtttaat agctgcttct cagggaccag atagataagc    300

ttattttgat attccttaag ctcttggtga agttgttcga tttccataat ttccaggtca    360

cactggttat cccaaacttc t                                              381
```

<210> SEQ ID NO 62
<211> LENGTH: 906
<212> TYPE: DNA
<213> ORGANISM: Homo sapien

<400> SEQUENCE: 62

```
gtggaggtga aacggaggca agaaaggggg ctacctcagg agcgagggac aaagggggcg     60

tgaggcacct aggccgcggc accccggcga caggaagccg tcctgaaccg ggctaccggg    120

taggggaagg gcccgcgtag tcctcgcagg gccccagagc tggagtcggc tccacagccc    180

cgggccgtcg gcttctcact tcctggacct ccccggcgcc cgggcctgag gactggctcg    240

gcggagggag aagaggaaac agacttgagc agctccccgt tgtctcgcaa ctccactgcc    300

gaggaactct catttcttcc ctcgctcctt cacccccac ctcatgtaga aaggtgctga     360

agcgtccgga gggaagaaga acctgggcta ccgtcctggc cttcccmccc ccttcccggg    420

gcgctttggt gggcgtggag ttggggttgg gggggtgggt gggggttctt ttttggagtg    480

ctggggaact tttttccctt cttcaggtca ggggaaaggg aatgcccaat tcagagagac    540

atgggggcaa gaaggacggg agtggaggag cttctggaac tttgcagccg tcatcgggag    600

gcggcagctc taacagcaga gagcgtcacc gcttggtatc gaagcacaag cggcataagt    660

ccaaacactc caaagacatg ggttggtga cccccgaagc agcatccctg ggcacagtta     720

tcaaaccttt ggtggagtat gatgatatca gctctgattc cgacaccttc tccgatgaca    780

tggccttcaa actagaccga agggagaacg acgaacgtcg tggatcagat cggagcgacc    840

gcctgcacaa acatcgtcac caccagcaca ggcgttcccg ggacttacta aaagctaaac    900

agaccg                                                               906
```

<210> SEQ ID NO 63
<211> LENGTH: 491
<212> TYPE: DNA
<213> ORGANISM: Homo sapien

<400> SEQUENCE: 63

```
gacatgtttg cctgcagggg accagagaca atgggattag ccagtgctca ctgttcttta     60

tgcttccaga gaggatgggg acagctctca ggtcagaatc caggctgaga aggccatgct    120

ggttggggc ccccggaagc acggtccgga tcctccctgg catcagcgta gacccgctgc     180

tcaggcttgg ggtaccaaac tcatgctctg tactgttttg gccccatgcg gtgagaggaa    240

aacctagaaa aagattggtc gtgctaagga atcagctgcc ccctcatcct ccgcatccaa    300

tgctggtgac aacatattcc ctctcccagg acacagactc ggtgactcca cactgggctg    360

agtggcctct ggaggctcgt ggcctaaggc agggctccgt aaggctgatc ggctgaactg    420

ggtggggtga gggtttctga cccttcgctt cccatcccat aaccgctgtc aatgagctca    480

cactgtggtc a                                                         491
```

-continued

<210> SEQ ID NO 64
<211> LENGTH: 511
<212> TYPE: DNA
<213> ORGANISM: Homo sapien

<400> SEQUENCE: 64
gatggcatgg tcgttgctaa tgtgcctgct gggatggagc acttcctcct gtgagcccag 60
gggacccgcc tgtccctgga gcttggggca aggagggaag agtgatacca ggaaggtggg 120
gctgcagcca ggggccagag tcagttcagg gagtggtcct cggccctcaa agctcctccg 180
gggactgctc aggagtgatg gtgccctgga gtttgcccca acttccctgg ccaccctgga 240
aggtgcctgg ctgctccagg cctctaggct gggctgatgg gtttctccag gacacaagta 300
tcattaaagc caccctctcc tcagcttgtc aggccgcaca tgtgggacag gctgtgctca 360
caaccccctc gcctgccctg ccctccatca ggaggagcca gtggaacctt cggaaagctc 420
ccagcatctc agcagccctc aaaagtcgtc ctggggcaag ctctggttct cctgactgga 480
ggtcatctgg gcttggcctg ctctctctcg c 511

<210> SEQ ID NO 65
<211> LENGTH: 394
<212> TYPE: DNA
<213> ORGANISM: Homo sapien

<400> SEQUENCE: 65
taaaaaagtg taacaaaggt ttatttagac tttcttcatg cccccagatc caggatgtct 60
atgtaaaccg ttatcttaca aagaaagcac aatatttggt ataaactaag tcagtgactt 120
gcttaactga aatagcgtcc atccaaaagt gggtttaagg taaaactacc tgacgatatt 180
ggcggggatc ctgcagtttg gactgcttgc cgggtttgtc cagggttccg ggtctgttct 240
tggcactcat ggggacaggc atcctgctcg tctgtggggc cccgctggag cccttacgtg 300
aagctgaagg tatcgaccst agggggctct agggcagtgg gaccttcatc cggaactaac 360
aagggtcggg gagaggcctc ttgggctatg tggg 394

<210> SEQ ID NO 66
<211> LENGTH: 359
<212> TYPE: DNA
<213> ORGANISM: Homo sapien

<400> SEQUENCE: 66
caagcgttcc tttatggatg taaattcaaa cagtcatgct gagccatccc gggctgacag 60
tcacgttwaa gacactaggt cgggcgccac agtgccaccc aaggagaaga agaatttgga 120
atttttccat gaagatgtac ggaaatctga tgttgaatat gaaaatggcc cccaaatgga 180
attccaaaag gttaccacag ggctgtaag acctagtgac cctcctaagt gggaaagagg 240
aatggagaat agtatttctg atgcatcaag aacatcagaa tataaaactg agatcataat 300
gaaggaaaat tccatatcca atatgagttt actcagagac agtagaaact attcccagg 359

<210> SEQ ID NO 67
<211> LENGTH: 450
<212> TYPE: DNA
<213> ORGANISM: Homo sapien
<220> FEATURE:
<221> NAME/KEY: misc_feature
<222> LOCATION: (1)...(450)
<223> OTHER INFORMATION: n = A,T,C or G

<400> SEQUENCE: 67

-continued

```
taggaataac aaatgtttat tcagaaatgg ataagtaata cataatcacc cttcatctct     60

taatgcccct tcctctcctt ctgcacagga gacacagatg ggtaacatag aggcatggga    120

agtggaggag gacacaggac tagcccacca ccttctcttc ccggtctccc aagatgactg    180

cttatagagt ggaggaggca aacaggtccc ctcaatgtac cagatggtca cctatagcac    240

cagctccaga tggccacgtg gttgcagctg gactcaatga aactctgtga caaccagaag    300

atacctgctt tgggatgaga gggaggataa agccatgcag ggaggatatt taccatccct    360

accctaagca cagtgcaagc agtgagcccc cggctcccag tacctgaaaa accaaggcct    420

actgnctttt ggatgctctc ttgggccacg                                      450


<210> SEQ ID NO 68
<211> LENGTH: 511
<212> TYPE: DNA
<213> ORGANISM: Homo sapien

<400> SEQUENCE: 68

aagcctcctg ccctggaaat ctggagcccc ttggagctga gctggacggg gcagggaggg     60

gctgagaggc aagaccgtct ccctcctgct gcagctgctt ccccagcagc cactgctggg    120

cacagcagaa acgccagcag agaaaatggg agccgagagt ccttagccct ggagctgagg    180

ctgcctctgg gctgacccgc tggctgtacg tggccagaac tggggttggc atctggcatc    240

catttgaggc cagggtggag gaaagggagg ccaacagagg aaaacctatt cctgctgtga    300

caacacagcc cttgtcccac gcagcctaag tgcagggagc gtgatgaagt caggcagcca    360

gtcggggagg acgaggtaac tcagcagcaa tgtcaccttg tagcctatgc gctcaatggc    420

ccggaggggc agcaaccccc cgcacacgtc agccaacagc agtgcctctg caggcaccaa    480

gagagcgatg atggacttga gcgccgtgtt c                                    511


<210> SEQ ID NO 69
<211> LENGTH: 511
<212> TYPE: DNA
<213> ORGANISM: Homo sapien

<400> SEQUENCE: 69

gtttggcaga agacatgttt aataacattt tcatatttaa aaaatacagc aacaattctc     60

tatctgtcca ccatcttgcc ttgcccttcc tggggctgag gcagacaaag gaaaggtaat    120

gaggttaggg cccccaggcg ggctaagtgc tattggcctg ctcctgctca aagagagcca    180

tagccagctg ggcacggccc cctagcccct ccaggttgct gaggcggcag cggtggtaga    240

gttcttcact gagccgtggg ctgcagtctc gcagggagaa cttctgcacc agccctggct    300

ctacggcccg aaagaggtgg agccctgaga accggaggaa aacatccatc acctccagcc    360

cctccagggc ttcctcctct tcctggcctg ccagttcacc tgccagccgg gctcgggccg    420

ccaggtagtc agcgttgtag aagcagccct ccgcagaagc ctgccggtca aatctccccg    480

ctataggagc cccccgggag gggtcagcac c                                    511


<210> SEQ ID NO 70
<211> LENGTH: 511
<212> TYPE: DNA
<213> ORGANISM: Homo sapien

<400> SEQUENCE: 70

caagttgaac gtcaggcttg gcagaggtgg agtgtagatg aaaacaaagg tgtgattatg     60

aagaggatgt gagtcctttg ggtgtaggag agaaaggctg ttgagcttct atttcaagat    120
```

-continued

```
acttttacct gtgcaaaaag cacattttcc acctccttct catggcattt gtgtaaggtg    180

agtatgattc ctattccatc tgcattttag aggtgaagaa taacgtacaa gggattcagt    240

gattagcaag ggacccctca ctaagtgttg atggagttag gacagagctc agctgtttga    300

atctcagagc ccaggcagct ggagctgggt aggatcctgg agctggcact aatgtgaggt    360

gcattccctc caacccaggc tcagatccgg aacctgaccg tgctgacccc cgaaggggag    420

gcagggctga gctggcccgt tgggctccct gctcctttca caccacactc tcgctttgag    480

gtgctgggct gggactactt cacagagcag c                                    511

<210> SEQ ID NO 71
<211> LENGTH: 511
<212> TYPE: DNA
<213> ORGANISM: Homo sapien

<400> SEQUENCE: 71

tggcctgggc aggattggga gagaggtagc tacccggatg cagtcctttg ggatgaagac     60

tatagggtat gaccccatca tttccccaga ggtctcggcc tcctttggtg ttcagcagct    120

gcccctggag gagatctggc ctctctgtga tttcatcact gtgcacactc ctctcctgcc    180

ctccacgaca ggcttgctga atgacaacac ctttgcccag tgcaagaagg gggtgcgtgt    240

ggtgaactgt gcccgtggag ggatcgtgga cgaaggcgcc ctgctccggg ccctgcagtc    300

tggccagtgt gccggggctg cactggacgt gtttacggaa gagccgccac gggaccgggc    360

cttggtggac catgagaatg tcatcagctg tccccacctg ggtgccagca ccaaggaggc    420

tcagagccgc tgtggggagg aaattgctgt tcagttcgtg gacatggtga aggggaaatc    480

tctcacgggg gttgtgaatg cccaggccct t                                    511

<210> SEQ ID NO 72
<211> LENGTH: 2017
<212> TYPE: DNA
<213> ORGANISM: Homo sapien

<400> SEQUENCE: 72

agccagatgg ctgagagctg caagaagaag tcaggatcat gatggctcag tttcccacag     60

cgatgaatgg agggccaaat atgtgggcta ttacatctga agaacgtact aagcatgata    120

aacagtttga taacctcaaa ccttcaggag gttacataac aggtgatcaa gcccgtactt    180

ttttcctaca gtcaggtctg ccggccccgg ttttagctga aatatgggcc ttatcagatc    240

tgaacaagga tgggaagatg gaccagcaag agttctctat agctatgaaa ctcatcaagt    300

taaagttgca gggccaacag ctgcctgtag tcctccctcc tatcatgaaa caacccccta    360

tgttctctcc actaatctct gctcgttttg ggatgggaag catgcccaat ctgtccattc    420

atcagccatt gcctccagtt gcacctatag caacaccctt gtcttctgct acttcaggga    480

ccagtattcc tcccctaatg atgcctgctc ccctagtgcc ttctgttagt acatcctcat    540

taccaaatgg aactgccagt ctcattcagc ctttatccat tccttattct tcttcaacat    600

tgcctcatgc atcatcttac agcctgatga tgggaggatt tggtggtgct agtatccaga    660

aggcccagtc tctgattgat ttaggatcta gtagctcaac ttcctcaact gcttccctct    720

cagggaactc acctaagaca gggacctcag agtgggcagt tcctcagcct tcaagattaa    780

agtatcggca aaaatttaat agtctagaca aaggcatgag cggatacctc tcaggttttc    840

aagctagaaa tgcccttctt cagtcaaatc tctctcaaac tcagctagct actatttgga    900
```

-continued

```
ctctggctga catcgatggt gacggacagt tgaaagctga agaatttatt ctggcgatgc    960

acctcactga catggccaaa gctggacagc cactaccact gacgttgcct cccgagcttg   1020

tccctccatc tttcagaggg ggaaagcaag ttgattctgt taatggaact ctgccttcat   1080

atcagaaaac acaagaagaa gagcctcaga agaaactgcc agttactttt gaggacaaac   1140

ggaaagccaa ctatgaacga ggaaacatgg agctggagaa gcgacgccaa gtgttgatgg   1200

agcagcagca gagggaggct gaacgcaaag cccagaaaga gaaggaagag tgggagcgga   1260

aacagagaga actgcaagag caagaatgga agaagcagct ggagttggag aaacgcttgg   1320

agaaacagag agagctggag agacagcggg aggaagagag gagaaaggag atagaaagac   1380

gagaggcagc aaaacaggag cttgagagac aacgccgttt agaatgggaa agactccgtc   1440

ggcaggagct gctcagtcag aagaccaggg aacaagaaga cattgtcagg ctgagctcca   1500

gaaagaaaag tctccacctg gaactggaag cagtgaatgg aaaacatcag cagatctcag   1560

gcagactaca agatgtccaa atcagaaagc aaacacaaaa gactgagcta gaagttttgg   1620

ataaacagtg tgacctggaa attatggaaa tcaaacaact tcaacaagag cttaaggaat   1680

atcaaaataa gcttatctat ctggtccctg agaagcagct attaaacgaa agaattaaaa   1740

acatgcagct cagtaacaca cctgattcag ggatcagttt acttcataaa aagtcatcag   1800

aaaaggaaga attatgccaa agacttaaag aacaattaga tgctcttgaa aaagaaactg   1860

catctaagct ctcagaaatg gattcattta acaatcagct gaaggaactc agagaaagct   1920

ataatacaca gcagttagcc cttgaacaac ttcataaaat caaacgtgac aaattgaagg   1980

aaatcgaaag aaaaagatta gagcaaaaaa aaaaaaa                            2017
```

<210> SEQ ID NO 73
<211> LENGTH: 414
<212> TYPE: DNA
<213> ORGANISM: Homo sapien

<400> SEQUENCE: 73

```
atggcagtga cattcaccat catgggaacc accttccctt ttcttcagga ttctctgtag     60

tggaagagag cacccagtgt tgggctgaaa acatctgaaa gtagggagaa gaacctaaaa    120

taatcagtat ctcagagggc tctaaggtgc caagaagtct cactggacat ttaagtgcca    180

acaaaggcat actttcggaa tcgccaagtc aaaactttct aacttctgtc tctctcagag    240

acaagtgaga ctcaagagtc tactgcttta gtggcaacta cagaaaactg gtgttaccca    300

gaaaaacagg agcaattaga aatggttcca atatttcaaa gctccgcaaa caggatgtgc    360

tttcctttgc ccatttaggg tttcttctct ttcctttctc tttattaacc acta          414
```

<210> SEQ ID NO 74
<211> LENGTH: 1567
<212> TYPE: DNA
<213> ORGANISM: Homo sapien

<400> SEQUENCE: 74

```
atatctagaa gtctggagtg agcaaacaag agcaagaaac aaaaagaagc caaaagcaga     60

aggctccaat atgaacaaga taaatctatc ttcaaagaca tattagaagt tgggaaaata    120

attcatgtga actagacaag tgtgttaaga gtgataagta aaatgcacgt ggagacaagt    180

gcatccccag atctcaggga cctccccctg cctgtcacct ggggagtgag aggacaggat    240

agtgcatgtt ctttgtctct gaatttttag ttatatgtgc tgtaatgttg ctctgaggaa    300

gcccctggaa agtctatccc aacatatcca catcttatat tccacaaatt aagctgtagt    360
```

-continued

```
atgtacccta agacgctgct aattgactgc cacttcgcaa ctcaggggcg gctgcatttt    420
agtaatgggt caaatgattc actttttatg atgcttccaa aggtgccttg gcttctcttc    480
ccaactgaca aatgccaaag ttgagaaaaa tgatcataat tttagcataa acagagcagt    540
cggcgacacc gattttataa ataaactgag caccttcttt ttaaacaaac aaatgcgggt    600
ttatttctca gatgatgttc atccgtgaat ggtccaggga aggacctttc accttgacta    660
tatggcatta tgtcatcaca agctctgagg cttctccttt ccatcctgcg tggacagcta    720
agacctcagt tttcaatagc atctagagca gtgggactca gctggggtga tttcgccccc    780
catctccggg ggaatgtctg aagacaattt tgttacctca atgagggagt ggaggaggat    840
acagtgctac taccaactag tggataaagg ccagggatgc tgctcaacct cctaccatgt    900
acaggacgtc tccccattac aactacccaa tccgaagtgt caactgtgtc aggactaaga    960
aaccctggtt ttgagtagaa aagggcctgg aaagagggga gccaacaaat ctgtctgctt   1020
cctcacatta gtcattggca aataagcatt ctgtctcttt ggctgctgcc tcagcacaga   1080
gagccagaac tctatcgggc accaggataa catctctcag tgaacagagt tgacaaggcc   1140
tatgggaaat gcctgatggg attatcttca gcttgttgag cttctaagtt tctttccctt   1200
cattctaccc tgcaagccaa gttctgtaag agaaatgcct gagttctagc tcaggttttc   1260
ttactctgaa tttagatctc cagacccttc ctggccacaa ttcaaattaa ggcaacaaac   1320
atataccttc catgaagcac acacagactt ttgaaagcaa ggacaatgac tgcttgaatt   1380
gaggccttga ggaatgaagc tttgaaggaa aagaatactt tgtttccagc cccttcccca   1440
cactcttcat gtgttaacca ctgccttcct ggaccttgga gccacggtga ctgtattaca   1500
tgttgttata gaaaactgat tttagagttc tgatcgttca agagaatgat taaatataca   1560
tttccta                                                             1567
```

<210> SEQ ID NO 75
<211> LENGTH: 240
<212> TYPE: DNA
<213> ORGANISM: Homo sapien

<400> SEQUENCE: 75

```
tcgagcggcc gcccgggcag gtccttcaga cttggactgt gtcacactgc caggcttcca     60
gggctccaac ttgcagacgg cctgttgtgg gacagtctct gtaatcgcga aagcaaccat    120
ggaagacctg ggggaaaaca ccatggtttt atccaccctg agatctttga acaacttcat    180
ctctcagcgt gcggagggag gctctggact ggatatttct acctcggccg cgaccacgct    240
```

<210> SEQ ID NO 76
<211> LENGTH: 330
<212> TYPE: DNA
<213> ORGANISM: Homo sapien
<220> FEATURE:
<221> NAME/KEY: misc_feature
<222> LOCATION: (1)...(330)
<223> OTHER INFORMATION: n = A,T,C or G

<400> SEQUENCE: 76

```
tagcgyggtc gcggccgagg yctgcttytc tgtccagccc agggcctgtg gggtcagggc     60
ggtgggtgca gatggcatcc actccggtgg cttccccatc tttctctggc ctgagcaagg    120
tcagcctgca gccagagtac agagggccaa cactggtgtt cttgaacaag ggccttagca    180
ggccctgaag grccctctct gtagtgttga acttcctgga gccaggccac atgttctcct    240
```

-continued

```
cataccgcag gytagygatg gtgaagttga gggtgaaata gtattmangr agatggctgg    300

caracctgcc cgggcggccg ctcsaaatcc                                     330


<210> SEQ ID NO 77
<211> LENGTH: 361
<212> TYPE: DNA
<213> ORGANISM: Homo sapien

<400> SEQUENCE: 77

agcgtggtcg cggccgaggt gtccttcagg gtctgcttat gcccttgttc aagaacacca     60

gtgtcagctc tctgtactct ggttgcagac tgaccttgct caggcctgag aaggatgggg    120

cagccaccag agtggatgct gtctgcaccc atcgtcctga ccccaaaagc cctggactgg    180

acagagagcg gctgtactgg aagctgagcc agctgaccca cggcatcact gagctgggcc    240

cctacaccct ggacagggac agtctctatg tcaatggttt cacccatcgg agctctgtac    300

ccaccaccag caccggggtg gtcagcgagg agccattcaa cctgcccggg cggccgctcg    360

a                                                                    361


<210> SEQ ID NO 78
<211> LENGTH: 356
<212> TYPE: DNA
<213> ORGANISM: Homo sapien
<220> FEATURE:
<221> NAME/KEY: misc_feature
<222> LOCATION: (1)...(356)
<223> OTHER INFORMATION: n = A,T,C or G

<400> SEQUENCE: 78

ttggggnttt mgagcggccg cccgggcagg taccggggtg gtcagcgagg agccattcac     60

actgaacttc accatcaaca acctgcggta tgaggagaac atgcagcacc ctggctccag    120

gaagttcaac accacggaga gggtccttca gggcctgctc aggtccctgt tcaagagcac    180

cagtgttggc cctctgtact ctggctgcag actgactttg ctcagacttg agaaacatgg    240

ggcagccact ggagtggacg ccatctgcac cctccgcctt gatcccactg gtcctggact    300

ggacagagag cggctatact gggagctgag ccagtcctct ggcggngacn ccnctt        356


<210> SEQ ID NO 79
<211> LENGTH: 226
<212> TYPE: DNA
<213> ORGANISM: Homo sapien

<400> SEQUENCE: 79

agcgtggtcg cggccgaggt ccagtcgcag catgctcttt ctcctgccca ctggcacagt     60

gaggaagatc tctgctgtca gtgagaaggc tgtcatccac tgagatggca gtcaaaagtg    120

catttaatac acctaacgta tcgaacatca tagcttggcc caggttatct catatgtgct    180

cagaacactt acaatagcct gcagacctgc ccgggcggcc gctcga                   226


<210> SEQ ID NO 80
<211> LENGTH: 444
<212> TYPE: DNA
<213> ORGANISM: Homo sapien
<220> FEATURE:
<221> NAME/KEY: misc_feature
<222> LOCATION: (1)...(444)
<223> OTHER INFORMATION: n = A,T,C or G

<400> SEQUENCE: 80

tgtggtgttg aacttcctgg agncagggtg acccatgtcc tccccatact gcaggttggt     60
```

-continued

```
gatggtgaag ttgagggtga atggtaccag gagagggcca gcagccataa ttgtsgrgck    120

gsmgmssgag gmwggwgtyy cwgaggttcy rarrtccact gtggaggtcc caggagtgct    180

ggtggtgggc acagagstcy gatgggtgaa accattgaca tagagactgt tcctgtccag    240

ggtgtagggg cccagctctt yratgycatt ggycagttkg ctyagctccc agtacagccr    300

ctctckgyyg mgwccagsgc ttttggggtc aagatgatgg atgcagatgg catccactcc    360

agtggctgct ccatccttct cggacctgag agaggtcagt ctgcagccag agtacagagg    420

gccaacactg gtgttctttg aata                                           444
```

<210> SEQ ID NO 81
<211> LENGTH: 310
<212> TYPE: DNA
<213> ORGANISM: Homo sapien

<400> SEQUENCE: 81

```
tcgagcggcc gcccgggcag gtcaggaagc acattggtct tagagccact gcctcctgga     60

ttccacctgt gctgcggaca tctccaggga gtgcagaagg gaagcaggtc aaactgctca    120

gatcagtcag actggctgtt ctcagttctc acctgagcaa ggtcagtctg cagccagagt    180

acagagggcc aacactggtg ttcttgaaca agggcttgag cagaccctgc agaaccctct    240

tccgtggtgt tgaacttcct ggaaaccagg gtgttgcatg tttttcctca taatgcaagg    300

ttggtgatgg                                                           310
```

<210> SEQ ID NO 82
<211> LENGTH: 571
<212> TYPE: DNA
<213> ORGANISM: Homo sapien
<220> FEATURE:
<221> NAME/KEY: misc_feature
<222> LOCATION: (1)...(571)
<223> OTHER INFORMATION: n = A,T,C or G

<400> SEQUENCE: 82

```
acggtttcaa tggacacttt tattgtttac ttaatggatc atcaattttg tctcactacc     60

tacaaatgga atttcatctt gtttccatgc tgagtagtga aacagtgaca aagctaatca    120

taataaccta catcaaaaga gaactaagct aacactgctc actttctttt taacaggcaa    180

aatataaata tatgcactct anaatgcaca atggtttagt cactaaaaaa ttcaaatggg    240

atcttgaaga atgtatgcaa atccagggtg cagtgaagat gagctgagat gctgtgcaac    300

tgtttaaggg ttcctggcac tgcatctctt ggccactagc tgaatcttga catggaaggt    360

tttagctaat gccaagtgga gatgcagaaa atgctaagtt gacttagggg ctgtgcacag    420

gaactaaaag gcaggaaagt actaaatatt gctgagagca tccaccccag gaaggacttt    480

accttccagg agctccaaac tggcaccacc cccagtgctc acatggctga ctttatcctc    540

cgtgttccat ttggcacagc aagtggcagt g                                   571
```

<210> SEQ ID NO 83
<211> LENGTH: 551
<212> TYPE: DNA
<213> ORGANISM: Homo sapien

<400> SEQUENCE: 83

```
aaggctggtg ggtttttgat cctgctggag aacctccgct ttcatgtgga ggaagaaggg     60

aagggaaaag atgcttctgg gaacaaggtt aaagccgagc cagccaaaat agaagctttc    120
```

-continued

```
cgagcttcac tttccaagct aggggatgtc tatgtcaatg atgcttttgg cactgctcac    180

agagcccaca gctccatggt aggagtcaat ctgccacaga aggctggtgg gtttttgatg    240

aagaaggagc tgaactactt tgcaaaggcc ttggagagcc cagagcgacc cttcctggcc    300

atcctgggcg gagctaaagt tgcagacaag atccagctca tcaataatat gctggacaaa    360

gtcaatgaga tgattattgg tggtggaatg gcttttacct tccttaaggt gctcaacaac    420

atggagattg gcacttctct gtttgatgaa gagggagcca agattgtcaa agacctaatg    480

tccaaagctg agaagaatgg tgtgaagatt accttgcctg ttgactttgt cactgctgac    540

aagtttgatg a                                                         551
```

<210> SEQ ID NO 84
<211> LENGTH: 571
<212> TYPE: DNA
<213> ORGANISM: Homo sapien

<400> SEQUENCE: 84

```
tttgttcctt acatttttct aaagagttac ttaaatcagt caactggtct ttgagactct     60

taagttctga ttccaactta gctaattcat tctgagaact gtggtatagg tggcgtgtct    120

cttctagctg ggacaaaagt tctttgtttt ccccctgtag agtatcacag accttctgct    180

gaagctggac ctctgtctgg gccttggact cccaaatctg cttgtcatgt tcaagcctgg    240

aaatgttaat ctttaattct tccatatgga tggacatctg tctaagttga tcctttagaa    300

cactgcaatt atcttctttg agtctaattt cttcttcttt gctttgaatc gcatcactaa    360

acttcctctc ccatttctta gcttcatcta tcaccctgtc acgatcatcc tggagggaag    420

acatgctctt agtaaaggct gcaagctggg tcacagtact gtccaagttt tcctgaagtt    480

gctgaacttc cttgtctttc ttgttcaaag taacctgaat ctctccaatt gtctcttcca    540

agtggacttt ttctctgcgc aaagcatcca g                                   571
```

<210> SEQ ID NO 85
<211> LENGTH: 561
<212> TYPE: DNA
<213> ORGANISM: Homo sapien

<400> SEQUENCE: 85

```
tcattgcctg tgatggcatc tggaatgtga tgagcagcca ggaagttgta gatttcattc     60

aatcaaagga ttcagcatgt ggtggaagct gtgaggcaag agaaacaaga actgtatggc    120

aagttaagaa gcacagaggc aaacaagaag gagacagaaa agcagttgca ggaagctgag    180

caagaaatgg aggaaatgaa agaaaagatg agaaagtttg ctaaatctaa acagcagaaa    240

atcctagagc tggaagaaga gaatgaccgg cttagggcag aggtgcaccc tgcaggagat    300

acagctaaag agtgtatgga aacacttctt tcttccaatg ccagcatgaa ggaagaactt    360

gaaagggtca aaatggagta tgaaaccctt tctaagaagt ttcagtcttt aatgtctgag    420

aaagactctc taagtgaaga ggttcaagat ttaaagcatc agatagaagg taatgtatct    480

aaacaagcta acctagaggc caccgagaaa catgataacc aaacgaatgt cactgaagag    540

ggaacacagt ctataccagg t                                              561
```

<210> SEQ ID NO 86
<211> LENGTH: 795
<212> TYPE: DNA
<213> ORGANISM: Homo sapien

<400> SEQUENCE: 86

-continued

```
aagccaataa tcaccattta ttacttaata tatgccaacc actgtacttg gcagttcaca     60

aattctcacc gttacaacaa ccccatgagg tatttattcc cattctatag atagggaaac    120

cacagctcaa gtaagttagg aaactgagcc aagtatacac agaatacgaa gtggcaaaac    180

tagaaggaaa gactgacact gctatctgct ggcctccagt gtcctggctc ttttcacacg    240

ggttcaatgt ctccagcgct gctgctgctg ctgcattacc atgccctcat tgtttttctt    300

cctctggtgt tcaactgcat ccttcaaaga atctaactca ttccagagac cacttatttc    360

tttctctctt tctgaaatta cttttaataa ttcttcatga gggggaaaag aagatgcctg    420

ttggtagttt tgttgtttaa gctgctcaat ttgggactta aacaatttgt tttcatcttg    480

tacatcctgt aacagctgtg ttttgctaga aagatcactc tccctctctt ttagcatggc    540

ttctaacctc ttcaattcat tttccttttc tttcaacaca atctcaagtt cttcaaactg    600

tgatgcagaa gaggcctctt tcaagttatg ttgtgctact tcctgaacat gtgcttttaa    660

agattcattt tcttcttgaa gatcctgtaa ccacttccct gtattggcta ggtctttctc    720

tttctcttcc aaaacagcct tcatggtatt catctgttcc tcttttcctt ttaataagtt    780

caggagcttc agaac                                                     795
```

<210> SEQ ID NO 87
<211> LENGTH: 594
<212> TYPE: DNA
<213> ORGANISM: Homo sapien

<400> SEQUENCE: 87

```
caagcttttt tttttttttt aaaaagtgtt agcattaatg ttttattgtc acgcagatgg     60

caactgggtt tatgtcttca tattttatat ttttgtaaat taaaaaaatt acaagtttta    120

aatagccaat ggctggttat attttcagaa aacatgatta gactaattca ttaatggtgg    180

cttcaagctt ttccttattg gctccagaaa attcacccac cttttgtccc ttcttaaaaa    240

actggaatgt tggcatgcat ttgacttcac actctgaagc aacatcctga cagtcatcca    300

catctacttc aaggaatatc acgttggaat acttttcaga gagggaatga aagaaaggct    360

tgatcatttt gcaaggccca caccacgtgg ctgagaagtc aactactaca agtttatcac    420

ctgcagcgtc caaggcttcc tgaaaagcag tcttgctctc gatctgcttc accatcttgg    480

ctgctggagt ctgacgagcg gctgtaagga ccgatggaaa tggatccaaa gcaccaaaca    540

gagcttcaag actcgctgct tggcttgaat tcggatccga tatcgccatg gcct          594
```

<210> SEQ ID NO 88
<211> LENGTH: 557
<212> TYPE: DNA
<213> ORGANISM: Homo sapien

<400> SEQUENCE: 88

```
aagtgttagc attaatgttt tattgtcacg cagatggcaa ctgggtttat gtcttcatat     60

tttatatttt tgtaaattaa aaaaattmca agttttaaat agccaatggc tggttatatt    120

ttcagaaaac atgattagac taattcatta atggtggctt caagcttttc cttattggct    180

ccagaaaatt cacccacctt ttgtcccttc ttaaaaaact ggaatgttgg catgcatttg    240

acttcacact ctgaagcaac atcctgacag tcatccacat ctacttcaag gaatatcacg    300

ttggaatact tttcagagag ggaatgaaag aaaggcttga tcattttgca aggcccacac    360

cacgtggctg agaagtcaac tactacaagt ttatcacctg cagcgtccaa ggcttcctga    420
```

-continued

```
aaagcagtct tgctctcgat ctgcttcacc atcttggctg ctggagtctg acgagcggct    480

gtaaggaccg atggaaatgg atccaaagca ccaaacagag cttcaagact cgctgcttgg    540

catgaattcg gatccga                                                   557


<210> SEQ ID NO 89
<211> LENGTH: 561
<212> TYPE: DNA
<213> ORGANISM: Homo sapien
<220> FEATURE:
<221> NAME/KEY: misc_feature
<222> LOCATION: (1)...(561)
<223> OTHER INFORMATION: n = A,T,C or G

<400> SEQUENCE: 89

tacaaacttt attgaaacgc acacgcgcac acacacaaac acccctgtgg atagggaaaa     60

gcacctggcc acagggtcca ctgaaacggg gaggggatgg cagcttgtaa tgtggctttt    120

gccacaaccc ccttctgaca gggaaggcct tagattgagg ccccacctcc catggtgatg    180

gggagctcag aatggggtcc agggagaatt tggttagggg gaggtgctag ggaggcatga    240

gcagagggca ccctccgagt ggggtcccga gggctgcaga gtcttcagta ctgtccctca    300

cagcagctgt ctcaaggctg ggtccctcaa aggggcgtcc cagcgcgggg cctccctgcg    360

caaacacttg gtacccctgg ctgcgcagcg gaagccagca ggacagcagt ggcgccgatc    420

agcacaacag acgccctggc ggtagggaca gcaggcccag ccctgtcggt tgtctcggca    480

gcaggtctgg ttatcatggc agaagtgtcc ttcccacact tcacgtcctt cacacccacg    540

tganggctac nggccaggaa g                                              561


<210> SEQ ID NO 90
<211> LENGTH: 561
<212> TYPE: DNA
<213> ORGANISM: Homo sapien

<400> SEQUENCE: 90

cccgtgggtg ccatccacgg agttgttacc tgatctttgg aagcaggatc gcccgtctgc     60

actgcagtgg aagccccgtg ggcagcagtg atggccatcc ccgcatgcca cggcctctgg    120

gaaggggcag caactggaag tccctgagac ggtaaagatg caggagtggc cggcagagca    180

gtgggcatca acctggcagg ggccacccag atgcctgctc agtgttgtgg gccatttgtc    240

cagaagggga cggcagcagc tgtagctggc tcctccgggg tccaggcagc aggccacagg    300

gcagaactga ccatctgggc accgcgttcc agccaccagc cctgctgtta aggccaccca    360

gctcaccagg gtccacatgg tctgcctgcg tccgactccg cggtccttgg gccctgatgg    420

ttctacctgc tgtgagctgc ccagtgggaa gtatggctgc tgccaatgcc caacgccacc    480

tgctgctccg atcacctgca ctgctgcccc aagacactgt gtgtgacctg atccagagta    540

agtgcctctc caaggagaac g                                              561


<210> SEQ ID NO 91
<211> LENGTH: 541
<212> TYPE: DNA
<213> ORGANISM: Homo sapien
<220> FEATURE:
<221> NAME/KEY: misc_feature
<222> LOCATION: (1)...(541)
<223> OTHER INFORMATION: n = A,T,C or G

<400> SEQUENCE: 91

gaatcacctt tctggtttag ctagtacttt gtacagaaca atgaggtttc ccacagcgga     60
```

-continued gtctccctgg gctctgtttg gctctcggta aggcaggcct acaccttttc ctctcctcta 120
tggagagggg aatatgcatt aaggtgaaaa gtcaccttcc aaaagtgaga aagggattcg 180
attgctgctt caggactgtg gaattatttg gaatgtttta caaatggttg ctacaaaaca 240
acaaaaaagg taattacaaa atgtgtacat cacaacatgc tttttaaaga cattatgcat 300
tgtgctcaca ttcccttaaa tgttgtttcc aaaggtgctc agcctctagc ccagctggat 360
tctccgggaa gaggcagaga cagtttggcg aaaaagacac agggaaggag ggggtggtga 420
aaggagaaag cagccttcca gttaaagatc agccctcagt taaaggtcag cttcccgcan 480
gctggcctca ngcggagtct gggtcagagg gaggagcagc agcagggtgg gactggggcg 540
t 541

<210> SEQ ID NO 92
<211> LENGTH: 551
<212> TYPE: DNA
<213> ORGANISM: Homo sapien

<400> SEQUENCE: 92
aaccggagcg cgagcagtag ctgggtgggc accatggctg ggatcaccac catcgaggcg 60
gtgaagcgca agatccaggt tctgcagcag caggcagatg atgcagagga gcgagctgag 120
cgcctccagc gagaagttga gggagaaagg cgggcccggg aacaggctga ggctgaggtg 180
gcctccttga accgtaggat ccagctggtt gaagaagagc tggaccgtgc tcaggagcgc 240
ctggccactg ccctgcaaaa gctggaagaa gctgaaaaag ctgctgatga gagtgagaga 300
ggtatgaagg ttattgaaaa ccgggcctta aaagatgaag aaaagatgga actccaggaa 360
atccaactca aagaagctaa gcacattgca gaagaggcag ataggaagta tgaagaggtg 420
gctcgtaagt tggtgatcat tgaaggagac ttggaacgca cagaggaacg agctgagctg 480
gcagagtccc gttgccgaga gatggatgag cagattagac tgatggacca gaacctgaag 540
tgtctgagtg c 551

<210> SEQ ID NO 93
<211> LENGTH: 531
<212> TYPE: DNA
<213> ORGANISM: Homo sapien

<400> SEQUENCE: 93
gagaacttgg cctttattgt gggcccagga gggcacaaag gtcaggaggc ccaagggagg 60
gatctggttt tctggatagc caggtcatag catgggtatc agtaggaatc cgctgtagct 120
gcacaggcct cacttgctgc agttccgggg agaacacctg cactgcatgg cgttgatgac 180
ctcgtggtac acgacagagc cattggtgca gtgcaagggc acgcgcatgg gctccgtcct 240
cgagggcagg cagcaggagc attgctcctg cacatcctcg atgtcaatgg agtacacagc 300
tttgctggca cactttccct ggcagtaatg aatgtccact tcctcttggg acttacaatc 360
tcccactttg atgtactgca ccttggctgt gatgtctttg caatcaggct cctcacatgt 420
gtcacagcag gtgcctggaa ttttcacgat tttgcctcct tcagccagac acttgtgttc 480
atcaaatggt gggcagcccg tgaccctctt ctcccagatg tactctcctc t 531

<210> SEQ ID NO 94
<211> LENGTH: 531
<212> TYPE: DNA
<213> ORGANISM: Homo sapien
<220> FEATURE:

-continued

<221> NAME/KEY: misc_feature
<222> LOCATION: (1)...(531)
<223> OTHER INFORMATION: n = A,T,C or G

<400> SEQUENCE: 94
gcctggacct tgccggatca gtgccacaca gtgacttgct tggcaaatgg ccagaccttg 60
ctgcagagtc atcgtgtcaa ttgtgaccat ggaccccggc cttcatgtgc caacagccag 120
tctcctgttc gggtggagga gacgtgtggc tgccgctgga cctgcccttg tgtgtgcacg 180
ggcagttcca ctcggcacat cgtcaccttc gatgggcaga atttcaagct tactggtagc 240
tgctcctatg tcatctttca aaacaaggag caggacctgg aagtgctcct ccacaatggg 300
gcctgcagcc ccggggcaaa acaagcctgc atgaagtcca ttgagattaa gcatgctggc 360
gtctctgctg agctgcacag taacatggag atggcagtgg atgggagact ggtccttgcc 420
ccgtacgttg gtgaaaacat ggaagtcagc atctacggcg ctatcatgta tgaagtcagg 480
tttacccatc ttggccacat cctcacatac accgccncaa aacaacgagt t 531

<210> SEQ ID NO 95
<211> LENGTH: 605
<212> TYPE: DNA
<213> ORGANISM: Homo sapien

<400> SEQUENCE: 95
agatcaacct ctgctggtca ggaggaatgc cttccttgtc ttggatcttt gctttgacgt 60
tctcgatagt rwcaactkkr ytsramskma agkgyratgr wmttksywgw rasyktmwwm 120
rsgraraytt agacayccm cctcwgagac gsagkaccar gtgcagaggt ggactctttc 180
tggatgttgt agtcagacag ggtgcgtcca tcttccagct gtttcccagc aaagatcaac 240
ctctgctgat caggagggat gccttcctta tcttggatct ttgccttgac attctcgatg 300
gtgtcactgg gctccacctc gagggtgatg gtcttaccag tcagggtctt cacgaagaty 360
tgcatcccac ctctgagacg gagcaccagg tgcagggtrg actctttctg gatgttgtag 420
tcagacaggg tgcgyccatc ttccagctgc tttccsagca aagatcaacc tctgctggtc 480
aggaggratg ccttccttgt cytggatctt tgcyttgacr ttctcratgg tgtcactcgg 540
ctccacttcg agagtgatgg tcttaccagt cagggtcttc acgaagatct gcatcccacc 600
tctaa 605

<210> SEQ ID NO 96
<211> LENGTH: 531
<212> TYPE: DNA
<213> ORGANISM: Homo sapien

<400> SEQUENCE: 96
aagtcacaaa cagacaaaga ttattaccag ctgcaagcta tattagaagc tgaacgaaga 60
gacagaggtc atgattctga gatgattgga gaccttcaag ctcgaattac atctttacaa 120
gaggaggtga agcatctcaa acataatctc gaaaaagtgg aaggagaaag aaaagaggct 180
caagacatgc ttaatcactc agaaaaggaa aagaataatt tagagataga tttaaactac 240
aaacttaaat cattacaaca acggttagaa caagaggtaa atgaacacaa agtaaccaaa 300
gctcgtttaa ctgacaaaca tcaatctatt gaagaggcaa agtctgtggc aatgtgtgag 360
atggaaaaaa agctgaaaga agaaagagaa gctcgagaga aggctgaaaa tcgggttgtt 420
cagattgaga aacagtgttc catgctagac gttgatctga agcaatctca gcagaaacta 480
gaacatttga ctggaaataa agaaaggatg gaggatgaag ttaagaatct a 531

-continued

<210> SEQ ID NO 97
<211> LENGTH: 1017
<212> TYPE: DNA
<213> ORGANISM: Homo sapien
<220> FEATURE:
<221> NAME/KEY: misc_feature
<222> LOCATION: (1)...(1017)
<223> OTHER INFORMATION: n = A,T,C or G

<400> SEQUENCE: 97
cgcctccacc atgtccatca gggtgaccca gaagtcctac aaggtgtcca cctctggccc 60
ccgggccttc agcagccgct cctacacgag tgggcccggt tcccgcatca gctcctcgag 120
cttctcccga gtgggcagca gcaactttcg cggtggcctg ggcggcggct atggtggggc 180
cagcggcatg ggaggcatca ccgcagttac ggtcaaccag agcctgctga gccccttgt 240 cctggaggtg gaccccaaca tccaggccgt gcgcacccag gagaaggagc agatcaagac 300
cctcaacaac aagtttgcct ccttcataga caaggtacgg ttcctggagc agcagaacaa 360
gatgctggag accaagtgga gcctcctgca gcagcagaag acggctcgaa gcaacatgga 420
caacatgttc gagagctaca tcaacarcct taggcggcag ctggagactc tgggccagga 480
gaagctgaag ctggaggcgg agcttggcaa catgcagggg ctggtggagg acttcaagaa 540
caagtatgag gatgagatca ataagcgtac agagatggag aacgaatttg tcctcatcaa 600
gaaggatgtg gatgaagctt acatgaacaa ggtagagctg gagtctcgcc tggaagggct 660
gaccgacgag atcaacttcc tcaggcagct gtatgaagag gagatccggg agctgcagtc 720
ccagatctcg gacacatctg tggtgctgtc catggacaac agccgctccc tggacatgga 780
cagcatcatt gctgaggtca aggcacagta cgaggatatt gccaaccgca gccgggctga 840
ggctgagagc atgtaccagg tcaagtatga ggagctgcag agcctggctg ggaagcacgg 900
ggatgacctg cggcgcacaa agactgagat ctctgagatg aacccggaac atcagcccgg 960
ctncaggctg agattgaggg cctcaaaggc caganggctt ncctggangn ccgccat 1017

<210> SEQ ID NO 98
<211> LENGTH: 561
<212> TYPE: DNA
<213> ORGANISM: Homo sapien

<400> SEQUENCE: 98
cccggagcca gccaacgagc ggaaaatggc agacaatttt tcgctccatg atgcgttatc 60
tgggtctgga aacccaaacc ctcaaggatg gcctggcgca tgggggaacc agcctgctgg 120
ggcagggggc tacccagggg cttcctatcc tggggcctac cccgggcagg cacccccagg 180
ggcttatcct ggacaggcac ctccaggcgc ctaccctgga gcacctggag cttatcccgg 240
agcacctgca cctggagtct acccagggcc acccagcggc cctggggcct acccatcttc 300
tggacagcca agtgccaccg gagcctaccc tgccactggc ccctatggcg cccctgctgg 360
gccactgatt gtgccttata acctgccttt gcctgggga gtggtgcctc gcatgctgat 420
aacaattctg ggcacggtga agcccaatgc aaacagaatt gctttagatt tccaaagagg 480
gaatgatgtt gccttccact ttaacccacg cttcaatgag aacaacagga gagtcattgg 540
ttgcaataca aagctggata a 561

<210> SEQ ID NO 99
<211> LENGTH: 636
<212> TYPE: DNA

-continued

<213> ORGANISM: Homo sapien

<400> SEQUENCE: 99
gggaatgcaa caactttatt gaaaggaaag tgcaatgaaa tttgttgaaa ccttaaaagg 60
ggaaacttag acaccccccc tcragcgmag kaccargtgc araggtggac tctttctgga 120
tgttgtagtc agacagggtr cgwccatctt ccagctgttt yccrgcaaag atcaacctct 180
gctgatcagg aggratgcct tccttatctt ggatctttgc cttgacattc tcgatggtgt 240
cactgggctc cacctcgagg gtgatggtct taccagtcag ggtcttcacg aagatytgca 300
tcccacctct gagacggagc accaggtgca gggtrgactc tttctggatg ttgtagtcag 360
acagggtgcg yccatcttcc agctgctttc csagcaaaga tcaacctctg ctggtcagga 420
ggratgcctt ccttgtcytg gatctttgcy ttgacrttct caatggtgtc actcggctcc 480
acttcgagag tgatggtctt accagtcagg gtcttcacga agatctgcat cccacctcta 540
agacggagca ccaggtgcag ggtggactct ttctggatgg ttgtagtcag acagggtgcg 600
tccatcttcc agctgtttcc cagcaaagat caacct 636

<210> SEQ ID NO 100
<211> LENGTH: 697
<212> TYPE: DNA
<213> ORGANISM: Homo sapien

<400> SEQUENCE: 100
aggttgatct ttgctgggaa acagctggaa gatggacgca ccctgtctga ctacaaccat 60
ccagaaagag tccaccctgc acctggtgct ccgtcttaga ggtgggatgc agatcttcgt 120
gaagaccctg actggtaaga ccatcactct cgaagtggag ccgagtgaca ccattgagaa 180
ygtcaargca aagatccarg acaaggaagg catyccctcct gaccagcaga ggttgatctt 240
tgctsggaaa gcagctggaa gatggrcgca ccctgtctga ctacaacatc cagaaagagt 300
cyaccctgca cctggtgctc cgtctcagag gtgggatgca ratcttcgtg aagaccctga 360
ctggtaagac catcaccctc gaggtggagc ccagtgacac catcgagaat gtcaaggcaa 420
agatccaaga taaggaaggc atccctcctg atcagcagag gttgatcttt gctgggaaac 480
agctggaaga tggacgcacc ctgtctgact acaacatcca gaaagagtcc acctytgcac 540
ytggtmctbc gtctyagagg kgggrtgcaa atctwmgtkw agacactcac tkkyaagryy 600
atcamcmwtg akktcgakys castkwcact wtcrakaamg tyrwwgcawa gatccmagac 660
aaggaaggca ttcctcctga ccagcagagg ttgatct 697

<210> SEQ ID NO 101
<211> LENGTH: 451
<212> TYPE: DNA
<213> ORGANISM: Homo sapien

<400> SEQUENCE: 101
atggagtctc actctgtcga ccaggctgga gcgctgtggt gcgatatcgg ctcactgcag 60
tctccacttc ctgggttcaa gcgatcctcc tgcctcagcc tcccgagtag ctgggactac 120
aggcaggcgt caccataatt tttgtatttt tagtagagac atggtttcgc catgttggct 180
gggctggtct cgaactcctg acctcaagtg atctgtcctg gcctcccaaa gtgttgggat 240
tacaggcgaa agccaacgct cccggccagg gaacaacttt agaatgaagg aaatatgcaa 300
aagaacatca catcaaggat caattaatta ccatctatta attactatat gtgggtaatt 360
atgactattt cccaagcatt ctacgttgac tgcttgagaa gatgtttgtc ctgcatggtg 420

-continued

```
gagagtggag aagggccagg attcttaggt t                                451

<210> SEQ ID NO 102
<211> LENGTH: 571
<212> TYPE: DNA
<213> ORGANISM: Homo sapien

<400> SEQUENCE: 102

agcgcggtct tccggcgcga gaaagctgaa ggtgatgtgg ccgccctcaa ccgacgcatc   60

cagctcgttg aggaggagtt ggacagggct caggaacgac tggccacggc cctgcagaag  120

ctggaggagg cagaaaaagc tgcagatgag agtgagagag gaatgaaggt gatagaaaac  180

cgggccatga aggatgagga gaagatggag attcaggaga tgcagctcaa agaggccaag  240

cacattgcgg aagaggctga ccgcaaatac gaggaggtag ctcgtaagct ggtcatcctg  300

gagggtgagc tggagagggc agaggagcgt gcggaggtgt ctgaactaaa atgtggtgac  360

ctggaagaag aactcaagaa tgttactaac aatctgaaat ctctggaggc tgcatctgaa  420

aagtattctg aaaaggagga caaatatgaa gaagaaatta aacttctgtc tgacaaactg  480

aaagaggctg agacccgtgc tgaatttgca gagagaacgg ttgcaaaact ggaaaagaca  540

attgatgacc tggaagagaa acttgcccag c                                571

<210> SEQ ID NO 103
<211> LENGTH: 451
<212> TYPE: DNA
<213> ORGANISM: Homo sapien

<400> SEQUENCE: 103

gtgcacaggt cccatttatt gtagaaaata ataataatta cagtgatgaa tagctcttct   60

taaattacaa aacagaaacc acaaagaagg aagaggaaaa accccaggac ttccaagggt  120

gaagctgtcc cctcctccct gccaccctcc caggctcatt agtgtccttg gaaggggcag  180

aggactcaga ggggatcagt ctccaggggc cctgggctga agcgggtgag gcagagagtc  240

ctgaggccac agagctgggc aacctgagcc gcctctctgg ccccctcccc caccactgcc  300

caaacctgtt tacagcacct tcgcccctcc cctctaaacc cgtccatcca ctctgcactt  360

cccaggcagg tgggtgggcc aggcctcagc catactcctg ggcgcgggtt tcggtgagca  420

aggcacagtc ccagaggtga tatcaaggcc t                                451

<210> SEQ ID NO 104
<211> LENGTH: 441
<212> TYPE: DNA
<213> ORGANISM: Homo sapien

<400> SEQUENCE: 104

gcaaggaact ggtctgctca cacttgctgg cttgcgcatc aggactggct ttatctcctg   60

actcacggtg caaaggtgca ctctgcgaac gttaagtccg tccccagcgc ttggaatcct  120

acggccccca cagccggatc ccctcagcct tccaggtcct caactcccgt ggacgctgaa  180

caatggcctc catggggcta caggtaatgg gcatcgcgct ggccgtcctg ggctggctgg  240

ccgtcatgct gtgctgcgcg ctgcccatgt ggcgcgtgac ggccttcatc ggcagcaaca  300

ttgtcacctc gcagaccatc tgggagggcc tatggatgaa ctgcgtggtg cagagcaccg  360

gccagatgca gtgcaaggtg tacgactcgc tgctggcact gccgcaggac ctgcaggcgg  420

cccgcgccct cgtcatcatc a                                           441
```

-continued

<210> SEQ ID NO 105
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 105
tgcaaaaggg acacaggggt tcaaaaataa aaatttctct tccccctccc caaacctgta 60
ccccagctcc ccgaccacaa cccccttcct cccccgggga aagcaagaag gagcaggtgt 120
ggcatctgca gctgggaaga gagaggccgg ggaggtgccg agctcggtgc tggtctcttt 180
ccaaatataa atacntgtgt cagaactgga aaatcctcca gcacccacca cccaagcact 240
ctccgttttc tgccggtgtt tggagagggg cggggggcag gggcgccagg caccggctgg 300
ctgcggtcta ctgcatccgc tgggtgtgca ccccgcgagc ctcctgctgc tcattgtaga 360
agagatgaca ctcggggtcc ccccggatgg tgggggctcc ctggatcagc ttcccggtgt 420
tggggttcac acaccagcac tccccacgct gcccgttcag agacatcttg cactgtttga 480
ggttgtacag gccatgcttg tcacagttg 509

<210> SEQ ID NO 106
<211> LENGTH: 571
<212> TYPE: DNA
<213> ORGANISM: Homo sapien

<400> SEQUENCE: 106
gggttggagg gactggttct ttatttcaaa aagacacttg tcaatattca gtatcaaaac 60
agttgcacta ttgatttctc tttctcccaa tcggccccaa agagaccaca taaaaggaga 120
gtacatttta agccaataag ctgcaggatg tacacctaac agacctccta gaaaccttac 180
cagaaaatgg ggactgggta gggaaggaaa cttaaaagat caacaaactg ccagcccacg 240
gactgcagag gctgtcacag ccagatgggg tggccagggt gccacaaacc caaagcaaag 300
tttcaaaata atataaaatt taaaaagttt tgtacataag ctattcaaga tttctccagc 360
actgactgat acaaagcaca attgagatgg cacttctaga gacagcagct tcaaacccag 420
aaaagggtga tgagatgagt ttcacatggc taaatcagtg gcaaaaacac agtcttcttt 480
ctttctttct ttcaaggagg caggaaagca attaagtggt cacctcaaca taagggggac 540
atgatccatt ctgtaagcag ttgtgaaggg g 571

<210> SEQ ID NO 107
<211> LENGTH: 555
<212> TYPE: DNA
<213> ORGANISM: Homo sapien

<400> SEQUENCE: 107
caggaaccgg agcgcgagca gtagctgggt gggcaccatg gctgggatca ccaccatcga 60
ggcggtgaag cgcaagatcc aggttctgca gcagcaggca gatgatgcag aggagcgagc 120
tgagcgcctc cagcgagaag ttgagggaga aaggcgggcc cgggaacagg ctgaggctga 180
ggtggcctcc ttgaaccgta ggatccagct ggttgaagaa gagctggacc gtgctcagga 240
gcgcctggcc actgccctgc aaaagctgga agaagctgaa aaagctgctg atgagagtga 300
gagaggtatg aaggttattg aaaaccgggc cttaaaagat gaagaaaaga tggaactcca 360
ggaaatccaa ctcaaagaag ctaagcacat tgcagaagag gcagatagga agtatgaaga 420

-continued

```
ggtggctcgt aagttggtga tcattgaagg agacttggaa cgcacagagg aacgagctga    480

gctggcagag tcccgttgcc gagagatgga tgagcagatt agactgatgg accagaacct    540

gaagtgtctg agtgc                                                     555
```

<210> SEQ ID NO 108
<211> LENGTH: 541
<212> TYPE: DNA
<213> ORGANISM: Homo sapien

<400> SEQUENCE: 108

```
atctacgtca tcaatcaggc tggagacacc atgttcaatc gagctaagct gctcaatatt     60

ggctttcaag aggccttgaa ggactatgat tacaactgct ttgtgttcag tgatgtggac    120

ctcattccga tggacgaccg taatgcctac aggtgttttt cgcagccacg gcacatttct    180

gttgcaatgg acaagttcgg gtttagcctg ccatatgttc agtattttgg aggtgtctct    240

gctctcagta aacaacagtt tcttgccatc aatggattcc ctaataatta ttggggttgg    300

ggaggagaag atgacgacat ttttaacaga ttagttcata aaggcatgtc tatatcacgt    360

ccaaatgctg tagtagggag gtgtcgaatg atccggcatt caagagacaa gaaaaatgag    420

cccaatcctc agaggtttga ccggatcgca catacaaagg aaacgatgcg cttcgatggt    480

ttgaactcac ttacctacaa ggtgttggat gtcagagata cccgttatat acccaaatca    540

c                                                                    541
```

<210> SEQ ID NO 109
<211> LENGTH: 411
<212> TYPE: DNA
<213> ORGANISM: Homo sapien

<400> SEQUENCE: 109

```
ctagacctct aattaaaagg cacaatcatg ctggagaatg aacagtctga ccccgagggc     60

cacagcgaat tttagggaag gaggcaaaga ggtgagaagg gaaaggaaag aaggaaggaa    120

ggagaacaat aagaactgga gacgttgggt gggtcaggga gtgtggtgga ggctcggaga    180

gatggtaaac aaacctgact gctatgagtt ttcaacccca tagtctaggg ccatgagggc    240

gtcagttctt ggtggctgag ggtccttcca cccagcccac ctgggggagt ggagtgggga    300

gttctgccag gtaagcagat gttgtctccc aagttcctga cccagatgtc tggcaggata    360

acgctgacct gttccctcaa caagggacct gaaagtaatt ttgctcttta c             411
```

<210> SEQ ID NO 110
<211> LENGTH: 451
<212> TYPE: DNA
<213> ORGANISM: Homo sapien

<400> SEQUENCE: 110

```
ccgaattcaa gcgtcaacga tccytccctt accatcaaat caattggcca ccaatggtac     60

tgaacctacg agtacaccga ctacgggcgg actaatcttc aactcctaca tacttccccc    120

attattccta gaaccaggcg acctgcgact ccttgacgtt gacaatcgag tagtactccc    180

gattgaagcc cccattcgta taataattac atcacaagac gtcttgcact catgagctgt    240

ccccacatta ggcttaaaaa cagatgcaat tcccggacgt ctaagccaaa ccactttcac    300

cgctacacga ccgggggtat actacggtca atgctctgaa atctgtggag caaaccacag    360

tttcatgccc atcgtcctag aattaattcc cctaaaaatc tttgaaatag ggcccgtatt    420
```

-continued taccctatag cacccccctct accccctcta g 451

<210> SEQ ID NO 111
<211> LENGTH: 541
<212> TYPE: DNA
<213> ORGANISM: Homo sapien

<400> SEQUENCE: 111
gctcttcaca cttttattgt taattctctt cacatggcag atacagagct gtcgtcttga 60
agaccaccac tgaccaggaa atgccacttt tacaaaatca tccccccttt tcatgattgg 120
aacagttttc ctgaccgtct gggagcgttg aagggtgacc agcacatttg cacatgcaaa 180
aaaggagtga ccccaaggcc tcaaccacac ttcccagagc tcaccatggg ctgcaggtga 240
cttgccaggt ttggggttcg tgagctttcc ttgctgctgc ggtggggagg ccctcaagaa 300
ctgagaggcc ggggtatgct tcatgagtgt taacatttac gggacaaaag cgcatcatta 360
ggataaggaa cagccacagc acttcatgct tgtgagggtt agctgtagga gcgggtgaaa 420
ggattccagt ttatgaaaat ttaaagcaaa caacggtttt tagctgggtg ggaaacagga 480
aaactgtgat gtcggccaat gaccaccatt tttctgccca tgtgaaggtc cccatgaaac 540
c 541

<210> SEQ ID NO 112
<211> LENGTH: 521
<212> TYPE: DNA
<213> ORGANISM: Homo sapien

<400> SEQUENCE: 112
caagcgcttg gcgtttggac ccagttcagt gaggttcttg ggttttgtgc ctttggggat 60
tttggtttga cccaggggtc agccttagga aggtcttcag gaggaggccg agttcccctt 120
cagtaccacc cctctctccc cactttccct ctcccggcaa catctctggg aatcaacagc 180
atattgacac gttggagccg agcctgaaca tgcccctcgg ccccagcaca tggaaaaccc 240
ccttccttgc ctaaggtgtc tgagtttctg gctcttgagg catttccaga cttgaaattc 300
tcatcagtcc attgctcttg agtctttgca gagaacctca gatcaggtgc acctgggaga 360
aagactttgt ccccacttac agatctatct cctcccttgg gaagggcagg gaatggggac 420
ggtgtatgga ggggaaggga tctcctgcgc ccttcattgc cacacttggt gggaccatga 480
acatctttag tgtctgagct tctcaaatta ctgcaatagg a 521

<210> SEQ ID NO 113
<211> LENGTH: 568
<212> TYPE: DNA
<213> ORGANISM: Homo sapien

<400> SEQUENCE: 113
agcgtcaaat cagaatggaa aagactcaaa accatcatca acaccaagat caaaaggaca 60
agratccttc aagaaacagg aaaaaactcc taaaacacca aaaggaccta gttctgtaga 120
agacattaaa gcaaaaatgc aagcaagtat agaaaaaggt ggttctcttc ccaaagtgga 180
agccaaattc atcaattatg tgaagaattg cttccggatg actgaccaag aggctattca 240
agatctctgg cagtggagga agtctcttta agaaaatagt ttaaacaatt tgttaaaaaa 300
ttttccgtct tatttcattt ctgtaacagt tgatatctgg ctgtcctttt tataatgcag 360
agtgagaact ttccctaccg tgtttgataa atgttgtcca ggttctattg ccaagaatgt 420
gttgtccaaa atgcctgttt agtttttaaa gatggaactc caccctttgc ttggttttaa 480

-continued gtatgtatgg aatgttatga taggacatag tagtagcggt ggtcagacat ggaaatggtg 540
ggsmgacaaa aatatacatg tgaaataa 568

<210> SEQ ID NO 114
<211> LENGTH: 483
<212> TYPE: DNA
<213> ORGANISM: Homo sapien

<400> SEQUENCE: 114
tccgaattcc aagcgaatta tggacaaacg attcctttta gaggattact tttttcaatt 60
tcggttttag taatctaggc tttgcctgta aagaatacaa cgatggattt taaatactgt 120
ttgtggaatg tgtttaaagg attgattcta gaacctttgt atatttgata gtatttctaa 180
ctttcatttc tttactgttt gcagttaatg ttcatgttct gctatgcaat cgtttatatg 240
cacgtttctt taattttttt agattttcct ggatgtatag tttaaacaac aaaaagtcta 300
tttaaaactg tagcagtagt ttacagttct agcaaagagg aaagttgtgg ggttaaactt 360
tgtattttct ttcttataga ggcttctaaa aaggtatttt tatatgttct ttttaacaaa 420
tattgtgtac aacctttaaa acatcaatgt ttggatcaaa acaagaccca gcttattttc 480
tgc 483

<210> SEQ ID NO 115
<211> LENGTH: 521
<212> TYPE: DNA
<213> ORGANISM: Homo sapien

<400> SEQUENCE: 115
tgtggtggcg cgggctgagg tggaggccca ggactctgac cctgcccctg ccttcagcaa 60
ggcccccggc agcgccggcc actacgaact gccgtgggtt gaaaaatata ggccagtaaa 120
gctgaatgaa attgtcggga atgaagacac cgtgagcagg ctagaggtct ttgcaaggga 180
aggaaatgtg cccaacatca tcattgcggg ccctccagga accggcaaga ccacaagcat 240
tctgtgcttg gcccgggccc tgctgggccc agcactcaaa gatgccatgt tggaactcaa 300
tgcttcaaat gacaggggca ttgacgttgt gaggaataaa attaaaatgt ttgctcaaca 360
aaaagtcact cttcccaaag gccgacataa gatcatcatt ctggatgaag cagacagcat 420
gaccgacgga gcccagcaag ccttgaggag aaccatggaa atctactcta aaaccactcg 480
ttcgcccttg cttgtaatgc ttcggataag atcatcgagc c 521

<210> SEQ ID NO 116
<211> LENGTH: 501
<212> TYPE: DNA
<213> ORGANISM: Homo sapien

<400> SEQUENCE: 116
ctttgcaaag cttttatttc atgtctgcgg catggaatcc acctgcacat ggcatcttag 60
ctgtgaagga gaaagcagtg cacgagaagg aatgagtggg cggaaccaac ggcctccaca 120
agctgccttc cagcagcctg ccaaggccat ggcagagaga gactgcaaac aaacacaagc 180
aaacagagtc tcttcacagc tggagtctga aagctcatag tggcatgtgt gaatctgaca 240
aaattaaaag tgtgcatagt ccattacatg cataaaacac taataataat cctgtttaca 300
cgtgactgca gcaggcaggt ccagctccac cactgccctc ctgccacatc acatcaagtg 360
ccatggttta gagggttttt catatgtaat tcttttattc tgtaaaaggt aacaaaatat 420

-continued

```
acagaacaaa actttccctt tttaaaacta atgttacaaa tctgtattat cacttggata    480

taaatagtat ataagctgat c                                              501


<210> SEQ ID NO 117
<211> LENGTH: 451
<212> TYPE: DNA
<213> ORGANISM: Homo sapien
<220> FEATURE:
<221> NAME/KEY: misc_feature
<222> LOCATION: (1)...(451)
<223> OTHER INFORMATION: n = A,T,C or G

<400> SEQUENCE: 117

caagggatat atgttgaggg tacrgrgtga cactgaacag atcacaaagc acgagaaaca     60

ttagttctct ccctccccag cgtctccttc gtctccctgg ttttccgatg tccacagagt    120

gagattgtcc ctaagtaact gcatgatcag agtgctgkct ttataagact cttcattcag    180

cgtatccaat tcagcaattg cttcatcaaa tgccgttttt gccaggctac aggccttttc    240

aggagagttt agaatctcat agtaaaagac tgagaaattt agtgccagac caagacgaat    300

tgggtgtgta ggctgcattn ctttcttact aatttcaaat gcttcctggt aagcctgctg    360

ggagttcgac acaagtggtt tgtttgttgc tccagatgcc acttcagaaa gatacctaaa    420

ataatctcct ttcattttca aagtagaaca c                                   451


<210> SEQ ID NO 118
<211> LENGTH: 501
<212> TYPE: DNA
<213> ORGANISM: Homo sapien

<400> SEQUENCE: 118

tccggagccg gggtagtcgc cgccgccgcc gccggtgcag ccactgcagg caccgctgcc     60

gccgcctgag tagtgggctt aggaaggaag aggtcatctc gctcggagct tcgctcggaa    120

gggtctttgt tccctgcagc cctcccacgg gaatgacaat ggataaaagt gagctggtac    180

agaaagccaa actcgctgag caggctgagc gatatgatga tatggctgca gccatgaagg    240

cagtcacaga acaggggcat gaactctcca acgaagagag aaatctgctc tctgttgcct    300

acaagaatgt ggtaaggccg cccgccgctc ttcctggcgt gtcatctcca gcattgagca    360

gaaaacagag aggaatgaga agaagcagca gatgggcaaa gagtaccgtg agaagataga    420

ggcagaactg caggacatct gcaatgatgt tctggagctt gttggacaaa tatcttattc    480

caatgctaca caacccagaa a                                              501


<210> SEQ ID NO 119
<211> LENGTH: 391
<212> TYPE: DNA
<213> ORGANISM: Homo sapien

<400> SEQUENCE: 119

aaaaagcagc argttcaaca caaaatagaa atctcaaatg taggatagaa caaaaccaag     60

tgtgtgaggg gggaagcaac agcaaaagga agaaatgaga tgttgcaaaa aagatggagg    120

agggttcccc tctcctctgg ggactgactc aaacactgat gtggcagtat acaccattcc    180

agagtcaggg gtgttcattc ttttttggga gtaagaaaag gtggggatta agaagacgtt    240

tctggaggct tagggaccaa ggctggtctc tttccccccct cccaacccccc ttgatccctt    300

tctctgatca ggggaaagga gctcgaatga gggaggtaga gttggaaagg gaaaggattc    360

cacttgacag aatgggacag actccttccc a                                   391
```

-continued

<210> SEQ ID NO 120
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 120
tggcaatagc acagccatcc aggagctctt cargcgcatc tcggagcagt tcactgccat 60
gttccgccgg aaggccttcc tccactggta cacaggcgag ggcatggacg agatggagtt 120
caccgaggct gagagcaaca tgaacgacct cgtctctgag tatcaagcag taccaggatg 180
ccaccgcaga agaggaggag gatttcggtg aggaggccga agaggaggcc taaggcagag 240
cccccatcac ctcaggcttc tcagttccct tagccgtctt actcaactgc ccctttcctc 300
tccctcagaa tttgtgtttg ctgcctctat cttgtttttt gttttttctt ctggggggt 360 ctagaacagt gcctggcaca tagtaggcgc tcaataaata cttggttgnt gaatgtctcc 420
t 421

<210> SEQ ID NO 121
<211> LENGTH: 206
<212> TYPE: DNA
<213> ORGANISM: Homo sapien

<400> SEQUENCE: 121
agctggcgct agggctcggt tgtgaaatac agcgtrgtca gcccttgcgc tcagtgtaga 60
aacccacgcc tgtaaggtcg gtcttcgtcc atctgctttt ttctgaaata cactaagagc 120
agccacaaaa ctgtaacctc aaggaaacca taaagcttgg agtgccttaa tttttaacca 180
gtttccaata aaacggttta ctacct 206

<210> SEQ ID NO 122
<211> LENGTH: 131
<212> TYPE: DNA
<213> ORGANISM: Homo sapien

<400> SEQUENCE: 122
ggagatgaag atgaggaagc tgagtcagct acgggcargc gggcagctga agatgatgag 60
gatgacgatg tcgataccaa gaagcagaag accgacgagg atgactagac agcaaaaaag 120
gaaaagttaa a 131

<210> SEQ ID NO 123
<211> LENGTH: 231
<212> TYPE: DNA
<213> ORGANISM: Homo sapien
<220> FEATURE:
<221> NAME/KEY: misc_feature
<222> LOCATION: (1)...(231)
<223> OTHER INFORMATION: n = A,T,C or G

<400> SEQUENCE: 123
gatgaaaatt aaatacttaa attaatcaaa aggcactacg ataccaccta aaacctactg 60
cctcagtggc agtakgctaa kgaagatcaa gctacagsac atyatctaat atgaatgtta 120
gcaattacat akcargaagc atgtttgctt tccagaagac tatggnacaa tggtcattwg 180
ggcccaagag gatatttggc cnggaaagga tcaagataga tnaangtaaa g 231

-continued

<210> SEQ ID NO 124
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 124
gagtagcaac gcaaagcgct tggtattgag tctgtgggsg acttcggttc cggtctctgc 60
agcagccgtg atcgcttagt ggagtgctta gggtagttgg ccaggatgcc gaatatcaaa 120
atcttcagca ggcagctccc accaggactt atctcasaaa attgctgacc gcctgggcct 180
ggagctaggc aaggtggtga ctaagaaatt cagcaaccag gagacctgtg tggaaattgg 240
tgaaagtgta ccgtggagag gatgtctaca ttgttcagag tggntgtggc gaaatcaatg 300
acaatttaat ggagcttttg atcatgatta atgcctgcaa gattgcttca gccagccggg 360
ttactgcagt catcccatgc ttcccttatg ccccggcagg ataagaaaga tnagagccgg 420
gccgccaatc tcagccaagc ttggtgcaaa tatgctatct gtagcagtgc agatcatatt 480
atcaccatgg acctacatgc ttctcaaatt canggctttt t 521

<210> SEQ ID NO 125
<211> LENGTH: 341
<212> TYPE: DNA
<213> ORGANISM: Homo sapien
<220> FEATURE:
<221> NAME/KEY: misc_feature
<222> LOCATION: (1)...(341)
<223> OTHER INFORMATION: n = A,T,C or G

<400> SEQUENCE: 125
atgcaaaagg ggacacaggg ggttcaaaaa taaaaatttc tcttccccct ccccaaacct 60
gtaccccagc tccccgacca caaccccctt cctcccccgg ggaaagcaag aaggagcagg 120
tgtggcatct gcagctggga agagagaggc cggggaggtg ccgagctcgg tgctggtctc 180
tttccaaata taaatacgtg tgtcagaact ggaaaatcct ccagcaccca ccacccaagc 240
actctccgtt ttctgccggt gtttggagag gggcggnggg caggggcgcc aggcaccggc 300
tggctgcggt ctactgcatc cgctgggtgt gcaccccgcg a 341

<210> SEQ ID NO 126
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 126
aggttggaga aggtcatgca ggtgcagatt gtccaggskc agccacaggg tcaagcccaa 60
caggcccaga gtggcactgg acagaccatg caggtgatgc agcagatcat cactaacaca 120
ggagagatcc agcagatccc ggtgcagctg aatgccggcc agctgcagta tatccgctta 180
gcccagcctg tatcaggcac tcaagttgtg cagggacaga tccagacact tgccaccaat 240
gctcaacaga ttacacagac agaggtccag caaggacagc agcagttcaa gccagttcac 300
aagatggaca gcagctctac cagatccagc aagtcaccat gcctgcgggc cangacctcg 360
ccagcccatg ttcatccagt caagccaacc agcccttcna cgggcaggcc ccccaggtga 420

```
ccggcgactg aagggcctga gctggcaagg ccaangacac ccaacacaat ttttgccata    480

cagcccccag gcaatgggca cagcctttct tcccagagga c                        521
```

<210> SEQ ID NO 127
<211> LENGTH: 351
<212> TYPE: DNA
<213> ORGANISM: Homo sapien

<400> SEQUENCE: 127

```
tgagatttat tgcatttcat gcagcttgaa gtccatgcaa aggrgactag cacagttttt     60

aatgcattta aaaaataaaa gggaggtggg cagcaaacac acaaagtcct agtttcctgg    120

gtccctggga gaaaagagtg tggcaatgaa tccacccact ctccacaggg aataaatctg    180

tctcttaaat gcaaagaatg tttccatggc ctctggatgc aaatacacag agctctgggg    240

tcagagcaag ggatggggag aggaccacga gtgaaaaagc agctacacac attcacctaa    300

ttccatctga gggcaagaac aacgtggcaa gtcttggggg tagcagctgt t             351
```

<210> SEQ ID NO 128
<211> LENGTH: 521
<212> TYPE: DNA
<213> ORGANISM: Homo sapien

<400> SEQUENCE: 128

```
tccagacatg ctcctgtcct aggcggggag caggaaccag acctgctatg ggaagcagaa     60

agagttaagg gaaggtttcc tttcattcct gttccttctc ttttgctttt gaacagtttt    120

taaatatact aatagctaag tcatttgcca gccaggtccc ggtgaacagt agagaacaag    180

gagcttgcta agaattaatt ttgctgtttt tcaccccatt caaacagagc tgccctgttc    240

cctgatggag ttccattcct gccagggcac ggctgagtaa cacgaagcca ttcaagaaag    300

gcgggtgtga aatcactgcc accccatgga cagacccctc actcttcctt cttagccgca    360

gcgctactta ataaatatat ttatactttg aaattatgat aaccgatttt tcccatgcgg    420

catcctaagg gcacttgcca gctcttatcc ggacagtcaa gcactgttgt tggacaacag    480

ataaaggaaa agaaaaagaa gaaaacaacc gcaacttctg t                        521
```

<210> SEQ ID NO 129
<211> LENGTH: 521
<212> TYPE: DNA
<213> ORGANISM: Homo sapien

<400> SEQUENCE: 129

```
tgagacggac cactggcctg gtccccccctc atktgctgtc gtaggacctg acatgaaacg     60

cagatctagt ggcagagagg aagatgatga ggaacttctg agacgtcggc agcttcaaga    120

agagcaatta atgaagctta actcaggcct gggacagttg atcttgaaag aagagatgga    180

gaaagagagc cgggaaaggt catctctgtt agccagtcgc tacgattctc ccatcaactc    240

agcttcacat attccatcat ctaaaactgc atctctccct ggctatggaa gaaatgggct    300

tcaccggcct gtttctaccg acttcgctca gtataacagc tatggggatg tcagcggggg    360

agtgcgagat taccagacac ttccagatgg ccacatgcct gcaatgagaa tggaccgagg    420

agtgtctatg cccaacatgt tggaaccaaa gatatttcca tatgaaatgc tcatggtgac    480

caacagaggg ccgaaaccaa atctcagaga ggtggacaga a                        521
```

<210> SEQ ID NO 130

-continued

```
<211> LENGTH: 270
<212> TYPE: DNA
<213> ORGANISM: Homo sapien

<400> SEQUENCE: 130

tcactttatt tttcttgtat aaaaacccta tgttgtagcc acagctggag cctgagtccg     60

ctgcacggag actctggtgt gggtcttgac gaggtggtca gtgaactcct gataggggaga    120

cttggtgaat acagtctcct tccagaggtc gggggtcagg tagctgtagg tcttagaaat    180

ggcatcaaag gtggccttgg cgaagttgcc caggtggca gtgcagcccc gggctgaggt     240

gtagcagtca tcgataccag ccatcatgag                                     270


<210> SEQ ID NO 131
<211> LENGTH: 341
<212> TYPE: DNA
<213> ORGANISM: Homo sapien

<400> SEQUENCE: 131

ctggaatata gacccgtgat cgacaaaact ttgaacgagg ctgactgtgc caccgtcccg     60

ccagccattc gctcctactg atgagacaag atgtggtgat gacagaatca gcttttgtaa    120

ttatgtataa tagctcatgc atgtgtccat gtcataactg tcttcatacg cttctgcact    180

ctggggaaga aggagtacat tgaagggaga ttggcaccta gtggctggga gcttgccagg    240

aacccagtgg ccagggagcg tggcacttac ctttgtccct tgcttcattc ttgtgagatg    300

ataaaactgg gcacagctct taaataaaat ataaatgaac a                        341


<210> SEQ ID NO 132
<211> LENGTH: 844
<212> TYPE: DNA
<213> ORGANISM: Homo sapien
<220> FEATURE:
<221> NAME/KEY: misc_feature
<222> LOCATION: (1)...(844)
<223> OTHER INFORMATION: n = A,T,C or G

<400> SEQUENCE: 132

tgaatgggga ggagctgacc caggaaatgg agcttgngga gaccaggcct gcaggggatg     60

gaaccttcca gaagtgggca tctgtggtgg tgcctcttgg gaaggagcag aagtacacat    120

gccatgtgga acatgagggg ctgcctgagc ccctcaccct gagatggggc aaggaggagc    180

ctccttcatc caccaagact aacacagtaa tcattgctgt tccggttgtc cttggagctg    240

tggtcatcct tggagctgtg atggcttttg tgatgaagag gaggagaaac acaggtggaa    300

aaggaggggga ctatgctctg gctccaggct cccagagctc tgatatgtct ctcccagatt    360

gtaaagtgtg aagacagctg cctggtgtgg acttggtgac agacaatgtc ttcacacatc    420

tcctgtgaca tccagagacc tcagttctct ttagtcaagt gtctgatgtt ccctgtgagt    480

ctgcgggctc aaagtgaaga actgtggagc ccagtccacc cctgcacacc aggaccctat    540

ccctgcactg ccctgtgttc ccttccacag ccaaccttgc tgctccagcc aaacattggt    600

ggacatctgc agcctgtcag ctccatgcta ccctgacctt caactcctca cttccacact    660

gagaataata atttgaatgt gggtggctgg agagatggct cagcgctgac tgctcttcca    720

aaggtcctga gttcaaatcc cagcaaccac atggtggctc acaaccatct gtaatgggat    780

ctaataccct cttctgcagt gtctgaagac asctacagtg tacttacata taataataaa    840

taag                                                                 844
```

-continued

<210> SEQ ID NO 133
<211> LENGTH: 601
<212> TYPE: DNA
<213> ORGANISM: Homo sapien

<400> SEQUENCE: 133
ggccgggcgc gcgcgccccc gccacacgca cgccgggcgt gccagtttat aaagggagag 60
agcaagcagc gagtcttgaa gctctgtttg gtgctttgga tccatttcca tcggtcctta 120
cagccgctcg tcagactcca gcagccaaga tggtgaagca gatcgagagc aagactgctt 180
ttcaggaagc cttggacgct gcaggtgata aacttgtagt agttgacttc tcagccacgt 240
ggtgtgggcc ttgcaaaatg atcaagcctt tctttcattc cctctctgaa aagtattcca 300
acgtgatatt ccttgaagta gatgtggatg actgtcagga tgttgcttca gagtgtgaag 360
tcaaatgcat gccaacattc cagtttttta agaagggaca aaaggtgggt gaattttctg 420
gagccaataa ggaaaagctt gaagccacca ttaatgaatt agtctaatca tgttttctga 480
aaatataacc agccattggc tatttaaaac ttgtaatttt tttaatttac aaaaatataa 540
aatatgaaga cataaacccm gttgccatct gcgtgacaat aaaacattaa tgctaacact 600
t 601

<210> SEQ ID NO 134
<211> LENGTH: 421
<212> TYPE: DNA
<213> ORGANISM: Homo sapien

<400> SEQUENCE: 134
tcacataaga aatttaagca agttacrcta tcttaaaaaa cacaacgaat gcattttaat 60
agagaaaccc ttccctccct ccacctccct cccccaccct cctcatgaat taagaatcta 120
agagaagaag taaccataaa accaagtttt gtggaatcca tcatccagag tgcttacatg 180
gtgattaggt taatattgcc ttcttacaaa atttctattt taaaaaaaat tataaccttg 240
attgcttatt acaaaaaaat tcagtacaaa agttcaatat attgaaaaat gcttttcccc 300
tccctcacag caccgtttta tatatagcag agaataatga agagattgct agtctagatg 360
gggcaatctt caaattacac caagacgcac agtggtttat ttaccctccc cttctcataa 420
g 421

<210> SEQ ID NO 135
<211> LENGTH: 511
<212> TYPE: DNA
<213> ORGANISM: Homo sapien

<400> SEQUENCE: 135
ggaaaggatt caagaattag aggacttgct tgctrragaa aaagacaact ctcgtcgcat 60
gctgacagac aaagagagag agatggcgga aataagggat caaatgcagc aacagctgaa 120
tgactatgaa cagcttcttg atgtaaagtt agccctggac atggaaatca gtgcttacag 180
gaaactctta gaaggcgaag aagagaggtt gaagctgtct ccaagccctt cttcccgtgt 240
gacagtatcc cgagcatcct caagtcgtag tgtaccgtac aactagagga aagcggaaga 300
gggttgatgt ggaagaatca gaggcgaagt agtagtgtta gcatctctca ttccgcctca 360
accactggaa atgtttgcat cgaagaaatt gatgttgatg ggaaatttat cccgcttgaa 420
gaacacttct gaacaggatc aaccaatggg aaggcttggg agatgatcag aaaaattgga 480
gacacatcag tcagttataa atatacctca a 511

-continued

<210> SEQ ID NO 136
<211> LENGTH: 341
<212> TYPE: DNA
<213> ORGANISM: Homo sapien

<400> SEQUENCE: 136
catgggtttc accaggttgg ccaggctgct cttgaactsc tgacctcagg tgatccaccc 60
gcctcggcct cccaaagtgc tgggattaca ggcgtgagcc accacgcccg gcccccaaag 120
ctgtttcttt tgtctttagc gtaaagctct cctgccatgc agtatctaca taactgacgt 180
gactgccagc aagctcagtc actccgtggt ctttttctct ttccagttct tctctctctc 240
ttcaagttct gcctcagtga aagctgcagg tccccagtta agtgatcagg tgagggttct 300
ttgaacctgg ttctatcagt cgaattaatc cttcatgatg g 341

<210> SEQ ID NO 137
<211> LENGTH: 551
<212> TYPE: DNA
<213> ORGANISM: Homo sapien

<400> SEQUENCE: 137
gatgtgttgg accctctgtg tcaaaaaaaa cctcacaaag aatcccctgc tcattacaga 60
agaagatgca tttaaaatat gggttatttt caacttttta tctgaggaca agtatccatt 120
aattattgtg tcagaagaga ttgaatacct gcttaagaag cttacagaag ctatgggagg 180
aggttggcag caagaacaat ttgaacatta taaaatcaac tttgatgaca gtaaaaatgg 240
cctttctgca tgggaactta ttgagcttat tggaaatgga cagtttagca aaggcatgga 300
ccggcagact gtgtctatgg caattaatga agtctttaat gaacttatat tagatgtgtt 360
aaagcagggt tacatgatga aaaagggcca cagacggaaa aactggactg aaagatggtt 420
tgtactaaaa cccaacataa tttcttacta tgtgagtgag gatctgaagg ataagaaagg 480
agacattctc ttggatgaaa attgctgtgt agaagtcctt gcctgacaaa agatggaaag 540
aaatgccttt t 551

<210> SEQ ID NO 138
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 138
gactggttct ttatttcaaa aagacacttg tcaatattca gtrtcaaaac agttgcacta 60
ttgatttctc tttctcccaa tcggccccaa agagaccaca taaaaggaga gtacatttta 120
agccaataag ctgcaggatg tacacctaac agacctccta gaaaccttac cagaaaatgg 180
ggactgggta gggaaggaaa cttaaaagat caacaaactg ccagcccacg gactgcagag 240
gctgtcacag ccagatgggg tggccagggt gccacaaacc caaagcaaag tttcaaaata 300
atataaaatt taaaaagttt tgtacataag ctattcaaga tttctccagc actgactgat 360
acaaagcaca attgagatgg cacttctaga gacagcagct tcaaacccag aaaagggtga 420
tgagatgaag tttcacatgg ctaaatcagt ggcaaaaaca cagtcttctt tctttctttc 480
tttcaaggan gcaggaaagc aattaagtgg tcaccttaac ataaggggga c 531

-continued

<210> SEQ ID NO 139
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 139

```
tgggtgggca ccatggctgg gatcaccacc atcgaggcgg tgaagcgcaa gatccaggtt     60

ctgcagcagc aggcagatga tgcagaggag cgagctgagc gcctccagcg agaagttgag    120

ggagaaaggc gggcccggga acaggctgag gctgaggtgg cctccttgaa ccgtaggatc    180

cagctggttg aagaagagct ggaccgtgct caggagcgcc tggccactgc cctgcaaaag    240

ctggaagaag ctgaaaaagc tgctgatgag agtgagagag gtatgaaggt tattgaaaac    300

cgggccttaa aagatgaaga aaagatggaa ctccaggaaa tccaactcaa agaagctaag    360

cacattgcag aagaggcaga taggaagtat gaagaggtgg ctcgtaagtt ggtgatcatt    420

gaaggagact tggaaccgca cagaaggaac gagcttgagc ttggcaaaag tcccgttgcc    480

cagagatggg atgaaccaga ttagactgat ggaccanaac c                        521
```

<210> SEQ ID NO 140
<211> LENGTH: 571
<212> TYPE: DNA
<213> ORGANISM: Homo sapien
<220> FEATURE:
<221> NAME/KEY: misc_feature
<222> LOCATION: (1)...(571)
<223> OTHER INFORMATION: n = A,T,C or G

<400> SEQUENCE: 140

```
aggggcngcg ggtgcgtggg ccactgggtg accgacttag cctggccaga ctctcagcac     60

ctggaagcgc cccgagagtg acagcgtgag gctgggaggg aggacttggc ttgagcttgt    120

taaactctgc tctgagcctc cttgtcgcct gcatttagat ggctcccgca aagaagggtg    180

gcgagaagaa aaagggccgt tctgccatca acgaagtggt aacccgagaa tacaccatca    240

acattcacaa gcgcatccat ggagtgggct tcaagaagcg tgcacctcgg gcactcaaag    300

agattcggaa atttgccatg aaggagatgg gaactccaga tgtgcgcatt gacaccaggc    360

tcaacaaagc tgtctgggcc aaaggaataa ggaatgtgcc ataccgaatc cggtgtgcgg    420

ctgtccagaa aacgtaatga ggatgaagat tcaccaaata agctatatac tttggttacc    480

tatgtacctg ttaccacttt caaaaatcta cagacagtca atgtggatga gaactaatcg    540

ctgatcgtca gatcaaataa agttataaaa t                                   571
```

<210> SEQ ID NO 141
<211> LENGTH: 531
<212> TYPE: DNA
<213> ORGANISM: Homo sapien

<400> SEQUENCE: 141

```
tcgggagcca cacttggccc tcttcctctc caaagsgcca gaacctcctt ctctttggag     60

aatggggagg cctcttggag acacagaggg tttcaccttg gatgacctct agagaaattg    120

cccaagaagc ccaccttctg gtcccaacct gcagaccccca cagcagtcag ttggtcaggc    180

cctgctgtag aaggtcactt ggctccattg cctgcttcca accaatgggc aggagagaag    240

gcctttattt ctcgcccacc cattcctcct gtaccagcac ctccgttttc agtcagtgtt    300
```

-continued

```
gtccagcaac ggtaccgttt acacagtcac ctcagacaca ccatttcacc tcccttgcca    360

agctgttagc cttagagtga ttgcagtgaa cactgtttac acaccgtgaa tccattccca    420

tcagtccatt ccagttggca ccagcctgaa ccatttggta cctggtgtta actggagtcc    480

tgtttacaag gtggagtcgg ggcttgctga cttctcttca tttgagggca c             531
```

<210> SEQ ID NO 142
<211> LENGTH: 491
<212> TYPE: DNA
<213> ORGANISM: Homo sapien
<220> FEATURE:
<221> NAME/KEY: misc_feature
<222> LOCATION: (1)...(491)
<223> OTHER INFORMATION: n = A,T,C or G

<400> SEQUENCE: 142

```
acctagacag aaggtgggtg agggaggact ggtaggaggc tgaggcaatt ccttggtagt     60

ttgtcctgaa accctactgg agaagtcagc atgaggcacc tactgagaga agtgcccaga    120

aactgctgac tgcatctgtt aagagttaac agtaaagagg tagaagtgtg tttctgaatc    180

agagtggaag cgtctcaagg gtcccacagt ggaggtccct gagctacctc ccttccgtga    240

gtgggaagag tgaagcccat gaagaactga gatgaagcaa ggatggggtt cctgggctcc    300

aggcaagggc tgtgctctct gcagcaggga gccccacgag tcagaagaaa agaactaatc    360

atttgttgca agaaaccttg cccggatact agcggaaaac tggaggcggn ggtgggggca    420

caggaaagtg gaagtgattt gatggagagc agagaagcct atgcacagtg gccgagtcca    480

cttgtaaagt g                                                         491
```

<210> SEQ ID NO 143
<211> LENGTH: 515
<212> TYPE: DNA
<213> ORGANISM: Homo sapien

<400> SEQUENCE: 143

```
ttcaagcaat tgtaacaagt atatgtagat tagagtgagc aaaatcatat acaattttca     60

tttccagttg ctattttcca aattgttctg taatgtcgtt aaaattactt aaaaattaac    120

aaagccaaaa attatattta tgacaagaaa gccatcccta cattaatctt acttttccac    180

tcaccggccc atctccttcc tctttttcct aactatgcca ttaaaactgt tctactgggc    240

cgggcgtgtg gctcatgcct gtaatcccag cattttggga ggccaaggca ggcggatcat    300

gaggtcaaga gattgagacc atcctggcca acatggtgaa accccgcctc gactaagaat    360

acaaaaatta gctgggcatg gtggcgcatg cctgtagtct cagctactcg ggaggctgag    420

gcagaagaat cgcttgaacc cgggaggcag aggatgcagt gagccccgat cgcgccactg    480

cactctagcc tgggcgacag actgagactc tgctc                               515
```

<210> SEQ ID NO 144
<211> LENGTH: 340
<212> TYPE: DNA
<213> ORGANISM: Homo sapien

<400> SEQUENCE: 144

```
tgtgccagtc tacaggccta tcagcagcga ctccttcagc aacagatggg gtcccctgtt     60

cagcccaacc ccatgagccc ccagcagcat atgctcccaa atcaggccca gtccccacac    120

ctacaaggcc agcagatccc taattctctc tccaatcaag tgcgctctcc ccagcctgtc    180

ccttctccac ggccacagtc ccagcccccc cactccagtc cttccccaag gatgcagcct    240
```

-continued cagccttctc cacaccacgt ttccccacag acaagttccc cacatcctgg actggtagtt 300
gcccaggcca accccatgga acaagggcat tttgccagcc 340

<210> SEQ ID NO 145
<211> LENGTH: 630
<212> TYPE: DNA
<213> ORGANISM: Homo sapien

<400> SEQUENCE: 145
tgtaaaaact tgtttttaat tttgtataaa ataaaggtgg tccatgccca cgggggctgt 60
aggaaatcca agcagaccag ctggggtggg gggatgtagc ctacctcggg ggactgtctg 120
tcctcaaaac gggctgagaa ggcccgtcag gggcccaggt cccacagaga ggcctgggat 180
actcccccaa cccgaggggc agactgggca gtggggagcc cccatcgtgc cccagaggtg 240
gccacaggct gaaggagggg cctgaggcac cgcagcctgc aacccccagg gctgcagtcc 300
actaactttt tacagaataa aaggaacatg gggatgggga aaaaagcacc aggtcaggca 360
gggcccgagg gccccagatc ccaggagggc caggactcag gatgccagca ccaccctagc 420
agctcccaca gctcctggca caggaggccg ccacggattg gcacaggccg ctgctggcca 480
tcacgccaca tttggagaac ttgtcccgac agaggtcagc tcggaggagc tcctcgtggg 540
cacacactgt acgaacacag atctccttgt taatgacgta cacacggcgg aggctgcggg 600
gacagggcac gggaggtctc agccccactt 630

<210> SEQ ID NO 146
<211> LENGTH: 521
<212> TYPE: DNA
<213> ORGANISM: Homo sapien

<400> SEQUENCE: 146
atggctgctg gatttaggtg gtaatagggg ctgtgggcca taaatctgaa gccttgagaa 60
ccttgggtct ggagagccat gaagagggaa ggaaaagagg gcaagtcctg aacctaacca 120
atgacctgat ggattgctcg accaagacac agaagtgaag tctgtgtctg tgcacttccc 180
acagactgga gtttttggtg ctgaatagag ccagttgcta aaaaattggg ggtttggtga 240
agaaatctga ttgttgtgtg tattcaatgt gtgattttaa aaataaacag caacaacaat 300
aaaaaccctg actggctgtt ttttccctgt attctttaca actatttttt gaccctctga 360
aaattattat acttcaccta aatggaagac tgctgtgttt gtggaaattt tgtaattttt 420
taatttattt tattctctct cctttttatt ttgcctgcag aatccgttga gagactaata 480
aggcttaata tttaattgat ttgtttaata tgtatataaa t 521

<210> SEQ ID NO 147
<211> LENGTH: 562
<212> TYPE: DNA
<213> ORGANISM: Homo sapien

<400> SEQUENCE: 147
ggcatgcgag cgcactcggc ggacgcaagg gcggcgggga gcacacggag cactgcaggc 60
gccgggttgg gacagcgtct tcgctgctgc tggatagtcg tgttttcggg gatcgaggat 120
actcaccaga aaccgaaaat gccgaaacca atcaatgtcc gagttaccac catggatgca 180
gagctggagt ttgcaatcca gccaaataca actggaaaac agctttttga tcaggtggta 240
aagactatcg gcctccggga agtgtggtac tttggcctcc actatgtgga taataaagga 300

-continued

```
tttcctacct ggctgaagct ggataagaag gtgtctgccc aggaggtcag gaaggagaat    360

cccctccagt tcaagttccg ggccaaagtt ctaccctgaa gatgtggctg aggagctcat    420

ccaggacatc acccagaaac ttttcttcct tcaagtgaag gaaggaatcc ttagcgatga    480

gatctactgc ccccettgar actgccgtgc tcttggggtc ctacgcttgt gcatgccaag    540

tttggggact accaccaaga ag                                             562
```

<210> SEQ ID NO 148
<211> LENGTH: 820
<212> TYPE: DNA
<213> ORGANISM: Homo sapien

<400> SEQUENCE: 148

```
gaaggagtcg ggatactcag cattgatgca ccccaatttc aaagcggcat tcttcggcag     60

gtctctggga caatctctag ggtcactacc tggaaactcg ttagggtaca actgaatgct    120

gaaaggaaag aacacctgca gaaccggaca gaaattcacc ccggcgatca gctgattgat    180

ctcggtcgac cagaagtcat ggctaaagat gacgaggacg ttgtcaattc cctgggcttt    240

tcgaagtgag tccagcagca gtctgaggta ttcgggccgg ttatgcacct ggaccaccag    300

caccagctcc cggggggccc aggtgccagc cttatctaca ttcctcaggg tctgatcaaa    360

gttcagctgg tacaccaggg accggtaccg cagcgtcagg ttgtccgctc gggctggggg    420

accgccggga ccagggaagc cgccgacacg ttggagaccc tgcggatgcc cacagccaca    480

gaggggtggt ccccaccgcg gccgccggca ccccgcgcgg gttcggcgtc cagcaacggt    540

ggggcgaggg cctcgttctt cctttgtcgc ccattgctgc tccagaggac gaagccgcag    600

gcggccacca cgagcgtcag gattagcacc ttccgtttgt agatgcggaa cctcatggtc    660

tccagggccg ggagcgcagc tacagctcga gcgtcggcgc cgccgctagg agccgcggct    720

cggcttcgtc tccgtcctct ccattcagca ccacgggtcc cggaaaaagc tcagccscgg    780

tcccaaccgc accctagctt cgttacctgc gcctcgcttg                          820
```

<210> SEQ ID NO 149
<211> LENGTH: 501
<212> TYPE: DNA
<213> ORGANISM: Homo sapien

<400> SEQUENCE: 149

```
cagattttta tttgcagtcg tcactggggc cgtttcttgc tgcttatttg tctgctagcc     60

tgctcttcca gctgcatggc caggcgcaag gccttgatga catctcgcag ggctgagaaa    120

tgcttggctt gctgggccag agcagattcc gctttgttca caaaggtctc caggtcatag    180

tctggctgct cggtcatctc agagagctca agccagtctg gtccttgctg tatgatctcc    240

ttgagctctt ccatagcctt ctcctccagc tccctgatct gagtcatggc ttcgttaaag    300

ctggacatct gggaagacag ttcctcctct tccttggata aattgcctgg aatcagcgcc    360

ccgttagagc aggcttccat ctcttctgtt tccatttgaa tcaactgctc tccactgggc    420

ccactgtggg ggctcagctc cttgaccctg ctgcatatct taagggtgtt taaaggatat    480

tcacaggagc ttatgcctgg t                                              501
```

<210> SEQ ID NO 150
<211> LENGTH: 511
<212> TYPE: DNA
<213> ORGANISM: Homo sapien
<220> FEATURE:
<221> NAME/KEY: misc_feature -continued
<222> LOCATION: (1)...(511)
<223> OTHER INFORMATION: n = A,T,C or G

<400> SEQUENCE: 150
ctcctcttgg tacatgaacc caagttgaaa gtggacttaa caaagtatct ggagaaccaa 60
gcattctgct ttgactttgc atttgatgaa acagcttcga atgaagttgt ctacaggttc 120
acagcaaggc cactggtaca gacaatcttt gaaggtggaa aagcaacttg ttttgcatat 180
ggccagacag gaagtggcaa gacacatact atgggcggag acctctctgg gaaagcccag 240
aatgcatcca aagggatcta tgccatggcc ttccgggacg tcttcttctg aagaatcaac 300
cctgctaccg gaagttgggc ctggaagtct atgtgacatt cttcgagatc tacaatggga 360
agctgtttga cctgctcaac aagaaggcca agcttgcgcg tgctggaaga cggcaagcaa 420
caggtgcaag tggtgggggc ttgcaggaac atctggntaa ctctgcttga tgatggcant 480
caagatgatc gacatgggca gcgcctgcag a 511

<210> SEQ ID NO 151
<211> LENGTH: 566
<212> TYPE: DNA
<213> ORGANISM: Homo sapien

<400> SEQUENCE: 151
tcccgaattc aagcgacaaa ttggawagtg aaatggaaga tgcctatcat gaacatcagg 60
caaatctttt gcgccaagat ctgatgagac gacaggaaga attaagacgc atggaagaac 120
ttcacaatca agaaatgcag aaacgtaaag aaatgcaatt gaggcaagag gaggaacgac 180
gtagaagaga ggaagagatg atgattcgtc aacgtgagat ggaagaacaa atgaggcgcc 240
aaagagagga aagttacagc cgaatgggct acatggatcc acgggaaaga gacatgcgaa 300
tgggtggcgg aggagcaatg aacatgggag atccctatgg ttcaggaggc cagaaatttc 360
cacctctagg aggtggtggt ggcataggtt atgaagctaa tcctggcgtt ccaccagcaa 420
ccatgagtgg ttccatgatg ggaagtgaca tgcgtactga gcgctttggg cagggaggtg 480
cggggcctgt gggtggacag ggtcctagag gaatggggcc tggaactcca gcaggatatg 540
gtagagggag agaagagtac gaaggc 566

<210> SEQ ID NO 152
<211> LENGTH: 518
<212> TYPE: DNA
<213> ORGANISM: Homo sapien

<400> SEQUENCE: 152
ttcgtgaaga ccctgactgg taagaccatc actctcgaag tggagcccga gtgacaccat 60
tgagaatgtc aaggcaaaga tccaagacaa ggaaggcatc cctcctgacc agcakaggtt 120
gatctttgct gggaaacagc tggaagatgg acgcaccctg tctgactaca acatccagaa 180
agagtccacc ctgcacctgg tgctccgtct cagaggtggg atgcaaatct tcgtgaagac 240
cctgactggt aagaccatca ccctcgaggt ggagcccagt gacaccatcg agaatgtcaa 300
ggcaaagatc caagataagg aaggcatccc tcctgatcag cagaggttga tctttgctgg 360
gaaacagctg gaagatggac gcaccctgtc tgactacaac atccagaaag agtccactct 420
gcacttggtc ctgcgcttga ggggggtgt ctaagtttcc ccttttaagg tttcaacaaa 480
tttcattgca ctttcctttc aataaagttg ttgcattc 518

<210> SEQ ID NO 153

-continued

<211> LENGTH: 542
<212> TYPE: DNA
<213> ORGANISM: Homo sapien

<400> SEQUENCE: 153
gcgcgggtgc gtgggccact gggtgaccga cttagcctgg ccagactctc agcacctgga 60
agcgccccga gagtgacagc gtgaggctgg gagggaggac ttggcttgag cttgttaaac 120
tctgctctga gcctccttgt cgcctgcatt tagatggctc ccgcaaagaa gggtggcgag 180
aagaaaaagg gccgttctgc catcaacgaa gtggtaaccc gagaatacac catcaacatt 240
cacaagcgca tccatggagt gggcttcaag aagcgtgcac ctcgggcact caaagagatt 300
cggaaatttg ccatgaagga gatgggaact ccagatgtgc gcattgacac caggctcaac 360
aaagctgtct gggccaaagg aataaggaat gtgccatacc gaatccgtgt gcggctgtcc 420
agaaaacgta atgaggatga agattcacca aataagctat atactttggt tacctatgta 480
cctgttacca ctttcaaaaa tctacagaca gtcaatgtgg atgagaacta atcgctgatc 540
gt 542

<210> SEQ ID NO 154
<211> LENGTH: 411
<212> TYPE: DNA
<213> ORGANISM: Homo sapien

<400> SEQUENCE: 154
aattctttat ttaaatcaac aaactcatct tcctcaagcc ccagaccatg gtaggcagcc 60
ctccctctcc atcccctcac cccacccctt agccacagtg aagggaatgg aaaatgagaa 120
gccacgaggg cccctgccag ggaaggctgc cccagatgtg tggtgagcac agtcagtgca 180
gctgtggctg gggcagcagc tgccacaggc tcctccctat aaattaagtt cctgcagcca 240
cagctgtggg agaagcatac ttgtagaagc aaggccagtc cagcatcaga aggcagaggc 300
agcatcagtg actcccagcc atggaatgaa cggaggacac agagctcaga gacagaacag 360
gccaggggga agaaggagag acagaatagg ccagggcatg gcggtgaggg a 411

<210> SEQ ID NO 155
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 155
tgatgaatct gggtgggctg gcagtagccc gagatgatgg gctcttctct ggggatccca 60
actggttccc taagaaatcc aaggagaatc ctcggaactt ctcggataac cagctgcaag 120
agggcaagaa cgtgatcggg ttacagatgg gcaccaaccg cggggcgtct cangcaggca 180
tgactggcta cgggatgcca cgccagatcc tctgatccca ccccaggcct tgcccctgcc 240
ctcccacgaa tggttaatat atatgtagat atatatttta gcagtgacat tcccagagag 300
ccccagagct ctcaagctcc tttctgtcag ggtggggggt tcaagcctgt cctgtcacct 360
ctgaagtgcc tgctggcatc ctctccccca tgcttactaa tacattccct tccccatagc 420
c 421

<210> SEQ ID NO 156
<211> LENGTH: 670

-continued

<212> TYPE: DNA
<213> ORGANISM: Homo sapien

<400> SEQUENCE: 156
agcggagctc cctcccctgg tggctacaac ccacacacgc caggctcagg catcgagcag 60
aactccagcg actgggtaac cactgacatt caggtgaagg tgcgggacac ctacctggat 120
acacaggtgg tgggacagac aggtgtcatc cgcagtgtca cgggggggcat gtgctctgtg 180 tacctgaagg acagtgagaa ggttgtcagc atttccagtg agcacctgga gcctatcacc 240
cccaccaaga acaacaaggt gaaagtgatc ctgggcgagg atcgggaagc cacgggcgtc 300
ctactgagca ttgatggtga ggatggcatt gtccgtatgg accttgatga gcagctcaag 360
atcctcaacc tccgcttcct ggggaagctc ctggaagcct gaagcaggca gggccggtgg 420
acttcgtcgg atgaagagtg atcctccttc cttccctggc ccttggctgt gacacaagat 480
cctcctgcag ggctaggcgg attgttctgg atttcctttt gtttttcctt ttaggtttcc 540
atcttttccc tccctggtgc tcattggaat ctgagtagag tctgggggag ggtccccacc 600
ttcctgtacc tcctccccac agcttgcttt tgttgtaccg tctttcaata aaaagaagct 660
gtttggtcta 670

<210> SEQ ID NO 157
<211> LENGTH: 421
<212> TYPE: DNA
<213> ORGANISM: Homo sapien

<400> SEQUENCE: 157
ggttcacagc actgctgctt gtgtgttgcc ggccaggaat tccaggctca caaggctatc 60
ttagcagctc gttctccggt ttttagtgcc atgtttgaac atgaaatgga ggagagcaaa 120
aagaatcgag ttgaaatcaa tgatgtggag cctgaagttt ttaaggaaat gatgtgcttc 180
atttacacgg ggaaggctcc aaacctcgac aaaatggctg atgatttgct ggcagctgct 240
gacaagtatg ccctggagcg cttaaaggtc atgtgtgagg atgccctctg cagtaacctg 300
tccgtggaga acgctgcaga aattctcatc ctggccgacc tccacagtgc agatcagttg 360
aaaactcagg cagtggattt catcaactat catgcttcgg atgtcttgga gacctcttgg 420
g 421

<210> SEQ ID NO 158
<211> LENGTH: 321
<212> TYPE: DNA
<213> ORGANISM: Homo sapien

<400> SEQUENCE: 158
tcgtagccat ttttctgctt ctttggagaa tgacgccaca ctgactgctc attgtcgttg 60
gttccatgcc aattggtgaa atagaacctc atccggtagt ggagccggag ggacatcttg 120
tcatcaacgg tgatggtgcg atttggagca taccagagct tggtgttctc gccatacagg 180
gcaaagaggt tgtgacaaag aggagagata cggcatgcct gtgcagccct gatgcacagt 240
tcctctgctg tgtactctcc actgcccagc cggaggggct ccctgtccga cagatagaag 300
atcacttcca cccctggctt g 321

<210> SEQ ID NO 159
<211> LENGTH: 596
<212> TYPE: DNA
<213> ORGANISM: Homo sapien -continued

<400> SEQUENCE: 159

```
tggcacactg ctcttaagaa actatgawga tctgagattt ttttgtgtat gtttttgact     60
cttttgagtg gtaatcatat gtgtctttat agatgtacat acctccttgc acaaatggag    120
gggaattcat tttcatcact gggagtgtcc ttagtgtata aaaaccatgc tggtatatgg    180
cttcaagttg taaaaatgaa agtgacttta aaagaaaata ggggatggtc caggatctcc    240
actgataaga ctgtttttaa gtaacttaag gacctttggg tctacaagta tatgtgaaaa    300
aaatgagact tactgggtga ggaaattcat tgtttaaaga tggtcgtgtg tgtgtgtgtg    360
tgtgtgtgtg ttgtgttgtg ttttgttttt taagggaggg aatttattat ttaccgttgc    420
ttgaaattac tgkgtaaata tatgtytgat aatgatttgc tytttgvcma ctaaaattag    480
gvctgtataa gtwctaratg cmtccctggg kgttgatytt ccmagatatt gatgatamcc    540
cttaaaattg taaccygcct tttccctttt gctytcmatt aaagtctatt cmaaag        596
```

<210> SEQ ID NO 160
<211> LENGTH: 515
<212> TYPE: DNA
<213> ORGANISM: Homo sapien

<400> SEQUENCE: 160

```
gggggtaggc tctttattag acggttattg ctgtactaca gggtcagagt gcagtgtaag     60
cagtgtcaga ggcccgcgtt cagcccaaga atgtggattt tctctcccta ttgatcacag    120
tgggtgggtt tcttcagaaa agccccagag gcagggacca gtgagctcca aggttagaag    180
tggaactgga aggcttcagt cacatgctgc ttccacgctt ccaggctggg cagcaaggag    240
gagatgccca tgacgtgcca ggtctcccca tctgacacca gtgaagtctg gtaggacagc    300
agccgcacgc ctgcctctgc caggaggcca atcatggtag gcagcattgc agggtcagag    360
gtctgagtcc ggaataggag caggggcagg tccctgcgga gaggcacttc tggcctgaag    420
acagctccat tgagcccctg cagtacaggy gtagtgcctt ggaccaagcc cacagcctgg    480
taaggggcgc ctgccagggc cacggccagg aggca                               515
```

<210> SEQ ID NO 161
<211> LENGTH: 936
<212> TYPE: DNA
<213> ORGANISM: Homo sapien

<400> SEQUENCE: 161

```
taatttctta gtcgtttgga atccttaagc atgcaaaagc tttgaacaga agggttcaca     60
aaggaaccag ggttgtctta tggcatccag ttaagccaga gctgggaatg cctctgggtc    120
atccacatca ggagcagaag cacttgactt gtcggtcctg ctgccacggt ttgggcgccc    180
accacgccca cgtccacctc gtcctcccct gccgccacgt cctgggcggc caaggtctcc    240
aaaattgatc tccagctgag acgttatatc atttgctggc ttccggaaat gatggtccat    300
aaccgaatct tcagcatgag cctcttcact ctttgattta tgaagaacaa atcccttctt    360
ccactgccca tcagcacctt catttggttt tcggatatta aattctactt ttgcccggtc    420
cttattttga atagccttcc actcatccaa agtcatctct tttggaccct cctcttttac    480
ctcttcaact tcattctcct tattttcagt gtctgccact ggatgatgtt cttcaccttc    540
aggtgtttcc tcagtcacat ttgattgatc caagtcagtt aattcgtctt tgacagttcc    600
ccagttgtga gatccgctac ctccacgttt gtcctcgtgc ttcaggccag atctatcact    660
tccactatgc ctatcaaatt cacgtttgcc acgagaatca aatccatctc ctcggcccat    720
```

-continued tccacgtcca cggccccctc gacctcttcc aagaccacca cgacctcgaa taggtcggtc 780
aataatcggt ctatcaactg aaaattcgcc tccttcaccc ttttcttcaa gtggcttttc 840
gaatcttcgt tcacgaggtg gtcgcctttc tggtcttcta tcaattattt tcccttcacc 900
ctgaagttgt tgatcaggtc ttcttccaac tcgtgc 936

<210> SEQ ID NO 162
<211> LENGTH: 950
<212> TYPE: DNA
<213> ORGANISM: Homo sapien

<400> SEQUENCE: 162
aagcggatgg acctgagtca gccgaatcct agccccttcc cttgggcctg ctgtggtgct 60
cgacatcagt gacagacgga agcagcagac catcaaggct acgggaggcc cggggcgctt 120
gcgaagatga agtttggctg cctctccttc cggcagcctt atgctggctt tgtcttaaat 180
ggaatcaaga ctgtggagac gcgctggcgt cctctgctga gcagccagcg gaactgtacc 240
atcgccgtcc acattgctca cagggactgg gaaggcgatg cctgtcggga gctgctggtg 300
gagagactcg ggatgactcc tgctcagatt caggccttgc tcaggaaagg ggaaaagttt 360
ggtcgaggag tgatagcggg actcgttgac attggggaaa ctttgcaatg ccccgaagac 420
ttaactcccg atgaggttgt ggaactagaa aatcaagctg cactgaccaa cctgaagcag 480
aagtacctga ctgtgatttc aaaccccagg tggttactgg agcccatacc taggaaagga 540
ggcaaggatg tattccaggt agacatccca gagcacctga tccctttggg gcatgaagtg 600
tgacaagtgt gggctcctga aaggaatgtt ccrgagaaac cagctaaatc atggcacctt 660
caatttgcca tcgtgacgca gacctgtata aattaggtta aagatgaatt tccactgctt 720
tggagagtcc cacccactaa gcactgtgca tgtaaacagg ttcctttgct cagatgaagg 780
aagtaggggg tggggctttc cttgtgtgat gcctccttag gcacacaggc aatgtctcaa 840
gtactttgac cttagggtag aaggcaaagc tgccagtaaa tgtctcagca ttgctgctaa 900
ttttggtcct gctagtttct ggattgtaca aataaatgtg ttgtagatga 950

<210> SEQ ID NO 163
<211> LENGTH: 475
<212> TYPE: DNA
<213> ORGANISM: Homo sapien
<220> FEATURE:
<221> NAME/KEY: misc_feature
<222> LOCATION: (1)...(475)
<223> OTHER INFORMATION: n = A,T,C or G

<400> SEQUENCE: 163
tcgagcggcc gcccgggcag gtgtcggagt ccagcacggg aggcgtggtc ttgtagttgt 60
tctccggctg cccattgctc tcccactcca cggcgatgtc gctgggatag aagcctttga 120
ccaggcaggt caggctgacc tggttcttgg tcatctcctc ccgggatggg ggcagggtgt 180
acacctgtgg ttctcggggc tgccctttgg ctttggagat ggttttctcg atgggggctg 240
ggagggcttt gttggagacc ttgcacttgt actccttgcc attcaaccag tcctggtgca 300
ngacggtgag gacgctnacc acacggtacg ngctggtgta ctgctcctcc cgcggctttg 360
tcttggcatt atgcacctcc acgccgtcca cgtaccaatt gaacttgacc tcagggtctt 420
cgtggctcac gtccaccacc acgcatgtaa cctcaaanct cggncgcgan cacgc 475

<210> SEQ ID NO 164

-continued

<211> LENGTH: 476
<212> TYPE: DNA
<213> ORGANISM: Homo sapien

<400> SEQUENCE: 164
agcgtggtcg cggccgaggt ctgaggttac atgcgtggtg gtggacgtga gccacgaaga 60
ccctgaggtc aagttcaact ggtacgtgga cggcgtggag gtgcataatg ccaagacaaa 120
gccgcgggag gagcagtaca acagcacgta ccgtgtggtc agcgtcctca ccgtcctgca 180
ccaggactgg ctgaatggca aggagtacaa gtgcaaggtc tccaacaaag ccctcccagc 240
ccccatcgag aaaaccatct ccaaagccaa agggcagccc cgagaaccac aggtgtacac 300
cctgccccca tcccgggagg agatgaccaa gaaccaggtc agcctgacct gcctggtcaa 360
aggcttctat cccagcgaca tcgcccgtgg agtgggagag caatgggcag ccggagaaca 420
actacaagac cacgcctccc gtgctggact ccgacacctg ccgggcggcc gctcga 476

<210> SEQ ID NO 165
<211> LENGTH: 256
<212> TYPE: DNA
<213> ORGANISM: Homo sapien
<220> FEATURE:
<221> NAME/KEY: misc_feature
<222> LOCATION: (1)...(256)
<223> OTHER INFORMATION: n = A,T,C or G

<400> SEQUENCE: 165
agcgtggttn cggccgaggt cccaaccaag gctgcancct ggatgccatc aaagtcttct 60
gcaacatgga gactggtgag acctgcgtgt accccactca gcccagtgtg gcccagaaga 120
actggtacat cagcaagaac cccaaggaca agaggcatgt ctggttcggc gagagcatga 180
ccgatggatt ccagttcgag tatggcggcc agggctccga ccctgccgat gtggacctgc 240
ccgggcggnc gctcga 256

<210> SEQ ID NO 166
<211> LENGTH: 332
<212> TYPE: DNA
<213> ORGANISM: Homo sapien

<400> SEQUENCE: 166
agcgtggtcg cggccgaggt caagaacccc gcccgcacct gccgtgacct caagatgtgc 60
cactctgact ggaagagtgg agagtactgg attgacccca accaaggctg caacctggat 120
gccatcaaag tcttctgcaa catggagact ggtgagacct gcgtgtaccc cactcagccc 180
agtgtggccc agaagaactg gtacatcagc aagaacccca aggacaagag gcatgtctgg 240
ttcggcgaga gcatgaccga tggattccag ttcgagtatg gcggccaggg ctccgaccct 300
gccgatgtgg acctgcccgg gcggccgctc ga 332

<210> SEQ ID NO 167
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 167
tcgagcggtc gcccgggcag gtccacatcg gcagggtcgg agccctggcc gccatactcg 60
aactggaatc catcggncat gctctcgccg aaccagacat gcctcttgnc cttggggttc 120

-continued ttgctgatgt accagntctt ctgggccaca ctgggctgag tggggtacac gcaggtctca 180
ccantctcca tgttgcanaa gactttgatg gcatccaggt tgcagccttg gttggggtca 240
atccagtact ctccactctt ccagacagag tggcacatct tgaggtcacg gcaggtgcgg 300
gcggggttct tgacctcggt cgcgaccacg ct 332

<210> SEQ ID NO 168
<211> LENGTH: 276
<212> TYPE: DNA
<213> ORGANISM: Homo sapien
<220> FEATURE:
<221> NAME/KEY: misc_feature
<222> LOCATION: (1)...(276)
<223> OTHER INFORMATION: n = A,T,C or G

<400> SEQUENCE: 168
tcgagcggcc gcccgggcag gtcctcctca gagcggtagc tgttcttatt gccccggcag 60
cctccataga tnaagttatt gcangagttc ctctccacgt caaagtacca gcgtgggaag 120
gatgcacggc aaggcccagt gactgcgttg gcggtgcagt attcttcata gttgaacata 180
tcgctggagt ggacttcaga atcctgcctt ctgggagcac ttgggacaga ggaatccgct 240
gcattcctgc tggtggacct cggccgcgac cacgct 276

<210> SEQ ID NO 169
<211> LENGTH: 276
<212> TYPE: DNA
<213> ORGANISM: Homo sapien

<400> SEQUENCE: 169
agcgtggtcg cggccgaggt ccaccagcag gaatgcagcg gattcctctg tcccaagtgc 60
tcccagaagg caggattctg aagaccactc cagcgatatg ttcaactatg aagaatactg 120
caccgccaac gcagtcactg ggccttgccg tgcatccttc ccacgctggt actttgacgt 180
ggagaggaac tcctgcaata acttcatcta tggaggctgc cggggcaata agaacagcta 240
ccgctctgag gaggacctgc ccgggcggcc gctcga 276

<210> SEQ ID NO 170
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 170
tcgagcggcc gcccgggcag gtccacatcg gcagggtcgg agccctggcc gccatactcg 60
aactggaatc catcggtcat gctctcgccg aaccagacat gcctcttgtc cttggggttc 120
ttgctgatgt accagttctt ctgggccaca ctgggctgag tggggtacac gcaggtctca 180
ccagtctcca tgttgcagaa gactttgatg gcatccaggt tgcagccttg gttggggtca 240
atccagtact ctccactctt ccagccagaa tggcacatct tgaggtcacg gcangtgcgg 300
gcggggttct tgacctcggc cgcgaccacg ct 332

<210> SEQ ID NO 171
<211> LENGTH: 333
<212> TYPE: DNA
<213> ORGANISM: Homo sapien -continued

<400> SEQUENCE: 171
agcgtggtcg cggccgaggt caagaaaccc cgccccgcacc tgccgtgacc tcaagatgtg 60
ccactctggc tggaagagtg gagagtactg gattgacccc aaccaaggct gcaacctgga 120
tgccatcaaa gtcttctgca acatggagac tggtgagacc tgcgtgtacc ccactcagcc 180
cagtgtggcc cagaagaact ggtacatcag caagaacccc aaggacaaga ggcatgtctg 240
gctcggcgag agcatgaccg atggattcca gttcgagtat ggcggccagg gctccgaccc 300
tgccgatgtg gacctgcccg ggcggccgct cga 333

<210> SEQ ID NO 172
<211> LENGTH: 527
<212> TYPE: DNA
<213> ORGANISM: Homo sapien
<220> FEATURE:
<221> NAME/KEY: misc_feature
<222> LOCATION: (1)...(527)
<223> OTHER INFORMATION: n = A,T,C or G

<400> SEQUENCE: 172
agcgtggtcg cggccgaggt cctgtcagag tggcactggt agaagntcca ggaaccctga 60
actgtaaggg ttcttcatca gtgccaacag gatgacatga aatgatgtac tcagaagtgt 120
cctgnaatgg ggcccatgan atggttgnct gagagagagc ttcttgtcct acattcggcg 180
ggtatggtct tggcctatgc cttatggggg tggccgttgn gggcggtgng gtccgcctaa 240
aaccatgttc ctcaaagatc atttgttgcc caacactggg ttgctgacca naagtgccag 300
gaagctgaat accatttcca gtgtcatacc cagggtgggt gacgaaaggg gtcttttgaa 360
ctgtggaagg aacatccaag atctctgntc catgaagatt ggggtgtgga agggttacca 420
gttggggaag ctcgctgtct ttttccttcc aatcangggc tcgctcttct gaatattctt 480
cagggcaatg acataaattg tatattcggt tcccggttcc aggccag 527

<210> SEQ ID NO 173
<211> LENGTH: 635
<212> TYPE: DNA
<213> ORGANISM: Homo sapien
<220> FEATURE:
<221> NAME/KEY: misc_feature
<222> LOCATION: (1)...(635)
<223> OTHER INFORMATION: n = A,T,C or G

<400> SEQUENCE: 173
tcgagcggcc gcccgggcag gtccaccaca cccaattcct tgctggtatc atggcagccg 60
ccacgtgcca ggattaccgg ctacatcatc aagtatgaga agcctgggtc tcctcccaga 120
gaagtggtcc ctcggccccg ccctggtgtc acagaggcta ctattactgg cctggaaccg 180
ggaaccgaat atacaattta tgtcattgcc ctgaagaata atcagaagag cgagcccctg 240
attggaagga aaaagacaga cgagcttccc caactggtaa cccttccaca ccccaatctt 300
catggaccag agatcttgga tgttccttcc acagttcaaa agaccccttt cgtcacccac 360
cctgggtatg acactggaaa tggtattcag cttcctggca cttctggtca gcaacccagt 420
gttgggcaac aaatgatctt tgangaacat ggntttaggc ggaccacacc ggccacaacg 480
ggcaccccca taaggcatag gccaagaaca tacccgncga atgtaggaca agaagctctn 540
tctcanacaa ncatctcatg ggccccattc cangacactt ctgagtacat canttcatgg 600
catcctggtg gcactgataa aaacccttac agtta 635

-continued

<210> SEQ ID NO 174
<211> LENGTH: 572
<212> TYPE: DNA
<213> ORGANISM: Homo sapien
<220> FEATURE:
<221> NAME/KEY: misc_feature
<222> LOCATION: (1)...(572)
<223> OTHER INFORMATION: n = A,T,C or G

<400> SEQUENCE: 174
agcgtggtcg cgggcgaggt cctgtcagag tggcactggt agaagttcca ggaaccctga 60
actgtaaggg ttcttcatca gtgccaacag gatgacatga aatgatgtac tcagaagtgt 120
cctggaatgg ggcccatgag atggttgtct gagagagagc ttcttgtcct acattcggcg 180
ggtatggtct tggcctatgc cttatggggg tggccgttgt gggcggtgtg gtccgcctaa 240
aaccatgttc ctcaaagatc atttgttgcc caacactggg ttgctgacca gaagtgccag 300
gaagctgaat accatttcca gtgtcatacc cagggtgggt gacgaaaggg gtcttttgaa 360
ctgtggaagg aacatccaag atctctggtc catgaagatt ggggtgtgga agggttacca 420
gttggggaag ctcgtctgtc tttttccttc caatcanggg ctcgctcttc tgattattct 480
tcagggcaat gacataaatt gtatattcgg ntcccgggtn cagccaataa taataaccct 540
ctgtgacacc anggcggggc cgaagganca ct 572

<210> SEQ ID NO 175
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 175
agcgtggtcg cggccgaggt cctcaccaga ggtaccacct acaacatcat agtggaggca 60
ctgaaagacc agcagaggca taaggttcgg gaagaggttg ttaccgtggg caactctgtc 120
aacgaaggct tgaaccaacc tacggatgac tcgtgctttg accoctacac agtttcccat 180 tatgccgttg gagatgagtg ggaacgaatg tctgaatcag gctttaaact gttgtgccag 240
tgcttangct ttggaagtgg tcatttcaga tgtgattcat ctagatggtg ccatgacaat 300
ggtgtgaact acaagattgg agagaagtgg gaccgtcagg gagaaaatgg acctgcccgg 360
gcggccgctc ga 372

<210> SEQ ID NO 176
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 176
tcgagcggcc gcccgggcag gtccattttc tccctgacgg tcccacttct ctccaatctt 60
gtagttcaca ccattgtcat ggcaccatct agatgaatca catctgaaat gaccacttcc 120
aaagcctaag cactggcaca acagtttaaa gcctgattca gacattcgtt cccactcatc 180
tccaacggca taatgggaaa ctgtgtaggg gtcaaagcac gagtcatccg taggttggtt 240
caagccttcg ntgacagagt tgcccacggt aacaacctct tcccgaacct tatgcctctg 300

-continued ctggtctttc agtgcctcca ctatgatgtt gtaggtggta cctctggtga ggacctcggc 360
cgcgaccacg ct 372

<210> SEQ ID NO 177
<211> LENGTH: 269
<212> TYPE: DNA
<213> ORGANISM: Homo sapien
<220> FEATURE:
<221> NAME/KEY: misc_feature
<222> LOCATION: (1)...(269)
<223> OTHER INFORMATION: n = A,T,C or G

<400> SEQUENCE: 177
agcgtggccg cggccgaggt ccattggctg gaacggcatc aacttggaag ccagtgatcg 60
tctcagcctt ggttctccag ctaatggtga tggngggtctc agtagcatct gtcacacgag 120
cccttcttgg tgggctgaca ttctccagag tggtgacaac accctgagct ggtctgcttg 180
tcaaagtgtc cttaagagca tagacactca cttcatattt ggcgnccacc ataagtcctg 240
atacaaccac ggaatgacct gtcaggaac 269

<210> SEQ ID NO 178
<211> LENGTH: 529
<212> TYPE: DNA
<213> ORGANISM: Homo sapien

<400> SEQUENCE: 178
tcgagcggcc gcccgggcag gtcctcagac cgggttctga gtacacagtc agtgtggttg 60
ccttgcacga tgatatggag agccagcccc tgattggaac ccagtccaca gctattcctg 120
caccaactga cctgaagttc actcaggtca cacccacaag cctgagcgcc cagtggacac 180
cacccaatgt tcagctcact ggatatcgag tgcgggtgac cccccaaggag aagaccggac 240 caatgaaaga aatcaacctt gctcctgaca gctcatccgt ggttgtatca ggacttatgg 300
cggccaccaa atatgaagtg agtgtctatg ctcttaagga cactttgaca agcagaccag 360
ctcagggtgt tgtcaccact ctggagaatg tcagcccacc aagaagggct cgtgtgacag 420
atgctactga gaccaccatc accattagct ggagaaccaa gactgagacg atcactggct 480
tccaagttga tgccgttcca gccaatggac ctcggccgcg accacgctt 529

<210> SEQ ID NO 179
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 179
agcgtggtcg cggccgaggt ctggccgaac tgccagtgta cagggaagat gtacatgtta 60
tagntcttct cgaagtcccg ggccagcagc tccacggggt ggtctcctgc ctccaggcgc 120
ttctcattct catggatctt cttcacccgc agcttctgct tctcagtcag aaggttgttg 180
tcctcatccc tctcatacag ggtgaccagg acgttcttga gccagtcccg catgcgcagg 240
gggaattcgg tcagctcaga gtccaggcaa ggggggatgt atttgcaagg cccgatgtag 300
tccaagtgga gcttgtggcc cttcttggtg ccctccaagg tgcactttgt ggcaaagaag 360
tggcaggaag agtcgaaggt cttgttgtca ttgctgcaca ccttctcaaa ctcgccaatg 420
ggggctgggc agacctgccc gggcggccgc tcga 454

-continued

<210> SEQ ID NO 180
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 180
tcgagcggcc gcccgggcag gtctgcccag cccccattgg cgagtttgag aaggngtgca 60
gcaatgacaa caagaccttc gactcttcct gccacttctt tgccacaaag tgcaccctgg 120
agggcaccaa gaagggccac aagctccacc tggactacat cgggccttgc aaatacatcc 180
ccccttgcct ggactctgag ctgaccgaat tccccctgcg catgcgggac tggctcaaga 240
acgtcctggt caccctgtat gagagggatg aggacaacaa ccttctgact gagaagcana 300
agctgcgggt gaagaanatc catgagaatg anaagcgcct gnaggcanga gaccaccccg 360
tggagctgct ggcccgggac ttcgagaaga actataacat gtacatcttc cctgtacact 420
ggcagttcgg ccagacctcg gccgcgacca cgct 454

<210> SEQ ID NO 181
<211> LENGTH: 102
<212> TYPE: DNA
<213> ORGANISM: Homo sapien
<220> FEATURE:
<221> NAME/KEY: misc_feature
<222> LOCATION: (1)...(102)
<223> OTHER INFORMATION: n = A,T,C or G

<400> SEQUENCE: 181
agcgtggntg cggacgacgc ccacaaagcc attgtatgta gttttanttc agctgcaaan 60
aataccncca gcatccacct tactaaccag catatgcaga ca 102

<210> SEQ ID NO 182
<211> LENGTH: 337
<212> TYPE: DNA
<213> ORGANISM: Homo sapien
<220> FEATURE:
<221> NAME/KEY: misc_feature
<222> LOCATION: (1)...(337)
<223> OTHER INFORMATION: n = A,T,C or G

<400> SEQUENCE: 182
tcgagcggtc gcccgggcag gtctgggcgg atagcaccgg gcatattttg gaatggatga 60
ggtctggcac cctgagcagc ccagcgagga cttggtctta gttgagcaat ttggctagga 120
ggatagtatg cagcacggtt ctgagtctgt gggatagctg ccatgaagna acctgaagga 180
ggcgctggct ggtangggtt gattacaggg ctgggaacag ctcgtacact tgccattctc 240
tgcatatact ggntagtgag gcgagcctgg cgctcttctt tgcgctgagc taaagctaca 300
tacaatggct ttgnggacct cggccgcgac cacgctt 337

<210> SEQ ID NO 183
<211> LENGTH: 374
<212> TYPE: DNA
<213> ORGANISM: Homo sapien

<400> SEQUENCE: 183
tcgagcggcc gcccgggcag gtccattttc tccctgacgg tcccacttct ctccaatctt 60

-continued

```
gtagttcaca ccattgtcat gacaccatct agatgaatca catctgaaat gaccacttcc    120

aaagcctaag cactggcaca acagtttaaa gcctgattca gacattcgtt cccactcatc    180

tccaacggca taatgggaaa ctgtgtaggg gtcaaagcac gagtcatccg taggttggtt    240

caagccttcg ttgacagaag ttgcccacgg taacaacctc ttcccgaacc ttatgcctct    300

gctggtcttt caagtgcctc cactatgatg ttgtaggtgg cacctctggt gaggacctcg    360

gccgcgacca cgct                                                      374
```

<210> SEQ ID NO 184
<211> LENGTH: 375
<212> TYPE: DNA
<213> ORGANISM: Homo sapien
<220> FEATURE:
<221> NAME/KEY: misc_feature
<222> LOCATION: (1)...(375)
<223> OTHER INFORMATION: n = A,T,C or G

<400> SEQUENCE: 184

```
agcgtggttt gcggccgagg tcctcaccan aggtgccacc tacaacatca tagtggaggc     60

actgaaagac cagcagaggc ataaggttcg ggaagaggtt gttaccgtgg gcaactctgt    120

caacgaaggc ttgaaccaac ctacggatga ctcgtgcttt gacccctaca cagnttccca    180

ttatgccgtt ggagatgagt gggaacgaat gtctgaatca ggctttaaac tgttgtgcca    240

gtgcttangc tttggaagtg gtcatttcag atgtgattca tctanatggt gtcatgacaa    300

tggtgngaac tacaagattg gagagaagtg gnaccgtcag ggganaaaat ggacctgccc    360

gggcggcncg ctcga                                                     375
```

<210> SEQ ID NO 185
<211> LENGTH: 148
<212> TYPE: DNA
<213> ORGANISM: Homo sapien
<220> FEATURE:
<221> NAME/KEY: misc_feature
<222> LOCATION: (1)...(148)
<223> OTHER INFORMATION: n = A,T,C or G

<400> SEQUENCE: 185

```
agcgtggtcg cggccgaggt ctggcttnct gctcangtga ttatcctgaa ccatccaggc     60

caaataagcg ccggctatgc ccctgnattg gattgccaca cggctcacat tgcatgcaag    120

tttgctgagc tgaaggaaaa gattgatc                                       148
```

<210> SEQ ID NO 186
<211> LENGTH: 397
<212> TYPE: DNA
<213> ORGANISM: Homo sapien
<220> FEATURE:
<221> NAME/KEY: misc_feature
<222> LOCATION: (1)...(397)
<223> OTHER INFORMATION: n = A,T,C or G

<400> SEQUENCE: 186

```
tcgagcggcc gcccgggcag gtccaattga aacaaacagt tctgagaccg ttcttccacc     60

actgattaag agtggggngg cgggtattag ggataatatt catttagcct tctgagcttt    120

ctgggcagac ttggtgacct tgccagctcc agcagccttc tggtccactg ctttgatgac    180

acccaccgca actgtctgtc tcatatcacg aacagcaaag cgacccaaag gtggatagtc    240

tgagaagctc tcaacacaca tgggcttgcc aggaaccata tcaacaatgg gcagcatcac    300

cagacttcaa gaatttaagg gccatcttcc agctttttac cagaacggcg atcaatcttt    360
```

-continued

```
tccttcagct cagcaaactt gcatgcaatg tgagccg                          397


<210> SEQ ID NO 187
<211> LENGTH: 584
<212> TYPE: DNA
<213> ORGANISM: Homo sapien
<220> FEATURE:
<221> NAME/KEY: misc_feature
<222> LOCATION: (1)...(584)
<223> OTHER INFORMATION: n = A,T,C or G

<400> SEQUENCE: 187

tcgagcggcc gcccgggcag gtccagaggg ctgtgctgaa gtttgctgct gccactggag    60

ccactccaat tgctggccgc ttcactcctg gaaccttcac taaccagatc caggcagcct   120

tccgggagcc acggcttctt gtggntactg accccagggc tgaccaccag cctctcacgg   180

aggcatctta tgttaaccta cctaccattg cgctgtgtaa cacagattct cctctgcgct   240

atgtggacat tgccatccca tgcaacaaca agggagctca ctcagngggg tttgatgtgg   300

tggatgctgg ctcgggaagt tctgcgcatg cgtggcacca tttcccgtga acacccatgg   360

gangncatgc ctgatctgga cttctacaga gatcctgaag agattgaaaa agaagaacag   420

gctgnttgct ganaaagcaa gtgaccaagg angaaatttc angggtgaaa nggactgctc   480

ccgctcctga attcactgct actcaacctg angntgcaga ctggtcttga aggngnacan   540

gggccctctg ggcctattta agcancttcg gtcgcgaaca cgnt                    584


<210> SEQ ID NO 188
<211> LENGTH: 579
<212> TYPE: DNA
<213> ORGANISM: Homo sapien
<220> FEATURE:
<221> NAME/KEY: misc_feature
<222> LOCATION: (1)...(579)
<223> OTHER INFORMATION: n = A,T,C or G

<400> SEQUENCE: 188

agcgtgngtc gcggccgagg tgctgaatag gcacagaggg cacctgtaca ccttcagacc    60

agtctgcaac ctcaggctga gtagcagtga actcaggagc gggagcagtc cattcaccct   120

gaaattcctc cttggncact gccttctcag cagcagcctg ctcttctttt tcaatctctt   180

caggatctct gtagaagtac agatcaggca tgacctccca tgggtgttca cgggaaatgg   240

tgccacgcat gcgcagaact tcccgagcca gcatccacca catcaaaccc actgagtgag   300

ctcccttgtt gttgcatggg atgggcaatg tccacatagc gcagaggaga atctgtgtta   360

cacagcgcaa tggtaggtag gttaacataa gatgcctccg cgagaagctg gtggtcagcc   420

ctggggtcaa gtaaccacaa gaagccgtgg ctcccggaag gctgcctgga tctggttagt   480

gaaggntcca ggagtgaagc ggccaacaat tggagtggct tcagtggcaa gcagcaaact   540

tcagcacaag ccctctggac ctgcccggcg gccgctcga                          579


<210> SEQ ID NO 189
<211> LENGTH: 374
<212> TYPE: DNA
<213> ORGANISM: Homo sapien
<220> FEATURE:
<221> NAME/KEY: misc_feature
<222> LOCATION: (1)...(374)
<223> OTHER INFORMATION: n = A,T,C or G

<400> SEQUENCE: 189
```

-continued

```
tcgagcggcc gcccgggcag gtccattttc tccctgacgg ncccacttct ctccaatctt     60

gtagttcaca ccattgtcat ggcaccatct agatgaatca catctgaaat gaccacttcc    120

aaagcctaag cactggcaca acagtttaaa gcctgattca gacattcgtt cccactcatc    180

tccaacggca taatgggaaa ctgtgtaggg gtcaaagcac gagtcatccg taggttggtt    240

caagccttcg ttgacagagt tgcccacggt aacaacctcn tccccgaacc ttatgcctct    300

gctgggcttt cagngcctcc actatgatgn tgtagggggg cacctctggn gangacctcg    360

gccgcgacca cgct                                                      374
```

<210> SEQ ID NO 190
<211> LENGTH: 373
<212> TYPE: DNA
<213> ORGANISM: Homo sapien
<220> FEATURE:
<221> NAME/KEY: misc_feature
<222> LOCATION: (1)...(373)
<223> OTHER INFORMATION: n = A,T,C or G

<400> SEQUENCE: 190

```
agcgtggtcg cggccgaggt cctcaccaga ggtgccacct acaacatcat agtggaggca     60

ctgaaagacc agcagaggca taaggctcgg gaagaggttg ttaccgtggg caactctgtc    120

aacgaaggct tgaaccaacc tacggatgac tcgtgctttg acccctacac agtttcccat    180

tatgccgttg gagatgagtg ggaacgaatg tctgaatcag gctttaaact gttgtgccag    240

tgcttangct ttggaagtgg gtcatttcag atgtgattca tctagatggt gccatgacaa    300

tggngngaac tacaagattg gagagaagtg gnaccgncag ggagaaaatg gacctgcccg    360

ggcggccgct cga                                                       373
```

<210> SEQ ID NO 191
<211> LENGTH: 354
<212> TYPE: DNA
<213> ORGANISM: Homo sapien
<220> FEATURE:
<221> NAME/KEY: misc_feature
<222> LOCATION: (1)...(354)
<223> OTHER INFORMATION: n = A,T,C or G

<400> SEQUENCE: 191

```
agcgtggtcg cggccgaggt ccacatcggc agggtcggag ccctggccgc catactcgaa     60

ctggaatcca tcggtcatgc tctcgccgaa ccagacatgc ctcttgtcct tggggttctt    120

gctgatgtac cagttcttct gggccacact gggctgagtg gggtacacgc aggtctcacc    180

agtctccatg ttgcagaaga ctttgatggc atccaggntg caaccttggt tggggtcaat    240

ccagtactct ccactcttcc agccagagtg gcacatcttg aggtcacggc aggtgcggnc    300

gggggntttt gcggctgccc tctggncttc ggntgtnctc natctgctgg ctca          354
```

<210> SEQ ID NO 192
<211> LENGTH: 587
<212> TYPE: DNA
<213> ORGANISM: Homo sapien
<220> FEATURE:
<221> NAME/KEY: misc_feature
<222> LOCATION: (1)...(587)
<223> OTHER INFORMATION: n = A,T,C or G

<400> SEQUENCE: 192

```
tcgagcggcc gcccgggcag gtctcgcggt cgcactggtg atgctggtcc tgttggtccc     60

cccggccctc ctggacctcc tggccccccct ggtcctccca gcgctggttt cgacttcagc    120
```

-continued

```
ttcctgcccc agccacctca agagaaggct cacgatggtg gccgctacta ccgggctgat    180

gatgccaatg tggttcgtga ccgtgacctc gaggtggaca ccaccctcaa gagcctgagc    240

cagcagatcg agaacatccg gagcccagag ggcagncgca agaaccccgc ccgcacctgc    300

cgtgacctca agatgtgcca ctctgactgg aagagtggag agtactggat tgaccccaac    360

caagctgcaa cctggatgcc atcaaagtct tctgcaacat ggagactggt gagacctgcg    420

tgtaccccac tcagcccagt gtggcccaaa agaactggta catcagcaag aaccccaagg    480

acaagaagca tgtctggttc ggcgagaaca tgaccgatgg attccagttc gagtatggcg    540

ggcagggctc cgaccctgcc gatggggacc ttggccgcga acacgct                  587
```

<210> SEQ ID NO 193
<211> LENGTH: 98
<212> TYPE: DNA
<213> ORGANISM: Homo sapien
<220> FEATURE:
<221> NAME/KEY: misc_feature
<222> LOCATION: (1)...(98)
<223> OTHER INFORMATION: n = A,T,C or G

<400> SEQUENCE: 193

```
agcgtggnng cggccgaggt ataaatatcc agnccatatc ctccctccac acgctganag     60

atgaagctgt ncaaagatct cagggtggan aaaaccat                             98
```

<210> SEQ ID NO 194
<211> LENGTH: 240
<212> TYPE: DNA
<213> ORGANISM: Homo sapien

<400> SEQUENCE: 194

```
tcgagcggcc gcccgggcag gtccttcaga cttggactgt gtcacactgc caggcttcca     60

gggctccaac ttgcagacgg cctgttgtgg gacagtctct gtaatcgcga aagcaaccat    120

ggaagacctg ggggaaaaca ccatggtttt atccaccctg agatctttga acaacttcat    180

ctctcagcgt gcggagggag gctctggact ggatatttct acctcggccg cgaccacgct    240
```

<210> SEQ ID NO 195
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 195

```
cgagcgggcg accgggcagg tncagactcc aatccanana accatcaagc cagatgtcag     60

aagctacacc atcacaggtt tacaaccagg cactgactac aaganctacc tgcacacctt    120

gaatgacaat gctcggagct cccctgtggt catcgacgcc tccactgcca ttgatgcacc    180

atccaacctg cgtttcctgg ccaccacacc caattccttg ctggtatcat ggcagccgcc    240

acgtgccagg attaccggta catcatcnag tatganaagc ctgggcctcc tcccagagaa    300

gnggtccctc ggccccgccc tgntgtccca naggntacta ttactgngcc ngcaaccggc    360

aaccgatatc nattttgnca ttggccttca acaataatta                           400
```

<210> SEQ ID NO 196
<211> LENGTH: 494
<212> TYPE: DNA

-continued

<213> ORGANISM: Homo sapien
<220> FEATURE:
<221> NAME/KEY: misc_feature
<222> LOCATION: (1)...(494)
<223> OTHER INFORMATION: n = A,T,C or G

<400> SEQUENCE: 196
agcgtggttc gcggccgang tcctgtcaga gtggcactgg tagaagttcc aggaaccctg 60
aactgtaagg gttcttcatc agngccaaca ggatgacatg aaatgatgta ctcagaagtg 120
tcctggaatg gggcccatga gatggttgtc tgagagagag cttcttgncc tgtctttttc 180
cttccaatca ggggctcgct cttctgatta ttcttcaggg caatgacata aattgtatat 240
tcgggtcccg gntccaggcc agtaatagta ncctctgtga caccagggcg gngccgaggg 300
accacttctc tgggaggaga cccaggcttc tcatacttga tgatgtaacc ggtaatcctg 360
gcacgtggcg gctgccatga taccagcaag gaattggggt gtggtggcca ggaaacgcag 420
gttggatggn gcatcaatgg cagtggaggc cgtcgatgac cacaggggga gctccgacat 480
tgtcattcaa ggtg 494

<210> SEQ ID NO 197
<211> LENGTH: 118
<212> TYPE: DNA
<213> ORGANISM: Homo sapien
<220> FEATURE:
<221> NAME/KEY: misc_feature
<222> LOCATION: (1)...(118)
<223> OTHER INFORMATION: n = A,T,C or G

<400> SEQUENCE: 197
agcgtggncg cggccgaggt gcagcgcggg ctgtgccacc ttctgctctc tgcccaacga 60
taaggagggt ncctgccccc aggagaacat taactntccc cagctcggcc tctgccgg 118

<210> SEQ ID NO 198
<211> LENGTH: 403
<212> TYPE: DNA
<213> ORGANISM: Homo sapien
<220> FEATURE:
<221> NAME/KEY: misc_feature
<222> LOCATION: (1)...(403)
<223> OTHER INFORMATION: n = A,T,C or G

<400> SEQUENCE: 198
tcgagcggcc gcccgggcag gtttttttttg ctgaaagtgg ntactttatt ggntgggaaa 60
gggagaagct gtggtcagcc caagagggaa tacagagncc cgaaaaaggg gagggcaggt 120
gggctggaac cagacgcagg gccaggcaga aactttctct cctcactgct cagcctggtg 180
gtggctggag ctcanaaatt gggagtgaca caggacacct tcccacagcc attgcggcgg 240
catttcatct ggccaggaca ctggctgtcc acctggcact ggtcccgaca gaagcccgag 300
ctggggaaag ttaatgttca cctgggggca ggaaccctcc ttatcattgn gcagagagca 360
gaaggtggca cagcccgcgc tgcacctcgg ccgcgaccac gct 403

<210> SEQ ID NO 199
<211> LENGTH: 167
<212> TYPE: DNA
<213> ORGANISM: Homo sapien
<220> FEATURE:
<221> NAME/KEY: misc_feature
<222> LOCATION: (1)...(167)
<223> OTHER INFORMATION: n = A,T,C or G

<400> SEQUENCE: 199
tcgagcggcc gcccgggcag gtccaccata agtcctgata caaccacgga tgagctgtca 60
ggagcaaggt tgatttcttt cattggtccg gncttctcct tgggggncac ccgcactcga 120
tatccagtga gctgaacatt gggtggcgtc cactgggcgc tcaggct 167

<210> SEQ ID NO 200
<211> LENGTH: 252
<212> TYPE: DNA
<213> ORGANISM: Homo sapien
<220> FEATURE:
<221> NAME/KEY: misc_feature
<222> LOCATION: (1)...(252)
<223> OTHER INFORMATION: n = A,T,C or G

<400> SEQUENCE: 200
tcgagcggtt cgcccgggca ggtccaccac acccaattcc ttgctggtat catggcagcc 60
gccacgtgcc aggattaccg gctacatcat caagtatgag aagcctgggt ctcctcccag 120
agaagcggtc cctcggcccc gccctggtgt cacagaggct actattactg gcctggaacc 180
gggaaccgaa tatacaattt atgtcattgn cctgaagaat aatcannaan agcgancccc 240
tgattggaag ga 252

<210> SEQ ID NO 201
<211> LENGTH: 91
<212> TYPE: DNA
<213> ORGANISM: Homo sapien

<400> SEQUENCE: 201
agcgtggtcg cggccgaggt tgtacaagct tttttttttt tttttttttt tttttttttt 60
tttttttttt tttttttttt tttttttttt t 91

<210> SEQ ID NO 202
<211> LENGTH: 368
<212> TYPE: DNA
<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 202
tcgagcggnc gcccgggcag gtctgccaac accaagattg gcccccgccg catccacaca 60
gtccgtgtgc ggggaggtaa caagaaatac cgtgccctga ggttggacgt ggggaatttc 120
tcctggggct cagagtgttg tactcgtaaa acaaggatca tcgatgttgt ctacaatgca 180
tctaataacg agctggttcg taccaagacc ctggtgaaga attgcatcgt gctcatcgac 240
agcacaccgt accgacagtg gtacgagtcc cactatgcgc tgcccctggg ccgcaagaag 300
ggagccaagc tgactcctga ggaagaagag attttaaaca aaaaacgatc taanaaaaaa 360
aaaacaat 368

<210> SEQ ID NO 203
<211> LENGTH: 340
<212> TYPE: DNA
<213> ORGANISM: Homo sapien

<400> SEQUENCE: 203
agcgtggtcg cggccgaggt gaaatggtat tcagcttcct ggcacttctg gtcagcaacc 60
cagtgttggg caacaaatga tctttgagga acatggtttt aggcggacca caccgcccac 120
aacggccacc cccataaggc ataggccaag accatacccg ccgaatgtag gacaagaagc 180
tctctctcag acaaccatct catgggcccc attccaggac acttctgagt acatcatttc 240
atgtcatcct gttggcactg atgaagaacc cttacagttc agggttcctg gaacttctac 300
cagtgccact ctgacaggac ctgcccgggc ggccgctcga 340

<210> SEQ ID NO 204
<211> LENGTH: 341
<212> TYPE: DNA
<213> ORGANISM: Homo sapien

<400> SEQUENCE: 204
tcgagcggcc gcccgggcag gtcctgtcag agtggcactg gtagaagttc caggaaccct 60
gaactgtaag ggttcttcat cagtgccaac aggatgacat gaaatgatgt actcagaagt 120
gtcctggaat ggggcccatg agatggttgt ctgagagaga gcttcttgtc ctacattcgg 180
cgggtatggt cttggcctat gccttatggg ggtggccgtt gtgggcggtg tggtccgcct 240
aaaaccatgt tcctcaaaga tcatttgttg cccaacactg ggttgctgac cagaagtgcc 300
aggaagctga ataccatttc acctcggccg cgaccacgct a 341

<210> SEQ ID NO 205
<211> LENGTH: 770
<212> TYPE: DNA
<213> ORGANISM: Homo sapien
<220> FEATURE:
<221> NAME/KEY: misc_feature
<222> LOCATION: (1)...(770)
<223> OTHER INFORMATION: n = A,T,C or G

<400> SEQUENCE: 205
tcgagcggcc gcccgggcag gtctcccttc ttgcggccca ggggcagcgc atagtgggac 60
tcgtaccact gtcggtacgg tgtgctgtcg atgagcacga tgcaattctt caccagggtc 120
ttggtacgaa ccagctcgtt attagatgca ttgtagacaa catcgatgat ccttgtttta 180
cgagtacaac actctgagcc ccaggagaaa ttccccacgt ccaacctcag ggcacggtat 240
ttcttgttac ctccccgcac acggactgtg tggatgcggc gggggccaag ctgactcctg 300
aggaagaaga gattttaaac aaaaaacgat ctaaaaaaat tcagaagaaa tatgatgaaa 360
ggaaaaagaa tgccaaaatc agcagtctcc tggaggagca gttccagcag ggcaagcttc 420
ttgcgtgcat cgcttcaagg ccgggacagt gtgaccgagc agatggctat gtgctagagg 480
gcaaagaagt ggagttctat cttaagaaaa tcagggccca gaatggtgng tcttcaacta 540
atccaaaggg gagtttcaga ccagtgcaat cagcaaaaac attgatactg ntggccaaat 600
ttattggtgc agggcttgca cantangann ggctgggtct tggggcttgg attggnacaa 660
gctttggcag ccttttcttt ggttttgcca aaaacctttt gntgaagang anacctnggg 720
cggacccctt aaccgattcc acnccnggng gcgttctang gncccncttg 770

<210> SEQ ID NO 206
<211> LENGTH: 810
<212> TYPE: DNA
<213> ORGANISM: Homo sapien
<220> FEATURE:
<221> NAME/KEY: misc_feature
<222> LOCATION: (1)...(810)
<223> OTHER INFORMATION: n = A,T,C or G

<400> SEQUENCE: 206
agcgtggtcg cggccgaggt ctgctgcttc agcgaagggt ttctggcata accaatgata 60

-continued

```
aggctgccaa agactgttcc aataccagca ccagaaccag ccactcctac tgttgcagca    120

cctgcaccaa taaatttggc agcagtatca atgtctctgc tgattgcact ggtctgaaac    180

tccctttgga ttagctgaga cacaccattc tgggccctga ttttcctaag atagaactcc    240

aactctttgc cctctagcac atagccatct gctcggtcac actgtcccgg ccttgaagcg    300

atgcacgcaa gaagcttgcc ctgctggaac tgctcctcca ggagactgct gattttggca    360

ttctttttcc tttcatcata tttcttctga attttttag atcgtttttt gtttaaaatc    420

tcttcttcct caggagtcag cttggccccc gccgcatcca cacagtccgt gtgcggggag    480

gtaacaagaa ataccgtgcc ctgaggttgg acgtggggaa tttctcctgg ggctcagagt    540

ggtgtactcg taaaacaagg atcatcgatg gtgnctacaa tgcatctaat aacgagctgg    600

gtcggaccca aagaacctgg ngaanaaatg gatcgnctca tcgacaggac accgtacccg    660

acaggggnac gantcccact atgcgcttgc ccctgggccg caanaaagga aaactgcccg    720

ggcggccntc gaaagcccaa ttntggaaaa aatccatcac actgggnggc cngtcgagca    780

tgcatntana ggggcccatt ccccctnann                                     810
```

<210> SEQ ID NO 207
<211> LENGTH: 257
<212> TYPE: DNA
<213> ORGANISM: Homo sapien

<400> SEQUENCE: 207

```
tcgagcggcc gcccgggcag gtccccaacc aaggctgcaa cctggatgcc atcaaagtct     60

tctgcaacat ggagactggt gagacctgcg tgtaccccac tcagcccagt gtggcccaga    120

agaactggta catcagcaag aaccccaagg acaagaggca tgtctggttc ggcgagagca    180

tgaccgatgg attccagttc gagtatggcg gccagggctc cgaccctgcc gatgtggacc    240

tcggccgcga ccacgct                                                   257
```

<210> SEQ ID NO 208
<211> LENGTH: 257
<212> TYPE: DNA
<213> ORGANISM: Homo sapien

<400> SEQUENCE: 208

```
agcgtggtcg cggccgaggt ccacatcggc agggtcggag ccctggccgc catactcgaa     60

ctggaatcca tcggtcatgc tctcgccgaa ccagacatgc ctcttgtcct tggggttctt    120

gctgatgtac cagttcttct gggccacact gggctgagtg gggtacacgc aggtctcacc    180

agtctccatg ttgcagaaga ctttgatggc atccaggttg cagccttggt tggggacctg    240

cccgggcggc cgctcga                                                   257
```

<210> SEQ ID NO 209
<211> LENGTH: 747
<212> TYPE: DNA
<213> ORGANISM: Homo sapien
<220> FEATURE:
<221> NAME/KEY: misc_feature
<222> LOCATION: (1)...(747)
<223> OTHER INFORMATION: n = A,T,C or G

<400> SEQUENCE: 209

```
tcgagcggcc gcccgggcag gtccaccaca cccaattcct tgctggtatc atggcagccg     60

ccacgtgcca ggattaccgg ctacatcatc aagtatgaga agcctgggtc tcctcccaga    120
```

-continued

```
gaagtggtcc ctcggccccg ccctggtgtc acagaggcta ctattactgg cctggaaccg    180

ggaaccgaat atacaattta tgtcattgcc ctgaagaata atcagaagag cgagcccctg    240

attggaagga aaaagacaga cgagcttccc caactggtaa cccttccaca ccccaatctt    300

catggaccag agatcttgga tgttccttcc acagttcaaa agaccccttt cgtcacccac    360

cctgggtatg acactggaaa tggtattcag cttcctggca cttctggtca gcaacccagt    420

gttgggcaac aaatgatctt tgaggaacat ggntttaggc ggaccacacc gcccacaacg    480

gccaccccca taaggcatag gccaagacca tacccgccga atgtaggaca agaagctntn    540

tntcanacac catntnatgg gccccattcc aggacacttc tgagtacatc atttatgnca    600

tctgtggcac ttgatgaaaa cccttacagt tcagggttct ggaactttta ccaggcctnt    660

tacaggactn ggccggacnc cttaagccna ttncaccctg gggcgttcta nggtcccact    720

cgnncactgg ngaaaatggc tactgtn                                        747
```

<210> SEQ ID NO 210
<211> LENGTH: 872
<212> TYPE: DNA
<213> ORGANISM: Homo sapien
<220> FEATURE:
<221> NAME/KEY: misc_feature
<222> LOCATION: (1)...(872)
<223> OTHER INFORMATION: n = A,T,C or G

<400> SEQUENCE: 210

```
agcgtggtcg cggccgaggt ccactagagg tctgtgtgcc attgcccagg cagagtctct     60

gcgttacaaa ctcctaggag ggcttgctgt gcggagggcc tgctatggtg tgctgcggtt    120

catcatggag agtggggcca aaggctgcga ggttgtggtg tctgngaaac tccnaggaca    180

ngagggctaa attccatgaa gtttgtggat ggcctgatga tccacaatcg gagaccctgt    240

taactactac cgtctnaccn cctgctgtnc ncccccnttt ctgctnaana catngggntn    300

ntncttgncc ntccttgggt ngaanatnna atngcctncc cnttcntanc nctactngnt    360

ccananttgg cctttaaana atccnccttg ccttnnncac tgttcanntn tttnntcgta    420

aaccctatna nttnnattan atnntnnnnn nctcaccccc ctcntcattn anccnatang    480

ctnnnaantc cttnanncct cccncccnnt ncnctcntac tnantncttc tnncccatta    540

cnnagctctt tcntttaana taatgnngcc nngctctnca tntctacnat ntgnnnaatn    600

cccccncccc cnancgnntt tttgacctnn naacctcctt tcctcttccc tncnnaaatt    660

ncnnanttcc ncnttccnnc ntttcggntn ntcccatnct ttccannnct tcantctanc    720

ncnctncaac ttattttcct ntcatccctt nttctttaca nncccccctnn tctactcnnc    780

nnttncatta natttgaaac tnccacnnct anttncctcn ctctacnntt ttattttncg    840

ntcnctctac ntaatantttt aatnanttnt cn                                 872
```

<210> SEQ ID NO 211
<211> LENGTH: 517
<212> TYPE: DNA
<213> ORGANISM: Homo sapien
<220> FEATURE:
<221> NAME/KEY: misc_feature
<222> LOCATION: (1)...(517)
<223> OTHER INFORMATION: n = A,T,C or G

<400> SEQUENCE: 211

```
tcgagcggcc gcccgggcag gtctgccaag gagaccctgt tatgctgtgg ggactggctg     60

gggcatggca ggcggctctg gcttcccacc cttctgttct gagatggggg tggtgggcag    120
```

-continued

```
tatctcatct ttgggttcca caatgctcac gtggtcaggc aggggcttct tagggccaat    180

cttaccagtt gggtcccagg gcagcatgat cttcaccttg atgcccagca caccctgtct    240

gagcaacacg tggcgcacaa gcagtgtcaa cgtagtaagt taacagggtc tccgctgtgg    300

atcatcaggc catccacaaa cttcatggat ttagccctct gtcctcggag tttcccagac    360

accacaacct cgcagccttt ggccccactc tccatgatga accgcagcac accatagcag    420

gccctccgca caagcaagcc ctcctaagaa tttgtaacgc ananactctg ctggcaatgg    480

cacacaaacc tctagtggac ctcggncgcg accacgc                             517
```

```
<210> SEQ ID NO 212
<211> LENGTH: 695
<212> TYPE: DNA
<213> ORGANISM: Homo sapien
<220> FEATURE:
<221> NAME/KEY: misc_feature
<222> LOCATION: (1)...(695)
<223> OTHER INFORMATION: n = A,T,C or G

<400> SEQUENCE: 212

tcgagcggcc gcccgggcag gtctggtcca ggatagcctg cgagtcctcc tactgctact     60

ccagacttga catcatatga atcatactgg ggagaatagt tctgaggacc agtagggcat    120

gattcacaga ttccaggggg gccaggagaa ccaggggacc ctggttgtcc tggaatacca    180

gggtcaccat ttctcccagg aataccagga gggcctggat ctcccttggg gccttgaggt    240

ccttgaccat taggagggcg agtaggagca gttggaggct gtgggcaaac tgcacaacat    300

tctccaaatg gaatttctgg gttggggcag tctaattctt gatccgtcac atattatgtc    360

atcgcagaga acggatcctg agtcacagac acatatttgg catggttctg gcttccagac    420

atctctatcc gncataggac tgaccaagat gggaacatcc tccttcaaca agcttnctgt    480

tgtgccaaaa ataatagtgg gatgaagcag accgagaagt anccagctcc cctttttgca    540

caaagcntca tcatgtctaa atatcagaca tgagacttct ttgggcaaaa aaggagaaaa    600

agaaaaagca gttcaaagta nccnccatca agttggttcc ttgcccnttc agcacccggg    660

ccccgttata aaacacctng ggccggaccc ccctt                               695
```

```
<210> SEQ ID NO 213
<211> LENGTH: 804
<212> TYPE: DNA
<213> ORGANISM: Homo sapien
<220> FEATURE:
<221> NAME/KEY: misc_feature
<222> LOCATION: (1)...(804)
<223> OTHER INFORMATION: n = A,T,C or G

<400> SEQUENCE: 213

agcgtggtcg cggccgaggt gttttatgac gggcccggtg ctgaagggca gggaacaact     60

tgatggtgct actttgaact gcttttcttt tctccttttt gcacaaagag tctcatgtct    120

gatatttaga catgatgagc tttgtgcaaa aggggagctg gctacttctc gctctgcttc    180

atcccactat tattttggca caacaggaag ctgttgaagg aggatgttcc catcttggtc    240

agtcctatgc ggatagagat gtctggaagc cagaaccatg ccaaatatgt gtctgtgact    300

caggatccgt tctctgcgat gacataatat gtgacgatca agaattagac tgccccaacc    360

cagaaattcc atttggagaa tgttgtgcag tttgcccaca gcctccaact gctcctactc    420

gccctcctaa tggtcaagga cctcaaggcc ccaagggaga tccaggccct cctggtattc    480
```

-continued

```
ctgggagaaa tggtgaccct ggtattccag gacaaccagg gtcccctggt tctcctggcc    540

cccctggaat cnggngaatc atgccctact ggtcctcaaa ctattctccc anatgattca    600

tatgatgtca agtctgggat agcnagtang ganggactcg caggctattc tggaccanac    660

ctgccggggg ggcgttcgaa agcccgaatc tgcanannth cnttcacact ggcggccgtc    720

gagctgcttt aaaagggcca ttccnccttt agngnggggg antacaatta ctnggcggcg    780

ttttanancg cgngnctggg aaat                                            804
```

<210> SEQ ID NO 214
<211> LENGTH: 594
<212> TYPE: DNA
<213> ORGANISM: Homo sapien
<220> FEATURE:
<221> NAME/KEY: misc_feature
<222> LOCATION: (1)...(594)
<223> OTHER INFORMATION: n = A,T,C or G

<400> SEQUENCE: 214

```
agcgtggtcg cggccgaggt ccacatcggc agggtcggag ccctggccgc catactcgaa     60

ctggaatcca tcggtcatgc tctcgccgaa ccagacatgc ctcttgtcct tggggttctt    120

gctgatgtac cagttcttct gggccacact gggctgagtg gggtacacgc aggtctcacc    180

agtctccatg ttgcagaaga ctttgatggc atccaggttg cagccttggt tggggtcaat    240

ccagtactct ccactcttcc agtcagagtg gcacatcttg aggtcacggc aggtgcgggc    300

ggggttcttg cggctgccct ctgggctccg gatgttctcg atctgctggc tcaggctctt    360

gagggtggtg tccacctcga ggtcacggtc acgaaccaca ttggcatcat cagcccggta    420

gtagcggcca ccatcgtgag ccttctcttg angtggctgg ggcaggaact gaagtcgaaa    480

ccagcgctgg gaggaccagg gggaccaana ggtccaggaa gggcccgggg gggaccaaca    540

ggaccagcat caccaagtgc gacccgcgag aacctgcccg gccgnccgct cgaa          594
```

<210> SEQ ID NO 215
<211> LENGTH: 590
<212> TYPE: DNA
<213> ORGANISM: Homo sapien
<220> FEATURE:
<221> NAME/KEY: misc_feature
<222> LOCATION: (1)...(590)
<223> OTHER INFORMATION: n = A,T,C or G

<400> SEQUENCE: 215

```
tcgagcgnnc gcccgggcag gtctcgcggt cgcactggtg atgctggtcc tgttggtccc     60

cccggccctc ctggacctcc tggtccccct ggtcctccca gcgctggttt cgacttcagc    120

ttcctgcccc agccacctca agagaaggct cacgatggtg gccgctacta ccgggctgat    180

gatgccaatg tggttcgtga ccgtgacctc gaggtggaca ccaccctcaa gagcctgagc    240

cagcagatcg agaacatccg gagcccagag ggcagccgca agaaccccgc ccgcacctgc    300

cgtgacctca agatgtgcca ctctgactgg aagagtggag agtactggat tgaccccaac    360

caaggctgca acctggatgc catcaaagtc ttctgcaaca tggagactgg tgagacctgc    420

gtgtacccca ctcagcccag tgtggcccag aagaactggt acatcagcaa gaaccccaag    480

gacaagaggc atgtctggtt cggcgagagc atgaccgatg gattccagtt cgagtatggc    540

ggccagggct cccaccctgc cgatgtggac ctccggccgc gaccaccctt               590
```

<210> SEQ ID NO 216
<211> LENGTH: 801

-continued

<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 216
tngagcggcc gcccgggcag gntgnnaacg ctggtcctgc tggtcctcct ggcaaggctg 60
gtgaagatgg tcaccctgga aaacccggac gacctggtga gagaggagtt gttggaccac 120
agggtgctcg tggtttccct ggaactcctg gacttcctgg cttcaaaggc attaggggac 180
acaatggtct ggatggattg aagggacagc ccggtgctcc tggtgtgaag ggtgaacctg 240
gtgcccctgg tgaaaatgga actccaggtc aaacaggagc ccgtgggctt cctggtgaga 300
gaggaccgtg ttggtgcccc tggcccanac ctcggccgcg accacgctaa gcccgaattt 360
ccagcacact ggnggccgtt actantggat ccgagctcgg taccaagctt ggcgtaatca 420
tggtcatagc tgtttcctgn gtgaaattgt tatccgctca caatttcaca cancatacga 480
agccggaaag cataaagtgt aaagccttgg ggtgctaatg agtgagctaa ctcncattaa 540
attgcgttgc gctcactgcc cgcttttcca nnngggaaac cntggcntng ccngcttgcn 600
ttaantgaaa tccgccnacc cccggggaaa agncggtttg cngtattggg gcncttttc 660 cctttcctcg gnttacttga nttantgggc tttggncgnt tcgggttgng gcgancnggt 720
tcaacntcac nccaaaggng gnaanacggt tttcccanaa tccgggggnt ancccaangn 780
aaaacatnng ncnaangggc t 801

<210> SEQ ID NO 217
<211> LENGTH: 349
<212> TYPE: DNA
<213> ORGANISM: Homo sapien
<220> FEATURE:
<221> NAME/KEY: misc_feature
<222> LOCATION: (1)...(349)
<223> OTHER INFORMATION: n = A,T,C or G

<400> SEQUENCE: 217
agcgtggttn gcggccgagg tctgggccag gggcaccaac acgtcctctc tcaccaggaa 60
gcccacgggc tcctgtttga cctggagttc cattttcacc aggggcacca ggttcaccct 120
tcacaccagg agcaccgggc tgtcccttca atccatncag accattgtgn cccctaatgc 180
ctttgaagcc aggaagtcca ggagttccag ggaaaccacc gagcaccctg tggtccaaca 240
actcctctct caccaggtcg tccgggtttt ccagggtgac catcttcacc agccttgcca 300
ggaggaccag caggaccagc gttaccaacc tgcccgggcg gccgctcga 349

<210> SEQ ID NO 218
<211> LENGTH: 372
<212> TYPE: DNA
<213> ORGANISM: Homo sapien

<400> SEQUENCE: 218
tcgagcggcc gcccgggcag gtccattttc tccctgacgg tcccacttct ctccaatctt 60
gtagttcaca ccattgtcat ggcaccatct agatgaatca catctgaaat gaccacttcc 120
aaagcctaag cactggcaca acagtttaaa gcctgattca gacattcgtt cccactcatc 180
tccaacggca taatgggaaa ctgtgtaggg gtcaaagcac gagtcatccg taggttggtt 240
caagccttcg ttgacagagt tgcccacggt aacaacctct tcccgaacct tatgcctctg 300

-continued

```
ctggtctttc agtgcctcca ctatgatgtt gtaggtggca cctctggtga ggacctcggc    360

cgcgaccacg ct                                                        372


<210> SEQ ID NO 219
<211> LENGTH: 374
<212> TYPE: DNA
<213> ORGANISM: Homo sapien

<400> SEQUENCE: 219

agcgtggtcg cggccgaggt cctcaccaga ggtgccacct acaacatcat agtggaggca     60

ctgaaagacc agcagaggca taaggttcgg gaagaggttg ttaccgtggg caactctgtc    120

aacgaaggct tgaaccaacc tacggatgac tcgtgctttg acccctacac agtttcccat    180

tatgccgttg gagatgagtg ggaacgaatg tctgaatcag gctttaaact gttgtgccag    240

tgcttaggct ttggaagtgg tcatttcaag atgtgattca tctagatggt gccatgacaa    300

tggtgtgaac tacaagattg gagagaagtg ggaccgtcag ggagaaaatg gacctgcccg    360

ggccggccgc tcga                                                      374


<210> SEQ ID NO 220
<211> LENGTH: 828
<212> TYPE: DNA
<213> ORGANISM: Homo sapien
<220> FEATURE:
<221> NAME/KEY: misc_feature
<222> LOCATION: (1)...(828)
<223> OTHER INFORMATION: n = A,T,C or G

<400> SEQUENCE: 220

tcgagcgnnc gcccgggcag gtccagtagt gccttcggga ctgggttcac ccccaggtct     60

gcggcagttg tcacagcgcc agccccgctg gcctccaaag catgtgcagg agcaaatggc    120

accgagatat tccttctgcc actgttctcc tacgtggtat gtcttcccat catcgtaaca    180

cgttgcctca tgagggtcac acttgaattc tccttttccg ttcccaagac atgtgcagct    240

catttggctg gctctatagt ttggggaaag tttgttgaaa ctgtgccact gacctttact    300

tcctccttct ctactggagc tttcgtacct tccacttctg ctgttggtaa aatggtggat    360

cttctatcaa tttcattgac agtacccact tctcccaaac atccagggaa atagtgattt    420

cagagcgatt aggagaacca aattatgggg cagaaataag gggcttttcc acaggttttc    480

ctttggagga agatttcagt ggtgacttta aaagaatact caacagtgtc ttcatcccca    540

tagcaaaaga agaaacngta aatgatggaa ngcttctgga gatgccnnca tttaagggac    600

ncccagaact tcaccatcta caggacctac ttcagtttac annaagncac atantctgac    660

tcanaaagga cccaagtagc nccatggnca gcactttnag cctttcccct ggggaaaann    720

ttacnttctt aaancctngg ccnngacccc cttaagncca aattntggaa aanttccntn    780

cnnctggggg gcngttcnac atgcntttna agggcccaat tnccccnt                 828


<210> SEQ ID NO 221
<211> LENGTH: 476
<212> TYPE: DNA
<213> ORGANISM: Homo sapien

<400> SEQUENCE: 221

tcgagcggcc gcccgggcag gtgtcggagt ccagcacggg aggcgtggtc ttgtagttgt     60

tctccggctg cccattgctc tcccactcca cggcgatgtc gctgggatag aagcctttga    120

ccaggcaggt caggctgacc tggttcttgg tcatctcctc ccgggatggg ggcagggtgt    180
```

-continued acacctgtgg ttctcggggc tgccctttgg ctttggagat ggttttctcg atgggggctg 240
ggagggcttt gttggagacc ttgcacttgt actccttgcc attcagccag tcctggtgca 300
ggacggtgag gacgctgacc acacggtacg tgctgttgta ctgctcctcc cgcggctttg 360
tcttggcatt atgcacctcc acgccgtcca cgtaccagtt gaacttgacc tcagggtctt 420
cgtggctcac gtccaccacc acgcatgtaa cctcagacct cggccgcgac cacgct 476

<210> SEQ ID NO 222
<211> LENGTH: 477
<212> TYPE: DNA
<213> ORGANISM: Homo sapien

<400> SEQUENCE: 222
agcgtggtcg cggccgaggt ctgaggttac atgcgtggtg gtggacgtga gccacgaaga 60
ccctgaggtc aagttcaact ggtacgtgga cggcgtggag gtgcataatg ccaagacaaa 120
gccgcgggag gagcagtaca acagcacgta ccgtgtggtc agcgtcctca ccgtcctgca 180
ccaggactgg ctgaatggca aggagtacaa gtgcaaggtc tccaacaaag ccctcccagc 240
ccccatcgag aaaaccatct ccaaagccaa agggcaagcc ccgagaacca caggtgtaca 300
ccctgccccc atcccgggag gagatgacca agaaccaggt cagcctgacc tgcctggtca 360
aaggcttcta tcccagcgac atcgccgtgg agtgggagag caatgggcag ccggagaaca 420
actacaagac cacgcctccc gtgctggact ccgacacctg cccgggcggc cgctcga 477

<210> SEQ ID NO 223
<211> LENGTH: 361
<212> TYPE: DNA
<213> ORGANISM: Homo sapien

<400> SEQUENCE: 223
tcgagcggcc gcccgggcag gttgaatggc tcctcgctga ccaccccggt gctggtggtg 60
ggtacagagc tccgatgggt gaaaccattg acatagagac tgtccctgtc cagggtgtag 120
gggcccagct cagtgatgcc gtgggtcagc tggctcagct tccagtacag ccgctctctg 180
tccagtccag ggcttttggg gtcaggacga tgggtgcaga cagcatccac tctggtggct 240
gccccatcct tctcaggcct gagcaaggtc agtctgcaac cagagtacag agagctgaca 300
ctggtgttct tgaacaaggg cataagcaga ccctgaagga cacctcggcc gcgaccacgc 360
t 361

<210> SEQ ID NO 224
<211> LENGTH: 361
<212> TYPE: DNA
<213> ORGANISM: Homo sapien

<400> SEQUENCE: 224
agcgtggtcg cggccgaggt gtccttcagg gtctgcttat gcccttgttc aagaacacca 60
gtgtcagctc tctgtactct ggttgcagac tgaccttgct caggcctgag aaggatgggg 120
cagccaccag agtggatgct gtctgcaccc atcgtcctga ccccaaaagc cctggactgg 180
acagagagcg gctgtactgg aagctgagcc agctgaccca cggcatcact gagctgggcc 240
cctacaccct ggacagggac agtctctatg tcaatggttt cacccatcgg agctctgtac 300
ccaccaccag caccggggtg gtcagcgagg agccattcaa cctgcccggg cggccgctcg 360
a 361

-continued

<210> SEQ ID NO 225
<211> LENGTH: 766
<212> TYPE: DNA
<213> ORGANISM: Homo sapien
<220> FEATURE:
<221> NAME/KEY: misc_feature
<222> LOCATION: (1)...(766)
<223> OTHER INFORMATION: n = A,T,C or G

<400> SEQUENCE: 225
agcgtggtcg cggccgaggt cctgtcagag tggcactggt agaagttcca ggaaccctga 60
actgtaaggg ttcttcatca gtgccaacag gatgacatga aatgatgtac tcagaagtgt 120
cctggaatgg ggcccatgag atggttgtct gagagagagc ttcttgtcct acattcggcg 180
ggtatggtct tggcctatgc cttatggggg tggccgttgt gggcggtgtg gtccgcctaa 240
aaccatgttc ctcaaagatc atttgttgcc caacactggg ttgctgacca gaagtgccag 300
gaagctgaat accatttcca gtgtcatacc cagggtgggt gacgaaaggg gtcttttgaa 360
ctgtggaagg aacatccaag atctctggtc catgaagatt ggggtgtgga agggttacca 420
gttggggaag ctcgtctgtc tttttccttc caatcagggg ctcgctcttc tgattattct 480
tcagggcaat gacataaatt gtatattcgg tcccggttcc aggccagtaa tagtagcctc 540
tgtgacacca gggcggggcc gagggaccct tctnttggaa gagaccagct tctcatactt 600
gatgatgagn ccggtaatcc tggcacgtgg nggttgcatg atnccaccaa ggaaatnggn 660
gggggnggac ctgcccggcg gccgttcnaa agcccaattc cacacacttg gnggccgtac 720
tatggatccc actcngtcca acttggngga atatggcata actttt 766

<210> SEQ ID NO 226
<211> LENGTH: 364
<212> TYPE: DNA
<213> ORGANISM: Homo sapien

<400> SEQUENCE: 226
tcgagcggcc gcccgggcag gtccttgacc ttttcagcaa gtgggaaggt gtaatccgtc 60
tccacagaca aggccaggac tcgtttgtac ccgttgatga tagaatgggg tactgatgca 120
acagttgggt agccaatctg cagacagaca ctggcaacat tgcggacacc ctccaggaag 180
cgagaatgca gagtttcctc tgtgatatca agcacttcag ggttgtagat gctgccattg 240
tcgaacacct gctggatgac cagcccaaag gagaaggggg agatgttgag catgttcagc 300
agcgtggctt cgctggctcc cactttgtct ccagtcttga tcagacctcg gccgcgacca 360
cgct 364

<210> SEQ ID NO 227
<211> LENGTH: 275
<212> TYPE: DNA
<213> ORGANISM: Homo sapien

<400> SEQUENCE: 227
agcgtggtcg cggccgaggt ctgtcctaca gtcctcagga ctctactccc tcagcagcgt 60
ggtgaccgtg ccctccagca acttcggcac ccagacctac acctgcaacg tagatcacaa 120
gcccagcaac accaaggtgg acaagagagt tgagcccaaa tcttgtgaca aaactcacac 180
atgcccaccg tgcccagcac ctgaactcct gggggaccg tcagtcttcc tcttccccccg 240 catcccccctt ccaaacctgc ccgggcggcc gctcg 275

-continued

```
<210> SEQ ID NO 228
<211> LENGTH: 275
<212> TYPE: DNA
<213> ORGANISM: Homo sapien

<400> SEQUENCE: 228

cgagcggccg cccgggcagg tttggaaggg ggatgcgggg gaagaggaag actgacggtc     60

cccccaggag ttcaggtgct gggcacggtg ggcatgtgtg agttttgtca caagatttgg    120

gctcaactct cttgtccacc ttggtgttgc tgggcttgtg atctacgttg caggtgtagg    180

tctgggtgcc gaagttgctg gagggcacgg tcaccacgct gctgagggag tagagtcctg    240

aggactgtag gacagacctc ggccgcgacc acgct                               275


<210> SEQ ID NO 229
<211> LENGTH: 40
<212> TYPE: DNA
<213> ORGANISM: Homo sapien
<220> FEATURE:
<221> NAME/KEY: misc_feature
<222> LOCATION: (1)...(40)
<223> OTHER INFORMATION: n = A,T,C or G

<400> SEQUENCE: 229

nggnnggtcc ggncngncag gaccactcnt cttcgaaata                           40


<210> SEQ ID NO 230
<211> LENGTH: 208
<212> TYPE: DNA
<213> ORGANISM: Homo sapien

<400> SEQUENCE: 230

agcgtggtcg cggccgaggt cctcacttgc ctcctgcaaa gcaccgatag ctgcgctctg     60

gaagcgcaga tctgttttaa agtcctgagc aatttctcgc accagacgct ggaagggaag    120

tttgcgaatc agaagttcag tggacttctg ataacgtcta atttcacgga gcgccacagt    180

accaggacct gcccgggcgg ccgctcga                                       208


<210> SEQ ID NO 231
<211> LENGTH: 208
<212> TYPE: DNA
<213> ORGANISM: Homo sapien
<220> FEATURE:
<221> NAME/KEY: misc_feature
<222> LOCATION: (1)...(208)
<223> OTHER INFORMATION: n = A,T,C or G

<400> SEQUENCE: 231

tcgagcggcc gcccgggcag gtcctggtac tgnggcgctc cgtgaaatta gacgttatca     60

gaagtccact gaacttctga ttcgcaaact tcccttccag cgtctggtgc gagaaattgc    120

tcaggacttt aaaacagatc tgcgcttcca gagcgcagct atcggtgctt tgcaggaggc    180

aagtgaggac ctcggccgcg accacgct                                       208


<210> SEQ ID NO 232
<211> LENGTH: 332
<212> TYPE: DNA
<213> ORGANISM: Homo sapien

<400> SEQUENCE: 232

tcgagcggcc gcccgggcag gtccacatcg gcagggtcgg agccctggcc gccatactcg     60

aactggaatc catcggtcat gctctcgccg aaccagacat gcctcttgtc cttggggttc    120
```

-continued

```
ttgctgatgt accagttctt ctgggccaca ctgggctgag tggggtacac gcaggtctca    180

ccagtctcca tgttgcagaa gactttgatg gcatccaggt tgcagccttg gttggggtca    240

atccagtact ctccactctt ccagtcagag tggcacatct tgaggtcacg gcaggtgcgg    300

gcggggttct tgacctcggc cgcgaccacg ct                                  332
```

<210> SEQ ID NO 233
<211> LENGTH: 415
<212> TYPE: DNA
<213> ORGANISM: Homo sapien
<220> FEATURE:
<221> NAME/KEY: misc_feature
<222> LOCATION: (1)...(415)
<223> OTHER INFORMATION: n = A,T,C or G

<400> SEQUENCE: 233

```
gtgggnttga acccntttna nctccgcttg gtaccgagct cggatccact agtaacggcc     60

gccagtgtgc tggaattcgg cttagcgtgg tcgcggccga ggtcaagaac cccgcccgca    120

cctgccgtga cctcaagatg tgccactctg actggaagag tggagagtac tggattgacc    180

ccaaccaagg ctgcaacctg gatgccatca aagtcttctg caacatggag actggtgaga    240

cctgcgtgta ccccactcag cccagtgtgg cccagaagaa ctggtacatc agcaagaacc    300

ccaaggacaa gaggcatgtc tggttcggcg agagcatgac cgatggattc cagttcgagt    360

atggcggcca gggctccgac cctgccgatg tggacctgcc cgggcggccg ctcga         415
```

<210> SEQ ID NO 234
<211> LENGTH: 776
<212> TYPE: DNA
<213> ORGANISM: Homo sapien
<220> FEATURE:
<221> NAME/KEY: misc_feature
<222> LOCATION: (1)...(776)
<223> OTHER INFORMATION: n = A,T,C or G

<400> SEQUENCE: 234

```
agcgtggtcg cggccgaggt ctgggatgct cctgctgtca cagtgagata ttacaggatc     60

acttacggag aaacaggagg aaatagccct gtccaggagt tcactgtgcc tgggagcaag    120

tctacagcta ccatcagcgg ccttaaacct ggagttgatt ataccatcac tgtgtatgct    180

gtcactggcc gtggagacag ccccgcaagc agcaagccaa tttccattaa ttaccgaaca    240

gaaattgaca aaccatccca gatgcaagtg accgatgttc aggacaacag cattagtgtc    300

aagtggctgc cttcaagttc ccctgttact ggttacagag taaccaccac tcccaaaaat    360

ggaccaggac caacaaaaac taaaactgca ggtccagatc aaacagaaat gactattgaa    420

ggcttgcagc ccacagtgga gtatgtggtt aagtgtctat gctcagaatc caagcggaga    480

gaagtcagcc tctggttcag actgnaagta accaacattg atcgcctaaa ggactggcat    540

tcactgatgn ggatgccgat tccatcaaaa ttgnttggga aaacccacag ggcaagttt     600

ncangtcnag gnggacctac tcgagccctg aggatggaat ccttgactnt tccttnncct    660

gatggggaaa aaaaaccttn aaaacttgaa ggacctgccc gggcggccgt ncaaaaccca    720

attccacccc cttgggggcg ttctatgggn cccactcgga ccaaacttgg ggtaan        776
```

<210> SEQ ID NO 235
<211> LENGTH: 805
<212> TYPE: DNA
<213> ORGANISM: Homo sapien
<220> FEATURE:
<221> NAME/KEY: misc_feature -continued
<222> LOCATION: (1)...(805)
<223> OTHER INFORMATION: n = A,T,C or G

<400> SEQUENCE: 235
tcgagcggcc gcccgggcag gtccttgcag ctctgcagtg tcttcttcac catcaggtgc 60
agggaatagc tcatggattc catcctcagg gctcgagtag gtcaccctgt acctggaaac 120
ttgcccctgt gggctttccc aagcaatttt gatggaatcg gcatccacat cagtgaatgc 180
cagtccttta gggcgatcaa tgttggttac tgcagtctga accagaggct gactctctcc 240
gcttggattc tgagcataga cactaaccac atactccact gtgggctgca agccttcaat 300
agtcatttct gtttgatctg gacctgcagt tttagttttt gttggtcctg gtccattttt 360
gggagtggtg gttactctgt aaccagtaac aggggaactt gaaggcagcc acttgacact 420
aatgctgttg tcctgaacat cggtcacttg catctgggat ggtttgtcaa tttctgttcg 480
gtaattaatg gaaattggct tgctgcttgc ggggcttgtc tccacggcca gtgacagcat 540
acacagtgat ggtataatca actccaggtt taagccgctg atggtagctg aaactttgct 600
ccaggcacaa gtgaactcct gacagggcta tttcctnctg ttctccgtaa gtgatcctgt 660
aatatctcac tgggacagca ggangcattc caaaacttcg ggcgngaccc cctaagccga 720
attntgcaat atncatcaca ctggcgggcg ctcgancatt cattaaaagg cccaatcncc 780
cctataggga gtntantaca attng 805

<210> SEQ ID NO 236
<211> LENGTH: 262
<212> TYPE: DNA
<213> ORGANISM: Homo sapien

<400> SEQUENCE: 236
tcgagcggcc gcccgggcag gtcacttttg gtttttggtc atgttcggtt ggtcaaagat 60
aaaaactaag tttgagagat gaatgcaaag gaaaaaaata ttttccaaag tccatgtgaa 120
attgtctccc attttttttgg cttttgaggg ggttcagttt gggttgcttg tctgtttccg 180
ggttgggggg aaagttggtt gggtgggagg gagccaggtt gggatggagg gagtttacag 240
gaagcagaca gggccaacgt cg 262

<210> SEQ ID NO 237
<211> LENGTH: 372
<212> TYPE: DNA
<213> ORGANISM: Homo sapien

<400> SEQUENCE: 237
agcgtggtcg cggccgaggt cctcaccaga ggtgccacct acaacatcat agtggaggca 60
ctgaaagacc agcagaggca taaggttcgg gaagaggttg ttaccgtggg caactctgtc 120
aacgaaggct tgaaccaacc tacggatgac tcgtgctttg acccctacac agtttcccat 180
tatgccgttg gagatgagtg ggaacgaatg tctgaatcag gctttaaact gttgtgccag 240
tgcttaggct ttggaagtgg tcatttcaga tgtgattcat ctagatggtg ccatgacaat 300
ggtgtgaact acaagattgg agagaagtgg gaccgtcagg gagaaaatgg acctgcccgg 360
gcggccgctc ga 372

<210> SEQ ID NO 238
<211> LENGTH: 372
<212> TYPE: DNA
<213> ORGANISM: Homo sapien -continued

<400> SEQUENCE: 238

```
tcgagcggcc gcccgggcag gtccattttc tccctgacgg tcccacttct ctccaatctt     60
gtagttcaca ccattgtcat ggcaccatct agatgaatca catctgaaat gaccacttcc    120
aaagcctaag cactggcaca acagtttaaa gcctgattca gacattcgtt cccactcatc    180
tccaacggca taatgggaaa ctgtgtaggg gtcaaagcac gagtcatccg taggttggtt    240
caagccttcg ttgacagagt tgcccacggt aacaacctct tcccgaacct tatgcctctg    300
ctggtctttc agtgcctcca ctatgatgtt gtaggtggca cctctggtga ggacctcggc    360
cgcgaccacg ct                                                        372
```

<210> SEQ ID NO 239
<211> LENGTH: 720
<212> TYPE: DNA
<213> ORGANISM: Homo sapien
<220> FEATURE:
<221> NAME/KEY: misc_feature
<222> LOCATION: (1)...(720)
<223> OTHER INFORMATION: n = A,T,C or G

<400> SEQUENCE: 239

```
tcgagcggcc gcccgggcag gtccaccata agtcctgata caaccacgga tgagctgtca     60
ggagcaaggt tgatttcttt cattggtccg gtcttctcct tgggggtcac ccgcactcga    120
tatccagtga gctgaacatt gggtggtgtc cactgggcgc tcaggcttgt gggtgtgacc    180
tgagtgaact tcaggtcagt tggtgcagga atagtggtta ctgcagtctg aaccagaggc    240
tgactctctc cgcttggatt ctgagcatag acactaacca catactccac tgtgggctgc    300
aagccttcaa tagtcatttc tgtttgatct ggacctgcag ttttagtttt tgttggtcct    360
ggtccatttt tgggagtggt ggttactctg taaccagtaa caggggaact tgaaggcagc    420
cacttgacac taatgctgtt gtcctgaaca tcggtcactt gcatctggga tggtttgnca    480
atttctgttc ggtaattaat ggaaattggc ttgctgcttg cggggctgtc tccacggcca    540
gtgacagcat acacagngat ggnatnatca actccaagtt taaggccctg atggtaactt    600
taaacttgct cccagccagn gaacttccgg acagggtatt tcttctggtt ttccgaaagn    660
gancctggaa tnntctcctt gganeagaag gancntccaa aacttgggcc ggaacccctt    720
```

<210> SEQ ID NO 240
<211> LENGTH: 691
<212> TYPE: DNA
<213> ORGANISM: Homo sapien
<220> FEATURE:
<221> NAME/KEY: misc_feature
<222> LOCATION: (1)...(691)
<223> OTHER INFORMATION: n = A,T,C or G

<400> SEQUENCE: 240

```
agcgtggtcg cggccgaggt cctgtcagag tggcactggt agaagttcca ggaaccctga     60
actgtaaggg ttcttcatca gtgccaacag gatgacatga aatgatgtac tcagaagtgt    120
cctggaatgg ggcccatgag atggttgtct gagagagagc ttcttgtcct acattcggcg    180
ggtatggtct tggcctatgc cttatggggg tggccgttgt gggcggtgtg gtccgcctaa    240
aaccatgttc ctcaaagatc atttgttgcc caacactggg ttgctgacca gaagtgccag    300
gaagctgaat accatttcca gtgtcatacc cagggtgggt gacgaaaggg gtcttttgaa    360
ctgtggaagg aacatccaag atctctggtc catgaagatt ggggtgtgga agggttacca    420
gttggggaag ctcgtctgtc tttttccttc caatcagggg ctcgctcttc tgattattct    480
```

-continued tcagggcaat gacataaatt gtatattcgg ttcccggttc caggccagta atagtagcct 540
cttgtgacac caggcggggc ccanggacca cttctctggg angagaccca gcttctcata 600
cttgatgatg taacccggta atcctgcacg tggcggctgn catgatacca ncaaggaatt 660
gggtgnggng gacctgcccg gcggccctcn a 691

<210> SEQ ID NO 241
<211> LENGTH: 808
<212> TYPE: DNA
<213> ORGANISM: Homo sapien
<220> FEATURE:
<221> NAME/KEY: misc_feature
<222> LOCATION: (1)...(808)
<223> OTHER INFORMATION: n = A,T,C or G

<400> SEQUENCE: 241
agcgtggtcg cggccgaggt ctgggatgct cctgctgtca cagtgagata ttacaggatc 60
acttacggag aaacaggagg aaatagccct gtccaggagt tcactgtgcc tgggagcaag 120
tctacagcta ccatcagcgg ccttaaacct ggagttgatt ataccatcac tgtgtatgct 180
gtcactggcc gtggagacag ccccgcaagc agcaagccaa tttccattaa ttaccgaaca 240
gaaattgaca aaccatccca gatgcaagtg accgatgttc aggacaacag cattagtgtc 300
aagtggctgc cttcaagttc ccctgttact ggttacagag taaccaccac tcccaaaaat 360
ggaccaggac caacaaaaac taaaactgca ggtccagatc aaacagaaat gactattgaa 420
ggcttgcagc ccacagtgga gtatgtggtt agtgtctatg ctcagaatcc aagcggagag 480
agtcagcctc tggttcagac tgcagtaacc actattcctg caccaactga cctgaagttc 540
actcaggtca cacccacaag cctgagccgc cagtggacac cacccaatgt tcactcactg 600
gatatcgagt gcgggtgacc cccaaggaga agacccggac ccatgaaaga aatcaacctt 660
gctcctgaca gctcatccgn gggtgtatca ggacttatgg gggactgccc cggcnggccg 720
ntcgaaancg aattntgaaa tttccttcnc actgggnggc gnttcgagct tncttntana 780
nggcccaatt cncctntagn gggtcgtn 808

<210> SEQ ID NO 242
<211> LENGTH: 26
<212> TYPE: DNA
<213> ORGANISM: Homo sapien
<220> FEATURE:
<221> NAME/KEY: misc_feature
<222> LOCATION: (1)...(26)
<223> OTHER INFORMATION: n = A,T,C or G

<400> SEQUENCE: 242
agcgtggtcg cggccgaggt cnagga 26

<210> SEQ ID NO 243
<211> LENGTH: 697
<212> TYPE: DNA
<213> ORGANISM: Homo sapien
<220> FEATURE:
<221> NAME/KEY: misc_feature
<222> LOCATION: (1)...(697)
<223> OTHER INFORMATION: n = A,T,C or G

<400> SEQUENCE: 243
tcgagcggcc gcccgggcag gtccaccaca cccaattcct tgctggtatc atggcagccg 60
ccacgtgcca ggattaccgg ctacatcatc aagtatgaga agcctgggtc tcctcccaga 120

-continued gaagtggtcc ctcggccccg ccctggtgtc acagaggcta ctattactgg cctggaaccg 180
ggaaccgaat atacaattta tgtcattgcc ctgaagaata atcagaagag cgagcccctg 240
attggaagga aaaagacaga cgagcttccc caactggtaa cccttccaca ccccaatctt 300
catggaccag agatcttgga tgttccttcc acagttcaaa agaccccttt cgtcacccac 360
cctgggtatg acactggaaa tggtattcag cttcctggca cttctggtca gcaacccagt 420
gttgggcaac aaatgatctt tgaggaacat ggttttaggc ggaccacacc gcccacaacg 480
ggcaccccca taaggnatag gccaagacca taccccgccg aatgtaggac aagaagctct 540
ntctcaacaa ccatctcatg ggccccattc caggacactt ctgagtacat catttcatgt 600
catcctggtg ggcacttgat gaanaaccct tacagttcag ggttcctgga acttctacca 660
gngccacttc tgacaggan ttgggcgnga ccacccct 697

<210> SEQ ID NO 244
<211> LENGTH: 373
<212> TYPE: DNA
<213> ORGANISM: Homo sapien

<400> SEQUENCE: 244
agcgtggtcg cggccgaggt ccattttctc cctgacggtc ccacttctct ccaatcttgt 60
agttcacacc attgtcatgg caccatctag atgaatcaca tctgaaatga ccacttccaa 120
agcctaagca ctggcacaac agtttaaagc ctgattcaga cattcgttcc cactcatctc 180
caacggcata atgggaaact gtgtaggggt caaagcacga gtcatccgta ggttggttca 240
agccttcgtt gacagagttg cccacggtaa caacctcttc ccgaacctta tgcctctgct 300
ggtctttcag tgcctccact atgatgttgt aggtggcacc tctggtgagg acctgcccgg 360
gcggcccgct cga 373

<210> SEQ ID NO 245
<211> LENGTH: 307
<212> TYPE: DNA
<213> ORGANISM: Homo sapien

<400> SEQUENCE: 245
agcgtggtcg cggccgaggt gtgccccaga ccaggaattc ggcttcgacg ttggccctgt 60
ctgcttcctg taaactccct ccatcccaac ctggctccct cccacccaac caactttccc 120
cccaacccgg aaacagacaa gcaacccaaa ctgaaccccc tcaaaagcca aaaaaatggg 180
agacaatttc acatggactt tggaaaatat ttttttcctt tgcattcatc tctcaaactt 240
agtttttatc tttgaccaac cgaacatgac caaaaaccaa aagtgacctg cccgggcggc 300
cgctcga 307

<210> SEQ ID NO 246
<211> LENGTH: 372
<212> TYPE: DNA
<213> ORGANISM: Homo sapien

<400> SEQUENCE: 246
tcgagcggcc gcccgggcag gtcctcacca gaggtgccac ctacaacatc atagtggagg 60
cactgaaaga ccagcagagg cataaggttc gggaagaggt tgttaccgtg ggcaactctg 120
tcaacgaagg cttgaaccaa cctacggatg actcgtgctt tgacccctac acagtttccc 180
attatgccgt tggagatgag tgggaacgaa tgtctgaatc aggctttaaa ctgttgtgcc 240
agtgcttagg ctttggaagt ggtcatttca gatgtgattc atctagatgg tgccatgaca 300

-continued

```
atggtgtgaa ctacaagatt ggagagaagt gggaccgtca gggagaaaat ggacctcggc    360

cgcgaccacg ct                                                        372


<210> SEQ ID NO 247
<211> LENGTH: 348
<212> TYPE: DNA
<213> ORGANISM: Homo sapien
<220> FEATURE:
<221> NAME/KEY: misc_feature
<222> LOCATION: (1)...(348)
<223> OTHER INFORMATION: n = A,T,C or G

<400> SEQUENCE: 247

tcgagcggcc gcccgggcag gtaccggggt ggtcagcgag gagccattca cactgaactt     60

caccatcaac aacctgcggt atgaggagaa catgcagcac cctggctcca ggaagttcaa    120

caccacggag agggtccttc agggcctgct caggtccctg ttcaagagca ccagtgttgg    180

ccctctgtac tctggctgca gactgacttt gctcagacct gagaaacatg ggcagccac     240

tggagtggac gccatctgca ccctccgcct tgatcccact ggtnctggac tggacanana    300

gcggctatac ttgggagctg anccnaacct ttggcggnga cnccnctt                348


<210> SEQ ID NO 248
<211> LENGTH: 304
<212> TYPE: DNA
<213> ORGANISM: Homo sapien
<220> FEATURE:
<221> NAME/KEY: misc_feature
<222> LOCATION: (1)...(304)
<223> OTHER INFORMATION: n = A,T,C or G

<400> SEQUENCE: 248

gaggactggc tcagctccca gtatagccgc tctctgtcca gtccaggacc agtgggatca     60

aggcggaggg tgcagatggc gtccactcca gtggctgccc catgtttctc aagtctgagc    120

aaagncagtc tgcagccaga gtacagaggg ccaacactgg tgctcttgaa cagggacctg    180

agcaggccct gaaggaccct ctccgtggtg ttgaacttcc tggagccagg gtgctgcatg    240

ttctcctcat accgcaggtt gttgatggtg aagttcagtg tgaatggctc ctcgctgacc    300

accc                                                                 304


<210> SEQ ID NO 249
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 249

agcgtggtcg cggccgaggt ccaccacacc caattccttg ctggtatcat ggcagccgcc     60

acgtgccagg attaccggct acatcatcaa gtatgagaag cctgggtctc ctcccagaga    120

agtggtccct cggccccgcc ctggtgtcac agaggctact attactggcc tggaaccggg    180

aaccgaatat acaatttatg tcattgccct gaagaataat cagaagagcg agcccctgat    240

tggaaggaaa aagacagacg agcttcccca actggtaacc cttccacacc ccaatcttca    300

tggaccanan ancttggatn gtcctttcac nggttnaaaa aaccctttc gcccccccac    360

cttggggatt aaccttggga aanggggatt tnaccnttcc                          400
```

-continued

<210> SEQ ID NO 250
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 250
tcgagcggcc gcccgggcag gtcctgtcag agtggcactg gtagaagttc caggaaccct 60
gaactgtaag ggttcttcat cagtgccaac aggatgacat gaaatgatgt actcagaagt 120
gtcctggaat ggggcccatg agatggttgt ctgagagaga gcttcttgtc ctacattcgg 180
cgggtatggt cttggcctat gccttatggg ggtggccgtt gtgggcggtg tggtccgcct 240
aaaaccatgt tcctcaaaga tcatttgttg cccaacactg ggttgctgac cagaagtgcc 300
aggaagctga ataccatttc cagtgtcata cccagggngg gtgaccaaag ggggtcnttt 360
ngacctggng aaaggaacca tccaaaanct ctgncccatg 400

<210> SEQ ID NO 251
<211> LENGTH: 514
<212> TYPE: DNA
<213> ORGANISM: Homo sapien
<220> FEATURE:
<221> NAME/KEY: misc_feature
<222> LOCATION: (1)...(514)
<223> OTHER INFORMATION: n = A,T,C or G

<400> SEQUENCE: 251
agcgtggncg cggccgaggt ctgaggatgt aaactcttcc caggggaagg ctgaagtgct 60
gaccatggtg ctactgggtc cttctgagtc agatatgtga ctgatgngaa ctgaagtagg 120
tactgtagat ggtgaagtct gggtgtccct aaatgctgca tctccagagc cttccatcat 180
taccgtttct tcttttgcta tgggatgaga cactgttgag tattctctaa agtcaccact 240
gaaatcttcc tccaaaggaa aacctgtgga aaagcccctt atttctgccc cataatttgg 300
ttctcctaat cnctctgaaa tcactatttc cctggaangt ttgggaaaaa nngggcnacc 360
tgncantgga aantggatan aaagatccca ccattttacc caacnagcag aaagtgggaa 420
nggtaccgaa aagctccaag taanaaaaag gagggaagta aaggtcaagt gggcaccagt 480
ttcaaacaaa actttcccca aactatanaa ccca 514

<210> SEQ ID NO 252
<211> LENGTH: 501
<212> TYPE: DNA
<213> ORGANISM: Homo sapien
<220> FEATURE:
<221> NAME/KEY: misc_feature
<222> LOCATION: (1)...(501)
<223> OTHER INFORMATION: n = A,T,C or G

<400> SEQUENCE: 252
aagcggccgc ccgggcaggn ncagnagtgc cttcgggact gggntcaccc ccaggtctgc 60
ggcagttgtc acagcgccag ccccgctggc ctccaaagca tgtgcaggag caaatggcac 120
cgagatattc cttctgccac tgttctccta cgtggtatgt cttcccatca tcgtaacacg 180
ttgcctcatg agggtcacac ttgaattctc cttttccgtt cccaagacat gtgcagctca 240
tttggctggc tctatagttt ggggaaagtt tgttgaaact gtgccactga cctttacttc 300
ctccttctct actggagctt tccgtacctt ccacttctgc tgntggnaaa aagggnggaa 360

-continued cntcttatca atttcattgg acagtanccc nctttctncc caaaacatnc aagggaaaat 420
attgattncn agagcggatt aaggaacaac ccnaattatg ggggccagaa ataaaggggg 480
cttttccaca ggtnttttcc t 501

<210> SEQ ID NO 253
<211> LENGTH: 226
<212> TYPE: DNA
<213> ORGANISM: Homo sapien

<400> SEQUENCE: 253
tcgagcggcc gcccgggcag gtctgcaggc tattgtaagt gttctgagca catatgagat 60
aacctgggcc aagctatgat gttcgatacg ttaggtgtat taaatgcact tttgactgcc 120
atctcagtgg atgacagcct tctcactgac agcagagatc ttcctcactg tgccagtggg 180
caggagaaag agcatgctgc gactggacct cggccgcgac cacgct 226

<210> SEQ ID NO 254
<211> LENGTH: 226
<212> TYPE: DNA
<213> ORGANISM: Homo sapien

<400> SEQUENCE: 254
agcgtggtcg cggccgaggt ccagtcgcag catgctcttt ctcctgccca ctggcacagt 60
gaggaagatc tctgctgtca gtgagaaggc tgtcatccac tgagatggca gtcaaaagtg 120
catttaatac acctaacgta tcgaacatca tagcttggcc caggttatct catatgtgct 180
cagaacactt acaatagcct gcagacctgc ccgggcggcc gctcga 226

<210> SEQ ID NO 255
<211> LENGTH: 427
<212> TYPE: DNA
<213> ORGANISM: Homo sapien
<220> FEATURE:
<221> NAME/KEY: misc_feature
<222> LOCATION: (1)...(427)
<223> OTHER INFORMATION: n = A,T,C or G

<400> SEQUENCE: 255
cgagcggccg cccgggcagg tccagactcc aatccagaga accaccaagc cagatgtcag 60
aagctacacc atcacaggtt tacaaccagg cactgactac aagatctacc tgtacacctt 120
gaatgacaat gctcggagct cccctgtggt catcgacgcc tccactgcca ttgatgcacc 180
atccaacctg cgtttcctgg ccaccacacc caattccttg ctggtatcat ggcagccgcc 240
acgtgccagg attaccggct acatcatcaa gtatgagaag cctgggtctc ctcccagaga 300
agtggtccct cggccccgcc ctggtgncac agaagctact attactggcc tggaaccggg 360
aaccgaatat acaatttatg tcattgccct gaagaataat canaagagcg agcccctgat 420
tggaagg 427

<210> SEQ ID NO 256
<211> LENGTH: 535
<212> TYPE: DNA
<213> ORGANISM: Homo sapien
<220> FEATURE:
<221> NAME/KEY: misc_feature
<222> LOCATION: (1)...(535)
<223> OTHER INFORMATION: n = A,T,C or G

<400> SEQUENCE: 256

-continued

```
agcgtggtcg cggccgaggt cctgtcagag tggcactggt agaagttcca ggaaccctga     60

actgtaaggg ttcttcatca gtgccaacag gatgacatga aatgatgtac tcagaagtgt    120

cctggaatgg ggcccatgag atggttgtct gagagagagc ttcttgtcct gtctttttcc    180

ttccaatcag ggctcgctc ttctgattat tcttcagggc aatgacataa attgtatatt    240

cggttcccgg ttccaggcca gtaatagtag cctctgtgac accagggcgg ggccgaggga    300

ccacttctct gggaggagac ccaggcttct catacttgat gatgtanccg gtaatcctgg    360

caccgtggcg gctgccatga taccagcaag gaattgggtg tggtggccaa gaaacgcagg    420

ttggatggtg catcaatggc agtggaggcg tcgatnacca caggggagct ccgancattg    480

tcattcaagg tggacaggta gaatcttgta atcaggtgcc tggtttgtaa acctg         535
```

<210> SEQ ID NO 257
<211> LENGTH: 544
<212> TYPE: DNA
<213> ORGANISM: Homo sapien
<220> FEATURE:
<221> NAME/KEY: misc_feature
<222> LOCATION: (1)...(544)
<223> OTHER INFORMATION: n = A,T,C or G

<400> SEQUENCE: 257

```
tcgagcggcc gcccgggcag gtttcgtgac cgtgacctcg aggtggacac caccctcaag     60

agcctgagcc agcagatcga gaacatccgg agcccagagg gcagccgcaa gaaccccgcc    120

cgcacctgcc gtgacctcaa gatgtgccac tctgactgga agagtggaga gtactggatt    180

gaccccaacc aaggctgcaa cctggatgcc atcaaagtct tctgcaacat ggagactggt    240

gagacctgcg tgtaccccac tcagcccagt gtggcccaga agaactggta catcagcaag    300

aaccccaagg acaagaagca tgtctggttc ggcgaaagca tgaccgatgg attccagttc    360

gagtatggcg gccagggctc cgaccctgcc gatgtggacc tcggccgcga ccacgctaag    420

cccgaattcc agcacactgg cggccgttac tagtgggatc cgagcttcgg taccaagctt    480

ggcgtaatca tgggncatag ctgtttcctg ngtgaaaatg gtattccgct tcacaatttc    540

ccac                                                                 544
```

<210> SEQ ID NO 258
<211> LENGTH: 418
<212> TYPE: DNA
<213> ORGANISM: Homo sapien

<400> SEQUENCE: 258

```
agcgtggtcg cggccgaggt ccacatcggc agggtcggag ccctggccgc catactcgaa     60

ctggaatcca tcggtcatgc tctcgccgaa ccagacatgc ctcttgtcct tggggttctt    120

gctgatgtac cagttcttct gggccacact gggctgagtg gggtacacgc aggtctcacc    180

agtctccatg ttgcagaaga ctttgatggc atccaggttg cagccttggt tggggtcaat    240

ccagtactct ccactcttcc agtcagagtg gcacatcttg aggtcacggc aggtgcgggc    300

ggggttcttg cggctgccct ctgggctccg gatgttctcg atctgctggc tcaagctctt    360

gaagggtggt gtccacctcg aggtcacggt cacgaaacct gcccgggcgg ccgctcga      418
```

<210> SEQ ID NO 259
<211> LENGTH: 377
<212> TYPE: DNA
<213> ORGANISM: Homo sapien
<220> FEATURE:
<221> NAME/KEY: misc_feature
<222> LOCATION: (1)...(377)
<223> OTHER INFORMATION: n = A,T,C or G

<400> SEQUENCE: 259
agcgtggtcg cggccgaggt caagaacccc gcccgcacct gccgtgacct caagatgtgc 60
cactctgact ggaagagtgg agagtactgg attgacccca accaaggctg caacctggat 120
gccatcaaag tcttctgcaa catggagact ggtgagacct gcgtgtaccc cactcagccc 180
agtgtggccc agaagaactg gtacatcagc aagaacccca aggacaagag gcatgtctgg 240
ttcggcgaga gcatgaccga tggattccag ttcgagtatg gcggccaggg ctccgaccct 300
gccgatgtgg acctgcccgn gccggnccgc tcgaaaagcc cnaatttcca gncacacttg 360
gccggccgtt actactg 377

<210> SEQ ID NO 260
<211> LENGTH: 332
<212> TYPE: DNA
<213> ORGANISM: Homo sapien

<400> SEQUENCE: 260
tcgagcggcc gcccgggcag gtccacatcg gcagggtcgg agccctggcc gccatactcg 60
aactggaatc catcggtcat gctctcgccg aaccagacat gcctcttgtc cttggggttc 120
ttgctgatgt accagttctt ctgggccaca ctgggctgag tggggtacac gcaggtctca 180
ccagtctcca tgttgcagaa gactttgatg gcatccaggt tgcagccttg gttggggtca 240
atccagtact ctccactctt ccagtcagag tggcacatct tgaggtcacg gcaggtgcgg 300
gcggggttct tgacctcggc cgcgaccacg ct 332

<210> SEQ ID NO 261
<211> LENGTH: 94
<212> TYPE: DNA
<213> ORGANISM: Homo sapien

<400> SEQUENCE: 261
cgagcggccg cccgggcagg tccccccct tttttttttt tttttttttt tttttttttt 60
tttttttttt tttttttttt tttttttttt tttt 94

<210> SEQ ID NO 262
<211> LENGTH: 650
<212> TYPE: DNA
<213> ORGANISM: Homo sapien
<220> FEATURE:
<221> NAME/KEY: misc_feature
<222> LOCATION: (1)...(650)
<223> OTHER INFORMATION: n = A,T,C or G

<400> SEQUENCE: 262
agcgtggtcg cggccgaggt ctggcattcc ttcgacttct ctccagccga gcttcccaga 60
acatcacata tcactgcaaa aatagcattg catacatgga tcaggccagt ggaaatgtaa 120
agaaggccct gaagctgatg gggtcaaatg aaggtgaatt caaggctgaa ggaaatagca 180
aattcaccta cacagttctg gaggatggtt gcacgaaaca cactggggaa tggagcaaaa 240
cagtctttga atatcgaaca cgcaaggctg tgagactacc tattgtagat attgcaccct 300
atgacattgg tggtcctgat caagaatttg gtgtggacgt tggccctgtt tgctttttat 360
aaaccaaact ctatctgaaa tcccaacaaa aaaaatttaa ctccatatgt gntcctcttg 420
ttctaatctt ggcaaccagt gcaagtgacc gacaaaattc cagttattta tttccaaaat 480

-continued gtttggaaac agtataattt gacaaagaaa aaaggatact tctctttttt tggctggtcc 540
accaaataca attcaaaagg ctttttggtt ttattttttt anccaattcc aatttcaaaa 600
tgtctcaatg gngcttataa taaaataaac tttcaccctt nttttntgat 650

<210> SEQ ID NO 263
<211> LENGTH: 573
<212> TYPE: DNA
<213> ORGANISM: Homo sapien
<220> FEATURE:
<221> NAME/KEY: misc_feature
<222> LOCATION: (1)...(573)
<223> OTHER INFORMATION: n = A,T,C or G

<400> SEQUENCE: 263
agcgtggtcg cggccgaggt ctgggatgct cctgctgtca cagtgagata ttacaggatc 60
acttacggag aaacaggagg aaatagccct gtccaggagt tcactgtgcc tgggagcaag 120
tctacagcta ccatcagcgg ccttaaacct ggagttgatt ataccatcac tgtgtatgct 180
gtcactggcc gtggagacag ccccgcaagc agcaagccaa tttccattaa ttaccgaaca 240
gaaattgaca aaccatccca gatgcaagtg accgatgttc aggacaacag cattagtgtc 300
aagtggctgc cttcaagttc ccctgttact ggttacagaa gtaaccacca ctcccaaaaa 360
tggaccagga ccaacaaaaa ctaaaactgc aggtccagat caaacagaaa atggactatt 420
gaaggcttgc agcccacagt ggaagtatgt ggntaggngt ctatgctcag aatcccaagc 480
cggagaaagt cagccttctg gtttagactg cagtaaccaa cattgatcgc cctaaaggac 540
tggncattca cttggatggt ggatgtccaa ttc 573

<210> SEQ ID NO 264
<211> LENGTH: 550
<212> TYPE: DNA
<213> ORGANISM: Homo sapien
<220> FEATURE:
<221> NAME/KEY: misc_feature
<222> LOCATION: (1)...(550)
<223> OTHER INFORMATION: n = A,T,C or G

<400> SEQUENCE: 264
tcgagcggcc gcccgggcag gtccttgcag ctctgcagng tcttcttcac catcaggtgc 60
agggaatagc tcatggattc catcctcagg gctcgagtag gtcaccctgt acctggaaac 120
ttgcccctgt gggctttccc aagcaatttt gatggaatcg acatccacat cagngaatgc 180
cagtccttta gggcgatcaa tgttggttac tgcagtctga accagaggct gactctctcc 240
gcttggattc tgagcataga cactaaccac atactccact gtgggctgca agccttcaat 300
agtcatttct gtttgatctg gacctgcagt tttaagtttt tggtggtcct gncccatttt 360
tgggaagtgg ggggttactc tgtaaccagt aacaggggaa cttgaaggca gccacttgac 420
actaatgctg ttgtcctgaa catcggtcac ttgcatctgg ggatggtttt gacaatttct 480
ggttcggcaa attaatggaa attggcttgc tgcttggcgg ggctgnctcc acgggccagt 540
gacagcatac 550

<210> SEQ ID NO 265
<211> LENGTH: 596
<212> TYPE: DNA
<213> ORGANISM: Homo sapien
<220> FEATURE:
<221> NAME/KEY: misc_feature
<222> LOCATION: (1)...(596)
<223> OTHER INFORMATION: n = A,T,C or G -continued

<400> SEQUENCE: 265
tcgagcggcc gcccgggcag gtccttgcag ctctgcagtg tcttcttcac catcaggtgc 60
agggaatagc tcatggattc catcctcagg gctcgagtag gtcaccctgt acctggaaac 120
ttgcccctgt gggctttccc aagcaatttt gatggaatcg acatccacat cagtgaatgc 180
cagtccttta gggcgatcaa tgttggttac tgcagtctga accagaggct gactctctcc 240
gcttggattc tgagcataga cactaaccac atactccact gtgggctgca agccttcaat 300
agtcatttct gtttgatctg gacctgcagt tttaagtttt tgttggncct gnnccatttt 360
tggggaaggg gtggttactc ttgtaaccag taacagggga acttgaagca gccacttgac 420
actaatgctg gtggcctgaa catcggtcac ttgcatctgg gatggtttgg tcaatttctg 480
ttcggtaatt aatgggaaat tggcttactg gcttgcgggg gctgtctcca cggncagtga 540
caagcataca caggngatgg gtataatcaa ctccaggttt aaggccnctg atggta 596

<210> SEQ ID NO 266
<211> LENGTH: 506
<212> TYPE: DNA
<213> ORGANISM: Homo sapien
<220> FEATURE:
<221> NAME/KEY: misc_feature
<222> LOCATION: (1)...(506)
<223> OTHER INFORMATION: n = A,T,C or G

<400> SEQUENCE: 266
agcgtggtcg cggccgaggt ctgggatgct cctgctgtca cagtgagata ttacaggatc 60
acttacggag aaacaggagg aaatagccct gtccaggagt tcactgtgcc tgggagcaag 120
tctacagcta ccatcagcgg ccttaaacct ggagttgatt ataccatcac tgtgtatgct 180
gtcactggcc gtggagacag ccccgcaagc agtaagccaa tttccattaa ttaccgaaca 240
gaaattgaca aaccatccca gatgcaagtg accgatgttc aggacaacag cattagtgtc 300
aagtggctgc cttcaagttc ccctgttact ggttacagag taaccaccac tcccaaaaat 360
gggaccagga ccaacaaaaa actaaaactg canggtccag atcaaacaga aatgactatt 420
gaaggcttgc agcccacagt ggagtatgtg ggttagtgtc tatgctcaga atnccaagcg 480
gagagagtca gcctctggtt cagact 506

<210> SEQ ID NO 267
<211> LENGTH: 548
<212> TYPE: DNA
<213> ORGANISM: Homo sapien
<220> FEATURE:
<221> NAME/KEY: misc_feature
<222> LOCATION: (1)...(548)
<223> OTHER INFORMATION: n = A,T,C or G

<400> SEQUENCE: 267
tcgagcggcc gcccgggcag gtcagcgctc tcaggacgtc accaccatgg cctgggctct 60
gctcctcctc accctcctca ctcagggcac agggtcctgg gcccagtctg ccctgactca 120
gcctccctcc gcgtccgggt ctcctggaca gtcagtcacc atctcctgca ctggaaccag 180
cagtgacgtt ggtgcttatg aatttgtctc ctggtaccaa caacacccag gcaaggcccc 240
caaactcatg atttctgagg tcactaagcg gccctcaggg gtccctgatc gcttctctgg 300
ctccaagtct ggcaacacgg cctccctgac cgtctctggg ctccangctg aggatgangc 360
tgattattac tggaagctca tatgcaggca acaacaattg ggtgttcggc ggaagggacc 420

-continued

```
aagctgaccg tnctaaggtc aagcccaagg cttgcccccc tcggtcactc tgttcccacc    480

ctcctctgaa gaagctttca agccaacaan gncacactgg gtgtgtctca taagtggact    540

ttctaccc                                                             548
```

<210> SEQ ID NO 268
<211> LENGTH: 584
<212> TYPE: DNA
<213> ORGANISM: Homo sapien
<220> FEATURE:
<221> NAME/KEY: misc_feature
<222> LOCATION: (1)...(584)
<223> OTHER INFORMATION: n = A,T,C or G

<400> SEQUENCE: 268

```
agcgtggtcg cggccgaggt ctgtagcttc tgtgggactt ccactgctca ggcgtcaggc     60

tcaggtagct gctggccgcg tacttgttgt tgctttgntt ggagggtgtg gtggtctcca    120

ctcccgcctt gacggggctg ctatctgcct tccaggccac tgtcacggct cccgggtaga    180

agtcacttat gagacacacc agtgtggcct tgttggcttg aagctcctca gaggagggtg    240

ggaacagagt gaccgagggg gcagccttgg gctgacctag gacggtcagc ttggtccctc    300

cgccgaacac ccaattgttg ttgcctgcat atgagctgca gtaataatca gcctcatcct    360

cagcctggag cccagagacn gtcaagggag gcccgtgttt gccaagactt ggaagccaga    420

naagcgatca gggacccctg agggccgctt tacngacctc aaaaaatcat gaatttgggg    480

ggcctttgcc tgggngttgg ttggtnacca gnaaaacaaa atttcataaa gcaccaacgt    540

cactgctggt ttccagtgca ngaanatggt gaactgaant gtcc                     584
```

<210> SEQ ID NO 269
<211> LENGTH: 368
<212> TYPE: DNA
<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 269

```
agcgtggtcg cggccgaggt ccagcatcag gagccccgcc ttgccggctc tggtcatcgc     60

ctttcttttt gtggcctgaa acgatgtcat caattcgcag tagcagaact gccgtctcca    120

ctgctgtctt ataagtctgc agcttcacag ccaatggctc ccatatgccc agttccttca    180

tgtccaccaa agtacccgtc tcaccattta caccccaggt ctcacagttc tcctgggtgt    240

gcttggcccg aagggaggta agtanacgga tggtgctggt cccacagttc tggatcaggg    300

tacgaggaat gacctctagg gcctgggcna caagccctgt atggacctgc ccgggcgggc    360

ccgctcga                                                             368
```

<210> SEQ ID NO 270
<211> LENGTH: 368
<212> TYPE: DNA
<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 270

```
tcgagcggcc gcccgggcag gtccatacag ggctgttgcc caggccctag aggncattcc     60

ttgtaccctg atccagaact gtgggaccag caccatccgt ctacttacct cccttcgggc    120
```

-continued

```
caagcacacc caggagaact gtgagacctg gggtgtaaat ggngagacgg gtactttggt    180

ggacatgaag gaactgggca tatgggagcc attggctgng aagctgcana cttataagac    240

agcagtggag acggcagttc tgctactgcg aattgatgac atcgtttcag gccacaaaaa    300

gaaaggcgat gaccanagcc ggcaaggcgg ggcttcctga tgctggacct cggccgccga    360

ccacgctt                                                             368
```

<210> SEQ ID NO 271
<211> LENGTH: 424
<212> TYPE: DNA
<213> ORGANISM: Homo sapien
<220> FEATURE:
<221> NAME/KEY: misc_feature
<222> LOCATION: (1)...(424)
<223> OTHER INFORMATION: n = A,T,C or G

<400> SEQUENCE: 271

```
agcgtggtcg cggccgaggt ccactagagg tctgtgtgcc attgcccagg cagagtctct     60

gcgttacaaa ctcctaggag ggcttgctgt gcggagggcc tgctatggtg tgctgcggtt    120

catcatggag agtggggcca aaggctgcga ggttgtggtg tctgggaaac tccgaggaca    180

gagggctaaa tccatgaagt ttgtggatgg cctgatgatc cacagcggag accctgttaa    240

ctactacgtt gacactgctg tgcgccacgt gttgctcana cagggtgtgc tgggcatcaa    300

ggtgaagatc atgctgccct gggacccanc tggcaaaaat ggcccttaaa aaccccttgc    360

cntgaccacg tgaaccattt gtgngaaccc caagatgaan atacttgccc accacccccc    420

attc                                                                 424
```

<210> SEQ ID NO 272
<211> LENGTH: 541
<212> TYPE: DNA
<213> ORGANISM: Homo sapien
<220> FEATURE:
<221> NAME/KEY: misc_feature
<222> LOCATION: (1)...(541)
<223> OTHER INFORMATION: n = A,T,C or G

<400> SEQUENCE: 272

```
tcgagcggcc gcccgggcag gtctgccaag gagaccctgt tatgctgtgg ggactggctg     60

gggcatggca ggcggctctg gcttcccacc cttctgttct gagatggggg tggtgggcag    120

tatctcatct ttgggttcca caatgctcac gtggtcaggc aggggcttct tagggccaat    180

cttaccagtt gggtcccagg gcagcatgat cttcaccttg atgcccagca caccctgtct    240

gagcaacacg tggcgcacag cagtgtcaac gtagtagtta acagggtctc cgctgtggat    300

catcaggcca tccacaaact tcatggattt agccctctgt cctcggagtt tcccaaaaca    360

ccacaacctc gccagccttt gggccccact tcttcatgaa tgaaaccgca gcacaccatt    420

ancaaggccc ttccgcacag gnaagccctt cctaaggagt tttgtaaacg caaaaaactc    480

ttgcctgggg caaatgggca cacagacctn tantnggacc ttggnccgcg aaccaccgct    540

t                                                                    541
```

<210> SEQ ID NO 273
<211> LENGTH: 579
<212> TYPE: DNA
<213> ORGANISM: Homo sapien
<220> FEATURE:
<221> NAME/KEY: misc_feature
<222> LOCATION: (1)...(579)

-continued

<223> OTHER INFORMATION: n = A,T,C or G

<400> SEQUENCE: 273
agcgtggtcg cggccgaggt ctggccctcc tggcaaggct ggtgaagatg gtcaccctgg 60
aaaacccgga cgacctggtg agagaggagt tgttggacca cagggtgctc gtggtttccc 120
tggaactcct ggacttcctg gcttcaaagg cattagggga cacaatggtc tggatggatt 180
gaagggacag cccggtgctc ctggtgtgaa gggtgaacct ggngcccctg gtgaaaatgg 240
aactccaggt caaacaggag cccgngggct tcctggngag agaggacgtg ttggtgcccc 300
tggcccanac ctgcccgggc ggccgctcna aaagccgaaa tccagnacac tggcggccgn 360
tactantgga atccgaactt cggtaccaaa gcttggccgt aatcatggcc atagcttgtt 420
ccctggggng gaaattggta ttccgctncc aattccacac aacataccga acccggaaag 480
cattaaagtg taaaagccct ggggggcct aaatgangtg agcntaactc ncatttaatt 540
ggcgttgcgc ttcactgccc cgcttttcca gtccgggna 579

<210> SEQ ID NO 274
<211> LENGTH: 330
<212> TYPE: DNA
<213> ORGANISM: Homo sapien
<220> FEATURE:
<221> NAME/KEY: misc_feature
<222> LOCATION: (1)...(330)
<223> OTHER INFORMATION: n = A,T,C or G

<400> SEQUENCE: 274
tcgagcggcc gcccgggcag gtctgggcca ggggcaccaa cacgtcctct ctcaccagga 60
agcccacggg ctcctgtttg acctggagtt ccattttcac caggggcacc aggttcaccc 120
ttcacaccag gagcaccggg ctgtcccttc aatccatcca gaccattgtg ncccctaatg 180
cctttgaagc caggaagtcc aggagttcca gggaaaccac gagcaccctg tggtccaaca 240
actcctctct caccaggtcg tccgggtttt ccagggtgac catcttcacc agccttgcca 300
ggagggccag acctcggccg cgaccacgct 330

<210> SEQ ID NO 275
<211> LENGTH: 97
<212> TYPE: DNA
<213> ORGANISM: Homo sapien
<220> FEATURE:
<221> NAME/KEY: misc_feature
<222> LOCATION: (1)...(97)
<223> OTHER INFORMATION: n = A,T,C or G

<400> SEQUENCE: 275
ancgtggtcg cggccgaggt cctcaccaga ggtgncacct acaacatcat agtggaggca 60
ctgaaagacc ancagaggca taaggttcgg gaagagg 97

<210> SEQ ID NO 276
<211> LENGTH: 610
<212> TYPE: DNA
<213> ORGANISM: Homo sapien
<220> FEATURE:
<221> NAME/KEY: misc_feature
<222> LOCATION: (1)...(610)
<223> OTHER INFORMATION: n = A,T,C or G

<400> SEQUENCE: 276
tcgagcggcc gcccgggcag gtccattttc tccctgacgg tcccacttct ctccaatctt 60
gtagttcaca ccattgtcat ggcaccatct agatgaatca catctgaaat gaccacttcc 120

-continued

```
aaagcctaag cactggcaca acagtttaaa gcctgattca gacattcgtt cccactcatc    180

tccaacggca taatgggaaa ctgtgtaggg gtcaaagcac gagtcatccg taggttggtt    240

caagccttcg ttgacagagt tgtccacggt aacaacctct tcccgaacct tatgcctctg    300

ctggtctttc agtgcctcca ctatgatgtt gtaggtggca cctctggtga ggacctcngn    360

ccngaacaac gcttaagccc gnattctgca gaataatccc atcacacttg gcggccgctt    420

cgancatgca tcntaaaagg ggccccaatt tcccccttat aagngaancc gtatttncca    480

atttcactgg ncccgccgnt tttacaaacg ncggtgaact ggggaaaaac cctggcggtt    540

acccaacttt aatcgccntt ggcagcacaa tccccccttt tcgnccancn tgggcgtaaa    600

taaccgaaaa                                                           610
```

```
<210> SEQ ID NO 277
<211> LENGTH: 38
<212> TYPE: DNA
<213> ORGANISM: Homo sapien
<220> FEATURE:
<221> NAME/KEY: misc_feature
<222> LOCATION: (1)...(38)
<223> OTHER INFORMATION: n = A,T,C or G

<400> SEQUENCE: 277

ancgnggtcg cggccgangt ntttttttctt nttttttt                            38
```

```
<210> SEQ ID NO 278
<211> LENGTH: 443
<212> TYPE: DNA
<213> ORGANISM: Homo sapien
<220> FEATURE:
<221> NAME/KEY: misc_feature
<222> LOCATION: (1)...(443)
<223> OTHER INFORMATION: n = A,T,C or G

<400> SEQUENCE: 278

agcgtggtcg cggccgaggt ctgaggttac atgcgtggtg gtggacgtga gccacgaaga     60

ccctgaggtc aagttcaact ggtacgtgga cggcgtggag gtgcataatg ccaagacaaa    120

gccgcgggag gagcagtaca acagcacgta ccgggnggtc agcgtcctca ccgtcctgca    180

ccagaattgg ttgaatggca aggagtacaa gngcaaggtt tccaacaaag ccntcccagc    240

ccccntcgaa aaaaccattt ccaaagccaa agggcagccc cgagaaccac aggtgtacac    300

cctgcccccca tcccgggagg aaaagancaa naaccnggtt cagccttaac ttgcttggtc    360

naangctttt tatcccaacg nacttccccc ntggaantgg gaaaaaccaa tgggccaanc    420

cgaaaaacaa ttacaanaac ccc                                            443
```

```
<210> SEQ ID NO 279
<211> LENGTH: 348
<212> TYPE: DNA
<213> ORGANISM: Homo sapien
<220> FEATURE:
<221> NAME/KEY: misc_feature
<222> LOCATION: (1)...(348)
<223> OTHER INFORMATION: n = A,T,C or G

<400> SEQUENCE: 279

tcgagcggcc gcccgggcag gtgtcggagt ccagcacggg aggcgtggtc ttgtagttgt     60

tctccggctg cccattgctc tcccactcca cggcgatgtc gctgggatag aagcctttga    120

ccaggcaggt caggctgacc tggttcttgg tcatctcctc ccgggatggg ggcagggtga    180
```

-continued

```
acacctgggg ttctcggggc ttgccctttg gttttgaana tggttttctc gatgggggct    240

ggaagggctt tgttgnaaac cttgcacttg actccttgcc attcacccag ncctggngca    300

ggacggngag gacnctnacc acacggaacc gggctggtgg actgctcc                 348


<210> SEQ ID NO 280
<211> LENGTH: 149
<212> TYPE: DNA
<213> ORGANISM: Homo sapien
<220> FEATURE:
<221> NAME/KEY: misc_feature
<222> LOCATION: (1)...(149)
<223> OTHER INFORMATION: n = A,T,C or G

<400> SEQUENCE: 280

agcgtggtcg cggacgangt cctgtcagag tggnactggt agaagttcca ngaaccctga     60

actgtaaggg ttcttcatca gtgccaacag gatgacatga aatgatgtac tcagaagngn    120

cctggaatgg ggcccatgan atggttgcc                                      149


<210> SEQ ID NO 281
<211> LENGTH: 404
<212> TYPE: DNA
<213> ORGANISM: Homo sapien
<220> FEATURE:
<221> NAME/KEY: misc_feature
<222> LOCATION: (1)...(404)
<223> OTHER INFORMATION: n = A,T,C or G

<400> SEQUENCE: 281

tcgagcggcc gcccgggcag gtccaccaca cccaattcct tgctggtatc atggcagccg     60

ccacgtgcca ggattaccgg ctacatcatc aagtatgaga agcctgggtc tcctcccaga    120

gaagtggtcc ctcggccccg ccctggtgtc acagaggcta ctattactgg cctggaaccg    180

ggaaccgaat atacaattta tgtcattgcc ctgaagaata atcagaagag cgagcccctg    240

attggaagga aaaagacaga cgagcttccc caactggtaa cccttccaca ccccaatctt    300

catggaccag agatcttgga tgttccttcc acagttcaaa agacccettt cggcaccccc    360

cctgggtatg aacctgggaa aanggnantt aanctttcct ggca                     404


<210> SEQ ID NO 282
<211> LENGTH: 507
<212> TYPE: DNA
<213> ORGANISM: Homo sapien
<220> FEATURE:
<221> NAME/KEY: misc_feature
<222> LOCATION: (1)...(507)
<223> OTHER INFORMATION: n = A,T,C or G

<400> SEQUENCE: 282

agcgtggtcg cggccgaggt ctgggatgct cctgctgtca cagtgagata ttacaggatc     60

acttacggag aaacaggagg aaatagccct gtccaggagt tcactgtgcc tgggagcaag    120

tctacagcta ccatcagcgg ccttaaacct ggagttgatt ataccatcac tgtgtatgct    180

gtcactggcc gtggagacag ccccgcaagc agcaagccaa tttccattaa ttaccgaaca    240

gaaattgaca aaccatccca gatgcaagtg accgatgttc aggacaacag cattagtgtc    300

aagtggctgc cttcaaggtn ccctggtact gggttacaga ntaaccacca ctcccaaaaa    360

tggaccagga accacaaaaa cttaaactgc agggtccaga tcaaaacaga aatgactatt    420

gaangcttgc agcccacagt gggagtatgn gggtagtgnc tatgcttcag aatccaagcg    480

gaaaaangtc aagccttntg ggttcaa                                        507
```

-continued

<210> SEQ ID NO 283
<211> LENGTH: 325
<212> TYPE: DNA
<213> ORGANISM: Homo sapien
<220> FEATURE:
<221> NAME/KEY: misc_feature
<222> LOCATION: (1)...(325)
<223> OTHER INFORMATION: n = A,T,C or G

<400> SEQUENCE: 283
tcgagcggcc gcccgggcag gtccttgcag ctctgcagtg tcttcttcac catcaggtgc 60
agggaatagc tcatggattc catcctcagg gctcgagtag gtcaccctgt acctggaaac 120
ttgcccctgt gggctttccc aagcaatttt gatggaatcg acatccacat cagtgaatgc 180
cagtccttta gggcgatcaa tgttggttac tgcagnctga accagaggct gactctctcc 240
gcttggattc tgagcataga cactaaccac atactccact gtgggctgca anccttcaat 300
aanncatttc tgtttgatct ggacc 325

<210> SEQ ID NO 284
<211> LENGTH: 331
<212> TYPE: DNA
<213> ORGANISM: Homo sapien
<220> FEATURE:
<221> NAME/KEY: misc_feature
<222> LOCATION: (1)...(331)
<223> OTHER INFORMATION: n = A,T,C or G

<400> SEQUENCE: 284
tcgagcggcc gcccgggcag gtctggtggg gtcctggcac acgcacatgg gggngttgnt 60
ctnatccagc tgcccagccc ccattggcga gtttgagaag gtgtgcagca atgacaacaa 120
naccttcgac tcttcctgcc acttctttgc cacaaagtgc accctggagg gcaccaagaa 180
gggccacaag ctccacctgg actacatcgg gccttgcaaa tacatccccc cttgcctgga 240
ctctgagctg accgaattcc cccttgcgca tgcgggactg gctcaagaac cgtcctggca 300
cccttgtatg anagggatga agacacnacc c 331

<210> SEQ ID NO 285
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 285
agcgtggtcg cggccgaggt ctgtcctaca gtcctcagga ctctactccc tcagcagcgt 60
ggtgaccgtg ccctccagca acttcggcac ccagacctac acctgcaacg tagatcacaa 120
gcccagcaac accaaggtgg acaagagagt tgagcccaaa tcttgtgaca aaactcacac 180
atgcccaccg tgcccagcac ctgaactcct ggggggaccg tcagtcttcc tcttcccccg 240
catccccctt ccaaacctgc ccgggcggcc gctcgaaagc cgaattccag cacactggcg 300
gccggtacta gtgganccna acttggnanc caacctggng gaantaatgg gcataanctg 360
tttctggggg gaaattggta tccngtttac aattcccnca caacatacga gccggaagca 420
taaaagngta aaagcctggg ggnggcctan tgaagtgaag ctaaactcac attaattngc 480
gttgccgctc actggcccgc ttttccagc 509

<210> SEQ ID NO 286
<211> LENGTH: 336
<212> TYPE: DNA
<213> ORGANISM: Homo sapien
<220> FEATURE:
<221> NAME/KEY: misc_feature
<222> LOCATION: (1)...(336)
<223> OTHER INFORMATION: n = A,T,C or G

<400> SEQUENCE: 286
tcgagcggcc gcccgggcag gtttggaagg gggatgcggg ggaagaggaa gactgacggt 60
ccccccagga gttcaggtgc tgggcacggt gggcatgtgt gagttttgtc acaagatttg 120
ggctcaactc tcttgtccac cttggtgttg ctgggcttgt gatctacgtt gcaggtgtag 180
gtctgggngc cgaagttgct ggagggcacg gtcaccacgc tgctgaggga gtagagtcct 240
gaggactgta ngacagacct cggccgngac cacgctaagc cgaattctgc agatatccat 300
cacactggcg gccgctccga gcatgcattt tagagg 336

<210> SEQ ID NO 287
<211> LENGTH: 30
<212> TYPE: DNA
<213> ORGANISM: Homo sapien
<220> FEATURE:
<221> NAME/KEY: misc_feature
<222> LOCATION: (1)...(30)
<223> OTHER INFORMATION: n = A,T,C or G

<400> SEQUENCE: 287
agcgtggncg cggacganga caacaacccc 30

<210> SEQ ID NO 288
<211> LENGTH: 316
<212> TYPE: DNA
<213> ORGANISM: Homo sapien
<220> FEATURE:
<221> NAME/KEY: misc_feature
<222> LOCATION: (1)...(316)
<223> OTHER INFORMATION: n = A,T,C or G

<400> SEQUENCE: 288
tcgagcggcc gcccgggcag gnccacatcg gcagggtcgg agccctggcc gccatactcg 60
aactggaatc catcggtcat gctcttgccg aaccagacat gcctcttgtc cttggggttc 120
ttgctgatgn accagttctt ctgggccaca ctgggctgag tggggtacac gcaggtctca 180
ccagtctcca tgttgcagaa gactttgatg gcatccaggt tgcagccttg gttggggtca 240
atccagtact ctccactctt ccagtcagag tggcacatct tgaggtcacg gcaggtgcgg 300
gcggggttct tgacct 316

<210> SEQ ID NO 289
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 289
agcgtggtcg cggccgaggt ccagcctgga gataanggtg aaggtggtgc ccccggactt 60
ccaggtatag ctggacctcg tggtagccct ggtgagagag gtgaaactgg ccctccagga 120
cctgctggtt tccctggtgc tcctggacag aatggtgaac ctggnggtaa aggagaaaga 180

-continued

```
ggggctccgg ntganaaagg tgaaggaggc cctcctgnat tggcaggggc cccangactt    240

agaggtggag ctggcccccc tggccccgaa ggaggaaagg gtgctgctgg tcctcctggg    300

ccacctgg                                                             308
```

<210> SEQ ID NO 290
<211> LENGTH: 324
<212> TYPE: DNA
<213> ORGANISM: Homo sapien
<220> FEATURE:
<221> NAME/KEY: misc_feature
<222> LOCATION: (1)...(324)
<223> OTHER INFORMATION: n = A,T,C or G

<400> SEQUENCE: 290

```
tcgagcggcc gcccgggcag gtctgggcca ggaggaccaa taggaccagt aggacccctt     60

gggccatctt tccctgggac accatcagca cctggaccgc ctggttcacc cttgtcaccc    120

tttggaccag gacttccaag acctcctctt tctccaggca ttccttgcag accaggagta    180

ccancagcac caggtggccc aggaggacca gcagcaccct ttcctccttc gggaccaggg    240

ggaccagctc cacctctaag tcctggggcc cctgccaatc caggagggcc tccttcacct    300

ttctcacccg gagcccctct ttct                                           324
```

<210> SEQ ID NO 291
<211> LENGTH: 278
<212> TYPE: DNA
<213> ORGANISM: Homo sapien
<220> FEATURE:
<221> NAME/KEY: misc_feature
<222> LOCATION: (1)...(278)
<223> OTHER INFORMATION: n = A,T,C or G

<400> SEQUENCE: 291

```
tcgagcggcc gcccgggcag gtccaccggg atattcgggg gtctggcagg aatgggaggc     60

atccagaacg agaaggagac catgcaaagc ctgaacgacc gcctggcctc ttacctggac    120

agagtgagga gcctggagac cgacaaccgg aggctggaga gcaaaatccg ggagcacttg    180

gagaagaagg gaccccaggt cagagactgg agccattact tcaagatcat cgaggacctg    240

agggctcana tcttcgcaaa tactgcngac aatgcccg                            278
```

<210> SEQ ID NO 292
<211> LENGTH: 299
<212> TYPE: DNA
<213> ORGANISM: Homo sapien
<220> FEATURE:
<221> NAME/KEY: misc_feature
<222> LOCATION: (1)...(299)
<223> OTHER INFORMATION: n = A,T,C or G

<400> SEQUENCE: 292

```
atgcgnggtc gcggccgang accanctctg gctcatactt gactctaaag ncntcaccag     60

nanttacggn cattgccaat ctgcagaacg atgcgggcat tgtccgcant atttgcgaag    120

atctgagccc tcaggncctc gatgatcttg aagtaanggc tccagtctct gacctggggt    180

cccttcttct ccaagtgctc ccggattttg ctctccagcc tccggttctc ggtctccaag    240

ncttctcact ctgtccagga aaagaggcca ggcggncgat cagggctttt gcatggact     299
```

<210> SEQ ID NO 293
<211> LENGTH: 101
<212> TYPE: DNA

-continued

<213> ORGANISM: Homo sapien

<400> SEQUENCE: 293
agcgtggtcg cggccgaggt tgtacaagct tttttttttt tttttttttt tttttttttt 60
tttttttttt tttttttttt tttttttttt tttttttttt t 101

<210> SEQ ID NO 294
<211> LENGTH: 285
<212> TYPE: DNA
<213> ORGANISM: Homo sapien
<220> FEATURE:
<221> NAME/KEY: misc_feature
<222> LOCATION: (1)...(285)
<223> OTHER INFORMATION: n = A,T,C or G

<400> SEQUENCE: 294
tcgagcggcc gcccgggcag gtctgccaac accaagattg gcccccgccg catccacaca 60
gttngtgtgc ggggaggtaa caagaaatac cgtgccctga ggntggacgn ggggaatttc 120
tcctggggct cagagtgttg tactcgtaaa acaaggatca tcgatgttgt ctacaatgca 180
tctaataacg agctggttcg taccaagacc ctggtgaaga attgcatcgt gctcatngac 240
agcacaccgt accgacagtg ggtaccgaag tcccactatg cncct 285

<210> SEQ ID NO 295
<211> LENGTH: 216
<212> TYPE: DNA
<213> ORGANISM: Homo sapien

<400> SEQUENCE: 295
tcgagcggcc gcccgggcag gtccaccaca cccaattcct tgctggtatc atggcagccg 60
ccacgtgcca ggattaccgg ctacatcatc aagtatgaga agcctgggtc tcctcccaga 120
gaagtggtcc ctcggccccg ccctggtgtc acagaggcta ctattactgg cctggaaccg 180
ggaaccgaat atacaattta tgtcattgcc ctgaag 216

<210> SEQ ID NO 296
<211> LENGTH: 414
<212> TYPE: DNA
<213> ORGANISM: Homo sapien
<220> FEATURE:
<221> NAME/KEY: misc_feature
<222> LOCATION: (1)...(414)
<223> OTHER INFORMATION: n = A,T,C or G

<400> SEQUENCE: 296
agcgtgntcn cggccgagga tggggaagct cgnctgtctt tttccttcca atcaggggct 60
nnntcttctg attattcttc agggcaanga cataaattgt atattcggnt cccggttcca 120
gnccagtaat agtagcctct gtgacaccag ggcggggccg agggaccact tctctgggag 180
gagacccagg cttctcatac ttgatgatga agccggtaat cctggcacgt gggcggctgc 240
catgatacca ccaangaatt gggtgtggtg gacctgcccg ggcgggccgc tcgaaaancc 300
gaattcntgc aagaatatcc atcacacttg ggcgggccgn tcgaaccatg catcntaaaa 360
gggccccaat ttccccccta ttaggngaag ccncatttaa caaattccac ttgg 414

<210> SEQ ID NO 297
<211> LENGTH: 376
<212> TYPE: DNA
<213> ORGANISM: Homo sapien
<220> FEATURE:
<221> NAME/KEY: misc_feature -continued
<222> LOCATION: (1)...(376)
<223> OTHER INFORMATION: n = A,T,C or G

<400> SEQUENCE: 297
tcgagcggcc gcccgggcag gtctcgcggt cgcactggtg atgctggtcc tgttggtccc 60
cccggccctc ctggacctcc tggtccccct ggtcctccca gcgctggttt cgacttcagc 120
ttcctgcccc agccacctca agagaaggct cacgatggtg gccgctacta ccgggctgat 180
gatgccaatg tggttcgtga ccgtgacctc gaggtggaca ccaccctcaa gagccttgag 240
ccagcagaat cgaaaacatt cggaacccaa gaagggcaag cccgcaaaga aaccccgccc 300
gcacctggcc gngaacctcc aagaangtgc ccacntcttg actgggaaaa aaagggaaaa 360
ntacttggaa ttggac 376

<210> SEQ ID NO 298
<211> LENGTH: 357
<212> TYPE: DNA
<213> ORGANISM: Homo sapien
<220> FEATURE:
<221> NAME/KEY: misc_feature
<222> LOCATION: (1)...(357)
<223> OTHER INFORMATION: n = A,T,C or G

<400> SEQUENCE: 298
agcgtggtcg cggccgaggt ccacatcggc agggtcggag ccctggccgc catactcgaa 60
ctggaatcca tcggtcatgc tctcgccgaa ccagacatgc ctcttgtcct tggggttctt 120
gctgatgtac cagttcttct gggccacact gggctgagtg gggtacacgc aggtctcacc 180
agtctccatg ttgcagaaga ctttgatggc atccaggttg cagccttggt tggggtcaat 240
ccagtactct ccactcttcc agtcagaagt ggcacatctt gaggtcacgg cagggtgcgg 300
gcggggttct tgcgggctgc ccttctgggc tcccggaatg ttctnngaac ttgctgg 357

<210> SEQ ID NO 299
<211> LENGTH: 307
<212> TYPE: DNA
<213> ORGANISM: Homo sapien
<220> FEATURE:
<221> NAME/KEY: misc_feature
<222> LOCATION: (1)...(307)
<223> OTHER INFORMATION: n = A,T,C or G

<400> SEQUENCE: 299
agcgtggtcg cggccgaggt ccactagagg tctgtgtgcc attgcccagg cagagtctct 60
gcgttacaaa ctcctaggag ggcttgctgt gcggagggcc tgctatggtg tgctgcggtt 120
catcatggag agtggggcca aaggctgcga ggttgtggtg tctgggaaac tccgaggaca 180
gagggctaaa tccatgaagt ttgtggatgg cctgatgatc cacagcggag accctgttaa 240
ctactacgtt gacacttgct tgtgcgccac gtgttgctca nacangggtg ggctgggcat 300 caaggng 307

<210> SEQ ID NO 300
<211> LENGTH: 351
<212> TYPE: DNA
<213> ORGANISM: Homo sapien

<400> SEQUENCE: 300
tcgagcggcc gcccgggcag gtctgccaag gagaccctgt tatgctgtgg ggactggctg 60
gggcatggca ggcggctctg gcttcccacc cttctgttct gagatggggg tggtgggcag 120

-continued

```
tatctcatct ttgggttcca caatgctcac gtggtcaggc aggggcttct tagggccaat    180

cttaccagtt gggtcccagg gcagcatgat cttcaccttg atgcccagca caccctgtct    240

gagcaacacg tggcgcacag caagtgtcaa cgtaagtaag ttaacagggt ctccgctgtg    300

gatcatcagg ccatccacaa acttcatgga tttaaccctc tgtcctcgga g             351
```

<210> SEQ ID NO 301
<211> LENGTH: 330
<212> TYPE: DNA
<213> ORGANISM: Homo sapien

<400> SEQUENCE: 301

```
tcgagcggcc gcccgggcag gtgtttcaga ggttccaagg tccactgtgg aggtcccagg     60

agtgctggtg gtgggcacag aggtccgatg ggtgaaacca ttgacataga gactgttcct    120

gtccagggtg taggggccca gctctttgat gccattggcc agttggctca gctcccagta    180

cagccgctct ctgttgagtc cagggctttt ggggtcaaga tgatggatgc agatggcatc    240

cactccagtg gctgctccat ccttctcgga cctgagagag gtcagtctgc agccagagta    300

cagagggcca acactggtgt tctttgaata                                     330
```

<210> SEQ ID NO 302
<211> LENGTH: 317
<212> TYPE: DNA
<213> ORGANISM: Homo sapien
<220> FEATURE:
<221> NAME/KEY: misc_feature
<222> LOCATION: (1)...(317)
<223> OTHER INFORMATION: n = A,T,C or G

<400> SEQUENCE: 302

```
agcgtggtcg cggccgaggt ctgtactggg agctaagcaa actgaccaat gacattgaag     60

agctgggccc ctacaccctg gacaggaaca gtctctatgt caatggtttc acccatcaga    120

gctctgtgnc caccaccagc actcctggga cctccacagt ggatttcaga acctcaggga    180

ctccatcctc cctctccagc cccacaatta tggctgctgg ccctctcctg gtaccattca    240

ccctcaactt caccatcacc aacctgcagt atggggagga catgggtcac cctgnctcca    300

ggaagttcaa caccaca                                                   317
```

<210> SEQ ID NO 303
<211> LENGTH: 283
<212> TYPE: DNA
<213> ORGANISM: Homo sapien
<220> FEATURE:
<221> NAME/KEY: misc_feature
<222> LOCATION: (1)...(283)
<223> OTHER INFORMATION: n = A,T,C or G

<400> SEQUENCE: 303

```
tcgagcggcc gcccggacag gtctgggcgg atagcaccgg gcatattttg gaatggatga     60

ggtctggcac cctgagcagt ccagcgagga cttggtctta gttgagcaat ttggctagga    120

ggatagtatg cagcacggnt ctgagnctgt gggatagctg ccatgaagta acctgaagga    180

ggtgctggct ggtangggtt gattacaggg ttgggaacag ctcgtacact tgccattctc    240

tgcatatact ggttagtgag gtgagcctgg ccctcttctt ttg                      283
```

<210> SEQ ID NO 304
<211> LENGTH: 72
<212> TYPE: DNA
<213> ORGANISM: Homo sapien -continued
<220> FEATURE:
<221> NAME/KEY: misc_feature
<222> LOCATION: (1)...(72)
<223> OTHER INFORMATION: n = A,T,C or G

<400> SEQUENCE: 304
agcgtggtcg cggccgaggt gagccacagg tgaccggggc tgaagctggg gctgctggnc 60
ctgctggtcc tg 72

<210> SEQ ID NO 305
<211> LENGTH: 245
<212> TYPE: DNA
<213> ORGANISM: Homo sapien
<220> FEATURE:
<221> NAME/KEY: misc_feature
<222> LOCATION: (1)...(245)
<223> OTHER INFORMATION: n = A,T,C or G

<400> SEQUENCE: 305
cagcngctcc nacggggcct gngggaccaa caacaccgtt ttcaccctta ggccctttgg 60
ctcctctttc tcctttagca ccaggttgac cagcagcncc ancaggacca gcaaatccat 120
tggggccagc aggaccgacc tcaccacgtt caccagggct tccccgagga ccagcaggac 180
cagcaggacc agcagcccca gcttcgcccc ggtcacctgt ggctcacctc ggccgcgacc 240
acgct 245

<210> SEQ ID NO 306
<211> LENGTH: 246
<212> TYPE: DNA
<213> ORGANISM: Homo sapien
<220> FEATURE:
<221> NAME/KEY: misc_feature
<222> LOCATION: (1)...(246)
<223> OTHER INFORMATION: n = A,T,C or G

<400> SEQUENCE: 306
tcgagcggtc gcccgggcag gtccaccggg atagccgggg gtctggcagg aatgggaggc 60
atccagaacg agaaggagac catgcaaagc ctgaacgacc gcctggcctc ttacctggac 120
agagtgagga gcctggagac cganaaccgg aggctggana gcaaaatccg ggagcacttg 180
gagaagaagg gaccccaggt caagagactg gagccattac ttcaagatca tcgagggacc 240
tggagg 246

<210> SEQ ID NO 307
<211> LENGTH: 333
<212> TYPE: DNA
<213> ORGANISM: Homo sapien
<220> FEATURE:
<221> NAME/KEY: misc_feature
<222> LOCATION: (1)...(333)
<223> OTHER INFORMATION: n = A,T,C or G

<400> SEQUENCE: 307
agcgnggtcg cggccgaggt ccagctctgt ctcatacttg actctaaagt catcagcagc 60
aagacgggca ttgtcaatct gcagaacgat gcgggcattg tccgcagtat ttgcgaagat 120
ctgagccctc aggtcctcga tgatcttgaa gtaatggctc cagtctctga cctggggtcc 180
cttcttctcc aagtgctccc ggattttgct ctccagcctc cggttctcgg tctccaggct 240
cctcactctg tccaggtaag aaggcccagg cggtcgttca ggctttgcat ggtctccttc 300
tcgttctgga tgcctcccat tcctgccaga ccc 333

-continued

<210> SEQ ID NO 308
<211> LENGTH: 310
<212> TYPE: DNA
<213> ORGANISM: Homo sapien

<400> SEQUENCE: 308
tcgagcggcc gcccgggcag gtcaggaagc acattggtct tagagccact gcctcctgga 60
ttccacctgt gctgcggaca tctccaggga gtgcagaagg gaagcaggtc aaactgctca 120
gatcagtcag actggctgtt ctcagttctc acctgagcaa ggtcagtctg cagccagagt 180
acagagggcc aacactggtg ttcttgaaca agggcttgag cagaccctgc agaaccctct 240
tccgtggtgt tgaacttcct ggaaaccagg gtgttgcatg tttttcctca taatgcaagg 300
ttggtgatgg 310

<210> SEQ ID NO 309
<211> LENGTH: 429
<212> TYPE: DNA
<213> ORGANISM: Homo sapien

<400> SEQUENCE: 309
agcgtggtcg cggccgaggt ccacatcggc agggtcggag ccctggccgc catactcgaa 60
ctggaatcca tcggtcatgc tctcgccgaa ccagacatgc ctcttgtcct tggggttctt 120
gctgatgtac cagttcttct gggccacact gggctgagtg gggtacaccg caggtctcac 180
cagtctccat gttgcagaag actttgatgg catccaggtt gcagccttgg ttggggtcaa 240
tccagtactc tccactcttc cagtcagaag tgggcacatc ttgaggtcac cggcaggtgc 300
cgggccgggg gttcttgcgg cttgccctct gggctccgga tgttctcgat ctgcttggct 360
caggctcttg agggtgggtg tccacctcga ggtcacggtc accgaaacct gcccgggcgg 420
cccgctcga 429

<210> SEQ ID NO 310
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 310
tcgagcggtc gcccgggcag gtttcgtgac cgtgacctcg aggtggacac caccctcaag 60
agcctgagcc agcagatcga gaacatccgg agcccagagg gcagccgcaa gaaccccgcc 120
cgcacctgcc gtgacctcaa gatgtgccac tctgactgga agagtggaga gtactggatt 180
gaccccaacc aaggctgcaa cctggatgcc atcaaagtct tctgcaacat ggagactggt 240
gagacctgcg tgtaccccac tcagcccagt gtgggcccag aagaaactgg tacatcagca 300
aggaacccca aggacaagag gcattgtctt ggttcggcga gnagcatgac ccgatggatt 360
ccagtttcga gtattggcgg ccagggcttc ccgacccttg ccgatgtgga cctcggccgc 420
gaccaccgct 430

<210> SEQ ID NO 311
<211> LENGTH: 2996
<212> TYPE: DNA
<213> ORGANISM: Homo sapien

<400> SEQUENCE: 311

-continued

```
cagccaccgg agtggatgcc atctgcaccc accgccctga ccccacaggc cctgggctgg     60
acagagagca gctgtatttg gagctgagcc agctgaccca cagcatcact gagctgggcc    120
cctacaccct ggacagggac agtctctatg tcaatggttt cacacagcgg agctctgtgc    180
ccaccactag cattcctggg acccccacag tggacctggg aacatctggg actccagttt    240
ctaaacctgg tccctcggct gccagccctc tcctggtgct attcactctc aacttcacca    300
tcaccaacct gcggtatgag gagaacatgc agcaccctgg ctccaggaag ttcaacacca    360
cggagagggt ccttcagggc ctggtccctg ttcaagagca ccagtgttgg ccctctgtac    420
tctggctgca gactgacttt gctcaggcct gaaaaggatg ggacagccac tggagtggat    480
gccatctgca cccaccaccc tgaccccaaa agccctaggc tggacagaga gcagctgtat    540
tgggagctga gccagctgac ccacaatatc actgagctgg gcccctatgc cctggacaac    600
gacagcctct ttgtcaatgg tttcactcat cggagctctg tgtccaccac cagcactcct    660
gggaccccca cagtgtatct gggagcatct aagactccag cctcgatatt tggcccttca    720
gctgccagcc atctcctgat actattcacc ctcaacttca ccatcactaa cctgcggtat    780
gaggagaaca tgtggcctgg ctccaggaag ttcaacacta cagagagggt ccttcagggc    840
ctgctaaggc ccttgttcaa gaacaccagt gttggccctc tgtactctgg ctgcaggctg    900
accttgctca ggccagagaa agatggggaa gccaccggag tggatgccat ctgcacccac    960
cgccctgacc ccacaggccc tgggctggac agagagcagc tgtatttgga gctgagccag   1020
ctgacccaca gcatcactga gctgggcccc tacacactgg acagggacag tctctatgtc   1080
aatggtttca cccatcggag ctctgtaccc accaccagca ccggggtggt cagcgaggag   1140
ccattcacac tgaacttcac catcaacaac ctgcgctaca tggcggacat gggccaaccc   1200
ggctccctca agttcaacat cacagacaac gtcatgaagc acctgctcag tcctttgttc   1260
cagaggagca gcctgggtgc acggtacaca ggctgcaggg tcatcgcact aaggtctgtg   1320
aagaacggtg ctgagacacg ggtggacctc ctctgcacct acctgcagcc cctcagcggc   1380
ccaggtctgc ctatcaagca ggtgttccat gagctgagcc agcagaccca tggcatcacc   1440
cggctgggcc cctactctct ggacaaagac agcctctacc ttaacggtta caatgaacct   1500
ggtccagatg agcctcctac aactcccaag ccagccacca cattcctgcc tcctctgtca   1560
gaagccacaa cagccatggg gtaccacctg aagaccctca cactcaactt caccatctcc   1620
aatctccagt attcaccaga tatgggcaag ggctcagcta cattcaactc caccgagggg   1680
gtccttcagc acctgctcag acccttgttc cagaagagca gcatgggccc cttctacttg   1740
ggttgccaac tgatctccct caggcctgag aaggatgggg cagccactgg tgtggacacc   1800
acctgcacct accaccctga ccctgtgggc cccgggctgg acatacagca gctttactgg   1860
gagctgagtc agctgaccca tggtgtcacc caactgggct tctatgtcct ggacagggat   1920
agcctcttca tcaatggcta tgcaccccag aatttatcaa tccggggcga gtaccagata   1980
aatttccaca ttgtcaactg gaacctcagt aatccagacc ccacatcctc agagtacatc   2040
accctgctga gggacatcca ggacaaggtc accacactct acaaaggcag tcaactacat   2100
gacacattcc gcttctgcct ggtcaccaac ttgacgatgg actccgtgtt ggtcactgtc   2160
aaggcattgt tctcctccaa tttggacccc agcctggtgg agcaagtctt tctagataag   2220
accctgaatg cctcattcca ttggctgggc tccacctacc agttggtgga catccatgtg   2280
acagaaatgg agtcatcagt ttatcaacca acaagcagct ccagcaccca gcacttctac   2340
```

-continued

```
ctgaatttca ccatcaccaa cctaccatat tcccaggaca aagcccagcc aggcaccacc   2400

aattaccaga ggaacaaaag gaatattgag gatgcgctca accaactctt ccgaaacagc   2460

agcatcaaga gttatttttc tgactgtcaa gtttcaacat tcaggtctgt ccccaacagg   2520

caccacaccg ggtggactcc cctgtgtaac ttctcgccac tggctcggag agtagacaga   2580

gttgccatct atgaggaatt tctgcggatg acccggaatg gtacccagct gcagaacttc   2640

accctggaca ggagcagtgt ccttgtggat gggtattttc ccaacagaaa tgagccctta   2700

actgggaatt ctgaccttcc cttctgggct gtcatcctca tcggcttggc aggactcctg   2760

ggactcatca catgcctgat ctgcggtgtc ctggtgacca cccgccggcg gaagaaggaa   2820

ggagaataca acgtccagca acagtgccca ggctactacc agtcacacct agacctggag   2880

gatctgcaat gactggaact tgccggtgcc tggggtgcct ttcccccagc cagggtccaa   2940

agaagcttgg ctggggcaga aataaaccat attggtcgga cacaaaaaaa aaaaaa       2996
```

```
<210> SEQ ID NO 312
<211> LENGTH: 914
<212> TYPE: PRT
<213> ORGANISM: Homo sapien

<400> SEQUENCE: 312

Met Ser Met Val Ser His Ser Gly Ala Leu Cys Pro Pro Leu Ala Phe
 1               5                  10                  15

Leu Gly Pro Pro Gln Trp Thr Trp Glu His Leu Gly Leu Gln Phe Leu
            20                  25                  30

Asn Leu Val Pro Arg Leu Pro Ala Leu Ser Trp Cys Tyr Ser Leu Ser
        35                  40                  45

Thr Ser Pro Ser Pro Thr Cys Gly Met Arg Arg Thr Cys Ser Thr Leu
    50                  55                  60

Ala Pro Gly Ser Ser Thr Pro Arg Arg Gly Ser Phe Arg Ala Trp Ser
65                  70                  75                  80

Leu Phe Lys Ser Thr Ser Val Gly Pro Leu Tyr Ser Gly Cys Arg Leu
                85                  90                  95

Thr Leu Leu Arg Pro Glu Lys Asp Gly Thr Ala Thr Gly Val Asp Ala
            100                 105                 110

Ile Cys Thr His His Pro Asp Pro Lys Ser Pro Arg Leu Asp Arg Glu
        115                 120                 125

Gln Leu Tyr Trp Glu Leu Ser Gln Leu Thr His Asn Ile Thr Glu Leu
    130                 135                 140

Gly Pro Tyr Ala Leu Asp Asn Asp Ser Leu Phe Val Asn Gly Phe Thr
145                 150                 155                 160

His Arg Ser Ser Val Ser Thr Thr Ser Thr Pro Gly Thr Pro Thr Val
                165                 170                 175

Tyr Leu Gly Ala Ser Lys Thr Pro Ala Ser Ile Phe Gly Pro Ser Ala
            180                 185                 190

Ala Ser His Leu Leu Ile Leu Phe Thr Leu Asn Phe Thr Ile Thr Asn
        195                 200                 205

Leu Arg Tyr Glu Glu Asn Met Trp Pro Gly Ser Arg Lys Phe Asn Thr
    210                 215                 220

Thr Glu Arg Val Leu Gln Gly Leu Leu Arg Pro Leu Phe Lys Asn Thr
225                 230                 235                 240

Ser Val Gly Pro Leu Tyr Ser Gly Cys Arg Leu Thr Leu Leu Arg Pro
                245                 250                 255

Glu Lys Asp Gly Glu Ala Thr Gly Val Asp Ala Ile Cys Thr His Arg
```

-continued

```
            260                 265                 270

Pro Asp Pro Thr Gly Pro Gly Leu Asp Arg Glu Gln Leu Tyr Leu Glu
        275                 280                 285

Leu Ser Gln Leu Thr His Ser Ile Thr Glu Leu Gly Pro Tyr Thr Leu
    290                 295                 300

Asp Arg Asp Ser Leu Tyr Val Asn Gly Phe Thr His Arg Ser Ser Val
305                 310                 315                 320

Pro Thr Thr Ser Thr Gly Val Val Ser Glu Glu Pro Phe Thr Leu Asn
                325                 330                 335

Phe Thr Ile Asn Asn Leu Arg Tyr Met Ala Asp Met Gly Gln Pro Gly
            340                 345                 350

Ser Leu Lys Phe Asn Ile Thr Asp Asn Val Met Lys His Leu Leu Ser
        355                 360                 365

Pro Leu Phe Gln Arg Ser Ser Leu Gly Ala Arg Tyr Thr Gly Cys Arg
    370                 375                 380

Val Ile Ala Leu Arg Ser Val Lys Asn Gly Ala Glu Thr Arg Val Asp
385                 390                 395                 400

Leu Leu Cys Thr Tyr Leu Gln Pro Leu Ser Gly Pro Gly Leu Pro Ile
                405                 410                 415

Lys Gln Val Phe His Glu Leu Ser Gln Gln Thr His Gly Ile Thr Arg
            420                 425                 430

Leu Gly Pro Tyr Ser Leu Asp Lys Asp Ser Leu Tyr Leu Asn Gly Tyr
        435                 440                 445

Asn Glu Pro Gly Pro Asp Glu Pro Pro Thr Thr Pro Lys Pro Ala Thr
    450                 455                 460

Thr Phe Leu Pro Pro Leu Ser Glu Ala Thr Thr Ala Met Gly Tyr His
465                 470                 475                 480

Leu Lys Thr Leu Thr Leu Asn Phe Thr Ile Ser Asn Leu Gln Tyr Ser
                485                 490                 495

Pro Asp Met Gly Lys Gly Ser Ala Thr Phe Asn Ser Thr Glu Gly Val
            500                 505                 510

Leu Gln His Leu Leu Arg Pro Leu Phe Gln Lys Ser Ser Met Gly Pro
        515                 520                 525

Phe Tyr Leu Gly Cys Gln Leu Ile Ser Leu Arg Pro Glu Lys Asp Gly
    530                 535                 540

Ala Ala Thr Gly Val Asp Thr Thr Cys Thr Tyr His Pro Asp Pro Val
545                 550                 555                 560

Gly Pro Gly Leu Asp Ile Gln Gln Leu Tyr Trp Glu Leu Ser Gln Leu
                565                 570                 575

Thr His Gly Val Thr Gln Leu Gly Phe Tyr Val Leu Asp Arg Asp Ser
            580                 585                 590

Leu Phe Ile Asn Gly Tyr Ala Pro Gln Asn Leu Ser Ile Arg Gly Glu
        595                 600                 605

Tyr Gln Ile Asn Phe His Ile Val Asn Trp Asn Leu Ser Asn Pro Asp
    610                 615                 620

Pro Thr Ser Ser Glu Tyr Ile Thr Leu Leu Arg Asp Ile Gln Asp Lys
625                 630                 635                 640

Val Thr Thr Leu Tyr Lys Gly Ser Gln Leu His Asp Thr Phe Arg Phe
                645                 650                 655

Cys Leu Val Thr Asn Leu Thr Met Asp Ser Val Leu Val Thr Val Lys
            660                 665                 670

Ala Leu Phe Ser Ser Asn Leu Asp Pro Ser Leu Val Glu Gln Val Phe
        675                 680                 685
```

-continued

```
Leu Asp Lys Thr Leu Asn Ala Ser Phe His Trp Leu Gly Ser Thr Tyr
    690                 695                 700

Gln Leu Val Asp Ile His Val Thr Glu Met Glu Ser Ser Val Tyr Gln
705                 710                 715                 720

Pro Thr Ser Ser Ser Ser Thr Gln His Phe Tyr Leu Asn Phe Thr Ile
                725                 730                 735

Thr Asn Leu Pro Tyr Ser Gln Asp Lys Ala Gln Pro Gly Thr Thr Asn
            740                 745                 750

Tyr Gln Arg Asn Lys Arg Asn Ile Glu Asp Ala Leu Asn Gln Leu Phe
        755                 760                 765

Arg Asn Ser Ser Ile Lys Ser Tyr Phe Ser Asp Cys Gln Val Ser Thr
    770                 775                 780

Phe Arg Ser Val Pro Asn Arg His His Thr Gly Val Asp Ser Leu Cys
785                 790                 795                 800

Asn Phe Ser Pro Leu Ala Arg Arg Val Asp Arg Val Ala Ile Tyr Glu
                805                 810                 815

Glu Phe Leu Arg Met Thr Arg Asn Gly Thr Gln Leu Gln Asn Phe Thr
            820                 825                 830

Leu Asp Arg Ser Ser Val Leu Val Asp Gly Tyr Phe Pro Asn Arg Asn
        835                 840                 845

Glu Pro Leu Thr Gly Asn Ser Asp Leu Pro Phe Trp Ala Val Ile Leu
    850                 855                 860

Ile Gly Leu Ala Gly Leu Leu Gly Leu Ile Thr Cys Leu Ile Cys Gly
865                 870                 875                 880

Val Leu Val Thr Thr Arg Arg Arg Lys Lys Glu Gly Glu Tyr Asn Val
                885                 890                 895

Gln Gln Gln Cys Pro Gly Tyr Tyr Gln Ser His Leu Asp Leu Glu Asp
            900                 905                 910

Leu Gln
```

<210> SEQ ID NO 313
<211> LENGTH: 656
<212> TYPE: DNA
<213> ORGANISM: Homo sapiens

<400> SEQUENCE: 313

```
acagccagtc ggagctgcaa gtgttctggg tggatcgcgy atatgcactc aaaatgctct     60

ttgtaaagga aagccacaac atgtccaagg gacctgaggc gacttggagg ctgagcaaag    120

tgcagtttgt ctacgactcc tcggagaaaa cccacttcaa agacgcagtc agtgctggga    180

agcacacagc caactcgcac cacctctctg ccttggtcac ccccgctggg aagtcctatg    240

agtgtcaagc tcaacaaacc atttcactgg cctctagtga tccgcagaag acggtcacca    300

tgatcctgtc tgcggtccac atccaacctt ttgacattat ctcagatttt gtcttcagtg    360

aagagcataa atgcccagtg gatgagcggg agcaactgga agaaaccttg cccctgattt    420

tggggctcat cttgggcctc gtcatcatgg taacactcgc gatttaccac gtccaccaca    480

aaatgactgc caaccaggtg cagatccctc gggacagatc ccagtataag cacatgggct    540

agaggccgtt aggcaggcac cccctattcc tgctccccca actggatcag gtagaacaac    600

aaaagcactt ttccatcttg tacacgagat acaccaacat agctacaatc aaacag        656
```

<210> SEQ ID NO 314
<211> LENGTH: 519
<212> TYPE: DNA

-continued

<213> ORGANISM: Homo sapiens

<400> SEQUENCE: 314
tgtgcgtgga ccagtcagct tccgggtgtg actggagcag ggcttgtcgt cttcttcaga 60
gtcactttgc aggggttggt gaagctgctc ccatccatgt acagctccca gtctactgat 120
gtttaaggat ggtctcggtg gttaggccca ctagaataaa ctgagtccaa tacctctaca 180
cagttatgtt taactgggct ctctgacacc gggaggaagg tggcggggtt taggtgttgc 240
aaacttcaat ggttatgcgg ggatgttcac agagcaagct ttggtatcta gctagtctag 300
cattcattag ctaatggtgt cctttggtat ttattaaaat caccacagca tagggggact 360
ttatgtttag gttttgtcta agagttagct tatctgcttc ttgtgctaac agggctattg 420
ctaccaggga ctttggacat gggggccagc gtttggaaac ctcatctagt ttttttgaga 480
gataggccac tggccttgga cctcggccgc gaccacgct 519

<210> SEQ ID NO 315
<211> LENGTH: 441
<212> TYPE: DNA
<213> ORGANISM: Homo sapiens

<400> SEQUENCE: 315
cacagagcgt ttattgacac caccactcct gaaaattggg atttcttatt aggttcccct 60
aaaagttccc atgttgatta catgtaaata gtcacatata tacaatgaag gcagtttctt 120
cagaggcaac cagggtttat agtgctaggt aaatgtcatc tcttttgtgc tactgactca 180
ttgtcaaacg tctctgcact gttttcagcc tctccacgtt gcctctgtcc tgcttcttag 240
ttccttcttt gtgacaaacc aaaagaataa gaggatttag aacaggactg cttttcccct 300
atgatttaaa aattccaatg actttcgccc ttgggagaaa tttccaagga aatctctctc 360
gctcgctctc tccgttttcc tttgtgagct tctgggggag ggttagtggt gactttttga 420
tacgaaaaaa tgcattttgt g 441

<210> SEQ ID NO 316
<211> LENGTH: 247
<212> TYPE: DNA
<213> ORGANISM: Homo sapiens

<400> SEQUENCE: 316
tggcgcggct gctggatttc accttcttgc acctgccggt gagcgcctgg ggtctaaagg 60
ggcgggatac tccattatgg cccctcgccc tgtagggctg gaatagttag aaaaggcaac 120
ccagtctagc ttggtaagaa gagagacatg cccccaacct cggcgccctt tttcctcacg 180
atctgctgtc cttacttcag cgactgcagg agcttcacct gcaagaaaac agcattgagc 240
tgctgac 247

<210> SEQ ID NO 317
<211> LENGTH: 409
<212> TYPE: DNA
<213> ORGANISM: Homo sapiens

<400> SEQUENCE: 317
tgacagggct cctggagttg ttaagtcacc aagtagctgc aggggatgga cactgcccca 60
cacgatgtgg gatgaacagc agccttggtt tgtagcccag ggtgtccatg gatttgaccc 120
gaatgctccc tggaggccct gtggcgagga caggcactgg atggtccaga ccctctggct 180
ggaggagtgg tggagccagg actgggcctt cagccatgag ggctagaata acctgacctc 240
ttgcattcta acactgggtc attaatgaca cctttccagt ggatgttgca aaaaccaaca 300
ctgtcaggaa cctggccctg ggagggctca ggtgagctca caaggagagg tcaagccaag 360
ccaaagggta ggkaacacac aacaccaggg gaaaccagcc cccaaacca 409

<210> SEQ ID NO 318
<211> LENGTH: 320
<212> TYPE: DNA
<213> ORGANISM: Homo sapiens
<220> FEATURE:
<221> NAME/KEY: misc_feature
<222> LOCATION: (1)...(320)
<223> OTHER INFORMATION: n = A,T,C or G

<400> SEQUENCE: 318
caaggnagat cttaagnggg gtcntatgta agtgtgctcc tggctccagg gttcctggag 60
cctcacgagg tcaggggaac ccttgtagaa ctccaccagc agcatcatct cgtgaaggat 120
gtcattggtc aggaagctgt cctggacgta ggccatctcc acatccatgg ggatgccata 180
gtcactgggc ctttgctcgg gaggaggcat cacccagaaa ggcgagatct tggactcggg 240
gcctgggttg ccagaatagt aaggggagca nagcagggcg aggcagggct ggaagccatt 300
gctggagccc tgcagccgca 320

<210> SEQ ID NO 319
<211> LENGTH: 212
<212> TYPE: DNA
<213> ORGANISM: Homo sapiens
<220> FEATURE:
<221> NAME/KEY: misc_feature
<222> LOCATION: (1)...(212)
<223> OTHER INFORMATION: n = A,T,C or G

<400> SEQUENCE: 319
tgaagcaata gcgcccccat tttacaggcg gagcatggaa gccagagagg tgggtggggg 60
agggggtcct tccctggctc aggcagatgg gaagatgagg aagccgctga agacgctgtc 120
ggcctcagag ccctggtaaa tgtgaccctt tttggggtct ttttcaaccc anacctggtc 180
accctgctgc agacctcggc cgcgaccacg ct 212

<210> SEQ ID NO 320
<211> LENGTH: 769
<212> TYPE: DNA
<213> ORGANISM: Homo sapiens

<400> SEQUENCE: 320
tggaggtgta gcagtgagag gagatytcag gcaagagtgt cacagcagag ccctaaascc 60
tccaactcac cagtgagaga tgagactgcc cagtactcag ccttcatctc ctgggccacc 120
tggagggcgt ctttctccat cagcgcatac tgagcagggg tactcagatc cttcttggaa 180
cctacaagga agagaagcac actggaaggg tcattctcct tcagggcatc ggccagccac 240
tgcctgccat gggaggtgga aagtaaggga tgagtgagtc tgcagggccc ctcccactga 300
cattcatagg cccaattacc ccctctctgg tcctacatgc attcttcttc ttcctgacca 360
cccctctgtt ctgaaccctc tcttcccgga gcctcccatt atattgcagg atgctcactt 420
acttggtatg ttccagagat gccacatcat tcaggttgaa gacaatgatg atggcttgga 480
agagtggcag aaacagcccc aggttgacag ggaagacact actgctcatt tccccaatcc 540
ttccagctcc atatgagaaa gccatgtgca ctctgagacc cacctacccc acttcaccca 600

-continued

```
gccccttacc ttgagctcct ctatagtagg ttgatgcaat gcatttgaac ctctcctgcc    660

cagcggtatc ccaactggaa ggaaggaaga gtgaagcaca ggtatgtatc ttgggggtg    720

tgggtgctgg ggagaaggga tagctggaag gggtgtggaa gcactcaca               769


<210> SEQ ID NO 321
<211> LENGTH: 690
<212> TYPE: DNA
<213> ORGANISM: Homo sapiens
<220> FEATURE:
<221> NAME/KEY: misc_feature
<222> LOCATION: (1)...(690)
<223> OTHER INFORMATION: n = A,T,C or G

<400> SEQUENCE: 321

tgggctgtgg gcggcacctg tgctctgcag gccagacagc gatagaagcc tttgtctgtg     60

cctactcccc cggaggcaac tgggaggtca acgggaagac aatcatcccc tataagaagg    120

gtgcctggtg ttcgctctgc acagccagtg tctcaggctg cttcaaagcc tgggaccatg    180

caggggggct ctgtgaggtc cccaggaatc cttgtcgcat gagctgccag aaccatggac    240

gtctcaacat cagcacctgc cactgccact gtccccctgg ctacacgggc agatactgcc    300

aagtgaggtg cagcctgcag tgtgtgcacg gccggttccg ggaggaggag tgctcgtgcg    360

tctgtgacat cggctacggg ggagcccagt gtgccaccaa ggtgcatttt cccttccaca    420

cctgtgacct gaggatcgac ggagactgct tcatggtgtc ttcagaggca gacacctatt    480

acagaagcca ggatgaaatg tcagaggaat ggcggggtgc tggcccagat caagagccag    540

aaagtgcagg acatcctcgc cttctatctg ggccgcctgg agaccaccaa cgaggtgact    600

gacagtgact ttgagaccag gaacttctgg atngggctca cctacaagac cgccaaggac    660

tccttncgct gggccacagg ggagcaccag                                     690


<210> SEQ ID NO 322
<211> LENGTH: 104
<212> TYPE: DNA
<213> ORGANISM: Homo sapiens

<400> SEQUENCE: 322

gtcgcaagcc ggagcaccac catgtagcct ttcccgaagt accggacctt ctcctcctcc     60

acgctcacat cacggacatc atggagcagg accaccacct ggtc                     104


<210> SEQ ID NO 323
<211> LENGTH: 118
<212> TYPE: DNA
<213> ORGANISM: Homo sapiens

<400> SEQUENCE: 323

gggccctggg cgcttccaaa tgacccagga ggtggtctgc gacgaatgcc ctaatgtcaa     60

actagtgaat gaagaacgaa cactggaagt agaaatagag cctggggtga gagacgga     118


<210> SEQ ID NO 324
<211> LENGTH: 354
<212> TYPE: DNA
<213> ORGANISM: Homo sapiens

<400> SEQUENCE: 324

tgctctccgg gagcttgaag aagaaactgg ctacaaaggg gacattgccg aatgttctcc     60

agcggtctgt atggacccag gcttgtcaaa ctgtactata cacatcgtga cagtcaccat    120

taacggagat gatgccgaaa acgcaaggcc gaagccaaag ccaggggatg gagagtttgt    180
```

-continued

```
ggaagtcatt tctttaccca agaatgacct gctgcagaga cttgatgctc tggtagctga    240

agaacatctc acagtggacg ccagggtcta ttcctacgct ctagcgctga aacatgcaaa    300

tgcaaagcca tttgaagtgc ccttcttgaa attttaagcc caaatatgac actg          354
```

<210> SEQ ID NO 325
<211> LENGTH: 642
<212> TYPE: DNA
<213> ORGANISM: Homo sapiens
<220> FEATURE:
<221> NAME/KEY: misc_feature
<222> LOCATION: (1)...(642)
<223> OTHER INFORMATION: n = A,T,C or G

<400> SEQUENCE: 325

```
ncatgcttga atgggctcct ggtgagagat tgccccctgg tggtgaaaca atcgtgtgtg     60

cccactgata ccaagaccaa tgaaagagac acagttaagc agcaatccat ctcatttcca    120

ggcacttcaa taggtcgctg attggtcctt gcaccagcag tggtagtcgt acctatttca    180

gagaggtctg aaattcaggt tcttagtttg ccagggacag gccctacctt atattttttt    240

ccatcttcat catccacttc tgcttacagt ttgctgctta caataactta atgatggatt    300

gagttatctg ggtggtctct agccatctgg gcagtgtggt tctgtctaac caaagggcat    360

tggcctcaaa ccctgcattt ggtttagggg ctaacagagc tcctcagata atcttcacac    420

acatgtaact gctggagatc ttattctatt atgaataaga aacgagaagt ttttccaaag    480

tgttagtcag gatctgaagg ctgtcattca gataacccag cttttccttt tggcttttag    540

cccattcaga ctttgccaga gtcaagccaa ggattgcttt tttgctacag ttttctgcca    600

aatggcctag ttcctgagta cctggaaacc agagagaaag ag                        642
```

<210> SEQ ID NO 326
<211> LENGTH: 455
<212> TYPE: DNA
<213> ORGANISM: Homo sapiens

<400> SEQUENCE: 326

```
tccgtgagga tgagcttcga gtccttcacc aggcactgca ggggcacagt cacgtcaatc     60

accttcacct tctcgctctt cctgctcttg tcattgacaa acttcccgta ccaggcattg    120

acgatgatga ggcccattct ggactcttct gcctcaatta tccttcggac agattcctgc    180

atcagccgga cagcggactc cgcctcttgc ttcttctgca gcacatcggt ggcggcgctt    240

tccctctgct tctccaattc cttctctttc tgagccctga ggtatggttt gatgatcaga    300

cggtgcatgg caaagtagac cactagaggc ccccacggtgg catagaacat ggcgctgggc    360

agaagctggt ccgtcaagtg aatagggaag aagtatgtct gactggccct gttgagcttg    420

actttgagag aaacgccctg tggaactcca acgct                                455
```

<210> SEQ ID NO 327
<211> LENGTH: 321
<212> TYPE: DNA
<213> ORGANISM: Homo sapiens

<400> SEQUENCE: 327

```
ttcactgtga actcgcagtc ctcgatgaac tcgcacagat gtgacagccc tgtctccttg     60

ctctctgagt tctcttcaat gatgctgatg atgcagtcca cgatagcgcg cttatactca    120

aagccaccct cttcccgcag catggtgaac aggaagttca taaggacggc gtgtttgcga    180
```

-continued

```
ggatatttct gacacagggc actgatggcc tggacaacca ccaccttgaa ttcatccgag    240

atttctgaca tgaaggagga gatctgcttc atgaggcggt cgatgctgct ctcgctgccc    300

gtcttaagga gggtggtgat g                                              321


<210> SEQ ID NO 328
<211> LENGTH: 476
<212> TYPE: DNA
<213> ORGANISM: Homo sapiens
<220> FEATURE:
<221> NAME/KEY: misc_feature
<222> LOCATION: (1)...(476)
<223> OTHER INFORMATION: n = A,T,C or G

<400> SEQUENCE: 328

tgcaggaggg gccatggggg ctgtgaatgg gatgcagccc catggtgtcc ctgataaatc     60

cagtgtgcag tctgatgaag tctgggtggg tgtggtctac gggctggcag ctaccatgat    120

ccaagaggta atgcactcct tttcccatct ctccaccatc tgtatcctgg ccmagaaaaa    180

cttcccttca aaccaaccaa aatttccttt caaaggcata acccaaatgc catccttggt    240

ccggtctaat aaagcctccc ccatttttcc cctggtatgc attcccaggc tccctggcct    300

tncagggctt nctgtctgtg ggtcatagtt tatctcctcc cacttgctgg gagctccttg    360

aaggcaaaga ctctactgcc tccatctatc cagtggaagt ggctcttcag agggtgccaa    420

gttagtatgt atgactgtca tctctcccaa cagggcctga cttggsaggg cttcca        476


<210> SEQ ID NO 329
<211> LENGTH: 340
<212> TYPE: DNA
<213> ORGANISM: Homo sapiens

<400> SEQUENCE: 329

cgagggagat tgccagcacc ctgatggaga gtgagatgat ggagatcttg tcagtgctag     60

ctaagggtga ccacagccct gtcacaaggg ctgctgcagc ctgcctggac aaagcagtgg    120

aatatgggct tatccaaccc aaccaagatg gagagtgagg gggttgtccc tgggcccaag    180

gctcatgcac acgctaccta ttgtggcacg gagagtaagg acggaagcag ctttggctgg    240

tggtggctgg catgcccaat actcttgccc atcctcgctt gctgccctag gatgtcctct    300

gttctgagtc agcggccacg ttcagtcaca cagccctgct                          340


<210> SEQ ID NO 330
<211> LENGTH: 277
<212> TYPE: DNA
<213> ORGANISM: Homo sapiens

<400> SEQUENCE: 330

tgtcaccatc acattggtgc caaataccca gaagacatcg tagatgaaga gtccgcccag     60

caggatgcag ccagtgctga cattgttgag gtgcaggagc tctactccat taagggagaa    120

ggccaggcca aaaaggttgt tggcaatcca gtgcttcctc agcaggtacc agacgccaac    180

gatgctgctc aggcccaggc acaccaggtc cttggtgtca aattcataat tgatgatctc    240

ctccttgttt tcccagaacc ctgtgtgaag agcagac                             277


<210> SEQ ID NO 331
<211> LENGTH: 136
<212> TYPE: DNA
<213> ORGANISM: Homo sapiens

<400> SEQUENCE: 331
```

-continued

```
ttgcttccca cctcctttct ctgtcctctc ctgaggttct gccttacaat ggggacactg     60

atacaaacca cacacacaat gaggatgaaa acagataaca ggtaaaatga cctcacctgc    120

ccgggcggcc gctcga                                                    136


<210> SEQ ID NO 332
<211> LENGTH: 184
<212> TYPE: DNA
<213> ORGANISM: Homo sapiens

<400> SEQUENCE: 332

ttgtgagata aacgcagata ctgcaatgca ttaaaacgct tgaaatactc atcagggatg     60

ttgctgatct tattgttgtc taagtagaga gttagaagag agacagggag accagaaggc    120

agtctggcta tctgattgaa gctcaagtca aggtattcga gtgatttaag acctttaaaa    180

gcag                                                                 184


<210> SEQ ID NO 333
<211> LENGTH: 384
<212> TYPE: DNA
<213> ORGANISM: Homo sapiens

<400> SEQUENCE: 333

cggaaaactt cgaggaattg ctcaaagtgc tgggggtgaa tgtgatgctg aggaagattg     60

ctgtggctgc agcgtccaag ccagcagtgg agatcaaaca ggagggagac actttctaca    120

tcaaaacctc caccaccgtg cgcaccacag agattaactt caaggttggg gaggagtttg    180

aggagcagac tgtggatggg aggccctgta agagcctggt gaaatgggag agtgagaata    240

aaatggtctg tgagcagaag ctcctgaagg gagagggccc caagacctcg tggaccagag    300

aactgaccaa cgatggggaa ctgatcctga ccatgacggc ggatgacgtt gtgtgcacca    360

gggtctacgt ccgagagtga gcgg                                           384


<210> SEQ ID NO 334
<211> LENGTH: 169
<212> TYPE: DNA
<213> ORGANISM: Homo sapiens
<220> FEATURE:
<221> NAME/KEY: misc_feature
<222> LOCATION: (1)...(169)
<223> OTHER INFORMATION: n = A,T,C or G

<400> SEQUENCE: 334

cnacaaacag agcagacacc ctggatccgg tcctgctact ggccaggacg gctggaccgt     60

aaaattgaat ttccacttcc tgaccgccgc cagaagagat tgattttctc cactatcact    120

agcaagatga acctctctga ggaggttgac ttggaagact atgtngccc                169


<210> SEQ ID NO 335
<211> LENGTH: 185
<212> TYPE: DNA
<213> ORGANISM: Homo sapiens

<400> SEQUENCE: 335

ccaggtttgc agcccaggct gcacatcagg ggactgcctc gcaatacttc atgctgttgc     60

tgctgactga tggtgctgtg acggatgtgg aagccacacg tgaggctgtg gtgcgtgcct    120

cgaacctgcc catgtcagtg atcattgtgg gtgtgggtgg tgctgacttt gaggccatgg    180

agcag                                                                185
```

-continued

<210> SEQ ID NO 336
<211> LENGTH: 358
<212> TYPE: DNA
<213> ORGANISM: Homo sapiens
<220> FEATURE:
<221> NAME/KEY: misc_feature
<222> LOCATION: (1)...(358)
<223> OTHER INFORMATION: n = A,T,C or G

<400> SEQUENCE: 336
ctgcccctgc cttacggcgg ccaganacac acccaggatg gcattggccc caaacttgga 60
tttgttctca gtcccatcca actccagcat caggttgtcc agtttctctt gctccaccac 120
agagagacct gagctgatga gggctggcgc gatggtggag ttgatgtggt ccactgcctt 180
caggacacct ttgcctaagt aacgctgttt gtctccatcc ctcagctcca gggcctcata 240
gatgcccgta gaggctccac tgggcactgc agcccggaaa agacctttgg cagtatagag 300
atccacctcc actgtggggt tcccgcggga gtccaggatc tcccgggccc agatcttc 358

<210> SEQ ID NO 337
<211> LENGTH: 271
<212> TYPE: DNA
<213> ORGANISM: Homo sapiens
<220> FEATURE:
<221> NAME/KEY: misc_feature
<222> LOCATION: (1)...(271)
<223> OTHER INFORMATION: n = A,T,C or G

<400> SEQUENCE: 337
cacaaagcca ccagccnggg aaatcagaat ttacttgatg caactgactt gtaatagcca 60
gaaatcctgc ccagcatggg attcagaacc tggtctgcaa ccaaatccac cgtcaaagtt 120
catacaggat aaaacaaatt caattgcctt ttccacatta atagcatcaa gcttccccaa 180
caaagccaaa gttgccaccg cacaaaaaga gaatcttgtg tcaatttctc cctactttat 240
aaaagtagat ttttcacatc ccatgaagca g 271

<210> SEQ ID NO 338
<211> LENGTH: 326
<212> TYPE: DNA
<213> ORGANISM: Homo sapiens
<220> FEATURE:
<221> NAME/KEY: misc_feature
<222> LOCATION: (1)...(326)
<223> OTHER INFORMATION: n = A,T,C or G

<400> SEQUENCE: 338
ctgtgctccc gactngnnca tctcaggtac caccgactgc actgggcggg gccctctggg 60
gggaaaggct ccacggggca gggatacatc tcgaggccag tcatcctctg gaggcagccc 120
aatcaggtca aagattttgc ccaactggtc ggcttcagag tttccacaga agagaggctt 180
tcgacgaaac atctctgcaa agatacagcc aacactccac atgtccacag gtgttgcata 240
tgtggactgc agaagaactt cgggagctcg gtaccagagt gtaacaacca cgggtgtaag 300
tgccatctgg tagctgtaga ttctgg 326

<210> SEQ ID NO 339
<211> LENGTH: 260
<212> TYPE: DNA
<213> ORGANISM: Homo sapiens
<220> FEATURE:
<221> NAME/KEY: misc_feature
<222> LOCATION: (1)...(260)
<223> OTHER INFORMATION: n = A,T,C or G -continued

<400> SEQUENCE: 339
ttcacctgag gactcatttc gtgccctttg ttgacttcaa gcaaagncct tcanggtctn 60
caaggacgnc acatttccac ttgcgaatgn nctcanggct catcttgaag aanaagnanc 120
ccaagtgctg gatcccagac tcgggggtaa ccttgtgggt aagagctcat ccagtttatg 180
ctttaggacg tccanctact cgggggagct ggaagcctgc gtggatgcgg ccctgctgga 240
cctcggccgc gaccacgcta 260

<210> SEQ ID NO 340
<211> LENGTH: 220
<212> TYPE: DNA
<213> ORGANISM: Homo sapiens
<220> FEATURE:
<221> NAME/KEY: misc_feature
<222> LOCATION: (1)...(220)
<223> OTHER INFORMATION: n = A,T,C or G

<400> SEQUENCE: 340
ctggaagccc ggctnggnct ggcagcggaa ggagccaggc aggttcacgc agcggtgctg 60
gcagtagcgg tagcggcact cgtctatgtc cacacactcg ggcccgatct tgcggtaacc 120
atcagggcag gtgcactgat aggagccagg caagttatgg cagtcctggc tggggcgaca 180
gtcgtgcagg gcctgggcac actcgtccac atccacacag 220

<210> SEQ ID NO 341
<211> LENGTH: 384
<212> TYPE: DNA
<213> ORGANISM: Homo sapiens

<400> SEQUENCE: 341
ctgctaccag gggagcgaga gctgactatc ccagcctcgg ctaatgtatt ctacgccatg 60
gatggagctt cacacgattt cctcctgcgg cagcggcgaa ggtcctctac tgctacaccg 120
ggcgtcacca gtggcccgtc tgcctcagga actcctccga gtgagggagg agggggctcc 180
tttcccagga tcaaggccac agggaggaag attgcacggg cactgttctg aggaggaagc 240
cccgttggct tacagaagtc atggtgttca taccagatgt gggtagccat cctgaatggt 300
ggcaattata tcacattgag acagaaattc agaaagggag ccagccaccc tggggcagtg 360
aagtgccact ggtttaccag acag 384

<210> SEQ ID NO 342
<211> LENGTH: 245
<212> TYPE: DNA
<213> ORGANISM: Homo sapiens

<400> SEQUENCE: 342
ctggctaagc tcatcattgt tactggtggg caccatgtcc ttgaagcttc aggcaagcaa 60
tgtaaccaac aagaatgacc ccaagtccat caactctcga gtcttcattg gaaacctcaa 120
cacagctctg gtgaagaaat cagatgtgga gaccatcttc tctaagtatg gccgtgtggc 180
cggctgttct gtgcacaagg gctatgcctt tgttcagtac tccaatgagc gccatgcccg 240
ggcag 245

<210> SEQ ID NO 343
<211> LENGTH: 611
<212> TYPE: DNA
<213> ORGANISM: Homo sapiens -continued

<400> SEQUENCE: 343
ccaaaaaaat caagatttaa tttttttatt tgcactgaaa aactaatcat aactgttaat 60
tctcagccat ctttgaagct tgaaagaaga gtctttggta ttttgtaaac gttagcagac 120
tttcctgcca gtgtcagaaa atcctattta tgaatcctgt cggtattcct tggtatctga 180
aaaaaatacc aaatagtacc atacatgagt tatttctaag tttgaaaaat aaaaagaaat 240
tgcatcacac taattacaaa atacaagttc tggaaaaaat atttttcttc attttaaaac 300
tttttttaac taataatggc tttgaaagaa gaggcttaat ttgggggtgg taactaaaat 360
caaaagaaat gattgacttg agggtctctg tttggtaaga atacatcatt agcttaaata 420
agcagcagaa ggttagtttt aattatgtag cttctgttaa tattaagtgt tttttgtctg 480
ttttacctca atttgaacag ataagtttgc ctgcatgctg gacatgcctc agaaccatga 540
atagcccgta ctagatcttg ggaacatgga tcttagagtc ctttggaata agttcttata 600
taaatacccc c 611

<210> SEQ ID NO 344
<211> LENGTH: 311
<212> TYPE: DNA
<213> ORGANISM: Homo sapiens
<220> FEATURE:
<221> NAME/KEY: misc_feature
<222> LOCATION: (1)...(311)
<223> OTHER INFORMATION: n = A,T,C or G

<400> SEQUENCE: 344
nctcgaaaaa gcccaagaca gcagaagcag acacctccag tgaactagca aagaaaagca 60
aagaagtatt cagaaaagag atgtcccagt tcatcgtcca gtgcctgaac ccttaccgga 120
aacctgactg caaagtggga agaattacca caactgaaga ctttaaacat ctggctcgca 180
agctgactca cggtgttatg aataaggagc tgaagtactg taagaatcct gaggacctgg 240
agtgcaatga gaatgtgaaa cacaaaacca aggantacat taanaagtac atgcannaan 300
tttggggctt g 311

<210> SEQ ID NO 345
<211> LENGTH: 201
<212> TYPE: DNA
<213> ORGANISM: Homo sapiens

<400> SEQUENCE: 345
cacacggtca tcccgactgc caacctggag gcccaggccc tgtggaagga gccgggcagc 60
aatgtcacca tgagtgtgga tgctgagtgt gtgcccatgg tcagggacct tctcaggtac 120
ttctactccc gaaggattga catcaccctg tcgtcagtca agtgcttcca caagctggcc 180
tctgcctatg ggccaggca g 201

<210> SEQ ID NO 346
<211> LENGTH: 370
<212> TYPE: DNA
<213> ORGANISM: Homo sapiens

<400> SEQUENCE: 346
ctgctccagg gcgtggtgtg ccttcgtggc ctctgcctcc tccgaggagc caggctgtgt 60
tctcttcaga atgttctgga gcagcagttt gaggcgggtg atgcgttgga agggcagaat 120
cagaaaggac ttgagggaaa ggcgctggca gacggggtcg ctctccagct tctccaagac 180
ctcccggaaa ttgctgttgc tattcatcag gctctggaag gtgcgttcct gataggtctg 240

-continued

```
gttggtgaca taaggcaggt agacccggcg gaagtctggg gcgtggttca ggactacgtc    300

acatacttgg aaggagaaga tattgttctc aaagttctct tccaggtctg aaaggaacgt    360

ggcgctgacg                                                           370
```

<210> SEQ ID NO 347
<211> LENGTH: 416
<212> TYPE: DNA
<213> ORGANISM: Homo sapiens
<220> FEATURE:
<221> NAME/KEY: misc_feature
<222> LOCATION: (1)...(416)
<223> OTHER INFORMATION: n = A,T,C or G

<400> SEQUENCE: 347

```
ctgttgtgct gtgtatggac gtgggcttta ccatgagtaa ctccattcct ggtatagaat     60

ccccatttga acaagcaaag aaggtgataa ccatgtttgt acagcgacag gtgtttgctg    120

agaacaagga tgagattgct ttagtcctgt ttggtacaga tggcactgac aatccccttt    180

ctggtgggga tcagtatcag aacatcacag tgcacagaca tctgatgcta ccagattttg    240

atttgctgga ggacattgaa agcaaaatcc aaccaggttc tcaacaggct gacttcctgg    300

atgcactaat cgtgagcatg gatgtgattc aacatgaaac aataggaaag aagtttggag    360

aagaggcata ttgaaatatt cactgacctc aagcagcccg attcagcaaa agtcan        416
```

<210> SEQ ID NO 348
<211> LENGTH: 351
<212> TYPE: DNA
<213> ORGANISM: Homo sapiens

<400> SEQUENCE: 348

```
gtacaggaga ggatggcagg tgcagagcgg gcactgagct ctgcaggtga aagggctcgg     60

cagttggatg ctctcctgga ggctctgaaa ttgaaacggg caggaaatag tctggcagcc    120

tctacagcag aagaaacggc aggcagtgcc cagggacgag caggagacag atgccttcct    180

cttgtctcaa ctgcaaagag gcgttccttc ctctttcact aatcctcctc agcacagacc    240

ctttacgggt gtcaggctgg gggacagtaa ggtctttccc ttcccacaag gccatatctc    300

aggctgtctc agtgggggga aaccttggac aatacccggg ctttcttggg c             351
```

<210> SEQ ID NO 349
<211> LENGTH: 207
<212> TYPE: DNA
<213> ORGANISM: Homo sapiens
<220> FEATURE:
<221> NAME/KEY: misc_feature
<222> LOCATION: (1)...(207)
<223> OTHER INFORMATION: n = A,T,C or G

<400> SEQUENCE: 349

```
nccgggacat ctccaccctc aacagtggca agaagagcct ggagactgaa cacaaggcct     60

tgaccagtga gattgcactg ctgcagtcca ggctgaagac agagggctct gatctgtgcg    120

acagagtgag cgaaatgcag aagctggatg cacaggtcaa ggagctggtg ctgaagtcgg    180

cggtggaggc tgagcgcctg gtggctg                                        207
```

<210> SEQ ID NO 350
<211> LENGTH: 323
<212> TYPE: DNA
<213> ORGANISM: Homo sapiens -continued

<400> SEQUENCE: 350
ccatacaggg ctgttgccca ggccctagag gtcattcctc gtaccctgat ccagaactgt 60
ggggccagca ccatccgtct acttacctcc cttcgggcca agcacaccca ggagaactgt 120
gagacctggg gtgtaaatgg tgagacgggt actttggtgg acatgaagga actgggcata 180
tgggagccat tggctgtgaa gctgcagact tataagacag cagtggagac ggcagttctg 240
ctactgcgaa ttgatgacat cgtttcaggc cacgaaaaga aaggcgatga ccagagccgg 300
caaggcgggg ctcctgatgc tgg 323

<210> SEQ ID NO 351
<211> LENGTH: 353
<212> TYPE: DNA
<213> ORGANISM: Homo sapiens
<220> FEATURE:
<221> NAME/KEY: misc_feature
<222> LOCATION: (1)...(353)
<223> OTHER INFORMATION: n = A,T,C or G

<400> SEQUENCE: 351
cgccgcatcc cntggtccct tccantccct tttcctttnt cngggaacgt gtatgcggtt 60
tgtttttgtt ttgtagggtt tttttccttc tccacctctc cctgtctctt ttgctccatg 120
ttgtccgttt ctgtggggtt aggtttatgt ttttaatcat ctgaggtcac gtctatttcc 180
tccggactcg cctgcttggt ggcgattctc caccggttaa tatggtgcgt cccttttttc 240
ttttgttgcg aatctgagcc ttcttcctcc agcttctgcc ttttgaactt tgttcttcgg 300
ttctgaaacc atacttttac ctgagtttcc gtgaggctga ggctgtgtgc caa 353

<210> SEQ ID NO 352
<211> LENGTH: 467
<212> TYPE: DNA
<213> ORGANISM: Homo sapiens

<400> SEQUENCE: 352
ctgcccacac tgatcacttg cgagatgtcc ttagggtaca agaacaggaa ttgaagtctg 60
aatttgagca gaacctgtct gagaaactct ctgaacaaga attacaattt cgtcgtctca 120
gtcaagagca agttgacaac tttactctgg atataaatac tgcctatgcc agactcagag 180
gaatcgaaca ggctgttcag agccatgcag ttgctgaaga ggaagccaga aaagcccacc 240
aactctggct ttcagtggag gcattaaagt acagcatgaa gacctcatct gcagaaacac 300
ctactatccc gctgggtagt gcagttgagg ccatcaaagc caactgttct gataatgaat 360
tcacccaagc tttaaccgca gctatccctc cagagtccct gacccgtggg gtgtacagtg 420
aagagaccct tagagcccgt ttctatgctg ttcaaaaact ggcccga 467

<210> SEQ ID NO 353
<211> LENGTH: 350
<212> TYPE: DNA
<213> ORGANISM: Homo sapiens

<400> SEQUENCE: 353
ctgctgcagc cacagtagtt cctcccatgg tgggtggccc tcctggtcct gctggcccag 60
gaaatctgtc cccaccagga acagcccctg gaaaacggcc ccgtcctcta ccaccttgtg 120
gaaatgctgc acgggaactg cctcctggag gaccagcttt accttcccca gacatttgtc 180
ctgattgtgt agttttcctg gactgcattt caaattgact caggaactgt ttattgcatg 240
gagttacaac aggattctga ccatgaagtt ctcttttagg taacagatcc attaactttt 300

-continued

```
ttgaagatgc ttcagatcca acaccaacaa gggcaaaccc ctttgactgg              350


<210> SEQ ID NO 354
<211> LENGTH: 351
<212> TYPE: DNA
<213> ORGANISM: Homo sapiens

<400> SEQUENCE: 354

atttagatga gatctgaggc atggagacat ggagacagta tacagactcc tagatttaag     60

ttttaggttt tttgcttttc taatcaccaa ttcttatata caatgtatat tttagactcg    120

agcagatgat catcttcatc ttaagtcatt ccttttgact gagtatggca ggattagagg    180

gaatggcagt atagatcaat gtctttttct gtaaagtata ggaaaaacca gagaggaaaa    240

aaagagctga caattggaag gtagtagaaa attgacgata atttcttctt aacaaataat    300

agttgtatat acaaggaggc tagtcaacca gattttattt gttgagggcg a             351


<210> SEQ ID NO 355
<211> LENGTH: 308
<212> TYPE: DNA
<213> ORGANISM: Homo sapiens

<400> SEQUENCE: 355

ttttggcgca agttttacag attttattaa agtcgaagct attggtcttg gaagatgaaa     60

atgcaaatgt tgatgaggtg gaattgaagc cagatacctt aataaaatta tatcttggtt    120

ataaaaataa gaaattaagg gttaacatca atgtgccaat gaaaaccgaa cagaagcagg    180

aacaagaaac cacacacaaa aacatcgagg aagaccgcaa actactgatt caggcggcca    240

tcgtgagaat catgaagatg aggaaggttc tgaaacacca gcagttactt ggcgaggtcc    300

tcactcag                                                             308


<210> SEQ ID NO 356
<211> LENGTH: 207
<212> TYPE: DNA
<213> ORGANISM: Homo sapiens

<400> SEQUENCE: 356

ctgtcccaag tgctcccaga aggcaggatt ctgaagacca ctccagcgat atgttcaact     60

atgaagaata ctgcaccgcc aacgcagtca ctgggccttg ccgtgcatcc ttcccacgct    120

ggtactttga cgtggagagg aactcctgca ataacttcat ctatggaggc tgccggggca    180

ataagaacag ctaccgctct gaggagg                                        207


<210> SEQ ID NO 357
<211> LENGTH: 188
<212> TYPE: DNA
<213> ORGANISM: Homo sapiens
<220> FEATURE:
<221> NAME/KEY: misc_feature
<222> LOCATION: (1)...(188)
<223> OTHER INFORMATION: n = A,T,C or G

<400> SEQUENCE: 357

tcgaccacgc cctcgtagcg catgngctnc aggacgatgc tcagagtgat gaacaccccg     60

gtgcggccca cgccagcact gcagtgcacc gtgataggcc catcctgtcc aaactgctcc    120

ttggtcttat gcacctgccc gatgaagtca atgaatccct cgcctgtctt gggcacgccc    180

tgctctgg                                                             188
```

-continued

<210> SEQ ID NO 358
<211> LENGTH: 291
<212> TYPE: DNA
<213> ORGANISM: Homo sapiens

<400> SEQUENCE: 358
ctgggagcat cggcaagcta ctgccttaaa atccgatctc cccgagtgca caatttctgt 60
cccttttaag ggttcacaac actaaagatt tcacatgaaa gggttgtgat tgatttgagc 120
aggcaggcgg tacgtgacag gggctgcatg caccggtggt cagagagaaa cagaacaggg 180
cagggaattt cacaatgttc ttctatacaa tggctggaat ctatgaataa catcagtttc 240
taagttatgg gttgattttt aactactggg tttaggccag gcaggcccag g 291

<210> SEQ ID NO 359
<211> LENGTH: 117
<212> TYPE: DNA
<213> ORGANISM: Homo sapiens
<220> FEATURE:
<221> NAME/KEY: misc_feature
<222> LOCATION: (1)...(117)
<223> OTHER INFORMATION: n = A,T,C or G

<400> SEQUENCE: 359
gccaccacac tccagcctgg gcaatacagc aagactgtct caaaaaaaaa aaaaaaaaaa 60
cccaaaaaaa ctcaaaaang taatgaatga tacccaangn gccttttcta gaaaaag 117

<210> SEQ ID NO 360
<211> LENGTH: 394
<212> TYPE: DNA
<213> ORGANISM: Homo sapiens

<400> SEQUENCE: 360
ctgttcctct ggggtggtcc agttctagag tgggagaaag ggagtcaggc gcattgggaa 60
tcgtggttcc agtctggttg cagaatctgc acatttgcca agaaattttc cctgtttgga 120
aagtttgccc cagctttccc gggcacacca ccttttgtcc caagtgtctg ccggtcgacc 180
aatctgcctg ccacacattg accaagccag acccggttca cccagctcga ggatcccagg 240
ttgaagagtg gccccttgag gccctggaaa gaccaatcac tggacttctt cccttgagag 300
tcagaggtca cccgtgattc tgcctgcacc ttatcattga tctgcagtga tttctgcaaa 360
tcaagagaaa ctctgcaggg cactcccctg tttc 394

<210> SEQ ID NO 361
<211> LENGTH: 394
<212> TYPE: DNA
<213> ORGANISM: Homo sapiens
<220> FEATURE:
<221> NAME/KEY: misc_feature
<222> LOCATION: (1)...(394)
<223> OTHER INFORMATION: n = A,T,C or G

<400> SEQUENCE: 361
ctgggcggat agcaccgggc atattttntt natggatgag gtctggcacc ctgagcagtc 60
cagcgaggac ttggtcttag ttgagcaatt tggctaggag gatagtatgc agcacggttc 120
tgagtctgtg ggatagctgc catgaagtaa cctgaaggag gtgctggctg gtaggggttg 180
attacagggt tgggaacagc tcgtacactt gccattctct gcatatactg gttagtgagg 240
tgagcctggc gctcttcttt gcgctgagct aaagctacat acaatggctt tgtggacctc 300
ggccgcgacc acgctaagcc gaattccagc acactggcgg ccgttactag tggatccgag 360

-continued ctcggtacca agcttggcgt aatcatggtc atag 394

<210> SEQ ID NO 362
<211> LENGTH: 268
<212> TYPE: DNA
<213> ORGANISM: Homo sapiens

<400> SEQUENCE: 362
ctgcgcgtgg accagtcagc ttccgggtgt gactggagca gggcttgtcg tcttcttcag 60
agtcactttg caggggttgg tgaagctgct cccatccatg tacagctccc agtctactga 120
tgtttaagga tggtctcggt ggttaggccc actagaataa actgagtcca atacctctac 180
acagttatgt ttaactgggc tctctgacac cgggaggaag gtggcggggt ttaggtgttg 240
caaacttcaa tggttatgcg gggatgtt 268

<210> SEQ ID NO 363
<211> LENGTH: 323
<212> TYPE: DNA
<213> ORGANISM: Homo sapiens

<400> SEQUENCE: 363
ccttgacctt ttcagcaagt gggaaggtgt aatccgtctc cacagacaag gccaggactc 60
gtttgtaccc gttgatgata gaatggggta ctgatgcaac agttgggtag ccaatctgca 120
gacagacact ggcaacattg cggacaccct ccaggaagcg agaatgcaga gtttcctctg 180
tgatatcaag cacttcaggg ttgtagatgc tgccattgtc gaacacctgc tggatgacca 240
gcccaaagga gaagggggag atgttgagca tgttcagcag cgtggcttcg ctggctccca 300
ctttgtctcc agtcttgatc aga 323

<210> SEQ ID NO 364
<211> LENGTH: 393
<212> TYPE: DNA
<213> ORGANISM: Homo sapiens
<220> FEATURE:
<221> NAME/KEY: misc_feature
<222> LOCATION: (1)...(393)
<223> OTHER INFORMATION: n = A,T,C or G

<400> SEQUENCE: 364
ccaagctctc catcgtcccc gtgcgcagng gctactgggg gaacaagatc ggcaagcccc 60
acactgtccc ttgcaaggtg acaggccgct gcggctctgt gctggtacgc ctcatcactg 120
cacccagggg cactggcatc gtctccgcac ctgtgcctaa gaagctgctc atgatggctg 180
gcatcgatga ctgctacacc tcagcccggg gctgcactgc caccctgggc aacttcgcca 240
aggccacctt tgatgccatt tctaagacct acagctacct gacccccgac ctctggaagg 300
agactgtatt caccaagtct ccctatcagg agttcactga ccacctcgtc aagacccaca 360
ccagagtctc cgtgcagcgg actcaggctc cag 393

<210> SEQ ID NO 365
<211> LENGTH: 371
<212> TYPE: DNA
<213> ORGANISM: Homo sapiens

<400> SEQUENCE: 365
cctcctcaga gcggtagctg ttcttattgc cccggcagcc tccatagatg aagttattgc 60
aggagttcct ctccacgtca aagtaccagc gtgggaagga tgcacggcaa ggcccagtga 120

-continued

```
ctgcgttggc ggtgcagtat tcttcatagt tgaacatatc gctggagtgg tcttcagaat    180

cctgccttct gggagcactt gggacagagg aatccgctgc attcctgctg gtggacctcg    240

gccgcgacca cgctaagccg aattccagca cactggcggc cgttactagt ggatccgagc    300

tcggtaccaa gcttggcgta atcatggtca tagctgtttc ctgtgtgaaa ttgttatccg    360

ctcacaattc c                                                         371
```

<210> SEQ ID NO 366
<211> LENGTH: 393
<212> TYPE: DNA
<213> ORGANISM: Homo sapiens

<400> SEQUENCE: 366

```
atttcttgcc agatgggagc tctttggtga agactccttt cgggaaaagt tttttggctt     60

cttcttcagg gatggttgga aggaccatca cactatcccc atccttccaa tcaactgggg    120

tggcaaccct tttttctgct gtcagctgga gagagatgac taccctgaga atctcatcaa    180

agttcctgcc agtggtagct gggtagagga tagacagctt cagcttctta tcaggaccaa    240

aaacaaacac cacacgagct gccacaggca tgcccttttc atccttctct gctggatcca    300

gcatgcccaa caggatggca agctcccgat tcctatcatc gatgatggga aaaggtaact    360

tttctgtggg ctcttcacaa ttgtaagcat tga                                 393
```

<210> SEQ ID NO 367
<211> LENGTH: 327
<212> TYPE: DNA
<213> ORGANISM: Homo sapiens
<220> FEATURE:
<221> NAME/KEY: misc_feature
<222> LOCATION: (1)...(327)
<223> OTHER INFORMATION: n = A,T,C or G

<400> SEQUENCE: 367

```
ccagctctgt ctcatacttg actctaaagt cttnagcagc aagacgggca ttgnnaatct     60

gcagaacgat gcgggcattg tccacagtat ttgcgaagat ctgagccctc aggtcctcga    120

tgatcttgaa gtaatggctc cagtctctga cctggggtcc cttcttctcc aagtgctccc    180

ggattttgct ctccagcctc cggttctcgg tctccaggct cctcactctg tccaggtaag    240

aggccaggcg gtcgttcagg ctttgcatgg tctccttctc gttctggatg cctcccattc    300

ctgccagacc cccggctatc ccggtgg                                        327
```

<210> SEQ ID NO 368
<211> LENGTH: 306
<212> TYPE: DNA
<213> ORGANISM: Homo sapiens
<220> FEATURE:
<221> NAME/KEY: misc_feature
<222> LOCATION: (1)...(306)
<223> OTHER INFORMATION: n = A,T,C or G

<400> SEQUENCE: 368

```
ctggagaagg acttcagcag tttnaagaag tactgccaag tcatccgtgt cattgcccac     60

acccagatgc gcctgcttcc tctgcgccag aagaaggccc acctgatgga gatccaggtg    120

aacggaggca ctgtggccga gaagctggac tgggcccgcg agaggcttga gcagcaggta    180

cctgtgaacc aagtgtttgg gcaggatgag atgatcgacg tcatcggggt gaccaagggc    240

aaaggctaca aaggggtcac cagtcgttgg cacaccaaga agctgccccg caagacccac    300

cgagga                                                               306
```

-continued

<210> SEQ ID NO 369
<211> LENGTH: 394
<212> TYPE: DNA
<213> ORGANISM: Homo sapiens

<400> SEQUENCE: 369
tcgacccaca ccggaacacg gagagctggg ccagcattgg cacttgatag gatttcccgt 60
cggctgccac gaaagtgcgt ttctttgtgt tctcgggttg gaaccgtgat ttccacagac 120
ccttgaaata cactgcgttg acgaggacca gtctggtgag cacaccatca ataagatctg 180
gggacagcag attgtcaatc atatccctgg tttcattttt aacccatgca ttgatggaat 240
cacaggcaga ggctggatcc tcaaagttca cattccggac ctcacactgg aacacatctt 300
tgttccttgt aacaaaaggc acttcaattt cagaggcatt cttaacaaac acggcgttag 360
ccactgtcac aatgtcttta ttcttcttgg agac 394

<210> SEQ ID NO 370
<211> LENGTH: 653
<212> TYPE: DNA
<213> ORGANISM: Homo sapiens

<400> SEQUENCE: 370
ccaccacacc caattccttg ctggtatcat ggcagccgcc acgtgccagg attaccggct 60
acatcatcaa gtatgagaag cctgggtctc ctcccagaga agtggtccct cggccccgcc 120
ctggtgtcac agaggctact attactggcc tggaaccggg aaccgaatat acaatttatg 180
tcattgccct gaagaataat cagaagagcg agcccctgat tggaaggaaa aagacagacg 240
agcttcccca actggtaacc cttccacacc ccaatcttca tggaccagag atcttggatg 300
ttccttccac agttcaaaag accccctttcg tcacccaccc tgggtatgac actggaaatg 360
gtattcagct tcctggcact tctggtcagc aacccagtgt tgggcaacaa atgatctttg 420
aggaacatgg ttttaggcgg accacaccgc ccacaacggc cacccccata aggcataggc 480
caagaccata cccgccgaat gtaggacaag aagctctctc tcagacaacc atctcatggg 540
ccccattcca ggacacttct gagtacatca tttcatgtca tcctgttggc actgatgaag 600
aacccttaca gttcagggtt cctggaactt ctaccagtgc cactctgaca gga 653

<210> SEQ ID NO 371
<211> LENGTH: 268
<212> TYPE: DNA
<213> ORGANISM: Homo sapiens

<400> SEQUENCE: 371
ctgcccagcc cccattggcg agtttgagaa ggtgtgcagc aatgacaaca agaccttcga 60
ctcttcctgc cacttctttg ccacaaagtg caccctggag ggcaccaaga agggccacaa 120
gctccacctg gactacatcg ggccttgcaa atacatcccc ccttgcctgg actctgagct 180
gaccgaattc cccctgcgca tgcgggactg gctcaagaac gtcctggtca ccctgtatga 240
gagggatgag gacaacaacc ttctgact 268

<210> SEQ ID NO 372
<211> LENGTH: 392
<212> TYPE: DNA
<213> ORGANISM: Homo sapiens

<400> SEQUENCE: 372

-continued

```
gctggtgccc ctggtgaacg tggacctcct ggattggcag gggccccagg acttagaggt     60

ggaactggtc cccctggtcc cgaaggagga aagggtgctg ctggtcctcc tgggccacct    120

ggtgctgctg gtactcctgg tctgcaagga atgcctggag aaagaggagg tcttggaagt    180

cctggtccaa agggtgacaa gggtgaacca ggcggtccag gtgctgatgg tgtcccaggg    240

aaagatggcc caaggggtcc tactggtcct attggtcctc ctggcccagc tggccagcct    300

ggagataagg gtgaaggtgg tgccccccgga cttccaggta tagctggacc tcgtggtagc    360

cctggtgaga gaggtgaaac ctcggccgcg ac                                  392
```

<210> SEQ ID NO 373
<211> LENGTH: 388
<212> TYPE: DNA
<213> ORGANISM: Homo sapiens
<220> FEATURE:
<221> NAME/KEY: misc_feature
<222> LOCATION: (1)...(388)
<223> OTHER INFORMATION: n = A,T,C or G

<400> SEQUENCE: 373

```
ccaagcgctc agatcggcaa ggggcaccan ttttgatctg cccagtgcac agccccacaa     60

ccaggtcagc gatgaaggta tcttcagtct cccccgaacg atgagacacc atgacgcccc    120

aaccattggc ctgggccagc ttgcacgcct gaagagactc ggtcacggag ccaatctggt    180

tgactttgag caggaggcag ttgcaggact tctcgttcac ggccttggcg atcctctttg    240

ggttggtcac tgtgagatca tcccccacta cctggattcc tgcactggct gtgaacttct    300

gccaagctcc ccagtcatcc tggtcaaagg gatcttcgat agacaccact gggtagtcct    360

tgatgaagga cttgtacagg tcagccag                                       388
```

<210> SEQ ID NO 374
<211> LENGTH: 393
<212> TYPE: DNA
<213> ORGANISM: Homo sapiens

<400> SEQUENCE: 374

```
ctgacgaccg cgtgaacccc tgcattgggg gtgtcatcct cttccatgag acactctacc     60

agaaggcgga tgatgggcgt cccttccccc aagttatcaa atccaagggc ggtgttgtgg    120

gcatcaaggt agacaagggc gtggtccccc tggcagggac aaatggcgag actaccaccc    180

aagggttgga tgggctgtct gagcgctgtg cccagtacaa gaaggacgga gctgacttcg    240

ccaagtggcg ttgtgtgctg aagattgggg aacacacccc ctcagccctc gccatcatgg    300

aaaatgccaa tgttctggcc cgttatgcca gtatctgcca gcagaatggc attgtgccca    360

tcgtggagcc tgagatcctc cctgatgggg acc                                 393
```

<210> SEQ ID NO 375
<211> LENGTH: 394
<212> TYPE: DNA
<213> ORGANISM: Homo sapiens
<220> FEATURE:
<221> NAME/KEY: misc_feature
<222> LOCATION: (1)...(394)
<223> OTHER INFORMATION: n = A,T,C or G

<400> SEQUENCE: 375

```
ccacaaatgg cgtggtccat gtcatcaccn ttnttctgca gcctccagcc aacagacctc     60

aggaaagagg ggatgaactt gcagactctg cgcttgagat cttcaaacaa gcatcagcgt    120

tttccagggc ttcccagagg tctgtgcgac tagcccctgt ctatcaaaag ttattagaga    180
```

-continued ggatgaagca ttagcttgaa gcactacagg aggaatgcac cacggcagct ctccgccaat 240
ttctctcaga tttccacaga gactgtttga atgttttcaa aaccaagtat cacactttaa 300
tgtacatggg ccgcaccata atgagatgtg agccttgtgc atgtggggga ggagggagag 360
agatgtactt tttaaatcat gttcccccta aaca 394

<210> SEQ ID NO 376
<211> LENGTH: 392
<212> TYPE: DNA
<213> ORGANISM: Homo sapiens
<220> FEATURE:
<221> NAME/KEY: misc_feature
<222> LOCATION: (1)...(392)
<223> OTHER INFORMATION: n = A,T,C or G

<400> SEQUENCE: 376
ctgcccagcc cccattggcg agtttgattn ggtgtgcagc aatgacaaca agaccttcga 60
ctcttcctgc cacttctttg ccacaaagtg caccctggag ggcaccaaga agggccacaa 120
gctccacctg gactacatcg ggccttgcaa atacatcccc ccttgcctgg actctgagct 180
gaccgaattc cccctgcgca tgcgggactg gctcaagaac gtcctggtca ccctgtatga 240
gagggatgag gacaacaacc ttctgactga gaagcagaag ctgcgggtga agaagatcca 300
tgagaatgag aagcgcctgg aggcaggaga ccacccccgtg gagctgctgg cccgggactt 360
cgagaagaac tataacatgt acatcttccc tg 392

<210> SEQ ID NO 377
<211> LENGTH: 292
<212> TYPE: DNA
<213> ORGANISM: Homo sapiens

<400> SEQUENCE: 377
caatgtttga tgcttaaccc ccccaatttc tgtgagatgg atggccagtg caagcgtgac 60
ttgaagtgtt gcatgggcat gtgtgggaaa tcctgcgttt cccctgtgaa agcttgattc 120
ctgccatatg gaggaggctc tggagtcctg ctctgtgtgg tccaggtcct ttccaccctg 180
agacttggct ccaccactga tatcctcctt tggggaaagg cttggcacac agcaggcttt 240
caagaagtgc cagttgatca atgaataaat aaacgagcct atttctcttt gc 292

<210> SEQ ID NO 378
<211> LENGTH: 395
<212> TYPE: DNA
<213> ORGANISM: Homo sapiens

<400> SEQUENCE: 378
ctgctgcttc agcgaagggt ttctggcata tccaatgata aggctgccaa agactgttcc 60
aataccagca ccagaaccag ccactcctac tgttgcagca cctgcaccaa taaatttggc 120
agcagtatca atgtctctgc tgattgcact ggtctgaaac tccctttgga ttagctgaga 180
cacaccattc tgggccctga ttttcctaag atagaactcc aactctttgc cctctagcac 240
atagccatct gctcggccac actgtcccgg ccttgaagcg atgcacgcaa gaagcttgcc 300
ctgctggaac tgctcctcca ggagactgct gattttggca ttctttttcc tttcatcata 360
tttcttctga attttttaga tcgtttttttg tttaa 395

<210> SEQ ID NO 379
<211> LENGTH: 223
<212> TYPE: DNA

<213> ORGANISM: Homo sapiens

<400> SEQUENCE: 379

```
ccagatgaaa tgctgccgca atggctgtgg gaaggtgtcc tgtgtcactc ccaatttctg      60
agctccagcc accaccaggc tgagcagtga ggagagaaag tttctgcctg gccctgcatc     120
tggttccagc ccacctgccc tccccttttt cgggactctg tattccctct tgggctgacc     180
acagcttctc cctttcccaa ccaataaagt aaccactttc agc                       223
```

<210> SEQ ID NO 380
<211> LENGTH: 317
<212> TYPE: DNA
<213> ORGANISM: Homo sapiens
<220> FEATURE:
<221> NAME/KEY: misc_feature
<222> LOCATION: (1)...(317)
<223> OTHER INFORMATION: n = A,T,C or G

<400> SEQUENCE: 380

```
tcgaccacag tattccaacc ctcctgtgcn tngagaagtg atggagggtg ctgacaacca      60
gggtgcagga gaacaaggta gaccagtgag gcagaatatg tatcggggat atagaccacg     120
attccgcagg ggccctcctc gccaaagaca gcctagagag gacggcaatg aagaagataa     180
agaaaatcaa ggagatgaga cccaaggtca gcagccacct caacgtcggt accgccgcaa     240
cttcaattac cgacgcagac gcccagaaaa ccctaaacca caagatggca aagagacaaa     300
agcagccgat ccaccag                                                   317
```

<210> SEQ ID NO 381
<211> LENGTH: 392
<212> TYPE: DNA
<213> ORGANISM: Homo sapiens
<220> FEATURE:
<221> NAME/KEY: misc_feature
<222> LOCATION: (1)...(392)
<223> OTHER INFORMATION: n = A,T,C or G

<400> SEQUENCE: 381

```
cctgaaggaa gagctggcct acctgaatnn naaccatgag gaggaaatca gtacgctgag      60
gggccaagtg ggaggccagg tcagtgtgga ggtggattcc gctccgggca ccgatctcgc     120
caagatcctg agtgacatgc gaagccaata tgaggtcatg gccgagcaga accggaagga     180
tgctgaagcc tggttcacca gccggactga agaattgaac cgggaggtcg ctggccacac     240
ggagcagctc cagatgagca ggtccgaggt tactgacctg cggcgcaccc ttcagggtct     300
tgagattgag ctgcagtcac agacctcggc cgcgaccacg ctaagccgaa ttccagcaca     360
ctggcggccg ttactagtgg atccgagctc gg                                   392
```

<210> SEQ ID NO 382
<211> LENGTH: 234
<212> TYPE: DNA
<213> ORGANISM: Homo sapiens

<400> SEQUENCE: 382

```
cctcgatgtc taaatgagcg tggtaaagga tggtgcctgc tggggtctcg tagatacctc      60
gggacttcat tccaatgaag cggttctcca cgatgtcaat acggcccacg ccatgcttgc     120
ccgcgacttc gttcaggtac atgaagagct ccaaggaggt ctggtgggtg gtgccatcct     180
tgacgttggt caccttcaca gggacccctt ttttgaactc catctccaga atgt           234
```

-continued

<210> SEQ ID NO 383
<211> LENGTH: 396
<212> TYPE: DNA
<213> ORGANISM: Homo sapiens
<220> FEATURE:
<221> NAME/KEY: misc_feature
<222> LOCATION: (1)...(396)
<223> OTHER INFORMATION: n = A,T,C or G

<400> SEQUENCE: 383
ccttgacctt ttcagcaagt gggaaggtgt tttccgtctc cacagacaag gccaggactc 60
gtttgnaccc gttgatgata gaatggggta ctgatgcaac agttgggtag ccaatctgca 120
gacagacact ggcaacattg cggacaccca ggatttcaat ggtgcccctg gagattttag 180
tggtgatacc taaagcctgg aaaaaggagg tcttctcggg cccgagacca gtgttctggg 240
ctggcacagt gacttcacat ggggcaatgg caccagcacg ggcagcagac ctgcccgggc 300
ggccgctcga aagccgaatt ccagcacact ggcggccgtt actagtggat ccgagctcgg 360
taccaagctt ggcgtaatca tggtcatagc tgtttc 396

<210> SEQ ID NO 384
<211> LENGTH: 396
<212> TYPE: DNA
<213> ORGANISM: Homo sapiens

<400> SEQUENCE: 384
gctgaatagg cacagagggc acctgtacac cttcagacca gtctgcaacc tcaggctgag 60
tagcagtgaa ctcaggagcg ggagcagtcc attcaccctg aaattcctcc ttggtcactg 120
ccttctcagc agcagcctgc tcttcttttt caatctcttc aggatctctg tagaagtaca 180
gatcaggcat gacctcccat gggtgttcac gggaaatggt gccacgcatg cgcagaactt 240
cccgagccag catccaccac atcaaaccca ctgagtgagc tcccttgttg ttgcatggga 300
tggcaatgtc cacatagcgc agaggagaat ctgtgttaca cagcgcaatg gtaggtaggt 360
taacataaga tgcctccgtg agaggctggt ggtcag 396

<210> SEQ ID NO 385
<211> LENGTH: 2943
<212> TYPE: DNA
<213> ORGANISM: Homo sapiens

<400> SEQUENCE: 385
cagccaccgg agtggatgcc atctgcaccc accgccctga ccccacaggc cctgggctgg 60
acagagagca gctgtatttg gagctgagcc agctgaccca cagcatcact gagctgggcc 120
cctacaccct ggacagggac agtctctatg tcaatggttt cacacagcgg agctctgtgc 180
ccaccactag cattcctggg acccccacag tggacctggg aacatctggg actccagttt 240
ctaaacctgg tccctcggct gccagccctc tcctggtgct attcactctc aacttcacca 300
tcaccaacct gcggtatgag gagaacatgc agcaccctgg ctccaggaag ttcaacacca 360
cggagagggt ccttcagggc ctggtccctg ttcaagagca ccagtgttgg ccctctgtac 420
tctggctgca gactgacttt gctcaggcct gaaaaggatg ggacagccac tggagtggat 480
gccatctgca cccaccaccc tgaccccaaa agccctaggc tggacagaga gcagctgtat 540
tgggagctga gccagctgac ccacaatatc actgagctgg gcccctatgc cctggacaac 600
gacagcctct ttgtcaatgg tttcactcat cggagctctg tgtccaccac cagcactcct 660
gggaccccca cagtgtatct gggagcatct aagactccag cctcgatatt tggcccttca 720

-continued

```
gctgccagcc atctcctgat actattcacc ctcaacttca ccatcactaa cctgcggtat    780
gaggagaaca tgtggcctgg ctccaggaag ttcaacacta cagagagggt ccttcagggc    840
ctgctaaggc ccttgttcaa gaacaccagt gttggccctc tgtactctgg ctgcaggctg    900
accttgctca ggccagagaa agatggggaa gccaccggag tggatgccat ctgcacccac    960
cgccctgacc ccacaggccc tgggctggac agagagcagc tgtatttgga gctgagccag   1020
ctgacccaca gcatcactga gctgggcccc tacacactgg acagggacag tctctatgtc   1080
aatggtttca cccatcggag ctctgtaccc accaccagca ccggggtggt cagcgaggag   1140
ccattcacac tgaacttcac catcaacaac ctgcgctaca tggcggacat gggccaaccc   1200
ggctccctca agttcaacat cacagacaac gtcatgaagc acctgctcag tcctttgttc   1260
cagaggagca gcctgggtgc acggtacaca ggctgcaggg tcatcgcact aaggtctgtg   1320
aagaacggtg ctgagacacg ggtggacctc ctctgcacct acctgcagcc cctcagcggc   1380
ccaggtctgc ctatcaagca ggtgttccat gagctgagcc agcagaccca tggcatcacc   1440
cggctgggcc cctactctct ggacaaagac agcctctacc ttaacggtta caatgaacct   1500
ggtccagatg agcctcctac aactcccaag ccagccacca cattcctgcc tcctctgtca   1560
gaagccacaa cagccatggg gtaccacctg aagaccctca cactcaactt caccatctcc   1620
aatctccagt attcaccaga tatgggcaag ggctcagcta cattcaactc caccgagggg   1680
gtccttcagc acctgctcag acccttgttc cagaagagca gcatgggccc cttctacttg   1740
ggttgccaac tgatctccct caggcctgag aaggatgggg cagccactgg tgtggacacc   1800
acctgcacct accaccctga ccctgtgggc cccgggctgg acatacagca gctttactgg   1860
gagctgagtc agctgaccca tggtgtcacc caactgggct tctatgtcct ggacagggat   1920
agcctcttca tcaatggcta tgcaccccag aatttatcaa tccggggcga gtaccagata   1980
aatttccaca ttgtcaactg gaacctcagt aatccagacc cccacatcctc agagtacatc  2040
accctgctga gggacatcca ggacaaggtc accacactct acaaaggcag tcaactacat   2100
gacacattcc gcttctgcct ggtcaccaac ttgacgatgg actccgtgtt ggtcactgtc   2160
aaggcattgt tctcctccaa tttggacccc agcctggtgg agcaagtctt tctagataag   2220
accctgaatg cctcattcca ttggctgggc tccacctacc agttggtgga catccatgtg   2280
acagaaatgg agtcatcagt ttatcaacca acaagcagct ccagcaccca gcacttctac   2340
ctgaatttca ccatcaccaa cctaccatat tcccaggaca aagcccagcc aggcaccacc   2400
aattaccaga ggaacaaaag gaatattgag gatgcggcac cacaccgggg tggactccct   2460
gtgtaacttc tcgccactgg ctcggagagt agacagagtt gccatctatg aggaatttct   2520
gcggatgacc cggaatggta cccagctgca gaacttcacc ctggacagga gcagtgtcct   2580
tgtggatggg tattttccca acagaaatga gcccttaact gggaattctg accttccctt   2640
ctgggctgtc atcctcatcg gcttggcagg actcctggga ctcatcacat gcctgatctg   2700
cggtgtcctg gtgaccaccc gccggcggaa gaaggaagga gaatacaacg tccagcaaca   2760
gtgcccaggc tactaccagt cacacctaga cctggaggat ctgcaatgac tggaacttgc   2820
cggtgcctgg ggtgcctttc ccccagccag ggtccaaaga agcttggctg ggcagaaat    2880
aaaccatatt ggtcggaaaa aaaaaaaaaa aaaaaaaaaa aaaaaaaaaa aaaaaaaaaa   2940
aaa                                                                  2943
```

<210> SEQ ID NO 386
<211> LENGTH: 2608

-continued

<212> TYPE: DNA
<213> ORGANISM: Homo sapiens

<400> SEQUENCE: 386
gttcaagagc accagtgttg gccctctgta ctctggctgc agactgactt tgctcaggcc 60
tgaaaaggat gggacagcca ctggagtgga tgccatctgc acccaccacc ctgaccccaa 120
aagccctagg ctggacagag agcagctgta ttgggagctg agccagctga cccacaatat 180
cactgagctg ggcccctatg ccctggacaa cgacagcctc tttgtcaatg gtttcactca 240
tcggagctct gtgtccacca ccagcactcc tgggaccccc acagtgtatc tgggagcatc 300
taagactcca gcctcgatat ttggcccttc agctgccagc catctcctga tactattcac 360
cctcaacttc accatcacta acctgcggta tgaggagaac atgtggcctg gctccaggaa 420
gttcaacact acagagaggg tccttcaggg cctgctaagg cccttgttca agaacaccag 480
tgttggccct ctgtactctg gctgcaggct gaccttgctc aggccagaga aagatgggga 540
agccaccgga gtggatgcca tctgcaccca ccgccctgac ccccacaggcc ctgggctgga 600
cagagagcag ctgtatttgg agctgagcca gctgacccac agcatcactg agctgggccc 660
ctacacactg gacagggaca gtctctatgt caatggtttc acccatcgga gctctgtacc 720
caccaccagc accggggtgg tcagcgagga gccattcaca ctgaacttca ccatcaacaa 780
cctgcgctac atggcggaca tggccaacc cggctccctc aagttcaaca tcacagacaa 840
cgtcatgaag cacctgctca gtcctttgtt ccagaggagc agcctgggtg cacggtacac 900
aggctgcagg gtcatcgcac taaggtctgt gaagaacggt gctgagacac gggtggacct 960
cctctgcacc tacctgcagc ccctcagcgg cccaggtctg cctatcaagc aggtgttcca 1020
tgagctgagc cagcagaccc atggcatcac ccggctgggc ccctactctc tggacaaaga 1080
cagcctctac cttaacggtt acaatgaacc tggtccagat gagcctccta caactcccaa 1140
gccagccacc acattcctgc ctcctctgtc agaagccaca acagccatgg ggtaccacct 1200
gaagaccctc acactcaact tcaccatctc caatctccag tattcaccag atatgggcaa 1260
gggctcagct acattcaact ccaccgaggg ggtccttcag cacctgctca gacccttgtt 1320
ccagaagagc agcatgggcc ccttctactt gggttgccaa ctgatctccc tcaggcctga 1380
gaaggatggg gcagccactg gtgtggacac cacctgcacc taccaccctg accctgtggg 1440
ccccgggctg gacatacagc agctttactg ggagctgagt cagctgaccc atggtgtcac 1500
ccaactgggc ttctatgtcc tggacaggga tagcctcttc atcaatggct atgcacccca 1560
gaatttatca atccggggcg agtaccagat aaatttccac attgtcaact ggaacctcag 1620
taatccagac cccacatcct cagagtacat caccctgctg agggacatcc aggacaaggt 1680
caccacactc tacaaaggca gtcaactaca tgacacattc cgcttctgcc tggtcaccaa 1740
cttgacgatg gactccgtgt tggtcactgt caaggcattg ttctcctcca atttggaccc 1800
cagcctggtg gagcaagtct ttctagataa gaccctgaat gcctcattcc attggctggg 1860
ctccacctac cagttggtgg acatccatgt gacagaaatg gagtcatcag tttatcaacc 1920
aacaagcagc tccagcaccc agcacttcta cctgaatttc accatcacca acctaccata 1980
ttcccaggac aaagcccagc caggcaccac caattaccag aggaacaaaa ggaatattga 2040
ggatgcgctc aaccaactct tccgaaacag cagcatcaag agttattttt ctgactgtca 2100
agtttcaaca ttcaggtctg tccccaacag gcaccacacc ggggtggact ccctgtgtaa 2160
cttctcgcca ctggctcgga gagtagacag agttgccatc tatgaggaat ttctgcggat 2220

-continued

```
gacccggaat ggtacccagc tgcagaactt caccctggac aggagcagtg tccttgtgga   2280

tgggtatttt cccaacagaa atgagccctt aactgggaat tctgaccttc ccttctgggc   2340

tgtcatcctc atcggcttgg caggactcct gggactcatc acatgcctga tctgcggtgt   2400

cctggtgacc acccgccggc ggaagaagga aggagaatac aacgtccagc aacagtgccc   2460

aggctactac cagtcacacc tagacctgga ggatctgcaa tgactggaac ttgccggtgc   2520

ctggggtgcc tttcccccag ccagggtcca aagaagcttg gctggggcag aaataaacca   2580

tattggtcgg acacaaaaaa aaaaaaaa                                      2608
```

<210> SEQ ID NO 387
<211> LENGTH: 1761
<212> TYPE: DNA
<213> ORGANISM: Homo sapiens

<400> SEQUENCE: 387

```
ctgaacttca ccatcaacaa cctgcgctac atggcggaca tgggccaacc cggctccctc     60

aagttcaaca tcacagacaa cgtcatgaag cacctgctca gtcctttgtt ccagaggagc    120

agcctgggtg cacggtacac aggctgcagg gtcatcgcac taaggtctgt gaagaacggt    180

gctgagacac gggtggacct cctctgcagg taggtgcaga ggaggtccac ggcatcaccc    240

ggctgggccc ctactctctg gacaaagaca gcctctacct taacgctccc aagccagcca    300

ccacattcct gcctcctctg tcagaagcca caacagccat ggggtaccac ctgaagaccc    360

tcacactcaa cttcaccatc tccaatctcc agtattcacc agatatgggc aagggctcag    420

ctacattcaa ctccaccgag gggtccttc agcacctgct cagacccttg ttccagaaga     480

gcagcatggg cccctctac ttgggttgcc aactgatctc cctcaggcct gagaaggatg     540

gggcagccac tggtgtggac accacctgca cctaccaccc tgaccctgtg ggccccgggc    600

tggacataca gcagctttac tgggagctga gtcagctgac ccatggtgtc acccaactgg    660

gcttctatgt cctggacagg gatagcctct tcatcaatgg ctatgcaccc cagaatttat    720

caatccgggg cgagtaccag ataaatttcc acattgtcaa ctggaacctc agtaatccag    780

accccacatc ctcagagtac atcaccctgc tgagggacat ccaggacaag gtcaccacac    840

tctacaaagg cagtcaacta catgacacat tccgcttctg cctggtcacc aacttgacga    900

tggactccgt gttggtcact gtcaaggcat tgttctcctc caatttggac cccagcctgg    960

tggagcaagt ctttctagat aagaccctga atgcctcatt ccattggctg ggctccacct   1020

accagttggt ggacatccat gtgacagaaa tggagtcatc agtttatcaa ccaacaagca   1080

gctccagcac ccagcacttc tacctgaatt tcaccatcac caacctacca tattcccagg   1140

acaaagccca gccaggcacc accaattacc agaggaacaa aaggaatatt gaggatgcgc   1200

tcaaccaact cttccgaaac agcagcatca agagttattt ttctgactgt caagtttcaa   1260

cattcaggtc tgtccccaac aggcaccaca ccggggtgga ctccctgtgt aacttctcgc   1320

cactggctcg gagagtagac agagttgcca tctatgagga atttctgcgg atgacccgga   1380

atggtaccca gctgcagaac ttcaccctgg acaggagcag tgtccttgtg gatgggtatt   1440

ttcccaacag aaatgagccc ttaactggga attctgacct tcccttctgg gctgtcatcc   1500

tcatcggctt ggcaggactc ctgggactca tcacatgcct gatctgcggt gtcctggtga   1560

ccacccgccg gcggaagaag gaaggagaat acaacgtcca gcaacagtgc ccaggctact   1620

accagtcaca cctagacctg gaggatctgc aatgactgga acttgccggt gcctggggtg   1680

cctttccccc agccagggtc caaagaagct tggctggggc agaaataaac catattggtc   1740
```

-continued

```
ggacacaaaa aaaaaaaaaa a                                            1761


<210> SEQ ID NO 388
<211> LENGTH: 772
<212> TYPE: PRT
<213> ORGANISM: Homo sapiens

<400> SEQUENCE: 388

Met Ser Met Val Ser His Ser Gly Ala Leu Cys Pro Pro Leu Ala Phe
                5                   10                  15

Leu Gly Pro Pro Gln Trp Thr Trp Glu His Leu Gly Leu Gln Phe Leu
            20                  25                  30

Asn Leu Val Pro Arg Leu Pro Ala Leu Ser Trp Cys Tyr Ser Leu Ser
        35                  40                  45

Thr Ser Pro Ser Pro Thr Cys Gly Met Arg Arg Thr Cys Ser Thr Leu
    50                  55                  60

Ala Pro Gly Ser Ser Thr Pro Arg Arg Gly Ser Phe Arg Ala Trp Ser
 65                 70                  75                  80

Leu Phe Lys Ser Thr Ser Val Gly Pro Leu Tyr Ser Gly Cys Arg Leu
                85                  90                  95

Thr Leu Leu Arg Pro Glu Lys Asp Gly Thr Ala Thr Gly Val Asp Ala
            100                 105                 110

Ile Cys Thr His His Pro Asp Pro Lys Ser Pro Arg Leu Asp Arg Glu
        115                 120                 125

Gln Leu Tyr Trp Glu Leu Ser Gln Leu Thr His Asn Ile Thr Glu Leu
    130                 135                 140

Gly Pro Tyr Ala Leu Asp Asn Asp Ser Leu Phe Val Asn Gly Phe Thr
145                 150                 155                 160

His Arg Ser Ser Val Ser Thr Thr Ser Thr Pro Gly Thr Pro Thr Val
                165                 170                 175

Tyr Leu Gly Ala Ser Lys Thr Pro Ala Ser Ile Phe Gly Pro Ser Ala
            180                 185                 190

Ala Ser His Leu Leu Ile Leu Phe Thr Leu Asn Phe Thr Ile Thr Asn
        195                 200                 205

Leu Arg Tyr Glu Glu Asn Met Trp Pro Gly Ser Arg Lys Phe Asn Thr
    210                 215                 220

Thr Glu Arg Val Leu Gln Gly Leu Leu Arg Pro Leu Phe Lys Asn Thr
225                 230                 235                 240

Ser Val Gly Pro Leu Tyr Ser Gly Cys Arg Leu Thr Leu Leu Arg Pro
                245                 250                 255

Glu Lys Asp Gly Glu Ala Thr Gly Val Asp Ala Ile Cys Thr His Arg
            260                 265                 270

Pro Asp Pro Thr Gly Pro Gly Leu Asp Arg Glu Gln Leu Tyr Leu Glu
        275                 280                 285

Leu Ser Gln Leu Thr His Ser Ile Thr Glu Leu Gly Pro Tyr Thr Leu
    290                 295                 300

Asp Arg Asp Ser Leu Tyr Val Asn Gly Phe Thr His Arg Ser Ser Val
305                 310                 315                 320

Pro Thr Thr Ser Thr Gly Val Val Ser Glu Glu Pro Phe Thr Leu Asn
                325                 330                 335

Phe Thr Ile Asn Asn Leu Arg Tyr Met Ala Asp Met Gly Gln Pro Gly
            340                 345                 350

Ser Leu Lys Phe Asn Ile Thr Asp Asn Val Met Lys His Leu Leu Ser
        355                 360                 365
```

-continued

```
Pro Leu Phe Gln Arg Ser Ser Leu Gly Ala Arg Tyr Thr Gly Cys Arg
    370                 375                 380

Val Ile Ala Leu Arg Ser Val Lys Asn Gly Ala Glu Thr Arg Val Asp
385                 390                 395                 400

Leu Leu Cys Thr Tyr Leu Gln Pro Leu Ser Gly Pro Gly Leu Pro Ile
                405                 410                 415

Lys Gln Val Phe His Glu Leu Ser Gln Gln Thr His Gly Ile Thr Arg
            420                 425                 430

Leu Gly Pro Tyr Ser Leu Asp Lys Asp Ser Leu Tyr Leu Asn Gly Tyr
        435                 440                 445

Asn Glu Pro Gly Pro Asp Glu Pro Pro Thr Thr Pro Lys Pro Ala Thr
    450                 455                 460

Thr Phe Leu Pro Pro Leu Ser Glu Ala Thr Thr Ala Met Gly Tyr His
465                 470                 475                 480

Leu Lys Thr Leu Thr Leu Asn Phe Thr Ile Ser Asn Leu Gln Tyr Ser
                485                 490                 495

Pro Asp Met Gly Lys Gly Ser Ala Thr Phe Asn Ser Thr Glu Gly Val
            500                 505                 510

Leu Gln His Leu Leu Arg Pro Leu Phe Gln Lys Ser Ser Met Gly Pro
        515                 520                 525

Phe Tyr Leu Gly Cys Gln Leu Ile Ser Leu Arg Pro Glu Lys Asp Gly
    530                 535                 540

Ala Ala Thr Gly Val Asp Thr Thr Cys Thr Tyr His Pro Asp Pro Val
545                 550                 555                 560

Gly Pro Gly Leu Asp Ile Gln Gln Leu Tyr Trp Glu Leu Ser Gln Leu
                565                 570                 575

Thr His Gly Val Thr Gln Leu Gly Phe Tyr Val Leu Asp Arg Asp Ser
            580                 585                 590

Leu Phe Ile Asn Gly Tyr Ala Pro Gln Asn Leu Ser Ile Arg Gly Glu
        595                 600                 605

Tyr Gln Ile Asn Phe His Ile Val Asn Trp Asn Leu Ser Asn Pro Asp
    610                 615                 620

Pro Thr Ser Ser Glu Tyr Ile Thr Leu Leu Arg Asp Ile Gln Asp Lys
625                 630                 635                 640

Val Thr Thr Leu Tyr Lys Gly Ser Gln Leu His Asp Thr Phe Arg Phe
                645                 650                 655

Cys Leu Val Thr Asn Leu Thr Met Asp Ser Val Leu Val Thr Val Lys
            660                 665                 670

Ala Leu Phe Ser Ser Asn Leu Asp Pro Ser Leu Val Glu Gln Val Phe
        675                 680                 685

Leu Asp Lys Thr Leu Asn Ala Ser Phe His Trp Leu Gly Ser Thr Tyr
    690                 695                 700

Gln Leu Val Asp Ile His Val Thr Glu Met Glu Ser Ser Val Tyr Gln
705                 710                 715                 720

Pro Thr Ser Ser Ser Ser Thr Gln His Phe Tyr Leu Asn Phe Thr Ile
                725                 730                 735

Thr Asn Leu Pro Tyr Ser Gln Asp Lys Ala Gln Pro Gly Thr Thr Asn
            740                 745                 750

Tyr Gln Arg Asn Lys Arg Asn Ile Glu Asp Ala Ala Pro His Arg Gly
        755                 760                 765

Gly Leu Pro Val
    770
```

-continued

<210> SEQ ID NO 389
<211> LENGTH: 833
<212> TYPE: PRT
<213> ORGANISM: Homo sapiens

<400> SEQUENCE: 389

```
Phe Lys Ser Thr Ser Val Gly Pro Leu Tyr Ser Gly Cys Arg Leu Thr
                5                   10                  15

Leu Leu Arg Pro Glu Lys Asp Gly Thr Ala Thr Gly Val Asp Ala Ile
            20                  25                  30

Cys Thr His His Pro Asp Pro Lys Ser Pro Arg Leu Asp Arg Glu Gln
        35                  40                  45

Leu Tyr Trp Glu Leu Ser Gln Leu Thr His Asn Ile Thr Glu Leu Gly
    50                  55                  60

Pro Tyr Ala Leu Asp Asn Asp Ser Leu Phe Val Asn Gly Phe Thr His
65                  70                  75                  80

Arg Ser Ser Val Ser Thr Thr Ser Thr Pro Gly Thr Pro Thr Val Tyr
                85                  90                  95

Leu Gly Ala Ser Lys Thr Pro Ala Ser Ile Phe Gly Pro Ser Ala Ala
            100                 105                 110

Ser His Leu Leu Ile Leu Phe Thr Leu Asn Phe Thr Ile Thr Asn Leu
        115                 120                 125

Arg Tyr Glu Glu Asn Met Trp Pro Gly Ser Arg Lys Phe Asn Thr Thr
    130                 135                 140

Glu Arg Val Leu Gln Gly Leu Leu Arg Pro Leu Phe Lys Asn Thr Ser
145                 150                 155                 160

Val Gly Pro Leu Tyr Ser Gly Cys Arg Leu Thr Leu Leu Arg Pro Glu
                165                 170                 175

Lys Asp Gly Glu Ala Thr Gly Val Asp Ala Ile Cys Thr His Arg Pro
            180                 185                 190

Asp Pro Thr Gly Pro Gly Leu Asp Arg Glu Gln Leu Tyr Leu Glu Leu
        195                 200                 205

Ser Gln Leu Thr His Ser Ile Thr Glu Leu Gly Pro Tyr Thr Leu Asp
    210                 215                 220

Arg Asp Ser Leu Tyr Val Asn Gly Phe Thr His Arg Ser Ser Val Pro
225                 230                 235                 240

Thr Thr Ser Thr Gly Val Val Ser Glu Glu Pro Phe Thr Leu Asn Phe
                245                 250                 255

Thr Ile Asn Asn Leu Arg Tyr Met Ala Asp Met Gly Gln Pro Gly Ser
            260                 265                 270

Leu Lys Phe Asn Ile Thr Asp Asn Val Met Lys His Leu Leu Ser Pro
        275                 280                 285

Leu Phe Gln Arg Ser Ser Leu Gly Ala Arg Tyr Thr Gly Cys Arg Val
    290                 295                 300

Ile Ala Leu Arg Ser Val Lys Asn Gly Ala Glu Thr Arg Val Asp Leu
305                 310                 315                 320

Leu Cys Thr Tyr Leu Gln Pro Leu Ser Gly Pro Gly Leu Pro Ile Lys
                325                 330                 335

Gln Val Phe His Glu Leu Ser Gln Gln Thr His Gly Ile Thr Arg Leu
            340                 345                 350

Gly Pro Tyr Ser Leu Asp Lys Asp Ser Leu Tyr Leu Asn Gly Tyr Asn
        355                 360                 365

Glu Pro Gly Pro Asp Glu Pro Pro Thr Thr Pro Lys Pro Ala Thr Thr
    370                 375                 380
```

-continued

```
Phe Leu Pro Pro Leu Ser Glu Ala Thr Thr Ala Met Gly Tyr His Leu
385                 390                 395                 400

Lys Thr Leu Thr Leu Asn Phe Thr Ile Ser Asn Leu Gln Tyr Ser Pro
                405                 410                 415

Asp Met Gly Lys Gly Ser Ala Thr Phe Asn Ser Thr Glu Gly Val Leu
            420                 425                 430

Gln His Leu Leu Arg Pro Leu Phe Gln Lys Ser Ser Met Gly Pro Phe
        435                 440                 445

Tyr Leu Gly Cys Gln Leu Ile Ser Leu Arg Pro Glu Lys Asp Gly Ala
    450                 455                 460

Ala Thr Gly Val Asp Thr Thr Cys Thr Tyr His Pro Asp Pro Val Gly
465                 470                 475                 480

Pro Gly Leu Asp Ile Gln Gln Leu Tyr Trp Glu Leu Ser Gln Leu Thr
                485                 490                 495

His Gly Val Thr Gln Leu Gly Phe Tyr Val Leu Asp Arg Asp Ser Leu
            500                 505                 510

Phe Ile Asn Gly Tyr Ala Pro Gln Asn Leu Ser Ile Arg Gly Glu Tyr
        515                 520                 525

Gln Ile Asn Phe His Ile Val Asn Trp Asn Leu Ser Asn Pro Asp Pro
    530                 535                 540

Thr Ser Ser Glu Tyr Ile Thr Leu Leu Arg Asp Ile Gln Asp Lys Val
545                 550                 555                 560

Thr Thr Leu Tyr Lys Gly Ser Gln Leu His Asp Thr Phe Arg Phe Cys
                565                 570                 575

Leu Val Thr Asn Leu Thr Met Asp Ser Val Leu Val Thr Val Lys Ala
            580                 585                 590

Leu Phe Ser Ser Asn Leu Asp Pro Ser Leu Val Glu Gln Val Phe Leu
        595                 600                 605

Asp Lys Thr Leu Asn Ala Ser Phe His Trp Leu Gly Ser Thr Tyr Gln
    610                 615                 620

Leu Val Asp Ile His Val Thr Glu Met Glu Ser Ser Val Tyr Gln Pro
625                 630                 635                 640

Thr Ser Ser Ser Ser Thr Gln His Phe Tyr Leu Asn Phe Thr Ile Thr
                645                 650                 655

Asn Leu Pro Tyr Ser Gln Asp Lys Ala Gln Pro Gly Thr Thr Asn Tyr
            660                 665                 670

Gln Arg Asn Lys Arg Asn Ile Glu Asp Ala Leu Asn Gln Leu Phe Arg
        675                 680                 685

Asn Ser Ser Ile Lys Ser Tyr Phe Ser Asp Cys Gln Val Ser Thr Phe
    690                 695                 700

Arg Ser Val Pro Asn Arg His His Thr Gly Val Asp Ser Leu Cys Asn
705                 710                 715                 720

Phe Ser Pro Leu Ala Arg Arg Val Asp Arg Val Ala Ile Tyr Glu Glu
                725                 730                 735

Phe Leu Arg Met Thr Arg Asn Gly Thr Gln Leu Gln Asn Phe Thr Leu
            740                 745                 750

Asp Arg Ser Ser Val Leu Val Asp Gly Tyr Phe Pro Asn Arg Asn Glu
        755                 760                 765

Pro Leu Thr Gly Asn Ser Asp Leu Pro Phe Trp Ala Val Ile Leu Ile
    770                 775                 780

Gly Leu Ala Gly Leu Leu Gly Leu Ile Thr Cys Leu Ile Cys Gly Val
785                 790                 795                 800
```

-continued

```
Leu Val Thr Thr Arg Arg Arg Lys Lys Glu Gly Glu Tyr Asn Val Gln
                805                 810                 815

Gln Gln Cys Pro Gly Tyr Tyr Gln Ser His Leu Asp Leu Glu Asp Leu
            820                 825                 830

Gln


<210> SEQ ID NO 390
<211> LENGTH: 438
<212> TYPE: PRT
<213> ORGANISM: Homo sapiens

<400> SEQUENCE: 390

Met Gly Tyr His Leu Lys Thr Leu Thr Leu Asn Phe Thr Ile Ser Asn
                  5                  10                  15

Leu Gln Tyr Ser Pro Asp Met Gly Lys Gly Ser Ala Thr Phe Asn Ser
             20                  25                  30

Thr Glu Gly Val Leu Gln His Leu Leu Arg Pro Leu Phe Gln Lys Ser
         35                  40                  45

Ser Met Gly Pro Phe Tyr Leu Gly Cys Gln Leu Ile Ser Leu Arg Pro
     50                  55                  60

Glu Lys Asp Gly Ala Ala Thr Gly Val Asp Thr Thr Cys Thr Tyr His
 65                  70                  75                  80

Pro Asp Pro Val Gly Pro Gly Leu Asp Ile Gln Gln Leu Tyr Trp Glu
                 85                  90                  95

Leu Ser Gln Leu Thr His Gly Val Thr Gln Leu Gly Phe Tyr Val Leu
            100                 105                 110

Asp Arg Asp Ser Leu Phe Ile Asn Gly Tyr Ala Pro Gln Asn Leu Ser
        115                 120                 125

Ile Arg Gly Glu Tyr Gln Ile Asn Phe His Ile Val Asn Trp Asn Leu
    130                 135                 140

Ser Asn Pro Asp Pro Thr Ser Ser Glu Tyr Ile Thr Leu Leu Arg Asp
145                 150                 155                 160

Ile Gln Asp Lys Val Thr Thr Leu Tyr Lys Gly Ser Gln Leu His Asp
                165                 170                 175

Thr Phe Arg Phe Cys Leu Val Thr Asn Leu Thr Met Asp Ser Val Leu
            180                 185                 190

Val Thr Val Lys Ala Leu Phe Ser Ser Asn Leu Asp Pro Ser Leu Val
        195                 200                 205

Glu Gln Val Phe Leu Asp Lys Thr Leu Asn Ala Ser Phe His Trp Leu
    210                 215                 220

Gly Ser Thr Tyr Gln Leu Val Asp Ile His Val Thr Glu Met Glu Ser
225                 230                 235                 240

Ser Val Tyr Gln Pro Thr Ser Ser Ser Ser Thr Gln His Phe Tyr Leu
                245                 250                 255

Asn Phe Thr Ile Thr Asn Leu Pro Tyr Ser Gln Asp Lys Ala Gln Pro
            260                 265                 270

Gly Thr Thr Asn Tyr Gln Arg Asn Lys Arg Asn Ile Glu Asp Ala Leu
        275                 280                 285

Asn Gln Leu Phe Arg Asn Ser Ser Ile Lys Ser Tyr Phe Ser Asp Cys
    290                 295                 300

Gln Val Ser Thr Phe Arg Ser Val Pro Asn Arg His His Thr Gly Val
305                 310                 315                 320

Asp Ser Leu Cys Asn Phe Ser Pro Leu Ala Arg Arg Val Asp Arg Val
                325                 330                 335
```

-continued

```
Ala Ile Tyr Glu Glu Phe Leu Arg Met Thr Arg Asn Gly Thr Gln Leu
            340                 345                 350

Gln Asn Phe Thr Leu Asp Arg Ser Ser Val Leu Val Asp Gly Tyr Phe
        355                 360                 365

Pro Asn Arg Asn Glu Pro Leu Thr Gly Asn Ser Asp Leu Pro Phe Trp
    370                 375                 380

Ala Val Ile Leu Ile Gly Leu Ala Gly Leu Leu Gly Leu Ile Thr Cys
385                 390                 395                 400

Leu Ile Cys Gly Val Leu Val Thr Thr Arg Arg Arg Lys Lys Glu Gly
                405                 410                 415

Glu Tyr Asn Val Gln Gln Gln Cys Pro Gly Tyr Tyr Gln Ser His Leu
            420                 425                 430

Asp Leu Glu Asp Leu Gln
        435
```

<210> SEQ ID NO 391
<211> LENGTH: 2627
<212> TYPE: DNA
<213> ORGANISM: Homo sapiens

<400> SEQUENCE: 391

```
ccacgcgtcc gcccacgcgt ccggaaggca gcggcagctc cactcagcca gtacccagat     60

acgctgggaa ccttccccag ccatggcttc cctggggcag atcctcttct ggagcataat    120

tagcatcatc attattctgg ctggagcaat tgcactcatc attggctttg gtatttcagg    180

gagacactcc atcacagtca ctactgtcgc ctcagctggg aacattgggg aggatggaat    240

cctgagctgc acttttgaac ctgacatcaa ctttctgat atcgtgatac aatggctgaa    300

ggaaggtgtt ttaggcttgg tccatgagtt caaagaaggc aaagatgagc tgtcggagca    360

ggatgaaatg ttcagaggcc ggacagcagt gtttgctgat caagtgatag ttggcaatgc    420

ctctttgcgg ctgaaaaacg tgcaactcac agatgctggc acctacaaat gttatatcat    480

cacttctaaa ggcaagggga atgctaacct tgagtataaa actggagcct tcagcatgcc    540

ggaagtgaat gtggactata atgccagctc agagaccttg cggtgtgagg ctccccgatg    600

gttcccccag cccacagtgg tctgggcatc ccaagttgac cagggagcca acttctcgga    660

agtctccaat accagctttg agctgaactc tgagaatgtg accatgaagg ttgtgtctgt    720

gctctacaat gttacgatca acaacacata ctcctgtatg attgaaaatg acattgccaa    780

agcaacaggg gatatcaaag tgacagaatc ggagatcaaa aggcggagtc acctacagct    840

gctaaactca aaggcttctc tgtgtgtctc ttctttcttt gccatcagct gggcacttct    900

gcctctcagc ccttacctga tgctaaaata atgtgccttg gccacaaaaa agcatgcaaa    960

gtcattgtta caacagggat ctacagaact atttcaccac cagatatgac ctagttttat   1020

atttctggga ggaaatgaat tcatatctag aagtctggag tgagcaaaca agagcaagaa   1080

acaaaaagaa gccaaaagca gaaggctcca atatgaacaa gataaatcta tcttcaaaga   1140

catattagaa gttgggaaaa taattcatgt gaactagaca agtgtgttaa gagtgataag   1200

taaaatgcac gtggagacaa gtgcatcccc agatctcagg gacctccccc tgcctgtcac   1260

ctggggagtg agaggacagg atagtgcatg ttctttgtct ctgaattttt agttatatgt   1320

gctgtaatgt tgctctgagg aagcccctgg aaagtctatc ccaacatatc cacatcttat   1380

attccacaaa ttaagctgta gtatgtaccc taagacgctg ctaattgact gccacttcgc   1440

aactcagggg cggctgcatt ttagtaatgg gtcaaatgat tcacttttta tgatgcttcc   1500
```

-continued

```
aaaggtgcct tggcttctct tcccaactga caaatgccaa agttgagaaa aatgatcata   1560

attttagcat aaacagagca gtcggcgaca ccgattttat aaataaactg agcaccttct   1620

ttttaaacaa acaaatgcgg gtttatttct cagatgatgt tcatccgtga atggtccagg   1680

gaaggacctt tcaccttgac tatatggcat tatgtcatca caagctctga ggcttctcct   1740

ttccatcctg cgtggacagc taagacctca gttttcaata gcatctagag cagtgggact   1800

cagctggggt gatttcgccc cccatctccg ggggaatgtc tgaagacaat tttggttacc   1860

tcaatgaggg agtggaggag gatacagtgc tactaccaac tagtggataa aggccaggga   1920

tgctgctcaa cctcctacca tgtacaggac gtctccccat tacaactacc caatccgaag   1980

tgtcaactgt gtcaggacta agaaaccctg gttttgagta gaaaagggcc tggaaagagg   2040

ggagccaaca aatctgtctg cttcctcaca ttagtcattg gcaaataagc attctgtctc   2100

tttggctgct gcctcagcac agagagccag aactctatcg ggcaccagga taacatctct   2160

cagtgaacag agttgacaag gcctatggga aatgcctgat gggattatct tcagcttgtt   2220

gagcttctaa gtttctttcc cttcattcta ccctgcaagc caagttctgt aagagaaatg   2280

cctgagttct agctcaggtt ttcttactct gaatttagat ctccagaccc ttcctggcca   2340

caattcaaat taaggcaaca aacatatacc ttccatgaag cacacacaga cttttgaaag   2400

caaggacaat gactgcttga attgaggcct tgaggaatga agctttgaag gaaaagaata   2460

ctttgtttcc agccccccttc ccacactctt catgtgttaa ccactgcctt cctggacctt   2520

ggagccacgg tgactgtatt acatgttgtt atagaaaact gattttagag ttctgatcgt   2580

tcaagagaat gattaaatat acatttccta caccaaaaaa aaaaaaa                 2627
```

```
<210> SEQ ID NO 392
<211> LENGTH: 309
<212> TYPE: PRT
<213> ORGANISM: Homo sapiens

<400> SEQUENCE: 392

His Ala Ser Ala His Ala Ser Gly Arg Gln Arg Gln Leu His Ser Ala
                5                   10                  15

Ser Thr Gln Ile Arg Trp Glu Pro Ser Pro Ala Met Ala Ser Leu Gly
            20                  25                  30

Gln Ile Leu Phe Trp Ser Ile Ile Ser Ile Ile Ile Ile Leu Ala Gly
        35                  40                  45

Ala Ile Ala Leu Ile Ile Gly Phe Gly Ile Ser Gly Arg His Ser Ile
    50                  55                  60

Thr Val Thr Thr Val Ala Ser Ala Gly Asn Ile Gly Glu Asp Gly Ile
65                  70                  75                  80

Leu Ser Cys Thr Phe Glu Pro Asp Ile Lys Leu Ser Asp Ile Val Ile
                85                  90                  95

Gln Trp Leu Lys Glu Gly Val Leu Gly Leu Val His Glu Phe Lys Glu
            100                 105                 110

Gly Lys Asp Glu Leu Ser Glu Gln Asp Glu Met Phe Arg Gly Arg Thr
        115                 120                 125

Ala Val Phe Ala Asp Gln Val Ile Val Gly Asn Ala Ser Leu Arg Leu
    130                 135                 140

Lys Asn Val Gln Leu Thr Asp Ala Gly Thr Tyr Lys Cys Tyr Ile Ile
145                 150                 155                 160

Thr Ser Lys Gly Lys Gly Asn Ala Asn Leu Glu Tyr Lys Thr Gly Ala
                165                 170                 175
```

-continued

```
Phe Ser Met Pro Glu Val Asn Val Asp Tyr Asn Ala Ser Ser Glu Thr
            180                 185                 190

Leu Arg Cys Glu Ala Pro Arg Trp Phe Pro Gln Pro Thr Val Val Trp
        195                 200                 205

Ala Ser Gln Val Asp Gln Gly Ala Asn Phe Ser Glu Val Ser Asn Thr
    210                 215                 220

Ser Phe Glu Leu Asn Ser Glu Asn Val Thr Met Lys Val Val Ser Val
225                 230                 235                 240

Leu Tyr Asn Val Thr Ile Asn Asn Thr Tyr Ser Cys Met Ile Glu Asn
                245                 250                 255

Asp Ile Ala Lys Ala Thr Gly Asp Ile Lys Val Thr Glu Ser Glu Ile
            260                 265                 270

Lys Arg Arg Ser His Leu Gln Leu Leu Asn Ser Lys Ala Ser Leu Cys
        275                 280                 285

Val Ser Ser Phe Phe Ala Ile Ser Trp Ala Leu Leu Pro Leu Ser Pro
    290                 295                 300

Tyr Leu Met Leu Lys
305


<210> SEQ ID NO 393
<211> LENGTH: 282
<212> TYPE: PRT
<213> ORGANISM: Homo sapiens

<400> SEQUENCE: 393

Met Ala Ser Leu Gly Gln Ile Leu Phe Trp Ser Ile Ile Ser Ile Ile
                  5                  10                  15

Ile Ile Leu Ala Gly Ala Ile Ala Leu Ile Ile Gly Phe Gly Ile Ser
             20                  25                  30

Gly Arg His Ser Ile Thr Val Thr Thr Val Ala Ser Ala Gly Asn Ile
         35                  40                  45

Gly Glu Asp Gly Ile Leu Ser Cys Thr Phe Glu Pro Asp Ile Lys Leu
     50                  55                  60

Ser Asp Ile Val Ile Gln Trp Leu Lys Glu Gly Val Leu Gly Leu Val
 65                  70                  75                  80

His Glu Phe Lys Glu Gly Lys Asp Glu Leu Ser Glu Gln Asp Glu Met
                 85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240
```

-continued

```
Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280


<210> SEQ ID NO 394
<211> LENGTH: 20
<212> TYPE: PRT
<213> ORGANISM: Homo sapiens

<400> SEQUENCE: 394

Met Ala Ser Leu Gly Gln Ile Leu Phe Trp Ser Ile Ile Ser Ile Ile
 1               5                  10                  15

Ile Ile Leu Ala
            20


<210> SEQ ID NO 395
<211> LENGTH: 20
<212> TYPE: PRT
<213> ORGANISM: Homo sapiens

<400> SEQUENCE: 395

Ile Ile Ile Leu Ala Gly Ala Ile Ala Leu Ile Ile Gly Phe Gly Ile
 1               5                  10                  15

Ser Gly Arg His
            20


<210> SEQ ID NO 396
<211> LENGTH: 20
<212> TYPE: PRT
<213> ORGANISM: Homo sapiens

<400> SEQUENCE: 396

Ile Ser Gly Arg His Ser Ile Thr Val Thr Thr Val Ala Ser Ala Gly
 1               5                  10                  15

Asn Ile Gly Glu
            20


<210> SEQ ID NO 397
<211> LENGTH: 20
<212> TYPE: PRT
<213> ORGANISM: Homo sapiens

<400> SEQUENCE: 397

Gly Asn Ile Gly Glu Asp Gly Ile Leu Ser Cys Thr Phe Glu Pro Asp
 1               5                  10                  15

Ile Lys Leu Ser
            20


<210> SEQ ID NO 398
<211> LENGTH: 20
<212> TYPE: PRT
<213> ORGANISM: Homo sapiens

<400> SEQUENCE: 398

Asp Ile Lys Leu Ser Asp Ile Val Ile Gln Trp Leu Lys Glu Gly Val
 1               5                  10                  15

Leu Gly Leu Val
            20
```

-continued

<210> SEQ ID NO 399
<211> LENGTH: 20
<212> TYPE: PRT
<213> ORGANISM: Homo sapiens

<400> SEQUENCE: 399

Val Leu Gly Leu Val His Glu Phe Lys Glu Gly Lys Asp Glu Leu Ser
1 5 10 15

Glu Gln Asp Glu
20

<210> SEQ ID NO 400
<211> LENGTH: 20
<212> TYPE: PRT
<213> ORGANISM: Homo sapiens

<400> SEQUENCE: 400

Ser Glu Gln Asp Glu Met Phe Arg Gly Arg Thr Ala Val Phe Ala Asp
1 5 10 15

Gln Val Ile Val
20

<210> SEQ ID NO 401
<211> LENGTH: 20
<212> TYPE: PRT
<213> ORGANISM: Homo sapiens

<400> SEQUENCE: 401

Asp Gln Val Ile Val Gly Asn Ala Ser Leu Arg Leu Lys Asn Val Gln
1 5 10 15

Leu Thr Asp Ala
20

<210> SEQ ID NO 402
<211> LENGTH: 21
<212> TYPE: PRT
<213> ORGANISM: Homo sapiens

<400> SEQUENCE: 402

Val Gln Leu Thr Asp Ala Gly Thr Tyr Lys Cys Tyr Ile Ile Thr Ser
1 5 10 15

Lys Gly Lys Gly Asn
20

<210> SEQ ID NO 403
<211> LENGTH: 20
<212> TYPE: PRT
<213> ORGANISM: Homo sapiens

<400> SEQUENCE: 403

Lys Gly Lys Gly Asn Ala Asn Leu Glu Tyr Lys Thr Gly Ala Phe Ser
1 5 10 15

Met Pro Glu Val
20

<210> SEQ ID NO 404
<211> LENGTH: 20
<212> TYPE: PRT
<213> ORGANISM: Homo sapiens

<400> SEQUENCE: 404

-continued

```
Ser Met Pro Glu Val Asn Val Asp Tyr Asn Ala Ser Ser Glu Thr Leu
 1               5                  10                  15

Arg Cys Glu Ala
            20


<210> SEQ ID NO 405
<211> LENGTH: 20
<212> TYPE: PRT
<213> ORGANISM: Homo sapiens

<400> SEQUENCE: 405

Leu Arg Cys Glu Ala Pro Arg Trp Phe Pro Gln Pro Thr Val Val Trp
 1               5                  10                  15

Ala Ser Gln Val
            20


<210> SEQ ID NO 406
<211> LENGTH: 20
<212> TYPE: PRT
<213> ORGANISM: Homo sapiens

<400> SEQUENCE: 406

Trp Ala Ser Gln Val Asp Gln Gly Ala Asn Phe Ser Glu Val Ser Asn
 1               5                  10                  15

Thr Ser Phe Glu
            20


<210> SEQ ID NO 407
<211> LENGTH: 20
<212> TYPE: PRT
<213> ORGANISM: Homo sapiens

<400> SEQUENCE: 407

Asn Thr Ser Phe Glu Leu Asn Ser Glu Asn Val Thr Met Lys Val Val
 1               5                  10                  15

Ser Val Leu Tyr
            20


<210> SEQ ID NO 408
<211> LENGTH: 20
<212> TYPE: PRT
<213> ORGANISM: Homo sapiens

<400> SEQUENCE: 408

Val Ser Val Leu Tyr Asn Val Thr Ile Asn Asn Thr Tyr Ser Cys Met
 1               5                  10                  15

Ile Glu Asn Asp
            20


<210> SEQ ID NO 409
<211> LENGTH: 20
<212> TYPE: PRT
<213> ORGANISM: Homo sapiens

<400> SEQUENCE: 409

Met Ile Glu Asn Asp Ile Ala Lys Ala Thr Gly Asp Ile Lys Val Thr
 1               5                  10                  15

Glu Ser Glu Ile
            20


<210> SEQ ID NO 410
<211> LENGTH: 20
```

-continued

<212> TYPE: PRT
<213> ORGANISM: Homo sapiens

<400> SEQUENCE: 410

Thr Glu Ser Glu Ile Lys Arg Arg Ser His Leu Gln Leu Leu Asn Ser
1               5                   10                  15

Lys Ala Ser Leu
            20

<210> SEQ ID NO 411
<211> LENGTH: 20
<212> TYPE: PRT
<213> ORGANISM: Homo sapiens

<400> SEQUENCE: 411

Ser Lys Ala Ser Leu Cys Val Ser Ser Phe Phe Ala Ile Ser Trp Ala
1               5                   10                  15

Leu Leu Pro Leu
            20

<210> SEQ ID NO 412
<211> LENGTH: 20
<212> TYPE: PRT
<213> ORGANISM: Homo sapiens

<400> SEQUENCE: 412

Ser Ser Phe Phe Ala Ile Ser Trp Ala Leu Leu Pro Leu Ser Pro Tyr
1               5                   10                  15

Leu Met Leu Lys
            20

<210> SEQ ID NO 413
<211> LENGTH: 35
<212> TYPE: PRT
<213> ORGANISM: Homo sapiens

<400> SEQUENCE: 413

Ile Ser Gly Arg His Ser Ile Thr Val Thr Thr Val Ala Ser Ala Gly
1               5                   10                  15

Asn Ile Gly Glu Asp Gly Ile Leu Ser Cys Thr Phe Glu Pro Asp Ile
            20                  25                  30

Lys Leu Ser
        35

<210> SEQ ID NO 414
<211> LENGTH: 35
<212> TYPE: PRT
<213> ORGANISM: Homo sapiens

<400> SEQUENCE: 414

Val Leu Gly Leu Val His Glu Phe Lys Glu Gly Lys Asp Glu Leu Ser
1               5                   10                  15

Glu Gln Asp Glu Met Phe Arg Gly Arg Thr Ala Val Phe Ala Asp Gln
            20                  25                  30

Val Ile Val
        35

<210> SEQ ID NO 415
<211> LENGTH: 65
<212> TYPE: PRT
<213> ORGANISM: Homo sapiens

<400> SEQUENCE: 415

Lys Gly Lys Gly Asn Ala Asn Leu Glu Tyr Lys Thr Gly Ala Phe Ser
 1              5                   10                  15

Met Pro Glu Val Asn Val Asp Tyr Asn Ala Ser Ser Glu Thr Leu Arg
            20                  25                  30

Cys Glu Ala Pro Arg Trp Phe Pro Gln Pro Thr Val Val Trp Ala Ser
        35                  40                  45

Gln Val Asp Gln Gly Ala Asn Phe Ser Glu Val Ser Asn Thr Ser Phe
    50                  55                  60

Glu
65

<210> SEQ ID NO 416
<211> LENGTH: 10
<212> TYPE: PRT
<213> ORGANISM: Homo sapiens

<400> SEQUENCE: 416

Lys Leu Ser Asp Ile Val Ile Gln Trp Leu
 1              5                   10

<210> SEQ ID NO 417
<211> LENGTH: 10
<212> TYPE: PRT
<213> ORGANISM: Homo sapiens

<400> SEQUENCE: 417

Ser Leu Gly Gln Ile Leu Phe Trp Ser Ile
 1              5                   10

<210> SEQ ID NO 418
<211> LENGTH: 10
<212> TYPE: PRT
<213> ORGANISM: Homo sapiens

<400> SEQUENCE: 418

Leu Leu Asn Ser Lys Ala Ser Leu Cys Val
 1              5                   10

<210> SEQ ID NO 419
<211> LENGTH: 10
<212> TYPE: PRT
<213> ORGANISM: Homo sapiens

<400> SEQUENCE: 419

Ser Leu Cys Val Ser Ser Phe Phe Ala Ile
 1              5                   10

<210> SEQ ID NO 420
<211> LENGTH: 10
<212> TYPE: PRT
<213> ORGANISM: Homo sapiens

<400> SEQUENCE: 420

Val Leu Tyr Asn Val Thr Ile Asn Asn Thr
 1              5                   10

<210> SEQ ID NO 421
<211> LENGTH: 10
<212> TYPE: PRT
<213> ORGANISM: Homo sapiens

<400> SEQUENCE: 421

-continued

Ile Leu Phe Trp Ser Ile Ile Ser Ile Ile
1 5 10

<210> SEQ ID NO 422
<211> LENGTH: 10
<212> TYPE: PRT
<213> ORGANISM: Homo sapiens

<400> SEQUENCE: 422

Leu Leu Pro Leu Ser Pro Tyr Leu Met Leu
1 5 10

<210> SEQ ID NO 423
<211> LENGTH: 10
<212> TYPE: PRT
<213> ORGANISM: Homo sapiens

<400> SEQUENCE: 423

Cys Met Ile Glu Asn Asp Ile Ala Lys Ala
1 5 10

<210> SEQ ID NO 424
<211> LENGTH: 10
<212> TYPE: PRT
<213> ORGANISM: Homo sapiens

<400> SEQUENCE: 424

Lys Thr Gly Ala Phe Ser Met Pro Glu Val
1 5 10

<210> SEQ ID NO 425
<211> LENGTH: 10
<212> TYPE: PRT
<213> ORGANISM: Homo sapiens

<400> SEQUENCE: 425

Trp Ala Leu Leu Pro Leu Ser Pro Tyr Leu
1 5 10

<210> SEQ ID NO 426
<211> LENGTH: 10
<212> TYPE: PRT
<213> ORGANISM: Homo sapiens

<400> SEQUENCE: 426

Ile Ile Leu Ala Gly Ala Ile Ala Leu Ile
1 5 10

<210> SEQ ID NO 427
<211> LENGTH: 10
<212> TYPE: PRT
<213> ORGANISM: Homo sapiens

<400> SEQUENCE: 427

Gln Leu Thr Asp Ala Gly Thr Tyr Lys Cys
1 5 10

<210> SEQ ID NO 428
<211> LENGTH: 10
<212> TYPE: PRT
<213> ORGANISM: Homo sapiens

<400> SEQUENCE: 428

Ala Leu Leu Pro Leu Ser Pro Tyr Leu Met

-continued

```
 1               5                   10


<210> SEQ ID NO 429
<211> LENGTH: 10
<212> TYPE: PRT
<213> ORGANISM: Homo sapiens

<400> SEQUENCE: 429

Gln Leu Leu Asn Ser Lys Ala Ser Leu Cys
 1               5                   10


<210> SEQ ID NO 430
<211> LENGTH: 10
<212> TYPE: PRT
<213> ORGANISM: Homo sapiens

<400> SEQUENCE: 430

Ile Leu Ser Cys Thr Phe Glu Pro Asp Ile
 1               5                   10


<210> SEQ ID NO 431
<211> LENGTH: 10
<212> TYPE: PRT
<213> ORGANISM: Homo sapiens

<400> SEQUENCE: 431

Trp Leu Lys Glu Gly Val Leu Gly Leu Val
 1               5                   10


<210> SEQ ID NO 432
<211> LENGTH: 10
<212> TYPE: PRT
<213> ORGANISM: Homo sapiens

<400> SEQUENCE: 432

Leu Gln Leu Leu Asn Ser Lys Ala Ser Leu
 1               5                   10


<210> SEQ ID NO 433
<211> LENGTH: 10
<212> TYPE: PRT
<213> ORGANISM: Homo sapiens

<400> SEQUENCE: 433

Gln Ile Leu Phe Trp Ser Ile Ile Ser Ile
 1               5                   10


<210> SEQ ID NO 434
<211> LENGTH: 10
<212> TYPE: PRT
<213> ORGANISM: Homo sapiens

<400> SEQUENCE: 434

Gly Ile Ser Gly Arg His Ser Ile Thr Val
 1               5                   10


<210> SEQ ID NO 435
<211> LENGTH: 10
<212> TYPE: PRT
<213> ORGANISM: Homo sapiens

<400> SEQUENCE: 435

Phe Glu Pro Asp Ile Lys Leu Ser Asp Ile
 1               5                   10
```

-continued

<210> SEQ ID NO 436
<211> LENGTH: 9
<212> TYPE: PRT
<213> ORGANISM: Homo sapiens

<400> SEQUENCE: 436

Ala Leu Leu Pro Leu Ser Pro Tyr Leu
1 5

<210> SEQ ID NO 437
<211> LENGTH: 9
<212> TYPE: PRT
<213> ORGANISM: Homo sapiens

<400> SEQUENCE: 437

Ser Leu Cys Val Ser Ser Phe Phe Ala
1 5

<210> SEQ ID NO 438
<211> LENGTH: 9
<212> TYPE: PRT
<213> ORGANISM: Homo sapiens

<400> SEQUENCE: 438

Ile Leu Phe Trp Ser Ile Ile Ser Ile
1 5

<210> SEQ ID NO 439
<211> LENGTH: 9
<212> TYPE: PRT
<213> ORGANISM: Homo sapiens

<400> SEQUENCE: 439

Gln Leu Leu Asn Ser Lys Ala Ser Leu
1 5

<210> SEQ ID NO 440
<211> LENGTH: 9
<212> TYPE: PRT
<213> ORGANISM: Homo sapiens

<400> SEQUENCE: 440

Lys Val Val Ser Val Leu Tyr Asn Val
1 5

<210> SEQ ID NO 441
<211> LENGTH: 9
<212> TYPE: PRT
<213> ORGANISM: Homo sapiens

<400> SEQUENCE: 441

Ile Leu Ala Gly Ala Ile Ala Leu Ile
1 5

<210> SEQ ID NO 442
<211> LENGTH: 9
<212> TYPE: PRT
<213> ORGANISM: Homo sapiens

<400> SEQUENCE: 442

Trp Leu Lys Glu Gly Val Leu Gly Leu
1 5

<210> SEQ ID NO 443

-continued

<211> LENGTH: 9
<212> TYPE: PRT
<213> ORGANISM: Homo sapiens

<400> SEQUENCE: 443

Ile Ile Leu Ala Gly Ala Ile Ala Leu
1 5

<210> SEQ ID NO 444
<211> LENGTH: 9
<212> TYPE: PRT
<213> ORGANISM: Homo sapiens

<400> SEQUENCE: 444

Asn Val Thr Met Lys Val Val Ser Val
1 5

<210> SEQ ID NO 445
<211> LENGTH: 9
<212> TYPE: PRT
<213> ORGANISM: Homo sapiens

<400> SEQUENCE: 445

Glu Met Phe Arg Gly Arg Thr Ala Val
1 5

<210> SEQ ID NO 446
<211> LENGTH: 9
<212> TYPE: PRT
<213> ORGANISM: Homo sapiens

<400> SEQUENCE: 446

Ala Val Phe Ala Asp Gln Val Ile Val
1 5

<210> SEQ ID NO 447
<211> LENGTH: 9
<212> TYPE: PRT
<213> ORGANISM: Homo sapiens

<400> SEQUENCE: 447

Leu Leu Pro Leu Ser Pro Tyr Leu Met
1 5

<210> SEQ ID NO 448
<211> LENGTH: 9
<212> TYPE: PRT
<213> ORGANISM: Homo sapiens

<400> SEQUENCE: 448

Leu Leu Asn Ser Lys Ala Ser Leu Cys
1 5

<210> SEQ ID NO 449
<211> LENGTH: 9
<212> TYPE: PRT
<213> ORGANISM: Homo sapiens

<400> SEQUENCE: 449

Val Ile Gln Trp Leu Lys Glu Gly Val
1 5

<210> SEQ ID NO 450
<211> LENGTH: 9
<212> TYPE: PRT

-continued

```
<213> ORGANISM: Homo sapiens

<400> SEQUENCE: 450

Ala Ile Ser Trp Ala Leu Leu Pro Leu
 1               5


<210> SEQ ID NO 451
<211> LENGTH: 9
<212> TYPE: PRT
<213> ORGANISM: Homo sapiens

<400> SEQUENCE: 451

Ser Leu Gly Gln Ile Leu Phe Trp Ser
 1               5


<210> SEQ ID NO 452
<211> LENGTH: 9
<212> TYPE: PRT
<213> ORGANISM: Homo sapiens

<400> SEQUENCE: 452

Ile Ala Leu Ile Ile Gly Phe Gly Ile
 1               5


<210> SEQ ID NO 453
<211> LENGTH: 9
<212> TYPE: PRT
<213> ORGANISM: Homo sapiens

<400> SEQUENCE: 453

Cys Thr Phe Glu Pro Asp Ile Lys Leu
 1               5


<210> SEQ ID NO 454
<211> LENGTH: 9
<212> TYPE: PRT
<213> ORGANISM: Homo sapiens

<400> SEQUENCE: 454

Ile Val Gly Asn Ala Ser Leu Arg Leu
 1               5


<210> SEQ ID NO 455
<211> LENGTH: 9
<212> TYPE: PRT
<213> ORGANISM: Homo sapiens

<400> SEQUENCE: 455

Gly Gln Ile Leu Phe Trp Ser Ile Ile
 1               5
```